US012509454B2

(12) United States Patent
Barsanti et al.

(10) Patent No.: US 12,509,454 B2
(45) Date of Patent: Dec. 30, 2025

(54) THIADIAZOLYL DERIVATIVES

(71) Applicant: IDEAYA Biosciences, Inc., South San Francisco, CA (US)

(72) Inventors: Paul A. Barsanti, South San Francisco, CA (US); Hilary Plake Beck, South San Francisco, CA (US); Melissa Fleury, South San Francisco, CA (US); John E. Knox, South San Francisco, CA (US); Ethan DeNardo McSpadden, South San Francisco, CA (US); Brian Thomas Jones, South San Francisco, CA (US); Luisruben P. Martinez, South San Francisco, CA (US); Zhonghua Pei, South San Francisco, CA (US); Chenbo Wang, South San Francisco, CA (US)

(73) Assignee: IDEAYA Biosciences, Inc., South San Francisco, CA (US)

( * ) Notice: Subject to any disclaimer, the term of this patent is extended or adjusted under 35 U.S.C. 154(b) by 748 days.

(21) Appl. No.: 17/615,123

(22) PCT Filed: May 29, 2020

(86) PCT No.: PCT/US2020/035165
§ 371 (c)(1),
(2) Date: Nov. 30, 2021

(87) PCT Pub. No.: WO2020/243459
PCT Pub. Date: Dec. 3, 2020

(65) Prior Publication Data

US 2023/0078112 A1 Mar. 16, 2023

Related U.S. Application Data

(60) Provisional application No. 62/855,495, filed on May 31, 2019, provisional application No. 62/990,239, filed on Mar. 16, 2020.

(51) Int. Cl.

| | |
|---|---|
| ***C07D 417/14*** | (2006.01) |
| ***C07D 417/12*** | (2006.01) |
| ***C07D 487/04*** | (2006.01) |
| ***C07D 498/18*** | (2006.01) |

(52) U.S. Cl.
CPC ......... *C07D 417/14* (2013.01); *C07D 417/12* (2013.01); *C07D 487/04* (2013.01); *C07D 498/18* (2013.01)

(58) Field of Classification Search
CPC .. C07D 417/12; C07D 417/14; C07D 487/04; C07D 498/18
See application file for complete search history.

(56) References Cited

FOREIGN PATENT DOCUMENTS

| | | | | |
|---|---|---|---|---|
| EP | 3034500 A1 * | 6/2016 | | ......... A61K 31/4439 |
| WO | 2008/075068 A2 | 6/2008 | | |
| WO | 2019/079297 A1 | 4/2019 | | |

OTHER PUBLICATIONS

Tatiani Kent, et al. Nucleic Acids Research, 2016, vol. 44, No. 19, pp. 9381-9392 doi: 10.1093/nar/gkw721.
International Search Report for PCT/US2020/035165 dated Nov. 13, 2020.

* cited by examiner

*Primary Examiner* — Laura L Stockton
(74) *Attorney, Agent, or Firm* — Alice Bradney

(57) ABSTRACT

Disclosed herein are certain thiadiazolyl derivatives Formula (I):

(I)

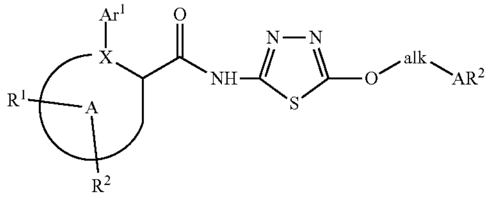

that inhibit DNA Polymerase Theta (Polθ) activity, in particular inhibit Polθ activity by inhibiting ATP dependent helicase domain activity of Polθ. Also, disclosed are pharmaceutical compositions comprising such compounds and methods of treating and/or preventing diseases treatable by inhibition of Polθ such as cancer, including homologous recombination (HR) deficient cancers.

7 Claims, No Drawings

THIADIAZOLYL DERIVATIVES

CROSS-REFERENCES TO RELATED APPLICATIONS

This application claims the benefit under 35 U.S.C. 119(e) of U.S. Provisional Application No. 62/855,495, filed on May 31, 2019 and U.S. Provisional Application No. 62/990,239, filed on Mar. 16, 2020, the contents of each is hereby incorporated by reference in their entirety for all purposes.

STATEMENT AS TO RIGHTS TO INVENTIONS MADE UNDER FEDERALLY SPONSORED RESEARCH AND DEVELOPMENT

Not applicable

REFERENCE TO A "SEQUENCE LISTING," A TABLE, OR A COMPUTER PROGRAM LISTING APPENDIX SUBMITTED ON A COMPACT DISK

Not applicable

FIELD

Disclosed herein are certain thiadiazolyl derivatives that inhibit DNA Polymerase Theta (Polθ) activity, in particular inhibit Polθ activity by inhibiting the ATP dependent helicase domain activity of Polθ. Also, disclosed are pharmaceutical compositions comprising such compounds and methods of treating and/or preventing diseases treatable by inhibition of Polθ such as cancer, including homologous recombination deficient (HRD) cancers.

BACKGROUND

Targeting DNA repair deficiencies has become a proven and effective strategy in cancer treatment. However, DNA repair deficient cancers often become dependent on backup DNA repair pathways, which present an "Achilles heel" that can be targeted to eliminate cancer cells, and is the basis of synthetic lethality. Synthetic lethality is exemplified by the success of poly (ADP-ribose) polymerase (PARP) inhibitors in treating BRCA-deficient breast and ovarian cancers (Audeh M. W., et al., Lancet (2010); 376 (9737): 245-51).

DNA damage repair processes are critical for genome maintenance and stability, among which, double strand breaks (DSBs) are predominantly repaired by the nonhomologous end joining (NHEJ) pathway in G1 phase of the cell cycle and by homologous recombination (HR) in S-G2 phases. A less addressed alternative end-joining (alt-EJ), also known as microhomology-mediated end-joining (MMEJ) pathway, is commonly considered as a "backup" DSB repair pathway when NHEJ or HR are compromised. Numerous genetic studies have highlighted a role for DNA polymerase theta (Polθ, encoded by POLQ) in stimulating MMEJ in higher organisms (Chan S. H., et al., PLoS Genet. (2010); 6: e1001005; Roerink S. F., et al., Genome research. (2014); 24: 954-962; Ceccaldi R., et. al., Nature (2015); 518: 258-62; and Mateos-Gomez P. A., et al., Nature (2015); 518: 254-57).

Polθ is distinct among human DNA polymerases, exhibiting not only a C-terminal DNA polymerase domain but also an N-terminal helicase domain separated by a long and lesser-conserved central domain of unknown function beyond Rad51 binding (Seki eta. A1, 2003, Shima et al 2003; Yousefzadeh and Wood 2013). The N-terminal ATPase/helicase domain belongs to the HELQ class of SF2 helicase super family. In homologous recombination deficient (HRD) cells, Polθ can carry out error-prone DNA synthesis at DNA damage sites through alt-EJ pathway. It has been shown that the helicase domain of Polθ causes suppression of HR pathway through disruption of Rad51 nucleoprotein complex formation involved in initiation of the HR-dependent DNA repair reactions following ionizing radiation. This anti-recombinase activity of Polθ promotes the alt-EJ pathway. In addition, the helicase domain of Polθ contributes to microhomology-mediated strand annealing (Chan S H et al., PLoS Genet. (2010); 6: e1001005; and Kawamura K et al., Int. J. Cancer (2004); 109: 9-16). Polθ efficiently promotes end-joining in alt-EJ pathway by employing this annealing activity when ssDNA overhangs contain >2 bp of microhomology (Kent T., et al., Elife (2016); 5: e13740), and Kent T., et al., Nat. Struct. Mol. Biol. (2015); 22: 230-237). This reannealing activity is achieved through coupled actions of Rad51 interaction followed by ATPase-mediated displacement of Rad51 from DSB damage sites. Once annealed, the primer strand of DNA can be extended by the polymerase domain of Polθ.

The expression of Polθ is largely absent in normal cells but upregulated in breast, lung, and ovarian cancers (Ceccaldi R., et al., Nature (2015); 518, 258-62). Additionally, the increase of Polθ expression correlates with poor prognosis in breast cancer (Lemee F et al., Proc Natl Acad Sci USA. (2010); 107: 13390-5). It has been shown that cancer cells with deficiency in HR, NHEJ or ATM are highly dependent on Polθ expression (Ceccaldi R., et al., Nature (2015); 518: 258-62, Mateos-Gomez P A et al., Nature (2015); 518: 254-57, and Wyatt D. W., et al., Mol. Cell (2016); 63: 662-73). Therefore, Polθ is an attractive target for novel synthetic lethal therapy in cancers containing DNA repair defects.

SUMMARY

Disclosed herein are certain thiadiazolyl derivatives that inhibit Polθ activity, in particular inhibit Polθ activity by inhibiting the ATP dependent helicase domain activity of Polθ. Also, disclosed are pharmaceutical compositions comprising such compounds and methods of treating and/or preventing diseases treatable by inhibition of Polθ such as cancer, including homologous recombination (HR) deficient cancers.

In a first aspect, provided is a compound of Formula (I):

(I)

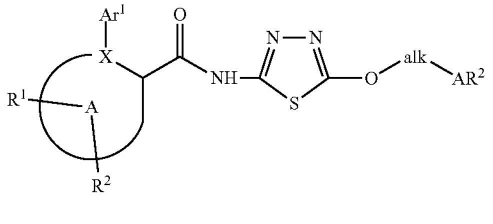

wherein:

X is —N— or —C—;

alk is alkylene;

ring A is phenyl or a five to ten membered heteroaryl ring containing, inclusive of X, one to four heteroatoms independently selected from nitrogen, oxygen, or sulfur;

$Ar^1$ is phenyl, heteroaryl, heterocyclyl, bicyclic heterocyclyl, bridged heterocyclyl, or spiroheterocyclyl, wherein each of the aforementioned ring is substituted with $R^a$, $R^b$, and/or $R^c$, wherein $R^a$ and $R^b$ are independently selected from hydrogen, alkyl, halo, haloalkyl, alkoxy, haloalkoxy, cycloalkyloxy, acyl, acylamino, monoalkylamino, dialkylamino, alkylsulfonyl, cyano, and hydroxy; or $R^a$ and $R^b$, when on adjacent ring vertices, combine to form a $C_{3-6}$ cycloalkyl or $R^a$ and $R^b$, when on the same ring vertex, combine to form oxo, and $R^f$ is selected from hydrogen, alkyl, halo, haloalkyl, alkoxy, haloalkoxy, hydroxy, hydroxyalkyl, alkoxyalkyl, aminoalkyl, heterocyclylalkyl, heterocyclyloxy, aminocarbonyl;

$Ar^2$ is phenyl, heteroaryl, or cycloalkyl, wherein said phenyl and heteroaryl are substituted with $R^d$, $R^e$ and/or $R^f$, wherein $R^d$ and $R^e$ are independently selected from hydrogen, alkyl, halo, haloalkyl, alkoxy, haloalkoxy, hydroxy, and cyano and $R^f$ is selected from hydrogen, alkyl, cycloalkyl, halo, haloalkyl, alkoxy, haloalkoxy, hydroxy, cyano, cyanomethyl, aminocarbonylmethyl, heteroaryl, and heterocyclyl, wherein said heteroaryl and heterocyclyl of $R^f$ are unsubstituted or substituted with one, two, or three substituents independently selected from alkyl, halo, haloalkyl, and hydroxy;

$R^1$ is hydrogen, alkyl, halo, haloalkyl, haloalkoxy, alkoxy, hydroxy, cyano, cyanoalkyl, carboxy, alkoxycarbonyl, acylamino, aminocarbonyl; optionally substituted heteroaryl, hydroxyalkyl, cycloalkyl, hydroxyalkynyl, alkoxyalkyl, aminoalkyl, aminocarbonylalkyl, sulfonylalkyl, aminosulfonylalkyl, optionally substituted heteroaralkyl, or optionally substituted heterocyclylalkyl; and $R^2$ is hydrogen, alkyl, halo, haloalkyl, haloalkoxy, or cyano; or a pharmaceutically acceptable salt thereof.

In a second aspect, provided is a pharmaceutical composition comprising a compound of Formula (I) or a pharmaceutically acceptable thereof and at least one pharmaceutically acceptable excipient.

In a third aspect, provided is a method for treating and/or preventing a disease characterized by overexpression of Polθ in a patient comprising administering to the patient a therapeutically effective amount of a compound of Formula (I) or a pharmaceutically acceptable salt thereof (or an embodiment thereof disclosed herein). In first embodiment of the third aspect, the patient is in recognized need of such treatment. In second embodiment of the third aspect and first embodiment contained therein, the compound of Formula (I) (or an embodiment thereof disclosed herein), or a pharmaceutically acceptable salt thereof is administered in a pharmaceutical composition. In third embodiment of the third aspect and first and second embodiments contained therein, the disease is a cancer.

In a fourth aspect, provided is a method for treating and/or preventing a homologous recombinant (HR) deficient cancer in a patient comprising administering to the patient a therapeutically effective amount of a compound of Formula (I) (or an embodiment thereof disclosed herein), or a pharmaceutically acceptable salt thereof. In first embodiment of the fourth aspect, the patient is in recognized need of such treatment. In second embodiment of the fourth aspect and first embodiment contained therein, the compound of Formula (I) (or an embodiment thereof disclosed herein), or a pharmaceutically acceptable salt thereof is administered in a pharmaceutical composition.

In a fifth aspect, provided is a method for inhibiting DNA repair by Polθ in a cancer cell comprising contacting the cell with an effective amount of a compound of Formula (I) (or an embodiment thereof disclosed herein), or a pharmaceutically acceptable salt thereof. In a first embodiment, the cancer is HR deficient cancer.

In a sixth aspect, provided is a method for treating and/or preventing a cancer in a patient, wherein the cancer is characterized by a reduction or absence of BRCA gene expression, the absence of the BRCA gene, or reduced function of BRCA protein, comprising administering to the subject a therapeutically effective amount of a compound of Formula (I) (or an embodiment thereof disclosed herein), or a pharmaceutically acceptable salt thereof, optionally in a pharmaceutical composition.

In a seventh aspect, provided is a compound of Formula (I) (or an embodiment thereof disclosed herein), or a pharmaceutically acceptable salt thereof for inhibiting DNA repair by Polθ in a cell. In a first embodiment, the cell is HR deficient cell.

In an eighth aspect, provided is a compound of Formula (I) (or an embodiment thereof disclosed herein), or a pharmaceutically acceptable salt thereof for use in the treatment and/or prevention of a disease in a patient, wherein the disease is characterized by overexpression of Polθ.

In a ninth aspect, provided is a compound of Formula (I) (or an embodiment thereof disclosed herein), or a pharmaceutically acceptable salt thereof for use in the treatment and/or prevention of a cancer in a patient, wherein the cancer is characterized by a reduction or absence of BRCA gene expression, the absence of the BRCA gene, or reduced function of BRCA protein.

In a tenth aspect, provided is a compound of Formula (I) (or an embodiment thereof disclosed herein), or a pharmaceutically acceptable salt thereof for use in the treatment and/or prevention of a HR deficient cancer in a patient.

In an eleventh aspect, provided is a compound of Formula (I) (or an embodiment thereof disclosed herein), or a pharmaceutically acceptable salt thereof for use in the treatment and/or prevention of a cancer that is resistant to poly(ADP-ribose) polymerase (PARP) inhibitor therapy in a patient. Examples of cancers resistant to PARP-inhibitors include, but are not limited to, breast cancer, ovarian cancer, lung cancer, bladder cancer, liver cancer, head and neck cancer, pancreatic cancer, gastrointestinal cancer, and colorectal cancer.

In any of the third to eleventh aspects, the cancer is lymphoma, soft tissue, rhabdoid, multiple myeloma, uterus, gastric, peripheral nervous system, rhabdomyosarcoma, bone, colorectal, mesothelioma, breast, ovarian, lung, fibroblast, central nervous system, urinary tract, upper aerodigestive, leukemia, kidney, skin, esophagus, and pancreas (data from large scale drop out screens in cancer cell lines indicate that some cell lines from the above cancers are dependent on polymerase theta for proliferation https://depmap.org/portal/).

In first embodiment, a HR-deficient cancer is breast cancer. Breast cancer includes, but is not limited to, lobular carcinoma in situ (LCIS), a ductal carcinoma in situ (DCIS), an invasive ductal carcinoma (IDC), inflammatory breast cancer, Paget disease of the nipple, Phyllodes tumor, Angiosarcoma, adenoid cystic carcinoma, low-grade adenosquamous carcinoma, medullary carcinoma, mucinous carcinoma, papillary carcinoma, tubular carcinoma, metaplastic carcinoma, micropapillary carcinoma, mixed carcinoma, or another breast cancer, including but not limited to triple negative, HER positive, estrogen receptor positive, progesterone receptor positive, HER and estrogen receptor positive, HER and progesterone receptor positive, estrogen and progesterone receptor positive, and HER and estrogen and progesterone receptor positive. In second embodiment, HR-deficient cancer is ovarian cancer. Ovarian cancer includes, but is not limited to, epithelial ovarian carcinomas (EOC), maturing teratomas, dysgerminomas, endodermal sinus tumors, granulosa-theca tumors, Sertoli-Leydig cell tumors, and primary peritoneal carcinoma.

BRIEF DESCRIPTION OF THE DRAWINGS

Not applicable

DETAILED DESCRIPTION

Before the present invention is further described, it is to be understood that the invention is not limited to the particular embodiments set forth herein, and it is also to be understood that the terminology used herein is for the purpose of describing particular embodiments only, and is not intended to be limiting.

The singular forms "a," "an," and "the" as used herein and in the appended claims include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

When needed, any definition herein may be used in combination with any other definition to describe a composite structural group. By convention, the trailing element of any such definition is that which attaches to the parent moiety. For example, the composite group alkoxyalkyl means that an alkoxy group is attached to the parent molecule through an alkyl group.

The publications discussed herein are provided solely for their disclosure prior to the filing date of the present application. Further, the dates of publication provided may be different from the actual publication dates, which may need to be independently confirmed.

Definitions:

Unless otherwise stated, the following terms used in the specification and claims are defined for the purposes of this application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl, pentyl, and the like. It will be recognized by a person skilled in the art that the term "alkyl" may include "alkylene" groups.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkylsulfonyl" means a —$SO_2R$ radical where R is alkyl as defined above, e.g., methylsulfonyl, ethylsulfonyl, 2-propylsulfonyl, and the like.

"Alkoxy" means a —OR radical where R is alkyl as defined above, e.g., methoxy, ethoxy, propoxy, or 2-propoxy, n-, iso-, or tert-butoxy, and the like.

"Alkoxycarbonyl" means a —COOR radical where R is alkyl as defined above, e.g., methoxycarbonyl, ethoxycarbonyl, propoxy, or 2-propoxycarbonyl, in-, iso-, or tert-butoxycarbonyl, and the like.

"Alkoxyalkyl" means a linear monovalent hydrocarbon radical of one to six carbon atoms or a branched monovalent hydrocarbon radical of three to six carbons substituted with one alkoxy group, as defined above, e.g., 2-methoxyethyl, 1-, 2-, or 3-methoxypropyl, 2-ethoxyethyl, and the like.

"Acyl" means a —C(O)R radical where R is alkyl as defined herein, e.g., methylcarbonyl, ethylcarbonyl, and the like.

"Acylamino" means a —NHC(O)R radical where R is alkyl as defined herein, e.g., methylcarbonylamino, ethylcarbonylamino, and the like.

"Amino" means a —$NH_2$.

"Aminoalkyl" means a linear monovalent hydrocarbon radical of one to six carbon atoms or a branched monovalent hydrocarbon radical of three to six carbons substituted with —NR'R" where R' and R" are independently hydrogen, alkyl, haloalkyl, hydroxyalkyl, alkoxyalkyl, or acyl, each as defined herein, e.g., aminomethyl, aminoethyl, methylaminomethyl, and the like.

"Aminocarbonyl" means a —CONRR' radical wherein R and R' are independently hydrogen or alkyl as defined herein, e.g., —$CONH_2$, methylaminocarbonyl, dimethylaminocarbonyl, and the like.

"Aminocarbonylalkyl" means alkyl radical as defined above that is substituted with —CONRR' radical wherein R and R' are independently hydrogen or alkyl as defined herein, e.g., —$(CH_2)_2CONH_2$, methylaminocarbonylmethyl, dimethylaminocarbonylethyl, and the like.

"Aminocarbonylmethyl" means a —$CH_2CONRR'$ radical wherein R and R' are independently hydrogen or alkyl as defined herein, e.g., —$CH_2CONH_2$, methylaminocarbonylmethyl, dimethylaminocarbonylmethyl, and the like.

"Aminosulfonylalkyl" means alkyl radical as defined above that is substituted with —$SO_2NRR'$ radical wherein R and R' are independently hydrogen or alkyl as defined herein, e.g., —$(CH_2)_2SO_2NH_2$, methylaminosulfonylmethyl, dimethylaminosulfonylethyl, and the like.

"Aryl" means a monovalent monocyclic or bicyclic aromatic hydrocarbon radical of 6 to 10 ring atoms e.g., phenyl or naphthyl.

"Bicyclic heterocyclyl" means a saturated monocyclic ring having 4 to 7 ring carbon ring atoms wherein one or two ring carbon atoms is(are) replaced by a heteroatom selected from N, O, or $S(O)_n$, (where n is an integer from 0 to 2) that is fused to phenyl, five or six-membered heteroaryl or heterocyclyl, each as defined herein. Exemplary bicyclic heterocyclyl groups include, but are not limited to,

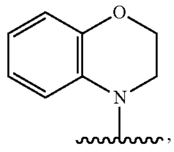,
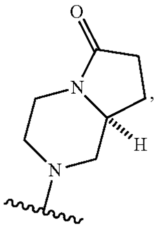, and the like.

"Bridged heterocyclyl" means a saturated monocyclic ring having 5 to 7 ring carbon ring atoms in which two non-adjacent ring atoms are linked by a (CRR')n group where n is 1 to 3 and each R is independently H or methyl (also may be referred to herein as "bridging" group) and further wherein one or two ring carbon atoms, including an atom in the bridging group, is replaced by a heteroatom selected from N, O, or $S(O)_n$, where n is an integer from 0 to 2. Bridged heterocyclyl is optionally substituted with one or two substituents independently selected from alkyl, halo, alkoxy, hydroxy, or cyano. Examples include, but are not limited to, 2-azabicyclo[2.2.2]octane, quinuclidine, 7-oxabicyclo[2.2.1]heptane, and the like.

"Cycloalkyl" means a monocyclic monovalent hydrocarbon radical of three to six carbon atoms which may be saturated or contains one double bond. Cycloalkyl may be unsubstituted or substituted with one or two substituents independently selected from alkyl, halo, alkoxy, hydroxy, or cyano. Examples include, but are not limited to, cyclopropyl, cyclobutyl, cyclopentyl, cyclohexyl, 1-cyanocycloprop-1-yl, 1-cyanomethylcycloprop-1-yl, 3-fluorocyclohexyl, and the like. When cycloalkyl contains a double bond, it may be referred to herein as cycloalkenyl.

"Cycloalkyloxy" means —O—R radical where R is cycloalkyl as defined above. Examples include, but are not limited to, cyclopropyloxy, cyclobutyloxy, and the like.

"Cyanoalkyl" means a linear monovalent hydrocarbon radical of one to six carbon atoms or a branched monovalent hydrocarbon radical of three to six carbons substituted with one cyano, as defined above, e.g., cyanomethyl, 2-cyanoethyl, and the like.

"Deuteroalkyl" means an alkyl radical as defined above wherein one to six hydrogen atoms in the alkyl radical are replaced by deuterium, e.g., $—CD_3$, $—CH_2CD_3$, and the like.

"Dialkylamino" means —NRR' radical where R and R' are independently alkyl as defined herein.

"Halo" means fluoro, chloro, bromo, or iodo, preferably fluoro or chloro.

"Haloalkyl" means alkyl radical as defined above, which is substituted with one to five halogen atoms, such as fluorine or chlorine, including those substituted with different halogens, e.g., $—CH_2Cl$, $—CF_3$, $—CHF_2$, $—CH_2CF_3$, $—CF_2CF_3$, $—CF(CH_3)_2$, and the like. When the alkyl is substituted with only fluoro, it can be referred to in this application as fluoroalkyl.

"Haloalkoxy" means a —OR radical where R is haloalkyl as defined above e.g., $—OCF_3$, $—OCHF_2$, and the like. When R is haloalkyl where the alkyl is substituted with only fluoro, it is referred to in this application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present, they are not both on the same carbon atom. Representative examples include, but are not limited to, hydroxymethyl, 2-hydroxy-ethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Hydroxyalkynyl" means a linear monovalent hydrocarbon radical of two to six carbon atoms or a branched monovalent hydrocarbon radical of three to six carbon atoms that contains a triple bond and is substituted with a hydroxy group.

"Heteroaryl" means a monovalent monocyclic or bicyclic aromatic radical of 5 to 10 ring atoms, unless otherwise stated, where one or more, (in one embodiment, one, two, or three), ring atoms are heteroatom selected from N, O, or S, the remaining ring atoms being carbon, unless stated otherwise. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzoxazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzothiadiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl, and the like. When the heteroaryl ring contains 5 or 6 ring atoms it is also referred to herein as five or six membered heteroaryl.

"Heterocyclyl" means a saturated or unsaturated monovalent monocyclic group of 4 to 8 ring atoms in which one or two ring atoms are heteroatom selected from N, O, or $S(O)_n$, where n is an integer from 0 to 2, the remaining ring atoms being C. Additionally, one or two ring carbon atoms in the heterocyclyl ring can optionally be replaced by a —CO— group. More specifically the term heterocyclyl includes, but is not limited to, azetidinyl, oxetanyl, pyrrolidino, piperidino, homopiperidino, 2-oxopyrrolidinyl, 2-oxopiperidinyl, morpholino, piperazino, tetrahydro-pyranyl, thiomorpholino, and the like. When the heterocyclyl ring is unsaturated it can contain one or two ring double bonds provided that the ring is not aromatic.

"Heterocyclyloxy" means a —O—R radical where R is heterocyclyl, as defined above.

"Heterocyclylalkyl" means a -(alkylene)-R radical where R is heterocyclyl, each group as defined herein.

"Monoalkylamino" means a —NHR radical where R is alkyl as defined above, e.g., methylamino, ethylamino, propylamino, or 2-propylamino, and the like.

"Oxo," as used herein, alone or in combination, refers to =(O).

"Optionally substituted heteroaralkyl" means -(alkylene)-heteroaryl, each as defined above, wherein heteroaryl is optionally substituted with one, two, or three substituents independently selected from alkyl, alkylsulfonyl, cycloalkyl, carboxy, alkoxycarbonyl, hydroxy, alkoxy, halo, haloalkyl, haloalkoxy, amino, alkylamino, dialkylamino, and cyano, unless stated otherwise.

"Optionally substituted heterocyclyl" means -(alkylene)-heterocyclyl, each as defined above, wherein heterocyclyl is optionally substituted with one, two, or three substituents independently selected from alkyl, alkylsulfonyl, cycloalkyl, carboxy, alkoxycarbonyl, hydroxy, hydroxyalkyl, alkoxy, alkoxyalkyl, aminoalkyl, halo, haloalkyl, haloalkoxy, and cyano, unless stated otherwise.

"Sulfonylalkyl" means alkyl radical as defined above that is substituted with —$SO_2R$ radical wherein R is alkyl as defined herein, e.g., methylsulfonylmethyl, ethylsulfonylethyl, and the like.

"Spiroheterocyclyl" means a saturated bicyclic ring having 6 to 10 ring atoms in which one, two, or three ring atoms are heteroatom selected from N, O, or $S(O)_n$, where n is an integer from 0 to 2, the remaining ring atoms being C and the rings are connected through only one atom, the connecting atom is also called the spiroatom, most often a quaternary carbon ("spiro carbon"). Examples include, but are not limited to, 2,6-diazaspiro[3.3]heptane, 2,6-diazaspiro[3.4]octane, 4-oxa-7-azaspiro[2.5]octane, 2-azaspiro[3.4]octane, 2-azaspiro[3.5]-nonane, 2,7-diazaspiro[4.4]nonane, and the like.

"Pharmaceutically acceptable salts" as used herein is meant to include salts of the active compounds which are prepared with relatively nontoxic acids or bases, depending on the particular substituents found on the compounds described herein. When compounds disclosed herein contain relatively acidic functionalities, base addition salts can be obtained by contacting the neutral form of such compounds with a sufficient amount of the desired base, either neat or in a suitable inert solvent. Examples of salts derived from pharmaceutically acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogen carbonic, phosphoric, monohydrogen phosphoric, dihydrogen phosphoric, sulfuric, monohydrogen sulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound can differ from the various salt forms in certain physical properties, such as solubility in polar solvents, but otherwise the salts are equivalent to the parent form of the compound for the purposes of the present invention.

The present disclosure also includes protected derivatives of compounds of the present disclosure. For example, when compounds of the present disclosure contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis,* $5^{th}$ Ed., John Wiley & Sons, Inc. (2014), the disclosure of which is incorporated herein by reference in its entirety. The protected derivatives of compounds of the present disclosure can be prepared by methods well known in the art.

The present disclosure also includes prodrugs of the compound of Formula (I) (and any embodiment thereof disclosed herein including specific compounds) or a pharmaceutically acceptable salt thereof. Prodrugs of the compounds described herein are those compounds that readily undergo chemical changes under physiological conditions to provide the compounds of the present invention. An example, without limitation, of a prodrug would be a compound which is administered as an ester (the "prodrug"), but then is metabolically hydrolyzed to the carboxylic acid, the active entity. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of Formulae (I) (and any embodiment thereof disclosed herein including specific compounds) can exist in unsolvated forms as well as solvated forms, including hydrated forms. In general, the solvated forms are equivalent to unsolvated forms and are intended to be encompassed within the scope of the present invention. Certain compounds of Formulae (I) may exist in multiple crystalline or amorphous forms. In general, all physical forms are equivalent for the uses contemplated by the present disclosure and are intended to be within the scope of the present disclosure.

Certain compounds of Formulae (I) (and any embodiment thereof disclosed herein including specific compounds) possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer to the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

Certain compounds of the present disclosure can exist as tautomers and/or geometric isomers. All possible tautomers and cis and trans isomers, as individual forms and mixtures thereof are within the scope of this disclosure. For example, certain hydroxy substituted compound of Formula (I) may exist as as tautomers as shown below:

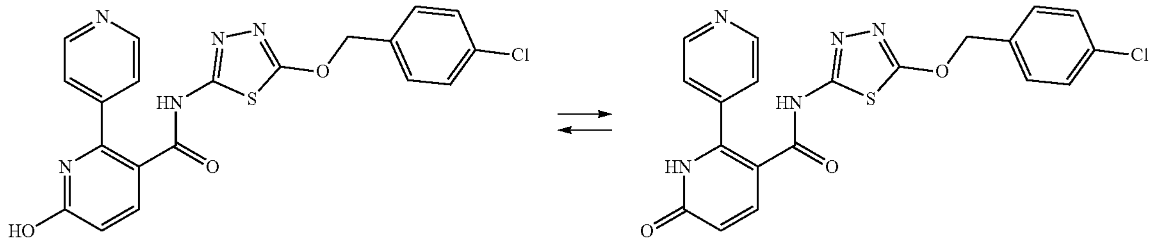 [SMILES: O=C(Nc1nnc(OCc2ccc(Cl)cc2)s1)c1ccc(O)nc1-c1ccncc1 ; O=C(Nc1nnc(OCc2ccc(Cl)cc2)s1)c1ccc(=O)[nH]c1-c1ccncc1]

The compounds of Formulae (I) (and any embodiment thereof disclosed herein including specific compounds) may also contain unnatural amounts of isotopes at one or more of the atoms that constitute such compounds. Unnatural amounts of an isotope may be defined as ranging from the amount found in nature to an amount 100% of the atom in question. that differ only in the presence of one or more isotopically enriched atoms. Exemplary isotopes that can be incorporated into compounds of the present invention, such as a compound of Formula (I) (and any embodiment thereof disclosed herein including specific compounds) include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{17}O$, $^{18}O$, $^{32}P$, $^{33}P$, $^{35}S$, $^{18}F$, $^{36}Cl$, $^{123}I$, and $^{125}I$, respectively. Isotopically labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, in compounds disclosed herein, including in Table 1 below one or more hydrogen atoms are replaced by $^{2}H$ or 3H, or one or more carbon atoms are replaced by $^{13}C$- or $^{14}C$-enriched carbon. Positron emitting isotopes such as $^{15}O$, $^{13}N$, $^{11}C$, and $^{15}F$ are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

“Pharmaceutically acceptable carrier or excipient” means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. “A pharmaceutically acceptable carrier/excipient” as used in the specification and claims includes both one and more than one such excipient.

“About,” as used herein, is intended to qualify the numerical values which it modifies, denoting such a value as variable within a margin of error. When no particular margin of error, such as a standard deviation to a mean value given in a chart or table of data, is recited, the term “about” should be understood to mean that range which would encompass ±10%, preferably ±5%, the recited value and the range is included.

“Disease” as used herein is intended to be generally synonymous, and is used interchangeably with, the terms “disorder,” “syndrome,” and “condition” (as in medical condition), in that all reflect an abnormal condition of the human or animal body or of one of its parts that impairs normal functioning, is typically manifested by distinguishing signs and symptoms, and causes the human or animal to have a reduced duration or quality of life.

“Patient” is generally synonymous with the term “subject” and as used herein includes all mammals including humans. Examples of patients include humans, livestock such as cows, goats, sheep, pigs, and rabbits, and companion animals such as dogs, cats, rabbits, and horses. Preferably, the patient is a human.

“In need of treatment” as used herein means the patient is being treated by a physician or other caregiver after diagnoses of the disease. For example, the patient has been diagnosed as having a disease linked to overexpression of Polθ or a homologous recombination (HR)-deficient cancer.

“Administration”, “administer” and the like, as they apply to, for example, a patient, cell, tissue, organ, or biological fluid, refer to contact of, for example, a compound of Formula (I), a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

“Therapeutically effective amount” as used herein means the amount of a compound of Formula (I) (and any embodiment thereof disclosed herein including specific compounds) or a pharmaceutically acceptable salt thereof that, when administered to a patient for treating a disease either alone or as part of a pharmaceutical composition and either in a single dose or as part of a series of doses, is sufficient to affect such treatment for the disease. The “therapeutically effective amount” will vary depending on the compound, the disease and its severity and the age, weight, etc., of the mammal to be treated. The therapeutically effective amount can be ascertained by measuring relevant physiological effects, and it can be adjusted in connection with the dosing regimen and diagnostic analysis of the subject’s condition, and the like. By way of example, measurement of the serum level of a compound of Formula (I) (or, e.g., a metabolite thereof) at a particular time post-administration may be indicative of whether a therapeutically effective amount has been used.

“Treating” or “treatment” of a disease includes:

(1) inhibiting the disease, i.e., arresting or reducing the development of the disease or its clinical symptoms; or (2) relieving the disease, i.e., causing regression of the disease or its clinical symptoms.

“Inhibiting”, “reducing,” or any variation of these terms in relation of Polθ, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of Polθ activity compared to its normal activity.

The term "preventing" refers to causing the clinical symptoms of the disease not to develop in a mammal that may be exposed to or predisposed to the disease but does not yet experience or display symptoms of the disease.

The term "homologous recombination" refers to the cellular process of genetic recombination in which nucleotide sequences are exchanged between two similar or identical DNA.

The term "homologous recombination (HR) deficient cancer" refers to a cancer that is characterized by a reduction or absence of a functional HR repair pathway. HR deficiency may arise from absence of one or more HR-associated genes or presence of one or more mutations in one or more HR-associated genes. Examples of HR-associated genes include BRCA1, BRCA2, RAD54, RAD51B, Ct1P (Choline Transporter-Like Protein), PALB2 (Partner and Localizer of BRCA2), XRCC2 (X-ray repair complementing defective repair in Chinese hamster cells 2), RECQL4 (RecQ Protein-Like 4), BLM (Bloom syndrome, RecQ helicase-like), WRN (Werner syndrome, one or more HR-associated genes) Nbs 1 (Nibrin), and genes encoding Fanconi anemia (FA) proteins or FA-like genes e.g, FANCA, FANCB, FANCC, FANCD1 (BRCA2), FANCD2, FANCE, FANCF, FANCG, FANCI, FANJ (BRIP1), FANCL, FANCM, FANCN (RALB2), FANCP (SLX4), FANCS (BRCA1), RAD51C, and XPF.

The term "Polθ overexpression" refers to the increased expression or activity of Polθ in a diseases cell e.g., cancerous cell, relative to expression or activity of Polθ in a normal cell (e.g., non-diseased cell of the same kind). The amount of Polθ can be at least 2-fold, at least 3-fold, at least 4-fold, at least 5-fold, at least 10-fold, or more relative to the Polθ expression in a normal cell. Examples of Polθ cancers include, but are not limited to, breast, ovarian, cervical, lung, colorectal, gastric, bladder and prostate cancers.

Representative compound of Formula (I) are listed in Table 1 below:

| Cpd # | Structure | Name |
|---|---|---|
| 1 | 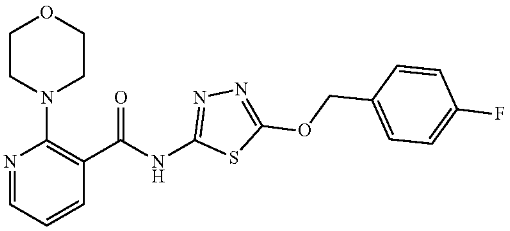 [SMILES: O=C(Nc1nnc(OCc2ccc(F)cc2)s1)c1cccnc1N1CCOCC1] | N-(5-((4-fluorobenzyl)oxy)-1,3,4-thiadiazol-2-yl)-2-morpholinonicotinamide |
| 2 | 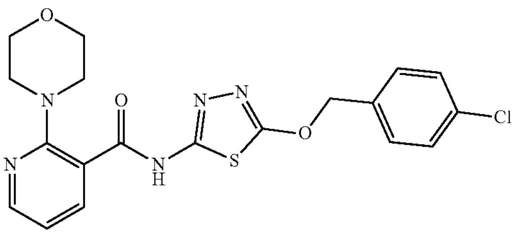 [SMILES: O=C(Nc1nnc(OCc2ccc(Cl)cc2)s1)c1cccnc1N1CCOCC1] | N-(5-((4-chlorobenzyl)oxy)-1,3,4-thiadiazol-2-yl)-2-morpholinonicotinamide |
| 3 | 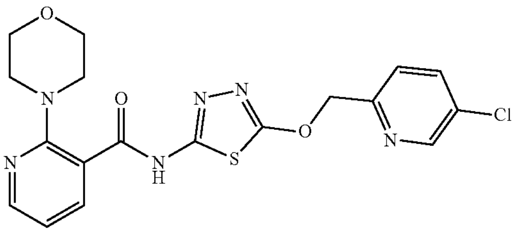 [SMILES: O=C(Nc1nnc(OCc2ccc(Cl)cn2)s1)c1cccnc1N1CCOCC1] | N-(5-((5-chloropyridin-2-yl)methoxy)-1,3,4-thiadiazol-2-yl)-2-morpholinonicotinamide |
| 4 | 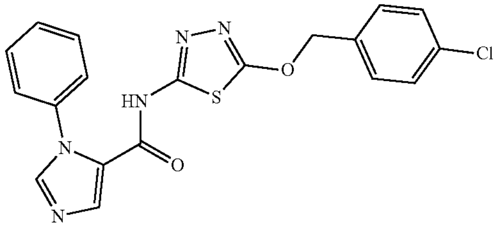 [SMILES: O=C(Nc1nnc(OCc2ccc(Cl)cc2)s1)c1cncn1-c1ccccc1] | N-(5-((4-chlorobenzyl)oxy)-1,3,4-thiadiazol-2-yl)-1-phenyl-1H-imidazole-5-carboxamide |

-continued

| Cpd # | Structure | Name |
|---|---|---|
| 5 | 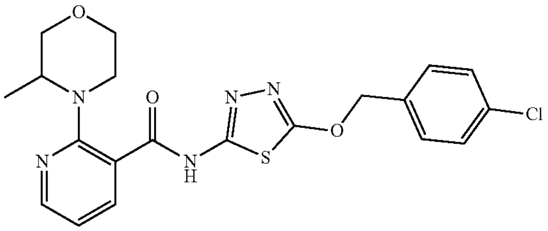 [SMILES: CC1COCCN1c1ncccc1C(=O)Nc1nnc(OCc2ccc(Cl)cc2)s1] | N-(5-((4-chlorobenzyl)oxy)-1,3,4-thiadiazol-2-yl)-2-(3-methymethylmorpholino) nicotinamide |
| 6 | 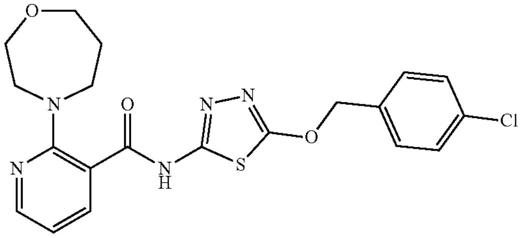 | N-(5-((4-chlorobenzyl)oxy)-1,3,4-thiadiazol-2-yl)-2-(1,4-oxazepan-4-yl)nicotinamide |
| 7 | 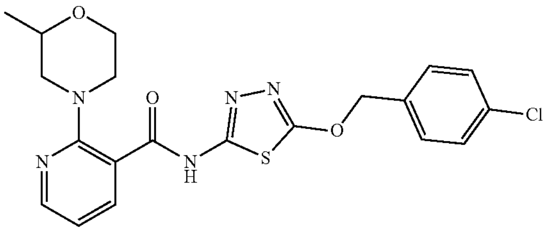 [SMILES: CC1CN(c2ncccc2C(=O)Nc2nnc(OCc3ccc(Cl)cc3)s2)CCO1] | N-(5-((4-chlorobenzyl)oxy)-1,3,4-thiadiazol-2-yl)-2-(2-methylmorpholino)nicotinamide |
| 8 | 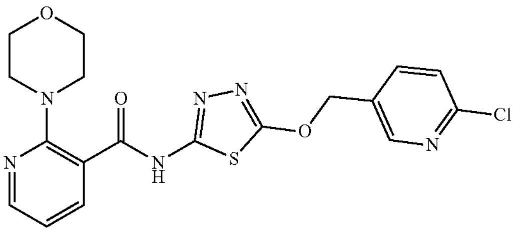 [SMILES: O=C(Nc1nnc(OCc2ccc(Cl)nc2)s1)c1cccnc1N1CCOCC1] | N-(5-((6-chloropyridin-3-yl)methoxy)-1,3,4-thiadiazol-2-yl)-2-morpholinonicotinamide |
| 9 | 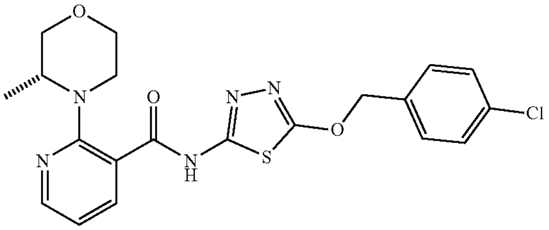 [SMILES: C[C@@H]1COCCN1c1ncccc1C(=O)Nc1nnc(OCc2ccc(Cl)cc2)s1] | (R)-N-(5-((4-chlorobenzyl)oxy)-1,3,4-thiadiazol-2-yl)-2-(3-methylmorpholino)nicotinamide |
| 10 | 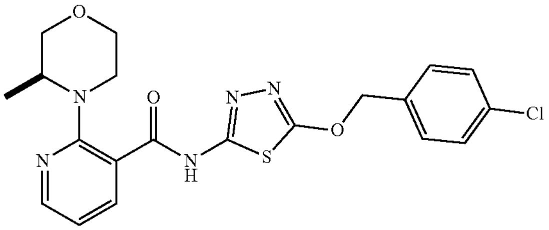 [SMILES: C[C@H]1COCCN1c1ncccc1C(=O)Nc1nnc(OCc2ccc(Cl)cc2)s1] | (S)-N-(5-((4-chlorobenzyl)oxy)-1,3,4-thiadiazol-2-yl)-2-(3-methylmorpholmo)nicotinamide |

-continued

| Cpd # | Structure | Name |
|---|---|---|
| 11 | 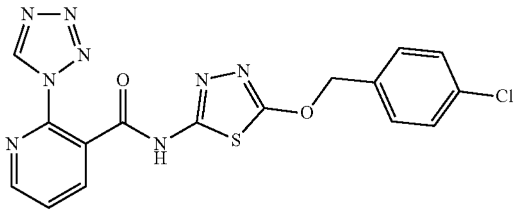 [SMILES: O=C(Nc1nnc(OCc2ccc(Cl)cc2)s1)c1cccnc1-n1cnnn1] | N-(5-((4-chlorobenzyl)oxy)-1,3,4-thiadiazol-2-yl)-2-(1H-tetrazol-1-yl)nicotinamide |
| 12 | 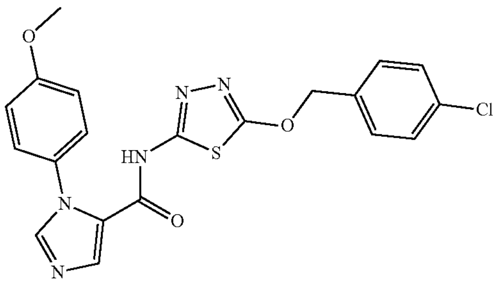 [SMILES: COc1ccc(-n2cncc2C(=O)Nc2nnc(OCc3ccc(Cl)cc3)s2)cc1] | N-(5-((4-chlorobenzyl)oxy)-1,3-4-thiadiazol-2-yl)-1-(4-methoxyphenyl)-1H-imidazole-5-carboxamide |
| 13 | 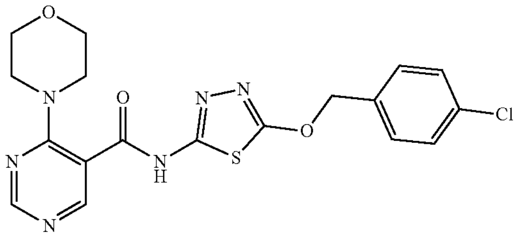 [SMILES: O=C(Nc1nnc(OCc2ccc(Cl)cc2)s1)c1cncnc1N1CCOCC1] | N-(5-((4-chlorobenzyl)oxy)-1,3,4-thiadiazol-2-yl)-4-morpholinopyrimidine-5-carboxamide |
| 14 | 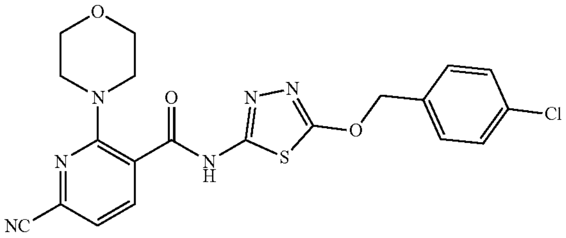 [SMILES: N#Cc1ccc(C(=O)Nc2nnc(OCc3ccc(Cl)cc3)s2)c(N2CCOCC2)n1] | N-(5-((4-chlorobenzyl)oxy)-1,3,4-thiadiazol-2-yl)-6-cyano-2-morpholinonicotinamide |
| 15 | 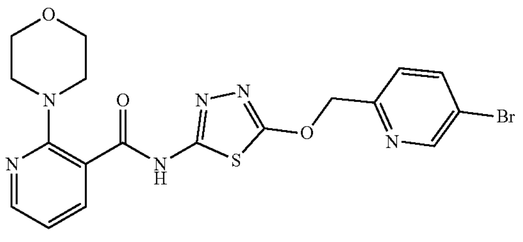 [SMILES: O=C(Nc1nnc(OCc2ccc(Br)cn2)s1)c1cccnc1N1CCOCC1] | N-(5-((5-bromopyridin-2-yl)methoxy)-1,3,4-thiadiazol-2-yl)-2-morpholinonicotinamide |
| 16 | 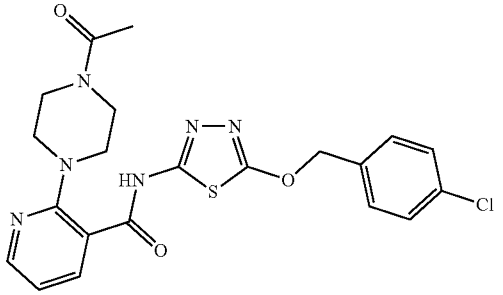 [SMILES: CC(=O)N1CCN(c2ncccc2C(=O)Nc2nnc(OCc3ccc(Cl)cc3)s2)CC1] | 2-(4-acetylpiperazin-1-yl)-N-(5-((4-chlorobenzyl)oxy)-1,3,4-thiadiazol-2-yl)nicotinamide |

-continued

| Cpd # | Structure | Name |
|---|---|---|
| 17 | 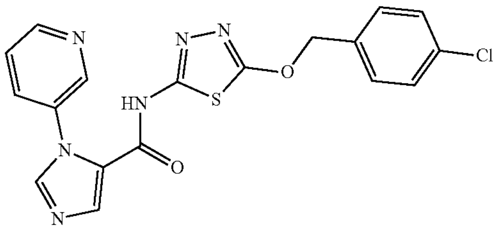 [SMILES: O=C(Nc1nnc(OCc2ccc(Cl)cc2)s1)c1cncn1-c1cccnc1] | N-(5-((4-chlorobenzyl)oxy)-1,3,4-thiadiazol-2-yl)-1-(pyridin-3-yl)-1H-imidazole-5-carboxamide |
| 18 | 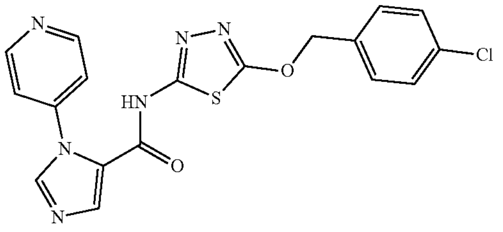 [SMILES: O=C(Nc1nnc(OCc2ccc(Cl)cc2)s1)c1cncn1-c1ccncc1] | N-(5-((4-chlorobenzyl)oxy)-1,3,4-thiadiazol-2-yl)-1-(pyridin-4-yl)-1H-imidazole-5-carboxamide |
| 19 | 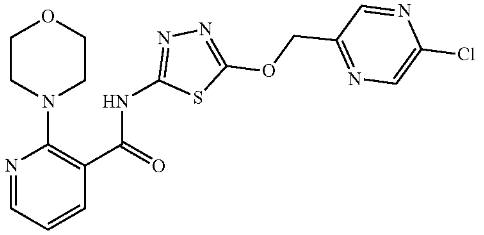 [SMILES: O=C(Nc1nnc(OCc2cnc(Cl)cn2)s1)c1cccnc1N1CCOCC1] | N-(5-((5-chloropyrazin-2-yl)methoxy)-1,3,4-thiadiazol-2-yl)-2-morpholinonicotinamide |
| 20 | 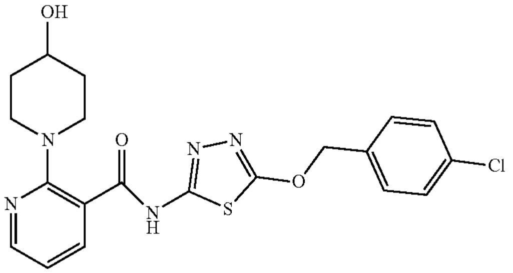 [SMILES: O=C(Nc1nnc(OCc2ccc(Cl)cc2)s1)c1cccnc1N1CCC(O)CC1] | N-(5-((5-chloropyridin-2-yl)methoxy)-1,3,4-thiadiazol-2-yl)-2-(4-hydroxypiperidin-1-yl)nicotinamide |
| 21 | 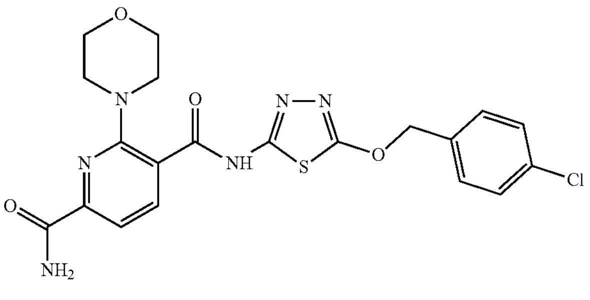 [SMILES: NC(=O)c1ccc(C(=O)Nc2nnc(OCc3ccc(Cl)cc3)s2)c(N2CCOCC2)n1] | N5-(5-((4-chlorobenzyl)oxy)-1,3,4-thiadiazol-2-yl)-6-morpholinopyridine-2,5-dicarboxamide |
| 22 | 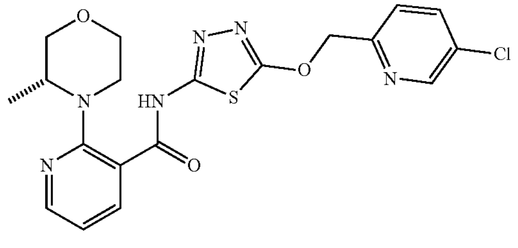 [SMILES: C[C@@H]1COCCN1c1ncccc1C(=O)Nc1nnc(OCc2ccc(Cl)cn2)s1] | (R)-N-(5-((5-chloropyridin-2-yl)methoxy)-1,3,4-thiadiazol-2-yl)-2-(3-methylmorpholino)nicotinamide |

-continued

| Cpd # | Structure | Name |
| --- | --- | --- |
| 23 | 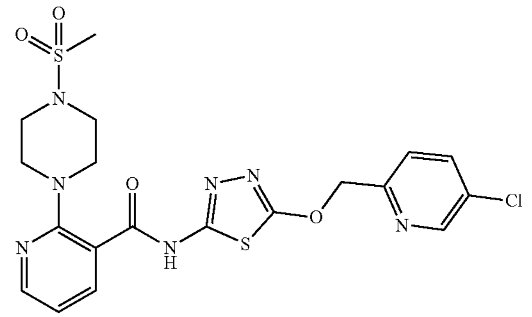 [SMILES: CS(=O)(=O)N1CCN(c2ncccc2C(=O)Nc2nnc(OCc3ccc(Cl)cn3)s2)CC1] | N-(5-((5-chloropyridin-2-yl)methoxy)-1,3,4-thiadiazol-2-yl)-2-(4-(methylsulfonyl)piperazin-1-yl)nicotinamide |
| 24 | 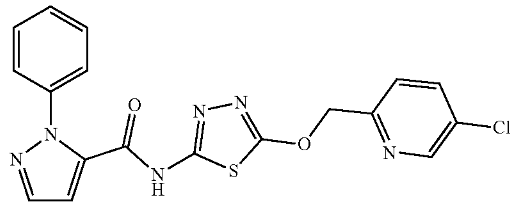 [SMILES: O=C(Nc1nnc(OCc2ccc(Cl)cn2)s1)c1ccnn1-c1ccccc1] | N-(5-((5-chloropyridin-2-yl)methoxy)-1,3,4-thiadiazol-2-yl)-1-phenyl-1H-pyrazole-5-carboxamide |
| 25 | 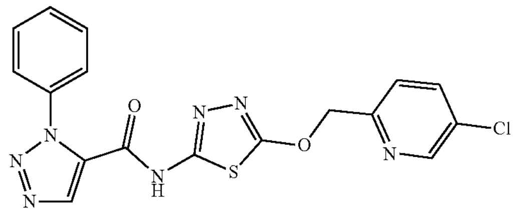 [SMILES: O=C(Nc1nnc(OCc2ccc(Cl)cn2)s1)c1cnnn1-c1ccccc1] | N-(5-((5-chloropyridin-2-yl)methoxy)-1,3,4-thiadiazol-2-yl)-1-phenyl-1H-1,2,3-triazole-5-carboxamide |
| 26 | 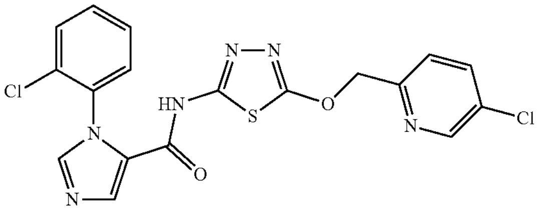 [SMILES: O=C(Nc1nnc(OCc2ccc(Cl)cn2)s1)c1cncn1-c1ccccc1Cl] | 1-(2-chlorophenyl)-N-(5-((5-chloropyridin-2-yl)methoxy)-1,3,4-thiadiazol-2-yl)-1H-imidazole-5-carboxamide |
| 27 | 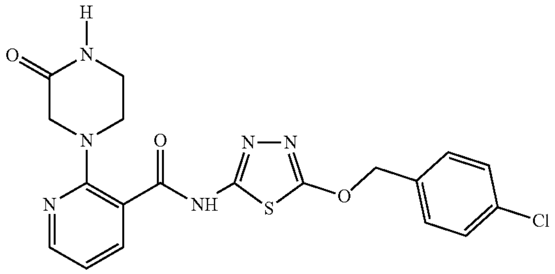 [SMILES: O=C1CN(c2ncccc2C(=O)Nc2nnc(OCc3ccc(Cl)cc3)s2)CCN1] | N-(5-((4-chlorobenzyl)oxy)-1,3,4-thiadiazol-2-yl)-2-(3-oxopiperazin-1-yl)nicotinamide-6-d |
| 28 | 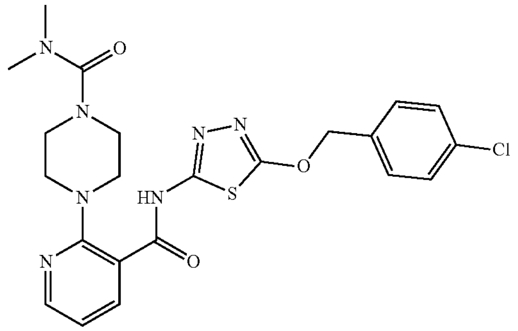 [SMILES: CN(C)C(=O)N1CCN(c2ncccc2C(=O)Nc2nnc(OCc3ccc(Cl)cc3)s2)CC1] | 4-(3-((5-((4-chlorobenzyl)oxy)-1,3,4-thiadiazol-2-yl)carbamoyl)pyridin-2-yl)-N,N-dimethylpiperazine-1-carboxamide |

-continued

| Cpd # | Structure | Name |
|---|---|---|
| 29 | 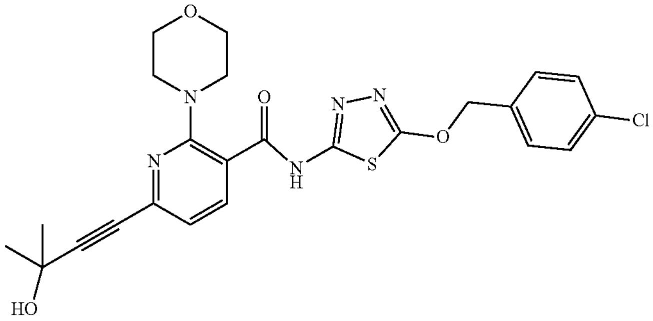 [SMILES: CC(C)(O)C#Cc1ccc(C(=O)Nc2nnc(OCc3ccc(Cl)cc3)s2)c(N2CCOCC2)n1] | N-(5-((4-chlorobenzyl)oxy)-1,3,4-thiadiazol-2-yl)-6-(3-hydroxy-3-methylbut-1-yn-1-yl)-2-morpholinonicotinamide |
| 30 | 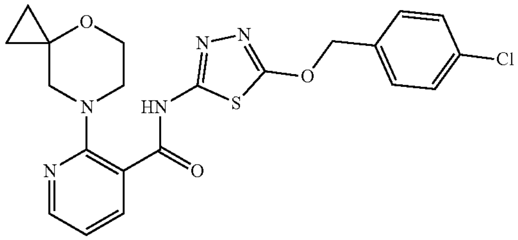 [SMILES: O=C(Nc1nnc(OCc2ccc(Cl)cc2)s1)c1cccnc1N1CCOC2(CC2)C1] | N-(5-((4-chlorobenzyl)oxy)-1,3,4-thiadiazol-2-yl)-2-(4-oxa-7-azaspiro[2.5]octan-7-yl)nicotinamide |
| 31 | 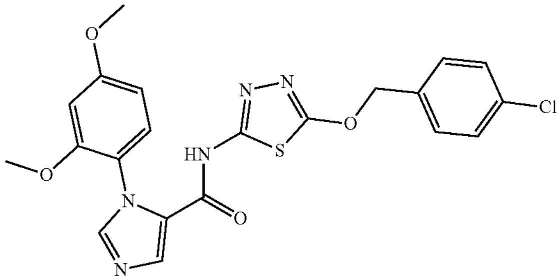 [SMILES: COc1ccc(-n2cncc2C(=O)Nc2nnc(OCc3ccc(Cl)cc3)s2)c(OC)c1] | N-(5-((4-chlorobenzyl)oxy)-1,3,4-thiadiazol-2-yl)-1-(2,4-dimethoxyphenyl)-1H-imidazole-5-carboxamide |
| 32 | 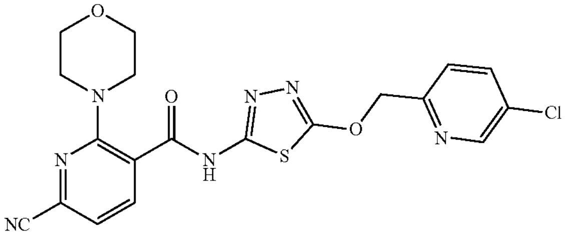 [SMILES: N#Cc1ccc(C(=O)Nc2nnc(OCc3ccc(Cl)cn3)s2)c(N2CCOCC2)n1] | N-(5-((5-chloropyridin-2-yl)methoxy)-1,3,4-thiadiazol-2-yl)-6-cyano-2-morpholinonicotinamide |
| 33 | 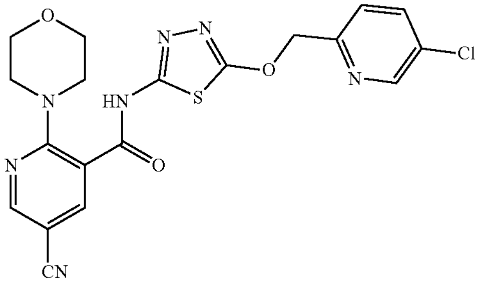 [SMILES: N#Cc1cnc(N2CCOCC2)c(C(=O)Nc2nnc(OCc3ccc(Cl)cn3)s2)c1] | N-(5-((5-chloropyridin-2-yl)methoxy)-1,3,4-thiadiazol-2-yl)-5-cyano-2-morpholinonicotinamide |

-continued

| Cpd # | Structure | Name |
|---|---|---|
| 34 | 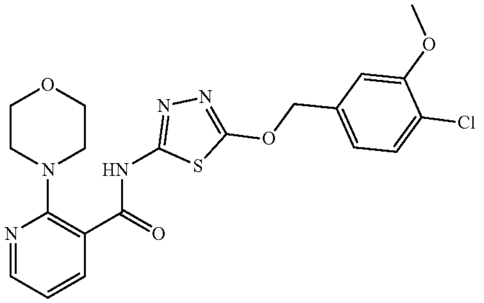 [SMILES: COc1cc(COc2nnc(NC(=O)c3cccnc3N3CCOCC3)s2)ccc1Cl] | N-(5-((4-chloro-3-methoxybenzyl)oxy)-1,3,4-thiadiazol-2-yl)-2-morpholinonicotinamide |
| 35 | 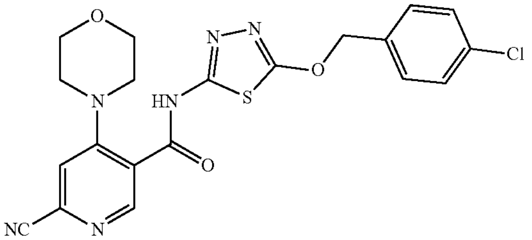 [SMILES: N#Cc1cc(N2CCOCC2)c(C(=O)Nc2nnc(OCc3ccc(Cl)cc3)s2)cn1] | N-(5-((4-chlorobenzyl)oxy)-1,3,4-thiadiazol-2-yl)-6-cyano-4-morpholinonicotinamide |
| 36 | 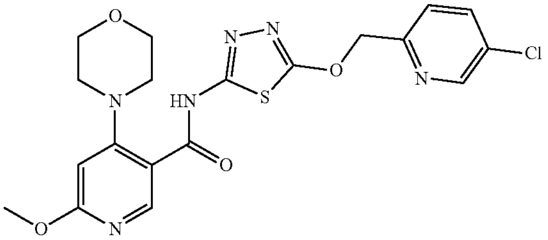 [SMILES: COc1cc(N2CCOCC2)c(C(=O)Nc2nnc(OCc3ccc(Cl)cn3)s2)cn1] | N-(5-((5-chloropyridin-2-yl)methoxy)-1,3,4-thiadiazol-2-yl)-6-methoxy-4-morpholinonicotinamide |
| 37 | 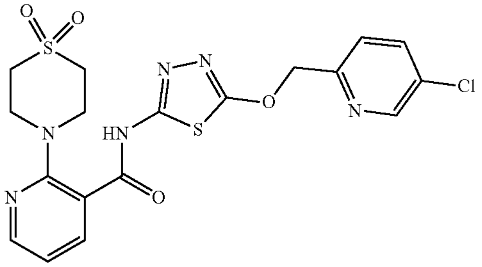 [SMILES: O=C(Nc1nnc(OCc2ccc(Cl)cn2)s1)c1cccnc1N1CCS(=O)(=O)CC1] | N-(5-((5-chloropyridin-2-yl)methoxy)-1,3,4-thiadiazol-2-yl)-2-(1,1-dioxidothiomorpholino)nicotinamide |
| 38 | 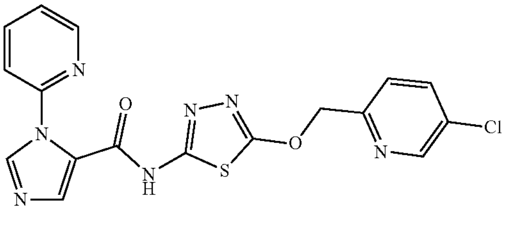 [SMILES: O=C(Nc1nnc(OCc2ccc(Cl)cn2)s1)c1cncn1-c1ccccn1] | N-(5-((5-chloropyridin-2-yl)methoxy)-1,3,4-thiadiazol-2-yl)-1-(pyridin-2-yl)-1H-imidazole-5-carboxamide |
| 39 | 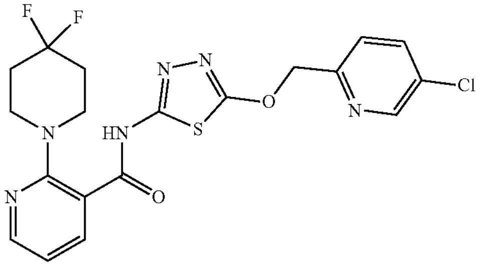 | N-(5-((5-chloropyridin-2-yl)methoxy)-1,3,4-thiadiazol-2-yl)-2-(4,4-difluoropiperidin-1-yl)nicotinamide |

-continued

| Cpd # | Structure | Name |
|---|---|---|
| 40 | 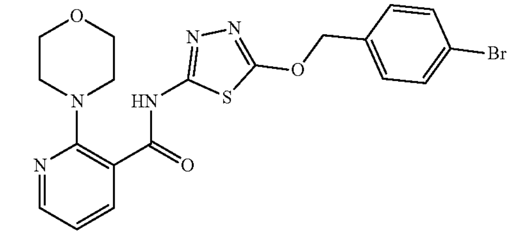 [SMILES: O=C(Nc1nnc(OCc2ccc(Br)cc2)s1)c1cccnc1N1CCOCC1] | N-(5-((4-bromobenzyl)oxy)-1,3,4-thiadiazol-2-yl)-2-morpholinonicotinamide |
| 41 | 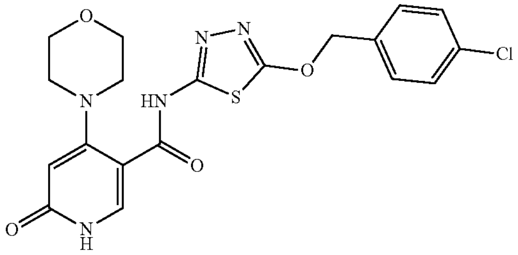 or 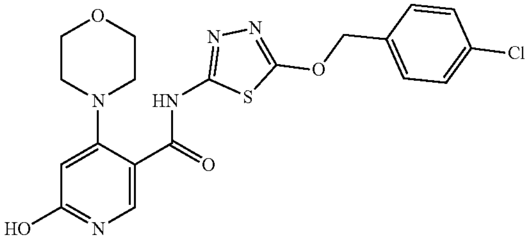 [SMILES: O=C(Nc1nnc(OCc2ccc(Cl)cc2)s1)c1cnc(O)cc1N1CCOCC1] | N-(5-((4-chlorobenzyl)oxy)-1,3,4-thiadiazol-2-yl)-4-morpholino-6-oxo-1,6-dihydropyridirin-3-carboxamide or its tautomer N-(5-((4-chlorobenzyl)oxy)-1,3,4-thiadiazol-2-yl)-6-hydroxy-4-morpholinonicotinamide |
| 42 | 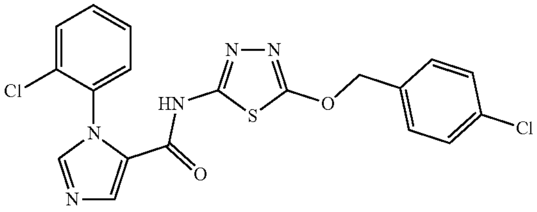 [SMILES: O=C(Nc1nnc(OCc2ccc(Cl)cc2)s1)c1cncn1-c1ccccc1Cl] | N-(5-((4-chlorobenzyl)oxy)-1,3,4-thiadiazol-2-yl)-1-(2-chlorophenyl)-1H-imidazole-5-carboxamide |
| 43 | 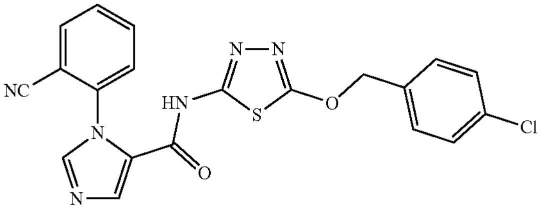 [SMILES: N#Cc1ccccc1-n1cncc1C(=O)Nc1nnc(OCc2ccc(Cl)cc2)s1] | N-(5-((4-chlorobenzyl)oxy)-1,3,4-thiadiazol-2-yl)-1-(2-cyanophenyl)-1H-imidazole-5-carboxamide |
| 44 | 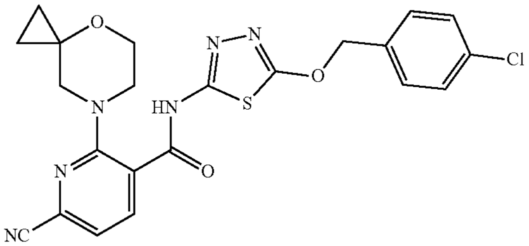 [SMILES: N#Cc1ccc(C(=O)Nc2nnc(OCc3ccc(Cl)cc3)s2)c(N2CCOC3(CC3)C2)n1] | N-(5-((4-chlorobenzyl)oxy)-1,3,4-thiadiazol-2-yl)-6-cyano-2-(4-oxa-7-azaspiro[2.5]octan-7-yl)nicotinamide |

-continued

| Cpd # | Structure | Name |
|---|---|---|
| 45 | 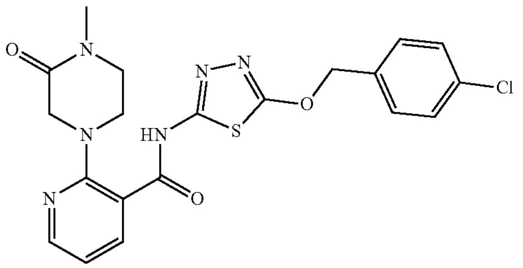 [SMILES: CN1CCN(c2ncccc2C(=O)Nc2nnc(OCc3ccc(Cl)cc3)s2)CC1=O] | N-(5-((4-chlorobenzyl)oxy)-1,3,4-thiadiazol-2-yl)-2-(4-methyl-3-oxopiperazin-1-yl)nicotinamide |
| 46 | 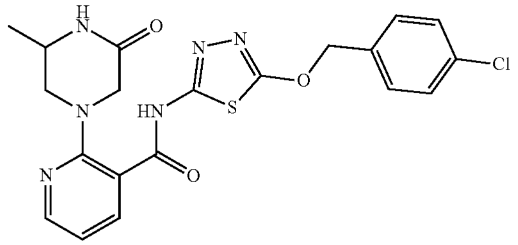 [SMILES: CC1CN(c2ncccc2C(=O)Nc2nnc(OCc3ccc(Cl)cc3)s2)CC(=O)N1] | N-(5-((4-chlorobenzyl)oxy)-1,3,4-thiadiazol-2-yl)-2-(3-methyl-5-oxopiperazin-1-yl)nicotinamide |
| 47 | 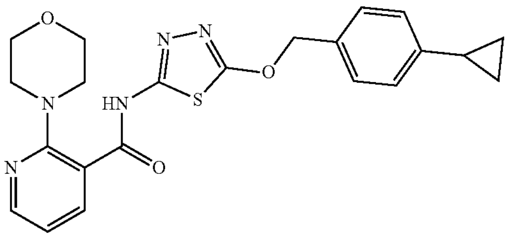 [SMILES: O=C(Nc1nnc(OCc2ccc(C3CC3)cc2)s1)c1cccnc1N1CCOCC1] | N-(5-((4-cyclopropylbenzyl)oxy)-1,3,4-thiadiazol-2-yl)-2-morpholinonicotinamide |
| 48 | 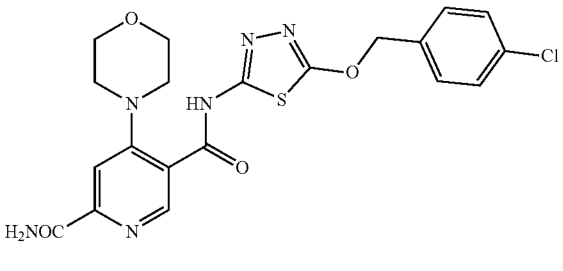 [SMILES: NC(=O)c1cc(N2CCOCC2)c(C(=O)Nc2nnc(OCc3ccc(Cl)cc3)s2)cn1] | N5-(5-((4-chlorobenzyl)oxy)-1,3,4-thiadiazol-2-yl)-4-morpholinopyridine-2,5-dicarboxamide |
| 49 | 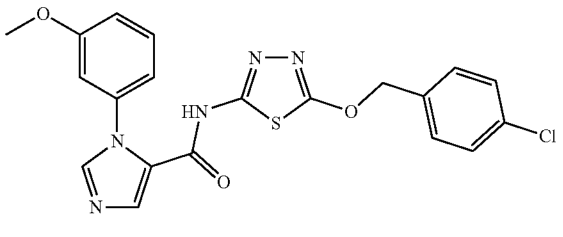 [SMILES: COc1cccc(-n2cncc2C(=O)Nc2nnc(OCc3ccc(Cl)cc3)s2)c1] | N-(5-((4-chlorobenzyl)oxy)-1,3,4-thiadiazol-2-yl)-1-(3-methoxyphenyl)-1H-imidazole-5-carboxamide |
| 50 | 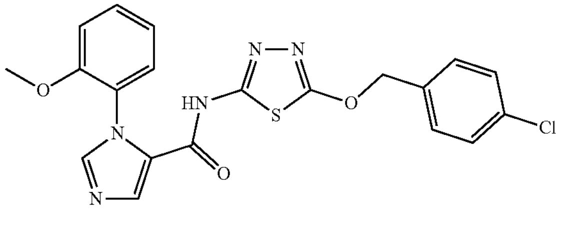 [SMILES: COc1ccccc1-n1cncc1C(=O)Nc1nnc(OCc2ccc(Cl)cc2)s1] | N-(5-((4-chlorobenzyl)oxy)-1,3,4-thiadiazol-2-yl)-1-(2-methoxyphenyl)-1H-imidazole-5-carboxamide |

-continued

| Cpd # | Structure | Name |
|---|---|---|
| 51 | 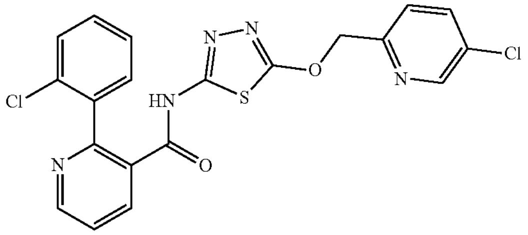 [SMILES: O=C(Nc1nnc(OCc2ccc(Cl)cn2)s1)c1cccnc1-c1ccccc1Cl] | 2-(2-chlorophenyl)-N-(5-((5-chloropyridin-2-yl)methoxy)-1,3,4-thiadiazol-2-yl)nicotinamide |
| 52 | 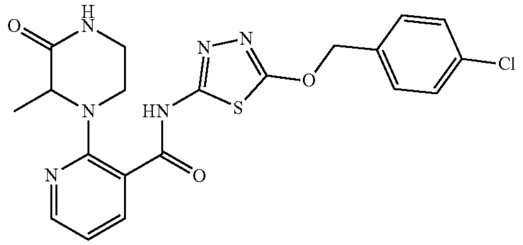 [SMILES: CC1C(=O)NCCN1c1ncccc1C(=O)Nc1nnc(OCc2ccc(Cl)cc2)s1] | N-(5-((4-chlorobenzyl)oxy)-1,3,4-thiadiazol-2-yl)-2-(2-methyl-3-oxopiperazin-1-yl)nicotinamide |
| 53 | 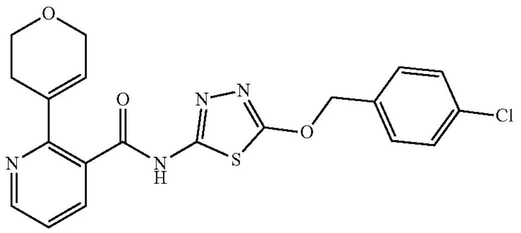 [SMILES: O=C(Nc1nnc(OCc2ccc(Cl)cc2)s1)c1cccnc1C1=CCOCC1] | N-(5-((4-chlorobenzyl)oxy)-1,3,4-thiadiazol-2-yl)-2-(3,6-dihydro-2H-pyran-4-yl)nicotinamide |
| 54 | 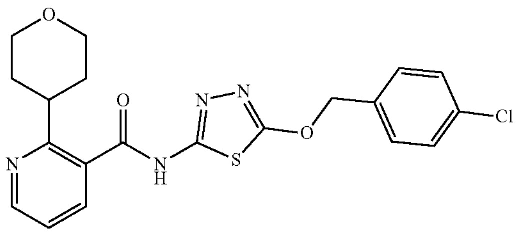 | N-(5-((4-chlorobenzyl)oxy)-1,3,4-thiadiazol-2-yl)-2-(tetrahydro-2H-pyran-4-yl)nicotinamide |
| 55 | 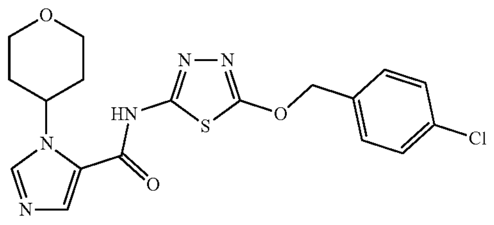 [SMILES: O=C(Nc1nnc(OCc2ccc(Cl)cc2)s1)c1cncn1C1CCOCC1] | N-(5-((4-chlorobenzyl)oxy)-1,3,4-thiadiazol-2-yl)-1-(tetrahydro-2H-pyran-4-yl)-1H-imidazole-5-carboxamide |
| 56 | 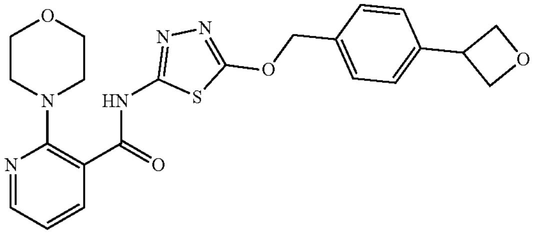 [SMILES: O=C(Nc1nnc(OCc2ccc(C3COC3)cc2)s1)c1cccnc1N1CCOCC1] | 2-morpholino-N-(5-((4-(oxetan-3-yl)benzyl)oxy)-1,3,4-thiadiazol-2-yl)nicotinamide-6-d |

-continued

| Cpd # | Structure | Name |
| --- | --- | --- |
| 57 | 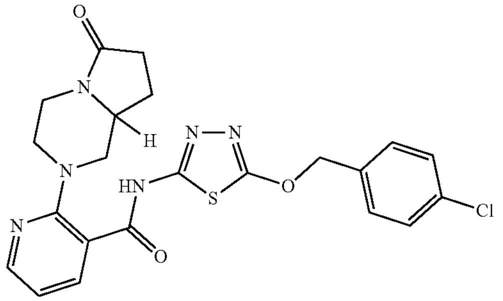 [SMILES: O=C(Nc1nnc(OCc2ccc(Cl)cc2)s1)c1cccnc1N1CCN2C(=O)CCC2C1] | N-(5-((4-chlorobenzyl)oxy)-1,3,4-thiadiazol-2-yl)-2-(6-oxohexahydropyrrolo[1,2-a]pyrazin-2(1H)-yl-8a-d)nicotinamide |
| 58 | 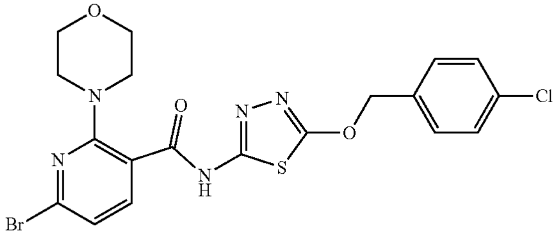 [SMILES: O=C(Nc1nnc(OCc2ccc(Cl)cc2)s1)c1ccc(Br)nc1N1CCOCC1] | 6-bromo-N-(5-((4-chlorobenzyl)oxy)-1,3,4-thiadiazol-2-yl)-2-morpholinonicotinamide |
| 59 | 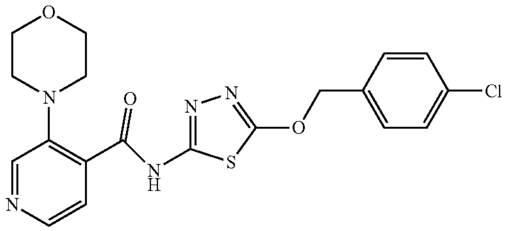 [SMILES: O=C(Nc1nnc(OCc2ccc(Cl)cc2)s1)c1ccncc1N1CCOCC1] | N-(5-((4-chlorobenzyl)oxy)-1,3,4-thiadiazol-2-yl)-3-morpholinoisonicotinamide |
| 60 | 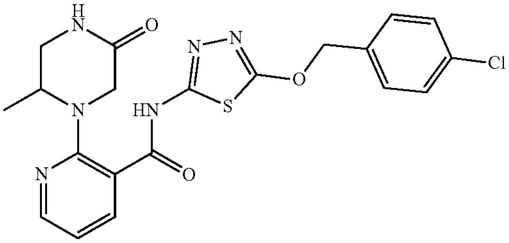 [SMILES: CC1CNC(=O)CN1c1ncccc1C(=O)Nc1nnc(OCc2ccc(Cl)cc2)s1] | N-(5-((4-chlorobenzyl)oxy)-1,3,4-thiadiazol-2-yl)-2-(2-methyl-5-oxopiperazin-1-yl)nicotinamide |
| 61 | 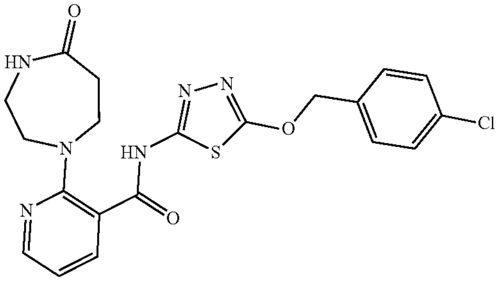 [SMILES: O=C1CCN(c2ncccc2C(=O)Nc2nnc(OCc3ccc(Cl)cc3)s2)CCN1] | N-(5-((4-chlorobenzyl)oxy)-1,3,4-thiadiazol-2-yl)-2-(5-oxo-1,4-diazepan-1-yl)nicotinamide |
| 62 | 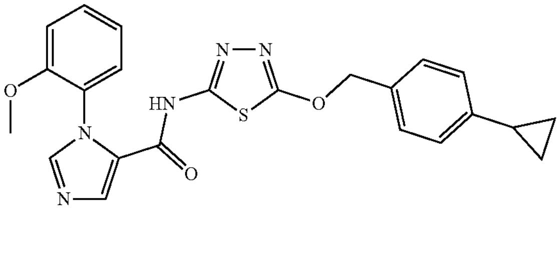 [SMILES: COc1ccccc1-n1cncc1C(=O)Nc1nnc(OCc2ccc(C3CC3)cc2)s1] | N-(5-((4-cyclopropylbenzyl)oxy)-1,3,4-thiadiazol-2-yl)-1-(2-methoxyphenyl)-1H-imidazole-5-carboxamide |

-continued

| Cpd # | Structure | Name |
|---|---|---|
| 63 | 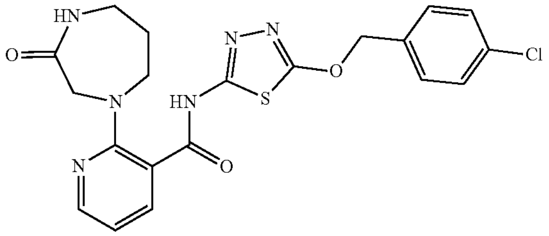 [SMILES: O=C1CN(c2ncccc2C(=O)Nc2nnc(OCc3ccc(Cl)cc3)s2)CCCN1] | N-(5-((4-chlorobenzyl)oxy)-1,3,4-thiadiazol-2-yl)-2-(3-oxo-1,4-diazepan-1-yl)nicotinamide |
| 64 | 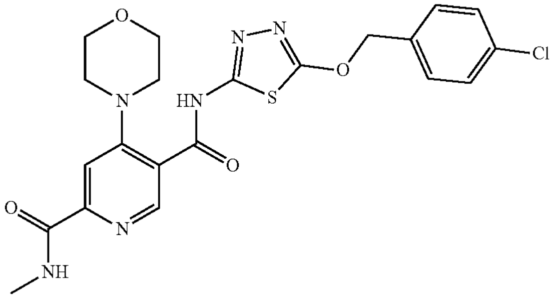 [SMILES: CNC(=O)c1cc(N2CCOCC2)c(C(=O)Nc2nnc(OCc3ccc(Cl)cc3)s2)cn1] | $N^5$-(5-((4-chlorobenzyl)oxy)-1,3,4-thiadiazol-2-yl)-N2-methyl-4-morpholinopyridine-2,5-dicarboxamide |
| 65 | 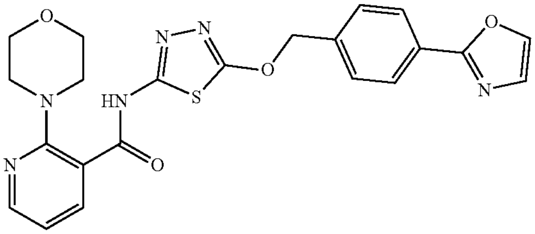 [SMILES: O=C(Nc1nnc(OCc2ccc(-c3ncco3)cc2)s1)c1cccnc1N1CCOCC1] | 2-morpholino-N-(5-((4-(oxazol-2-yl)benzyl)oxy)-1,3,4-thiadiazol-2-yl)nicotinamide |
| 66 | 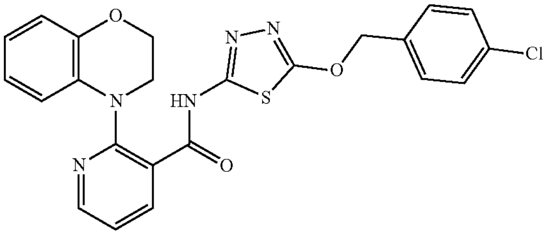 [SMILES: O=C(Nc1nnc(OCc2ccc(Cl)cc2)s1)c1cccnc1N1CCOc2ccccc21] | N-(5-((4-chlorobenzyl)oxy)-1,3,4-thiadiazol-2-yl)-2-(2,3-dihydro-4H-benzo[b][1,4]oxazin-4-yl)nicotinamide |
| 67 | 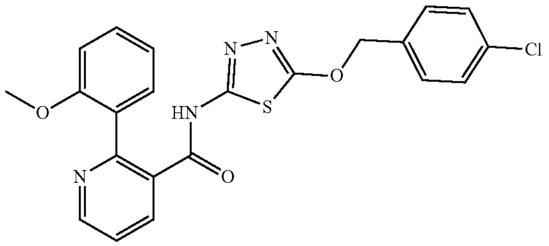 [SMILES: COc1ccccc1-c1ncccc1C(=O)Nc1nnc(OCc2ccc(Cl)cc2)s1] | N-(5-((4-chlorobenzyl)oxy)-1,3,4-thiadiazol-2-yl)-2-(2-methoxyphenyl)nicotinamide |

-continued

| Cpd # | Structure | Name |
|---|---|---|
| 68 | 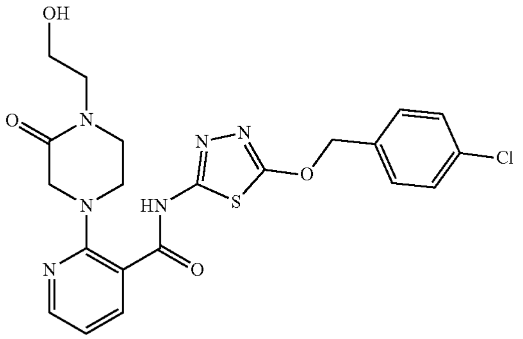 [SMILES: O=C(Nc1nnc(OCc2ccc(Cl)cc2)s1)c1cccnc1N1CCN(CCO)C(=O)C1] | N-(5-((4-chlorobenzyl)oxy)-1,3,4-thiadiazol-2-yl)-2-(4-(2-hydroxyethyl)-3-oxopiperazin-1-yl)nicotinamide |
| 69 | 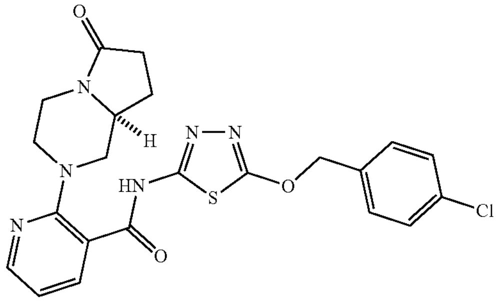 [SMILES: O=C(Nc1nnc(OCc2ccc(Cl)cc2)s1)c1cccnc1N1CCN2C(=O)CC[C@H]2C1] | (S)-N-(5-((4-chlorobenzyl)oxy)-1,3,4-thiadiazol-2-yl)-2-(6-oxohexahydropyrrolo[1,2-a]pyrazin-2(1H)-yl-8a-d)nicotinamide |
| 70 | 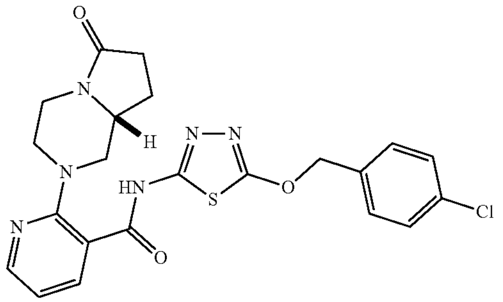 [SMILES: O=C(Nc1nnc(OCc2ccc(Cl)cc2)s1)c1cccnc1N1CCN2C(=O)CC[C@@H]2C1] | (R)-N-(5-((4-chlorobenzyl)oxy)-1,3,4-thiadiazol-2-yl)-2-(6-oxohexahydropyrrolo[1,2-a]pyrazin-2(1H)-yl-8a-d)nicotinamide |
| 71 | 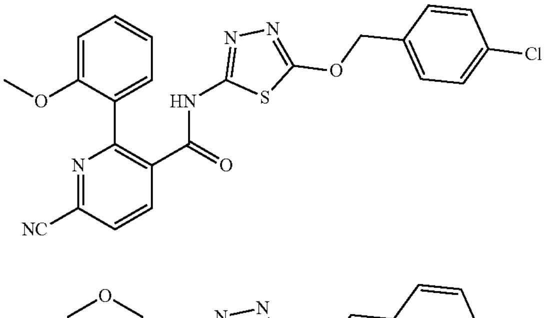 | N-(5-((4-chlorobenzyl)oxy)-1,3,4-thiadiazol-2-yl)-6-cyano-2-(2-methoxyphenyl)nicotinamide |
| 72 | 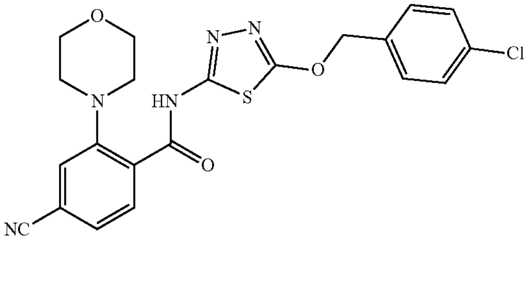 [SMILES: N#Cc1ccc(C(=O)Nc2nnc(OCc3ccc(Cl)cc3)s2)c(N2CCOCC2)c1] | N-(5-((4-chlorobenzyl)oxy)-1,3,4-thiadiazol-2-yl)-4-cyano-2-morpholinobenzamide |

-continued

| Cpd # | Structure | Name |
|---|---|---|
| 73 | 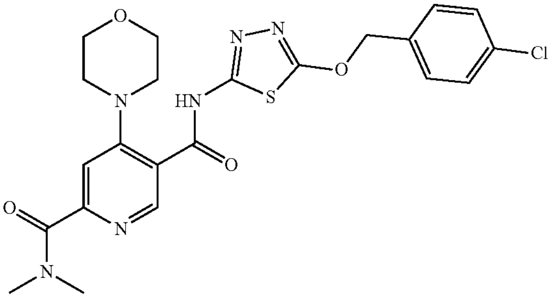 [SMILES: CN(C)C(=O)c1cc(N2CCOCC2)c(C(=O)Nc2nnc(OCc3ccc(Cl)cc3)s2)cn1] | N5-(5-((4-chlorobenzyl)oxy)-1,3,4-thiadiazol-2-yl)-N2,N2-dimethyl-4-morpholinopyridine-2,5-dicarboxamide |
| 74 | 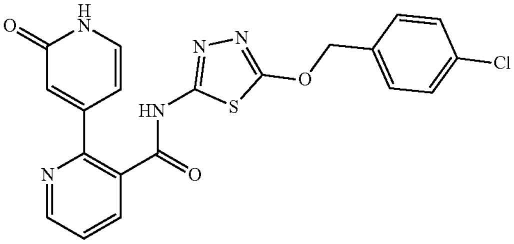 or 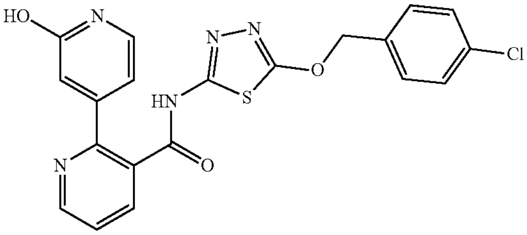 [SMILES: O=C(Nc1nnc(OCc2ccc(Cl)cc2)s1)c1cccnc1-c1ccnc(O)c1] | N-(5-((4-chlorobenzyl)oxy)-1,3,4-thiadiazol-2-yl)-2'-oxo-1',2'-dihydro-[2,4'-bipyridine]-3-carboxamide or its tautomer N-(5-((4-chlorobenzyl)oxy)-1,3,4-thiadiazol-2-yl)-2'-hydroxy-[2,4'-bipyridine]-3-carboxamide |
| 75 | 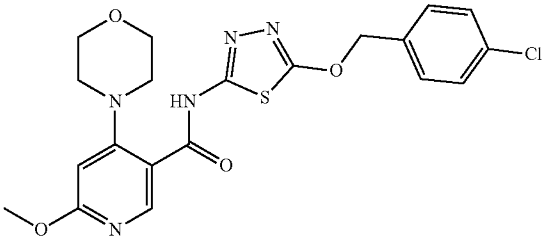 [SMILES: COc1cc(N2CCOCC2)c(C(=O)Nc2nnc(OCc3ccc(Cl)cc3)s2)cn1] | N-(5-((4-chlorobenzyl)oxy)-1,3,4-thiadiazol-2-yl)-6-methoxy-4-morpholinonicotinamide |
| 76 | 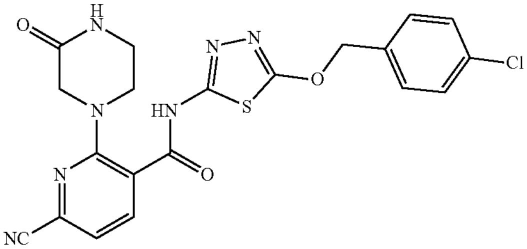 | N-(5-((4-chlorobenzyl)oxy)-1,3,4-thiadiazol-2-yl)-6-cyano-2-(3-oxopiperazin-1-yl)nicotinamide |
| 77 | 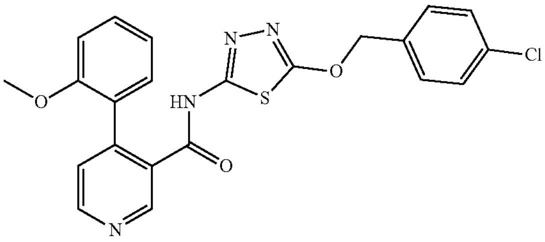 [SMILES: COc1ccccc1-c1ccncc1C(=O)Nc1nnc(OCc2ccc(Cl)cc2)s1] | N-(5-((4-chlorobenzyl)oxy)-1,3,4-thiadiazol-2-yl)-4-(2-methoxyphenyl)nicotinamide |

-continued

| Cpd # | Structure | Name |
|---|---|---|
| 78 | 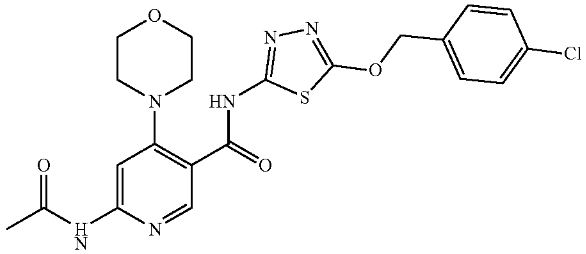 [SMILES: CC(=O)Nc1cc(N2CCOCC2)c(C(=O)Nc2nnc(OCc3ccc(Cl)cc3)s2)cn1] | 6-acetamido-N-(5-((4-chlorobenzyl)oxy)-1,3,4-thiadiazol-2-yl)-4-morpholinonicotinamide |
| 79 | 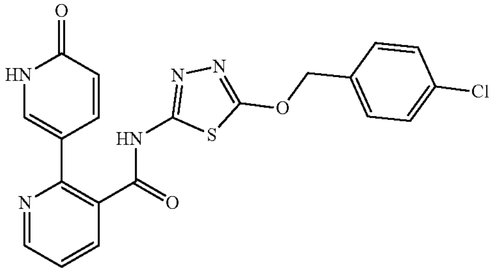 or 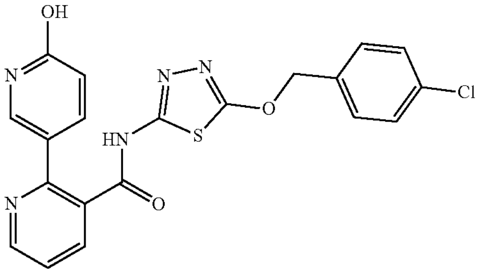 [SMILES: O=C(Nc1nnc(OCc2ccc(Cl)cc2)s1)c1cccnc1-c1ccc(O)nc1] | N-(5-((4-chlorobenzyl)oxy)-1,3,4-thiadiazol-2-yl)-6'-oxo-1',6'-dihydro-[2,3'-bipyridine]-3-carboxamide or its tautomer N-(5-((4-chlorobenzyl)oxy)-1,3,4-thiadiazol-2-yl)-6'-hydroxy-[2,3'-bipyridine]-3-carboxamide |
| 80 | 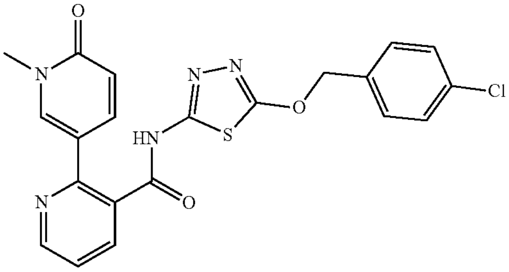 [SMILES: Cn1cc(-c2ncccc2C(=O)Nc2nnc(OCc3ccc(Cl)cc3)s2)ccc1=O] | N-(5-((4-chlorobenzyl)oxy)-1,3,4-thiadiazol-2-yl)-1'-methyl-6'-oxo-1',6'-dihydro-[2,3'-bipyridine]-3-carboxamido |
| 81 | 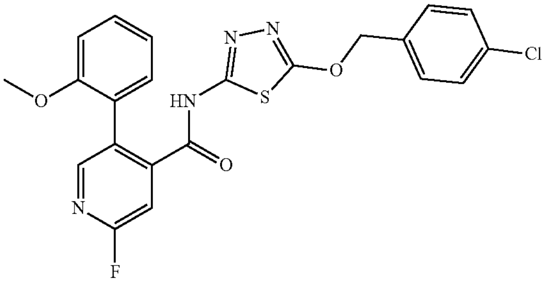 [SMILES: COc1ccccc1-c1cnc(F)cc1C(=O)Nc1nnc(OCc2ccc(Cl)cc2)s1] | N-(5-((4-chlorobenzyl)oxy)-1,3,4-thiadiazol-2-yl)-2-fluoro-5-(2-methoxyphenyl)-isonicotinamide |
| 82 | 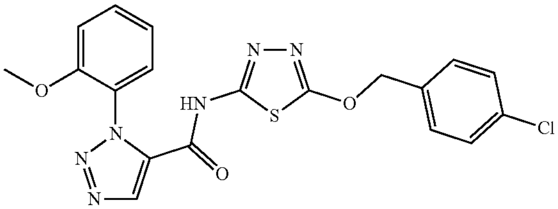 [SMILES: COc1ccccc1-n1nncc1C(=O)Nc1nnc(OCc2ccc(Cl)cc2)s1] | N-(5-((4-fluorobenzyl)oxy)-1,3,4-thiadiazol-2-yl)-1-(2-methoxyphenyl)-1H-1,2,3-triazole-5-carboxamide |

-continued

| Cpd # | Structure | Name |
| --- | --- | --- |
| 83 | 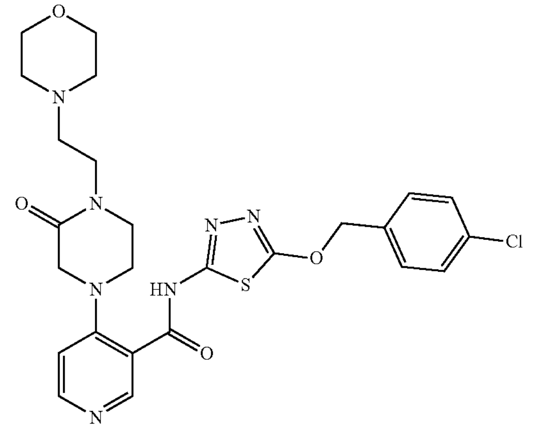 [SMILES: O=C(Nc1nnc(OCc2ccc(Cl)cc2)s1)c1cnccc1N1CCN(CCN2CCOCC2)C(=O)C1] | N-(5-((4-chlorobenzyl)oxy)-1,3,4-thiadiazol-2-yl)-4-(4-(2-morpholinoethyl)-3-oxopiperazin-1-yl)nicotinamide |
| 84 | 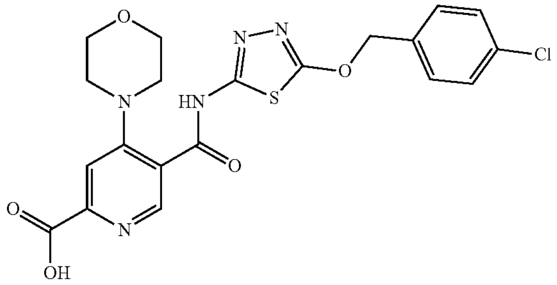 [SMILES: O=C(O)c1cc(N2CCOCC2)c(C(=O)Nc2nnc(OCc3ccc(Cl)cc3)s2)cn1] | 5-((5-((4-chlorobenzyl)oxy)-1,3,4-thiadiazol-2-yl)carbamoyl)-4-morpholinopicolinic acid |
| 85 | 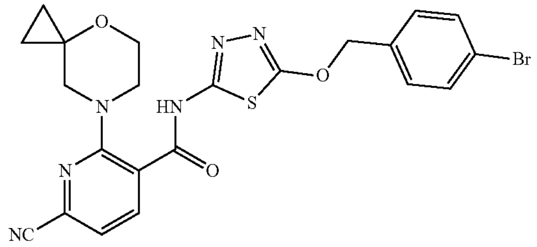 [SMILES: N#Cc1ccc(C(=O)Nc2nnc(OCc3ccc(Br)cc3)s2)c(N2CCOC3(CC3)C2)n1] | N-(5-((4-bromobenzyl)oxy)-1,3,4-thiadiazol-2-yl)-6-cyano-2-(4-oxa-7-azaspiro[2.5]octan-7-yl)nicotinamide |
| 86 | 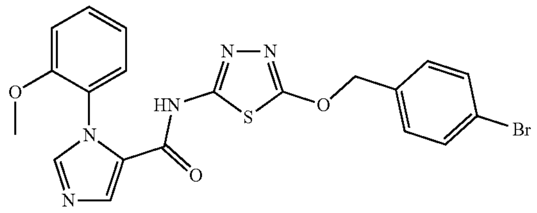 [SMILES: COc1ccccc1-n1cncc1C(=O)Nc1nnc(OCc2ccc(Br)cc2)s1] | N-(5-((4-bromobenzyl)oxy)-1,3,4-thiadiazol-2-yl)-1-(2-methoxyphenyl)-1H-imidazole-5-carboxamide |
| 87 | 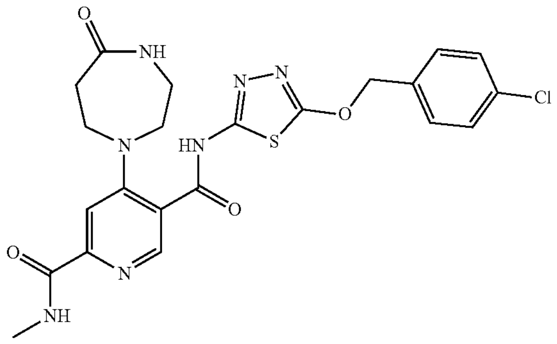 [SMILES: CNC(=O)c1cc(N2CCNC(=O)CC2)c(C(=O)Nc2nnc(OCc3ccc(Cl)cc3)s2)cn1] | N5-(5-((4-chlorobenzyl)oxy)-1,3,4-thiadiazol-2-yl)-N2-methyl-4-(5-oxo-1,4-diazepan-1-yl)pyridine-2,5-dicarboxamide |

-continued

| Cpd # | Structure | Name |
|---|---|---|
| 88 | 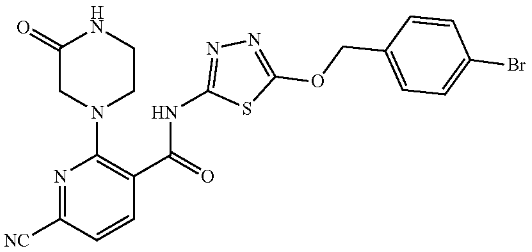 [SMILES: N#Cc1ccc(C(=O)Nc2nnc(OCc3ccc(Br)cc3)s2)c(N2CCNC(=O)C2)n1] | N-(5-((4-bromobenzyl)oxy)-1,3,4-thiadiazol-2-yl)-6-cyano-2-(3-oxopiperazin-1-yl)nicotinamide |
| 89 | 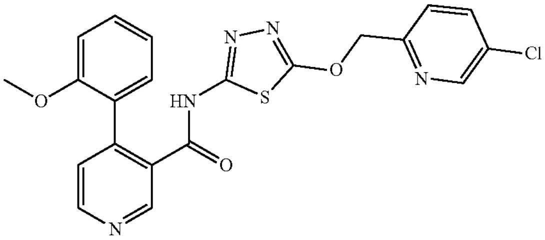 [SMILES: COc1ccccc1-c1ccncc1C(=O)Nc1nnc(OCc2ccc(Cl)cn2)s1] | N-(5-((5-chloropyridin-2-yl)methoxy)-1,3,4-thiadiazol-2-yl)-4-(2-methoxyphenyl)nicotinamide |
| 90 | 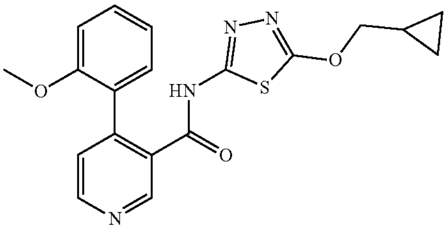 [SMILES: COc1ccccc1-c1ccncc1C(=O)Nc1nnc(OCC2CC2)s1] | N-(5-(cyclopropylmethoxy)-1,3,4-thiadiazol-2-yl)-4-(2-methoxyphenyl)nicotinamide |
| 91 | 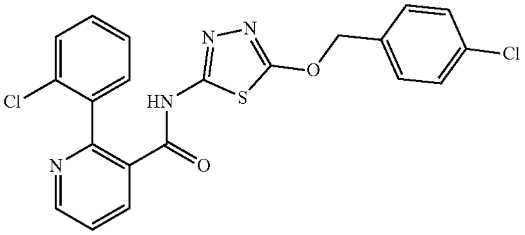 [SMILES: O=C(Nc1nnc(OCc2ccc(Cl)cc2)s1)c1cccnc1-c1ccccc1Cl] | 2-(2-chlorophenyl)-N-[5-[(4-chlorophenyl)methoxy]-1,3,4-thiadiazol-2-yl]pyridine-3- |
| 92 | 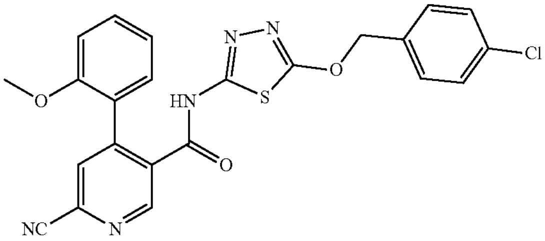 [SMILES: COc1ccccc1-c1cc(C#N)ncc1C(=O)Nc1nnc(OCc2ccc(Cl)cc2)s1] | N-(5-((4-chlorobenzyl)oxy)-1,3,4-thiadiazol-2-yl)-6-cyano-4-(2-methoxyphenyl)nicotinamide |
| 93 | 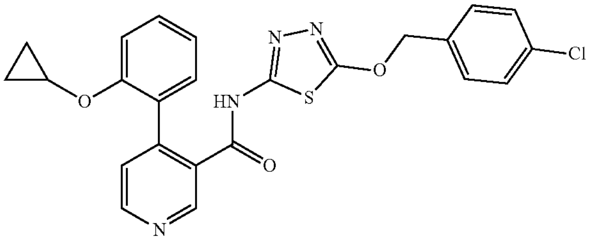 [SMILES: O=C(Nc1nnc(OCc2ccc(Cl)cc2)s1)c1cnccc1-c1ccccc1OC1CC1] | N-(5-((4-chlorobenzyl)oxy)-1,3,4-thiadiazol-2-yl)-4-(2-cyclopropoxyphenyl)nicotinamide |

-continued

| Cpd # | Structure | Name |
| --- | --- | --- |
| 94 | 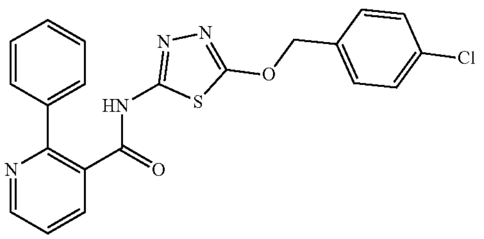 [SMILES: O=C(Nc1nnc(OCc2ccc(Cl)cc2)s1)c1cccnc1-c1ccccc1] | N-(5-((4-chlorobenzyl)oxy)-1,3,4-thiadiazol-2-yl)-2-phenylnicotinamide |
| 95 | 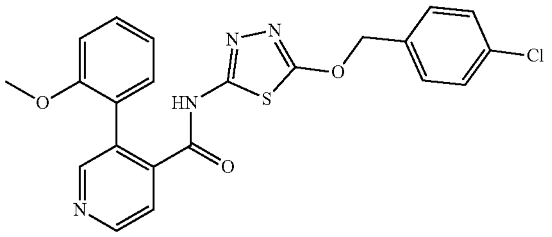 [SMILES: COc1ccccc1-c1cnccc1C(=O)Nc1nnc(OCc2ccc(Cl)cc2)s1] | N-(5-((4-chlorobenzyl)oxy)-1,3,4-thiadiazol-2-yl)-3-(2-methoxyphenyl)isonicotinamide |
| 96 | 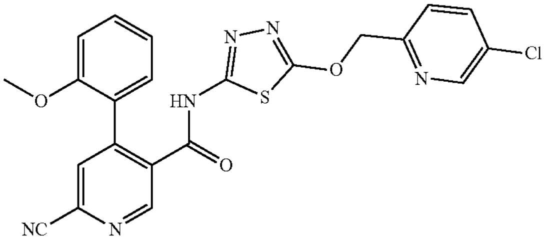 [SMILES: COc1ccccc1-c1cc(C#N)ncc1C(=O)Nc1nnc(OCc2ccc(Cl)cn2)s1] | N-(5-((5-chloropyridin-2-yl)methoxy)-1,3,4-thiadiazol-2-yl)-6-cyano-4-(2-methoxyphenyl)nicotinamide |
| 97 | 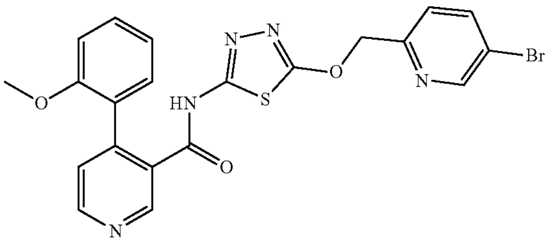 [SMILES: COc1ccccc1-c1ccncc1C(=O)Nc1nnc(OCc2ccc(Br)cn2)s1] | N-(5-((5-bromopyridin-2-yl)methoxy)-1,3,4-thiadiazol-2-yl)-4-(2-methoxyphenyl)nicotinamide |
| 98 | 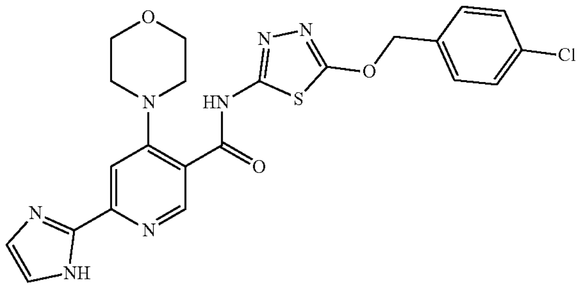 [SMILES: O=C(Nc1nnc(OCc2ccc(Cl)cc2)s1)c1cnc(-c2ncc[nH]2)cc1N1CCOCC1] | N-(5-((4-chlorobenzyl)oxy)-1,3,4-thiadiazol-2-yl)-6-(1H-imidazol-2-yl)-4-morpholinonicotinamide |
| 99 | 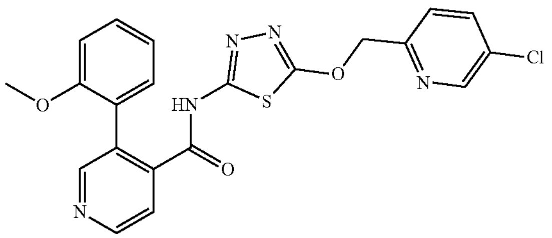 [SMILES: COc1ccccc1-c1cnccc1C(=O)Nc1nnc(OCc2ccc(Cl)cn2)s1] | N-[5-[(5-chloropyridin-2-yl)methoxy]-1,3,4-thiadiazol-2-yl]-3-(2-methoxyphenyl)pyridine-4-carboxamide |

-continued

| Cpd # | Structure | Name |
|---|---|---|
| 100 | 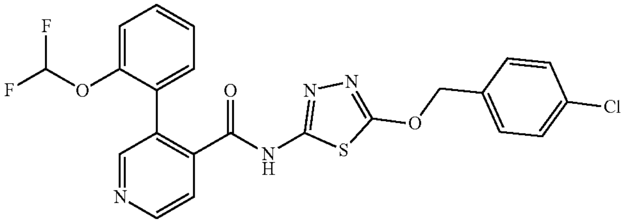 [SMILES: O=C(Nc1nnc(OCc2ccc(Cl)cc2)s1)c1ccncc1-c1ccccc1OC(F)F] | N-(5-((4-chlorobenzyl)oxy)-1,3,4-thiadiazol-2-yl)-3-(2-(difluoromethoxy)phenyl)isonicotinamide |
| 101 | 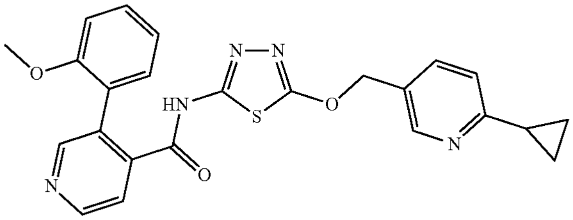 [SMILES: COc1ccccc1-c1cnccc1C(=O)Nc1nnc(OCc2ccc(C3CC3)nc2)s1] | N-[5-[(6-cyclopropylpyridin-3-yl)methoxy]-1,3,4-thiadiazol-2-yl]-3-(2-methoxyphenyl)pyridine-4-carboxamide |
| 102 | 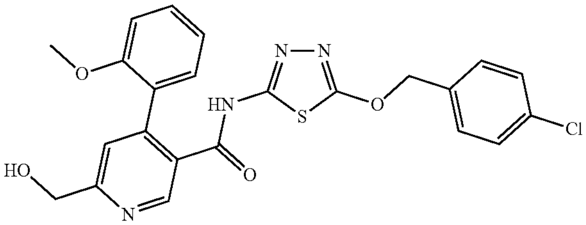 [SMILES: COc1ccccc1-c1cc(CO)ncc1C(=O)Nc1nnc(OCc2ccc(Cl)cc2)s1] | N-(5-((4-chlorobenzyl)oxy)-1,3,4-thiadiazol-2-yl)-6-(hydroxymethyl)-4-(2-methoxyphenyl)nicotinamide |
| 103 | 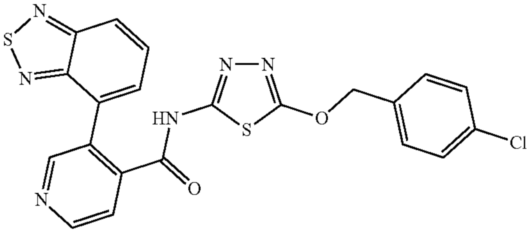 [SMILES: O=C(Nc1nnc(OCc2ccc(Cl)cc2)s1)c1ccncc1-c1cccc2nsnc12] | 3-(benzo[c][1,2.5]thiadiazol-4-yl)-N-(5-((4-chlorobenzyl)oxy)-1,3,4-thiadiazol-2-yl)isonicotinamide |
| 104 | 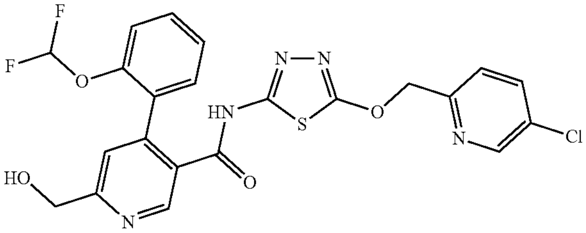 [SMILES: O=C(Nc1nnc(OCc2ccc(Cl)cn2)s1)c1cnc(CO)cc1-c1ccccc1OC(F)F] | N-(5-((5-chloropyridin-2-yl)methoxy)-1,3,4-thiadiazol-2-yl)-4-(2-(difluoromethoxy)phenyl)-6-(hydroxymethyl)nicotinamide |
| 105 | 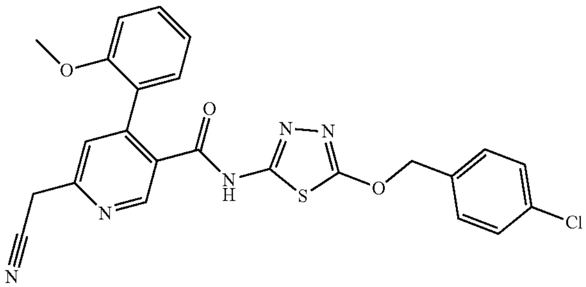 [SMILES: COc1ccccc1-c1cc(CC#N)ncc1C(=O)Nc1nnc(OCc2ccc(Cl)cc2)s1] | N-(5-((4-chlorobenzyl)oxy)-1,3,4-thiadiazol-2-yl)-6-(cyanomethyl)-4-(2-methoxyphenyl)nicotinamide |

-continued

| Cpd # | Structure | Name |
| --- | --- | --- |
| 106 | 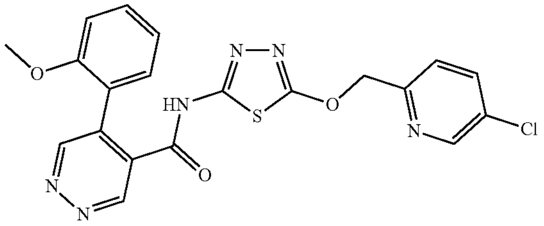 [SMILES: COc1ccccc1-c1cnncc1C(=O)Nc1nnc(OCc2ccc(Cl)cn2)s1] | N-(5-((5-chloropyridin-2-yl)methoxy)-1,3,4-thiadiazol-2-yl)-5-(2-methoxyphenyl)pyridazine-4-carboxamide |
| 107 | 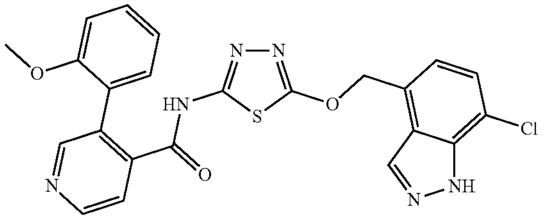 [SMILES: COc1ccccc1-c1cnccc1C(=O)Nc1nnc(OCc2ccc(Cl)c3[nH]ncc23)s1] | N-(5-((7-chloro-1H-indazol-4-yl)methoxy)-1,3,4-thiadiazol-2-yl)-3-(2-methoxyphenyl)isonicotinamide |
| 108 | 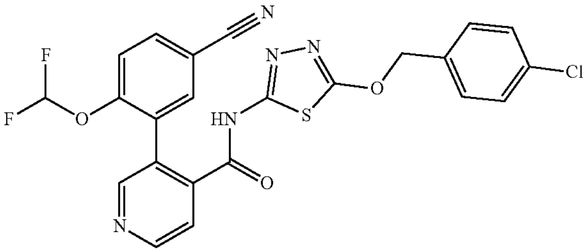 [SMILES: N#Cc1ccc(OC(F)F)c(-c2cnccc2C(=O)Nc2nnc(OCc3ccc(Cl)cc3)s2)c1] | N-(5-((4-chlorobenzyl)oxy)-1,3,4-thiadiazol-2-yl)-3-(5-cyano-2-(difluoromethoxy)phenyl)isonicotinamide |
| 109 | 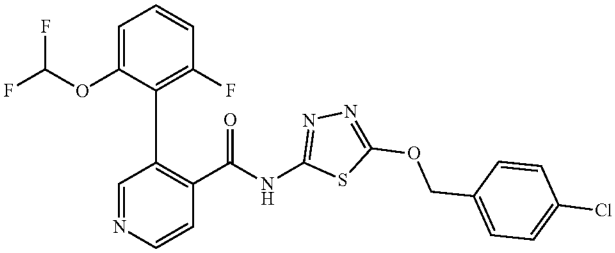 [SMILES: O=C(Nc1nnc(OCc2ccc(Cl)cc2)s1)c1ccncc1-c1c(F)cccc1OC(F)F] | N-(5-((4-chlorobenzyl)oxy)-1,3,4-thiadiazol-2-yl)-3-(2-(difluoromethoxy)-6-fluorophenyl)isonicotinamide |
| 110 | 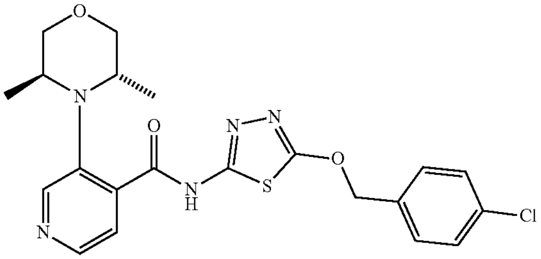 [SMILES: C[C@H]1COC[C@H](C)N1c1cnccc1C(=O)Nc1nnc(OCc2ccc(Cl)cc2)s1] | N-(5-((4-chlorobenzyl)oxy)-1,3,4-thiadiazol-2-yl)-3-((3S,5S)-3,5-dimethylmorpholino)isonicotinamide |
| 111 | 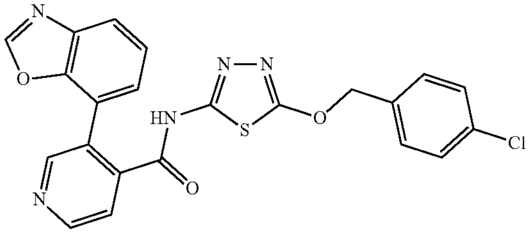 [SMILES: O=C(Nc1nnc(OCc2ccc(Cl)cc2)s1)c1ccncc1-c1cccc2ncoc12] | 3-(benzo[d]oxazol-7-yl)-N-(5-((4-chlorobenzyl)oxy)-1,3,4-thiadiazol-2-yl)isonicotinamide |

-continued

| Cpd # | Structure | Name |
| --- | --- | --- |
| 112 | 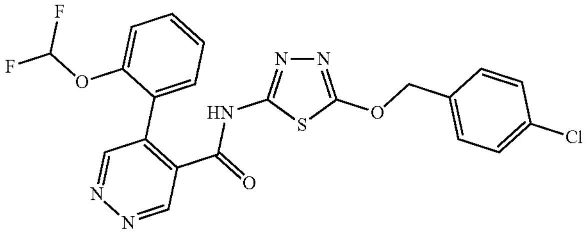 [SMILES: O=C(Nc1nnc(OCc2ccc(Cl)cc2)s1)c1cnncc1-c1ccccc1OC(F)F] | N-(5-((4-chlorobenzyl)oxy)-1,3,4-thiadiazol-2-yl)-5-(2-(difluoromethoxy)phenyl)pyridazine-4-carboxamide |
| 113 | 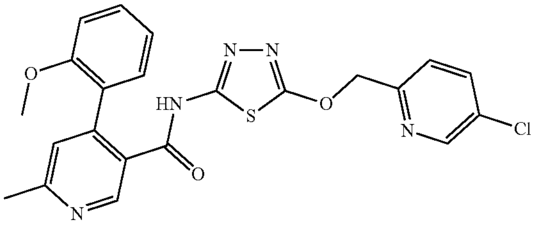 [SMILES: COc1ccccc1-c1cc(C)ncc1C(=O)Nc1nnc(OCc2ccc(Cl)cn2)s1] | N-(5-((5-chloropyridin-2-yl)methoxy)-1,3,4-thiadiazol-2-yl)-4-(2-methoxyphenyl)-6-methylnicotinamide |
| 114 | 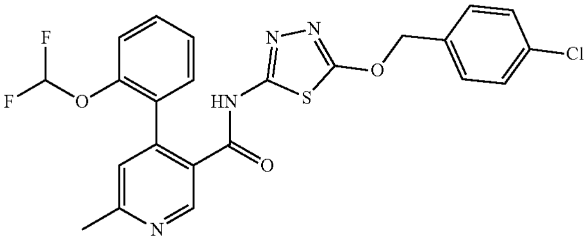 [SMILES: Cc1cc(-c2ccccc2OC(F)F)c(C(=O)Nc2nnc(OCc3ccc(Cl)cc3)s2)cn1] | N-[5-[(4-chlorophenyl)methoxy]-1,3,4-thiadiazol-2-yl]-4-[2-(difluoromethoxy)phenyl]-6-methylpyridine-3-carboxamide |
| 115 | 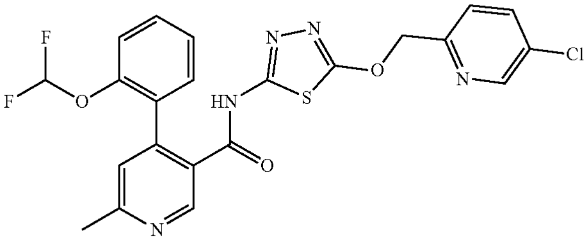 [SMILES: Cc1cc(-c2ccccc2OC(F)F)c(C(=O)Nc2nnc(OCc3ccc(Cl)cn3)s2)cn1] | N-[5-[(5-chloropyridin-2-yl)methoxy]-1,3,4-thiadiazol-2-yl]-4-[2-(difluoromethoxy)phenyl]-6-metbylpyridine-3-carboxamide |
| 116 | 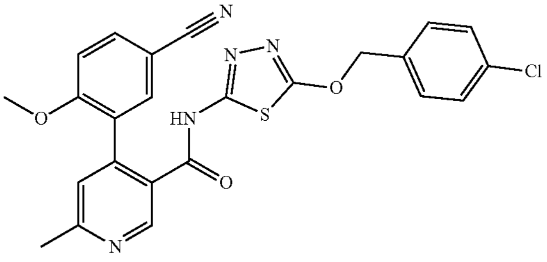 [SMILES: COc1ccc(C#N)cc1-c1cc(C)ncc1C(=O)Nc1nnc(OCc2ccc(Cl)cc2)s1] | N-[5-[(4-chlorophenyl)methoxy]-1,3,4-thiadiazol-2-yl]-4-(5-cyano-2-methoxyphenyl)-6-methylpyridine-3-carboxamide |
| 117 | 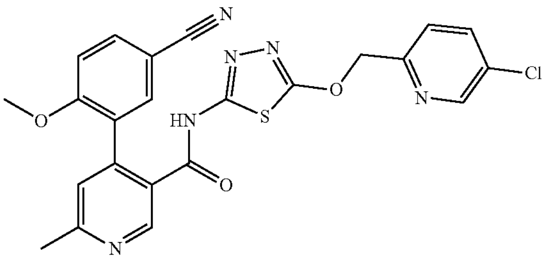 [SMILES: COc1ccc(C#N)cc1-c1cc(C)ncc1C(=O)Nc1nnc(OCc2ccc(Cl)cn2)s1] | N-[5-[(5-chloropyridin-2-yl)methoxy]-1,3,4-thiadiazol-2-yl]-4-(5-cyano-2-methoxyphenyl)-6-methylpyridine-3-carboxamide |

-continued

| Cpd # | Structure | Name |
|---|---|---|
| 118 | 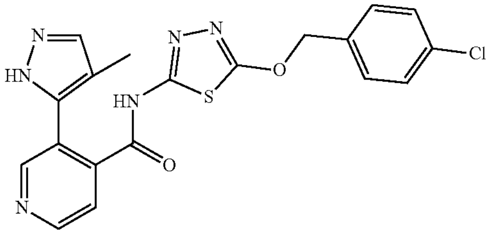 [SMILES: Cc1cn[nH]c1-c1cnccc1C(=O)Nc1nnc(OCc2ccc(Cl)cc2)s1] | N-(5-((4-chlorobenzyl)oxy)-1,3,4-thiadiazol-2-yl)-3-(4-methyl-1H-pyrazol-5-yl)isonicotinamide |
| 119 | 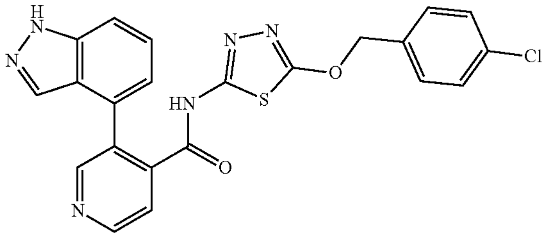 [SMILES: O=C(Nc1nnc(OCc2ccc(Cl)cc2)s1)c1ccncc1-c1cccc2[nH]ncc12] | N-(5-((4-chlorobenzyl)oxy)-1,3,4-thiadiazol-2-yl)-3-(1H-indazol-4-yl)isonicotinamide |
| 120 | 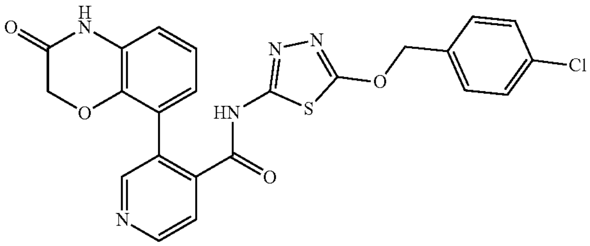 [SMILES: O=C1COc2c(cccc2-c2cnccc2C(=O)Nc2nnc(OCc3ccc(Cl)cc3)s2)N1] | N-(5-((4-chlorobenzyl)oxy)-1,3,4-thiadiazol-2-yl)-3-(3-oxo-3,4-dihydro-2H-benzo[b][1,4]oxazin-8-yl)isonicotinamide |
| 121 | 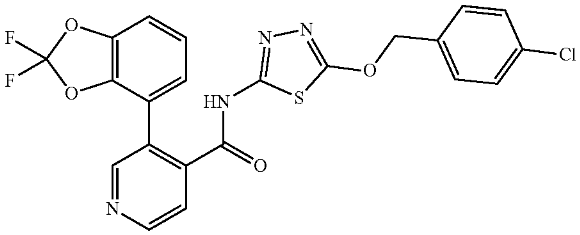 [SMILES: O=C(Nc1nnc(OCc2ccc(Cl)cc2)s1)c1ccncc1-c1cccc2c1OC(F)(F)O2] | N-(5-((4-chlorobenzyl)oxy)-1,3,4-thiadiazol-2-yl)-3-(2,2-difluorobenzo[d][1,3]dioxol-4-yl)isonicotinamide |
| 122 | 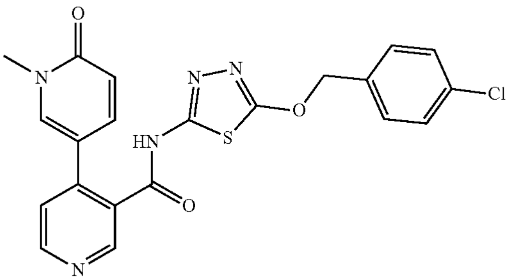 [SMILES: Cn1cc(-c2ccncc2C(=O)Nc2nnc(OCc3ccc(Cl)cc3)s2)ccc1=O] | N-(5-((4-chlorobenzyl)oxy)-1,3,4-thiadiazol-2-yl)-1-methyl-6-oxo-1,6-dihydro-[3,4'-bipyridine]-3'-carboxamide |
| 123 | 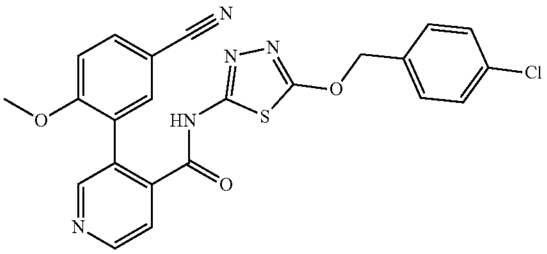 [SMILES: COc1ccc(C#N)cc1-c1cnccc1C(=O)Nc1nnc(OCc2ccc(Cl)cc2)s1] | N-(5-((4-chlorobenzyl)oxy)-1,3,4-thiadiazol-2-yl)-3-(5-cyano-2-methoxyphenyl)isonicotinamide |

-continued

| Cpd # | Structure | Name |
|---|---|---|
| 124 | 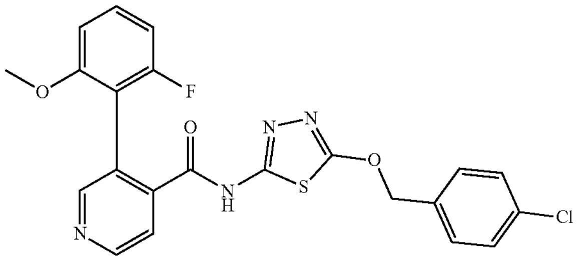 [SMILES: COc1cccc(F)c1-c1cnccc1C(=O)Nc1nnc(OCc2ccc(Cl)cc2)s1] | N-(5-((4-chlorobenzyl)oxy)-1,3,4-thiadiazol-2-yl)-3-(2-fluoro-6-methoxyphenyl)isonicotinamide |
| 125 | 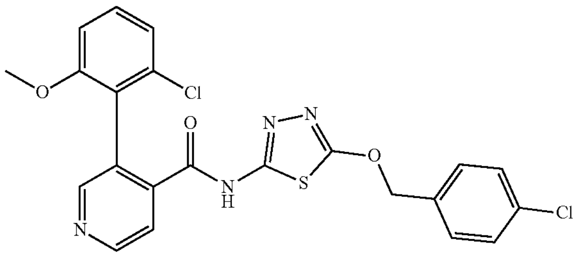 [SMILES: COc1cccc(Cl)c1-c1cnccc1C(=O)Nc1nnc(OCc2ccc(Cl)cc2)s1] | 3-(2-chloro-6-methoxyphenyl)-N-(5-((4-chlorobenzyl)oxy)-1,3,4-thiadiazol-2-yl)isonicotinamide |
| 126 | 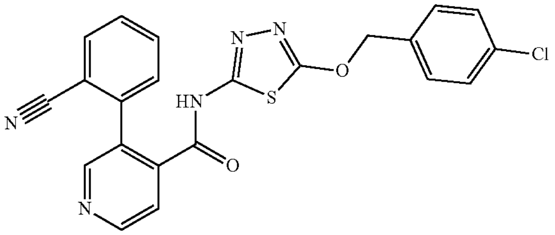 [SMILES: NCc1ccccc1-c1cnccc1C(=O)Nc1nnc(OCc2ccc(Cl)cc2)s1] | N-(5-((4-chlorobenzyl)oxy)-1,3,4-thiadiazol-2-yl)-3-(2-cyanophenyl)isonicotinamide |
| 127 | 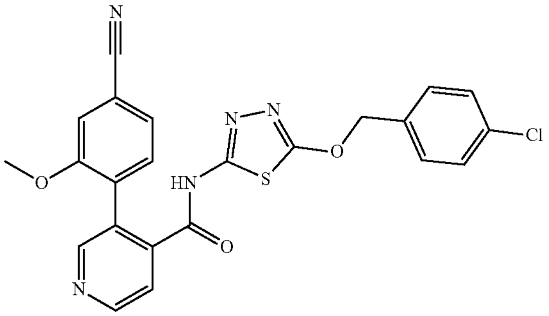 [SMILES: COc1cc(C#N)ccc1-c1cnccc1C(=O)Nc1nnc(OCc2ccc(Cl)cc2)s1] | N-(5-((4-chlorobenzyl)oxy)-1,3,4-thiadiazol-2-yl)-3-(4-cyano-2-methoxyphenyl)isonicotinamide |
| 128 | 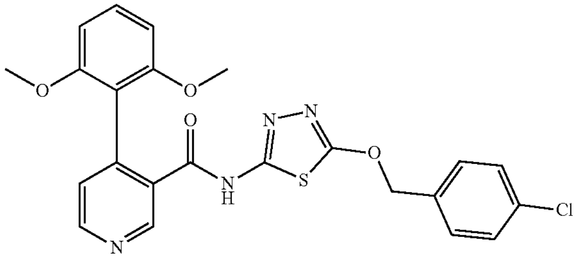 [SMILES: COc1cccc(OC)c1-c1ccncc1C(=O)Nc1nnc(OCc2ccc(Cl)cc2)s1] | N-(5-((4-chlorobenzyl)oxy)-1,3,4-thiadiazol-2-yl)-4-(2,6-dimethoxyphenyl)nicotinamide |

-continued

| Cpd # | Structure | Name |
|---|---|---|
| 129 | 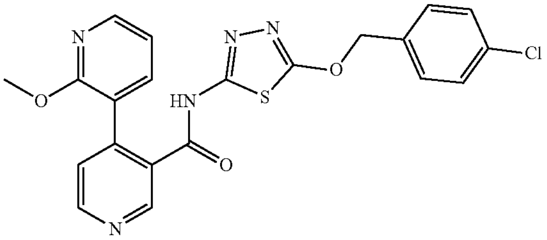 [SMILES: COc1ncccc1-c1ccncc1C(=O)Nc1nnc(OCc2ccc(Cl)cc2)s1] | N-(5-((4-chlorobenzyl)oxy)-1,3,4-thiadiazol-2-yl)-2-methoxy-[3,4'-bipyridine]-3'-carboxamide |
| 130 | 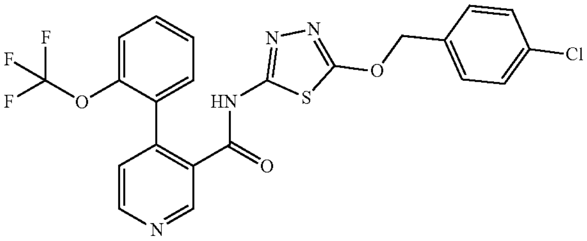 [SMILES: O=C(Nc1nnc(OCc2ccc(Cl)cc2)s1)c1cnccc1-c1ccccc1OC(F)(F)F] | N-(5-((4-chlorobenzyl)oxy)-1,3,4-thiadiazol-2-yl)-4-(2-(trifluoromethoxy)phenyl)nicotinamide |
| 131 | 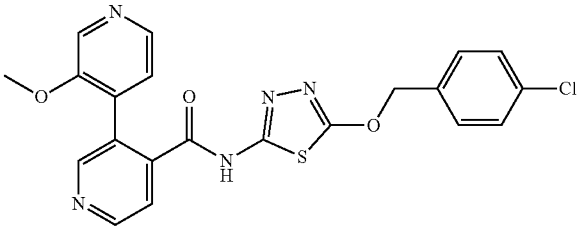 [SMILES: COc1cnccc1-c1cnccc1C(=O)Nc1nnc(OCc2ccc(Cl)cc2)s1] | N-(5-((4-chlorobenzyl)oxy)-1,3,4-thiadiazol-2-yl)-3'-methoxy-[3,4'-bipyridine]-4-carboxamide |
| 132 | 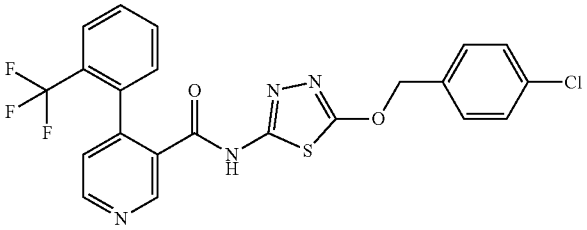 [SMILES: O=C(Nc1nnc(OCc2ccc(Cl)cc2)s1)c1cnccc1-c1ccccc1C(F)(F)F] | N-(5-((4-chlorobenzyl)oxy)-1,3,4-thiadiazol-2-yl)-4-(2-(trifluoromethyl)phenyl)nicotinamide |
| 133 | 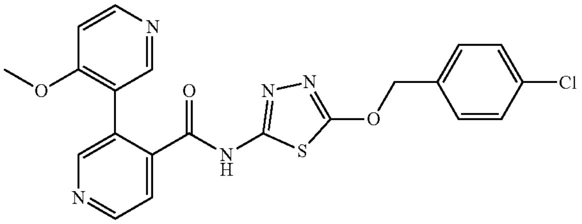 [SMILES: COc1ccncc1-c1cnccc1C(=O)Nc1nnc(OCc2ccc(Cl)cc2)s1] | N-(5-((4-chlorobenzyl)oxy)-1,3,4-thiadiazol-2-yl)-4'-methoxy-[3,3'-bipyridine]-4-carboxamide |
| 134 | 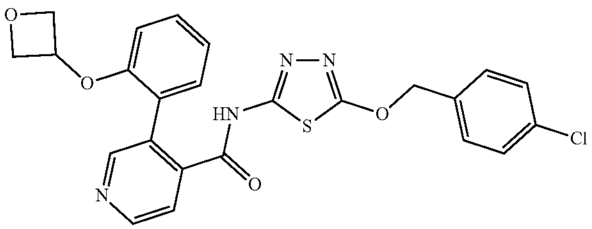 [SMILES: O=C(Nc1nnc(OCc2ccc(Cl)cc2)s1)c1ccncc1-c1ccccc1OC1COC1] | N-[5-[(4-chlorophenyl)methoxy]-1,3,4-thiadiazol-2-yl]-3-[2-(oxetan-3-yloxy)phenyl]pyridine-4-carboxamide |

-continued

| Cpd # | Structure | Name |
| --- | --- | --- |
| 135 | 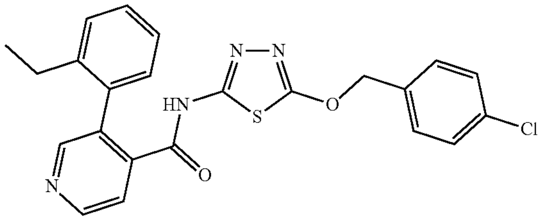 [SMILES: CCc1ccccc1-c1cnccc1C(=O)Nc1nnc(OCc2ccc(Cl)cc2)s1] | N-[5-[(4-chlorophenyl)methoxy]-1,3,4-thiadiazol-2-yl]-3-(2-ethylphenyl)pyridine-4-carboxamide |
| 136 | 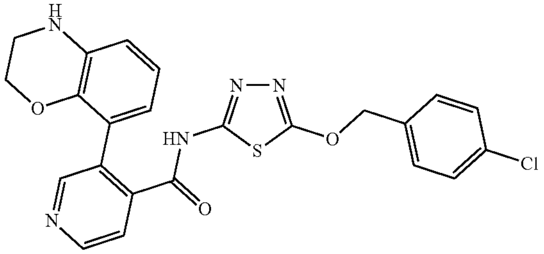 [SMILES: O=C(Nc1nnc(OCc2ccc(Cl)cc2)s1)c1ccncc1-c1cccc2c1OCCN2] | N-[5-[(4-chlorophenyl)methoxy]-1,3,4-thiadiazol-2-yl]-3-(3,4-dihydro-2H-1,4-benzoxazin-8-yl)pyridine-4-carboxamide |
| 137 | 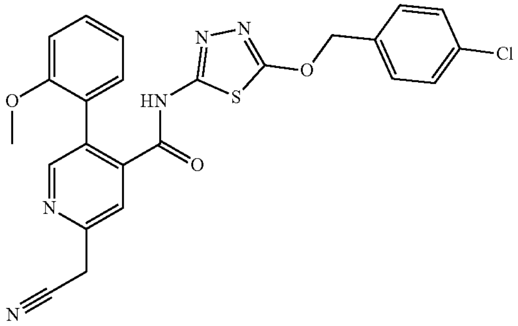 [SMILES: COc1ccccc1-c1cnc(CC#N)cc1C(=O)Nc1nnc(OCc2ccc(Cl)cc2)s1] | N-[5-[(4-chlorophenyl)methoxy]-1,3,4-thiadiazol-2-yl]-2-(cyanomethyl)-5-(2-methoxyphenyl)pyridine-4-carboxamide |
| 138 | 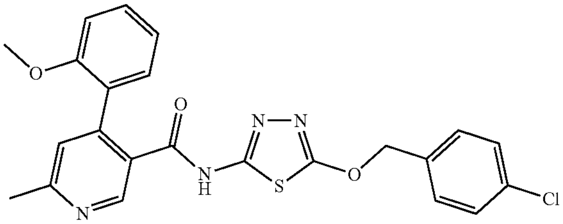 [SMILES: COc1ccccc1-c1cc(C)ncc1C(=O)Nc1nnc(OCc2ccc(Cl)cc2)s1] | N-[5-[(4-chlorophenyl)methoxy]-1,3,4-thiadiazol-2-yl]-4-(2-methoxyphenyl)-6-methylpyridine-3-carboxamide |
| 139 | 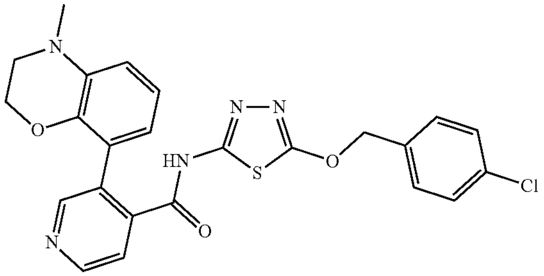 [SMILES: CN1CCOc2c(-c3cnccc3C(=O)Nc3nnc(OCc4ccc(Cl)cc4)s3)cccc21] | N-[5-[(4-chlorophenyl)methoxy]-1,3,4-thiadiazol-2-yl]-3-(4-methyl-2,3-dihydro-1,4-benzoxazin-8-yl)pyridine-4-carboxamide |
| 140 | 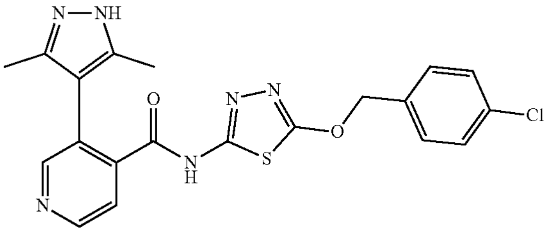 [SMILES: Cc1n[nH]c(C)c1-c1cnccc1C(=O)Nc1nnc(OCc2ccc(Cl)cc2)s1] | N-[5-[(4-chlorophenyl)methoxy]-1,3,4-thiadiazol-2-yl]-3-(3,5-dimethyl-1H-pyrazol-4-yl)pyridine-4-carboxamide |

-continued

| Cpd # | Structure | Name |
|---|---|---|
| 141 | 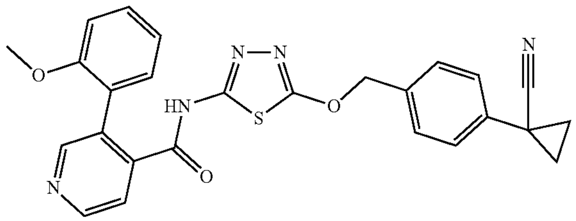 [SMILES: COc1ccccc1-c1cnccc1C(=O)Nc1nnc(OCc2ccc(C3(C#N)CC3)cc2)s1] | N-(5-[[4-(1-cyanocyclopropyl)phenyl]methoxy]-1,3,4-thiadiazol-2-yl)-3-(2-methoxyphenyl)pyridine-4-carboxamide |
| 142 | 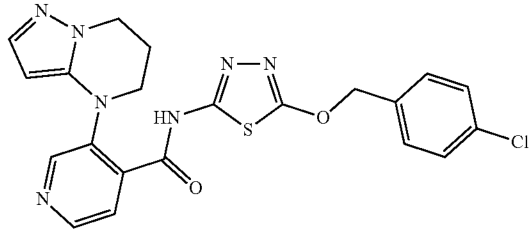 [SMILES: O=C(Nc1nnc(OCc2ccc(Cl)cc2)s1)c1ccncc1N1CCCn2nccc21] | N-[5-[(4-chlorophenyl)methoxy]-1,3,4-thiadiazol-2-yl]-3-[5H,6H,7H-pyrazolo[1,5-a]pyrimidin-4-yl]pyridine-4-carboxamide |
| 143 | 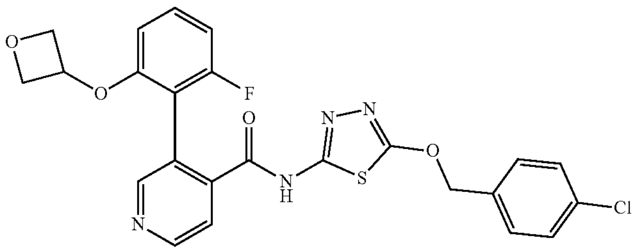 [SMILES: O=C(Nc1nnc(OCc2ccc(Cl)cc2)s1)c1ccncc1-c1c(F)cccc1OC1COC1] | N-(5-((4-chlorobenzyl)oxy)-1,3,4-thiadiazol-2-yl)-3-(2-fluoro-6-(oxetan-3-yloxy)phenyl)isonicotinamide |
| 144 | 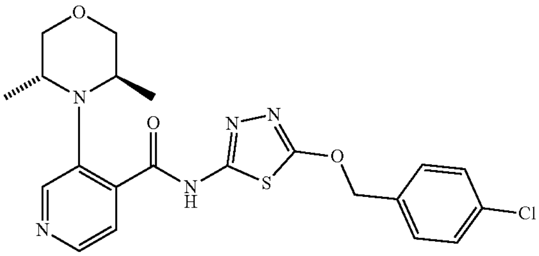 [SMILES: C[C@@H]1COC[C@@H](C)N1c1cnccc1C(=O)Nc1nnc(OCc2ccc(Cl)cc2)s1] | N-(5-((4-chlorobenzyl)oxy)-1,3,4-thiadiazol-2-yl)-3-((3R,5R)-3,5-dimethylmorpholino)isonicotinamide |
| 145 | 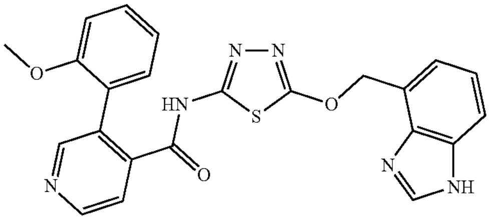 [SMILES: COc1ccccc1-c1cnccc1C(=O)Nc1nnc(OCc2cccc3[nH]cnc23)s1] | N-[5-(1H-1,3-benzodiazol-4-ylmethoxy)-1,3,4-thiadiazol-2-yl]-3-(2-methoxyphenyl)pyridine-4-carboxamide |
| 146 | 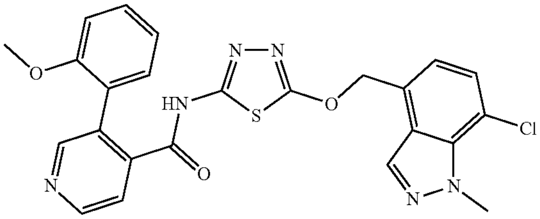 [SMILES: COc1ccccc1-c1cnccc1C(=O)Nc1nnc(OCc2ccc(Cl)c3c2cnn3C)s1] | N-[5-[(7-chloro-1-methylindazol-4-yl)methoxy]-1,3,4-thiadiazol-2-yl]-3-(2-methoxyphenyl)pyridine-4-carboxamide |

-continued

| Cpd # | Structure | Name |
|---|---|---|
| 147 | 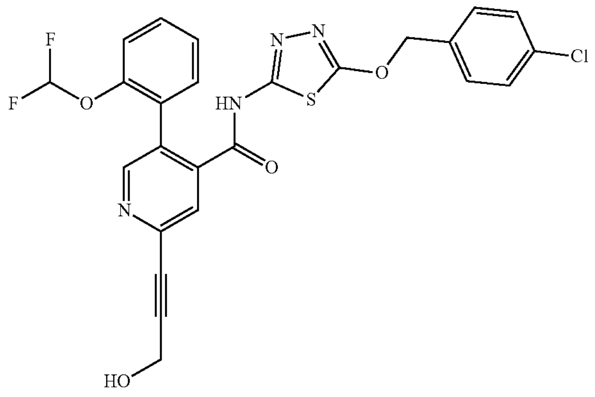 [SMILES: O=C(Nc1nnc(OCc2ccc(Cl)cc2)s1)c1cc(C#CCO)ncc1-c1ccccc1OC(F)F] | N-[5-[(4-chlorophenyl)methoxy]-1,3,4-thiadiazol-2-yl]-5-[2-(difluoromethoxy)phenyl]-2-(3-hydroxyprop-1-yn-1-yl)pyridine-4-carboxamide |
| 148 | 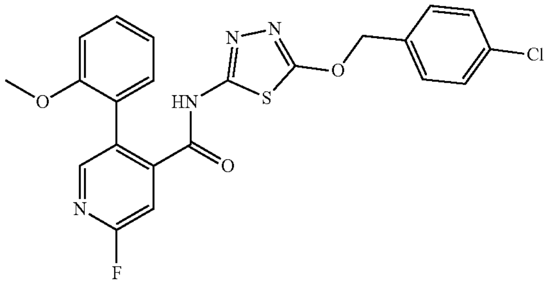 [SMILES: COc1ccccc1-c1cnc(F)cc1C(=O)Nc1nnc(OCc2ccc(Cl)cc2)s1] | N-(5-((4-chlorobenzyl)oxy)-1,3,4-thiadiazol-2-yl)-2-fluoro-5-(2-methoxyphenyl)isonicotinamide |
| 149 | 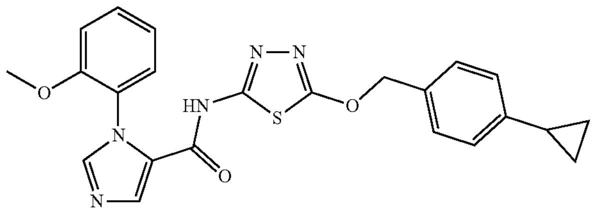 [SMILES: COc1ccccc1-n1cncc1C(=O)Nc1nnc(OCc2ccc(C3CC3)cc2)s1] | N-(5-((4-cyclopropylbenzyl)oxy)-1,3,4-thiadiazol-2-yl)-1-(2-methoxyphenyl)-1H-imidazole-5-carboxamide |
| 150 | 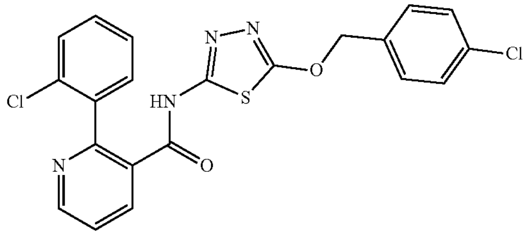 [SMILES: O=C(Nc1nnc(OCc2ccc(Cl)cc2)s1)c1cccnc1-c1ccccc1Cl] | N-(5-((4-chlorobenzyl)oxy)-1,3,4-thiadiazol-2-yl)-2-(2-chlorophenyl)nicotinamide |
| 151 | 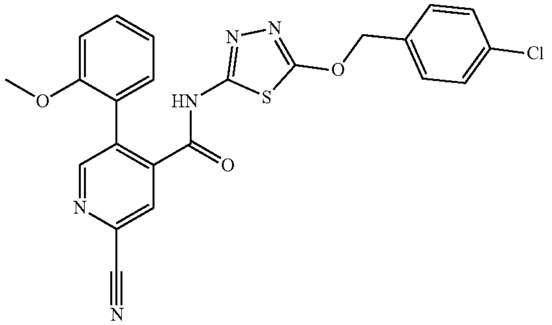 [SMILES: COc1ccccc1-c1cnc(C#N)cc1C(=O)Nc1nnc(OCc2ccc(Cl)cc2)s1] | N-(5-((4-chlorobenzyl)oxy)-1,3,4-thiadiazol-2-yl)-2-cyano-5-(2-methoxyphenyl)isonicotinamide |

-continued

| Cpd # | Structure | Name |
| --- | --- | --- |
| 152 | 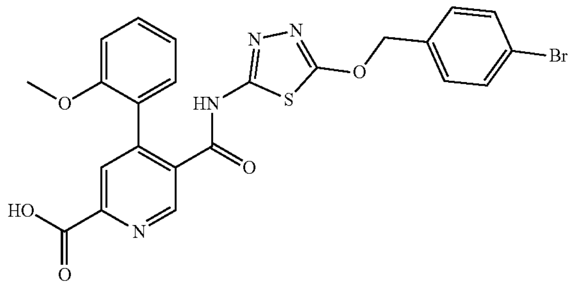 [SMILES: COc1ccccc1-c1cc(C(=O)O)ncc1C(=O)Nc1nnc(OCc2ccc(Br)cc2)s1] | 5-([5-[(4-bromophenyl)methoxy]-1,3,4-thiadiazol-2-yl]carbamoyl)-4-(2-methoxyphenyl)pyridine-2-carboxylic acid |
| 153 | 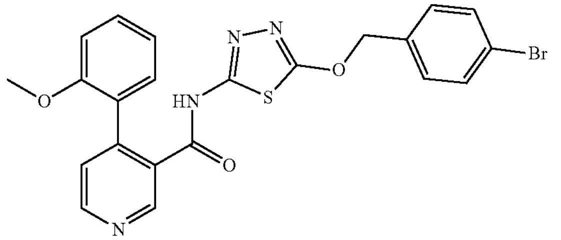 [SMILES: COc1ccccc1-c1ccncc1C(=O)Nc1nnc(OCc2ccc(Br)cc2)s1] | N-[5-[(4-bromophenyl)methoxy]-1,3,4-thiadiazol-2-yl]-4-(2-methoxyphenyl)pyridine-3-carboxamide |
| 154 | 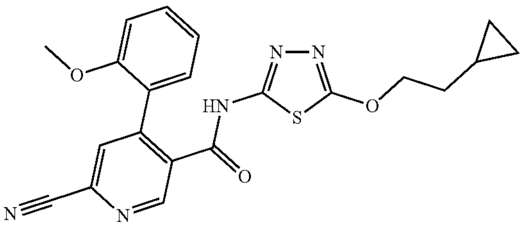 [SMILES: COc1ccccc1-c1cc(C#N)ncc1C(=O)Nc1nnc(OCCC2CC2)s1] | 6-cyano-N-(5-(2-cyclopropylethoxy)-1,3,4-thiadiazol-2-yl)-4-(2-methoxyphenyl)nicotinamide |
| 155 | 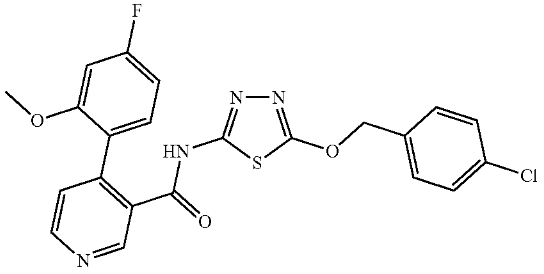 [SMILES: COc1cc(F)ccc1-c1ccncc1C(=O)Nc1nnc(OCc2ccc(Cl)cc2)s1] | N-[5-[(4-chlorophenyl)methoxy]-1,3,4-thiadiazol-2-yl]-4-(4-fluoro-2-methoxyphenyl)pyridine-3-carboxamide |
| 156 | 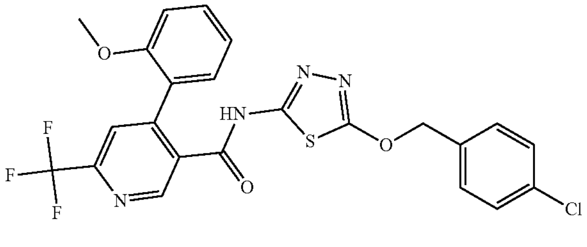 [SMILES: COc1ccccc1-c1cc(C(F)(F)F)ncc1C(=O)Nc1nnc(OCc2ccc(Cl)cc2)s1] | N-[5-[(4-chlorophenyl)methoxy]-1,3,4-thiadiazol-2-yl]-4-(2-methoxyphenyl)-6-(trifluoromethyl)pyridine-3-carboxamide |
| 157 | 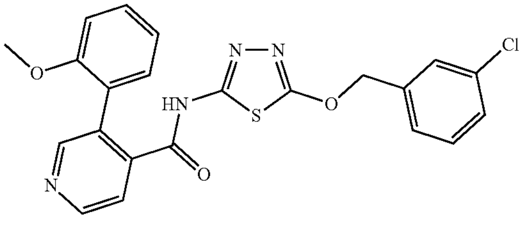 [SMILES: COc1ccccc1-c1cnccc1C(=O)Nc1nnc(OCc2cccc(Cl)c2)s1] | N-(5-((3-chlorobenzyl)oxy)-1,3,4-thiadiazol-2-yl)-3-(2-methoxyphenyl)isonicotinamide |

-continued

| Cpd # | Structure | Name |
|---|---|---|
| 158 | 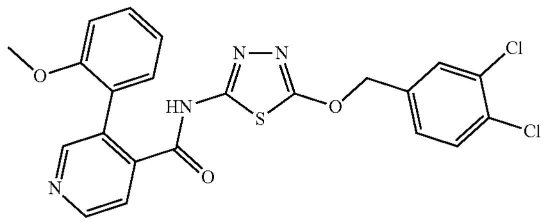 [SMILES: COc1ccccc1-c1cnccc1C(=O)Nc1nnc(OCc2ccc(Cl)c(Cl)c2)s1] | N-[5-[(3,4-dichlorophenyl)methoxy]-1,3,4-thiadiazol-2-yl]-3-(2-methoxyphenyl)pyridine-4-carboxamide |
| 159 | 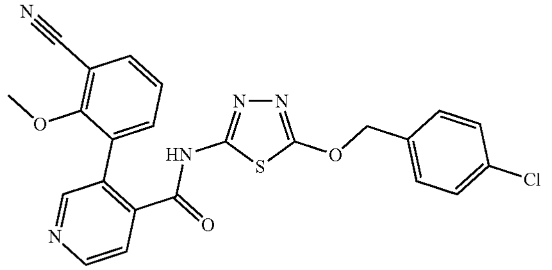 [SMILES: COc1c(C#N)cccc1-c1cnccc1C(=O)Nc1nnc(OCc2ccc(Cl)cc2)s1] | N-(5-((4-chlorobenzyl)oxy)-1,3,4-thiadiazol-2-yl)-3-(3-cyano-2-methoxyphenyl)isonicotinamide |
| 160 | 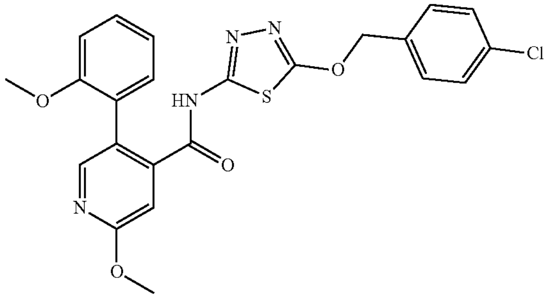 [SMILES: COc1cc(C(=O)Nc2nnc(OCc3ccc(Cl)cc3)s2)c(-c2ccccc2OC)cn1] | N-(5-((4-chlorobenzyl)oxy)-1,3,4-thiadiazol-2-yl)-2-methoxy-5-(2-methoxyphenyl)isonicotinamide |
| 161 | 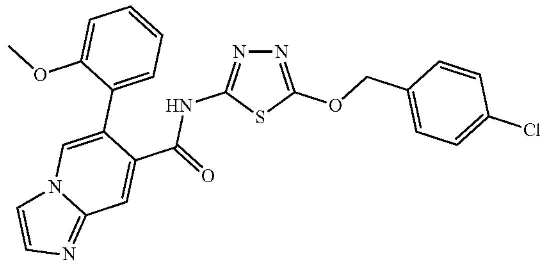 [SMILES: COc1ccccc1-c1cn2ccnc2cc1C(=O)Nc1nnc(OCc2ccc(Cl)cc2)s1] | N-(5-((4-chlorobenzyl)oxy)-1,3,4-thiadiazol-2-yl)-6-(2-methoxyphenyl)imidazo[1,2-a]pyridine-7-carboxamide |
| 162 | 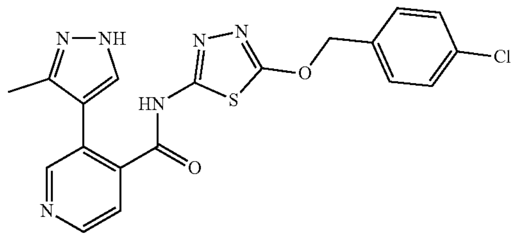 [SMILES: Cc1n[nH]cc1-c1cnccc1C(=O)Nc1nnc(OCc2ccc(Cl)cc2)s1] | N-(5-((4-chlorobenzyl)oxy)-1,3,4-thiadiazol-2-yl)-3-(3-methyl-1H-pyrazol-4-yl)isonicotinamide |

-continued

| Cpd # | Structure | Name |
|---|---|---|
| 163 | 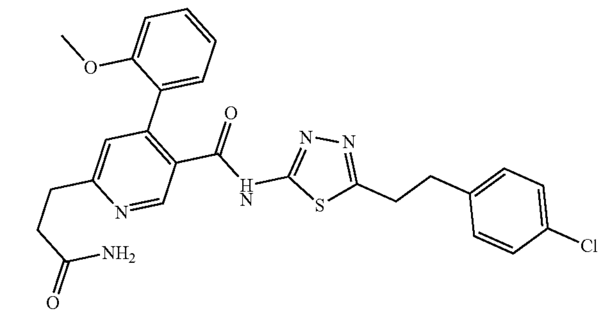 [SMILES: COc1ccccc1-c1cc(CCC(N)=O)ncc1C(=O)Nc1nnc(CCc2ccc(Cl)cc2)s1] | 6-(3-amino-3-oxopropyl)-N-(5-((4-chlorobenzyl)oxy)-1,3,4-thiadiazol-2-yl)-4-(2-methoxyphenyl)nicotinamide |
| 164 | 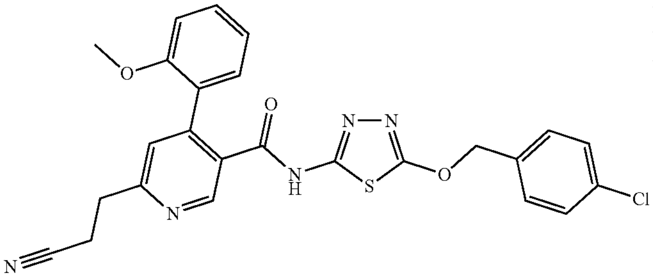 [SMILES: COc1ccccc1-c1cc(CCC#N)ncc1C(=O)Nc1nnc(OCc2ccc(Cl)cc2)s1] | N-[5-[(4-chlorophenyl)methoxy]-1,3,4-thiadiazol-2-yl]-6-(2-cyanoethyl)-4-(2-methoxyphenyl)pyridine-3-carboxamide |
| 165 | 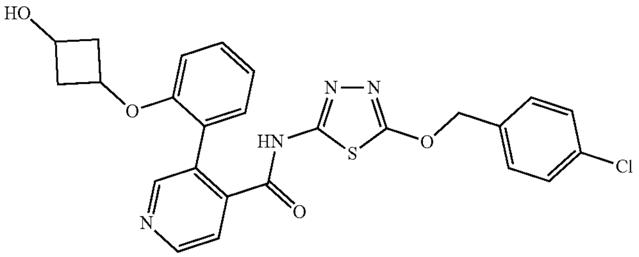 [SMILES: O=C(Nc1nnc(OCc2ccc(Cl)cc2)s1)c1ccncc1-c1ccccc1OC1CC(O)C1] | N-(5-((4-chlorobenzyl)oxy)-1,3,4-thiadiazol-2-yl)-3-(2-(3-hydroxycyclobutoxy)phenyl)isonicotinamide |
| 166 | 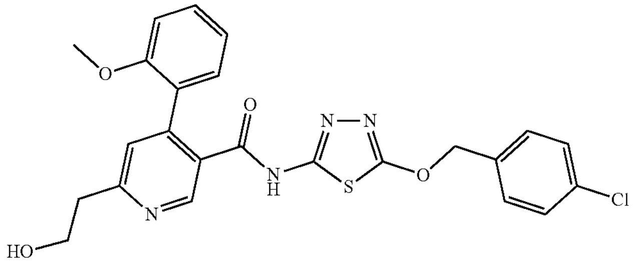 [SMILES: COc1ccccc1-c1cc(CCO)ncc1C(=O)Nc1nnc(OCc2ccc(Cl)cc2)s1] | N-(5-((4-chlorobenzyl)oxy)-1,3,4-thiadiazol-2-yl)-6-(2-hydroxyethyl)-4-(2-methoxyphenyl)nicotinamide |
| 167a | 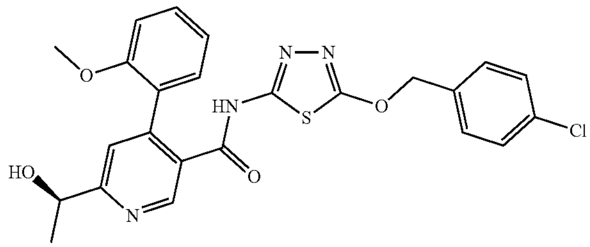 [SMILES: COc1ccccc1-c1cc([C@@H](C)O)ncc1C(=O)Nc1nnc(OCc2ccc(Cl)cc2)s1] | (R)-N-[5-[(4-chlorophenyl)methoxy]-1,3,4-thiadiazol-2-yl]-6-(1-hydroxyethyl)-4-(2-methoxyphenyl)pyridine-3-carboxamide |

-continued

| Cpd # | Structure | Name |
| --- | --- | --- |
| 167b | 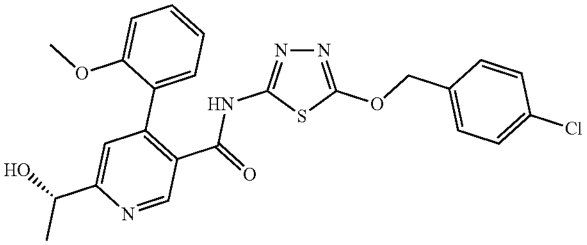 [SMILES: COc1ccccc1-c1cc([C@H](C)O)ncc1C(=O)Nc1nnc(OCc2ccc(Cl)cc2)s1] | (S)-N-[5-[(4-chlorophenyl)methoxy]-1,3,4-thiadiazol-2-yl]-6-(1-hydroxyethyl)-4-(2-methoxyphenyl)pyridine-3-carboxamide |
| 168 | 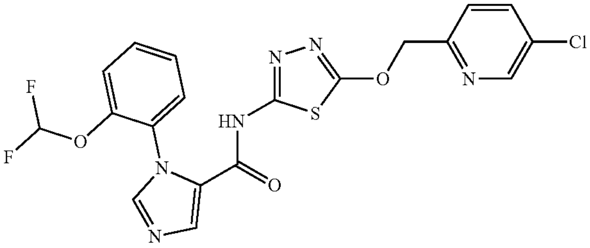 [SMILES: O=C(Nc1nnc(OCc2ccc(Cl)cn2)s1)c1cncn1-c1ccccc1OC(F)F] | N-[5-[(5-chloropyridin-2-yl)methoxy]-1,3,4-thiadiazol-2-yl]-3-[2-(difluoromethoxy)phenyl]imidazole-4-carboxamide |
| 169 | 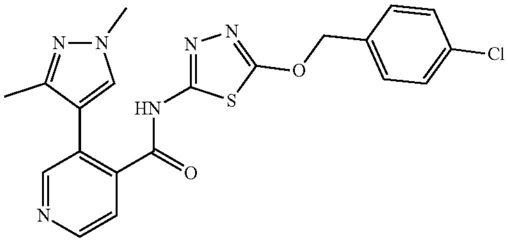 [SMILES: Cc1nn(C)cc1-c1cnccc1C(=O)Nc1nnc(OCc2ccc(Cl)cc2)s1] | N-[5-[(4-chlorophenyl)methoxy]-1,3,4-thiadiazol-2-yl]-3-(1,3-dimethylpyrazol-4-yl)pyridine-4-carboxamide |
| 170 | 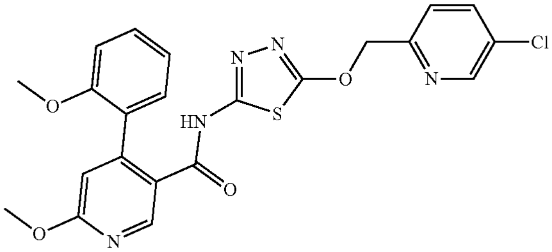 [SMILES: COc1cc(-c2ccccc2OC)c(C(=O)Nc2nnc(OCc3ccc(Cl)cn3)s2)cn1] | N-[5-[(5-chloropyridin-2-yl)methoxy]-1,3,4-thiadiazol-2-yl]-6-(hydroxymethyl)-4-(2-methoxyphenyl)pyridine-3-carboxamide |
| 171 | 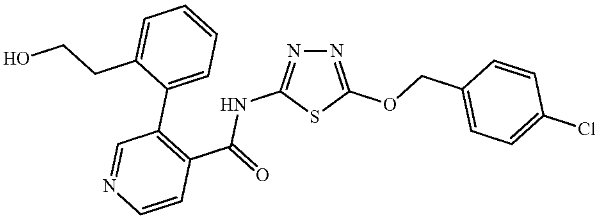 [SMILES: O=C(Nc1nnc(OCc2ccc(Cl)cc2)s1)c1ccncc1-c1ccccc1CCO] | N-(5-((4-chlorobenzyl)oxy)-1,3,4-thiadiazol-2-yl)-3-(2-(2-hydroxyethyl)phenyl)isonicotinamide |
| 172 | 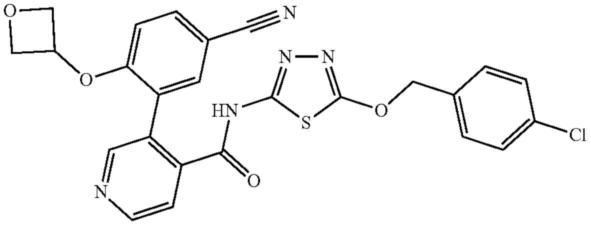 [SMILES: N#Cc1ccc(OC2COC2)c(-c2cnccc2C(=O)Nc2nnc(OCc3ccc(Cl)cc3)s2)c1] | N-(5-((4-chlorobenzyl)oxy)-1,3,4-thiadiazol-2-yl)-3-(5-cyano-2-(oxetan-3-yloxy)phenyl)isonicotinamide |

-continued

| Cpd # | Structure | Name |
|---|---|---|
| 173 | 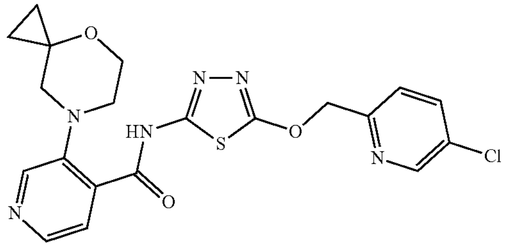 [SMILES: O=C(Nc1nnc(OCc2ccc(Cl)cn2)s1)c1ccncc1N1CCOC2(CC2)C1] | N-[5-[(5-chloropyridin-2-yl)methoxy]-1,3,4-thiadiazol-2-yl]-3-[4-oxa-7-azaspiro[2.5]octan-7-yl]pyridine-4-carboxamide |
| 174 | 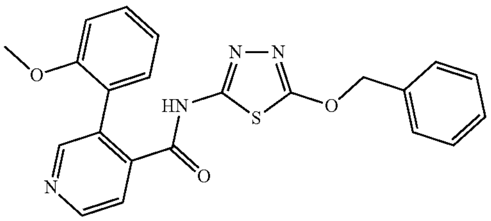 [SMILES: COc1ccccc1-c1cnccc1C(=O)Nc1nnc(OCc2ccccc2)s1] | N-(5-(benzyloxy)-1,3,4-thiadiazol-2-yl)-3-(2-methoxyphenyl)isonicotinamide |
| 175a | 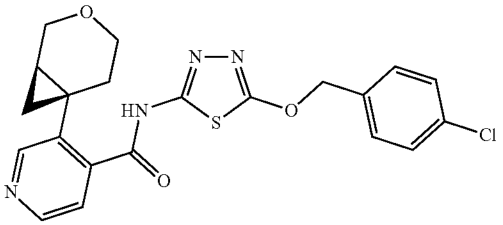 [SMILES: O=C(Nc1nnc(OCc2ccc(Cl)cc2)s1)c1ccncc1[C@@]12CCOC[C@@H]1C2] | 3-((1R,6S)-3-oxabicyclo[4.1.0]heptan-6-yl)-N-(5-((4-chlorobenzyl)oxy)-1,3,4-thiadiazol-2-yl)isonicotinamide |
| 175b | 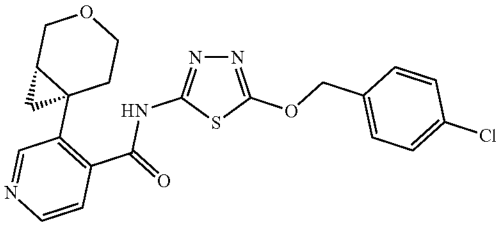 [SMILES: O=C(Nc1nnc(OCc2ccc(Cl)cc2)s1)c1ccncc1[C@]12CCOC[C@H]1C2] | 3-((1S,6R)-3-oxabicyclo[4.1.0]heptan-6-yl)-N-(5-((4-chlorobenzyl)oxy)-1,3,4-thiadiazol-2-yl)isonicotinamide |
| 176 | 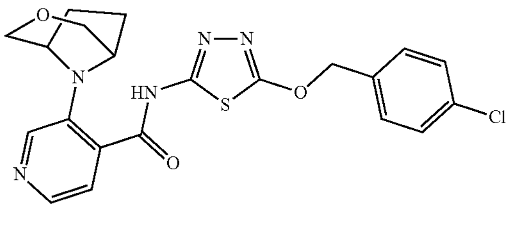 [SMILES: O=C(Nc1nnc(OCc2ccc(Cl)cc2)s1)c1ccncc1N1C2CCC1COC2] | N-[5-[(4-chlorophenyl)methoxy]-1,3,4-thiadiazol-2-yl]-3-[3-oxa-8-azabicyclo[3.2.1]octan-8-yl]pyridine-4-carboxamide |
| 177 | 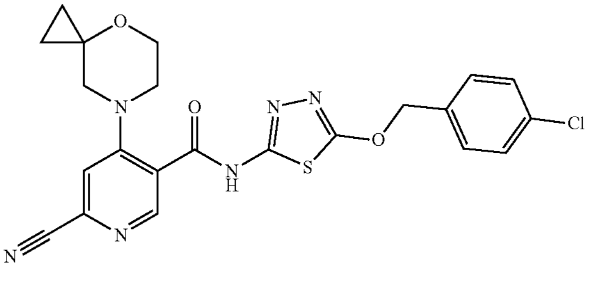 [SMILES: N#Cc1cc(N2CCOC3(CC3)C2)c(C(=O)Nc2nnc(OCc3ccc(Cl)cc3)s2)cn1] | N-[5-[(4-chlorophenyl)methoxy]-1,3,4-thiadiazol-2-yl]-6-cyano-4-[4-oxa-7-azaspiro[2.5]octan-7-yl]pyridine-3-carboxamide |

-continued

| Cpd # | Structure | Name |
|---|---|---|
| 178a | 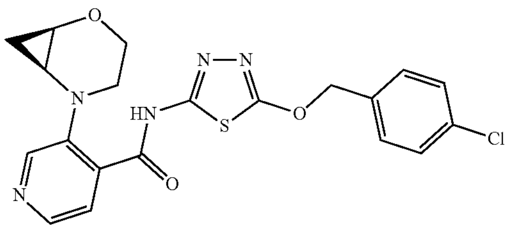 [SMILES: O=C(Nc1nnc(OCc2ccc(Cl)cc2)s1)c1ccncc1N1CCO[C@@H]2C[C@@H]21] | 3-((1R,6S)-2-oxa-5-azabicyclo[4.1,0]beptan-5-yl)-N-(5-((4-chlorobenzyl)oxy)-1,3,4-thiadiazol-2-yl)isonicotinamide |
| 178b | 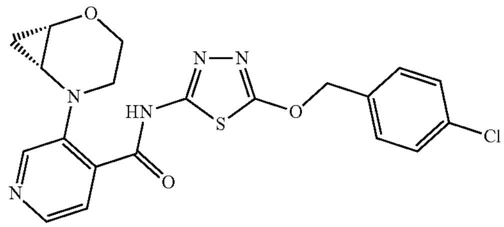 [SMILES: O=C(Nc1nnc(OCc2ccc(Cl)cc2)s1)c1ccncc1N1CCO[C@H]2C[C@H]21] | 3-((1S,6R)-2-oxa-5-azabicyclo[4.1,0]heptan-5-yl)-N-(5-((4-chlorobenzyl)oxy)-1,3,4-thiadiazol-2-yl)isonicotinamide |
| 179a | 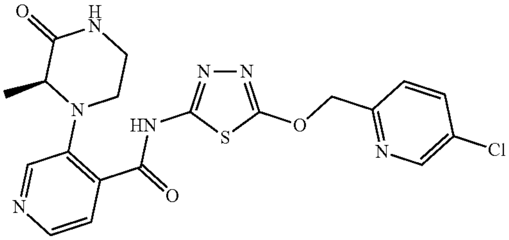 [SMILES: C[C@H]1C(=O)NCCN1c1cnccc1C(=O)Nc1nnc(OCc2ccc(Cl)cn2)s1] | (S)-N-(5-((5-chloropyridin-2-yl)methoxy)-1,3,4-thiadiazol-2-yl)-3-(2-methyl-3-oxopiperazin-1-yl)isonicotinamide |
| 179b | 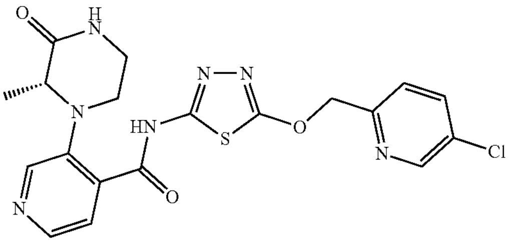 [SMILES: C[C@@H]1C(=O)NCCN1c1cnccc1C(=O)Nc1nnc(OCc2ccc(Cl)cn2)s1] | (R)-N-(5-((5-chloropyridin-2-yl)methoxy)-1,3,4-thiadiazol-2-yl)-3-(2-methyl-3-oxopiperazin-1-yl)isonicotinamide |
| 180 | 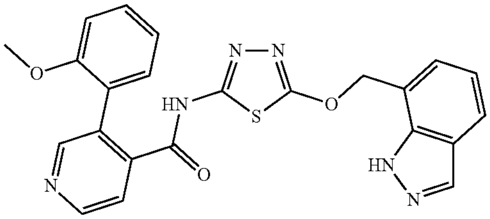 [SMILES: COc1ccccc1-c1cnccc1C(=O)Nc1nnc(OCc2cccc3cn[nH]c23)s1] | N-[5-(3H-1,3-benzodiazol-4-ylmethoxy)-1,3,4-thiadiazol-2-yl]-3-(2-methoxyphenyl)pyridine-4-carboxamide |
| 181 | 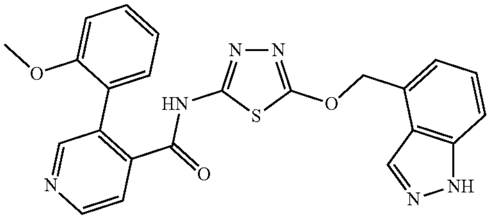 [SMILES: COc1ccccc1-c1cnccc1C(=O)Nc1nnc(OCc2cccc3[nH]ncc23)s1] | N-[5-(1H-indazol-4-ylmethoxy)-1,3,4-thiadiazol-2-yl]-3-(2-methoxyphenyl)pyridine-4-carboxamide |

-continued

| Cpd # | Structure | Name |
| --- | --- | --- |
| 182 | 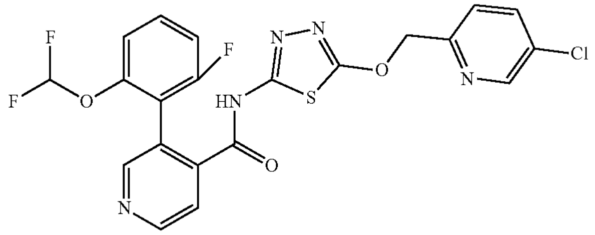 [SMILES: O=C(Nc1nnc(OCc2ccc(Cl)cn2)s1)c1ccncc1-c1c(F)cccc1OC(F)F] | N-(5-((5-chloropyridin-2-yl)methoxy)-1,3,4-thiadiazol-2-yl)-3-(2-(difluoromethoxy)-6-fluorophenyl)isonicotinamide |
| 183 | 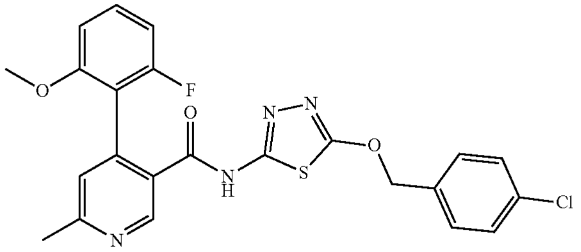 [SMILES: COc1cccc(F)c1-c1cc(C)ncc1C(=O)Nc1nnc(OCc2ccc(Cl)cc2)s1] | N-(5-((4-chlorobenzyl)oxy)-1,3,4-thiadiazol-2-yl)-4-(2-fluoro-6-methoxyphenyl)-6-methylnicotinamide |
| 184 | 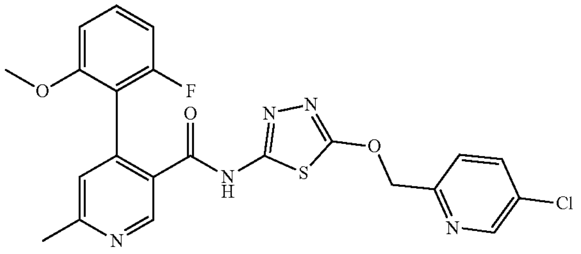 [SMILES: COc1cccc(F)c1-c1cc(C)ncc1C(=O)Nc1nnc(OCc2ccc(Cl)cn2)s1] | N-(5-((5-chloropyridin-2-yl)methoxy)-1,3,4-thiadiazol-2-yl)-4-(2-fluoro-6-methoxyphenyl)-6-methylnicotinamide |
| 185 | 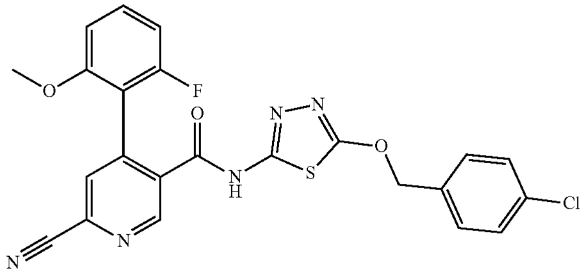 [SMILES: COc1cccc(F)c1-c1cc(C#N)ncc1C(=O)Nc1nnc(OCc2ccc(Cl)cc2)s1] | N-(5-((4-chlorobenzyl)oxy)-1,3,4-thiadiazol-2-yl)-6-cyano-4-(2-fluoro-6-methoxyphenyl)nicotinamide |
| 186 | 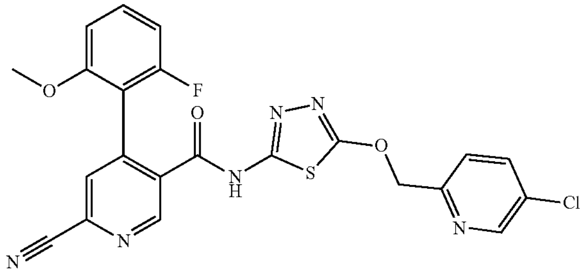 [SMILES: COc1cccc(F)c1-c1cc(C#N)ncc1C(=O)Nc1nnc(OCc2ccc(Cl)cn2)s1] | N-(5-((5-chloropyridin-2-yl)methoxy)-1,3,4-thiadiazol-2-yl)-6-cyano-4-(2-fluoro-6-methoxyphenyl)nicotinamide |
| 187 | 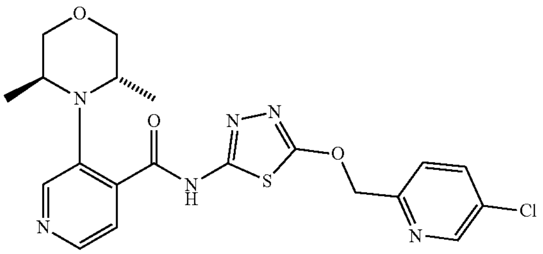 [SMILES: C[C@H]1COC[C@H](C)N1c1cnccc1C(=O)Nc1nnc(OCc2ccc(Cl)cn2)s1] | N-(5-((5-chloropyridin-2-yl)methoxy)-1,3,4-thiadiazol-2-yl)-3-((3S,5S)-3,5-dimethylmorpholino)isonicotinamide |

-continued

| Cpd # | Structure | Name |
| --- | --- | --- |
| 188 | 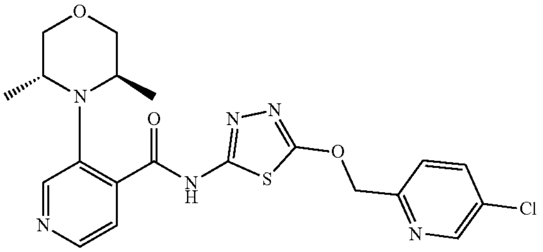 [SMILES: C[C@@H]1COC[C@@H](C)N1c1cnccc1C(=O)Nc1nnc(OCc2ccc(Cl)cn2)s1] | N-(5-((5-chloropyridin-2-yl)methoxy)-1,3,4-thiadiazol-2-yl)-3-((3R,5R)-3,5-dimethylmorpholino)isonicotinamide |
| 189 | 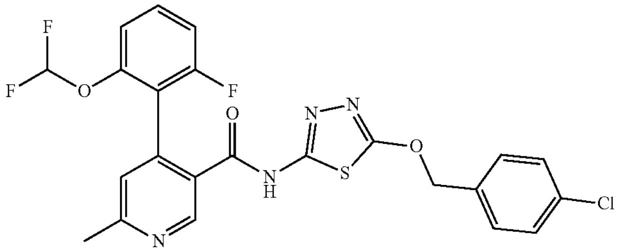 [SMILES: Cc1cc(-c2c(F)cccc2OC(F)F)c(C(=O)Nc2nnc(OCc3ccc(Cl)cc3)s2)cn1] | N-(5-((4-chlorobenzyl)oxy)-1,3,4-thiadiazol-2-yl)-4-(2-(difluoromethoxy)-6-fluorophenyl)-6-methylnicotinamide |
| 190 | 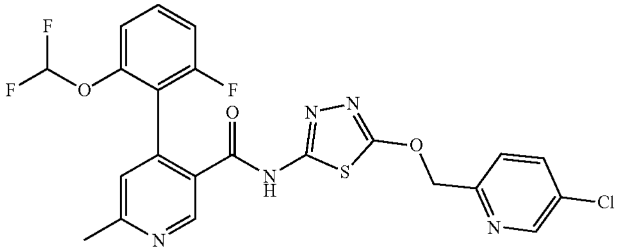 [SMILES: Cc1cc(-c2c(F)cccc2OC(F)F)c(C(=O)Nc2nnc(OCc3ccc(Cl)cn3)s2)cn1] | N-(5-((5-chloropyridin-2-yl)methoxy)-1,3,4-thiadiazol-2-yl)-4-(2-(difluoromethoxy)-6-fluorophenyl)-6-methylnicotinamide |
| 191 | 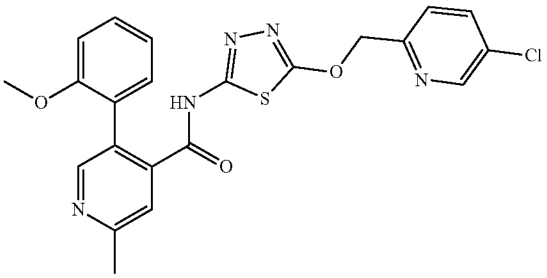 | N-[5-[(5-chloropyridin-2-yl)methoxy]-1,3,4-thiadiazol-2-yl]-5-(2-methoxyphenyl)-2-methylpyridine-4-carboxamide |
| 192 | 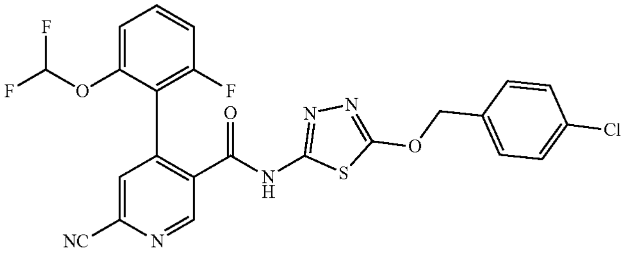 [SMILES: N#Cc1cc(-c2c(F)cccc2OC(F)F)c(C(=O)Nc2nnc(OCc3ccc(Cl)cc3)s2)cn1] | N-(5-((4-chlorobenzyl)oxy)-1,3,4-thiadiazol-2-yl)-6-cyano-4-(2-(difluoromethoxy)-6-fluorophenyl)nicotinamide |
| 193 | 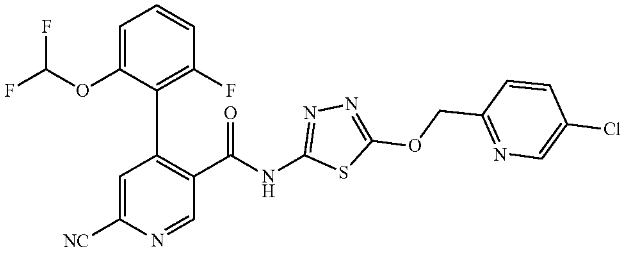 [SMILES: N#Cc1cc(-c2c(F)cccc2OC(F)F)c(C(=O)Nc2nnc(OCc3ccc(Cl)cn3)s2)cn1] | N-(5-((5-chloropyridin-2-yl)methoxy)-1,3,4-thiadiazol-2-yl)-6-cyano-4-(2-(difluoromethoxy)-6-fluorophenyl) nicotinamide |

-continued

| Cpd # | Structure | Name |
| --- | --- | --- |
| 194 | 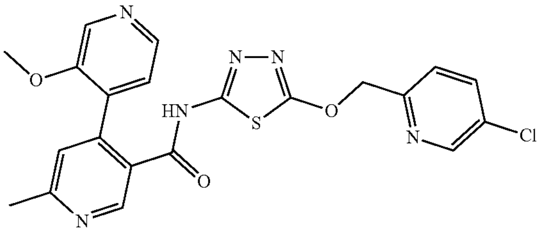 [SMILES: COc1cnccc1-c1cc(C)ncc1C(=O)Nc1nnc(OCc2ccc(Cl)cn2)s1] | N-(5-((5-chloropyridin-2-yl)methoxy)-1,3,4-thiadiazol-2-yl)-3'-methoxy-6-methyl-[4,4'-bipyridine]-3-carboxamide |
| 195 | 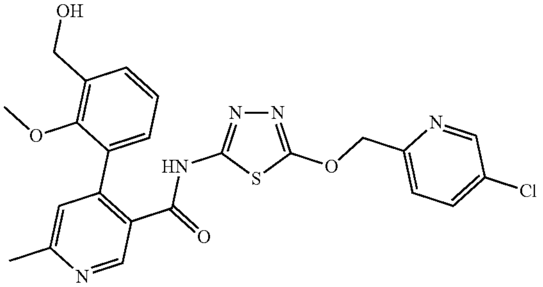 [SMILES: COc1c(CO)cccc1-c1cc(C)ncc1C(=O)Nc1nnc(OCc2ccc(Cl)cn2)s1] | N-[5-[(5-chloropyridin-2-yl)methoxy]-1,3,4-thiadiazol-2-yl]-4-[3-(hydroxymethyl)-2-methoxyphenyl]-6-methylpyridine-3-carboxamide |
| 196 | 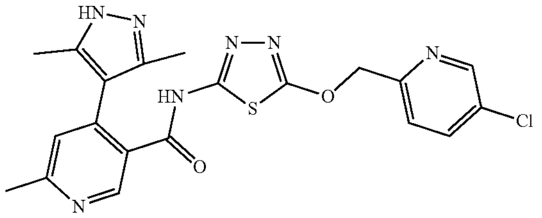 [SMILES: Cc1cc(-c2c(C)n[nH]c2C)c(C(=O)Nc2nnc(OCc3ccc(Cl)cn3)s2)cn1] | N-(5-((5-chloropyridin-2-yl)methoxy)-1,3,4-thiadiazol-2-yl)-4-(3,5-dimethyl-1H-pyrazol-4-yl)-6methylnicotinamide |
| 197 | 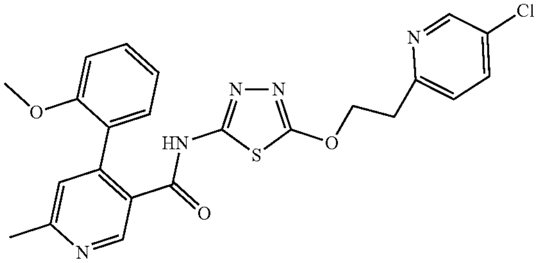 [SMILES: COc1ccccc1-c1cc(C)ncc1C(=O)Nc1nnc(OCCc2ccc(Cl)cn2)s1] | N-(5-(2-(5-chloropyridin-2-yl)ethoxy)-1,3,4-thiadiazol-2-yl)-4-(2-methoxyphenyl)-6-methylnicotinamide |
| 198 | 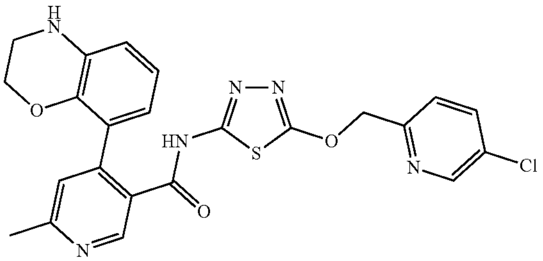 [SMILES: Cc1cc(-c2cccc3c2OCCN3)c(C(=O)Nc2nnc(OCc3ccc(Cl)cn3)s2)cn1] | N-(5-((5-chloropyridin-2-yl)methoxy)-1,3,4-thiadiazol-2-yl)-4-(3,4-dihydro-2H-benzo[b][1,4]oxazin-8-yl)-6-methylnicotinamide |
| 199 | 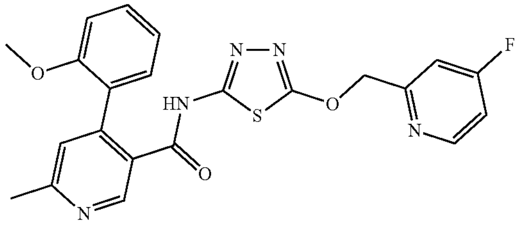 [SMILES: COc1ccccc1-c1cc(C)ncc1C(=O)Nc1nnc(OCc2cc(F)ccn2)s1] | N-(5-((4-fluoropyridin-2-yl)methoxy)-1,3,4-thiadiazol-2-yl)-4-(2-methoxyphenyl)-6-methylnicotinamide |

-continued

| Cpd # | Structure | Name |
|---|---|---|
| 200 | 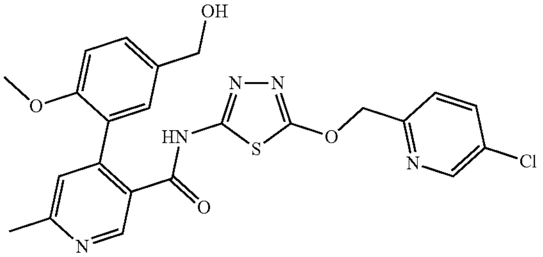 [SMILES: COc1ccc(CO)cc1-c1cc(C)ncc1C(=O)Nc1nnc(OCc2ccc(Cl)cn2)s1] | N-(5-((5-chloropyridin-2-yl)methoxy)-1,3,4-thiadiazol-2-yl)-4-(5-(hydroxymethyl)-2-methoxyphenyl)-6-methylnicotinamide |
| 201 | 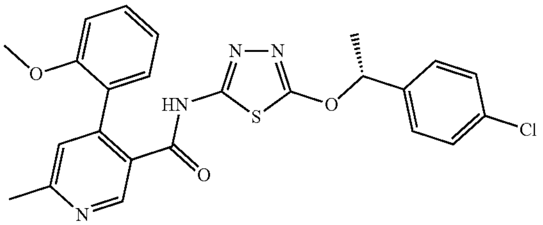 [SMILES: COc1ccccc1-c1cc(C)ncc1C(=O)Nc1nnc(O[C@H](C)c2ccc(Cl)cc2)s1] | N-[5-[(1R)-1-(4-chlorophenyl)ethoxy]-1,3,4-thiadiazol-2-yl]-4-(2-methoxyphenyl)-6-methylpyridine-3-carboxamide |
| 202 | 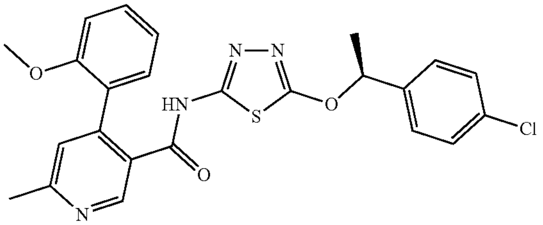 [SMILES: COc1ccccc1-c1cc(C)ncc1C(=O)Nc1nnc(O[C@@H](C)c2ccc(Cl)cc2)s1] | N-[5-[(1S)-1-(4-chlorophenyl)ethoxy]-1,3,4-thiadiazol-2-yl]-4-(2-methoxyphenyl)-6-methylpyridine-3-carboxamide |
| 203 | 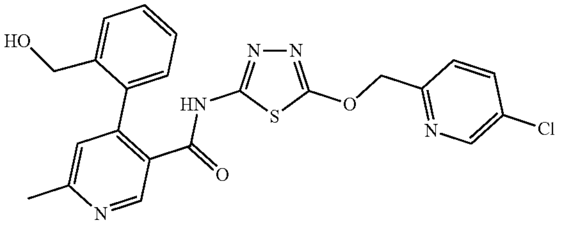 [SMILES: Cc1cc(-c2ccccc2CO)c(C(=O)Nc2nnc(OCc3ccc(Cl)cn3)s2)cn1] | N-[5-[(5-chloropyridin-2-yl)methoxy]-1,3,4-thiadiazol-2-yl]-4-[2-(hydroxymethyl)phenyl]-6-methylpyridine-3-carboxamide |
| 204 | 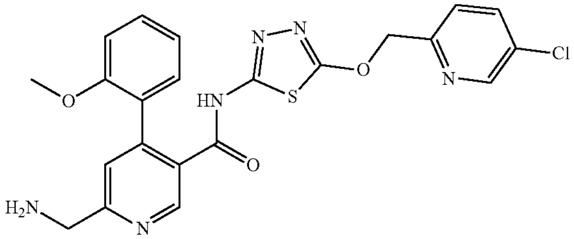 [SMILES: COc1ccccc1-c1cc(CN)ncc1C(=O)Nc1nnc(OCc2ccc(Cl)cn2)s1] | 6-(aminomethyl)-N-[5-[(5-chloropyridin-2-yl)methoxy]-1,3,4-thiadiazol-2-yl]-4-(2-methoxyphenyl)pyridine-3-carboxamide |
| 205 | 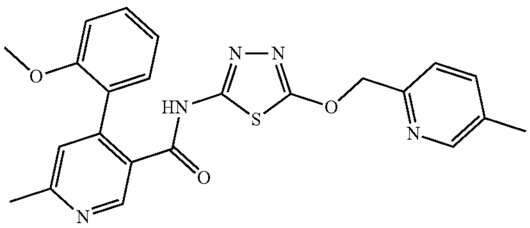 | 4-(2-methoxyphenyl)-6-methyl-N-(5-((5-methylpyridin-2-yl)methoxy)-1,3,4-thiadiazol-2-yl)nicotinamide |

-continued

| Cpd # | Structure | Name |
|---|---|---|
| 206 | 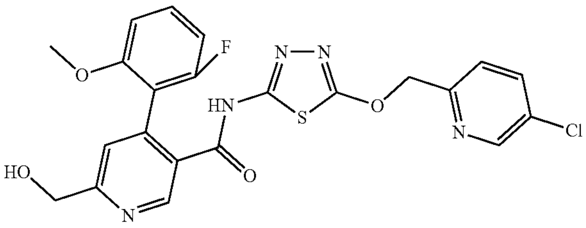 [SMILES: COc1cccc(F)c1-c1cc(CO)ncc1C(=O)Nc1nnc(OCc2ccc(Cl)cn2)s1] | N-[5-[(5-chloropyridin-2-yl)methoxy]-1,3,4-thiadiazol-2-yl]-4-(2-fluoro-6-methoxyphenyl)-6-(hydroxymethyl)pyridine-3-carboxamide |
| 207 | 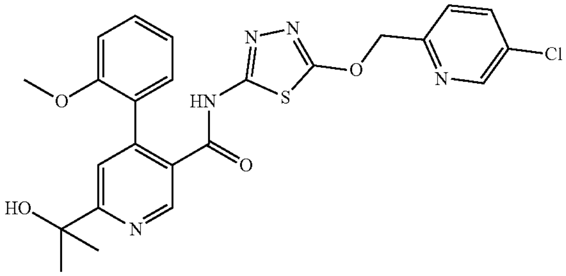 [SMILES: COc1ccccc1-c1cc(C(C)(C)O)ncc1C(=O)Nc1nnc(OCc2ccc(Cl)cn2)s1] | N-(5-((5-chloropyridin-2-yl)methoxy)-1,3,4-thiadiazol-2-yl)-6-(2-hydroxypropan-2-yl)-4-(2-methoxyphenyl)nicotinamide |
| 208 | 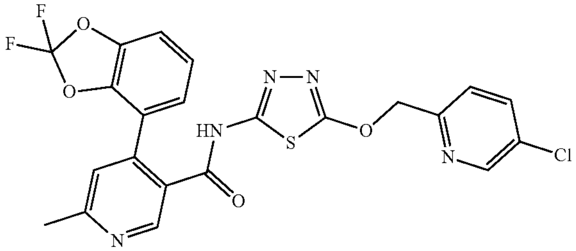 [SMILES: Cc1cc(-c2cccc3c2OC(F)(F)O3)c(C(=O)Nc2nnc(OCc3ccc(Cl)cn3)s2)cn1] | N-(5-((5-chloropyridin-2-yl)methoxy)-1,3,4-thiadiazol-2-yl)-4-(2,2-difluorobenzo[d][1,3]dioxol-4-yl)-6-methylnicotinamide |
| 209 | 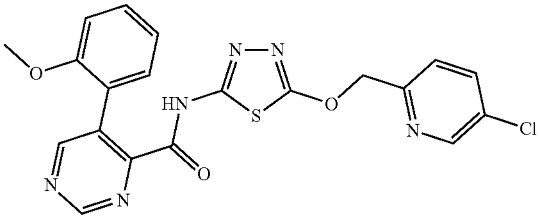 [SMILES: COc1ccccc1-c1cncnc1C(=O)Nc1nnc(OCc2ccc(Cl)cn2)s1] | N-(5-((5-chloropyridin-2-yl)methoxy)-1,3,4-thiadiazol-2-yl)-5-(2-methoxyphenyl)pyrimidine-4-carboxamide |
| 210 | 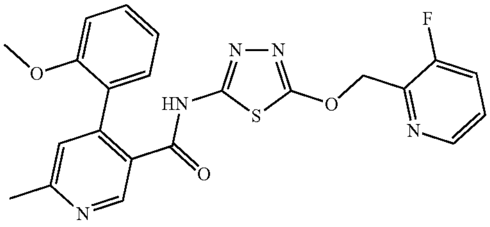 [SMILES: COc1ccccc1-c1cc(C)ncc1C(=O)Nc1nnc(OCc2ncccc2F)s1] | N-[5-[(3-fluoropyridin-2-yl)methoxy]-1,3,4-thiadiazol-2-yl]-4-(2-methoxyphenyl)-6-methylpyridine-3-carboxamide |
| 211 | 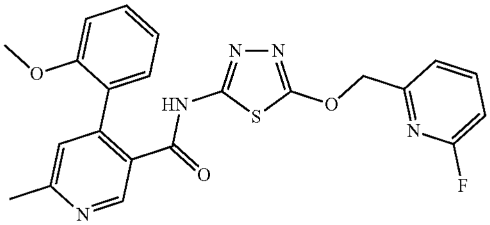 [SMILES: COc1ccccc1-c1cc(C)ncc1C(=O)Nc1nnc(OCc2cccc(F)n2)s1] | N-[5-[(6-fluoropyridin-2-yl)methoxy]-1,3,4-thiadiazol-2-yl]-4-(2-methoxyphenyl)-6-methylpyridine-3-carboxamide |

-continued

| Cpd # | Structure | Name |
| --- | --- | --- |
| 212 | 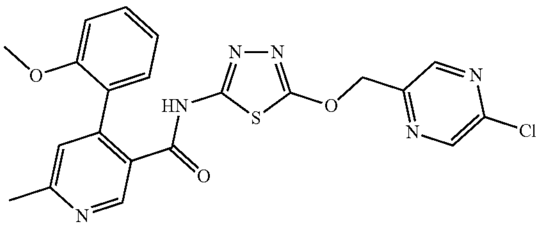 [SMILES: COc1ccccc1-c1cc(C)ncc1C(=O)Nc1nnc(OCc2cnc(Cl)cn2)s1] | N-[5-[(5-chloropyrazin-2-yl)methoxy]-1,3,4-thiadiazol-2-yl]-4-(2-methoxyphenyl)-6-methylpyridine-3-carboxamide |
| 213 | 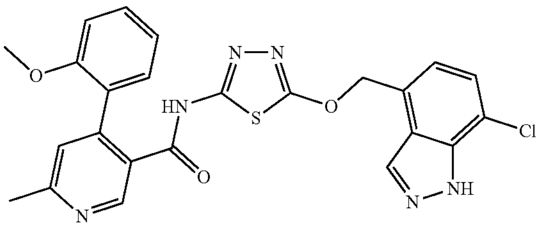 [SMILES: COc1ccccc1-c1cc(C)ncc1C(=O)Nc1nnc(OCc2ccc(Cl)c3[nH]ncc23)s1] | N-[5-[(7-chloro-1H-indazol-4-yl)methoxy]-1,3,4-thiadiazol-2-yl]-4-(2-methoxyphenyl)-6-methylpyridine-3-carboxamide |
| 214 | 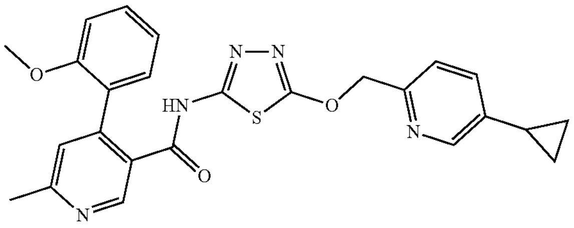 [SMILES: COc1ccccc1-c1cc(C)ncc1C(=O)Nc1nnc(OCc2ccc(C3CC3)cn2)s1] | N-(5-((5-cyclopropylpyridin-2-yl)methoxy)-1,3,4-thiadiazol-2-yl)-4-(2-methoxyphenyl)-6-methylnicolinamide |
| 215 | 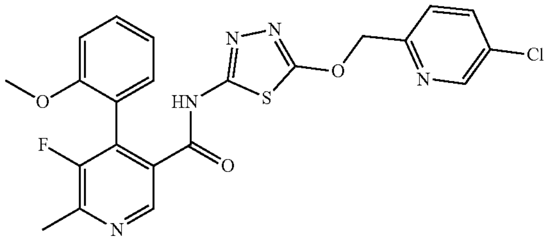 [SMILES: COc1ccccc1-c1c(C(=O)Nc2nnc(OCc3ccc(Cl)cn3)s2)cnc(C)c1F] | N-(5-((5-chloropyridin-2-yl)methoxy)-1,3,4-thiadiazol-2-yl)-5-fluoro-4-(2-methoxyphenyl)-6-methylnicotinamide |
| 216 | 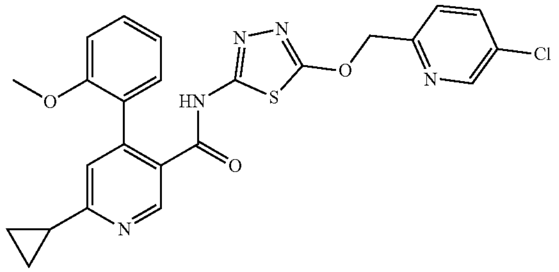 [SMILES: COc1ccccc1-c1cc(C2CC2)ncc1C(=O)Nc1nnc(OCc2ccc(Cl)cn2)s1] | N-[5-[(5-chloropyridin-2-yl)methoxy]-1,3,4-thiadiazol-2-yl]-6-cyclopropyl-4-(2-methoxyphenyl)pyridine-3-carboxamide |
| 217 | 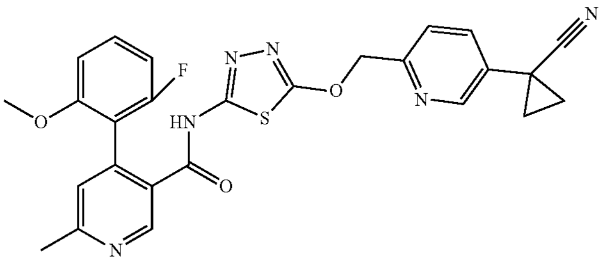 [SMILES: COc1cccc(F)c1-c1cc(C)ncc1C(=O)Nc1nnc(OCc2ccc(C3(C#N)CC3)cn2)s1] | N-(5-((5-(1-cyanocyclopropyl)pyridin-2-yl)methoxy)-1,3,4-thiadiazol-2-yl)-4-(2-fluoro-6-methoxyphenyl)-6-methylnicotinamide |

-continued

| Cpd # | Structure | Name |
| --- | --- | --- |
| 218 | 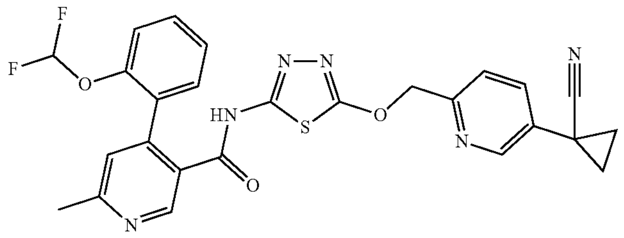 [SMILES: Cc1cc(-c2ccccc2OC(F)F)c(C(=O)Nc2nnc(OCc3ccc(C4(C#N)CC4)cn3)s2)cn1] | N-(5-[[5-(1-cyanocyclopropyl)pyridin-2-yl]methoxy]-1,3,4-thiadiazol-2-yl)-4-[2-(difluoromethoxy)phenyl]-6-methylpyridine-3-carboxamide |
| 219 | 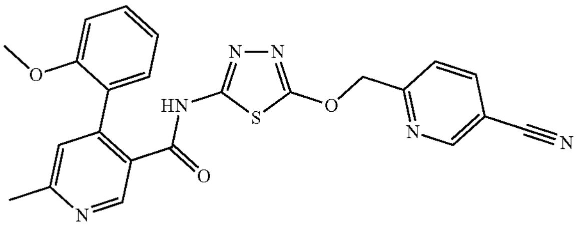 [SMILES: COc1ccccc1-c1cc(C)ncc1C(=O)Nc1nnc(OCc2ccc(C#N)cn2)s1] | N-(5-((5-cyanopyridin-2-yl)methoxy)-1,3,4-thiadiazol-2-yl)-4-(2-methoxyphenyl)-6-methylnicotinamide |
| 220 | 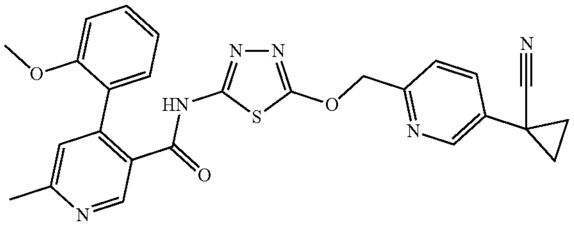 [SMILES: COc1ccccc1-c1cc(C)ncc1C(=O)Nc1nnc(OCc2ccc(C3(C#N)CC3)cn2)s1] | N-(5-[[5-(1-cyanocyclopropyl)pyridin-2-yl]methoxy]-1,3,4-thiadiazol-2-yl)-4-(2-methoxyphenyl)-6-methylpyridine-3-carboxamide |
| 221 | 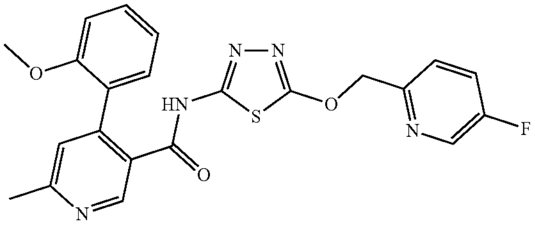 [SMILES: COc1ccccc1-c1cc(C)ncc1C(=O)Nc1nnc(OCc2ccc(F)cn2)s1] | N-[5-[(5-fluoropyridin-2-yl)methoxy]-1,3,4-thiadiazol-2-yl]-4-(2-methoxyphenyl)-6-methylpyridine-3-carboxamide |
| 222 | 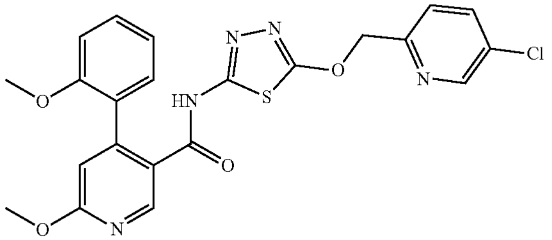 [SMILES: COc1cc(-c2ccccc2OC)c(C(=O)Nc2nnc(OCc3ccc(Cl)cn3)s2)cn1] | N-(5-((5-chloropyridin-2-yl)methoxy)-1,3,4-thiadiazol-2-yl)-6-methoxy-4-(2-methoxyphenyl)nicotinamide |
| 223 | 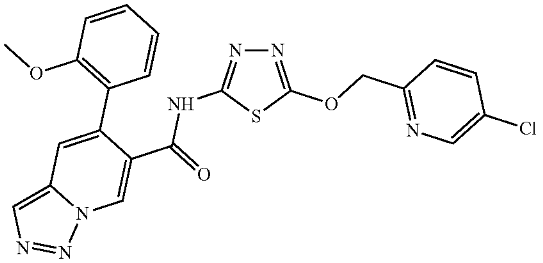 [SMILES: COc1ccccc1-c1cc2cnnn2cc1C(=O)Nc1nnc(OCc2ccc(Cl)cn2)s1] | N-[5-[(5-chloropyridin-2-yl)methoxy]-1,3,4-thiadiazol-2-yl]-5-(2-methoxyphenyl)-[1,2,3]triazolo[1,5-a]pyridine-6-carboxamide |

-continued

| Cpd # | Structure | Name |
|---|---|---|
| 224 | 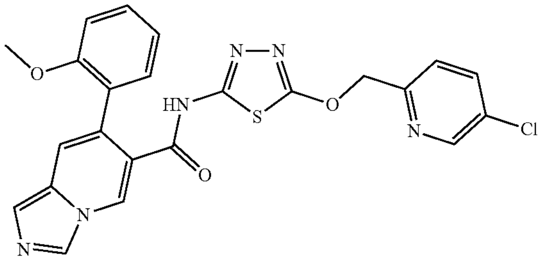 [SMILES: COc1ccccc1-c1cc2cncn2cc1C(=O)Nc1nnc(OCc2ccc(Cl)cn2)s1] | N-[5-[(5-chloropyridin-2-yl)methoxy]-1,3,4-thiadiazol-2-yl]-7-(2-methoxyphenyl)imidazo[1,5-a]pyridine-6-carboxamide |
| 225 | 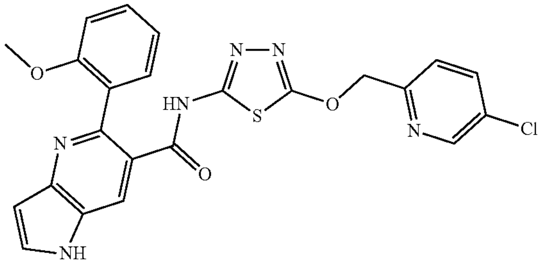 [SMILES: COc1ccccc1-c1nc2cc[nH]c2cc1C(=O)Nc1nnc(OCc2ccc(Cl)cn2)s1] | N-[5-[(5-chloropyridin-2-yl)methoxy]-1,3,4-thiadiazol-2-yl]-5-(2-methoxyphenyl)-1H-pyrrolo[3,2-b]pyridine-6-carboxamide |
| 226 | 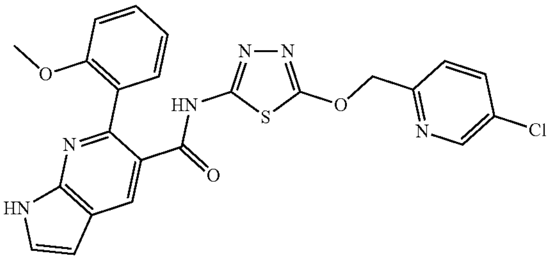 [SMILES: COc1ccccc1-c1nc2[nH]ccc2cc1C(=O)Nc1nnc(OCc2ccc(Cl)cn2)s1] | N-[5-[(5-chloropyridin-2-yl)methoxy]-1,3,4-thiadiazol-2-yl]-6-(2-methoxyphenyl)-1H-pyrrolo[2,3-b]pyridine-5-carboxamide |
| 227 | 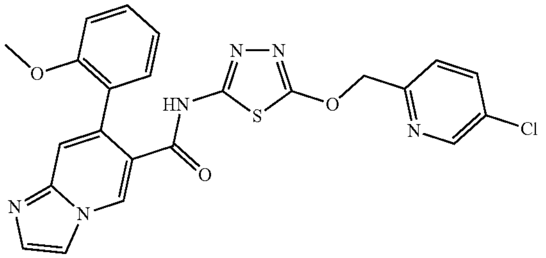 [SMILES: COc1ccccc1-c1cc2nccn2cc1C(=O)Nc1nnc(OCc2ccc(Cl)cn2)s1] | N-(5-((5-chloropyridin-2-yl)methoxy)-1,3,4-thiadiazol-2-yl)-7-(2-methoxyphenyl)imidazo[1,2-a]pyridine-6-carboxamide |
| 228 | 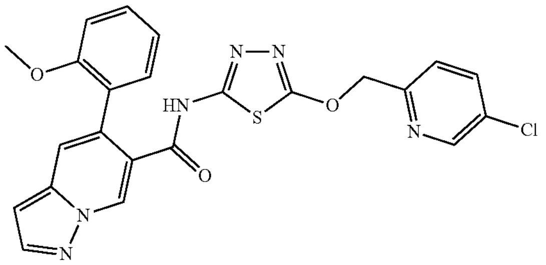 [SMILES: COc1ccccc1-c1cc2ccnn2cc1C(=O)Nc1nnc(OCc2ccc(Cl)cn2)s1] | N-[5-[(5-chloropyridin-2-yl)methoxy]-1,3,4-thiadiazol-2-yl]-5-(2-methoxyphenyl)pyrazolo[1,5-a]pyridine-6-carboxamide |
| 229 | 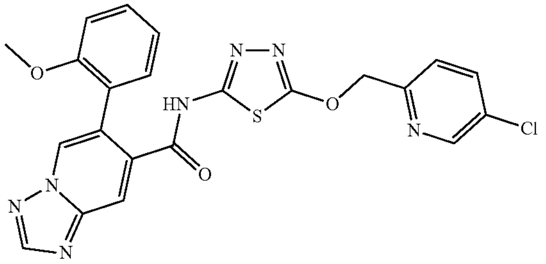 [SMILES: COc1ccccc1-c1cn2ncnc2cc1C(=O)Nc1nnc(OCc2ccc(Cl)cn2)s1] | N-(5-((5-chloropyridin-2-yl)methoxy)-1,3,4-thiadiazol-2-yl)-6-(2-tnethoxyphenyl)-[1,2,4]triazolo[1,5-a]pyridine-7-carboxamide |

-continued

| Cpd # | Structure | Name |
|---|---|---|
| 230 | 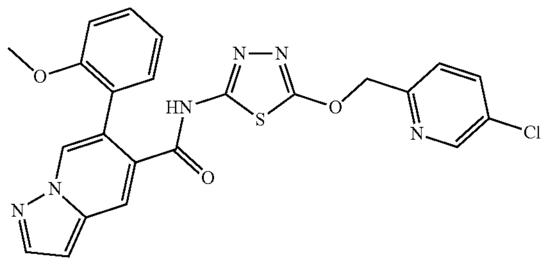 [SMILES: COc1ccccc1-c1cn2nccc2cc1C(=O)Nc1nnc(OCc2ccc(Cl)cn2)s1] | N-[5-[(5-chloropyridin-2-yl)methoxy]-1,3,4-thiadiazol-2-yl]-6-(2-methoxyphenyl)pyrazolo[1,5-a]pyridine-5-carboxamide |
| 231 | 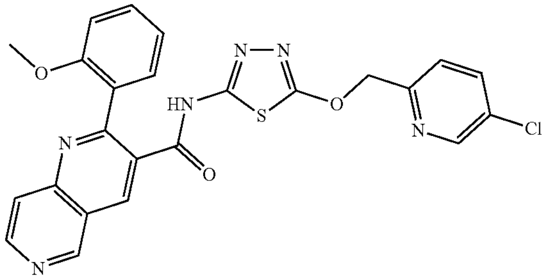 [SMILES: COc1ccccc1-c1nc2ccncc2cc1C(=O)Nc1nnc(OCc2ccc(Cl)cn2)s1] | N-(5-((5-chloropyridin-2-yl)methoxy)-1,3,4-thiadiazol-2-yl)-2-(2-methoxyphenyl)-1,6-naphthyridine-3-carboxamide |
| 232 | 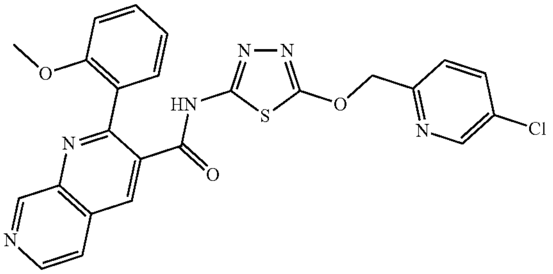 [SMILES: COc1ccccc1-c1nc2cnccc2cc1C(=O)Nc1nnc(OCc2ccc(Cl)cn2)s1] | N-(5-((5-chloropyridin-2-yl)methoxy)-1,3,4-thiadiazol-2-yl)-2-(2-methoxyphenyl)-1,7-naphthyridine-3-carboxamide |

Embodiments:

In further embodiments 1 to 16 below, the present disclosure includes:

1. In embodiment 1, provided is a compound of Formula (I), or a pharmaceutically acceptable salt thereof, where $R^1$, $R^2$, X, alk, ring A, $Ar^1$, and $Ar^2$ are as described in the Summary above. In a first subembodiment of embodiment 1, alk is methylene or ethylene. In a second subembodiment of embodiment 1, alk is $C_{1-3}$ alkylene. In a third subembodiment of embodiment 1, alk is methylmethylene.

2. In embodiment 2, the compound of embodiment 1, or a pharmaceutically acceptable salt thereof is wherein the compound has a structure of formula (Ia):

(Ia)

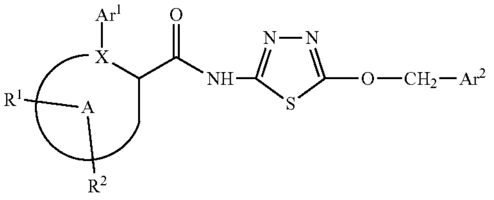

3. In embodiment 3, the compound of embodiment 1 or 2 or embodiments contained therein, or a pharmaceutically acceptable salt thereof is wherein ring A is phenyl or a five or six membered heteroaryl ring. In a first subembodiment of embodiment 3, ring A is phenyl, pyridinyl, pyridazinyl, pyrimidinyl, imidazolyl, pyrazolyl, triazolyl or imidazo[1,2-a]pyridinyl.

In a second subembodiment of embodiment 3, ring A is phenyl, pyridinyl, pyridazinyl, pyrimidinyl, imidazolyl, pyrazolyl, triazolyl, imidazo[1,2-a]pyridinyl, [1,2,3]triazolo[1,5-a]pyridinyl, imidazo[1,5-a]pyridinyl, pyrrolo[2,3-b]pyridinyl, pyrrolo[3,2-b]pyridinyl, pyrazolo[1,5-a]pyridinyl, [1,2,4]triazolo[1,5-a]pyridinyl, 1,6-naphthyridinyl, or 1,7-naphthyridinyl. In a subembodiment of embodiment 3, ring A is a nine or ten membered heteroaryl ring. In a subembodiment of embodiment 3, ring A is imidazo[1,2-a]pyridinyl, [1,2,3]triazolo[1,5-a]pyridinyl, imidazo[1,5-a]pyridinyl, pyrrolo[2,3-b]pyridinyl, pyrrolo[3,2-b]pyridinyl, pyrazolo[1,5-a]pyridinyl, [1,2,4]triazolo[1,5-a]pyridinyl, 1,6-naphthyridinyl, or 1,7-naphthyridinyl.

4. In embodiment 4, the compound of embodiment 1 or 2 or embodiments contained therein, or a pharmaceutically acceptable salt thereof is wherein ring A is a five or six membered heteroaryl ring. In a first subembodiment of embodiment 4, ring A is pyridinyl, pyridazinyl, pyrimidinyl, imidazolyl, pyrazolyl, or triazolyl. In a second subembodiment of embodiment 4, ring A is:

(i)
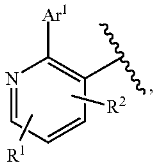
(ii)
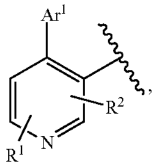
(iii)
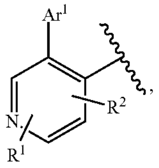
(iv)
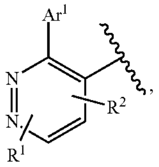
(v)
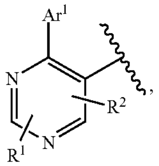
(vi)
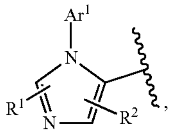
(vii)
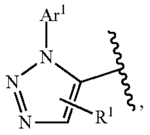
(viii)
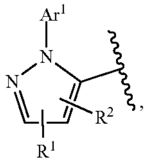
or
(ix)
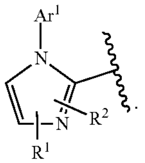
In a third subembodiment of embodiment 4, ring A is:
(i)
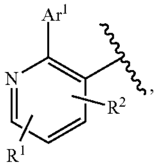
(ii)
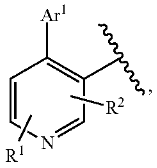
(iii)
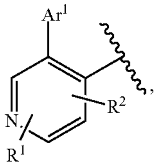
(iv)
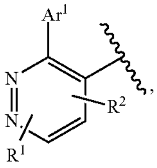
or
(v)
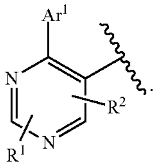
In a subembodiment of the third subembodiment, ring A is:
(i)
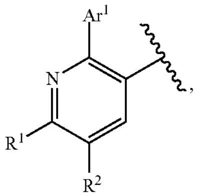
(ii)
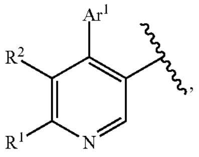
(iii)
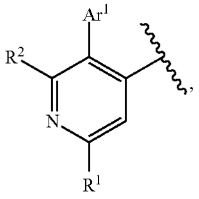

-continued (iv)

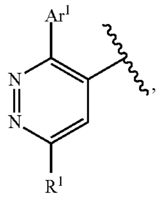

or (v)

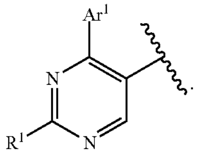

In a fourth subembodiment of embodiment 4, ring A is:

(i)

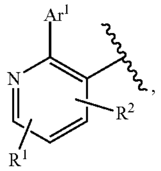

(ii)

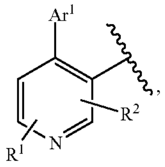

(iii)

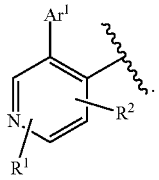

In a subembodiment of the fourth subembodiment, ring A is:

(i)

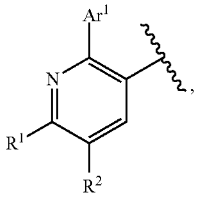

(ii)

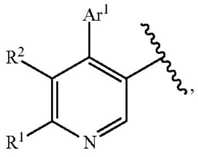

or

-continued (iii)

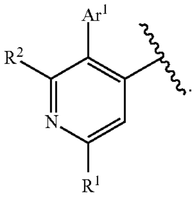

In a subembodiment of the fourth subembodiment, ring A is:

(i)

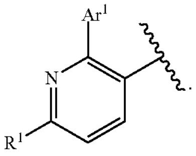

In a subembodiment of the fourth subembodiment, ring A is:

(ii)

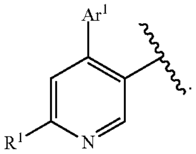

In a subembodiment of the fourth subembodiment, ring A is:

(iii)

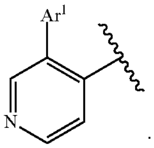

In a fifth subembodiment of embodiment 4, ring A is:

(vi)

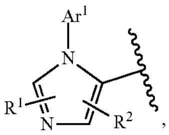

(vii)

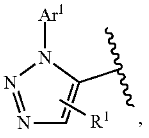

-continued (viii)

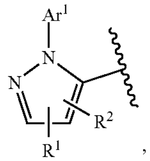

, or (ix)

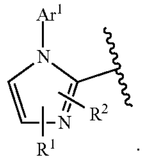

.

5. In embodiment 4, the compound of any one of embodiments 1 to 4 and subembodiment contained therein, or a pharmaceutically acceptable salt thereof is wherein ring A is phenyl.

6. In embodiment 6, the compound of any one of embodiments 1 to 5 and subembodiments contained therein, or a pharmaceutically acceptable salt thereof is wherein $Ar^1$ is heterocyclyl substituted with $R^a$, $R^b$, and/or $R^c$. In a first subembodiment of embodiment 6, $Ar^1$ is piperidinyl, piperazinyl, morpholinyl, homomorpholinyl, 2-oxopiperazinyl, 2-oxohomopiperazinyl, tetrahydropyranyl, 3,6-dihydro-2H-pyranyl, 2-oxo-1,2-dihydropyridinyl, thiomorpholinyl, or 1,1-dioxothiomorpholinyl substituted with $R^a$, $R^b$, and/or $R^c$. In a second subembodiment of embodiment 6, $Ar^1$ is piperidin-1-yl, piperazin-1-yl, morpholin-4-yl, homomorpholin-4-yl, 3-oxopiperazin-1-yl, 3-oxohomopiperazin-1-yl, 5-oxohomopiperazin-1-yl, tetrahydropyran-4-yl, 3,6-dihydro-2H-pyran-4-yl, 6-oxo-1,6-dihydropyridin-3-yl, 6-oxo-1,6-dihydropyridin-4-yl, thiomorpholin-4-yl, or 1,1-dioxothiomorpholin-4-yl substituted with $R^a$, $R^b$, and/or $R^c$. In a subembodiment of embodiment 6, $Ar^1$ is morpholin-4-yl substituted with $R^a$, $R^b$, and/or $R^c$. In a third subembodiment of embodiment 6 and first and second subembodiments contained therein, $R^a$ is hydrogen or alkyl, $R^b$ is hydrogen, alkyl, halo, haloalkyl, alkoxy, haloalkoxy, acyl, alkylsulfonyl, cyano, or hydroxy, and $R^c$ is selected from alkyl, halo, haloalkyl, alkoxy, haloalkoxy, hydroxy, hydroxyalkyl, alkoxyalkyl, aminoalkyl, heterocyclylalkyl, and aminocarbonyl. In a subembodiment of embodiment 6, $R^a$ and $R^b$, when on adjacent ring vertices, combine to form a cyclopropyl or cyclobutyl ring, and $R^c$ is hydrogen. In a subembodiment of embodiment 6, $R^a$ and $R^b$, when on adjacent ring vertices, combine to form a cyclopropyl ring, and $R^c$ is hydrogen. In a fourth subembodiment of embodiment 6 and first and second subembodiments contained therein, $Ar^1$ is substituted with $R^b$ and/or $R^c$ wherein $R^b$ is hydrogen, methyl, fluoro, cyano, methylsulfonyl, or methylcarbonyl and $R^c$ is hydrogen, methyl, ethyl, fluoro, difluoromethyl, trifluoromethyl, trifluoroethyl, methoxy, ethoxy, difluoromethoxy, trifluoromethoxy, trifluoroethoxy, hydroxy, 2-hydroxyethyl, 2-methoxyethyl, 2-aminoethyl, 2-morpholin-1-ylethyl, —$CONH_2$, methylaminocarbonyl, or dimethylaminocarbonyl. In a fifth subembodiment of embodiment 6, $Ar^1$ is morpholin-4-yl, homomorpholin-4-yl, 2-methylmorpholin-4-yl, 3-methylmorpholin-4-yl, 3R-methylmorpholin-4-yl, 3S-methylmorpholin-4-yl, 3-oxopiperazin-1-yl, 4-methyl-3-oxo-piperazin-1-yl, 2-methyl-3-oxopiperazin-1-yl, 6-methyl-3-oxopiperazin-1-yl, 5-methyl-3-oxopiperazin-1-yl, 3-oxohomopiperazin-1-yl, 5-oxohomopiperazin-1-yl, 4-dimethylaminocarbonylpiperazin-1-yl, tetrahydropyran-4-yl, 3,6-dihydro-2H-pyran-4-yl, 4-(2-hydroxyethyl)-3-oxopiperazin-1-yl, 6-oxo-1,6-dihydropyridin-4-yl, 6-oxo-1,6-dihydropyridin-3-yl, 1-methyl-6-oxo-1,6-dihydropyridin-3-yl, 4-(2-morpholin-4-ylethyl)-3-oxopiperazin-1-yl, 4-methylcarbonylpiperazin-1-yl, 4-methylsulfonylpiperazin-1-yl, 1,1-dioxothiomorpholin-4-yl, or 4,4-difluoropiperidin-1-yl.

7. In embodiment 7, the compound of any one of embodiments 1 to 6 and subembodiments contained therein, or a pharmaceutically acceptable salt thereof is wherein $Ar^1$ is bicyclic heterocyclyl substituted with $R^a$, $R^b$, and/or $R^c$. In a first subembodiment of embodiment 7, $Ar^1$ is 6-oxohexahydropyrrolo[1,2-a]pyrazin-2(1H)-yl or 2,3-dihydro-4H-benzo[b][1,4]oxazin-4-yl, each ring substituted with $R^a$, $R^b$, and/or $R^c$. In a subembodiment of embodiment 7, $Ar^1$ is selected from the group consisting of 6-oxohexahydropyrrolo[1,2-a]pyrazin-2(1H)-yl, 3-oxo-3,4-dihydro-2H-benzo[b][1,4]oxazin-8-yl, benzo[d][1,3]dioxol-4-yl, (3,4-dihydro-2H-1,4-benzoxazin-8-yl), [5H,6H,7H-pyrazolo[1,5-a]pyrimidin-4-yl] and 2,3-dihydro-4H-benzo[b][1,4]oxazin-4-yl, each ring substituted with $R^a$, $R^b$, and/or $R^c$. In a second subembodiment of embodiment 7 and first subembodiment contained therein, $R^a$ is hydrogen, $R^b$ is hydrogen, alkyl, halo, haloalkyl, alkoxy, haloalkoxy, acyl, alkylsulfonyl, cyano, or hydroxy, and $R^c$ is selected from alkyl, halo, haloalkyl, alkoxy, haloalkoxy, hydroxy, hydroxyalkyl, alkoxyalkyl, aminoalkyl, heterocyclylalkyl, and aminocarbonyl. In a third subembodiment of embodiment 7 and first and second subembodiments contained therein, $Ar^1$ is substituted with $R^b$ and/or $R^c$ wherein $R^b$ is hydrogen, methyl, fluoro, cyano, methylsulfonyl, or methylcarbonyl and $R^c$ is hydrogen, methyl, ethyl, fluoro, difluoromethyl, trifluoromethyl, trifluoroethyl, methoxy, ethoxy, difluoromethoxy, trifluoromethoxy, trifluoroethoxy, hydroxy, 2-hydroxyethyl, 2-methoxyethyl, 2-aminoethyl, 2-morpholin-1-ylethyl, —$CONH_2$, methylaminocarbonyl, or dimethylaminocarbonyl.

8. In embodiment 8, the compound of any one of embodiments 1 to 7 and subembodiments contained therein, or a pharmaceutically acceptable salt thereof is wherein $Ar^1$ is spiroheterocyclyl substituted with $R^a$, $R^b$, and/or $R^c$. In a first subembodiment of embodiment 8, $Ar^1$ is 4-oxa-7-azaspiro[2.5]octan-7-yl substituted with $R^a$, R, and/or $R^c$. In a second subembodiment of embodiment 8 and first subembodiment contained therein, $R^a$ is hydrogen, $R^b$ is hydrogen, alkyl, halo, haloalkyl, alkoxy, haloalkoxy, acyl, alkylsulfonyl, cyano, or hydroxy, and $R^c$ is selected from alkyl, halo, haloalkyl, alkoxy, haloalkoxy, hydroxy, hydroxyalkyl, alkoxyalkyl, aminoalkyl, heterocyclylalkyl, and aminocarbonyl. In a third subembodiment of embodiment 8 and first and second subembodiments contained therein, $Ar^1$ is substituted with $R^b$ and/or $R^c$ wherein $R^b$ is hydrogen, methyl, fluoro, cyano, methylsulfonyl, or methylcarbonyl and $R^c$ is hydrogen, methyl, ethyl, fluoro, difluoromethyl, trifluoromethyl, trifluoroethyl, methoxy, ethoxy, difluoromethoxy, trifluoromethoxy, trifluoroethoxy, hydroxy, 2-hydroxyethyl, 2-methoxyethyl, 2-aminoethyl, 2-morpholin-1-ylethyl, —$CONH_2$, methylaminocarbonyl, or dimethylaminocarbonyl.

9. In embodiment 9, the compound of any one of embodiments 1 to 8 and subembodiments contained therein, or a pharmaceutically acceptable salt thereof is wherein $Ar^1$ is phenyl substituted with $R^a$, $R^b$, and/or $R^c$. In a subembodiment of embodiment 9, wherein $Ar^1$ is

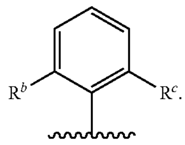

In a first subembodiment of embodiment 9, $R^a$ is hydrogen or alkyl, $R^b$ is hydrogen, alkyl, halo, haloalkyl, alkoxy, haloalkoxy, acyl, alkylsulfonyl, cyano, or hydroxy, and $R^c$ is selected from alkyl, halo, haloalkyl, alkoxy, haloalkoxy, hydroxy, hydroxyalkyl, alkoxyalkyl, aminoalkyl, heterocyclylalkyl, and aminocarbonyl. In a second subembodiment of embodiment 9, $Ar^1$ is substituted with $R^b$ and/or $R^c$ wherein $R^b$ is hydrogen, methyl, fluoro, cyano, methylsulfonyl, or methylcarbonyl and $R^c$ is hydrogen, methyl, ethyl, fluoro, difluoromethyl, trifluoromethyl, trifluoroethyl, methoxy, ethoxy, difluoromethoxy, trifluoromethoxy, trifluoroethoxy, hydroxy, 2-hydroxyethyl, 2-methoxyethyl, 2-aminoethyl, 2-morpholin-1-ylethyl, —$CONH_2$, methylaminocarbonyl, or dimethylaminocarbonyl. In a subembodiment of embodiment 9, wherein $Ar^1$ is

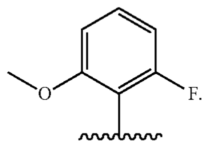 [SMILES: *c1c(F)cccc1OC]

In a third subembodiment of embodiment 9, $Ar^1$ is phenyl, 2-methoxyphenyl, 3-methoxyphenyl, 4-methoxyphenyl, 2,4-dimethoxyphenyl, 2-chlorophenyl, 2-cyanophenyl, or 2-cyclopropyl-oxyphenyl. In a third subembodiment of embodiment 9, $Ar^1$ is 2-methoxyphenyl. In a fourth subembodiment of embodiment 9, $Ar^1$ is 3-methoxyphenyl. In a fifth subembodiment of embodiment 9, $Ar^1$ is 2,4-dimethoxyphenyl.

10. In embodiment 10, the compound of any one of embodiments 1 to 9 and subembodiments contained therein, or a pharmaceutically acceptable salt thereof is wherein $Ar^1$ is heteroaryl substituted with $R^a$, $R^b$, and/or $R^c$. In a subembodiment of embodiment 10, $Ar^1$ is benzo[c][1,2,5]thiadiazolyl, benzo[d]oxazolyl, 1H-indazolyl, substituted with $R^a$, $R^b$, and/or $R^c$ where $R^a$ is hydrogen or alkyl, $R^b$ is hydrogen, alkyl, halo, haloalkyl, alkoxy, haloalkoxy, acyl, alkylsulfonyl, cyano, or hydroxy, and $R^c$ is selected from hydrogen alkyl, halo, haloalkyl, alkoxy, haloalkoxy, hydroxy, hydroxyalkyl, alkoxyalkyl, aminoalkyl, heterocyclylalkyl, and aminocarbony. In a first subembodiment of embodiment 10, $Ar^1$ is pyridinyl, pyrimidinyl, pyrazolyl, pyrrolyl, imidazolyl, or triazolyl substituted with $R^a$, $R^b$, and/or $R^c$ where $R^a$ is hydrogen or alkyl, $R^b$ is hydrogen, alkyl, halo, haloalkyl, alkoxy, haloalkoxy, acyl, alkylsulfonyl, cyano, or hydroxy, and $R^c$ is selected from alkyl, halo, haloalkyl, alkoxy, haloalkoxy, hydroxy, hydroxyalkyl, alkoxyalkyl, aminoalkyl, heterocyclylalkyl, and aminocarbonyl. In a second subembodiment of embodiment 10, $Ar^1$ is substituted with $R^b$ and/or $R^c$ wherein $R^b$ is hydrogen, methyl, fluoro, cyano, methylsulfonyl, or methylcarbonyl and $R^c$ is hydrogen, methyl, ethyl, fluoro, difluoromethyl, trifluoromethyl, trifluoroethyl, methoxy, ethoxy, difluoromethoxy, trifluoromethoxy, trifluoroethoxy, hydroxy, 2-hydroxyethyl, 2-methoxyethyl, 2-aminoethyl, 2-morpholin-1-ylethyl, —$CONH_2$, methylaminocarbonyl, or dimethylaminocarbonyl.

11. In embodiment 11, the compound of any one of embodiments 1 to 10 and subembodiments contained therein, or a pharmaceutically acceptable salt thereof is wherein $Ar^2$ is phenyl substituted with $R^d$, $R^e$ and/or $R^f$. In a first subembodiment of embodiment 11, $R^d$ is hydrogen, $R^e$ is hydrogen, alkyl, halo, haloalkyl, alkoxy, haloalkoxy, hydroxy, or cyano and $R^f$ is selected from hydrogen, alkyl, cycloalkyl, halo, haloalkyl, alkoxy, haloalkoxy, hydroxy, cyano, cyanomethyl, aminocarbonylmethyl, heteroaryl, and heterocyclyl, wherein said heteroaryl and heterocyclyl of $R^f$ are unsubstituted or substituted with one, two, or three substituents independently selected from alkyl, halo, haloalkyl, and hydroxy. In a subembodiment of embodiment 11, $R^f$ is cycloalkyl optionally substituted with cyano. In a first subembodiment of embodiment 11, $Ar^2$ is phenyl, 4-fluorophenyl, 4-chlorophenyl, 4-methoxyphenyl, 2-chloro-4-fluorophenyl, 4-cyanophenyl, 4-bromophenyl, 4-oxetan-3-ylphenyl, 4-chloro-3-methoxyphenyl, 4-cyclopropylphenyl, or 4-oxazol-2-ylphenyl. In a subembodiment of embodiment 11, $Ar^2$ is

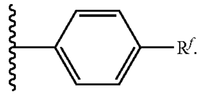

In a third subembodiment of embodiment 11, $Ar^2$ is 4-fluorophenyl. In a fourth subembodiment of embodiment 11, $Ar^2$ is 4-chlorophenyl.

12. In embodiment 12, the compound of any one of embodiments 1 to 11 and subembodiments contained therein, or a pharmaceutically acceptable salt thereof is wherein $Ar^2$ is heteroaryl substituted with $R^d$, $R^e$ and/or $R^f$. In a first subembodiment of embodiment 12, $R^d$ is hydrogen, $R^e$ is hydrogen, alkyl, halo, haloalkyl, alkoxy, haloalkoxy, hydroxy, or cyano and $R^f$ is selected from hydrogen, alkyl, cycloalkyl, halo, haloalkyl, alkoxy, haloalkoxy, hydroxy, cyano, cyanomethyl, aminocarbonylmethyl, heteroaryl, and heterocyclyl, wherein said heteroaryl and heterocyclyl of $R^f$ are unsubstituted or substituted with one, two, or three substituents independently selected from alkyl, halo, haloalkyl, and hydroxy. In a subembodiment of embodiment 12, $R^f$ is cycloalkyl optionally substituted with cyano. In a second subembodiment of embodiment 12 and first subembodiment contained therein $Ar^2$ is heteroaryl selected from pyridinyl or pyrimidinyl. In a subembodiment of embodiment 12 and subembodiments contained therein $Ar^2$ is

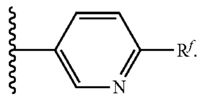

In a subembodiment of embodiment 12 and subembodiments contained therein $Ar^2$ is

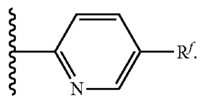

In a third subembodiment of embodiment 11, $Ar^2$ is 6-chloropyridin-3-yl, 6-bromopyridin-3-yl, or 5-chloropyazin-2-yl.

13. In embodiment 13, the compound of any one of embodiments 1 to 12 and subembodiments contained therein, or a pharmaceutically acceptable salt thereof is wherein $Ar^2$ cycloalkyl. In a first subembodiment of embodiment 13, $Ar^2$ is cycloalkyl is selected from cyclopropyl, cyclobutyl, cyclopentyl or cyclohexyl.

14. In embodiment 14, the compound of any one of embodiments 1 to 13 and subembodiments contained therein, or a pharmaceutically acceptable salt thereof is wherein $R^1$ is hydrogen, cyano, —$CONH_2$, methylaminocarbonyl, dimethylaminocarbonyl, imidazol-2-yl, methoxy, hydroxy, bromo, carboxy, or fluoro. In a subembodiment of embodiment 14, $R^1$ is hydrogen, alkyl, halo, haloalkyl, or cyano.

15. In embodiment 15, the compound of any one of embodiments 1 to 14 and subembodiments contained therein, or a pharmaceutically acceptable salt thereof is wherein $R^1$ is hydroxyalkyl, alkoxyalkyl, aminoalkyl, aminocarbonylalkyl, sulfonylalkyl, aminosulfonylalkyl, optionally substituted heteroaralkyl, or optionally substituted heterocyclylalkyl.

16. In embodiment 16, the compound of any one of embodiments 1 to 14 and subembodiments contained therein, or a pharmaceutically acceptable salt thereof is wherein $R^2$ is hydrogen, cyano, or fluoro, preferably hydrogen.

It is understood that the embodiments set forth above include combinations of one or more of embodiments and/or subembodiments listed therein. For example, the $Ar^1$ group listed in embodiment 10 and subembodiment therein, can independently combine with one or more of the embodiments 1-9, and 11-16 and/or subembodiments contained therein.

Assay

The ability of compounds of the disclosure to inhibit Polθ can be measured as described in Biological Example 1 below.

Pharmaceutical Composition

The compounds of Formula (I), or a pharmaceutically acceptable salt thereof, provided herein may be in the form of compositions suitable for administration to a subject. In general, such compositions are pharmaceutical compositions comprising a compound of Formula (I) or a pharmaceutically acceptable salt thereof and one or more pharmaceutically acceptable or physiologically acceptable excipients. In certain embodiments, the compound of Formula (I), or a pharmaceutically acceptable salt thereof is present in a therapeutically effective amount. The pharmaceutical compositions may be used in the methods disclosed herein; thus, for example, the pharmaceutical compositions can be administered ex vivo or in vivo to a subject in order to practice the therapeutic methods and uses described herein.

The pharmaceutical compositions can be formulated to be compatible with the intended method or route of administration; exemplary routes of administration are set forth herein. Furthermore, the pharmaceutical compositions may be used in combination with other therapeutically active agents or compounds as described herein in order to treat the diseases, disorders and conditions contemplated by the present disclosure.

The pharmaceutical compositions containing the active ingredient (e.g., a compound of Formula (I), a pharmaceutically acceptable salt thereof) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets, capsules, and the like. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl di-stearate may be employed. The tablets may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinyl acetate, methylcellulose, carboxymethylcellulose, protamine sulfate, or lactide and glycolide copolymers, polylactide and glycolide copolymers, or ethylene vinyl acetate copolymers in order to control delivery of an administered composition. For example, the oral agent can be entrapped in microcapsules prepared by coacervation techniques or by interfacial polymerization, by the use of hydroxymethyl cellulose or gelatin-microcapsules or poly (methyl methacrylate) microcapsules, respectively, or in a colloid drug delivery system. Colloidal dispersion systems include macromolecule complexes, nanocapsules, microspheres, microbeads, and lipid-based systems, including oil-in-water emulsions, micelles, mixed micelles, and liposomes. Methods for the preparation of the above-mentioned formulations are known in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, (hydroxypropyl)methyl cellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., poly-oxyethylene stearate), or condensation products of ethylene oxide with long chain aliphatic alcohols (e.g., for heptdecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of a compound of Formula (I), or a pharmaceutically acceptable salt thereof, and one or more pharmaceutically acceptable excipient. Suitable pharmaceutically acceptable excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time delay material such as glyceryl monostearate or glyceryl stearate alone, or in combination with a wax, may be employed. Any drug delivery apparatus may be used to deliver a compound of Formula (I), or a pharmaceutically acceptable salt thereof, including implants (e.g., implantable pumps) and catheter systems, slow injection pumps and devices, all of which are well known to the skilled artisan.

Depot injections, which are generally administered subcutaneously or intramuscularly, may also be utilized to release the compound of Formula (I), or a pharmaceutically acceptable salt thereof disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. The suspension may be formulated according to the known art using those suitable dispersing or wetting agents and suspending agents mentioned herein. The sterile injectable preparation may also be a sterile injectable solution or suspension in a non-toxic parenterally acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, NJ) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose, any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

A compound of Formula (I), or a pharmaceutically acceptable salt thereof may also be administered in the form of suppositories for rectal administration or sprays for nasal or inhalation use. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

Routes of Administration

Compounds of Formula (I), or a pharmaceutically acceptable salt thereof and compositions containing the same may be administered in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to administer the compounds of Formula (I), or a pharmaceutically acceptable salt thereof over a defined period of time. Particular embodiments of the present invention contemplate oral administration.

Combination Therapy

The present invention contemplates the use of compounds of Formula (I), or a pharmaceutically acceptable salt thereof in combination with one or more active therapeutic agents (e.g., chemotherapeutic agents) or other prophylactic or therapeutic modalities (e.g., radiation). In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the compounds of Formula (I), or a pharmaceutically acceptable salt thereof are administered or applied sequentially, e.g., where one agent is administered prior to one or more other agents. In other embodiments, the compounds of Formula (I), or a pharmaceutically acceptable salt thereof are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present disclosure.

The compounds of Formula (I), or a pharmaceutically acceptable salt thereof may be used in combination with at least one other (active) agent in any manner appropriate under the circumstances. In one embodiment, treatment with the at least one active agent and at least one compound of Formula (I), or a pharmaceutically acceptable salt thereof is maintained over a period of time. In another embodiment, treatment with the at least one active agent is reduced or discontinued (e.g., when the subject is stable), while treatment with the compound of Formula (I), or a pharmaceutically acceptable salt thereof is maintained at a constant dosing regimen. In a further embodiment, treatment with the at least one active agent is reduced or discontinued (e.g., when the subject is stable), while treatment with a compound of Formula (I), or a pharmaceutically acceptable salt thereof is reduced (e.g., lower dose, less frequent dosing or shorter treatment regimen). In yet another embodiment, treatment with the at least one active agent is reduced or discontinued (e.g., when the subject is stable), and treatment with the compound of Formula (I), or a pharmaceutically acceptable salt thereof is increased (e.g., higher dose, more frequent dosing or longer treatment regimen). In yet another embodiment, treatment with the at least one active agent is maintained and treatment with the compound of Formula (I), or a pharmaceutically acceptable salt thereof is reduced or discontinued (e.g., lower dose, less frequent dosing or shorter treatment regimen). In yet another embodiment, treatment with the at least one active agent and treatment with the compound of Formula (I), or a pharmaceutically acceptable salt thereof are reduced or discontinued (e.g., lower dose, less frequent dosing or shorter treatment regimen).

The present disclosure provides methods for treating cancer with a compound of Formula (I), or a pharmaceutically acceptable salt thereof and at least one additional therapeutic or diagnostic agent.

In some embodiments, the compound of Formula (I), or a pharmaceutically acceptable salt thereof is administered in combination with at least one additional therapeutic agent, selected from Temozolomide, Pemetrexed, Pegylated liposomal doxorubicin (Doxil), Eribulin (Halaven), Ixabepilone (Ixempra), Protein-bound paclitaxel (Abraxane), Oxaliplatin, Irinotecan, Venatoclax (bcl2 inhibitor), 5-azacytadine, Anti-CD20 therapeutics, such as Rituxan and obinutuzumab, Hormonal agents (anastrozole, exemestand, letrozole, zoladex, lupon eligard), CDK4/6 inhibitors, Palbociclib, Abemaciclib, CPI (Avelumab, Cemiplimab-rwlc, and Bevacizumab.

In certain embodiments, the present disclosure provides methods for treating cancer comprising administration of a compound of Formula (I), or a pharmaceutically acceptable salt thereof described herein in combination with a signal transduction inhibitor (STI) to achieve additive or synergistic suppression of tumor growth. As used herein, the term "signal transduction inhibitor" refers to an agent that selectively inhibits one or more steps in a signaling pathway. Examples of signal transduction inhibitors (STIs) useful in methods described herein include, but are not limited to: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); and (vi) phosphatidyl inositol kinase inhibitors. Agents involved in immunomodulation can also be used in combination with one or more compounds of Formula (I), or a pharmaceutically acceptable salt thereof described herein for the suppression of tumor growth in cancer patients.

In certain embodiments, the present disclosure provides methods for treating cancer comprising administration of a compound of Formula (I), or a pharmaceutically acceptable salt thereof described herein in combination with a chemotherapeutic agents. Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above. In a particular embodiment, compounds of the present disclosure are coadministered with a cytostatic compound selected from the group consisting of cisplatin, doxorubicin, taxol, taxotere and mitomycin C. In a particular embodiment, the cytostatic compound is doxorubicin.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, enzalutamide, apalutamide, abiraterone acetate, leuprolide, and goserelin; and pharmaceutically acceptable salts, acids or derivatives of any of the above. In certain embodiments, combination therapy comprises administration of a hormone or related hormonal agent.

The present disclosure also contemplates the use of the compounds of Formula (I), or a pharmaceutically acceptable salt thereof described herein in combination with immune checkpoint inhibitors. The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

Examples of immune checkpoint inhibitors include but are not limited to CTLA-4, PD-1, PD-L1, BTLA, TIM3, LAG3, OX40, 41BB, VISTA, CD96, TGFβ, CD73, CD39, A2AR, A2BR, IDO1, TDO2, Arginase, B7-H3, B7-H4. Cell-based modulators of anti-cancer immunity are also contemplated. Examples of such modulators include but are not limited to chimeric antigen receptor T-cells, tumor infiltrating T-cells and dendritic-cells.

The present disclosure contemplates the use of compounds of Formula (I), or a pharmaceutically acceptable salt thereof described herein in combination with inhibitors of the aforementioned immune-checkpoint receptors and ligands, for example ipilimumab, abatacept, nivolumab, pembrolizumab, atezolizumab, nivolumab, and durvalumab.

Additional treatment modalities that may be used in combination with a compound of Formula (I), or a pharmaceutically acceptable salt thereof disclosed herein include radiotherapy, a monoclonal antibody against a tumor antigen, a complex of a monoclonal antibody and toxin, a T-cell adjuvant, bone marrow transplant, or antigen presenting cells (e.g., dendritic cell therapy).

The present disclosure contemplates the use of compounds of Formula (I), or a pharmaceutically acceptable salt thereof described herein for the treatment of glioblastoma either alone or in combination with radiation and/or temozolomide (TMZ), avastin or lomustine.

The present disclosure encompasses pharmaceutically acceptable salts, acids or derivatives of any of the above.

Dosing

The compounds of Formula (I), or a pharmaceutically acceptable salt thereof provided herein may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The “median effective dose” or $ED_{50}$ of an agent is the dose or amount of an agent that produces a therapeutic response or desired effect in 50% of the population to which it is administered. Although the $ED_{50}$ is commonly used as a measure of reasonable expectance of an agent’s effect, it is not necessarily the dose that a clinician might deem appropriate taking into consideration all relevant factors. Thus, in some situations the effective amount is more than the calculated $ED_{50}$, in other situations the effective amount is less than the calculated $ED_{50}$, and in still other situations the effective amount is the same as the calculated $ED_{50}$.

In addition, an effective dose of a compound of Formula (I), or a salt thereof, as provided herein, may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In certain embodiments, the compounds of Formula (I), or a pharmaceutically acceptable salt thereof disclosed herein may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the compound of Formula (I), or a pharmaceutically acceptable salt thereof is contained in a "unit dosage form". The phrase "unit dosage form" refers to physically discrete units, each unit containing a predetermined amount of the compound of Formula (I), or a pharmaceutically acceptable salt thereof, either alone or in combination with one or more additional agents, sufficient to produce the desired effect. It will be appreciated that the parameters of a unit dosage form will depend on the particular agent and the effect to be achieved.

Kits

The present invention also contemplates kits comprising a compound of Formula (I), or a pharmaceutically acceptable salt thereof, and pharmaceutical compositions thereof. The kits are generally in the form of a physical structure housing various components, as described below, and may be utilized, for example, in practicing the methods described above.

A kit can include one or more of the compound of Formula (I), or a pharmaceutically acceptable salt thereof disclosed herein (provided in, e.g., a sterile container), which may be in the form of a pharmaceutical composition suitable for administration to a subject. The compound of Formula (I), or a pharmaceutically acceptable salt thereof can be provided in a form that is ready for use (e.g., a tablet or capsule) or in a form requiring, for example, reconstitution or dilution (e.g., a powder) prior to administration. When the compounds of Formula (I), or a pharmaceutically acceptable salt thereof are in a form that needs to be reconstituted or diluted by a user, the kit may also include diluents (e.g., sterile water), buffers, pharmaceutically acceptable excipients, and the like, packaged with or separately from the compounds of Formula (I), or a pharmaceutically acceptable salt thereof. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXAMPLES

The following examples and references (intermediates) are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: μg=microgram; μl or μL=microliter; mM=millimolar; μM=micromolar; THF=tetrahydrofuran; DIEA=diisopropylethylamine; EtOAc=ethyl acetate; NMP=N-methylpyridine, TFA=trifluoroacetic acid; DCM=dichloromethane; $Cs_2CO_3$=cesium carbonate; XPhos Pd G3=2-dicyclohexylphosphino-2',4',6'-triisopropyl-1,1'-biphenyl)[2-(2'-amino-1,1'-biphenyl)]palladium-(II) methanesulfonate; LiCl=lithium chloride; $POCl_3$=phosphoryl chloride; PE=petroleum ether; DMSO=dimethylsulfoxide; HCl=hydrochloric acid; $Na_2SO_4$=sodium sulfate; DMF=dimethylformamide; NaOH=sodium hydroxide; $K_2CO_3$=potassium carbonate; MeCN=acetonitrile; BOC=tert-butoxycarbonyl; MTBE=methyl tert-butyl ether; MeOH=methanol; $NaHCO_3$=sodium bicarbonate; $NaBH_3CN$=sodium cyanoborohydride; EtOH=ethanol; $PCl_5$=phosphorus pentachloride; $NH_4OAc$=ammonium acetate; $Et_2O$=ether; HOAc=acetic acid; $Ac_2O$=acetic anhydride; i-PrOH=isopropanol; NCS=N-chlorosuccinimide; $K_3PO_4$=potassium phosphate; Pd(dtbpf)$Cl_2$=1,1'-Bis(di-tert-butylphosphino)ferrocene]dichloro-palladium(II); $Zn(CN)_2$=Zinc cyanide; $Pd(PPh_3)_4$=tetrakis(triphenylphosphine)palladium(0); $Et_3N$=triethylamine; CuCN=copper cyanide; t-BuONO=tert-butyl nitrite; HATU=1-[bis(dimethylamino)methylene]-1H-1,2,3-triazolo[4,5-b]pyridinium 3-oxid hexafluorophosphate; DBU=1,8-diazabicyclo(5.4.0) undec-7-ene; $LiAlH_4$=lithium aluminium hydride; $NH_3$=ammonia; $H_2SO_4$=sulfuric acid; $H_2O_2$=hydrogen peroxide; EDCI=N-(3-dimethylaminopropyl)-N'-ethylcarbodiimide hydrochloride; HOBT=1-hydroxybenzotriazole hydrate; DHP=dihydropyran; TsOH=p-Toluenesulfonic acid; FA=formic acid; TCFH=N,N,N,N'-tetramethylchloroformamidinium hexafluorophosphate; NMI=N-methylimidazole; $Pd(dppf)Cl_2$=[1,1'-Bis(diphenylphosphino)ferrocene]dichloropalladium(II); $Pd(dppf)Cl_2$-DCM=[1,1'-Bis(diphenylphosphino)ferrocene]dichloropalladium(I), complex with dichloromethane.

SYNTHETIC EXAMPLES

General Procedures

General Procedure A

Amide Formation Using HATU

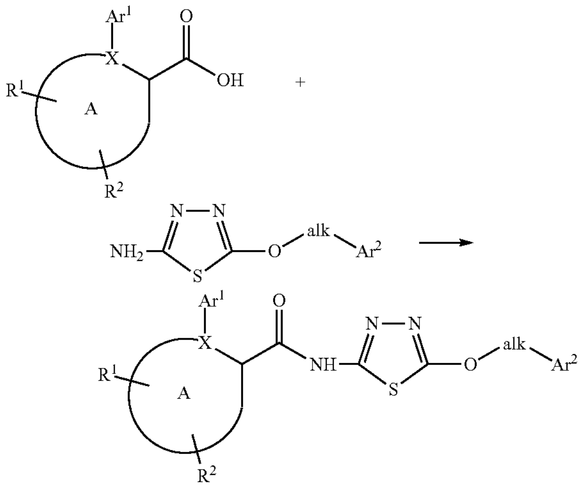

To a solution of carboxylic acid (1 eq.) and amine (1 eq.) in DMF (0.5 M) was added DIEA (2 eq.) and HATU (1.5 eq). The mixture was stirred overnight at room temperature under nitrogen.

General Procedure B

Amination of 2-chloropyridine

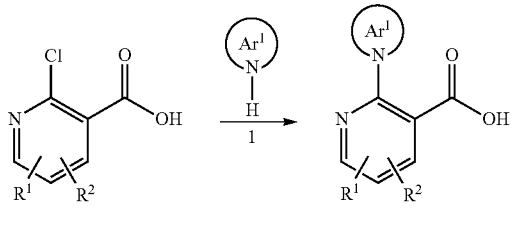

To a solution of 2-chloropyridine-3-carboxylic acid (1 eq.) in NMP (0.6 M) was added heterocyclyl of formula 1 (1 eq.) and DIEA (3 eq.) at room temperature under nitrogen. The mixture was stirred for 5 h at 80° C.

General Procedure C

Amination of 2-fluoroebenzene and 2-fluoropyridine

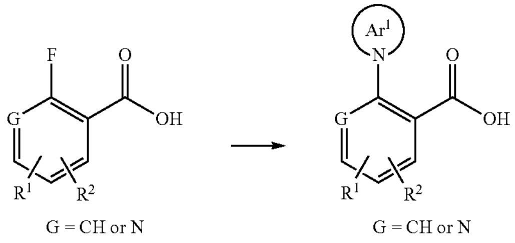

To a solution of aryl-carboxylic acid (1 eq.) in MeCN (0.7 M) was added heterocyclyl of formula 1 above (1.5 eq.) and DIEA (2 eq.) at room temperature under nitrogen. The mixture was stirred at 80° C. overnight.

General Procedure D

Amide Formation Using Propylphosphonic Anhydride

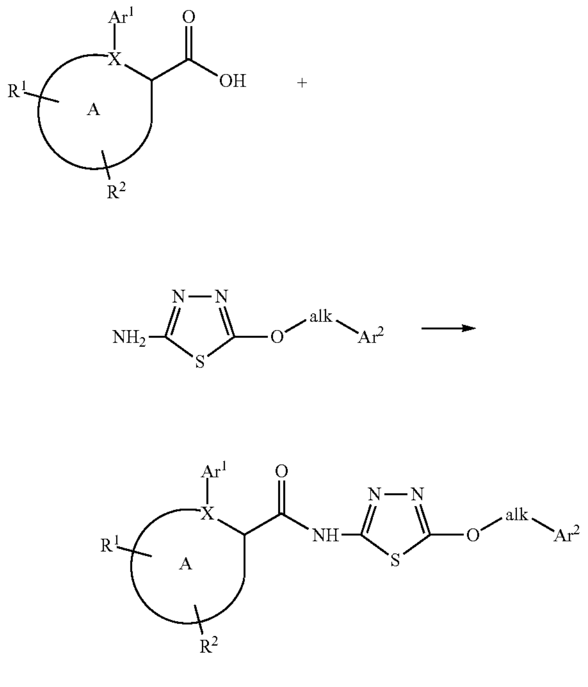

To a solution of carboxylic acid (1 eq.) and amine (1 eq.) in THF (0.5 M) was added T3P (1.5 eq.) and DIEA (2 eq.) under nitrogen. The mixture was stirred at 50° C. overnight.

General Procedure E

Arylamination Using Suzuki Coupling

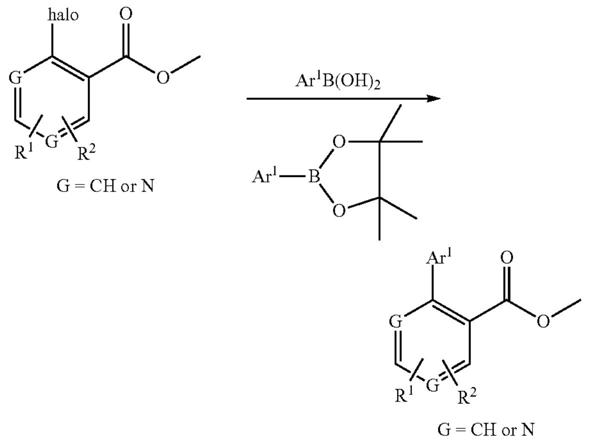

To a solution of aryl halogen (1 eq.) in dioxane:water (5:1, 0.4 M) was added boronic acid or boronic ester (1.5 eq.), $Pd(dppf)Cl_2$ (0.2 eq.) and $K_2CO_3$ (2 eq.). Mixture was stirred at 100° C. overnight.

General Procedure F

Ester Hydrolysis

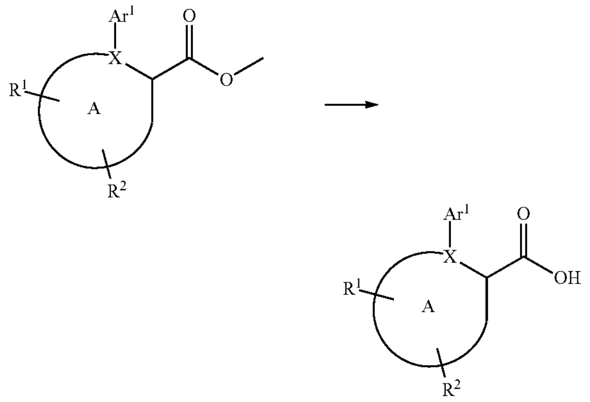

To a solution of ester (1 eq.) in methanol:water (1:1, 0.2 M) was added NaOH (5 eq). The mixture was stirred at room temperature for 1 h.

Intermediate A

Synthesis of 5-((4-fluorobenzyl)oxy)-1,3,4-thiadiazol-2-amine

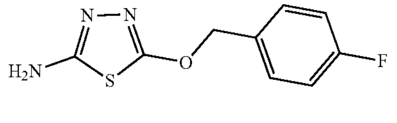 [SMILES: Nc1nnc(OCc2ccc(F)cc2)s1]

Step 1. Preparation of O-(4-fluorobenzyl) S-methyl carbonodithioate

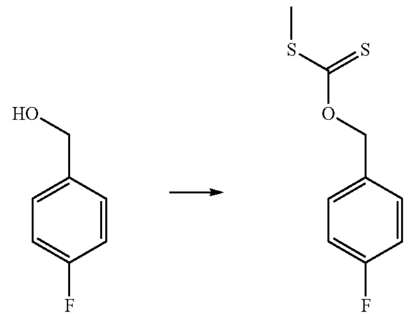

To a solution of (4-fluorophenyl)methanol (2.0 g, 15.9 mmol) in THF (20 mL) at 0° C. was added NaH (0.63 g, 15.9 mmol, 60% dispersion in oil). $CS_2$ (1.21 g, 15.9 mmol) was added dropwise over 5 min at 0° C. and the mixture was stirred for additional 30 min at 0° C. $CH_3I$ (2.25 g, 15.9 mmol) was added dropwise over 5 min at 0° C. The mixture was stirred for additional 6 h at 0° C. and then quenched with water. The aqueous layer was extracted with EtOAc and the mixture was concentrated under reduced pressure. The residue was purified by silica gel column chromatography, eluted with PE to afford the title compound as yellow oil.

Step 2. Preparation of 5-((4-fluorobenzyl)oxy)-1,3,4-thiadiazol-2-amine

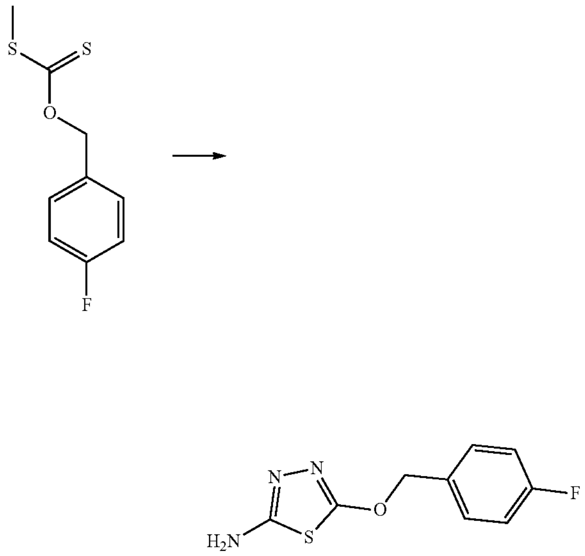

A mixture of O-(4-fluorobenzyl) S-methyl carbonodithioate (1.20 g, 5.548 mmol) and hydrazine hydrate (2.9 g, 5.8 mmol) in MeOH (12 mL) was stirred for 3 h at room temperature under nitrogen and then $Et_3N$ (1.1 g, 11.1 mmol) was added. BrCN (0.88 g, 8.308 mmol) was added and the reaction mixture was stirred for 3 h. The mixture was diluted with water and solids were collected by filtration and washed with MeOH to provide the title compound as a red solid.

Intermediate B

Synthesis of 5-((4-chlorobenzyl)oxy)-1,3,4-thiadiazol-2-amine

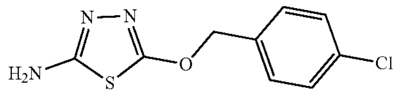 [SMILES: Nc1nnc(OCc2ccc(Cl)cc2)s1]

Step 1. Preparation of O-(4-chlorobenzyl) S-methyl carbonodithioate

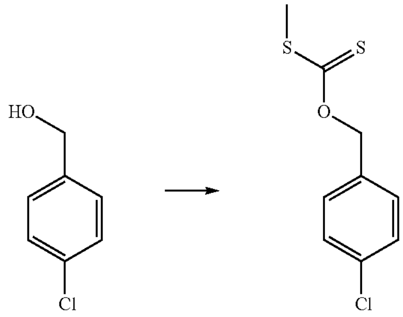

To a solution of (4-chlorophenyl)methanol (20 g, 140 mmol) in THF (200 mL) under nitrogen was added NaOH (11.2 g, 280 mmol) at 0° C. The mixture was stirred at 0° C. for 30 min and then $CS_2$ (12.8 g, 168 mmol) was added. The mixture was stirred at 0° C. for additional 30 min and then MeI (23.9 g, 168 mmol) was added. After 30 min water was added and the mixture was extracted with EtOAc. The combined organic layers were concentrated under reduce pressure to afford the title compound as a yellow oil.

Step 2. Preparation of 5-((4-chlorobenzyl)oxy)-1,3,4-thiadiazol-2-amine

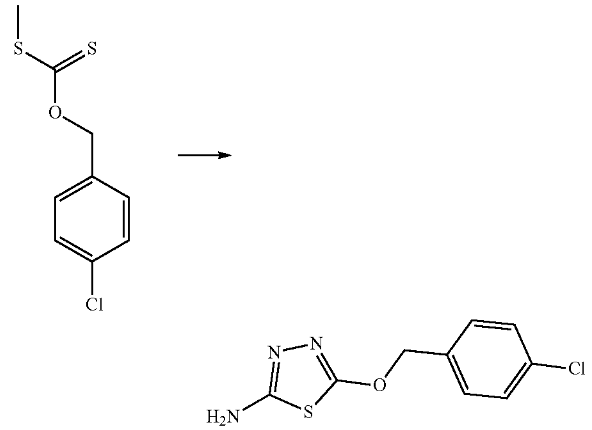

To a solution of O-(4-chlorobenzyl) S-methyl carbonodithioate (15 g, 64 mmol) in methanol (450 mL) under nitrogen was added hydrazine hydrate (3.2 g, 64 mmol) at 0° C. The mixture was stirred at 0° C. for 30 min and then concentrated under reduced pressure. The reside was diluted with MeOH and then $Et_3N$ (14 g, 139 mmol) and BrCN (8 g, 77 mmol) were added. The mixture was stirred for 30 min at room temperature. The solids were collected by filtration and washed with MeOH to afford the title compound as a yellow solid.

Additional Synthesis of Intermediate B

Synthesis of 5-((4-chlorobenzyl)oxy)-1,3,4-thiadiazol-2-amine

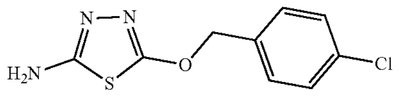 [SMILES: Nc1nnc(OCc2ccc(Cl)cc2)s1]

Step 1. Preparation of 5-((4-chlorobenzyl)oxy)-1,3,4-thiadiazol-2-amine

To a solution of NaH (42.0 g, 1.05 mol, 60.0/6 purity) in THF (750 mL) was added a solution of (4-chlorophenyl) methanol (100 g, 701 mmol) in THF (250 mL) dropwise at 5° C. The mixture was stirred at 5° C. for 4 h. Then 2-amino-5-bromo-1,3,4-thiadiazole (152 g, 842 mmol) was added to the mixture at 5° C. The mixture was stirred at 5° C. for 3 h. The mixture was poured into $H_2O$ and extracted with EtOAc (3×). The combined organic layers were dried over $Na_2SO_4$, filtered and concentrated under reduce pressure. The crude was purified by silica gel column chromatography, eluted with 9%-66% EtOAc in PE to afford a residue. The residue was diluted with MeOH and the slurry was stirred at 25° C. for 0.5 h. The solids were collected and diluted with MeOH. The slurry was stirred at 80° C. for 16 h. The solids were collected to afford the title compound (61.0 g, 18% yield) as a grey solid.

Intermediate C

Synthesis of 5-((5-chloropyridin-2-yl)methoxy-1,3,4-thiadiazol-2-amine

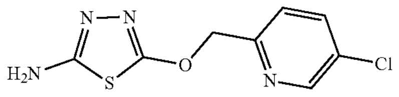

Step 1. O-((5-chloropyridin-2-yl)methyl) S-methyl carbonodithioate

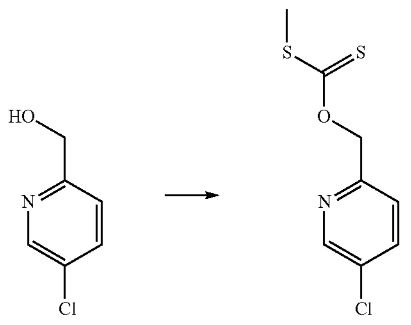

To a solution (5-chloropyridin-2-yl)methanol (3.0 g, 21 mmol) in THF (30 mL) at 0° C. was added NaOH (1.3 g, 31.5 mmol) under nitrogen. The mixture was stirred at 0° C. for 15 min. Then $CS_2$ (1.8 g, 23 mmol) was added and the mixture was stirred for 30 min at 0° C. Then MeI (3.3 g, 23 mmol) was added and the mixture was stirred for 30 min at 0° C. Then sat. $NH_4Cl$ (30 mL) was added and mixture warmed to room temperature. The aqueous layer was extracted with EtOAc (3x30 mL). The combined organic layers were concentrated under reduced pressure. The residue was purified by silica gel column chromatography, eluted with 1% EtOAc in PE to afford O-((5-chloropyridin-2-yl)methyl) S-methyl carbonodithioate as a yellow oil.

Step 2. Preparation of 5-((5-chloropyridin-2-yl)methoxy)-1,3,4-thiadiazol-2-amine

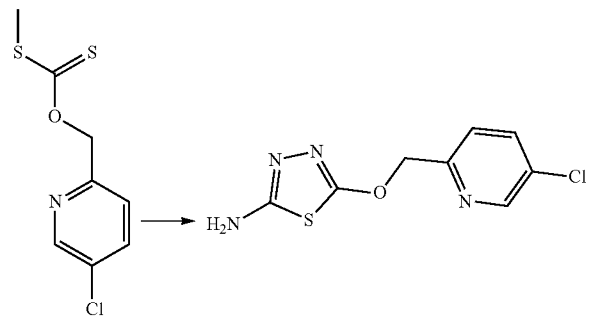

To a solution of O-((5-chloropyridin-2-yl)methyl) S-methyl carbonodithioate (1.8 g, 7.7 mmol) in MeOH (18 mL) was added hydrazine hydrate (387 mg, 7.7 mmol) under nitrogen. The mixture was stirred for 15 min at room temperature. Then BrCN (819 mg, 7.7 mmol) and $Et_3N$ (1638 mg, 15 mmol) were added. The mixture was stirred for 15 min at room temperature. A solid formed and the solid was collected by filtration. The solid was washed with MeOH (3x5 mL) to afford 5-((5-chloropyridin-2-yl)methoxy)-1,3,4-thiadiazol-2-amine as a gray solid.

Additional Synthesis of Intermediate C

Intermediate C

Synthesis of 5-((5-chloropyridin-2-yl)methoxy)-1,3,4-thiadiazol-2-amine

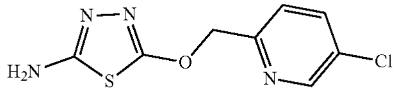

Step 1. Preparation of (5-chloropyridin-2-yl)methanol

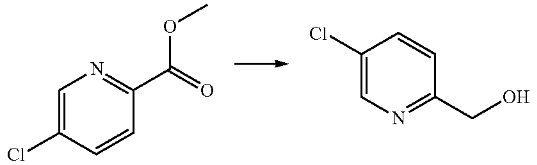

To a solution of methyl 5-chloropicolinate (95 g, 554 mmol) in MeOH (950 mL) was added $NaBH_4$ (42.0 g, 1.11 mol) in portions at 0° C. Then the mixture was stirred at rt for 2 h. The mixture was poured into $H_2O$. Mixture was cooled to 0° C. and 6 N HCl was added until pH of solution was 1~2. The temperature of the solution was 0-10° C. Then the mixture was concentrated under reduce pressure to remove MeOH. 6 N NaOH was added until the pH of the solution was 8~10. The mixture was extracted with EtOAc (3×). The combined organic layers were dried over $Na_2SO_4$, filtered and concentrated under reduce pressure to afford the title compound (158 g) as a yellow oil, which was used in the next step without further purification.

Step 2. Preparation of 5-((5-chloropyridin-2-yl)methoxy)-1,3,4-thiadiazol-2-amine

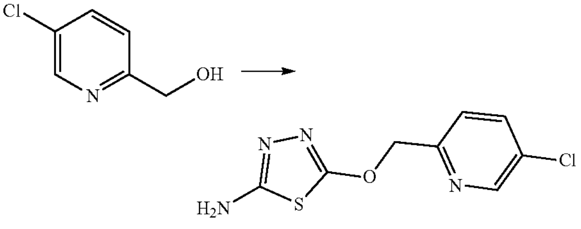

To a solution of NaH (65.7 g, 1.64 mol, 60.0% purity) in THF (1.20 L) was added a solution of (5-chloropyridin-2-yl)methanol (158 g, 1.10 mol) in THF (400 mL) at 5° C. dropwise. The mixture was stirred at 5° C. for 1 h. Then 2-amino-5-bromo-1,3,4-thiadiazole (237 g, 1.31 mol) was added in portions at 5° C. The mixture was stirred at 5° C. for 4 h. The mixture was poured into $H_2O$ and extracted with EtOAc (4×). The combined organic layer was dried over $Na_2SO_4$, filtered and concentrated under reduce pressure. The residue was diluted with MeOH and slurry was stirred at 25° C. for 0.5 h. The solids were collected and diluted with MeOH. The slurry was stirred at 80° C. for 2 h. The solids were collected to afford the title compound (57.6 g, 21% yield) as a grey solid.

Intermediate D

Synthesis of N-[5-[(4-chlorophenyl)methoxy]-1,3,4-thiadiazol-2-yl]-2-fluoropyridine-3-carboxamide

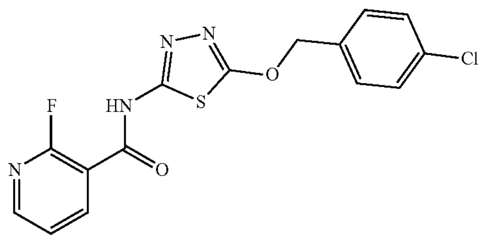 [SMILES: O=C(Nc1nnc(OCc2ccc(Cl)cc2)s1)c1cccnc1F]

To a solution of 2-fluoropyridine-3-carboxylic acid (1 g, 7.1 mmol) in $SOCl_2$ (1052 mg, 7.8 mmol) was added DMF (51.80 mg, 0.709 mmol) under nitrogen. The mixture was stirred 2 h at room temperature. The mixture was concentrated under reduced pressure. The residue was diluted with DCM (10 mL) and 5-((4-chlorobenzyl)oxy)-1,3,4-thiadiazol-2-amine (1679 mg, 6.9 mmol, Intermediate B) and $Et_3N$ (1434 mg, 14.2 mmol) were added. The mixture was stirred for 2 h at room temperature. The mixture was diluted with DCM (10 mL) and water (10 mL). The organic layer was concentrated under reduce pressure. The residue was re-crystallized from MeOH:water, 10:1 to afford N-[5-[(4-chlorophenyl)methoxy]-1,3,4-thiadiazol-2-yl]-2-fluoropyridine-3-carboxamide as an off-white solid.

Intermediate E

Synthesis of N-[5-[(4-chlorophenyl)methoxy]-1,3,4-thiadiazol-2-yl]-2-chloropyridine-3-carboxamide

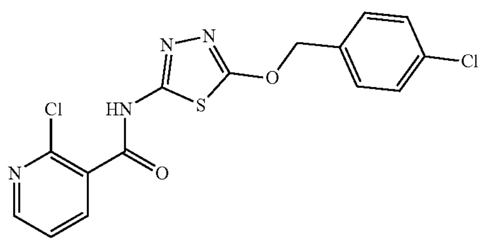 [SMILES: O=C(Nc1nnc(OCc2ccc(Cl)cc2)s1)c1cccnc1Cl]

The title compound was prepared using General Procedure D employing 2-chloropyridine-3-carboxylic acid and 5-((4-chlorobenzyl)oxy)-1,3,4-thiadiazol-2-amine (Intermediate B).

Intermediate F

N-(5-((5-chloropyridin-2-yl)methoxy)-1,3,4-thiadiazol-2-yl)-2-chloronicotinamide

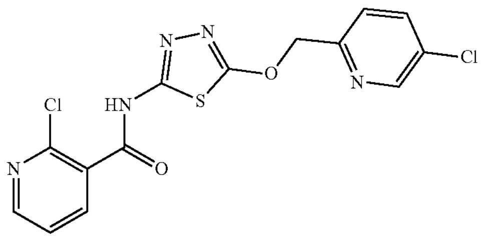 [SMILES: O=C(Nc1nnc(OCc2ccc(Cl)cn2)s1)c1cccnc1Cl]

The title compound was prepared using General Procedure D employing 2-chloropyridine-3-carboxylic acid and 5-((5-chloropyridin-2-yl)methoxy)-1,3,4-thiadiazol-2-amine (Intermediate C). The mixture was stirred at room temperature for 2 h. The mixture was diluted with ice water. The mixture was filtered and the solid was washed with ice water to give the desired product as an off-white solid.

Intermediate G

N-(5-((5-chloropyridin-2-yl)methoxy)-1,3,4-thiadiazol-2-yl)-2-fluoronicotinamide

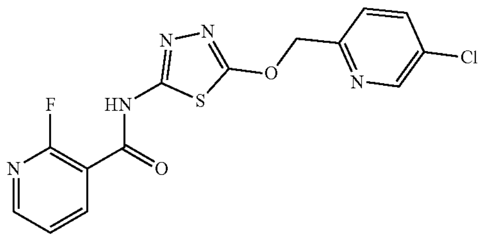 [SMILES: O=C(Nc1nnc(OCc2ccc(Cl)cn2)s1)c1cccnc1F]

The title compound was prepared using similar procedure as Intermediate F, replacing 2-chloropyridine-3-carboxylic acid with 2-fluoropyridine-3-carboxylic acid.

Intermediate H 3-(2-methoxyphenyl) pyridine-4-carboxylic acid

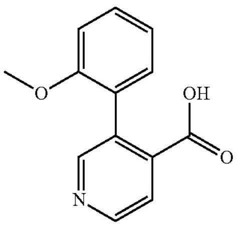

-continued

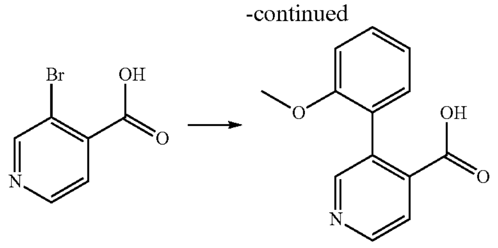

To a solution of 3-bromopyridine-4-carboxylic acid (2.0 g, 9.9 mmol) in dioxane (10 mL) and water (10 mL) was added 2-methoxyphenylboronic acid (2.3 g, 14.9 mmol), $Na_2CO_3$ (1.1 g, 9.9 mmol) and $Pd(PPh_3)_4$ (1.1 g, 0.99 mmol) at room temperature under nitrogen. The mixture was stirred at 100° C. overnight. The mixture was cooled to room temperature and diluted with water. The mixture was extracted with EtOAc (2×). The aqueous layer was acidified to pH 6 with HCl (1 M). A solid formed and mixture was filtered to afford title compound as a white solid.

Additional Synthesis of Intermediate H

Intermediate H 3-(2-methoxyphenyl) pyridine-4-carboxylic acid

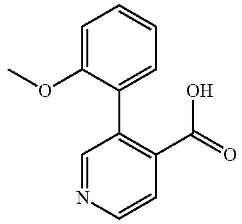 [SMILES: COc1ccccc1-c1cnccc1C(=O)O]

Step 1. Preparation of methyl 3-(2-methoxyphenyl)isonicotinate

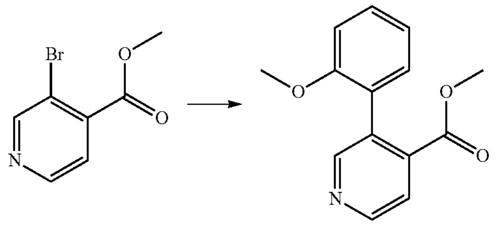

To a solution of methyl 3-bromoisonicotinate (150 g, 694 mmol) in dioxane (1.5 L) and $H_2O$ (150 mL) was added $K_2CO_3$ (95.9 g, 694 mmol), $Pd(dppf)Cl_2$ (25.4 g, 34.7 mmol) and compound 2-methoxyphenylboronic acid (126 g, 833 mmol). The mixture was stirred at 85° C. for 16 h. The mixture was poured into $H_2O$ and extracted with EtOAc (3×). The combined organic layers were dried over $Na_2SO_4$, filtered and concentrated under reduced pressure. The crude was purified by silica gel column chromatography, eluted with 9-100% EtOAc in PE to afford a residue. The residue was diluted with MTBE and the slurry was stirred at rt for 0.5 h to afford the title compound (94.0 g, 83% yield) as a white solid.

Step 2. Preparation of 3-(2-methoxyphenyl) pyridine-4-carboxylic acid

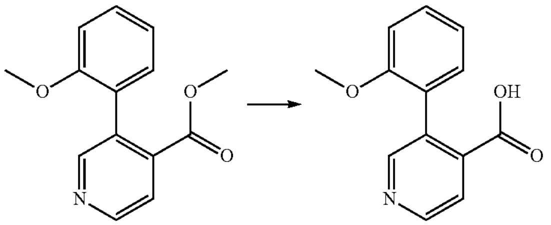

To a solution of methyl 3-(2-methoxyphenyl)isonicotinate (108 g, 444 mmol) in MeOH (648 mL) and $H_2O$ (648 mL) was added NaOH (53.2 g, 1.33 mol). The mixture was stirred at 50° C. for 2 h. The mixture was concentrated under reduced pressure. The residue was diluted with 2 N HCl until pH was 2-3. The mixture was filtered. The solid was washed with $H_2O$ (3×). The solid was dried under vacuum to afford the title compound (70.0 g, 79% yield) as a white solid, which was used to next step without further purification.

Example 1

Synthesis of N-(5-((4-fluorobenzyl)oxy)-1,3,4-thiadiazol-2-yl)-2-morpholinonicotinamide

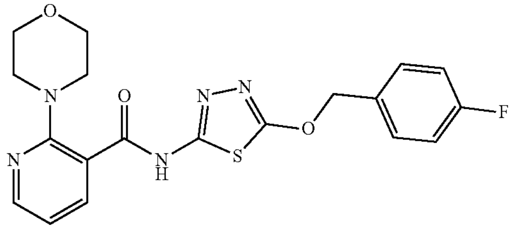 [SMILES: O=C(Nc1nnc(OCc2ccc(F)cc2)s1)c1cccnc1N1CCOCC1]

The title compound was prepared using General Procedure A employing 2-(morpholin-4-yl)pyridine-3-carboxylic acid and 5-((4-fluorobenzyl)oxy)-1,3,4-thiadiazol-2-amine (Intermediate A). The mixture was diluted with water (6 mL) and extracted with EtOAc (2×3 mL). The combined organic layers were concentrated under reduced pressure. The residue was purified by Prep-TLC (DCM:MeOH, 100:1) to afford N-(5-((4-fluorobenzyl)oxy)-1,3,4-thiadiazol-2-yl)-2-morpholinonicotinamide as a white solid. $^1H$ NMR (300 MHz; DMSO-$d_6$): δ3.21-3.24 (t, 4H), 3.65-3.68 (t, 4H), 5.49 (s, 2H), 6.98-7.02 (m, 1H), 7.22-7.30 (m, 2H), 7.57-7.61 (m, 2H), 7.90-7.93 (m, 1H), 8.35-8.37 (m, 1H), 12.87 (s, 1H). m/z 416 (M+H$^+$).

Example 2

Synthesis of N-(5-((4-chlorobenzyl)oxy)-1,3,4-thiadiazol-2-yl)-2-morpholinonicotinamide

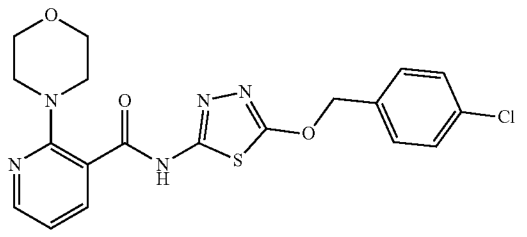 [SMILES: O=C(Nc1nnc(OCc2ccc(Cl)cc2)s1)c1cccnc1N1CCOCC1]

The title compound was prepared using General Procedure A employing 2-(morpholin-4-yl)pyridine-3-carboxylic acid and 5-((4-chlorobenzyl)oxy)-1,3,4-thiadiazol-2-amine (Intermediate B). The mixture was diluted with water and extracted with EtOAc (2×). The combined organic layers were concentrated under reduced pressure. The residue triturated with MeOH to afford N-(5-((4-chlorobenzyl)oxy)-1,3,4-thiadiazol-2-yl)-2-morpholinonicotinamide as a white solid. $^1$H NMR (300 MHz; DMSO-$d_6$): δ 3.17-3.25 (m, 4H), 3.65-3.68 (t, 4H), 5.51 (s, 2H), 6.98-7.02 (m, 1H), 7.48-7.58 (m, 4H), 7.90-7.93 (m, 1H), 8.35-8.38 (m, 1H), 12.89 (s, 1H) ppm. m/z 432 (M+H$^+$).

Example 3

Synthesis of N-[5-[(5-chloropyridin-2-yl)methoxy]-1,3,4-thiadiazol-2-yl]-2-(morpholin-4-yl)benzamide

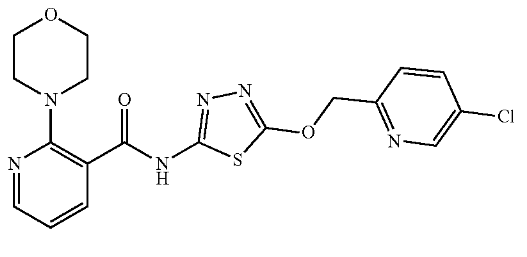 [SMILES: O=C(Nc1nnc(OCc2ccc(Cl)cn2)s1)c1cccnc1N1CCOCC1]

The title compound was prepared using General Procedure A employing 2-(morpholin-4-yl)pyridine-3-carboxylic acid and 5-((5-chloropyridin-2-yl)methoxy)-1,3,4-thiadiazol-2-amine (Intermediate C). The mixture was diluted with water (2 mL) and the mixture was extracted with EtOAc (4×2 mL). The combined organic layers were concentrated under reduced pressure. The residue was triturated with 3 mL MeOH to afford N-(5-((4-chlorobenzyl)oxy)-1,3,4-thiadiazol-2-yl)-2-morpholinonicotinamide as a white solid. $^1$H NMR (300 MHz; DMSO-$d_6$): δ 3.21-3.24 (t, 4H), 3.64-3.68 (t, 4H), 5.61 (s, 2H), 6.98-7.02 (m, 1H), 7.62-7.64 (d, 1H), 7.90-7.94 (m, 1H), 8.00-8.04 (m, 1H), 8.32-8.38 (m, 1H), 8.66-8.69 (m, 1H), 12.91 (s, 1H) ppm. m/z 433 (M+H$^+$).

Example 4

Synthesis of N-(5-((4-chlorobenzyl)oxy)-1,3,4-thiadiazol-2-yl)-1-phenyl-1H-imidazole-5-carboxamide

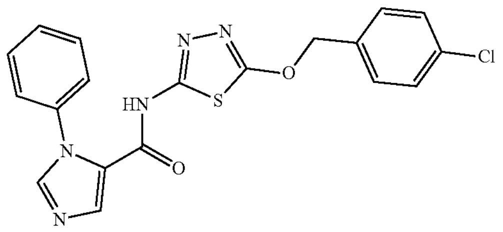 [SMILES: O=C(Nc1nnc(OCc2ccc(Cl)cc2)s1)c1cncn1-c1ccccc1]

The title compound was prepared according to General Procedure D using 1-phenyl-1H-imidazole-5-carboxylic acid and intermediate B to give N-(5-((4-chlorobenzyl)oxy)-1,3,4-thiadiazol-2-yl)-1-phenyl-1H-imidazole-5-carboxamide (20 mg, 6% yield). $^1$H NMR (400 MHz, DMSO-$d_6$) δ 12.82 (s, 1H), 8.15 (s, 1H), 8.10 (s, 1H), 7.53-7.45 (m, 7H), 7.41 (d, J=6.6 Hz, 2H), 5.46 (s, 2H) ppm. m/z 412 (M+H$^+$).

Example 5

Synthesis of (R) N-(5-((4-chlorobenzyl)oxy)-1,3,4-thiadiazol-2-yl)-2-(3-methylmorpholino)-nicotinamide and (S)—N-(5-((4-chlorobenzyl)oxy)-1,3,4-thiadiazol-2-yl)-2-(3-methylmorpholino) nicotinamide

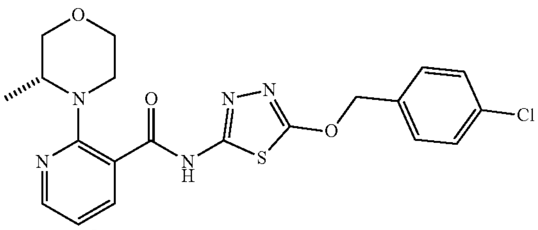

and

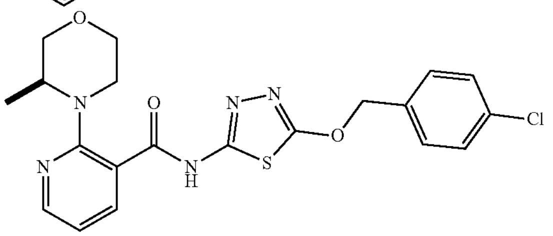

To a vial equipped with stir bar was added 2-chloro-N-(5-((4-chlorobenzyl)oxy)-1,3,4-thiadiazol-2-yl)nicotinamide Intermediate E (100 mg, 1 eq.) followed by addition of racemic 3-methylmorpholine (79 mg, 3 eq.) and THF (1.3 mL). DIPEA (0.274 mL, 6 eq.) was then added and the reaction was heated to 75° C. and allowed to stir for 8 h. Upon reaction completion, the mixture was diluted with water, and extracted with EtOAc. The combined organic extracts were washed with brine, dried over $Na_2SO_4$ and concentrated in vacuo. The crude residue was purified by column chromatography (silica gel, hexanes/ethyl acetate 0-100%) to give racemic mixture of (R) N-(5-((4-chlorobenzyl)oxy)-1,3,4-thiadiazol-2-yl)-2-(3-methylmorpholino)

nicotinamide and (S) N-(5-((4-chlorobenzyl)oxy)-1,3,4-thiadiazol-2-yl)-2-(3-methylmorpholino)nicotinamide as a racemic mixture (12 mg, 10% yield) as a white solid. $^1$H NMR (400 MHz, Chloroform-d) δ 8.55 (d, J=4.0 Hz, 1H), 8.49 (d, J=7.7 Hz, 1H), 7.44 (d, J=8.1 Hz, 2H), 7.37 (d, J=8.2 Hz, 2H), 7.32-7.25 (m, 1H), 5.49 (s, 2H), 4.04 (t, J=8.5 Hz, 3H), 3.27 (td, J=11.4, 10.6, 4.5 Hz, 1H), 3.23-3.09 (m, 2H), 2.98 (t, J=11.3 Hz, 1H), 1.23 (d, J=6.2 Hz, 3H) ppm. m/z 446 (M+H$^+$).

Example 6

Synthesis of N-(5-((4-chlorobenzyl)oxy)-1,3,4-thiadiazol-2-yl)-2-(1,4-oxazepan-4-yl)nicotinamide

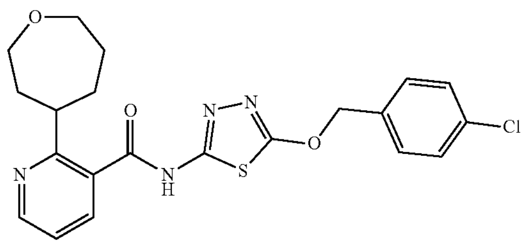 [SMILES: O=C(Nc1nnc(OCc2ccc(Cl)cc2)s1)c1cccnc1C1CCCOCC1]

Step 1. Preparation of 2-(1,4-oxazepan-4-yl)nicotinic acid

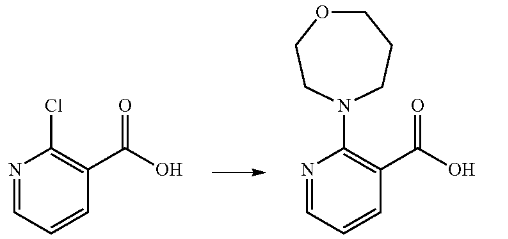 [SMILES: O=C(O)c1cccnc1Cl ; O=C(O)c1cccnc1N1CCCOCC1]

The title compound was prepared using General Procedure B employing 1, 4-oxazepane. The mixture was concentrated under reduced pressure. The residue was purified by reverse phase chromatography (column $C_{18}$ silica gel; mobile phase, with 5-100% MeCN in water). The residue was further purified using reverse phase Prep-HPLC [(XBridge Prep OBD $C_{18}$ column; gradient elution 2 to 15% ACN in (0.16% $NH_4HCO$; in water)] to afford 2-(1,4-oxazepan-4-yl)nicotinic acid as a light yellow solid.

Step 2. Preparation of N-(5-((4-chlorobenzyl)oxy)-1,3,4-thiadiazol-2-yl)-2-(1,4-oxazepan-4-yl)nicotinamide

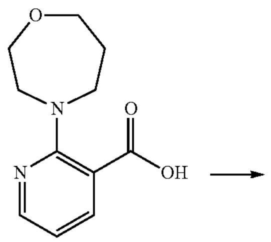

-continued

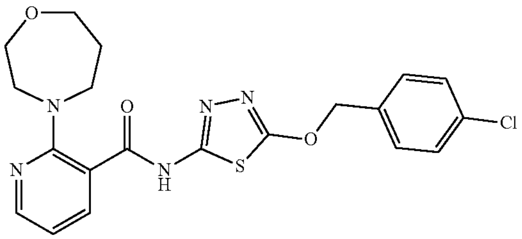

The title compound was prepared using General Procedure A employing 2-(1,4-oxazepan-4-yl)nicotinic acid and 5-((4-fluorobenzyl)oxy)-1,3,4-thiadiazol-2-amine (Intermediate A). The mixture was stirred for 2 days at room temperature. The mixture was diluted with water (5 mL). The mixture was extracted with EtOAc (3×3 mL) and the combined organic layers were concentrated under reduce pressure. The residue was purified by Prep-TLC (EtOAc: hexanes, 1:1) to afford N-(5-((4-chlorobenzyl)oxy)-1,3,4-thiadiazol-2-yl)-2-(1,4-oxazepan-4-yl)nicotinamide as a white solid. $^1$H NMR (300 MHz; DMSO-$d_6$): δ 1.80-1.90 (m, 2H), 3.46-3.52 (m, 2H), 3.53-3.60 (m, 4H), 3.73-3.74 (d, 2H), 5.49 (s, 2H), 6.73-6.77 (m, 1H), 7.48-7.56 (m, 4H), 7.75-7.78 (m, 1H), 8.22-8.24 (m, 1H), 12.82 (s, 1H) ppm. m/z 446 (M+H$^+$).

Example 7

Synthesis of (R)—N-(5-((4-chlorobenzyl)oxy)-1,3,4-thiadiazol-2-yl)-2-(2-methylmorpholino)nicotinamide and (S)—N-(5-((4-chlorobenzyl)oxy)-1,3,4-thiadiazol-2-yl)-2-(2-methylmorpholino) nicotinamide

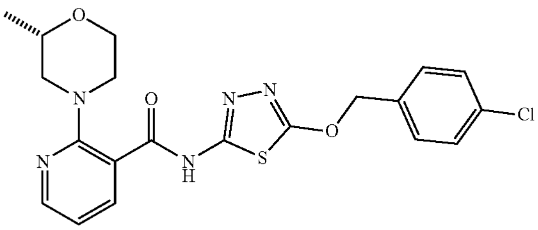

and

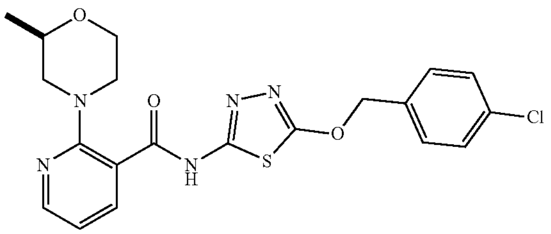

Step 1. Preparation of racemic 2-(2-methylmorpholin-4-yl)pyridine-3-carboxylic acid

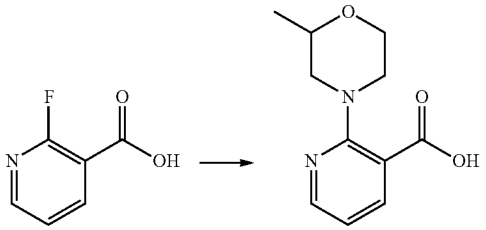 [SMILES: O=C(O)c1cccnc1F ; CC1CN(c2ncccc2C(=O)O)CCO1]

The title compound was prepared using General Procedure C employing racemic 2-methylmorpholine. The mixture was diluted with water. The aqueous layer was extracted with EtOAc (3×). The combined organic layers were concentrated under reduced pressure. The residue was purified by Prep-TLC (DCM:MeOH, 20:1) to afford racemic 2-(2-methylmorpholin-4-yl)pyridine-3-carboxylic acid as a white solid.

Step 2. Preparation of (R)—N-(5-((4-chlorobenzyl)oxy)-1,3,4-thiadiazol-2-yl)-2-(2-methylmorpholino)nicotinamide and (S)—N-(5-((4-chlorobenzyl)oxy)-1,3,4-thiadiazol-2-yl)-2-(2-methylmorpholino)nicotinamide

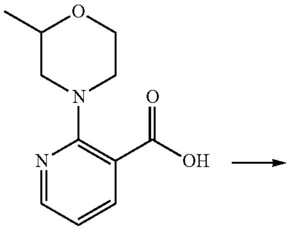

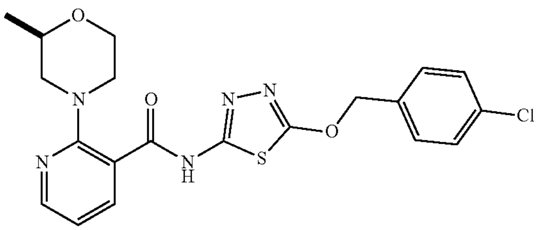

and

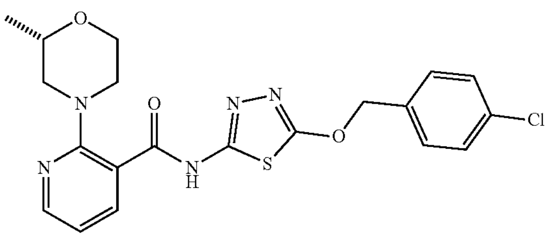

The title compounds were prepared using General Procedure A employing racemic 2-(2-methylmorpholin-4-yl)pyridine-3-carboxylic acid and 5-((4-chlorobenzyl)oxy)-1,3,4-thiadiazol-2-amine (Intermediate B). The mixture was diluted with water and extracted with EtOAc. The organic layers were concentrated under reduced pressure. The residue was purified by Prep-TLC (DCM:MeOH, 35:1) to afford as a racemic mixture of (R)—N-(5-((4-chlorobenzyl)oxy)-1,3,4-thiadiazol-2-yl)-2-(2-methylmorpholino)nicotinamide and (S)—N-(5-((4-chlorobenzyl)oxy)-1,3,4-thiadiazol-2-yl)-2-(2-methylmorpholino)nicotinamide as a white solid. $^1$H NMR (300 MHz; DMSO-$d_6$): δ 1.27 (s, 3H), 2.96-3.33 (m, 4H), 4.03-4.15 (m, 3H), 5.52 (s, 2H), 7.30-7.34 (m, 1H), 7.38-7.48 (m, 4H), 8.52-8.60 (m, 2H), 13.51 (s, 1H) ppm. m/z 446 (M+H$^+$).

Example 8

Synthesis of N-(5-((6-chloropyridin-3-yl)methoxy)-1,3,4-thiadiazol-2-yl)-2-morpholinonicotinamide

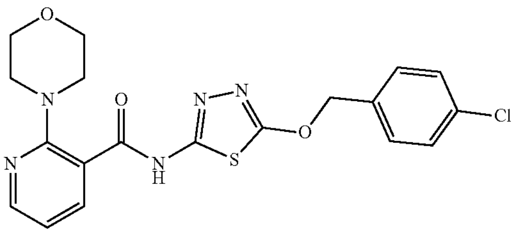 [SMILES: O=C(Nc1nnc(OCc2ccc(Cl)cc2)s1)c1cccnc1N1CCOCC1]

Step 1. Preparation of [(6-chloropyridin-3-yl)methoxy](methylsulfanyl)methanethione

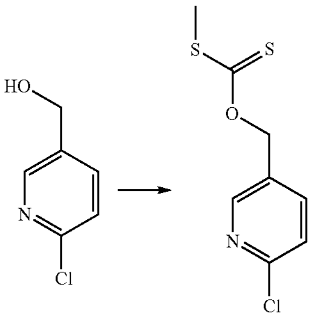

The title compound was prepared using a similar procedure as Intermediate B, Step 1 replacing (4-chlorophenyl)methanol with (6-chloropyridin-3-yl)methanol. The residue was purified by silica gel column chromatography, eluted with 1% EtOAc in PE to afford [(6-chloropyridin-3-yl)methoxy](methylsulfanyl)methanethione as yellow oil.

Step 2. Preparation of 5-[(6-chloropyridin-3-yl) methoxy]-1,3,4-thiadiazol-2-amine

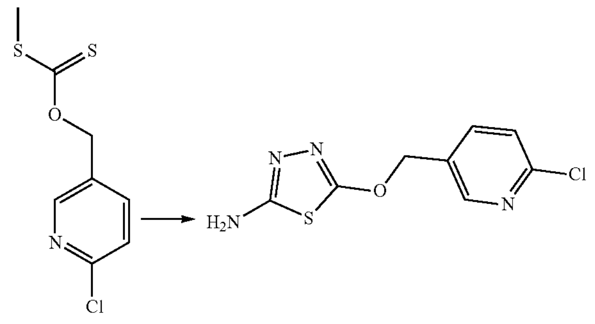

The title compound was prepared using a similar procedure as Intermediate B, Step 2 replacing O-(4-chlorobenzyl) S-methyl carbonodithioate with [(6-chloropyridin-3-yl) methoxy]-(methylsulfanyl)methanethione. The mixture was concentrated under reduce pressure. The residue with triturated with MeOH to afford 5-[(6-chloropyridin-3-yl) methoxy]-1,3,4-thiadiazol-2-amine as a white solid.

Step 3. Preparation of N-(5-((6-chloropyridin-3-yl) methoxy)-1,3,4-thiadiazol-2-yl)-2-morpholinonicotinamide

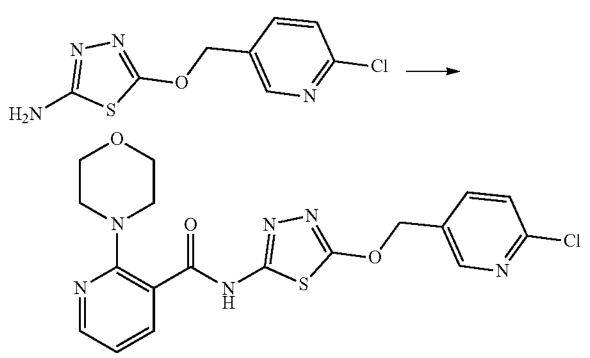

The title compound was prepared using General Procedure A employing 5-[(6-chloropyridin-3-yl)methoxy]-1,3,4-thiadiazol-2-amine and 2-(morpholin-4-yl)pyridine-3-carboxylic acid. The mixture was diluted with water. The aqueous layer was extracted with EtOAc (3×). The combined organic layers were concentrated under reduce pressure. The residue was purified by Prep-TLC (DCM:MeOH, 35:1). The residue was further purified by Prep-HPLC [column, XBridge Prep OBD $C_{18}$; mobile phase 15-25% ACN in (0.05% $NH_4OH$ in water)] to afford N-(5-((6-chloropyridin-3-yl)methoxy)-1,3,4-thiadiazol-2-yl)-2-morpholinonicotinamide as a white solid. $^1H$ NMR (400 MHz; DMSO-$d_6$): δ 3.23 (t, 4H), 3.66 (t, 4H), 5.56 (s, 2H), 6.97-7.01 (m, 1H), 7.59-7.62 (m, 1H), 7.90-7.92 (m, 1H), 8.03-8.06 (m, 1H), 8.35-8.36 (m, 1H), 8.59 (d, 1H), 12.90 (s, 1H) ppm. m/z 433 ($M+H^+$).

Example 9

Synthesis of (R)—N-(5-((4-chlorobenzyl)oxy)-1,3,4-thiadiazol-2-yl)-2-(3-methylmorpholino)nicotinamide

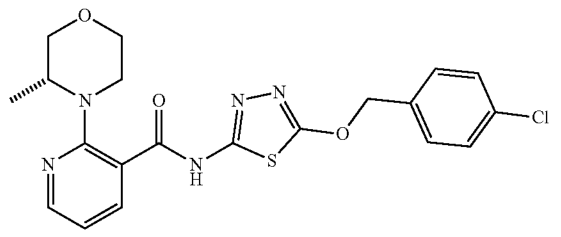 [SMILES: C[C@@H]1COCCN1c1ncccc1C(=O)Nc1nnc(OCc2ccc(Cl)cc2)s1]

To a vial equipped with stir bar was added 2-chloro-N-(5-((4-chlorobenzyl)oxy)-1,3,4-thiadiazol-2-yl)nicotinamide Intermediate E (200 mg, 1 eq.) followed by addition of (R)-3-methylmorpholine (159 mg, 3 eq.) and THF (2.6 mL). DIPEA (0.548 mL, 6 eq.) was then added and the reaction was heated to 75° C. and allowed to stir for 8 h. Upon reaction completion, the mixture was diluted with water and extracted with EtOAc. The combined organic extracts were washed with brine, dried over $Na_2SO_4$ and concentrated in vacuo. The crude residue was purified by column chromatography (silica gel, hexanes/ethyl acetate 0-100%) to give the title compound (28 mg, 12% yield) as a white solid. $^1H$ NMR (400 MHz, Chloroform-d) δ 8.55 (d, J=4.8 Hz, 1H), 8.50 (d, J=7.7 Hz, 1H), 7.44 (d, J=7.6 Hz, 2H), 7.38 (d, J=8.2 Hz, 2H), 7.32-7.24 (m, 1H), 5.49 (s, 2H), 4.08-4.00 (m, 3H), 3.28 (td, J=11.6, 4.3 Hz, 1H), 3.16 (dd, J=23.0, 12.2 Hz, 2H), 2.98 (t, J=11.2 Hz, 1H), 1.23 (d, J=6.1 Hz, 3H) ppm. m/z 446 ($M+H^+$).

Example 10

Synthesis of (S)—N-(5-((4-chlorobenzyl)oxy)-1,3,4-thiadiazol-2-yl)-2-(3-methyl-morpholino)nicotinamide

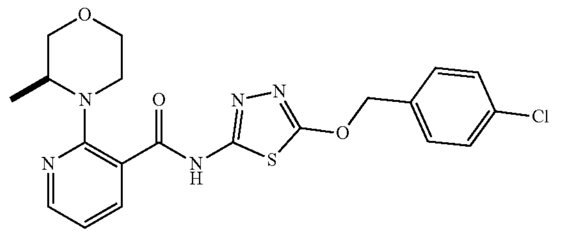 [SMILES: C[C@H]1COCCN1c1ncccc1C(=O)Nc1nnc(OCc2ccc(Cl)cc2)s1]

Proceeding analogously as described in Example 9 above but substituting (R)-3-methylmorpholine with (S)-3-methylmorpholine gave the title compound as a white solid. LC/MS [M+H]+ 445.92. 1H NMR (400 MHz, Chloroform-d) δ 8.55 (d, J=4.7 Hz, 1H), 8.49 (d, J=7.8 Hz, 1H), 7.43 (d, J=8.0 Hz, 2H), 7.37 (d, J=8.0 Hz, 2H), 7.32-7.24 (m, 1H), 5.49 (s, 2H), 4.11-3.93 (m, 3H), 3.26 (td, J=11.4, 10.8, 4.6 Hz, 1H), 3.22-3.07 (m, 2H), 2.97 (t, J=11.3 Hz, 1H), 1.23 (d, J=6.0 Hz, 3H) ppm. m/z 446 ($M+H^+$).

Example 11

Synthesis of N-(5-((4-chlorobenzyl)oxy)-1,3,4-thiadiazol-2-yl)-2-(1H-tetrazol-1-yl)nicotinamide

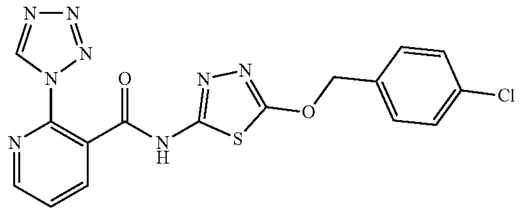 [SMILES: O=C(Nc1nnc(OCc2ccc(Cl)cc2)s1)c1cccnc1-n1cnnn1]

Step 1. Preparation of methyl 2-(H-tetrazol-1-yl)nicotinate

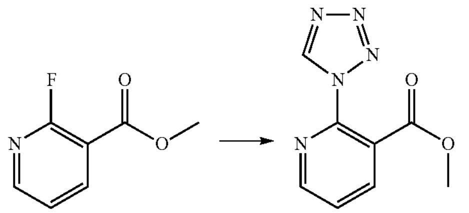

To a solution of tetrazole (0.68 g, 9.7 mmol) in NMP (15 mL) at 0° C. was added NaH (0.58 g, 14.5 mmol, 60% dispersion in oil) in portions under nitrogen. The mixture was stirred at 0° C. for 30 min then methyl 2-fluoropyridine-3-carboxylate (1.50 g, 9.7 mmol) was added. The mixture was heated to 80° C. and stirred at 80° C. for overnight. The mixture was cooled to room temperature and quenched with sat. $NH_4Cl$. The mixture was extracted with EtOAc (3×) and the combined organic layers were concentrated under reduce pressure. The residue was purified by reverse phase chromatography (column, $C_{18}$ silica gel; mobile phase, with 5-100% MeCN in water) to afford methyl 2-(1H-tetrazol-1-yl)nicotinate as white solid.

Step 2. Preparation of 2-(1H-tetrazol-1-yl)nicotinic acid

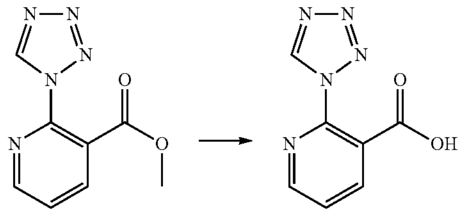

To a solution of methyl 2-(1H-tetrazol-1-yl)nicotinate (620 mg, 2.9 mmol) in MeOH (30 mL) was added a solution of NaOH (234 mg, 5.8 mmol) in $H_2O$ (6 mL). The mixture was stirred at room temperature for 4 h. HCl (1 M) was added until the pH of the mixture was 5. The mixture was concentrated under reduced pressure. The residue was purified by reverse phase chromatography (column, $C_{18}$ silica gel; mobile phase, with 5-100% MeCN in water) to afford 2-(1H-tetrazol-1-yl)nicotinic acid as a white solid.

Step 3. Preparation of N-(5-((4-chlorobenzyl)oxy)-1,3,4-thiadiazol-2-yl)-2-(1H-tetrazol-1-yl)nicotinamide

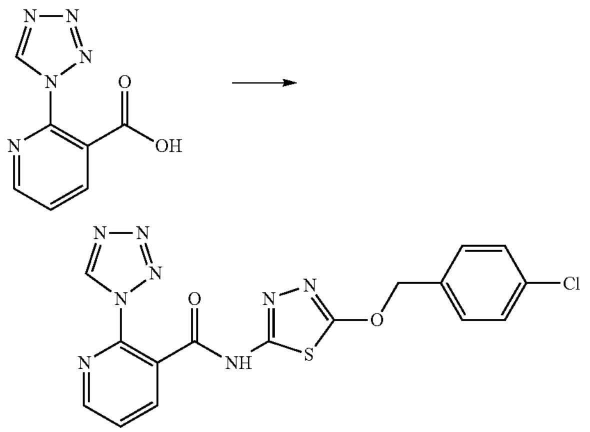

To a solution of 2-(1H-tetrazol-1-yl)nicotinic acid (200 mg, 1.0 mmol) in DMF (5 mL) was added 5-((4-chlorobenzyl)oxy)-1,3,4-thiadiazol-2-amine (253 mg, 1.0 mmol, Intermediate B), EDCI (301 mg, 1.6 mmol) and HOBT (212 mg, 1.6 mmol). The mixture was stirred at 50° C. overnight. The mixture was diluted with sat. NaCl (20 mL) and extracted with EtOAc (3×5 mL). The combined organic layers were concentrated under reduce pressure. The residue was re-crystallization from DCM:MeOH, 30:1 to afford N-(5-((4-chlorobenzyl)oxy)-1,3,4-thiadiazol-2-yl)-2-(1H-tetrazol-1-yl)nicotinamide as a white solid. $^1H$ NMR (300 MHz; DMSO-$d_6$): δ 5.50 (s, 2H), 7.47-7.56 (m, 4H), 7.82-7.93 (m, 1H), 8.39-8.49 (m, 1H), 8.83-8.88 (m, 1H), 10.21 (s, 1H), 13.05 (s, 1H) ppm. m/z 415 ($M+H^+$).

Example 12

Synthesis of N-(5-((4-chlorobenzyl)oxy)-1,3,4-thiadiazol-2-yl)-1-(4-methoxyphenyl)-1H-imidazole-5-carboxamide

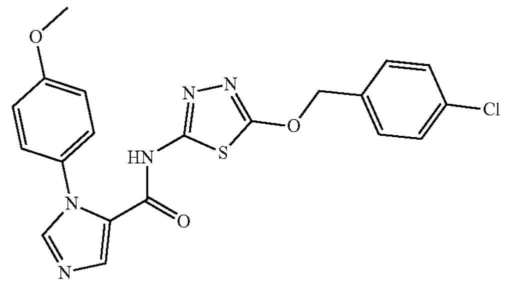 [SMILES: COc1ccc(-n2cncc2C(=O)Nc2nnc(OCc3ccc(Cl)cc3)s2)cc1]

Step 1. Preparation of ethyl 1-(4-methoxyphenyl)-1H-imidazole-5-carboxylate

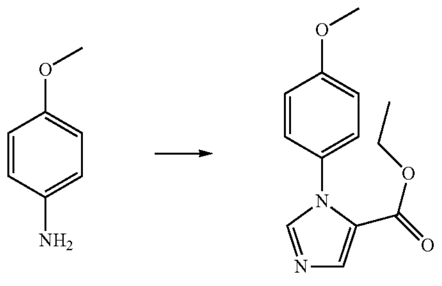

To a solution of p-Anisidine (3.0 g, 24.4 mmol) and ethyl glyoxylate (5.0 g, 24.4 mmol, 50% in toluene) in toluene (30 mL) under nitrogen was added sodium sulfate (17.3 g, 122 mmol). The mixture was stirred for 1 h at 120° C. The mixture was filtered and the filtration was concentrated under reduce pressure. The mixture was diluted with EtOH (30 mL) and purged with nitrogen. Then $K_2CO_3$ (2.2 g, 16.2 mmol) and p-toluenesulfonylmethyl isocyanide (2.4 g, 12.2 mmol) were added. The mixture was stirred at 50° C. for 4 h. The mixture was cooled to room temperature and quenched with water (30 mL). The mixture was extracted with EtOAc (6×30 mL). The combined organic layers were concentrated under reduced pressure. The residue was purified by silica gel column chromatography, eluted with 2% MeOH in DCM to afford ethyl 1-(4-methoxyphenyl)-1H-imidazole-5-carboxylate as a yellow solid.

Step 2. Preparation of 3-(4-methoxyphenyl)imidazole-4-carboxylic acid

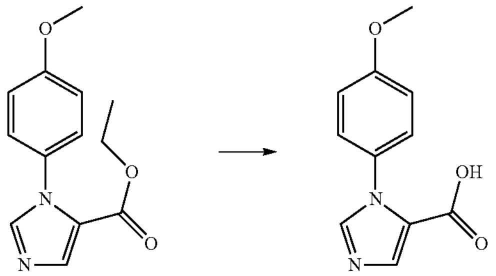 [SMILES: CCOC(=O)c1cncn1-c1ccc(OC)cc1 ; COc1ccc(-n2cncc2C(=O)O)cc1]

To a solution of ethyl 3-(4-methoxyphenyl)imidazole-4-carboxylate (400 mg, 1.6 mmol) in THF (4 mL) and water (4 mL) was added NaOH (130 mg, 3.2 mmol). The mixture was stirred at room temperature for 2 h. The mixture was diluted with water (15 mL). The mixture was acidified to pH 6 with HOAc. The mixture was extracted with EtOAc (2×5 mL). The combined organic layers were dried over $Na_2SO_4$ and concentrated under reduced pressure to afford 3-(4-methoxyphenyl)imidazole-4-carboxylic acid as a white solid.

Step 3. Preparation of N-(5-((4-chlorobenzyl)oxy)-1,3,4-thiadiazol-2-yl)-1-(4-methoxyphenyl)-1H-imidazole-5-carboxamide

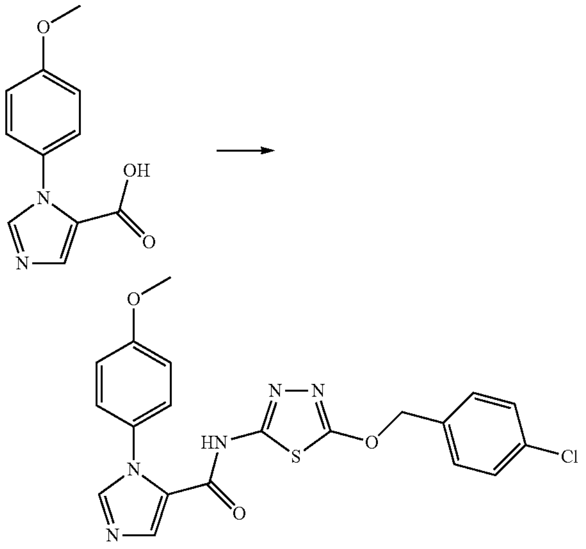

The title compound was prepared using General Procedure D employing 3-(4-methoxyphenyl)imidazole-4-carboxylic acid and 5-((4-chlorobenzyl)oxy)-1,3,4-thiadiazol-2-amine (Intermediate B). The mixture was cooled to room temperature and quenched with water. The aqueous layer was extracted with EtOAc (2×). The combining organic layer were concentrated under reduce pressure and the residue was triturated with MeOH to afford N-(5-((4-chlorobenzyl)oxy)-1,3,4-thiadiazol-2-yl)-1-(4-methoxyphenyl)-1H-imidazole-5-carboxamide as a brown solid. $^1H$ NMR (300 MHz; DMSO-$d_6$): δ 3.81 (s, 3H), 5.46 (s, 2H), 7.00-7.03 (m, 2H), 7.27-7.34 (m, 2H), 7.45-7.53 (m, 4H), 8.04-8.16 (m, 2H), 12.63-12.80 (br s, 1H) ppm. m/z 442 $(M+H^+)$.

Example 13

Synthesis of N-(5-((4-chlorobenzyl)oxy)-1,3,4-thiadiazol-2-yl)-4-morpholinopyrimidine-5-carboxamide Step 1. Preparation of methyl 2-chloro-4-(morpholin-4-yl)pyrimidine-5-carboxylate

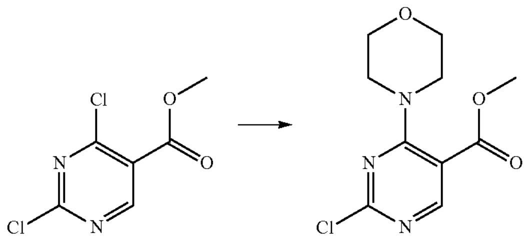 [SMILES: COC(=O)c1cnc(Cl)nc1Cl ; COC(=O)c1cnc(Cl)nc1N1CCOCC1]

To a solution of methyl 2,4-dichloropyrimidine-5-carboxylate (1.0 g, 4.8 mmol) in NMP (10 mL) at 0° C. was added DIEA (1.25 g, 9.7 mmol) under nitrogen. Then morpholine (0.42 g, 4.8 mmol) was added in portions. The mixture was stirred at 0° C. for 3 h. The mixture was diluted with EtOAc (10 mL) washed with water (3×10 mL). The aqueous layer was extracted with EtOAc (2×10 mL). The combined organic layers were concentrated under reduce pressure. The residue was purified by Prep-TLC (PE:EtOAc, 2:1) to afford methyl 2-chloro-4-(morpholin-4-yl)pyrimidine-5-carboxylate as a yellow solid.

Step 2. Preparation of 4-(morpholin-4-yl)pyrimidine-5-carboxylic acid

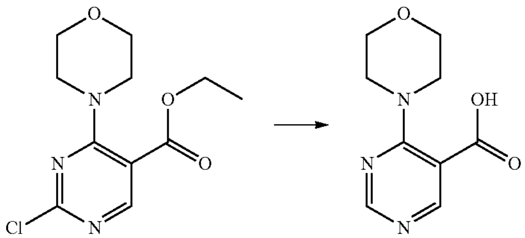 [SMILES: CCOC(=O)c1cnc(Cl)nc1N1CCOCC1 ; O=C(O)c1cncnc1N1CCOCC1]

To a solution of methyl 2-chloro-4-(morpholin-4-yl)pyrimidine-5-carboxylate (400 mg, 1.6 mmol) in MeOH was added 10% Pd/C (40 mg) and NaOH (311 mg, 7.8 mmol) and water (4 mL). The mixture was stirred at room temperature for 3 h under the of $H_2$ (g). The mixture was filtered through celite and the filtrate was concentrated under reduced pressure to afford 4-(morpholin-4-yl)pyrimidine-5-carboxylic acid as a white solid.

Step 3. Preparation of N-(5-((4-chlorobenzyl)oxy)-1,3,4-thiadiazol-2-yl)-4-morpholinopyrimidine-5-carboxamide

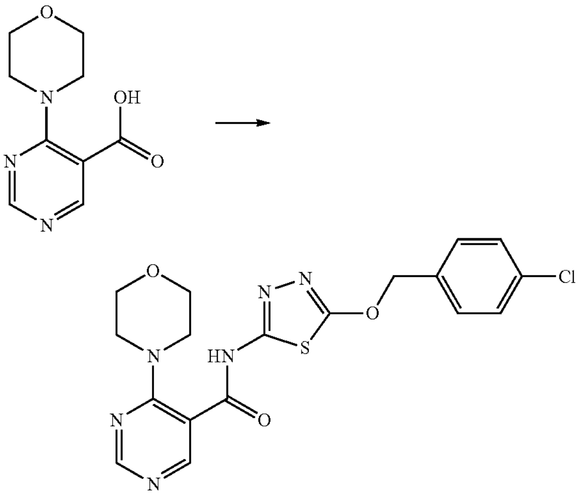

The title compound was prepared using General Procedure D employing 5-((4-chlorobenzyl)oxy)-1,3,4-thiadiazol-2-amine (Intermediate B) and 4-(morpholin-4-yl)pyrimidine-5-carboxylic acid. The mixture was cooled to room temperature and diluted with EtOAc. The mixture was washed with water (3×). The aqueous layer was extracted with EtOAc. The organic layer was concentrated under reduce pressure and the residue was purified by Prep-TLC (DCM:MeOH, 50:1) to afford N-(5-((4-chlorobenzyl)oxy)-1,3,4-thiadiazol-2-yl)-4-morpholinopyrimidine-5-carboxamide as a white solid. $^1$H NMR (300 MHz; DMSO-$d_6$): δ 3.48-3.50 (m, 4H), 3.61-3.64 (m, 4H), 5.51 (s, 2H), 7.48-7.51 (m, 2H), 7.54-7.56 (m, 2H), 8.47 (s, 1H), 8.61 (s, 1H), 13.01 (s, 1H) ppm. m/z 433 ($M+H^+$).

Example 14

Synthesis of N-(5-((4-chlorobenzyl)oxy)-1,3,4-thiadiazol-2-yl)-6-cyano-2-morpholinonicotinamide

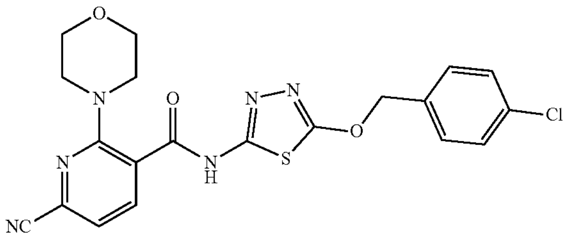 [SMILES: N#Cc1ccc(C(=O)Nc2nnc(OCc3ccc(Cl)cc3)s2)c(N2CCOCC2)n1]

Step 1. Preparation of 6-bromo-2-morpholinonicotinic acid

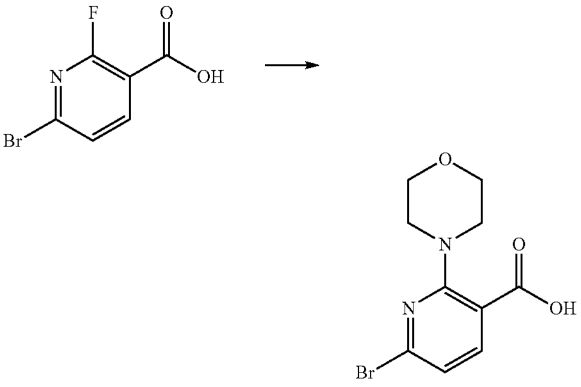

To a solution of 6-bromo-2-fluoropyridine-3-carboxylic acid (5.0 g, 22.7 mmol) in MeCN (50 mL) was added morpholine (4.0 g, 45.5 mmol), and DIEA (5.9 g, 45.4 mmol) under nitrogen. The mixture was stirred at 50° C. overnight. The mixture was concentrated under reduce pressure and the residue was purified by reverse flash chromatography (column, $C_{18}$ silica gel; mobile phase, 5-40% MeCN in water to afford 6-bromo-2-morpholinonicotinic acid as a brown solid.

Step 2. Preparation of 6-cyano-2-morpholinonicotinic acid

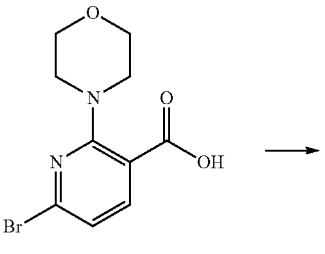

-continued

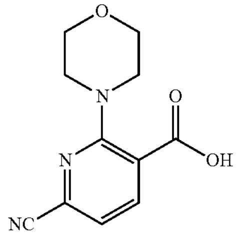

To a solution of 6-bromo-2-morpholinonicotinic acid (3.2 g, 11.1 mmol) in DMSO (32 mL) was added CuCN (5.0 g, 55.7 mmol) under nitrogen. The mixture was stirred at 120° C. for 4 h. Then the mixture was cooled to room temperature and diluted with EtOAc (20 mL). The mixture was filtered and the filtrate was concentrated under reduce pressure. The residue was purified by reverse flash chromatography (column, $C_{18}$ silica gel; mobile phase, 5-30% MeCN) in water to afford 6-cyano-2-morpholinonicotinic acid as a yellow green solid.

Step 3. Preparation of N-(5-((4-chlorobenzyl)oxy)-1,3,4-thiadiazol-2-yl)-6-cyano-2-morpholinonicotinamide

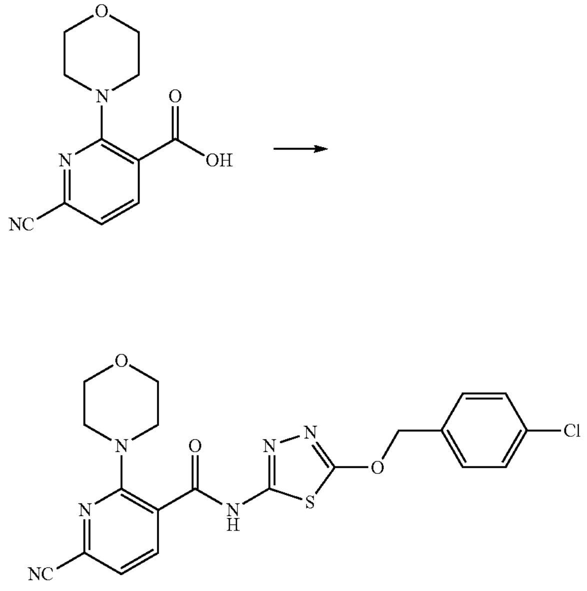

To a solution of 6-cyano-2-morpholinonicotinic acid (170 mg, 0.73 mmol) and 5-((4-chlorobenzyl)oxy)-1,3,4-thiadiazol-2-amine (211 mg, 0.88 mmol, Intermediate B) in DMF (2 mL) was added EDCI (210 mg, 1.09 mmol) and HOBT (148 mg, 1.1 mmol) under nitrogen. The mixture was stirred at 50° C. overnight. The mixture was diluted with water (10 mL) and extracted with EtOAc (3x5 mL). The combined organic layers were concentrated under reduce pressure and the residue was triturated with 1 mL MeOH to afford N-(5-((4-chlorobenzyl)oxy)-1,3,4-thiadiazol-2-yl)-6-cyano-2-morpholinonicotinamide as a light yellow solid. $^{1}H$ NMR (300 MHz; DMSO-$d_6$): δ 3.31-3.32 (m, 4H), 3.61-3.63 (m, 4H), 5.46-5.51 (m, 2H), 7.46-7.57 (m, 5H), 8.00-8.02 (m, 1H), 13.03 (s, 1H) ppm. m/z 457 ($M+H^+$).

Example 15

Synthesis of N-[5-[(5-bromopyridin-3-yl)oxy]-1,3,4-thiadiazol-2-yl]-2-(morpholin-4-yl) pyridine-3-carboxamide

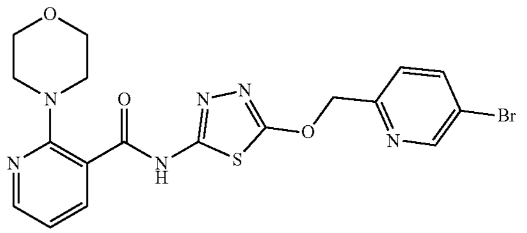 [SMILES: O=C(Nc1nnc(OCc2ccc(Br)cn2)s1)c1cccnc1N1CCOCC1]

Step 1. Preparation of 5-((5-bromopyridin-2-yl) methoxy)-1,3,4-thiadiazol-2-amine

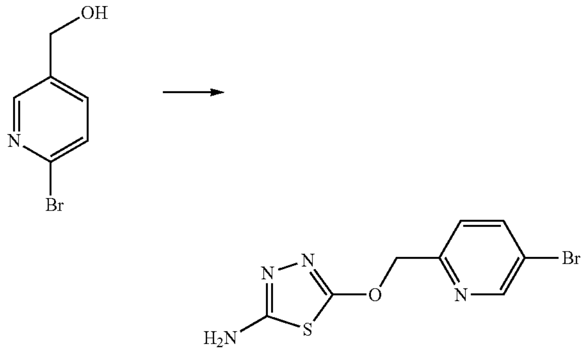

The title compound was prepared using similar procedure as Intermediate C replacing (5-chloropyridin-2-yl)methanol in Step 1 with (5-bromopyridin-2-yl) methanol.

Step 2. Preparation of N-[5-[(5-bromopyridin-3-yl) oxy]-1, 3, 4-thiadiazol-2-yl]-2-(morpholin-4-yl) pyridine-3-carboxamide

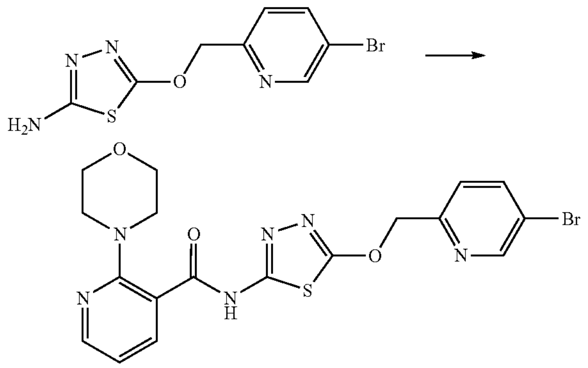

The title compound was prepared using General Procedure A employing 5-((5-bromopyridin-2-yl)methoxy)-1,3,4-thiadiazol-2-amine and 2-morpholinonicotinic acid. The mixture wash diluted with water and filtered. The filtrate was concentrated and the residue was purified by Prep-TLC (DCM:MeOH, 50:1) to afford N-[5-[(6-bromopyridin-3-yl) oxy]-1, 3, 4-thiadiazol-2-yl]-2-(morpholin-4-yl) pyridine-3-carboxamide as a white solid. $^{1}$H NMR (300 MHz; DMSO-$d_6$): δ 3.22-3.24 (m, 4H), 3.65-3.67 (m, 4H), 5.55 (s, 2H), 6.98-7.01 (m, 1H), 7.56-7.58 (m, 1H), 7.90-7.93 (m, 1H), 8.12-8.15 (m, 1H), 8.35-8.36 (m, 1H), 8.73-8.74 (m, 1H), 12.90 (s, 1H) ppm. m/z 479 (M+H$^+$).

Example 16

Synthesis of 2-(4-acetylpiperazin-1-yl)-N-(5-((4-chlorobenzyl)oxy)-1,3,4-thiadiazol-2-yl)nicotinamide

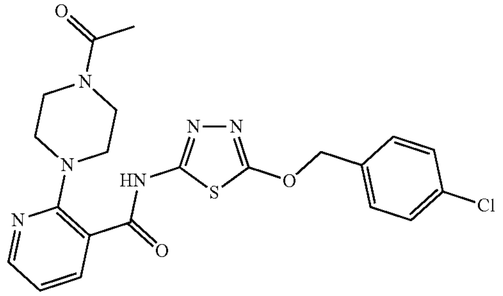 [SMILES: CC(=O)N1CCN(c2ncccc2C(=O)Nc2nnc(OCc3ccc(Cl)cc3)s2)CC1]

Proceeding analogously as described in Example 9 but substituting (R)-3-methylmorpholine with 1-(piperazin-1-yl)ethan-1-one gave crude product. The crude residue was purified via Prep-HPLC (column, C18 silica gel, mobile phase, 45-85% MeCN in water, with both eluents containing 0.1% FA) to the title compound as a white solid. LC/MS [M+H]$^+$ 472.95. $^{1}$H NMR (400 MHz, DMSO-$d_6$) δ 8.34 (d, J=4.6 Hz, 1H), 7.90 (d, J=7.4 Hz, 1H), 7.55 (d, J=8.2 Hz, 2H), 7.49 (d, J=8.1 Hz, 2H), 6.98 (dd, J=7.4, 4.9 Hz, 1H), 5.49 (s, 2H), 3.64-3.45 (m, 4H), 3.30-3.15 (m, 4H), 2.00 (s, 3H) ppm. m/z 473 (M+H$^+$).

Example 17

Synthesis of N-(5-((4-chlorobenzyl)oxy)-1,3,4-thiadiazol-2-yl)-1-(pyridin-3-yl)-1H-imidazole-5-carboxamide

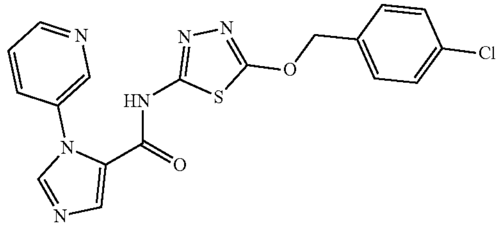 [SMILES: O=C(Nc1nnc(OCc2ccc(Cl)cc2)s1)c1cncn1-c1cccnc1]

The title compound was prepared using similar procedure as Example 12, replacing p-Anisidine in Step 1 with 3-aminopyridine to provide N-(5-((4-chlorobenzyl)oxy)-1,3,4-thiadiazol-2-yl)-1-(pyridin-3-yl)-1H-imidazole-5-carboxamide as a white solid. $^{1}$H NMR (300 MHz, DMSO-$d_6$): δ 5.47 (s, 2H), 7.45-7.58 (m, 5H), 7.92-7.95 (m, 1H), 8.21-8.25 (m, 2H), 8.66-8.67 (m, 2H), 12.87-12.95 (br s, 1H) ppm. m/z 413 (M+H$^+$).

Example 18

Synthesis of N-(5-((4-chlorobenzyl)oxy)-1,3,4-thiadiazol-2-yl)-1-(pyridin-4-yl)-1H-imidazole-5-carboxamide

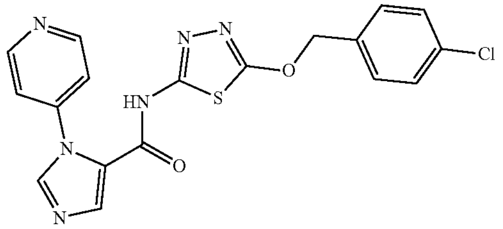 [SMILES: O=C(Nc1nnc(OCc2ccc(Cl)cc2)s1)c1cncn1-c1ccncc1]

Step 1. Preparation of 3-(pyridin-4-yl)imidazole-4-carboxylic acid

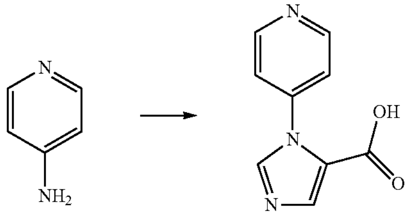 [SMILES: Nc1ccncc1 ; O=C(O)c1cncn1-c1ccncc1]

The title compound was prepared using similar procedure as Example 12, Step 1 and 2 replacing p-Anisidine in Step 1 with 4-aminopyridine.

Step 2. Preparation of N-(5-((4-chlorobenzyl)oxy)-1,3,4-thiadiazol-2-yl)-1-(pyridin-4-yl)-1H-imidazole-5-carboxamide

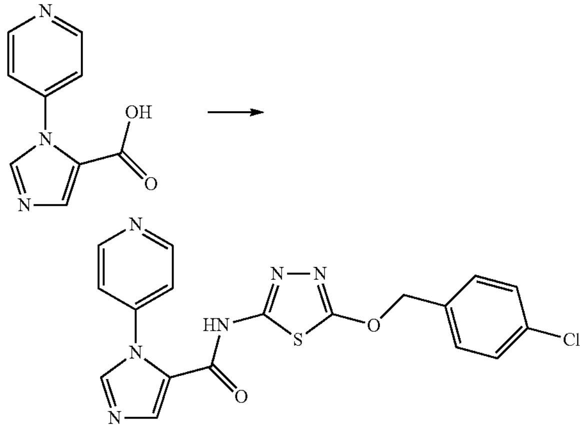

The title compound was prepared using General Procedure A employing 3-(pyridin-4-yl)imidazole-4-carboxylic acid and 5-((4-chlorobenzyl)oxy)-1,3,4-thiadiazol-2-amine (Intermediate B). The mixture was stirred at 50° C. for 4 h. The mixture was cooled to room temperature and diluted with water (10 mL) at room temperature. The mixture was extracted with EtOAc (2x5 mL). The combined organic layers were concentrated under reduced pressure and the residue triturated MeOH (2 mL) to afford N-(5-((4-chlorobenzyl)oxy)-1,3,4-thiadiazol-2-yl)-1-(pyridin-4-yl)-1H-imidazole-5-carboxamide as a white solid. $^1$H NMR (300 MHz; DMSO-$d_6$): δ 5.47 (s, 2H), 7.45-7.57 (m, 6H), 8.15-8.25 (m, 2H), 8.69-8.71 (m, 2H), 12.81-13.15 (br s, 1H) ppm. m/z 413 (M+H$^+$).

Example 19

Synthesis of N-[5-[(5-chloropyrazin-2-yl)methoxy]-1,3,4-thiadiazol-2-yl]-2-(morpholin-4-yl)pyridine-3-carboxamide

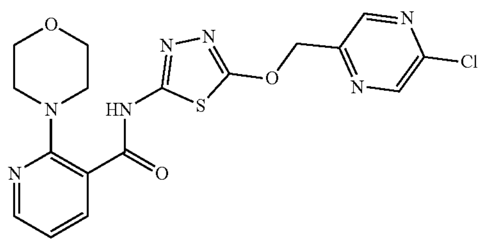 [SMILES: O=C(Nc1nnc(OCc2cnc(Cl)cn2)s1)c1cccnc1N1CCOCC1]

Step 1. Preparation of 5-[(5-chloropyrazin-2-yl)methoxy]-1,3,4-thiadiazol-2-amine

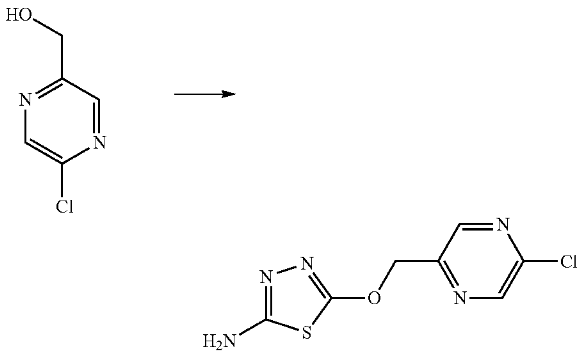

The title compound was prepared using similar procedure as Intermediate C replacing (5-chloropyridin-2-yl)methanol in Step 1 with (5-chloropyrazin-2-yl)methanol.

Step 2. Preparation of N-[5-[(5-chloropyrazin-2-yl)methoxy]-1,3,4-thiadiazol-2-yl]-2-(morpholin-4-yl)pyridine-3-carboxamide

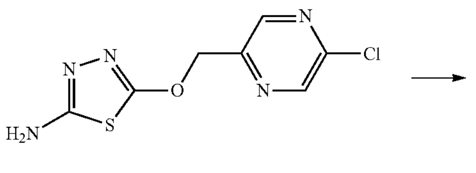

-continued

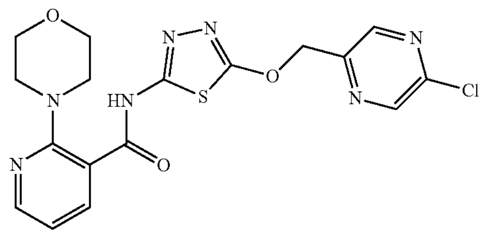

The title compound was prepared using General Procedure A employing 5-[(5-chloropyrazin-2-yl)methoxy]-1,3,4-thiadiazol-2-amine and 2-morpholinonicotinic acid. The mixture was diluted with water (10 mL). The aqueous layer was extracted with EtOAc (3x10 mL). The combined organic layers were concentrated under reduced pressure. The residue was triturated with MeOH (1 mL) to afford N-[5-[(5-chloropyrazin-2-yl)methoxy]-1,3,4-thiadiazol-2-yl]-2-(morpholin-4-yl)pyridine-3-carboxamide as a yellow solid. $^1$H NMR (300 MHz; DMSO-$d_6$): δ 3.22-3.25 (m, 4H), 3.61-3.68 (m, 4H), 5.67 (s, 2H), 6.98-7.03 (m, 1H), 7.91-7.96 (m, 1H), 8.36-8.38 (m, 1H), 8.75 (s, 1H), 8.86-8.87 (m, 1H), 12.92 (s, 1H) ppm. m/z 434 (M+H$^+$).

Example 20

Synthesis of N-(5-((4-chlorobenzyl)oxy)-1,3,4-thiadiazol-2-yl)-2-(4-hydroxypiperidin-1-yl)nicotinamide

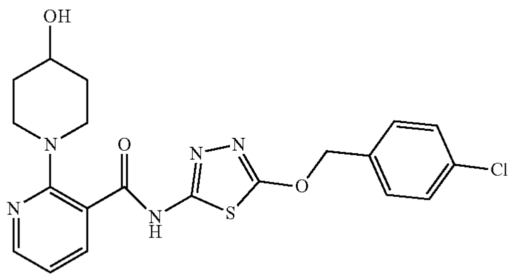 [SMILES: O=C(Nc1nnc(OCc2ccc(Cl)cc2)s1)c1cccnc1N1CCC(O)CC1]

Proceeding analogously as described in Example 22 but replacing (R)-3-methylmorpholine with 4-piperidinol gave crude product. The crude product was purified by reverse phase HPLC (water (0.1% formic acid) and MeCN (0.1% formic acid)) to afford the title compound as a white solid. $^1$H NMR (400 MHz, DMSO-$d_6$): δ 12.98 (s, 1H), 8.66 (s, 1H), 8.33 (d, J=4.7 Hz, 1H), 8.08-7.95 (m, 1H), 7.90 (d, J=7.6 Hz, 1H), 7.63 (d, J=8.3 Hz, 1H), 7.06-6.81 (m, 1H), 5.57 (s, 2H), 4.71 (d, J=4.0 Hz, 1H), 3.79-3.57 (m, 1H), 3.57-3.40 (m, 3H), 2.98 (t, J=11.2 Hz, 2H), 1.85-1.63 (m, 2H), 1.55-1.37 (m, 2H) ppm. m/z 447 (M+H$^+$).

Example 21

Synthesis of $N^5$-(5-((4-chlorobenzyl)oxy)-1,3,4-thiadiazol-2-yl)-6-morpholinopyridine-2,5-dicarboxamide

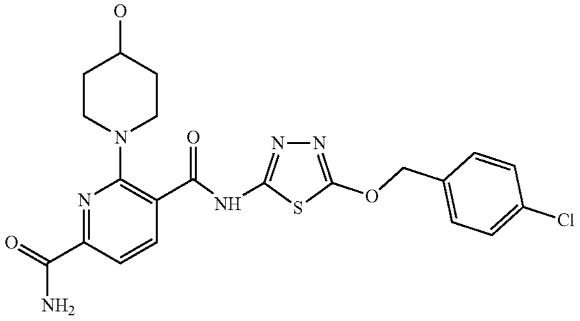 [SMILES: NC(=O)c1ccc(C(=O)Nc2nnc(OCc3ccc(Cl)cc3)s2)c(N2CCC(O)CC2)n1]

To a solution of N-(5-((4-chlorobenzyl)oxy)-1,3,4-thiadiazol-2-yl)-6-cyano-2-morpholino-nicotinamide (55 mg, 0.12 mmol, Example 14) in MeOH (3 mL) was added $H_2O_2$ (1.5 mL, 30% in water), water (0.6 mL) and NaOH (3.5 mg, 0.087 mmol). The mixture was stirred overnight at room temperature. The mixture was diluted with water (6 mL) and extracted with EtOAc (2×3 mL). The combining organic layers were concentrated under reduce pressure. The residue was purified by Prep-TLC (DCM:MeOH, 10:1). The residue was triturated with MeOH (1 mL) to afford $N^5$-(5-((4-chlorobenzyl)oxy)-1,3,4-thiadiazol-2-yl)-6-morpholino-pyridine-2,5-dicarboxamide as a white solid. $^1$H NMR (300 MHz; DMSO-$d_6$): δ 3.62 (s, 4H), 5.36-4.82 (m, 6H), 6.08 (s, 1H), 7.37-7.34 (m, 1H), 7.53-7.45 (m, 5H), 7.86-7.76 (m, 2H) ppm. m/z 475 (M+H$^+$).

Example 22

Synthesis of (R)—N-(5-((5-chloropyridin-2-yl)methoxy)-1,3,4-thiadiazol-2-yl)-2-(3-methylmorpholino)nicotinamide

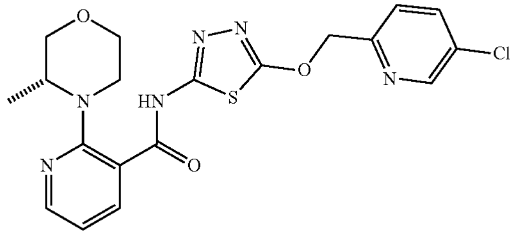 [SMILES: C[C@@H]1COCCN1c1ncccc1C(=O)Nc1nnc(OCc2ccc(Cl)cn2)s1]

To a vial equipped with stir bar was added 2-chloro-N-(5-((5-chloropyridin-2-yl)methoxy)-1,3,4-thiadiazol-2-yl) nicotinamide Intermediate F (200 mg, 1 eq.) followed by addition of (R)-3-methylmorpholine (158 mg, 3 eq.) and THF (2.6 mL). DIPEA (0.546 mL, 6 eq.) was then added and the reaction was heated to 75° C. and allowed to stir for 8 h. Upon reaction completion the mixture was diluted with water, and extracted with EtOAc. The combined organic extracts were washed with brine, dried over $Na_2SO_4$ and concentrated in vacuo. The crude residue was purified purified via reverse phase chromatography conditions (40%-80% MeCN/$H_2O$) to give the title compound (30 mg, 12% yield) as a white solid. 1H NMR (400 MHz, Chloroform-d) δ 8.60 (s, 1H), 8.56 (d, J=4.8 Hz, 1H), 8.50 (d, J=7.8 Hz, 1H), 7.73 (d, J=8.3 Hz, 1H), 7.51 (d, J=8.3 Hz, 1H), 7.32-7.25 (m, 1H), 5.61 (s, 2H), 4.10-3.98 (m 3H), 3.27 (td, J=11.3, 10.4, 4.8 Hz, 1H), 3.15 (dd, J=22.2, 12.2 Hz, 2H), 2.98 (t, J=11.3 Hz, 1H), 1.23 (d, J=6.2 Hz, 3H) ppm. m/z 447 (M+H$^+$).

Example 23

Synthesis of N-(5-((5-chloropyridin-2-yl)methoxy)-1,3,4-thiadiazol-2-yl)-2-(4-(methylsulfonyl)piperazin-1-yl)nicotinamide

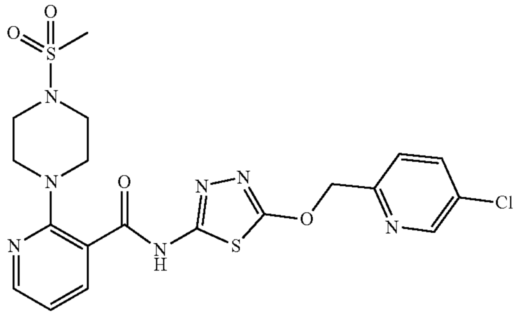 [SMILES: CS(=O)(=O)N1CCN(c2ncccc2C(=O)Nc2nnc(OCc3ccc(Cl)cn3)s2)CC1]

Proceeding analogously as described in Example 22, employing (methylsulfonyl)piperazine, hydrogen chloride and N-(5-((5-chloropyridin-2-yl)methoxy)-1,3,4-thiadiazol-2-yl)-2-fluoronicotinamide (Intermediate G) gave crude product. The residue was purified by Prep-HPLC (column, $C_{18}$ silica gel, mobile phase, 45%0-85% MeCN in water, with both eluents containing 0.1% FA) to give the title compound. $^1$H NMR (400 MHz; DMSO-$d_6$): δ 12.85 (br s, 1H), 8.66 (s, 1H), 8.35 (d, 1H), 8.01 (dd, 1H), 7.91 (d, 1H), 7.62 (d, 1H), 7.00-6.97 (m, 1H), 5.57 (s, 2H), 3.37-3.31 (m, 4H), 3.20-3.18 (m, 4H), 2.89 (s, 3H) ppm. m/z 510 (M+H$^+$).

Example 24

Synthesis of N-(5-((5-chloropyridin-2-yl)methoxy)-1,3,4-thiadiazol-2-yl)-1-phenyl-1H-pyrazole-5-carboxamide

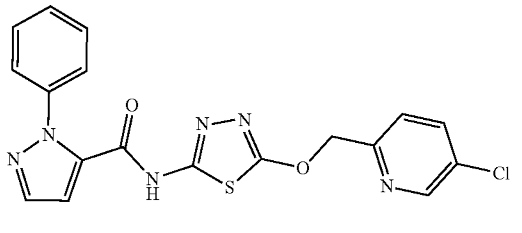 [SMILES: O=C(Nc1nnc(OCc2ccc(Cl)cn2)s1)c1ccnn1-c1ccccc1]

The title compound was prepared using General Procedure D employing 1-phenyl-1H-pyrazole-5-carboxylic acid and 5-((5-chloropyridin-2-yl)methoxy)-1,3,4-thiadiazol-2-amine (Intermediate C). The mixture was diluted with water and extracted with EtOAc. The combined organic layers were concentrated under reduce pressure. The residue was purified by reverse phase HPLC (column, $C_{18}$ silica; mobile phase 0-100% MeCN in water, with both eluents containing 0.1% FA water) to afford N-(5-((5-chloropyridin-2-yl) methoxy)-1,3,4-thiadiazol-2-yl)-1-phenyl-1H-pyrazole-5-carboxamide as a white solid. $^1$H NMR (400 MHz, DMSO-$d_6$) δ 13.05 (s, 1H), 8.65 (d, J=2.3 Hz, 1H), 8.04-7.94 (m, 1H), 7.85 (s, 1H), 7.59 (d, J=8.4 Hz, 1H), 7.44 (td, J=15.8, 14.5, 10.2 Hz, 7H), 5.55 (s, 2H) ppm. m/z 413 (M+H$^+$).

Example 25

Synthesis of N-(5-((5-chloropyridin-2-yl)methoxy)-1,3,4-thiadiazol-2-yl)-1-phenyl-1H-1,2,3-triazole-5-carboxamide

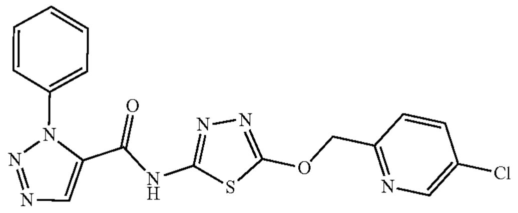 [SMILES: O=C(Nc1nnc(OCc2ccc(Cl)cn2)s1)c1cnnn1-c1ccccc1]

The title compound was prepared using General Procedure D employing 1-phenyl-1H-1,2,3-triazole-5-carboxylic acid and 5-((5-chloropyridin-2-yl)methoxy)-1,3,4-thiadiazol-2-amine (Intermediate C). The mixture was diluted with water and extracted with EtOAc (3×). The combined organic layers were concentrated under reduce pressure. The residue was purified by reverse phase HPLC (column, $C_{18}$ silica; mobile phase 0-100% MeCN in water, with both eluents containing 0.1% FA water) to afford N-(5-((5-chloropyridin-2-yl)methoxy)-1,3,4-thiadiazol-2-yl)-1-phenyl-1H-pyrazole-5-carboxamide as a white solid. $^1$H NMR (400 MHz, DMSO-$d_6$) δ 13.38 (s, 1H), 8.64 (d, J=2.2 Hz, 1H), 7.99 (dd, J=8.3, 2.4 Hz, 1H), 7.58 (s, 6H), 5.55 (s, 2H) ppm. m/z 414 (M+H$^+$).

Example 26

Synthesis of 3-(2-chlorophenyl)-N-[5-[(5-chloropyridin-2-yl)methoxy]-1,3,4-thiadiazol-2-yl]imidazole-4-carboxamide

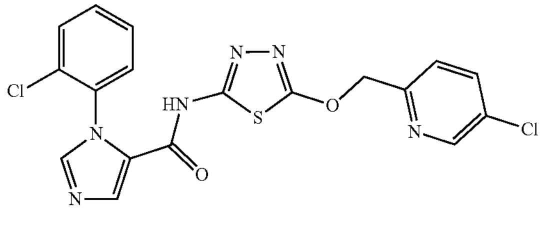 [SMILES: O=C(Nc1nnc(OCc2ccc(Cl)cn2)s1)c1cncn1-c1ccccc1Cl]

The title compound was prepared using similar procedure as Example 18, replacing 4-aminopyridine with 2-chloroaniline in Step 1 and employing (5-((5-chloropyridin-2-yl) methoxy)-1,3,4-thiadiazol-2-amine, Intermediate C) in Step 2. The mixture was stirred at 50° C. overnight and then cooled to room temperature and diluted with water. The mixture was extracted with EtOAc (3×) and the combined organic layers were concentrated under reduced pressure. The residue was purified by Prep-TLC (DCM:MeOH, 15:1) to afford 3-(2-chlorophenyl)-N-[5-[(5-chloropyridin-2-yl) methoxy]-1,3,4-thiadiazol-2-yl]imidazole-4-carboxamide as a yellow solid. $^1$H NMR (400 MHz; DMSO-$d_6$): δ 5.53 (s, 2H), 7.48-7.58 (m, 4H), 7.65-7.67 (m, 1H), 7.97-8.00 (m, 1H), 8.10 (s, 1H), 8.25 (s, 1H), 8.63-8.64 (m, 1H), 12.85 (s, 1H) ppm. m/z 447 (M+H$^+$).

Example 27

Synthesis of N-(5-((4-chlorobenzyl)oxy)-1,3,4-thiadiazol-2-yl)-2-(3-oxopiperazin-1-yl)nicotinamide

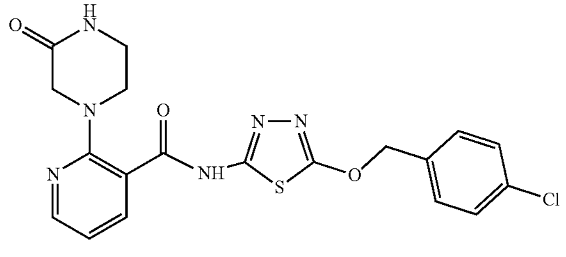 [SMILES: O=C1CN(c2ncccc2C(=O)Nc2nnc(OCc3ccc(Cl)cc3)s2)CCN1]

The title compound was prepared using General Procedure C, employing piperazin-2-one. Followed by General Procedure D employing 5-((4-chlorobenzyl)oxy)-1,3,4-thiadiazol-2-amine (Intermediate B). The mixture was diluted with EtOAc and washed with brine (2×). The aqueous layer was extracted with EtOAc. The combined organic layers were concentrated and the residue was purified by Prep-TLC (DCM:MeOH, 20:1). The residue was triturated with MeOH to afford N-(5-((4-chlorobenzyl)oxy)-1,3,4-thiadiazol-2-yl)-2-(3-oxopiperazin-1-yl)nicotinamide as a white solid. $^1$H NMR (400 MHz; DMSO-$d_6$): δ 3.22 (s, 2H), 3.44-3.47 (m, 2H), 3.78 (s, 2H), 5.50 (s, 2H), 6.94-6.97 (m, 1H), 7.48-7.56 (m, 4H), 7.87-7.89 (m, 1H), 8.02 (s, 1H), 8.32-8.33 (m, 1H), 12.84 (s, 1H) ppm. m/z 445 (M+H$^+$).

Example 28

Synthesis of 4-(3-((5-((4-chlorobenzyl)oxy)-1,3,4-thiadiazol-2-yl)carbamoyl)pyridin-2-yl)-N,N-dimethylpiperazine-1-carboxamide

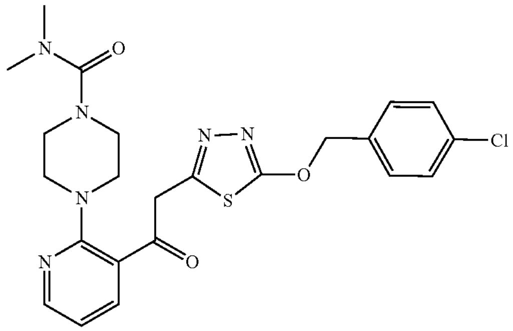 [SMILES: CN(C)C(=O)N1CCN(c2ncccc2C(=O)Cc2nnc(OCc3ccc(Cl)cc3)s2)CC1]

The title compound was prepared using General Procedure C, employing N,N-dimethylpiperazine-1-carboxamide. Followed by General Procedure A employing 5-((4-chlorobenzyl)oxy)-1,3,4-thiadiazol-2-amine (Intermediate B). The mixture was stirred at 50° C. for overnight. The mixture was cooled to room temperature and diluted with water. The mixture was extracted with EtOAc (2×). The combined organic layers were concentrated and the residue was purified by Prep-TLC (DCM:MeOH, 20:1). The residue was purified by Prep-HPLC [column, $C_{18}$ silica gel; mobile phase, 50-63% ACN in (0.16% $NH_4HCO_3$ in water)] to afford 4-(3-((5-((4-chlorobenzyl)oxy)-1,3,4-thiadiazol-2-yl)carbamoyl)pyridin-2-yl)-N,N-dimethylpiperazine-1-carboxamide as a white solid. $^1$H NMR (400 MHz; DMSO-$d_6$): δ 2.76 (s, 6H), 3.19-3.26 (m, 8H), 5.51 (s, 2H), 6.98-7.02 (m, 1H), 7.49-7.57 (m, 4H), 7.91-7.93 (m, 1H), 8.35-8.37 (m, 1H), 12.87 (s, 1H) ppm. m/z 502 (M+H$^+$).

Example 29

Synthesis of N-(5-((4-chlorobenzyl)oxy)-1,3,4-thiadiazol-2-yl)-6-(3-hydroxy-3-methylbut-1-yn-1-yl)-2-morpholinonicotinamide

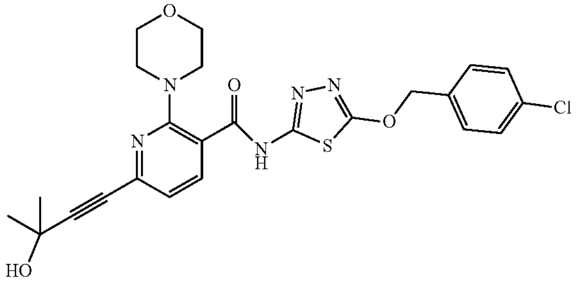 [SMILES: CC(C)(O)C#Cc1ccc(C(=O)Nc2nnc(OCc3ccc(Cl)cc3)s2)c(N2CCOCC2)n1]

Step 1. Preparation of 6-bromo-N-(5-((4-chlorobenzyl)oxy)-1,3,4-thiadiazol-2-yl)-2-morpholinonicotinamide

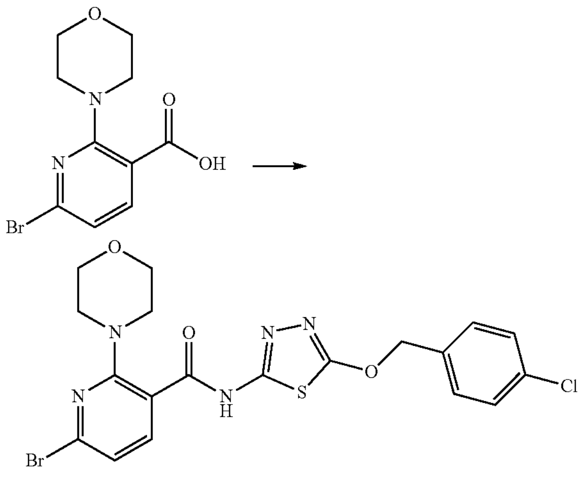

The title compound was prepared using General Procedure A employing 6-bromo-2-morpholinonicotinic acid (Step 1, Example 14) and 5-((4-chlorobenzyl)oxy)-1,3,4-thiadiazol-2-amine (Intermediate B). The mixture was diluted with water and extracted with EtOAc (3×). The combined organic layers were concentrated under reduce pressure. The residue was triturated with DCM:MeOH, 10:1 to afford 6-bromo-N-(5-((4-chlorobenzyl)oxy)-1,3,4-thiadiazol-2-yl)-2-morpholinonicotinamide as a white solid.

Step 2. Preparation of N-(5-((4-chlorobenzyl)oxy)-1,3,4-thiadiazol-2-yl)-6-(3-hydroxy-3-methylbut-1-yn-1-yl)-2-morpholinonicotinamide

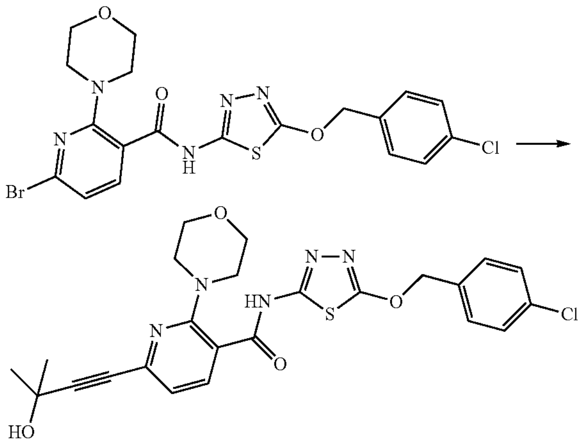

To a solution of 6-bromo-N-(5-((4-chlorobenzyl)oxy)-1,3,4-thiadiazol-2-yl)-2-morpholinonicotinamide (150 mg, 0.29 mmol) in DME (5 mL) was added 2-methyl-3-butyn-2-ol (37 mg, 0.44 mmol, 1.50), $PPh_3$ (123 mg, 0.47 mmol), CuI (22 mg, 0.12 mmol), and 10% Pd/C (15 mg, 10%) under nitrogen. The mixture was stirred at 80° C. for 3 h. The mixture was cooled to room temperature and filtered. The filtrate was concentrated under reduced pressure. The residue was purified by Prep-TLC (EtOAc:hexanes, 1:1) to afford N-(5-((4-chlorobenzyl)oxy)-1,3,4-thiadiazol-2-yl)-6-(3-hydroxy-3-methylbut-1-yn-1-yl)-2-morpholinonicotinamide as a white solid. $^1$H NMR (400 MHz; DMSO-$d_6$): δ 1.47 (s, 6H), 3.21-3.23 (d, 4H), 3.63-3.65 (m, 4H), 5.50-5.62 (m, 3H), 7.00-7.03 (m, 1H), 7.47-7.56 (m, 4H), 7.84-7.87 (m, 1H), 12.84 (s, 1H) ppm. m/z 433 (M+H$^+$).

Example 30

Synthesis of N-(5-((4-chlorobenzyl)oxy)-1,3,4-thiadiazol-2-yl)-2-(4-oxa-7-azaspiro[2.5]octan-7-yl)nicotinamide

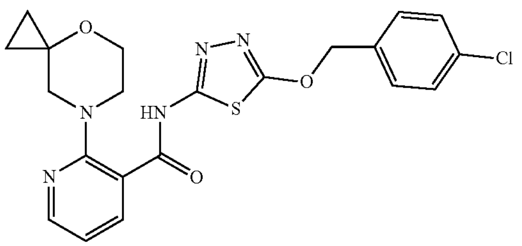 [SMILES: O=C(Nc1nnc(OCc2ccc(Cl)cc2)s1)c1cccnc1N1CCOC2(CC2)C1]

The title compound was prepared using General Procedure C, employing 4-oxa-7-azaspiro[2.5]octane. Followed by General Procedure A employing 5-((4-chlorobenzyl)oxy)-1,3,4-thiadiazol-2-amine (Intermediate B). The mixture was diluted with water and extracted with EtOAc (4×). The combined organic layers were concentrated under reduced pressure. The residue was triturated with MeOH to afford N-(5-((4-chlorobenzyl)oxy)-1,3,4-thiadiazol-2-yl)-2-

(4-oxa-7-azaspiro[2.5]octan-7-yl)nicotinamide as a white solid. $^1$H NMR (300 MHz; DMSO-$d_6$): δ 0.50-0.55 (m, 2H), 0.66-0.70 (m, 2H), 3.23 (s, 2H), 3.27-3.32 (m, 2H), 3.72-3.76 (m, 2H), 5.50 (s, 2H), 7.00-7.05 (m, 1H), 7.47-7.57 (m, 4H), 7.93-7.96 (m, 1H), 8.36-8.38 (m, 1H), 13.00 (s, 1H) ppm. m/z 458 (M+$H^+$).

Example 31

Synthesis of N-(5-((4-chlorobenzyl)oxy)-1,3,4-thiadiazol-2-yl)-1-(2,4-dimethoxyphenyl)-1H-imidazole-5-carboxamide

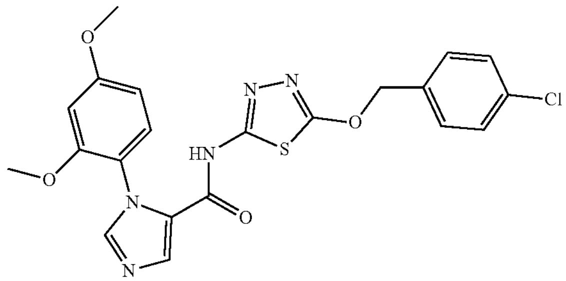 [SMILES: COc1ccc(-n2cncc2C(=O)Nc2nnc(OCc3ccc(Cl)cc3)s2)c(OC)c1]

The title compound was prepared using similar procedure as Example 18, replacing 4-aminopyridine with 2,4-dimethoxyaniline in Step 1 and employing (5-((4-chlorobenzyl)oxy)-1,3,4-thiadiazol-2-amine (Intermediate B) in Step 2. The mixture was stirred at 50° C. overnight and then cooled to room temperature and diluted with water. The mixture was extracted with EtOAc and the combined organic layers were concentrated under reduced pressure. The residue was triturated with MeOH to afford N-(5-((4-chlorobenzyl)oxy)-1,3,4-thiadiazol-2-yl)-1-(2,4-dimethoxyphenyl)-1H-imidazole-5-carboxamide as a white solid. $^1$H NMR (300 MHz; DMSO-$d_6$): δ 3.65 (s, 3H), 3.83 (s, 3H), 5.46 (s, 2H), 6.58-6.62 (m, 1H), 6.70-6.71 (m, 1H), 7.25-7.28 (m, 1H), 7.45-7.53 (m, 4H), 7.92 (s, 1H), 8.11 (s, 1H), 12.68 (s, 1H) ppm. m/z 472 (M+$H^+$).

Example 32

Synthesis of N-{5-[(5-chloro(2-pyridyl))methoxy](1,3,4-thiadiazol-2-yl)}(6-cyano-2-morpholin-4-ylnicotinamide

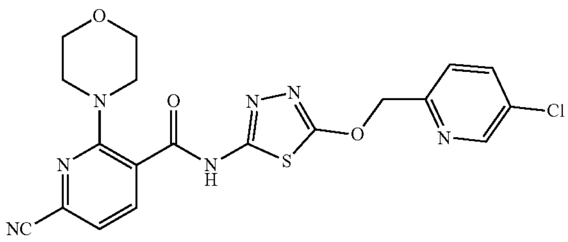 [SMILES: N#Cc1ccc(C(=O)Nc2nnc(OCc3ccc(Cl)cn3)s2)c(N2CCOCC2)n1]

The title compound was prepared using General Procedure A employing 6-cyano-2-morpholinonicotinic acid (Example 14, Step 3) and 5-((5-chloropyridin-2-yl)methoxy)-1,3,4-thiadiazol-2-amine (Intermediate C). The mixture was cooled to room temperature and filtered. The solid was washed with EtOAc to give N-{5-[(5-chloro(2-pyridyl))methoxy](1,3,4-thiadiazol-2-yl)}(6-cyano-2-morpholin-4-yl(3-pyridyl))carboxamide as a tan solid. $^1$H NMR (400 MHz; DMSO-$d_6$): δ 13.04 (br s, 1H), 8.66 (s, 1H), 8.01 (d, 2H), 7.63 (d, 1H), 7.47 (d, 1H), 5.57 (s, 2H), 3.64-3.61 (m, 4H), 3.33-3.30 (m, 4H), ppm. m/z 458 (M+$H^+$).

Example 33

Synthesis of N-(5-((5-chloropyridin-2-yl)methoxy)-1,3,4-thiadiazol-2-yl)-5-cyano-2-morpholinonicotinamide

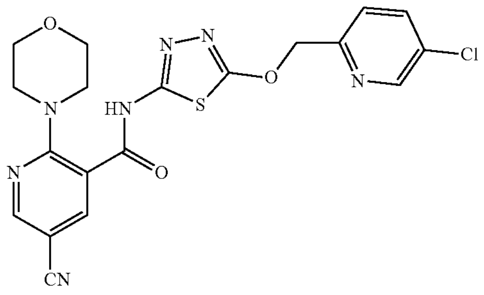 [SMILES: N#Cc1cnc(N2CCOCC2)c(C(=O)Nc2nnc(OCc3ccc(Cl)cn3)s2)c1]

Step 1. Preparation of methyl 5-bromo-2-morpholinonicotinate

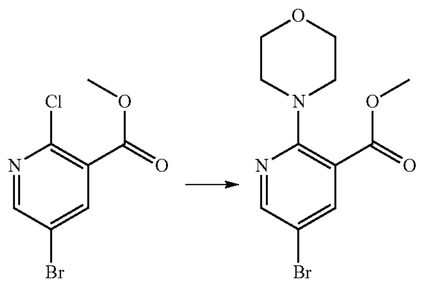 [SMILES: COC(=O)c1cc(Br)cnc1Cl ; COC(=O)c1cc(Br)cnc1N1CCOCC1]

To a solution of methyl 5-bromo-2-chloropyridine-3-carboxylate (1.0 g, 4.0 mmol) in DMF (10 mL) was added morpholine (0.70 g, 8.0 mmol), DIEA (1.0 g, 8.0 mmol) under nitrogen. The mixture was stirred at 100° C. overnight. The mixture was cooled to room temperature and diluted with water. The mixture was extracted with EtOAc (2×). The combined organic layers were concentrated under reduced pressure. The residue was purified by silica gel column chromatography, eluted with 9% EtOAc in PE to afford methyl 5-bromo-2-morpholinonicotinate as yellow oil.

Step 2. Preparation of methyl 5-cyano-2-morpholinonicotinate

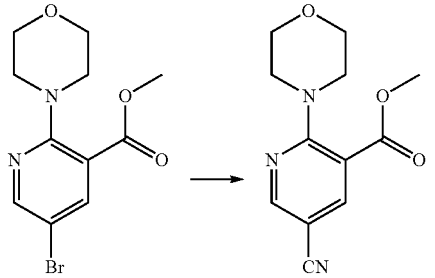 [SMILES: COC(=O)c1cc(Br)cnc1N1CCOCC1 ; COC(=O)c1cc(C#N)cnc1N1CCOCC1]

To a solution of methyl 5-bromo-2-morpholinonicotinate (1.1 g, 3.6 mmol) in DMF (11 mL) was added $Zn(CN)_2$ (0.84 g, 7.2 mmol) and $Pd(PPh_3)_4$ (0.41 g, 0.36 mmol) under nitrogen. The mixture was stirred at 100° C. for overnight. The mixture was diluted with water (20 mL) and extracted with EtOAc (2×10 mL). The combined organic layers were concentrated under reduced pressure. The residue was purified by silica gel column chromatography, eluted with 33% EtOAc in PE to afford methyl 5-cyano-2-morpholinonicotinate as an off-white solid.

Step 3. Preparation of 5-cyano-2-morpholinonicotinic acid

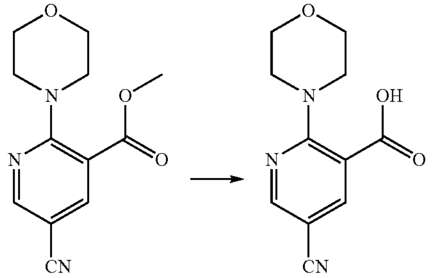 [SMILES: COC(=O)c1cc(C#N)cnc1N1CCOCC1 ; N#Cc1cnc(N2CCOCC2)c(C(=O)O)c1]

To a solution of methyl 5-cyano-2-morpholinonicotinate (770. mg, 3.1 mmol) in THF (7.7 mL) was added water (2 mL) and LiOH (179 mg, 7.5 mmol). The mixture was stirred overnight at room temperature. The mixture was diluted with water (20 mL) and was extracted with EtOAc (2×10 mL). Formic acid was added to the aqueous layer until pH was 3. The aqueous phase was concentrated under reduced pressure. The residue was purified by reverse phase chromatography (column, $C_{18}$ silica gel; mobile phase, with 0-40% MeCN in water) to afford 5-cyano-2-morpholinonicotinic acid as a white solid.

Step 4. Preparation of N-(5-((5-chloropyridin-2-yl)methoxy)-1,3,4-thiadiazol-2-yl)-5-cyano-2-morpholinonicotinamide

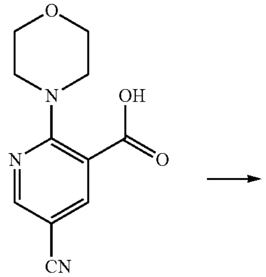

-continued

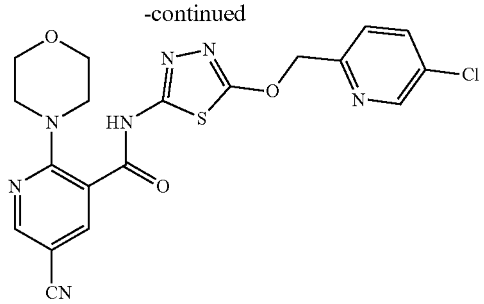

To a solution of 5-cyano-2-morpholinonicotinic acid (460 mg, 2.0 mmol) in DMF (5 mL) was added 5-((5-chloropyridin-2-yl)methoxy)-1,3,4-thiadiazol-2-amine (718 mg, 3.0 mmol, Intermediate C), EDCI (567 mg, 3.0 mmol) and HOBT (400 mg, 3.0 mmol) under nitrogen. The mixture was stirred overnight at room temperature and then was diluted with water (20 mL). The mixture was extracted with EtOAc (5×20 mL). The combining organic layer was concentrated under reduce pressure. The residue was diluted with MeOH (10 mL) and the mixture was filtered. The solid was washed with MeOH (1×3 mL) to afford N-(5-((5-chloropyridin-2-yl)methoxy)-1,3,4-thiadiazol-2-yl)-5-cyano-2-morpholinonicotinamide as a white solid. $^1H$ NMR (300 MHz; DMSO-$d_6$): δ 3.46-3.49 (m, 4H), 3.61-3.64 (m, 4H), 5.57 (s, 2H), 7.61-7.64 (m, 1H), 8.00-8.04 (m, 1H), 8.23-8.24 (m, 1H), 8.63-8.67 (m, 2H), 12.99 (s, 1H) ppm. m/z 458 ($M+H^+$).

Example 34

Synthesis of N-(5-((4-chloro-3-methoxybenzyl)oxy)-1,3,4-thiadiazol-2-yl)-2-morpholinonicotinamide

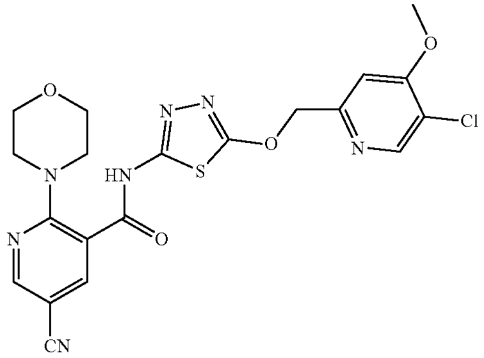 [SMILES: COc1cc(COc2nnc(NC(=O)c3cc(C#N)cnc3N3CCOCC3)s2)ncc1Cl]

Step 1. Preparation of 5-[(4-chloro-3-methoxyphenyl)methoxy]-1,3,4-thiadiazol-2-amine

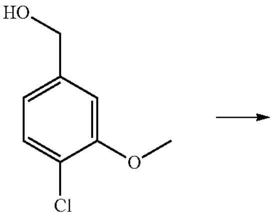

-continued

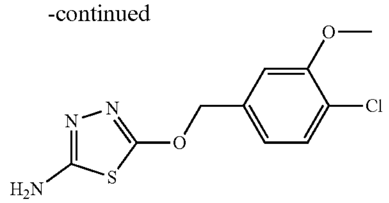

The title compound was prepared using similar procedure as Intermediate C replacing (5-chloropyridin-2-yl)methanol in Step 1 with (4-chloro-3-methoxyphenyl)methanol.

Step 2. Preparation of N-(5-((4-chloro-3-methoxybenzyl)oxy)-1,3,4-thiadiazol-2-yl)-2-morpholinonicotinamide

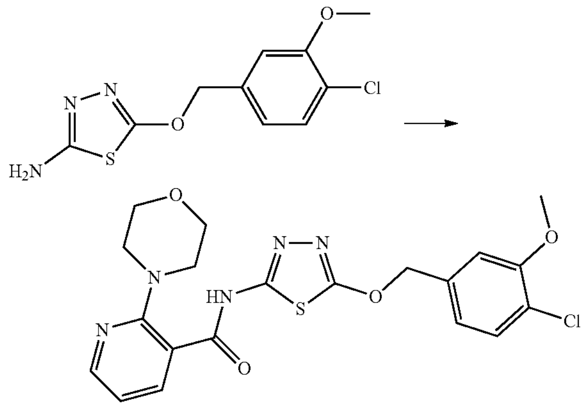

The title compound was prepared using General Procedure D employing 5-[(4-chloro-3-methoxyphenyl)methoxy]-1,3,4-thiadiazol-2-amine and 2-morpholinonicotinic acid. The mixture was diluted with water. The aqueous layer was extracted with EtOAc (3×). The combined organic layers were concentrated under reduced pressure. The residue was purified by Prep-TLC (DCM:MeOH, 35:1) to afford N-(5-((4-chloro-3-methoxybenzyl)oxy)-1,3,4-thiadiazol-2-yl)-2-morpholinonicotinamide as a white solid $^{1}H$ NMR (300 MHz; DMSO-$d_6$): δ 3.22-3.25 (m, 4H), 3.66-3.69 (m, 4H), 3.89 (s, 3H), 5.50 (s, 2H), 6.98-7.03 (m, 1H), 7.10-7.13 (m, 1H), 7.33-7.34 (m, 1H), 7.46-7.49 (m, 1H), 7.91-7.94 (m, 1H), 8.36-8.38 (m, 1H), 12.88 (s, 1H) ppm. m/z 462 ($M+H^+$).

Example 35

Synthesis of N-(5-((4-chlorobenzyl)oxy)-1,3,4-thiadiazol-2-yl)-6-cyano-4-morpholinonicotinamide

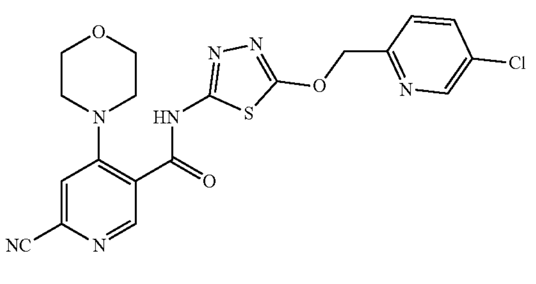 [SMILES: N#Cc1cc(N2CCOCC2)c(C(=O)Nc2nnc(OCc3ccc(Cl)cn3)s2)cn1]

Step 1. Preparation of ethyl 6-chloro-4-morpholinonicotinate

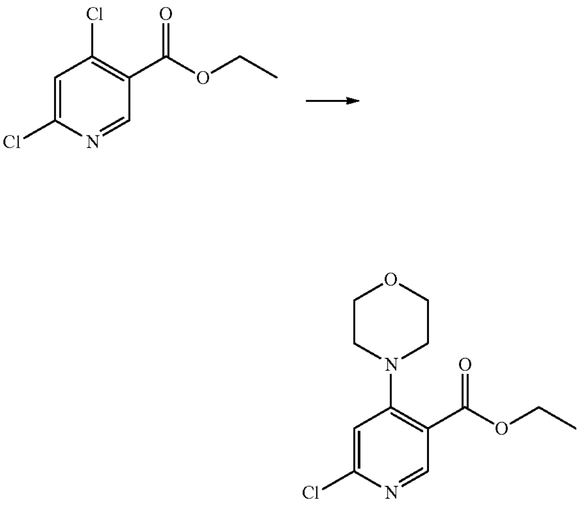

To a solution of morpholine (871 mg, 10 mmol) and $Et_3N$ (1.8 g, 18 mmol) in MeCN (20 mL) was added ethyl 4,6-dichloropyridine-3-carboxylate (2.0 g, 9.1 mmol) under nitrogen. The mixture was stirred overnight at room temperature. The mixture was concentrated under reduce pressure. The residue was triturated with PE:EtOAc, 30:1 to afford ethyl 6-chloro-4-morpholinonicotinate as a white solid.

Step 2. Preparation of 6-cyano-4-(morpholin-4-yl)pyridine-3-carboxylic acid

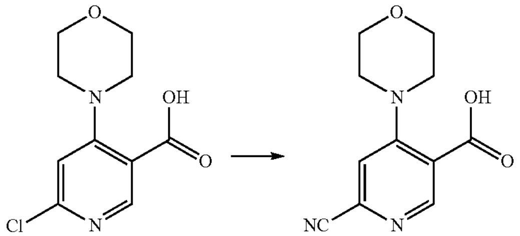 [SMILES: O=C(O)c1cnc(Cl)cc1N1CCOCC1 ; N#Cc1cc(N2CCOCC2)c(C(=O)O)cn1]

To a solution of 6-chloro-4-(morpholin-4-yl)pyridine-3-carboxylic acid (400 mg, 1.6 mmol) in DMF (4 mL) was added $Zn(CN)_2$ (387 mg, 3.3 mmol), Zn powder (323 mg, 4.9 mmol) and Pd(dppf)$Cl_2$ (181 mg, 0.25 mmol) under nitrogen. The mixture was stirred at 100° C. for 2 h. The mixture was cooled to room temperature and filtered. The solid was washed with DMF (2×2 mL). The filtrate was concentrated under reduce pressure and the residue was purified by reverse phase chromatography (column, $C_{18}$ silica gel; mobile phase, 0-100% MeCN in water) to afford 6-cyano-4-(morpholin-4-yl)pyridine-3-carboxylic acid as a yellow solid.

Step 3. Preparation of N-(5-((4-chlorobenzyl)oxy)-1,3,4-thiadiazol-2-yl)-6-cyano-4-morpholinonicotinamide

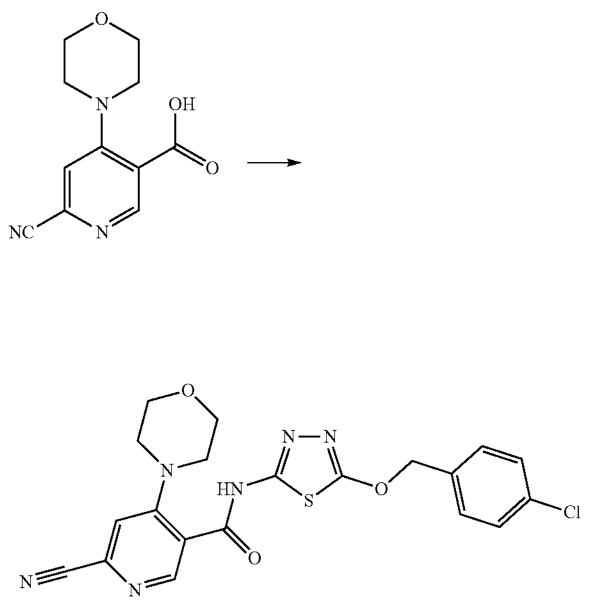

The title compound was prepared using General Procedure A employing 6-cyano-4-(morpholin-4-yl)pyridine-3-carboxylic acid and 5-((4-chlorobenzyl)oxy)-1,3,4-thiadiazol-2-amine (Intermediate B). The mixture was diluted with water and extracted with EtOAc (3×). The combined organic layers concentrated under reduce pressure. The residue was triturated with MeOH to afford N-(5-((4-chlorobenzyl)oxy)-1,3,4-thiadiazol-2-yl)-6-cyano-4-morpholinonicotinamide as a yellow solid. $^1$H NMR (300 MHz; DMSO-$d_6$): δ 3.26 (s, 4H), 3.64 (s, 4H), 5.51 (s, 2H), 7.48-7.57 (m, 4H), 7.70 (s, 1H), 8.47 (s, 1H), 13.04 (s, 1H) ppm. m/z 457 (M+H$^+$).

Example 36

Synthesis of N-(5-((5-chloropyridin-2-yl)methoxy)-1,3,4-thiadiazol-2-yl)-6-methoxy-4-morpholinonicotinamide

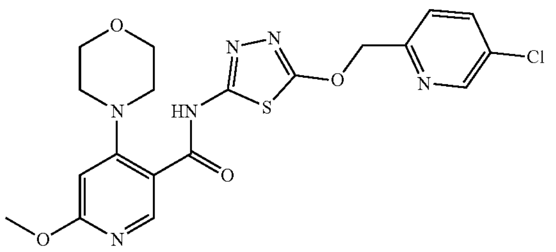 [SMILES: COc1cc(N2CCOCC2)c(C(=O)Nc2nnc(OCc3ccc(Cl)cn3)s2)cn1]

Step 1. Preparation of 6-methoxy-4-(morpholin-4-yl)pyridine-3-carboxylic acid

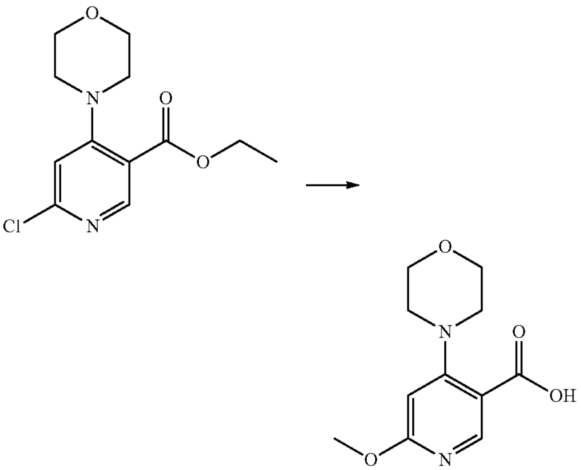

To a solution of ethyl 6-chloro-4-(morpholin-4-yl)pyridine-3-carboxylate (810 mg, 3.1 mmol, Example 35, Step 1) in MeOH (10 mL) at 0° C. was added sodium methoxide (199 mg, 3.7 mmol) under nitrogen. The mixture was stirred at 60° C. for overnight. Then NaOH (1.5 mL, 6.1 mmol, 4 M) was added and the mixture was stirred for 5 h at room temperature. The mixture was acidified to pH 6 with HOAc. The mixture was concentrated and the residue was purified by reverse phase chromatography (column, $C_{18}$ silica gel; mobile phase, with 10-50% MeCN in water) to afford 6-methoxy-4-(morpholin-4-yl)pyridine-3-carboxylic acid as a white solid.

Step 2. Preparation of N-(5-((5-chloropyridin-2-yl)methoxy)-1,3,4-thiadiazol-2-yl)-6-methoxy-4-morpholinonicotinamide

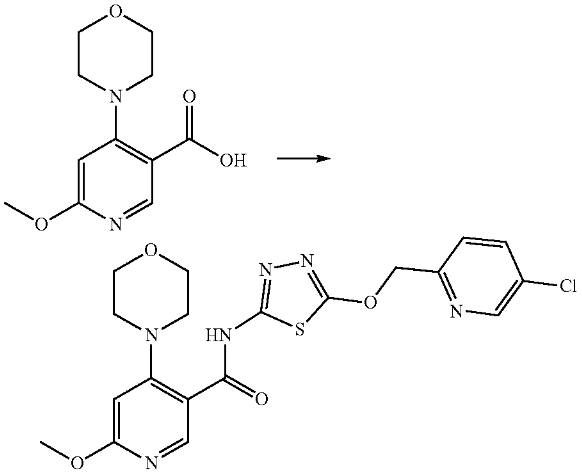

The title compound was prepared using General Procedure A employing 6-methoxy-4-(morpholin-4-yl)pyridine-3-carboxylic acid and 5-((5-chloropyridin-2-yl)methoxy)-1, 3,4-thiadiazol-2-amine (Intermediate C). The mixture was stirred at 50° C. overnight. The mixture was diluted with water and extracted with EtOAc (2×). The combined organic layers were concentrated under reduced pressure. The residue was triturated with MeOH (2 mL) to afford N-(5-((5-chloropyridin-2-yl)methoxy)-1,3,4-thiadiazol-2-yl)-6-methoxy-4-morpholinonicotinamide as a brown solid. $^1H$ NMR (300 MHz; DMSO-$d_6$): δ 3.02-3.05 (m, 4H), 3.66-3.69 (m, 4H), 3.88 (s, 3H), 5.57 (s, 2H), 6.37 (s, 1H), 7.62-7.65 (m, 1H), 8.00-8.04 (m, 1H), 8.26 (s, 1H), 8.66-8.67 (m, 1H), 12.65 (s, 1H) ppm. m/z 463 ($M+H^+$).

Example 37

Synthesis of N-(5-((5-chloropyridin-2-yl)methoxy)-1,3,4-thiadiazol-2-yl)-2-(1,1-dioxidothiomorpholino) nicotinamide

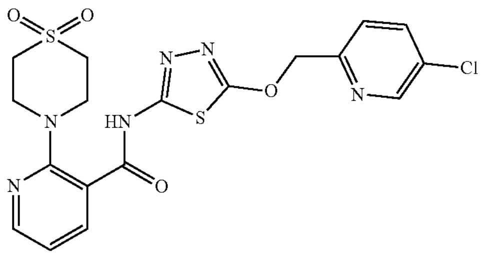 [SMILES: O=C(Nc1nnc(OCc2ccc(Cl)cn2)s1)c1cccnc1N1CCS(=O)(=O)CC1]

To a vial equipped with stir bar was added N-(5-((5-chloropyridin-2-yl)methoxy)-1,3,4-thiadiazol-2-yl)-2-fluoronicotinamide Intermediate G (100 mg, 1 eq.) followed by addition of thiomorpholine 1,1-dioxide (110 mg, 3 eq.) and DMF (1.2 mL). DIPEA (0.280 mL, 6 eq.) was then added and the reaction was heated to 75° C. and allowed to stir for 48 hours. Upon reaction completion the mixture was diluted with water and extracted with EtOAc. The combined organic extracts were washed with a 10% by weight solution of LiCl in $H_2O$, then brine, and dried over $Na_2SO_4$ and concentrated in vacuo. The crude residue was purified via reverse phase chromatography conditions (column, C18 silica gel, mobile phase, 40-80% MeCN in water, with both eluents containing 0.1% FA) to afford to give the title compound (7 mg, 5% yield) as a white solid. $^1H$ NMR (400 MHz, DMSO-$d_6$) δ 8.66 (s, 1H), 8.32 (d, J=4.7 Hz, 1H), 8.01 (d, J=8.0 Hz, 1H), 7.91 (d, J=7.5 Hz, 1H), 7.62 (d, J=8.4 Hz, 1H), 7.01 (t, J=6.2 Hz, 1H), 5.55 (s, 2H), 3.72 (bs, 4H), 3.18 (bs, 4H) ppm. m/z 481 ($M+H^+$).

Example 38

Synthesis of N-(5-((5-chloropyridin-2-yl)methoxy)-1,3,4-thiadiazol-2-yl)-1-(pyridin-2-yl)-1H-imidazole-5-carboxamide

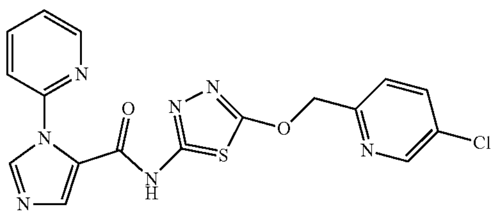

The title compound was prepared using General Procedure D employing 1-(pyridin-2-yl)-1H-imidazole-5-carboxylic acid and 5-((5-chloropyridin-2-yl)methoxy)-1,3,4-thiadiazol-2-amine (Intermediate C). The mixture was diluted with water and extracted with EtOAc (3×). The combined organic layers were concentrated under reduce pressure. The residue was purified by Prep-HPLC (column, $C_{18}$ silica gel; mobile phase, 0-100% MeCN in water, both containing 0.1% formic acid) to afford N-(5-((5-chloropyridin-2-yl)methoxy)-1,3,4-thiadiazol-2-yl)-1-phenyl-1H-pyrazole-5-carboxamide as a white solid. $^1H$ NMR (400 MHz, DMSO-$d_6$) δ 12.94 (s, 1H), 8.64 (d, J=2.2 Hz, 1H), 8.59-8.44 (m, 1H), 8.34-8.19 (m, 1H), 8.09-7.87 (m, 2H), 7.66-7.55 (m, 2H), 7.57-7.43 (m, 1H), 6.52 (s, 1H), 5.52 (s, 2H) ppm. m/z 414 ($M+H^+$).

Example 39

Synthesis of N-(5-((5-chloropyridin-2-yl)methoxy)-1,3,4-thiadiazol-2-yl)-2-(4,4-difluoropiperidin-1-yl) nicotinamide

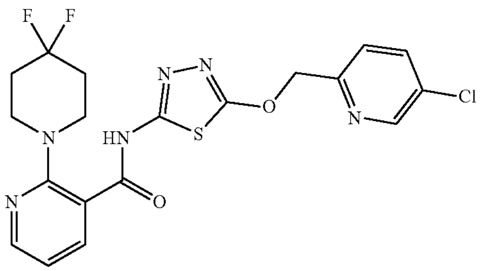 [SMILES: O=C(Nc1nnc(OCc2ccc(Cl)cn2)s1)c1cccnc1N1CCC(F)(F)CC1]

Proceeding analogously as described in Example 22, but using N-(5-((5-chloropyridin-2-yl)methoxy)-1,3,4-thiadiazol-2-yl)-2-fluoronicotinamide Intermediate G and 4,4-difluoropiperidine gave crude product. Purification by reverse phase chromatography (column, C18 silica gel; mobile phase, 40-80% MeCN in water, with both eluents containing 0.1% FA) gave the title compound as a white solid. 1H NMR (400 MHz, Chloroform-d) δ 8.61 (s, 1H), 8.54 (d, J=4.5 Hz, 1H), 8.48 (d, J=7.8 Hz, 1H), 7.75 (d, J=8.2 Hz, 1H), 7.32-7.26 (m, 1H), 5.63 (s, 2H), 3.44 (s, 4H), 2.31 (dt, J=13.5, 7.2 Hz, 4H) ppm. m/z 467 ($M+H^+$).

Example 40

Synthesis of N-(5-((4-bromobenzyl)oxy)-1,3,4-thiadiazol-2-yl)-2-morpholinonicotinamide

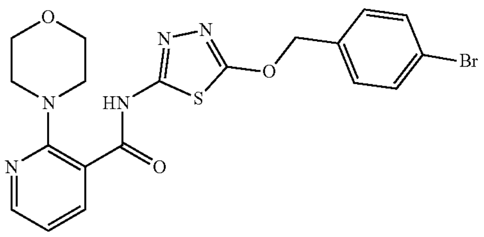 [SMILES: O=C(Nc1nnc(OCc2ccc(Br)cc2)s1)c1cccnc1N1CCOCC1]

Step 1. Preparation of 5-((4-bromobenzyl)oxy)-1,3,4-thiadiazol-2-amine

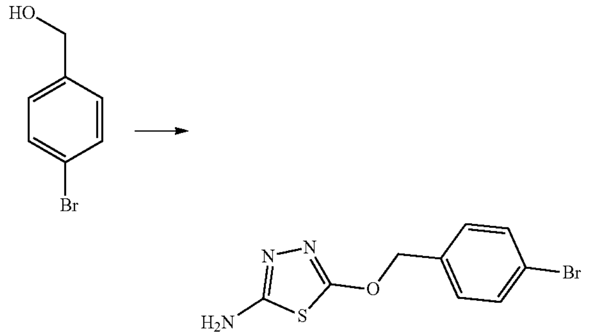

The title compound was prepared using similar procedure as Intermediate C replacing (5-chloropyridin-2-yl)methanol in Step 1 with p-bromobenzyl alcohol.

Step 2. Preparation of N-(5-((4-bromobenzyl)oxy)-1,3,4-thiadiazol-2-yl)-2-morpholinonicotinamide

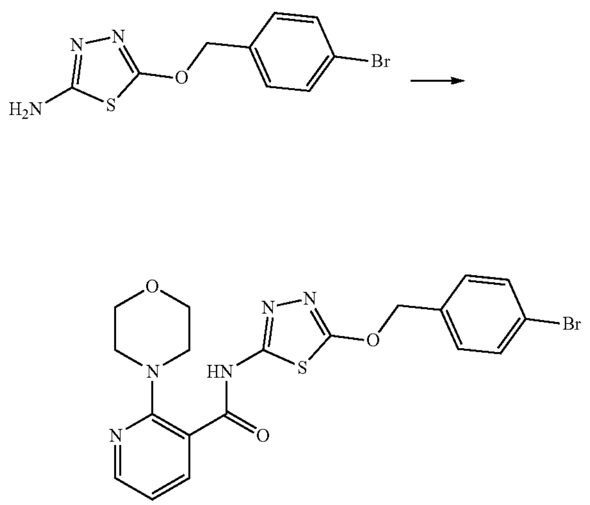

The title compound was prepared using General Procedure A employing 5-((4-bromobenzyl)-oxy)-1,3,4-thiadiazol-2-amine and 2-morpholinonicotinic acid. The mixture was diluted with water. The aqueous layer was extracted with EtOAc (3x). The combined organic layer was concentrated under reduced pressure. The residue was triturated with MeOH to afford N-(5-((4-bromobenzyl)oxy)-1,3,4-thiadiazol-2-yl)-2-morpholinonicotinamide as a pink solid. $^1$H NMR (400 MHz; DMSO-$d_6$): δ 3.22-3.25 (m, 4H), 3.66-3.68 (m, 4H), 5.45 (s, 2H), 7.00-7.02 (m, 1H), 7.48-7.52 (m, 2H), 7.62-7.65 (m, 2H), 7.91-7.93 (m, 1H), 8.36-8.37 (m, 1H), 12.88 (s, 1H) ppm. m/z 476 (M+H$^+$).

Example 41

Synthesis of N-(5-((4-chlorobenzyl)oxy)-1,3,4-thiadiazol-2-yl)-4-morpholino-6-oxo-1,6-dihydropyridine-3-carboxamide or its tautomer N-(5-((4-chlorobenzyl)oxy)-1,3,4-thiadiazol-2-yl)-6-hydroxy-4-morpholinonicotinamide

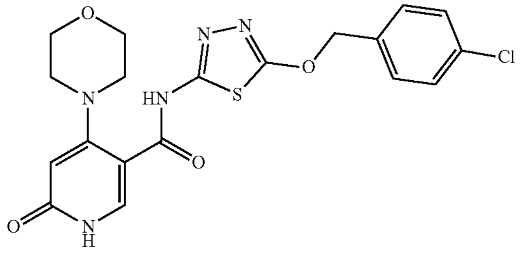

or its tautomeric gorm

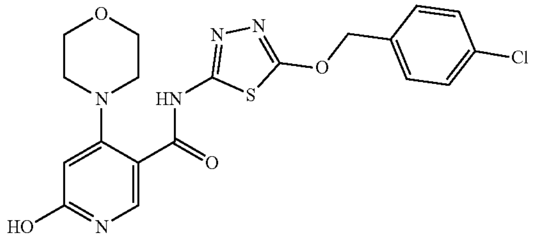

Step 1. Preparation of ethyl 4-(morpholin-4-yl)-6-oxo-1H-pyridine-3-carboxylate

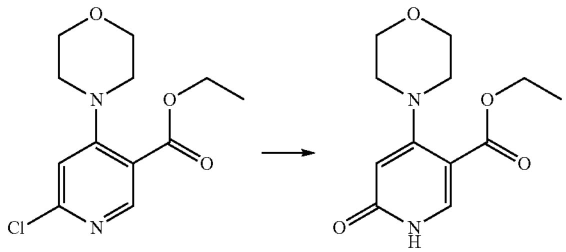 [SMILES: CCOC(=O)c1cnc(Cl)cc1N1CCOCC1 ; CCOC(=O)c1c[nH]c(=O)cc1N1CCOCC1]

A solution of ethyl 6-chloro-4-(morpholin-4-yl)pyridine-3-carboxylate (1.0 g, 3.7 mmol, Example 35, Step 1) in HOAc (10 mL) was stirred at 100° C. overnight. The mixture was cooled to room temperature and concentrated under reduced pressure. The residue was diluted by with sat. $NaHCO_3$ (10 mL) and the mixture was extracted with EtOAc (5×10 mL). The combined organic layers were concentrated under reduced pressure. The residue was purified by silica gel column chromatography, eluted with 5% MeOH in DCM to afford ethyl 4-(morpholin-4-yl)-6-oxo-1H-pyridine-3-carboxylate as a white solid.

Step 2. Preparation of 4-morpholino-6-oxo-5,6-dihydropyridine-3-carboxylic acid

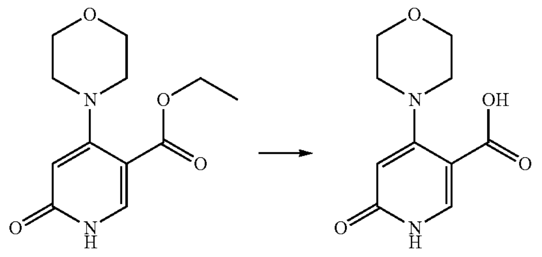 [SMILES: CCOC(=O)c1c[nH]c(=O)cc1N1CCOCC1 ; O=C(O)c1c[nH]c(=O)cc1N1CCOCC1]

To a solution of ethyl 4-(morpholin-4-yl)-6-oxo-1H-pyridine-3-carboxylate (430 mg, 1.7 mmol) in MeOH (4.3 mL) was added NaOH (136 mg, 3.4 mmol) and water (1.7 mL). The mixture was stirred at 100° C. for 48 h. The mixture was acidified to pH 6 with HCl (1 M). The mixture was concentrated under reduce pressure. The residue was purified by reverse phase chromatography (column, $C_{18}$ silica gel; mobile phase, with 0-50% MeCN in water, with both eluents containing 0.05% TFA). The residue was further purified by reverse phase chromatography 9 column, Prep T3 OBD Column; mobile phase, with 2-10% MeCN in water, with water containing 0.05% TFA0 to afford 4-morpholino-6-oxo-5,6-dihydropyridine-3-carboxylic acid as a white solid.

Step 3. Preparation of N-(5-((4-chlorobenzyl)oxy)-1,3,4-thiadiazol-2-yl)-4-morpholino-6-oxo-1,6-dihydropyridine-3-carboxamide

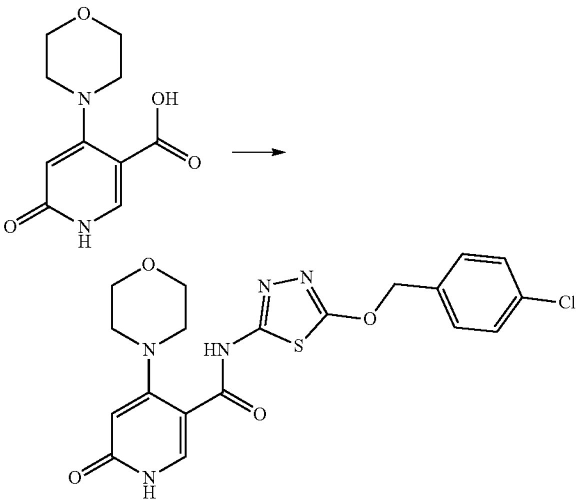

The title compound was prepared using General Procedure A employing and 5-((4-chlorobenzyl)oxy)-1,3,4-thiadiazol-2-amine (Intermediate B). The mixture was stirred at 50° C. overnight under nitrogen. The mixture was cooled room temperature and diluted with water. The mixture was extracted with EtOAc (2×). The combined organic layers were concentrated under reduced pressure. The residue was purified by Prep-TLC (DCM:MeOH, 25:1) to afford N-(5-((4-chlorobenzyl)oxy)-1,3,4-thiadiazol-2-yl)-4-morpholino-6-oxo-1,6-dihydropyridine-3-carboxamide as a white solid. $^1$H NMR (300 MHz; DMSO-$d_6$): δ 2.92 (s, 4H), 3.65-3.69 (m, 4H), 5.48 (s, 2H), 5.71 (s, 1H), 7.47-7.56 (m, 4H), 7.77 (s, 1H), 11.62 (s, 1H), 12.38 (s, 1H) ppm. m/z 448 (M+H$^+$).

Example 42

Synthesis of N-(5-((4-chlorobenzyl)oxy)-1,3,4-thiadiazol-2-yl)-1-(2-chlorophenyl)-1H-imidazole-5-carboxamide

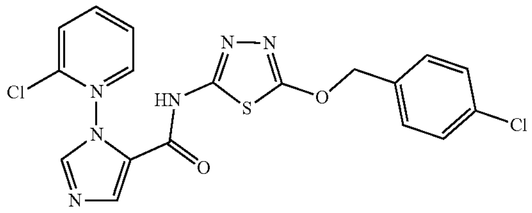

The title compound was prepared using similar procedure as Example 18, replacing 4-aminopyridine with 2-chloroaniline in Step 1 and employing 5-((4-chlorobenzyl)oxy)-1,3,4-thiadiazol-2-amine (Intermediate B) in Step 2. The mixture was diluted with water and extracted with EtOAc (2×). The combined organic layers were concentrated under reduce pressure. The residue was purified Prep-TLC with (DCM:MeOH, 35:1) to afford N-(5-((4-chlorobenzyl)oxy)-1,3,4-thiadiazol-2-yl)-1-(2-chlorophenyl)-1H-imidazole-5-carboxamide as a white solid. $^1$H NMR (300 MHz; DMSO-$d_6$): δ 5.44-5.47 (m, 2H), 7.45-7.60 (m, 7H), 7.65-7.68 (m, 1H), 8.11 (s, 1H), 8.27 (s, 1H), 12.85 (s, 1H) ppm. m/z 446 (M+H$^+$).

Example 43

Synthesis of N-(5-((4-chlorobenzyl)oxy)-1,3,4-thiadiazol-2-yl)-1-(2-cyanophenyl)-1H-imidazole-5-carboxamide

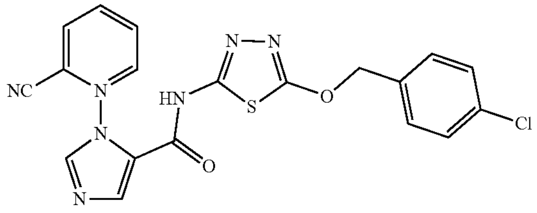

The title compound was prepared using similar procedure as Example 12, replacing p-Anisidine with 2-aminobenzonitrile and employing 5-((4-chlorobenzyl)oxy)-1,3,4-thiadiazol-2-amine (Intermediate B) in Step 2. The mixture was diluted with water and extracted with EtOAc (2×). The combined organic layers were concentrated under reduce pressure. The residue was triturated with to afford N-(5-((4-chlorobenzyl)oxy)-1,3,4-thiadiazol-2-yl)-1-(2-cyanophenyl)-1H-imidazole-5-carboxamide as a light yellow solid. $^1$H NMR (300 MHz; DMSO-$d_6$): δ 5.47 (s, 2H), 7.46-7.54 (m, 4H), 7.70-7.75 (m, 2H), 7.83-7.93 (m, 1H), 8.04-8.07 (m, 1H), 8.27-8.32 (m, 2H), 12.96-13.04 (br s, 1H) ppm. m/z 437 (M+H$^+$).

Example 44

Synthesis of N-(5-((4-chlorobenzyl)oxy)-1,3,4-thiadiazol-2-yl)-6-cyano-2-(4-oxa-7-azaspiro[2.5]octan-7-yl)nicotinamide

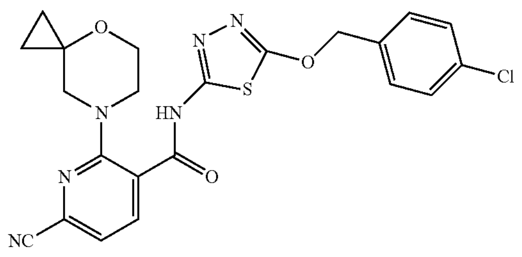 [SMILES: N#Cc1ccc(C(=O)Nc2nnc(OCc3ccc(Cl)cc3)s2)c(N2CCOC3(CC3)C2)n1]

Step 1. Preparation of 6-cyano-2-(4-oxa-7-azaspiro[2.5]octan-7-yl)nicotinic acid

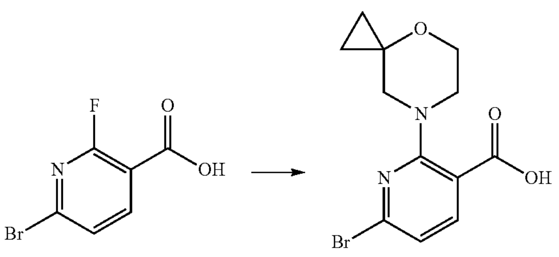 [SMILES: O=C(O)c1ccc(Br)nc1F ; O=C(O)c1ccc(Br)nc1N1CCOC2(CC2)C1]

The title compound was prepared using similar procedure as Example 14, Steps 1-2, replacing morpholine with 4-oxa-7-azaspiro[2.5]octane in Step 1.

Step 2. Preparation of N-(5-((4-chlorobenzyl)oxy)-1,3,4-thiadiazol-2-yl)-6-cyano-2-(4-oxa-7-azaspiro[2.5]octan-7-yl)nicotinamide

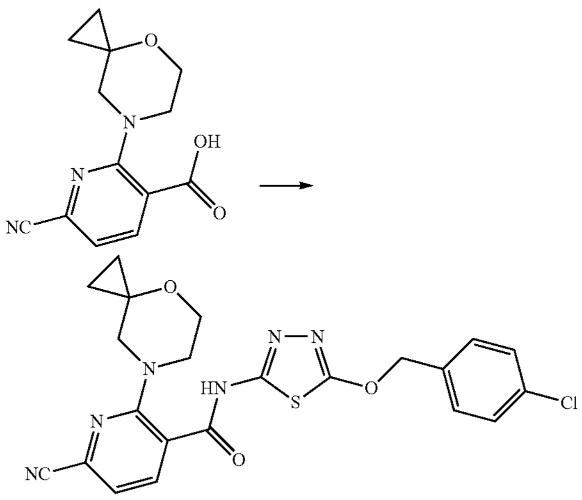

The title compound was prepared using General Procedure A employing 6-cyano-2-(4-oxa-7-azaspiro[2.5]octan-7-yl)nicotinic acid and 5-((4-chlorobenzyl)oxy)-1,3,4-thiadiazol-2-amine (Intermediate B). The mixture was diluted with water and extracted with EtOAc (3×). The combined organic layers were concentrated under reduced pressure. The residue was triturated with MeOH to afford N-(5-((4-chlorobenzyl)oxy)-1,3,4-thiadiazol-2-yl)-6-cyano-2-(4-oxa-7-azaspiro[2.5]octan-7-yl)nicotinamide as a yellow green solid. $^1H$ NMR (400 MHz; DMSO-$d_6$): δ 0.53-0.56 (m, 2H), 0.66-0.69 (m, 2H), 3.31-3.32 (m, 2H), 3.35-3.37 (m, 2H), 3.68-3.70 (m, 2H), 5.51 (s, 2H), 7.47-7.50 (m, 3H), 7.54-7.56 (m, 2H), 8.00-8.02 (m, 1H), 13.04 (s, 1H) ppm. m/z 483 $(M+H^+)$.

Example 45

Synthesis of N-[5-[(4-chlorophenyl)methoxy]-1,3,4-thiadiazol-2-yl]-2-(4-methyl-3-oxopiperazin-1-yl)pyridine-3-carboxamide

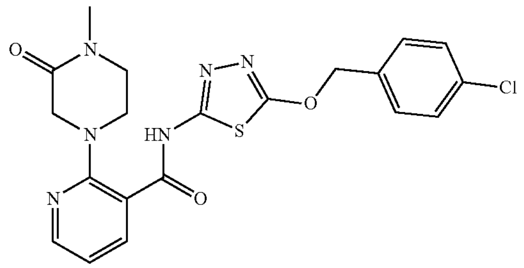 [SMILES: CN1CCN(c2ncccc2C(=O)Nc2nnc(OCc3ccc(Cl)cc3)s2)CC1=O]

To a solution of N-[5-[(4-chlorophenyl)methoxy]-1,3,4-thiadiazol-2-yl]-2-fluoropyridine-3-carboxamide (100 mg, 0.27 mmol, Intermediate D) in MeCN (1.0 mL), was added 1-methylpiperazin-2-one (34 mg, 0.3 mmol) and $Et_3N$ (55 mg, 0.55 mmol) under nitrogen. The mixture was stirred at 80° C. overnight. The mixture was cooled to room temperature and concentrated under reduce pressure. The residue was triturated with MeOH to afford N-[5-[(4-chlorophenyl)methoxy]-1,3,4-thiadiazol-2-yl]-2-(4-methyl-3-oxopiperazin-1-yl)pyridine-3-carboxamide as a yellow solid. $^1H$ NMR (400 MHz; DMSO-$d_6$): δ 2.82-2.85 (m, 3H), 3.32-3.34 (m, 2H), 3.54-3.57 (m, 2H), 3.83 (s, 2H), 5.51 (s, 2H), 6.95-6.98 (m, 1H), 7.48-7.56 (m, 4H), 7.88-7.90 (m, 1H), 8.32-8.34 (m, 1H), 12.74 (s, 1H) ppm. m/z 459 $(M+H^+)$.

Example 46

Synthesis of (R) N-(5-((4-chlorobenzyl)oxy)-1,3,4-thiadiazol-2-yl)-2-(3-methyl-5-oxopiperazin-1-yl)nicotinamide and (S) N-(5-((4-chlorobenzyl)oxy)-1,3,4-thiadiazol-2-yl)-2-(3-methyl-5-oxopiperazin-1-yl)nicotinamide

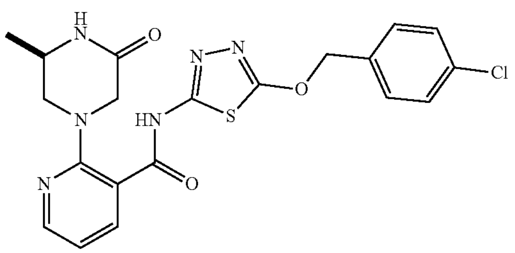 and

-continued

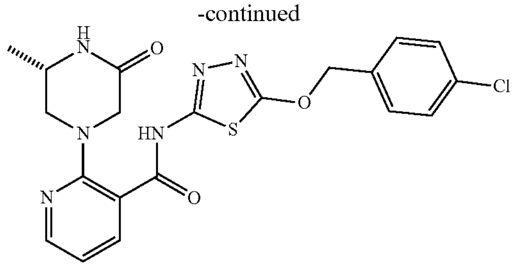

To a solution of N-[5-[(4-chlorophenyl)methoxy]-1,3,4-thiadiazol-2-yl]-2-fluoropyridine-3-carboxamide (100 mg, 0.27 mmol, Intermediate D) in NMP (I mL) was added racemic 6-methylpiperazin-2-one (125 mg, 1.1 mmol) and DIEA (74 mg, 0.55 mmol) under nitrogen. The mixture was stirred for 12 h at room temperature. The mixture was diluted with EtOAc (2 mL) and washed with water (2×). The organic layer was concentrated under reduce pressure. The reside was triturated with MeOH (2 mL) to afford a racemic mixture of (R) N-(5-((4-chlorobenzyl)oxy)-1,3,4-thiadiazol-2-yl)-2-(3-methyl-5-oxopiperazin-1-yl)nicotinamide and (S) N-(5-((4-chlorobenzyl)oxy)-1,3,4-thiadiazol-2-yl)-2-(3-methyl-5-oxopiperazin-1-yl)nicotinamide as a white solid. $^1$H NMR (400 MHz; DMSO-$d_6$): δ 1.00-1.02 (m, 3H), 3.00-3.05 (m, 1H), 3.55 (s, 1H), 3.65-3.79 (m, 3H), 5.51 (s, 2H), 6.93-6.96 (m, 1H), 7.48-7.56 (m, 4H), 7.86-7.89 (m, 1H), 8.07 (s, 1H), 8.32-8.33 (m, 1H), 12.84 (s, 1H) ppm. m/z 459 (M+H$^+$).

Example 47

Synthesis of N-(5-((4-cyclopropylbenzyl)oxy)-1,3,4-thiadiazol-2-yl)-2-morpholinonicotinamide

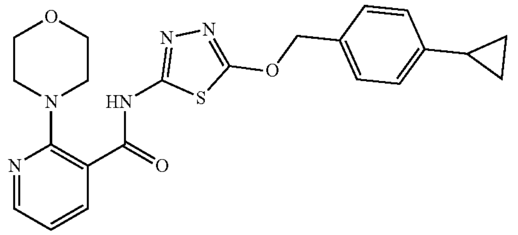 [SMILES: O=C(Nc1nnc(OCc2ccc(C3CC3)cc2)s1)c1cccnc1N1CCOCC1]

Step 1. Preparation of 5-[(4-cyclopropylphenyl)methoxy]-1,3,4-thiadiazol-2-amine

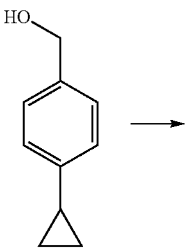

-continued

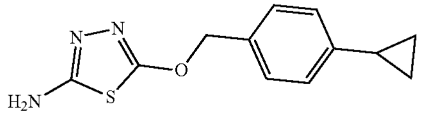

The title compound was prepared using similar procedure as Intermediate C replacing (5-chloropyridin-2-yl)methanol in Step 1 with (4-cyclopropylphenyl)methanol.

Step 2. Preparation of N-(5-((4-cyclopropylbenzyl)oxy)-1,3,4-thiadiazol-2-yl)-2-morpholinonicotinamide

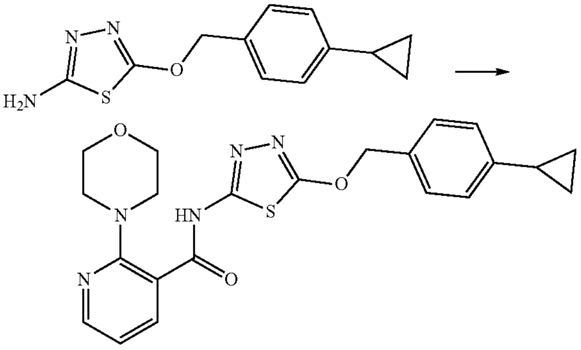

The title compound was prepared using General Procedure A employing 5-[(4-cyclopropylphenyl)methoxy]-1,3,4-thiadiazol-2-amine and 2-morpholinonicotinic acid. The mixture was diluted with water. The aqueous layer was extracted with EtOAc (3×). The combined organic layer was concentrated under reduced pressure. The residue was triturated with MeOH to afford N-(5-((4-cyclopropylbenzyl)oxy)-1,3,4-thiadiazol-2-yl)-2-morpholinonicotinamide as off-white solid. $^1$H NMR (300 MHz; DMSO-$d_6$): δ 0.61-0.71 (m, 2H), 0.96-0.99 (m, 2H), 1.89-1.98 (m, 1H), 3.21-3.24 (m, 4H), 3.65-3.68 (m, 4H), 5.43 (s, 2H), 6.97-7.01 (m, 1H), 7.10-7.13 (m, 2H), 7.37-7.40 (m, 2H), 7.89-7.92 (m, 1H), 8.34-8.37 (m, 1H), 12.85 (s, 1H) ppm. m/z 438 (M+H$^+$).

Example 48

Synthesis of $N^5$-(5-((4-chlorobenzyl)oxy)-1,3,4-thiadiazol-2-yl)-4-morpholinopyridine-2,5-dicarboxamide

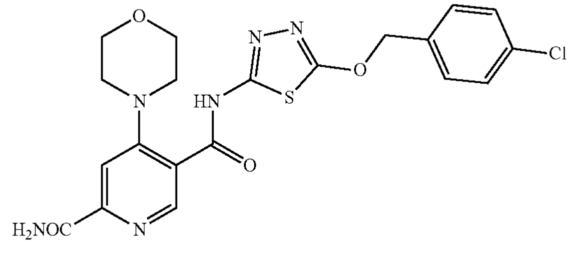 [SMILES: NC(=O)c1cc(N2CCOCC2)c(C(=O)Nc2nnc(OCc3ccc(Cl)cc3)s2)cn1]

The title compound was prepared using similar procedure as Example 21 employing N-(5-((4-chlorobenzyl)oxy)-1,3, 4-thiadiazol-2-yl)-6-cyano-4-morpholinonicotinamide, Example 35. The mixture was stirred at room temperature for 2 h. The mixture was cooled room temperature and diluted with water. The mixture was extracted with EtOAc (3×). The combined organic layers were concentrated under reduced pressure. The residue was purified by Prep-TLC with (DCM:MeOH, 35:1) to afford $N^5$-(5-((4-chlorobenzyl)oxy)-1,3,4-thiadiazol-2-yl)-4-morpholinopyridine-2,5-dicarboxamide as a yellow solid. $^1$H NMR (400 MHz; DMSO-$d_6$): δ 3.20 (s, 4H), 3.67 (s, 4H), 5.51 (s, 2H), 7.49-7.58 (m, 5H), 7.70-7.73 (m, 1H), 8.14-8.19 (m, 1H), 8.45 (s, 1H), 12.92-13.00 (br s, 1H) ppm. m/z 475 (M+H$^+$).

Example 49

Synthesis of N-(5-((4-chlorobenzyl)oxy)-1,3,4-thiadiazol-2-yl)-1-(3-methoxyphenyl)-1H-imidazole-5-carboxamide

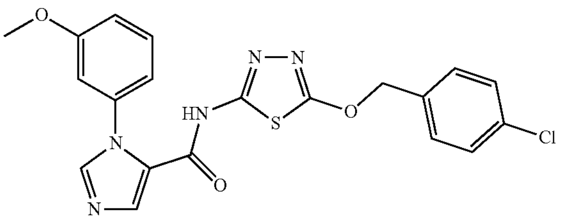 [SMILES: COc1cccc(-n2cncc2C(=O)Nc2nnc(OCc3ccc(Cl)cc3)s2)c1]

The title compound was prepared using similar procedure as Example 18, replacing 4-aminopyridine with 3-methoxyaniline in Step 1 and employing 5-((4-chlorobenzyl)oxy)-1,3,4-thiadiazol-2-amine (Intermediate B) in Step 2. The mixture was diluted with EtOAc and washed with water (2×). The organic layer was concentrated under reduced pressure. The residue was triturated with MeOH to afford N-(5-((4-chlorobenzyl)oxy)-1,3,4-thiadiazol-2-yl)-1-(3-methoxyphenyl)-1H-imidazole-5-carboxamide as an off-white solid. $^1$H NMR (300 MHz; DMSO-$d_6$): δ 3.78 (s, 3H), 5.47 (s, 2H), 6.95-7.01 (m, 3H), 7.36-7.53 (m, 5H), 8.12-8.16 (m, 2H), 12.80 (s, 1H) ppm. m/z 442 (M+H$^+$).

Example 50

Synthesis of N-(5-((4-chlorobenzyl)oxy)-1,3,4-thiadiazol-2-yl)-1-(2-methoxyphenyl)-1H-imidazole-5-carboxamide

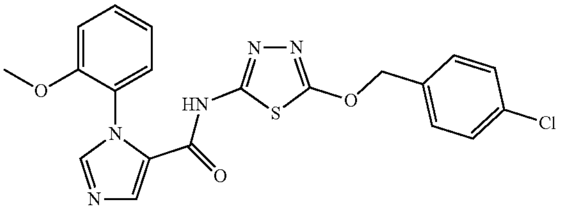 [SMILES: COc1ccccc1-n1cncc1C(=O)Nc1nnc(OCc2ccc(Cl)cc2)s1]

The title compound was prepared using similar procedure as Example 18, replacing 4-aminopyridine with 2-methoxyaniline in Step 1 and employing 5-((4-chlorobenzyl)oxy)-1,3,4-thiadiazol-2-amine (Intermediate B) in Step 2. The mixture was diluted with water and filtered. The solid was triturated with MeOH to afford N-(5-((4-chlorobenzyl)oxy)-1,3,4-thiadiazol-2-yl)-1-(2-methoxyphenyl)-1H-imidazole-5-carboxamide as an off-white solid. $^1$H NMR (400 MHz; DMSO-$d_6$): δ 3.64-3.66 (m, 3H), 5.44 (s, 2H), 7.02-7.07 (m, 1H), 7.15-7.17 (m, 1H), 7.34-7.36 (m, 1H), 7.41-7.52 (m, 5H), 7.97 (s, 1H), 8.09 (s, 1H), 12.71 (s, 1H) ppm. m/z 442 (M+H$^+$).

Example 51

Synthesis of 2-(2-chlorophenyl)-N-[5-[(5-chloropyridin-2-yl)methoxy]-1,3,4-thiadiazol-2-yl]pyridine-3-carboxamide

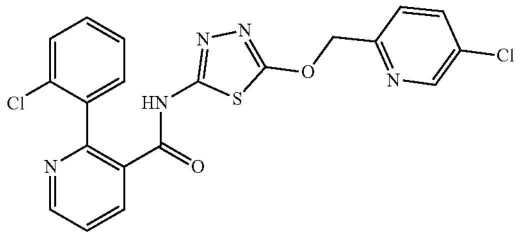 [SMILES: O=C(Nc1nnc(OCc2ccc(Cl)cn2)s1)c1cccnc1-c1ccccc1Cl]

Step 1. Preparation of methyl 2-(2-chlorophenyl)pyridine-3-carboxylate

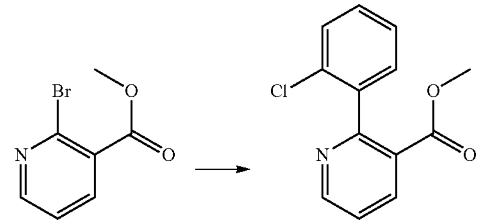 [SMILES: COC(=O)c1cccnc1Br ; COC(=O)c1cccnc1-c1ccccc1Cl]

The title compound was prepared using General Procedure E employing methyl 2-bromopyridine-3-carboxylate and 2-chlorophenylboronic acid. The mixture was cooled to rt and diluted with water. The mixture was extracted with EtOAc (3×). The combined organic layer was concentrated under reduce pressure. The residue was purified by silica gel column chromatography, eluted with 16% EtOAc in hexanes to afford methyl 2-(2-chlorophenyl)pyridine-3-carboxylate as a yellow solid.

Step 2. Preparation of 2-(2-chlorophenyl)pyridine-3-carboxylic acid

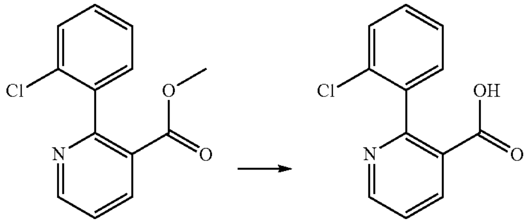 [SMILES: COC(=O)c1cccnc1-c1ccccc1Cl ; O=C(O)c1cccnc1-c1ccccc1Cl]

The title compound was prepared using General Procedure F employing methyl 2-(2-chlorophenyl)pyridine-3-carboxylate. The mixture was diluted with water and extracted with EtOAc (5×). The combined organic layers were concentrated under reduced pressure. The residue was purified by Prep-TLC (DCM:MeOH, 50:1) to afford 2-(2-chlorophenyl)pyridine-3-carboxylic acid as a white solid.

Step 3. Preparation of 2-(2-chlorophenyl)-N-[5-[(5-chloropyridin-2-yl)methoxy]-1,3,4-thiadiazol-2-yl]pyridine-3-carboxamide

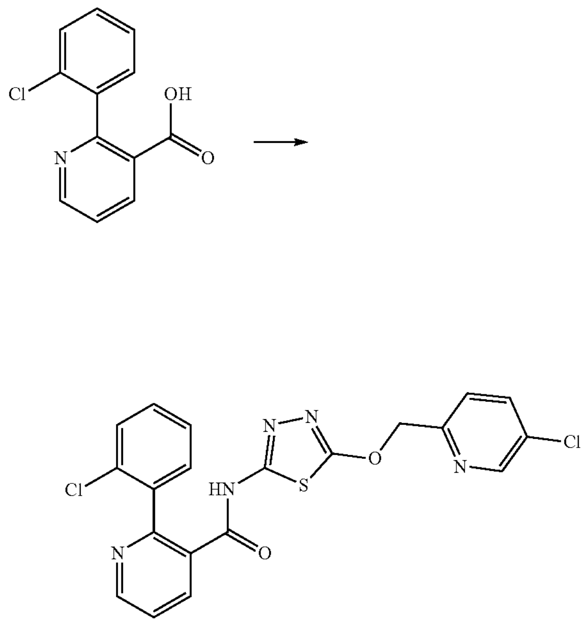

To a solution of 2-(2-chlorophenyl)pyridine-3-carboxylic acid (140 mg, 0.51 mmol) in DCM (1.4 mL) was added oxalyl chloride (98 mg, 0.77 mmol) and DMF (4 mg, 0.05 mmol) at room temperature. The mixture was stirred for 1 h. The mixture was concentrated under reduced pressure. The residue was dissolved in DCM (1.2 mL) and $Et_3N$ (130 mg, 1.3 mmol) and 5-((5-chloropyridin-2-yl)methoxy)-1,3,4-thiadiazol-2-amine (149 mg, 0.62 mmol, Intermediate C) were added. The mixture was stirred for 3 h at room temperature. The mixture was diluted with DCM was washed with water. The aqueous layer was extracted with EtOAc (3×). The combined organic layers were concentrated under reduced pressure. The residue was purified by Prep-TLC (DCM:MeOH, 50:1) to afford 2-(2-chlorophenyl)-N-[5-[(5-chloropyridin-2-yl)methoxy]-1,3,4-thiadiazol-2-yl]pyridine-3-carboxamide as a white solid. $^1H$ NMR (300 MHz; DMSO-$d_6$): δ 5.54 (s, 2H), 7.40-7.49 (m, 4H), 7.58-7.63 (m, 2H), 7.98-8.01 (m, 1H), 8.21-8.24 (m, 1H), 8.64-8.65 (m, 1H), 8.81-8.83 (m, 1H), 13.00 (s, 1H) ppm. m/z 458 ($M+H^+$).

Example 52

Synthesis of (R) N-(5-((4-chlorobenzyl)oxy)-1,3,4-thiadiazol-2-yl)-2-(2-methyl-3-oxopiperazin-1-yl)nicotinamide and (S) N-(5-((4-chlorobenzyl)oxy)-1,3,4-thiadiazol-2-yl)-2-(2-methyl-3-oxopiperazin-1-yl)nicotinamide

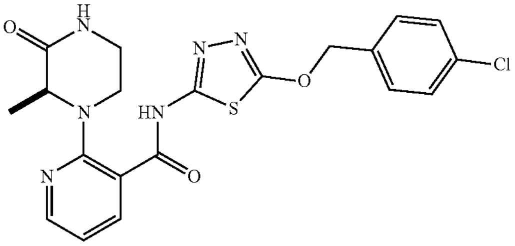

and

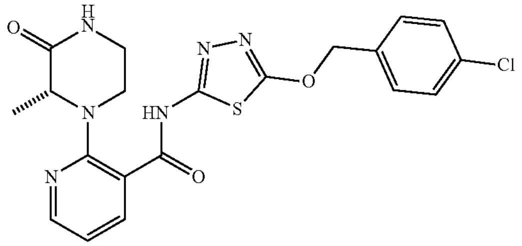

Step 1. Preparation of (R) 2-(2-methyl-3-oxopiperazin-1-yl)pyridine-3-carboxylic acid and (S) 2-(2-methyl-3-oxopiperazin-1-yl)pyridine-3-carboxylic acid

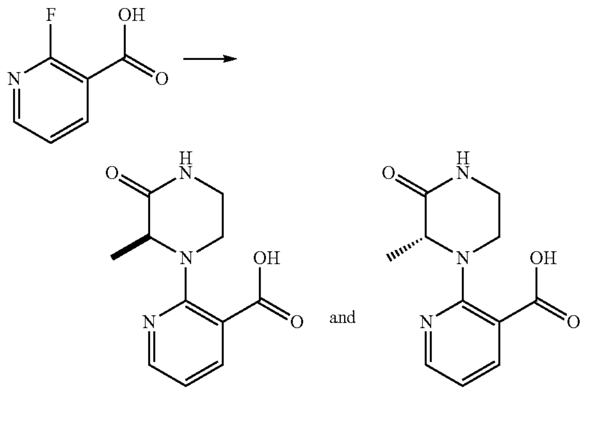

To a solution of 2-fluoropyridine-3-carboxylic acid (1.0 g, 7.1 mmol) in MeCN (10 mL) was added racemic 3-methylpiperazin-2-one (1618 mg, 14.2 mmol) and $Et_3N$ (1434 mg, 14.2 mmol). The mixture was stirred at 80° C. for 3 days. The mixture was cooled to room temperature and concentrated under reduce pressure. The residue was triturated with MeOH (5 mL) to afford a racemic mixture of (R) 2-(2-methyl-3-oxopiperazin-1-yl)pyridine-3-carboxylic acid and (S) 2-(2-methyl-3-oxopiperazin-1-yl)pyridine-3-carboxylic acid as a yellow solid.

Step 2. Preparation of (R) N-(5-((4-chlorobenzyl)oxy)-1,3,4-thiadiazol-2-yl)-2-(2-methyl-3-oxopiperazin-1-yl)nicotinamide and (S) N-(5-((4-chlorobenzyl)oxy)-1,3,4-thiadiazol-2-yl)-2-(2-methyl-3-oxopiperazin-1-yl)nicotinamide

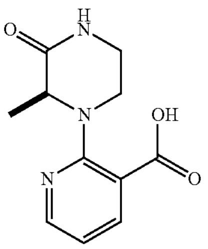

and

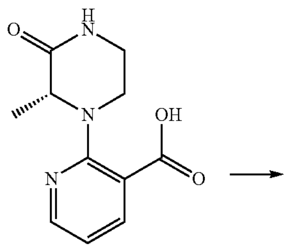

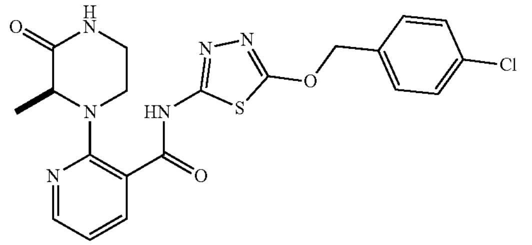

and

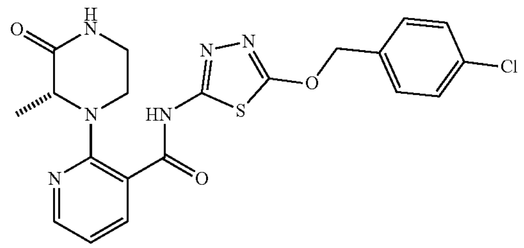

The title compound was prepared using General Procedure A employing a racemic mixture of (R) 2-(2-methyl-3-oxopiperazin-1-yl)pyridine-3-carboxylic acid and (S) 2-(2-methyl-3-oxopiperazin-1-yl)pyridine-3-carboxylic acid and 5-((4-chlorobenzyl)oxy)-1,3,4-thiadiazol-2-amine (Intermediate B). The mixture was stirred at 50° C. 4 h. The mixture was cooled room temperature and diluted with water. The mixture was extracted with EtOAc (3×). The combined organic layers were concentrated under reduced pressure. The residue was triturated with MeOH to afford a racemic mixture of (R) N-(5-((4-chlorobenzyl)oxy)-1,3,4-thiadiazol-2-yl)-2-(2-methyl-3-oxopiperazin-1-yl)nicotinamide and (S) N-(5-((4-chlorobenzyl)oxy)-1,3,4-thiadiazol-2-yl)-2-(2-methyl-3-oxopiperazin-1-yl)nicotinamide as a yellow solid. $^1$H NMR (300 MHz; DMSO-$d_6$): δ 1.24-1.32 (m, 3H), 3.10-3.14 (m, 1H), 3.35-3.41 (m, 2H), 3.51-3.57 (m, 1H), 4.25-4.32 (m, 1H), 5.51 (s, 2H), 6.93-6.98 (m, 1H), 7.48-7.57 (m, 4H), 7.86-7.89 (m, 2H), 8.32-8.35 (m, 1H), 12.97 (s, 1H) ppm. m/z 459 (M+H$^+$).

Example 53

Synthesis of N-(5-((4-chlorobenzyl)oxy)-1,3,4-thiadiazol-2-yl)-2-(3,6-dihydro-2H-pyran-4-yl)nicotinamide

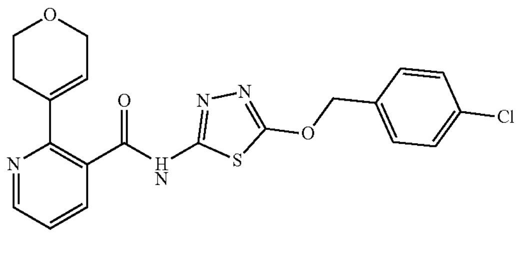 [SMILES: O=C(Nc1nnc(OCc2ccc(Cl)cc2)s1)c1cccnc1C1=CCOCC1]

Step 1. Preparation of methyl 2-(3,6-dihydro-2H-pyran-4-yl)pyridine-3-carboxylate

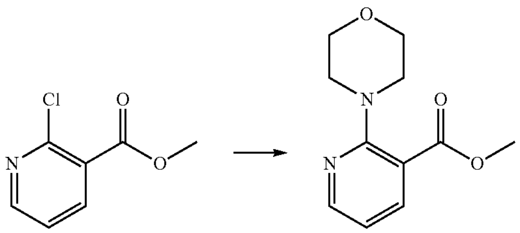 [SMILES: COC(=O)c1cccnc1Cl ; COC(=O)c1cccnc1N1CCOCC1]

The title compound was prepared using General Procedure E employing methyl 2-chloropyridine-3-carboxylate and 2-(3,6-dihydro-2H-pyran-4-yl)-4,4,5,5-tetramethyl-1,3,2-dioxaborolane. The mixture was stirred at 100° C. for 3 h. The mixture was cooled room temperature and diluted with water. The mixture was extracted with EtOAc (4×). The combined organic layers were concentrated under reduced pressure. The residue was purified by silica gel column chromatography, eluted with 33% EtOAc in PE to afford methyl 2-(3,6-dihydro-2H-pyran-4-yl)pyridine-3-carboxylate as yellow oil.

Step 2. Preparation of 2-(3,6-dihydro-2H-pyran-4-yl)nicotinic acid

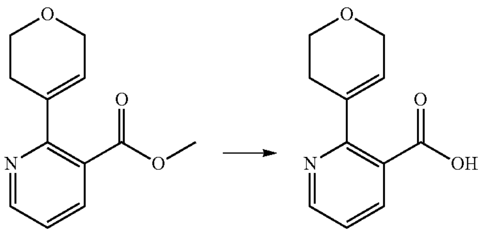 [SMILES: COC(=O)c1cccnc1C1=CCOCC1 ; O=C(O)c1cccnc1C1=CCOCC1]

The title compound was prepared using General Procedure F employing methyl 2-(3,6-dihydro-2H-pyran-4-yl)pyridine-3-carboxylate. The mixture was stirred at room temperature for 5 h and then diluted with water. The mixture was extracted with EtOAc (3×). The aqueous layer was neutralized to pH 6 with HOAc and the mixture was extracted with EtOAc (5×). The combined organic layers were concentrated under reduced pressure. The residue was purified using Prep-HPLC (column, $C_{18}$ silica gel; mobile phase, 10-50% MeCN in water, with both eluents containing 0.05% TFA) to afford 2-(3,6-dihydro-2H-pyran-4-yl)nicotinic acid as light-yellow oil.

Step 3. Preparation of N-(5-((4-chlorobenzyl)oxy)-1,3,4-thiadiazol-2-yl)-2-(3,6-dihydro-2H-pyran-4-yl) nicotinamide

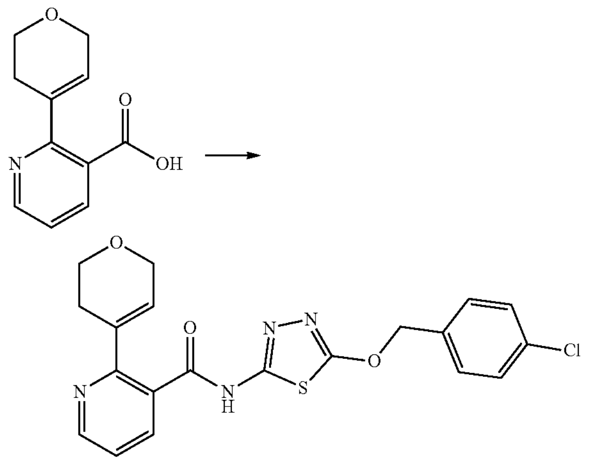

The title compound was prepared using General Procedure A employing 2-(3,6-dihydro-2H-pyran-4-yl)nicotinic acid and 5-((4-chlorobenzyl)oxy)-1,3,4-thiadiazol-2-amine (Intermediate B). The mixture was diluted with water. The mixture was extracted with EtOAc (2×). The combined organic layers were concentrated under reduced pressure. The residue was triturated with MeOH to afford N-(5-((4-chlorobenzyl)oxy)-1,3,4-thiadiazol-2-yl)-2-(3,6-dihydro-2H-pyran-4-yl)nicotinamide as a white solid. $^1$H NMR (400 MHz; DMSO-$d_6$): δ 2.51-2.54 (m, 2H), 3.75-3.78 (m, 2H), 4.06-4.07 (m, 2H), 5.50 (s, 2H), 5.92 (s, 1H), 7.39-7.43 (m, 1H), 7.46-7.57 (m, 4H), 7.93-7.96 (m, 1H), 8.66-8.69 (m, 1H), 12.89 (s, 1H) ppm. m/z 429 (M+H$^+$).

Example 54

Synthesis of N-[5-[(4-chlorophenyl)methoxy]-1,3,4-thiadiazol-2-yl]-2-(oxan-4-yl)pyridine-3-carboxamide

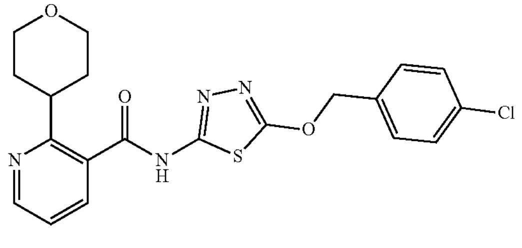

Step 1. Preparation of 2-(oxan-4-yl)pyridine-3-carboxylic acid

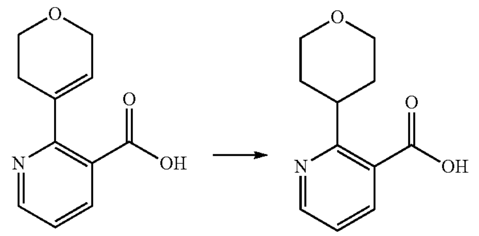 [SMILES: O=C(O)c1cccnc1C1=CCOCC1 ; O=C(O)c1cccnc1C1CCOCC1]

To a solution of 2-(3,6-dihydro-2H-pyran-4-yl)nicotinic acid (180 mg, 0.88 mmol, Example 53, Step 2), in MeOH (22 mL) was added 20% Pd/C (36 mg). The mixture was stirred at room temperature under hydrogen for 9 h. The mixture was filtered over celite and the filtrate was concentrated under reduced pressure to afford 2-(oxan-4-yl)pyridine-3-carboxylic acid as light-yellow oil.

Step 2. Preparation of N-[5-[(4-chlorophenyl) methoxy]-1,3,4-thiadiazol-2-yl]-2-(oxan-4-yl)pyridine-3-carboxamide

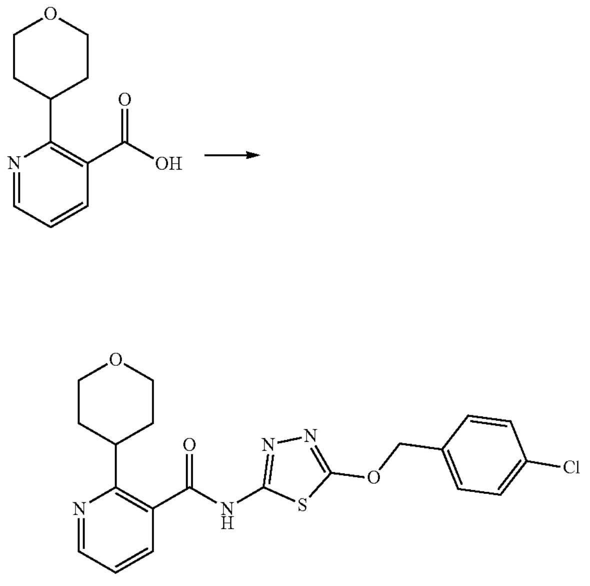 [SMILES: O=C(O)c1cccnc1C1CCOCC1 ; O=C(Nc1nnc(OCc2ccc(Cl)cc2)s1)c1cccnc1C1CCOCC1]

The title compound was prepared using General Procedure A employing 2-(oxan-4-yl)pyridine-3-carboxylic acid and 5-((4-chlorobenzyl)oxy)-1,3,4-thiadiazol-2-amine (Intermediate B). The mixture was diluted with water. The mixture was extracted with EtOAc (2×). The combined organic layers were concentrated under reduced pressure. The residue was purified by Prep-TLC (DCM:MeOH, 100.1) to afford N-[5-[(4-chlorophenyl)methoxy]-1,3,4-thiadiazol-2-yl]-2-(oxan-4-yl)pyridine-3-carboxamide as a white solid. $^1$H NMR (300 MHz; DMSO-$d_6$): δ 1.62-1.65 (m, 2H), 1.84-1.98 (m, 2H), 3.17-3.22 (m, 1H), 3.37-3.40 (m, 2H), 3.89-3.94 (m, 2H), 5.52 (s, 2H), 7.35-7.40 (m, 1H), 7.49-7.58 (m, 4H), 7.94-7.97 (m, 1H), 8.68-8.71 (m, 1H), 12.98 (s, 1H) ppm. m/z 431 (M+H$^+$).

Example 55

Synthesis of N-(5-((4-chlorobenzyl)oxy)-1,3,4-thiadiazol-2-yl)-1-(tetrahydro-2H-pyran-4-yl)-1H-imidazole-5-carboxamide

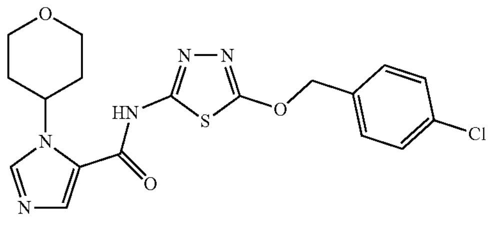 [SMILES: O=C(Nc1nnc(OCc2ccc(Cl)cc2)s1)c1cncn1C1CCOCC1]

Step 1. Preparation of 1-(tetrahydro-2H-pyran-4-yl)-1H-imidazole-5-carboxylic acid

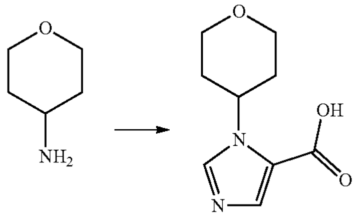 [SMILES: NC1CCOCC1 ; O=C(O)c1cncn1C1CCOCC1]

The title compound was prepared using similar procedure as Example 12, Steps 1-2 replacing p-Anisidine in Step 1 with oxan-4-amine.

Step 2. Preparation of N-(5-((4-chlorobenzyl)oxy)-1,3,4-thiadiazol-2-yl)-1-(tetrahydro-2H-pyran-4-yl)-1H-imidazole-5-carboxamide

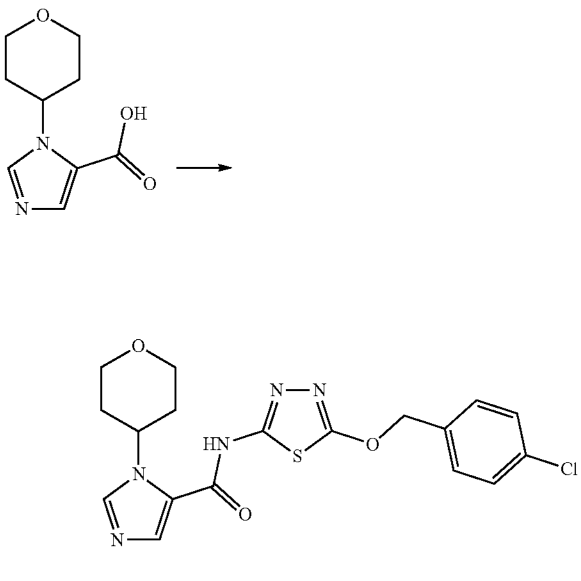 [SMILES: O=C(O)c1cncn1C1CCOCC1 ; O=C(Nc1nnc(OCc2ccc(Cl)cc2)s1)c1cncn1C1CCOCC1]

To a solution of 1-(tetrahydro-2H-pyran-4-yl)-1H-imidazole-5-carboxylic acid (110 mg, 0.61 mmol) in DCM (1.1 mL) was added DMF (4.5 mg, 0.06 mmol) and then oxalyl chloride (85 mg, 0.63 mmol) was added dropwise at room temperature under nitrogen. Following the addition, the mixture was concentrated under reduce pressure. The yellow solid was diluted with DCM (1.2 mL) and $Et_3N$ (113 mg, 1.1 mmol) and 5-((4-chlorobenzyl)oxy)-1,3,4-thiadiazol-2-amine (120 mg, 0.56 mmol, Intermediate B) were added at room temperature under nitrogen. The mixture was stirred at room temperature for 4 h. The mixture was diluted with water. The mixture was extracted with EtOAc (2×). The combined organic layers were concentrated under reduced pressure. The residue was triturated with MeOH (1 mL) to afford N-(5-((4-chlorobenzyl)oxy)-1,3,4-thiadiazol-2-yl)-1-(tetrahydro-2H-pyran-4-yl)-1H-imidazole-5-carboxamide as a white solid. $^1H$ NMR (300 MHz; DMSO-$d_6$): δ 1.89-1.98 (m, 4H), 3.40-3.49 (m, 2H), 3.95-3.99 (m, 2H), 5.05-5.10 (m, 1H), 5.50 (s, 2H), 7.47-7.56 (m, 4H), 8.10 (s, 1H), 8.23 (s, 1H), 12.67-12.79 (br s, 1H) ppm. m/z 420 ($M+H^+$).

Example 56

Synthesis of 2-morpholino-N-(5-((4-(oxetan-3-yl)benzyl)oxy)-1,3,4-thiadiazol-2-yl)nicotinamide

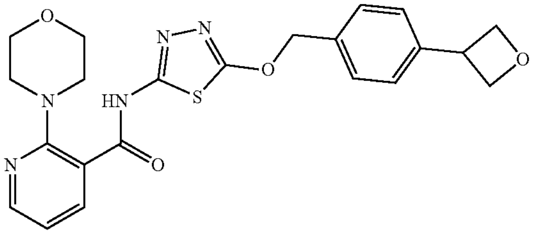 [SMILES: O=C(Nc1nnc(OCc2ccc(C3COC3)cc2)s1)c1cccnc1N1CCOCC1]

Step 1. Preparation of ((4-bromobenzyl)oxy)(tert-butyl)diphenylsilane

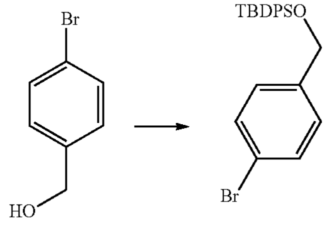

To a solution of p-bromobenzyl alcohol (5 g, 26.88 mmol) in THF (10 mL) was added imidazole (182.0 mg, 0.2688 mmol) and TBDPSCl (8.08 g, 29.57 mmol) under nitrogen. The mixture was stirred at room temperature overnight. The mixture was diluted with water and extracted with DCM (3×). The combined organic layers were concentrated under reduced pressure to afford ((4-bromobenzyl)oxy)(tert-butyl)diphenylsilane as a solid. The material was used in the next step without further purification.

Step 2. Preparation of tert-butyl((4-oxetan-3-yl)benzyl)oxy)diphenylsilane

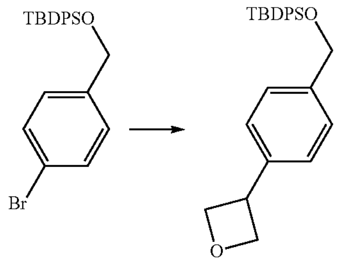

((4-Bromobenzyl)oxy)(tert-butyl)diphenylsilane (500 mg, 1.2 mmol), 3-iodooxetane (732 mg, 5.3 mmol), [Ir(dtbbpy)(ppy)$_2$][PF$_6$] (43 mg, 0.047 mmol), tris(trimethylsilyl)silane (532 mg, 2.4 mmol) and $Na_2CO_3$ (450 mg, 4.2 mmol) were combined and purged with nitrogen. Then DME (20 mL) was added. In a separate vial 4,4'-Di-tert-butyl-2,2-bipyridine (12 mg, 0.043 mmol), nickel(II) chloride (5 mg, 0.036 mmol) and 1,2-dimethoxyethane (9 mg, 0.039 mmol) were combined and purged with nitrogen and diluted with DME (10 mL). The mixture was stirred at room temperature for 20 min and then added into the Ir solution. The mixture was degassed with bubbling nitrogen for 10 minutes and then sealed. The mixture was stirred under 50 W blue LED lamp (7 cm away, with cooling fan to maintain 25° C.) for 3.5 days. The mixture was diluted with EtOAc (50 mL) and washed with water (20 mL×2). The organic layer was concentrated under reduce pressure and the residue was purified by Prep-TLC (PE:EtOAc, 4:1) to afford tert-butyl((4-(oxetan-3-yl)benzyl)oxy)diphenylsilane as a light yellow solid.

Step 3. Preparation of (4-(oxetan-3-yl)phenyl)methanol

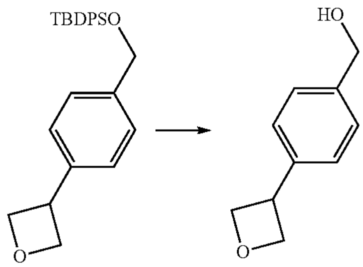

To a solution of tert-butyl([[4-(oxetan-3-yl)phenyl]methoxy])diphenylsilane (300 mg, 0.72 mmol) in THF (6 mL) was added TBAF (564 mg, 2.2 mmol). The mixture was stirred at room temperature for 40 minutes. The mixture was diluted with EtOAc (30 mL), washed with brine (3×5 mL) and concentrated under reduce pressure. The residue was purified by Prep-TLC (PE:EtOAc, 1:1) to afford (4-(oxetan-3-yl)phenyl)methanol as colorless oil.

Step 4. Preparation of S-methyl 0-(4-(oxetan-3-yl)benzyl) carbonodithioate

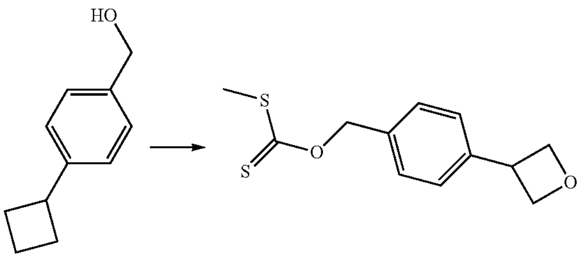 [SMILES: OCc1ccc(C2CCC2)cc1 ; CSC(=S)OCc1ccc(C2COC2)cc1]

To a solution of (4-(oxetan-3-yl)phenyl)methanol (80 mg, 0.49 mmol) in THF (5 mL) at 0° C. was added NaH (39 mg, 0.97 mmol, 60% dispersion in oil). The mixture was stirred at 0° C. for 20 min and then $CS_2$ (45 mg, 0.59 mmol) was added. The mixture was stirred at 0° C. for 10 min and then MeI (83 mg, 0.59 mmol) was added. The mixture was diluted with sat. $NH_4Cl$ (5 mL) and extracted with EtOAc (3×5 mL). The combined organic layers were concentrated under reduced pressure. The residue was purified by silica gel column chromatography, eluted with 9% EtOAc in hexanes to afford S-methyl 0-(4-(oxetan-3-yl)benzyl) carbonodithioate as a white solid.

Step 5. Preparation of 5-((4-(oxetan-3-yl)benzyl)oxy)-1,3,4-thiadiazol-2-amine

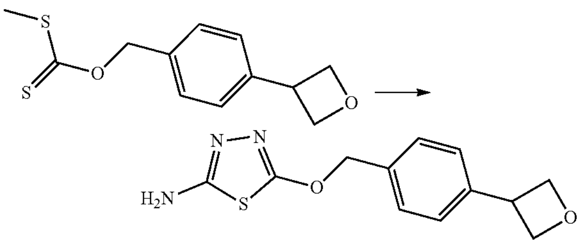

The title compound was prepared using similar procedure as Intermediate B, Step 2, replacing O-(4-chlorobenzyl) S-methyl carbonodithioate with S-methyl O-(4-(oxetan-3-yl)benzyl) carbonodithioate Step 6. Preparation of 2-morpholino-N-(5-((4-(oxetan-3-yl)benzyl)oxy)-1,3,4-thiadiazol-2-yl)nicotinamide

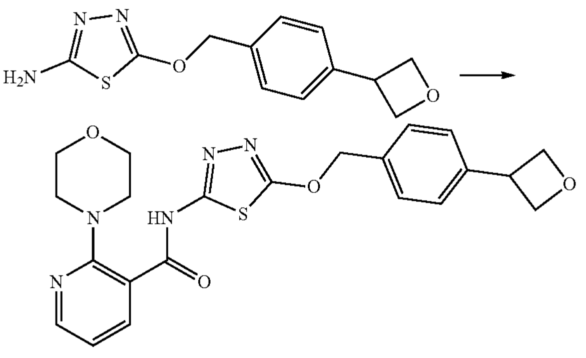

The title compound was prepared using General Procedure A employing 2-(morpholin-4-yl)pyridine-3-carboxylic acid and 5-((4-(oxetan-3-yl)benzyl)oxy)-1,3,4-thiadiazol-2-amine. The mixture was diluted with water and extracted with DCM (3×). The combined organic layers were purified by Prep-HPLC [column, XBridge Prep OBD $C_{18}$; mobile phase, 20-40% MeCN in (0.05% $NH_4OH$ in water)] to afford 2-morpholino-N-(5-((4-(oxetan-3-yl)benzyl)oxy)-1,3,4-thiadiazol-2-yl)nicotinamide as a white solid. $^1$H NMR (400 MHz; DMSO-$d_6$): δ 3.22-3.25 (m, 4H), 3.66-3.68 (m, 4H), 4.24-4.32 (m, 1H), 4.61-4.64 (m, 2H), 4.94-4.97 (m, 2H), 5.50 (s, 2H), 6.98-7.01 (m, 1H), 7.45-7.54 (m, 4H), 7.90-7.92 (m, 1H), 8.35-8.37 (m, 1H), 12.88 (s, 1H) ppm. m/z 454 (M+H$^+$).

Example 57

Synthesis of (R) N-(5-((4-chlorobenzyl)oxy)-1,3,4-thiadiazol-2-yl)-2-(6-oxohexahydropyrrolo[1,2-a]pyrazin-2(1H)-yl)nicotinamide and (S) N-(5-((4-chlorobenzyl)oxy)-1,3,4-thiadiazol-2-yl)-2-(6-oxohexahydropyrrolo[1,2-a]pyrazin-2(1H)-yl)nicotinamide

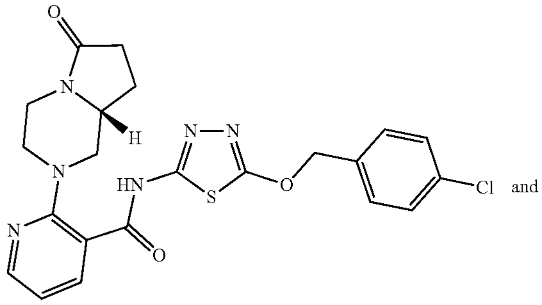

and

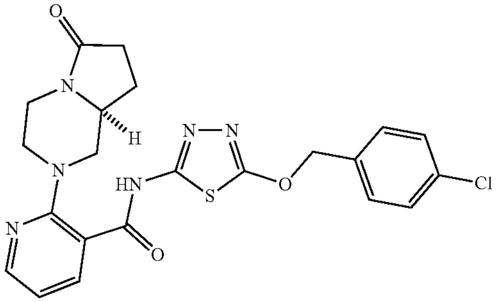

To a solution of racemic hexahydro-1H-pyrrolo[1,2-a]pyrazin-6-one (110 mg, 0.78 mmol) and N-[5-[(4-chlorophenyl)methoxy]-1,3,4-thiadiazol-2-yl]-2-fluoropyridine-3-carboxamide (200 mg, 0.55 mmol, Intermediate D) in NMP (1.5 mL) was added DIEA (202 mg, 1.6 mmol) under nitrogen. The mixture was stirred at 60° C. overnight. The mixture was diluted with water. The mixture was extracted with EtOAc (2×). The combined organic layers were washed with water (2×) and concentrated under reduced pressure. The residue was purified by Prep-TLC (DCM:MeOH, 20:1) to afford a racemic mixture of (R) N-(5-((4-chlorobenzyl)oxy)-1,3,4-thiadiazol-2-yl)-2-(6-oxohexahydropyrrolo[1,2-a]pyrazin-2(1H)-yl)nicotinamide and (S) N-(5-((4-chlorobenzyl)oxy)-1,3,4-thiadiazol-2-yl)-2-(6-oxohexahydropyrrolo[1,2-a]pyrazin-2(1H)-yl)nicotinamide as a white solid. $^1$H NMR (300 MHz; DMSO-$d_6$): δ 1.52-1.59 (m, 1H), 2.03-2.09 (m, 1H), 2.22-2.30 (m, 2H), 2.61-2.68 (m, 1H), 2.73-2.85 (m, 2H), 3.61-3.68 (m, 2H), 3.78-3.84 (m, 2H), 5.51 (s, 2H), 6.99-7.03 (m, 1H), 7.48-7.58 (m, 4H), 7.91-7.94 (m, 1H), 8.35-8.37 (m, 1H), 12.85 (s, 1H) ppm. m/z 485 (M+H$^+$).

Example 58

Synthesis of 6-bromo-N-(5-((4-chlorobenzyl)oxy)-1,3,4-thiadiazol-2-yl)-2-morpholinonicotinamide

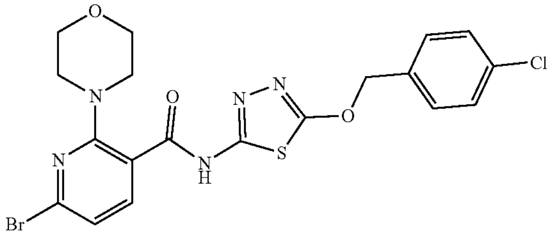 [SMILES: O=C(Nc1nnc(OCc2ccc(Cl)cc2)s1)c1ccc(Br)nc1N1CCOCC1]

The title compound was prepared using General Procedure A employing 6-bromo-2-morpholinonicotinic acid (Step 1, Example 14) and 5-((4-chlorobenzyl)oxy)-1,3,4-thiadiazol-2-amine (Intermediate B). The mixture was diluted with water and extracted with EtOAc (3×). The combined organic layers were concentrated under reduce pressure. The residue was triturated with DCM:MeOH, 10:1 to afford 6-bromo-N-(5-((4-chlorobenzyl)oxy)-1,3,4-thiadiazol-2-yl)-2-morpholinonicotinamide as a white solid. $^1$H NMR (300 MHz; DMSO-$d_6$): δ 3.26-3.32 (m, 4H), 3.61-3.64 (m, 4H), 5.50 (s, 2H), 7.06-7.09 (m, 1H), 7.47-7.56 (m, 4H), 7.72-7.75 (m, 1H), 12.83 (s, 1H) ppm. m/z 512 (M+H$^+$).

Example 59

Synthesis of N-(5-((4-chlorobenzyl)oxy)-1,3,4-thiadiazol-2-yl)-3-morpholinoisonicotinamide

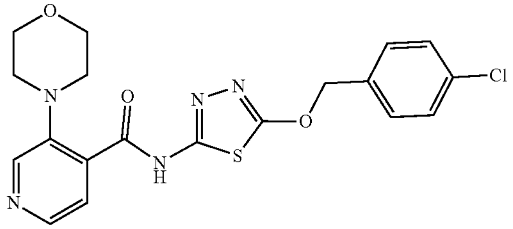 [SMILES: O=C(Nc1nnc(OCc2ccc(Cl)cc2)s1)c1ccncc1N1CCOCC1]

Step 1: Preparation of 3-morpholinoisonicotinic acid

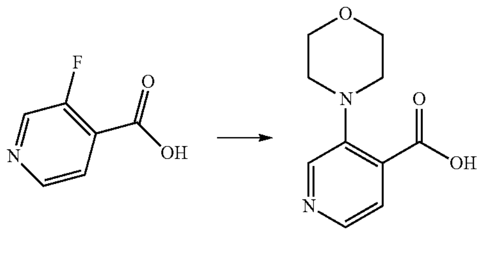 [SMILES: O=C(O)c1ccncc1F ; O=C(O)c1ccncc1N1CCOCC1]

To a solution of 3-fluoroisonicotinic acid (1 eq.) and morpholine (1.2 eq.) in THF at −78° C. was slowly added a solution of LiHMDS (3 eq., 1 M in THF). The mixture was slowly warm to room temperature and stirred for an additional 18 h. The mixture was quenched with 4M HCl in dioxane and the mixture was concentrated under reduced pressure. The residue was purified by flash chromatography, eluted with 0-12% MeOH in DCM to afford 3-morpholinoisonicotinic acid an orange solid. $^1$H NMR (400 MHz, DMSO-$d_6$) δ 14.11 (s, 1H), 8.55 (d, J=1.7 Hz, 1H), 8.34 (dd, J=4.9, 1.7 Hz, 1H), 7.53 (dd, J=4.9, 1.7 Hz, 1H), 3.80-3.68 (m, 4H), 3.16-3.03 (m, 4H).

Step 2. Preparation of N-(5-((4-chlorobenzyl)oxy)-1,3,4-thiadiazol-2-yl)-3-morpholino-isonicotinamide

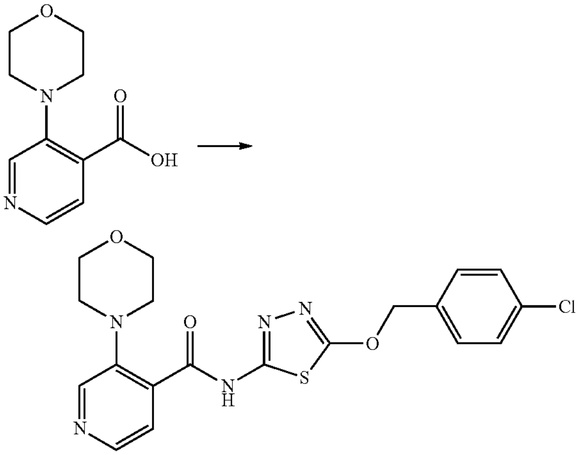

The title compound was prepared using General Procedure D employing 3-morpholinoisonicotinic acid and 5-((4-chlorobenzyl)oxy)-1,3,4-thiadiazol-2-amine (Intermediate B). The mixture was diluted with water and extracted with EtOAc (3×). The combined organic layers were concentrated under reduce pressure. The residue was purified by reverse phase HPLC (column, C18 silica gel; mobile phase, 0-100% MeCN in water, with both eluents containing 0.1% FA) to afford N-(5-((4-chlorobenzyl)oxy)-1,3,4-thiadiazol-2-yl)-3-morpholinoisonicotinamide as a white solid. $^1$H NMR (400 MHz, DMSO-$d_6$) δ 13.48 (s, 1H), 8.65 (s, 1H), 8.54-8.36 (m, 1H), 7.69-7.60 (m, 1H), 7.56 (dd, J=8.5, 1.9 Hz, 2H), 7.49 (dd, J=8.6, 2.0 Hz, 2H), 5.51 (s, 2H), 3.73 (t, J=4.3 Hz, 4H), 3.08 (t, J=4.2 Hz, 4H) ppm. m/z 432 (M+H$^+$).

Example 60

Synthesis of (R) N-(5-((4-chlorobenzyl)oxy)-1,3,4-thiadiazol-2-yl)-2-(2-methyl-5-oxopiperazin-1-yl) nicotinamide and (S) N-(5-((4-chlorobenzyl)oxy)-1,3,4-thiadiazol-2-yl)-2-(2-methyl-5-oxopiperazin-1-yl)nicotinamide

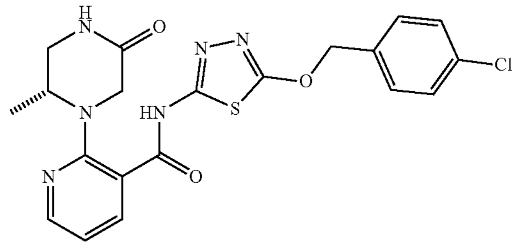

and

-continued

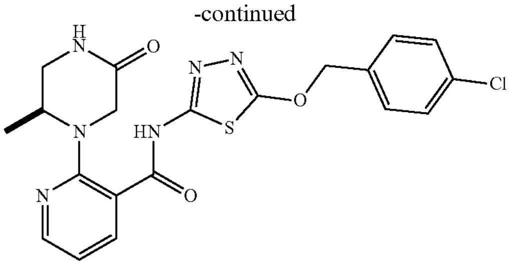

The title compound was prepared using similar procedure as Example 7, Steps 1-2, replacing racemic 2-methylmorpholine in Step 1 with racemic 5-methylpiperazin-2-one hydrochloride. The mixture was diluted with water. The mixture was extracted with EtOAc (2×). The combined organic layers were concentrated under reduced pressure. The residue was purified by Prep-TLC (DCM:MeOH, 50:1) to afford a racemic mixture of (R) N-(5-((4-chlorobenzyl)oxy)-1,3,4-thiadiazol-2-yl)-2-(2-methyl-5-oxopiperazin-1-yl)nicotinamide and (S) N-(5-((4-chlorobenzyl)oxy)-1,3,4-thiadiazol-2-yl)-2-(2-methyl-5-oxopiperazin-1-yl) nicotinamide as a white solid. $^1$H NMR (300 MHz; DMSO-$d_6$): δ 1.09-1.11 (m, 3H), 2.97-3.06 (m, 1H), 3.36-3.42 (m, 1H), 3.66-3.81 (m, 2H), 4.08-4.10 (m, 1H), 5.50 (s, 2H), 6.92-7.02 (m, 1H), 7.47-7.57 (m, 4H), 7.86-7.96 (m, 2H), 8.31-8.38 (m, 1H), 12.86 (s, 1H) ppm. m/z 459 (M+H$^+$).

Example 61

Synthesis of N-(5-((4-chlorobenzyl)oxy)-1,3,4-thiadiazol-2-yl)-2-(5-oxo-1,4-diazepan-1-yl)nicotinamide

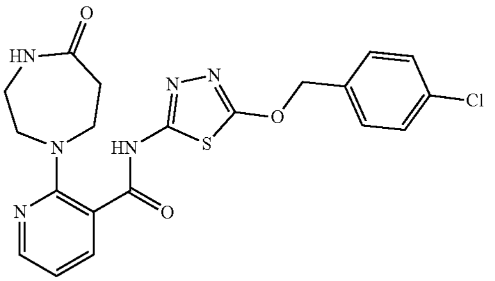 [SMILES: O=C1CCN(c2ncccc2C(=O)Nc2nnc(OCc3ccc(Cl)cc3)s2)CCN1]

To a solution of N-[5-[(4-chlorophenyl)methoxy]-1,3,4-thiadiazol-2-yl]-2-fluoropyridine-3-carboxamide (200 mg, 0.55 mmol, Intermediate D) in MeCN (2.0 mL), was added 1,4-diazepan-5-one (69 mg, 0.60 mmol) and $Et_3N$ (111 mg, 1.1 mmol) under nitrogen. The mixture was stirred at 60° C. overnight. The mixture was cooled to room temperature and diluted with water. The mixture was filtered and the solid was washed with MeOH (2 mL) to afford N-(5-((4-chlorobenzyl)oxy)-1,3,4-thiadiazol-2-yl)-2-(5-oxo-1,4-diazepan-1-yl)nicotinamide as a white solid. $^1$H NMR (400 MHz; DMSO-$d_6$): δ 2.56-2.58 (m, 4H), 3.20-3.25 (m, 2H), 3.51 (s, 2H), 5.50 (s, 2H), 6.87-6.91 (m, 1H), 7.45-7.57 (m, 5H), 7.83-7.88 (m, 1H), 8.28-8.30 (m, 1H), 12.84 (s, 1H) ppm. m/z 459 (M+H$^+$).

Example 62

Synthesis of N-(5-((4-cyclopropylbenzyl)oxy)-1,3,4-thiadiazol-2-yl)-1-(2-methoxyphenyl)-1H-imidazole-5-carboxamide

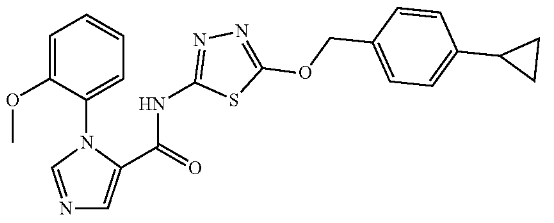 [SMILES: COc1ccccc1-n1cncc1C(=O)Nc1nnc(OCc2ccc(C3CC3)cc2)s1]

The title compound was prepared using similar procedure as Example 50 employing 5-[(4-cyclopropylphenyl)methoxy]-1,3,4-thiadiazol-2-amine (Example 47, Step 1) in Step 2. The mixture was diluted with water and extracted with DCM. The combined organic layers were concentrated under reduced pressure. The residue was triturated with MeOH to afford N-(5-((4-cyclopropylbenzyl)oxy)-1,3,4-thiadiazol-2-yl)-1-(2-methoxyphenyl)-1H-imidazole-5-carboxamide as a white solid. $^1$H NMR (300 MHz; DMSO-$d_6$): δ 0.62-0.66 (m, 2H), 0.94-0.98 (m, 2H), 1.87-1.96 (m, 1H), 3.66 (s, 3H), 5.39 (s, 2H), 7.03-7.11 (m, 3H), 7.16-7.18 (m, 1H), 7.33-7.37 (m, 3H), 7.42-7.48 (m, 1H), 7.95-7.98 (m, 1H), 8.10 (s, 11H), 12.62-12.71 (br s, 11H) ppm. m/z 448 (M+H$^+$).

Example 63

Synthesis of N-(5-((4-chlorobenzyl)oxy)-1,3,4-thiadiazol-2-yl)-2-(3-oxo-1,4-diazepan-1-yl)nicotinamide

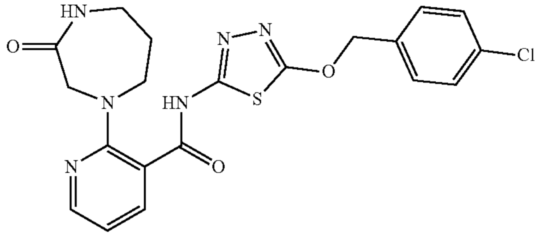 [SMILES: O=C1CN(c2ncccc2C(=O)Nc2nnc(OCc3ccc(Cl)cc3)s2)CCCN1]

The title compound was prepared using similar procedure as Example 61, replacing 1,4-diazepan-5-one with 1,4-diazepan-2-one. The mixture was cooled room temperature and diluted with EtOAc. The mixture was washed with water. The combined organic layer was concentrated under reduced pressure. The residue was purified by Prep-TLC (DCM:MeOH, 10:1). The residue was further triturated with MeOH to afford N-(5-((4-chlorobenzyl)oxy)-1,3,4-thiadiazol-2-yl)-2-(3-oxo-1,4-diazepan-1-yl)nicotinamide as a white solid. $^1$H NMR (400 MHz; DMSO-$d_6$): δ 1.90 (s, 2H), 2.96-2.97 (m, 2H), 3.36-3.39 (m, 2H), 4.02 (s, 2H), 5.49 (s, 2H), 6.82-6.86 (m, 1H), 7.41 (s, 1H), 7.47-7.56 (m, 4H), 7.78-7.84 (m, 1H), 8.22-8.27 (m, 1H), 12.74 (s, 1H) ppm. m/z 459 (M+H$^+$).

Example 64

Synthesis of N$^5$-(5-((4-chlorobenzyl)oxy)-1,3,4-thiadiazol-2-yl)-N2-methyl-4-morpholinopyridine-2,5-dicarboxamide

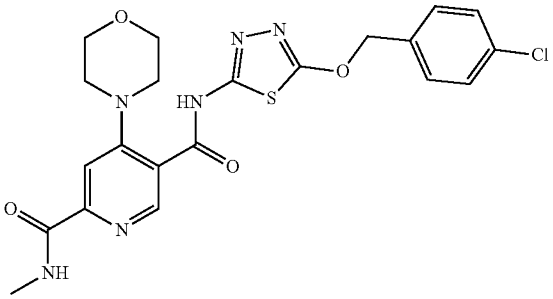 [SMILES: CNC(=O)c1cc(N2CCOCC2)c(C(=O)Nc2nnc(OCc3ccc(Cl)cc3)s2)cn1]

Step 1. Preparation of ethyl 6-(methylcarbamoyl)-4-morpholinonicotinate

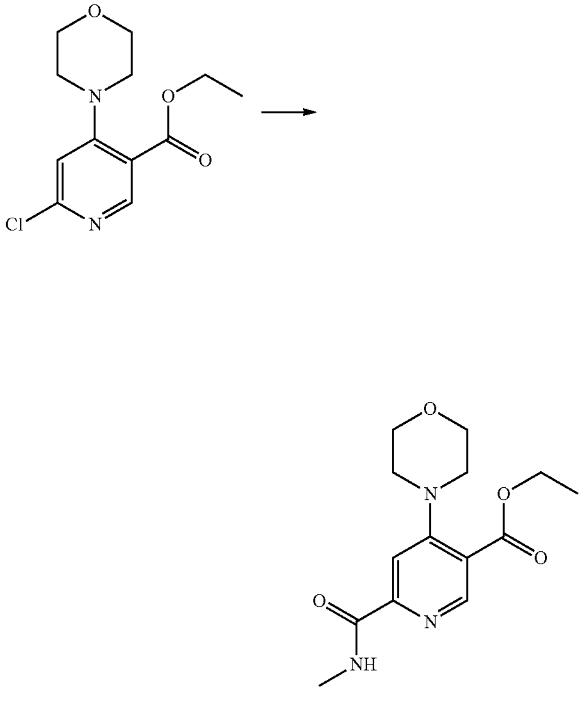

To a solution of ethyl 6-chloro-4-(morpholin-4-yl)pyridine-3-carboxylate (1.5 g, 5.5 mmol, Example 35, Step 1) in THF (15 mL) was added $Et_3N$ (1.1 g, 11.1 mmol), methylamine (2.80 mL, 5.6 mmol, 2 M in THF) and Pd(dppf)$Cl_2$ (405 mg, 0.55 mmol). The mixture was stirred at 110° C. for 4 h under CO (20 atm). The mixture was cooled room temperature and diluted with water. The mixture was extracted with EtOAc (5×). The combined organic layers were concentrated under reduced pressure. The residue was purified by Prep-TLC (DCM:MeOH, 50:1) to afford ethyl 6-(methylcarbamoyl)-4-morpholinonicotinate as a red solid.

Step 2. Preparation of 6-(methylcarbamoyl)-4-morpholinonicotinic acid

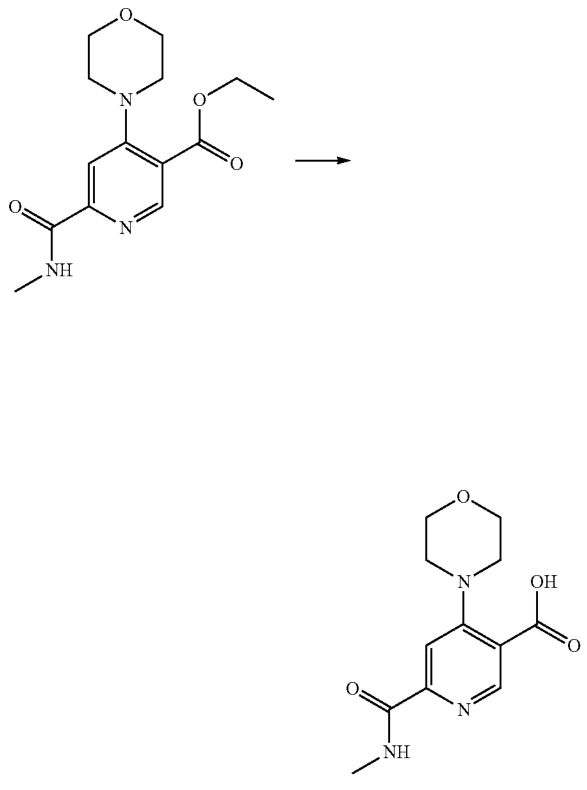

To a solution of ethyl 6-(methylcarbamoyl)-4-morpholinonicotinate (310 mg, 1.0 mmol) in MeOH (3 mL) and water (3 mL) was added NaOH (204 mg, 5.1 mmol. The mixture was stirred at room temperature overnight. The mixture was acidified to pH 6 with HCl (1 M). The mixture was concentrated under reduced pressure. The residue was purified by reverse phase chromatography (column, $C_{18}$ silica gel; mobile phase, with 10-50% MeOH in water) to afford 6-(methylcarbamoyl)-4-morpholinonicotinic acid as a colorless solid.

Step 3. Preparation of $N^5$-(5-((4-chlorobenzyl)oxy)-1,3,4-thiadiazol-2-yl)-N2-methyl-4-morpholinopyridine-2,5-dicarboxamide

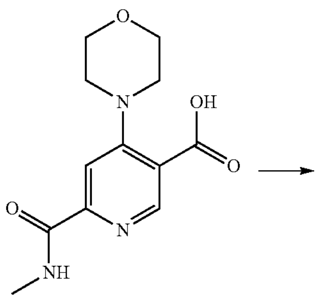

-continued

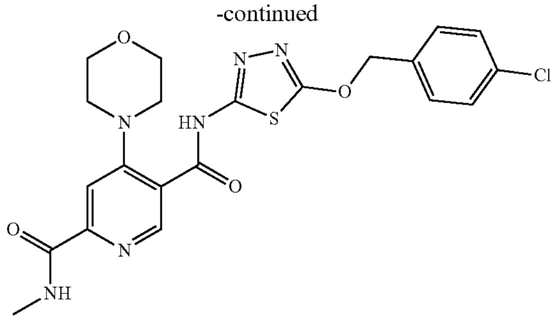

The title compound was prepared using General Procedure A employing 6-(methylcarbamoyl)-4-morpholinonicotinic acid and 5-((4-chlorobenzyl)oxy)-1,3,4-thiadiazol-2-amine (Intermediate B). The mixture was diluted with water. The mixture was extracted with EtOAc (2×). The combined organic layers were concentrated under reduced pressure. The residue was triturated with MeOH to afford $N^5$-(5-((4-chlorobenzyl)oxy)-1,3,4-thiadiazol-2-yl)-N2-methyl-4-morpholinopyridine-2,5-dicarboxamide as a white solid. $^1H$ NMR (400 MHz; DMSO-$d_6$): δ 2.81-2.82 (m, 3H), 3.18-3.21 (m, 4H), 3.60-3.69 (m, 4H), 5.52 (s, 2H), 7.49-7.58 (m, 5H), 8.46 (s, 1H), 8.80-8.82 (m, 1H), 12.93 (s, 1H) ppm. m/z 489 ($M+H^+$).

Example 65

Synthesis of 2-morpholino-N-(5-((4-(oxazol-2-yl)benzyl)oxy)-1,3,4-thiadiazol-2-yl)nicotinamide

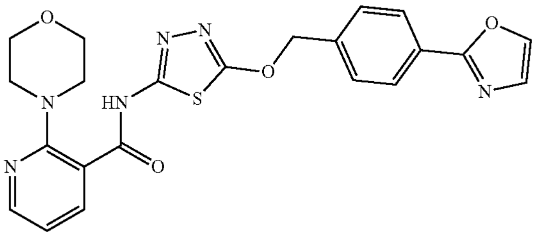 [SMILES: O=C(Nc1nnc(OCc2ccc(-c3ncco3)cc2)s1)c1cccnc1N1CCOCC1]

Step 1. Preparation of 2-(4-(((tert-butyldiphenylsilyl)oxy)methyl)phenyl)oxazole

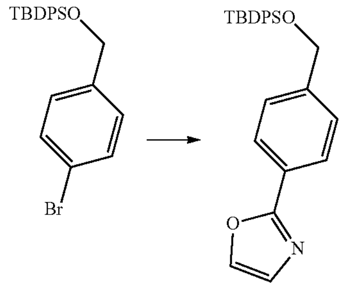

To a solution of ((4-bromobenzyl)oxy)(tert-butyl)diphenylsilane (1.5 g, 3.5 mmol, Example 56, step 1), in toluene (15 mL) was added 2-(tributylstannyl)-1,3-oxazole (1.9 g, 5.3 mmol) and $Pd(PPh_3)_4$ (0.4 g, 0.35 mmol) under nitrogen.

The mixture was stirred at 110° C. for overnight. The mixture was cooled to room temperature and diluted with water. The mixture was extracted with DCM (3×) and the combined organic layers were concentrated under reduced pressure. The residue was purified by silica gel column chromatography, eluted with 9% EtOAc in hexanes to afford 2-(4-(((tert-butyldiphenylsilyl)oxy)methyl)phenyl)oxazole as yellow oil.

Step 2. Preparation of 5-((4-(oxazol-2-yl)benzyl)oxy)-1,3,4-thiadiazol-2-amine

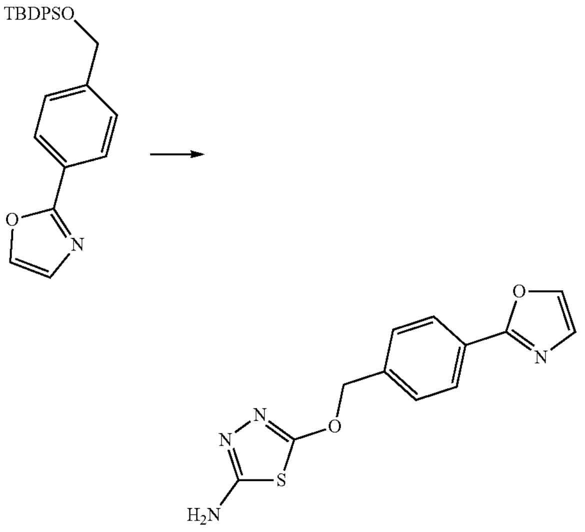

The title compound was prepared using similar procedure as Example 56, Step 3, 4 and 5 replacing tert-butyl([[4-(oxetan-3-yl)phenyl]methoxy])diphenylsilane in Step 3 with 2-(4-(((tert-butyldiphenylsilyl)oxy)methyl)phenyl)oxazole Step 3. Preparation of 2-morpholino-N-(5-((4-(oxazol-2-yl)benzyl)oxy)-1,3,4-thiadiazol-2-yl)nicotinamide

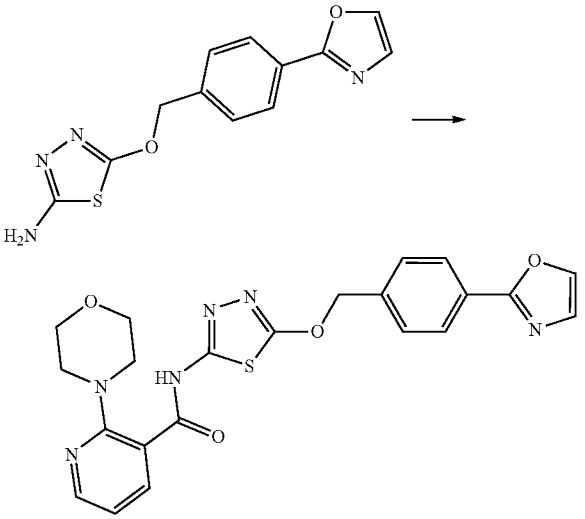

The title compound was prepared using General Procedure A employing 2-(morpholin-4-yl)pyridine-3-carboxylic acid and 5-((4-(oxazol-2-yl)benzyl)oxy)-1,3,4-thiadiazol-2-amine. The mixture was diluted with water and mixture was filtered. Solid was triturated with MeOH to afford 2-morpholino-N-(5-((4-(oxazol-2-yl)benzyl)oxy)-1,3,4-thiadiazol-2-yl)nicotinamide as a white solid. $^1$H NMR (400 MHz; DMSO-$d_6$): δ 3.18-3.25 (m, 4H), 3.66-3.69 (m, 4H), 5.59 (s, 2H), 6.98-7.02 (m, 1H), 7.42 (s, 1H), 7.67-7.70 (m, 2H), 7.91-7.94 (m, 1H), 8.00-8.06 (m, 2H), 8.26 (s, 1H), 8.36-8.38 (m, 1H), 12.89 (s, 1H) ppm. m/z 465 (M+H$^+$).

Example 66

Synthesis of N-(5-((4-chlorobenzyl)oxy)-1,3,4-thiadiazol-2-yl)-2-(2,3-dihydro-4H-benzo[b][1,4]oxazin-4-yl)nicotinamide

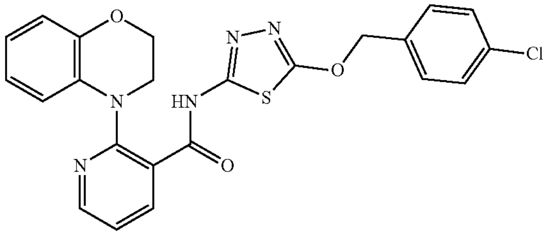 [SMILES: O=C(Nc1nnc(OCc2ccc(Cl)cc2)s1)c1cccnc1N1CCOc2ccccc21]

The title compound was prepared according to General Procedure D using Intermediate B and 2-(2,3-dihydro-4H-benzo[b][1,4]oxazin-4-yl)nicotinic acid, prepared according to General procedure C with 3,4-dihydro-2H-benzo[b][1,4]oxazine, to afford N-(5-((4-chlorobenzyl)oxy)-1,3,4-thiadiazol-2-yl)-2-(2,3-dihydro-4H-benzo[b][1,4]oxazin-4-yl)nicotinamide (14 mg, 15% yield.) as a white solid. 1H NMR (400 MHz, DMSO-d6) δ 8.48 (d, J=4.7 Hz, 1H), 7.95 (d, J=7.5 Hz, 1H), 7.49 (q, J=8.2 Hz, 4H), 7.17 (t, J=6.0 Hz, 1H), 6.73 (d, J=8.0 Hz, 2H), 6.67 (t, J=7.7 Hz, 1H), 6.52 (t, J=7.7 Hz, 1H), 5.43 (s, 2H), 4.31 (s, 2H), 3.81 (s, 2H) ppm. m/z 480 (M+H$^+$).

Example 67

Synthesis of N-(5-((4-chlorobenzyl)oxy)-1,3,4-thiadiazol-2-yl)-2-(2-methoxyphenyl)nicotinamide

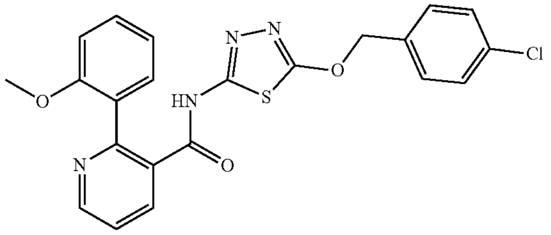

Step 1. Preparation of methyl 2-(2-methoxyphenyl)pyridine-3-carboxylate

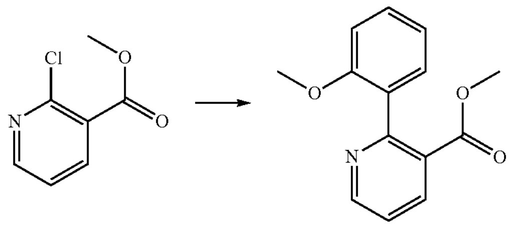

The title compound was prepared using General Procedure E employing methyl 2-chloropyridine-3-carboxylate and 2-methoxyphenylboronic acid. The mixture was cooled room temperature and diluted with water. The mixture was extracted with EtOAc (3×). The combined organic layers were concentrated under reduced pressure. The residue was purified by silica gel column chromatography, eluted with 17% EtOAc in PE to afford methyl 2-(2-methoxyphenyl) pyridine-3-carboxylate (as a white solid.

Step 2. Preparation of 2-(2-methoxyphenyl)pyridine-3-carboxylic acid

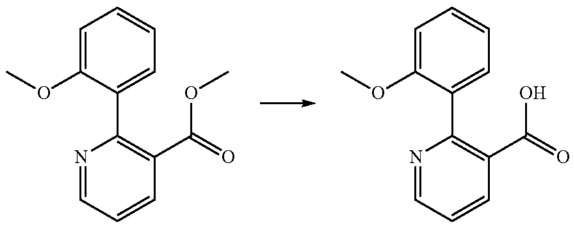

The title compound was prepared using General Procedure F employing methyl 2-(2-methoxyphenyl)pyridine-3-carboxylate. The mixture was stirred at 50° C. for 4 h. The mixture was acidified to pH 6 with HCl (1 M) and extracted with EtOAc (4×). The combined organic layers were concentrated under reduced pressure. The residue was purified by silica gel column chromatography, eluted with 33% EtOAc in PE to afford 2-(2-methoxyphenyl)pyridine-3-carboxylic acid as a white solid Step 3. Preparation of N-(5-((4-chlorobenzyl)oxy)-1,3,4-thiadiazol-2-yl)-2-(2-methoxyphenyl)nicotinamide

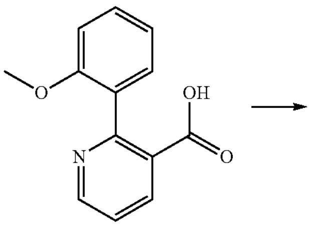

-continued

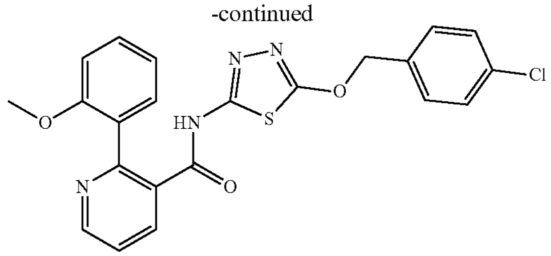

The title compound was prepared using General Procedure A employing 2-(2-methoxyphenyl)pyridine-3-carboxylic acid and 5-((4-chlorobenzyl)oxy)-1,3,4-thiadiazol-2-amine (Intermediate B). The mixture was diluted with water. The mixture was extracted with EtOAc (2×). The combined organic layers were concentrated under reduced pressure. The residue was triturated with MeOH. The residue was further purified by Prep-TLC (DCM:MeOH, 20:1) to afford N-(5-((4-chlorobenzyl)oxy)-1,3,4-thiadiazol-2-yl)-2-(2-methoxyphenyl)nicotinamide (90.8 mg, 22.98%) as a white solid. $^1$H NMR (400 MHz; DMSO-$d_6$): δ 3.49 (s, 3H), 5.47 (s, 2H), 6.93-6.95 (m, 1H), 7.05-7.13 (m, 1H), 7.36-7.40 (m, 1H), 7.47-7.54 (m, 6H), 8.03-8.04 (m, 1H), 8.77-8.78 (m, 1H), 12.70 (s, 1H) ppm. m/z 453 ($M+H^+$).

Example 68

Synthesis of N-(5-((4-chlorobenzyl)oxy)-1,3,4-thiadiazol-2-yl)-2-(4-(2-hydroxyethyl)-3-oxopiperazin-1-yl)nicotinamide

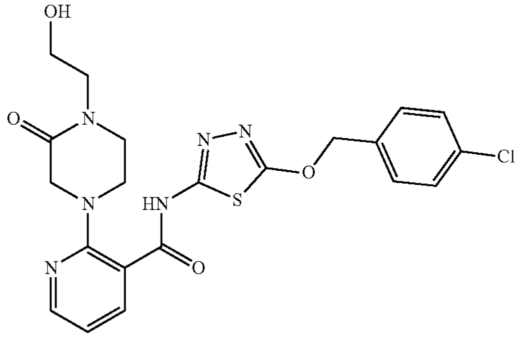 [SMILES: O=C(Nc1nnc(OCc2ccc(Cl)cc2)s1)c1cccnc1N1CCN(CCO)C(=O)C1]

Step 1. Preparation of benzyl 4-(2-acetoxyethyl)-3-oxopiperazine-1-carboxylate

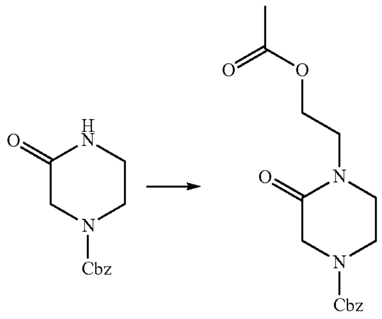 [SMILES: O=C1CN(C(=O)OCc2ccccc2)CCN1 ; CC(=O)OCCN1CCN(C(=O)OCc2ccccc2)CC1=O]

To a solution of benzyl 3-oxopiperazine-1-carboxylate (3.0 g, 12.8 mmol) in DMF (30 mL) was added 2-bromoethyl acetate (2.1 g, 12.8 mmol) dropwise under nitrogen. Then NaH (1.3 g, 32 mmol, 60% dispersion in oil) was added. The mixture was stirred overnight at room temperature. The mixture was diluted with sat. $NH_4Cl$. The mixture was extracted with EtOAc (2×). The combined organic layers were concentrated under reduced pressure. The residue was purified by silica gel column chromatography, eluted with 0.5% MeOH in DCM to afford benzyl 4-(2-acetoxyethyl)-3-oxopiperazine-1-carboxylate as a yellow solid.

Step 2. Preparation of 1-(2-hydroxyethyl)piperazin-2-one

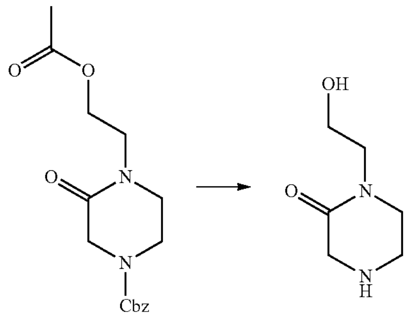 [SMILES: CC(=O)OCCN1CCN(C(=O)OCc2ccccc2)CC1=O ; O=C1CNCCN1CCO]

To a solution of benzyl 4-[2-(acetyloxy)ethyl]-3-oxopiperazine-1-carboxylate (2.4 g, 7.5 mmol) in MeOH (24 mL) and water (10 mL) was added $K_2CO_3$ (2.1 g, 15.0 mmol). The mixture was stirred for 2 h at room temperature. The mixture was diluted with $CHCl_3$ (24 mL).

The mixture was washed with brine (3×). The mixture was concentrated under reduced pressure. The residue was dissolved in MeOH (10 mL) and 10% Pd/C (100 mg) was added. The mixture was stirred for 2 h at room temperature under hydrogen. The mixture was filtered through celite. The filtrate was concentrated under reduced pressure to afford 1-(2-hydroxyethyl)piperazin-2-one as a white solid.

Step 3. Preparation of N-(5-((4-chlorobenzyl)oxy)-1,3,4-thiadiazol-2-yl)-2-(4-(2-hydroxy-ethyl)-3-oxopiperazin-1-yl)nicotinamide

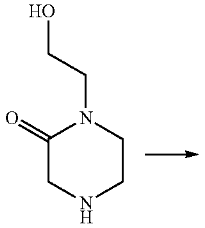

-continued

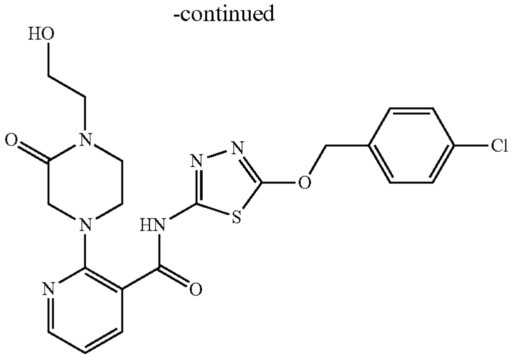

The title compound was prepared using similar procedure as Example 61, replacing 1,4-diazepan-5-one with 1-(2-hydroxyethyl)piperazin-2-one. The mixture was cooled to room temperature and diluted with EtOAc. The mixture was washed with water (3×). The organic layer was concentrated under reduced pressure. The residue was triturated with MeOH to afford N-(5-((4-chlorobenzyl)oxy)-1,3,4-thiadiazol-2-yl)-2-(4-(2-hydroxyethyl)-3-oxopiperazin-1-yl)nicotinamide as a white solid. $^1H$ NMR (400 MHz; DMSO-$d_6$): δ 3.35-3.38 (m, 2H), 3.44-3.52 (m, 4H), 3.55-3.58 (m, 2H), 3.83 (s, 2H), 4.68-4.71 (m, 1H), 5.51 (s, 2H), 6.92-6.95 (m, 1H), 7.48-7.50 (m, 2H), 7.54-7.56 (m, 2H), 7.87-7.89 (m, 1H), 8.31-8.33 (m, 1H), 12.82 (s, 1H) ppm. m/z 489 $(M+H^+)$.

Example 69

Synthesis of (R)—N-(5-((4-chlorobenzyl)oxy)-1,3,4-thiadiazol-2-yl)-2-(6-oxohexahydropyrrolo[1,2-a]pyrazin-2(1H)-yl)nicotinamide or (S)—N-(5-((4-chlorobenzyl)oxy)-1,3,4-thiadiazol-2-yl)-2-(6-oxohexahydropyrrolo[1,2-a]pyrazin-2(1H)-yl)nicotinamide

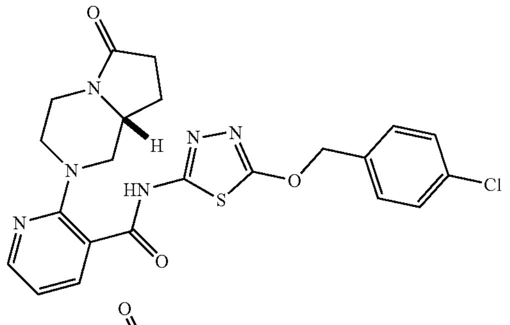

or

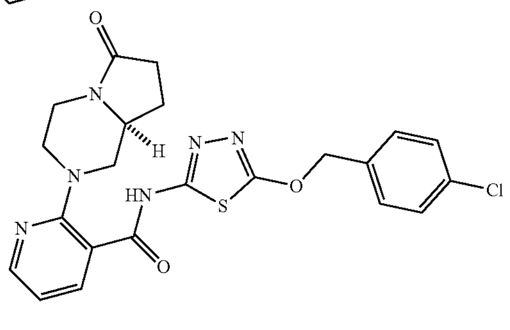

The racemic mixture (R) N-(5-((4-chlorobenzyl)oxy)-1,3,4-thiadiazol-2-yl)-2-(6-oxohexahydropyrrolo[1,2-a]

pyrazin-2(1H)-yl)nicotinamide and (S)—N-(5-((4-chlorobenzyl)oxy)-1,3,4-thiadiazol-2-yl)-2-(6-oxohexahydropyrrolo[1,2-a]pyrazin-2(1H)-yl)nicotinamide (Example 57) was purified using Prep-HPLC (column: CHIRALPAK IF-3; mobile phase A: 25% DCM in hexanes containing (0.1% $Et_2NH$), mobile phase B: EtOH, isocratic 30% B in A) to afford the title compound as a white solid, as the first eluting isomer. $^1H$ NMR (300 MHz; DMSO-$d_6$): δ 1.51-1.58 (m, 1H), 2.03-2.07 (m, 1H), 2.21-2.29 (m, 2H), 2.60-2.64 (m, 1H), 2.77-2.84 (m, 2H), 3.60-3.67 (m, 2H), 3.77-3.84 (m, 2H), 5.50 (s, 2H), 6.98-7.03 (m, 1H), 7.48-7.57 (m, 4H), 7.91-7.94 (m, 1H), 8.34-8.36 (m, 1H), 12.82 (s, 1H) ppm. m/z 485 (M+H$^+$).

Example 70

Synthesis of (R)—N-(5-((4-chlorobenzyl)oxy)-1,3,4-thiadiazol-2-yl)-2-(6-oxohexahydropyrrolo-[1,2-a]pyrazin-2(1H)-yl)nicotinamide or (S)—N-(5-((4-chlorobenzyl)oxy)-1,3,4-thiadiazol-2-yl)-2-(6-oxohexahydropyrrolo[1,2-a]pyrazin-2(1H)-yl)nicotinamide

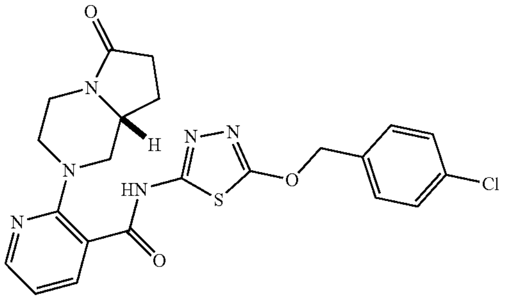

or

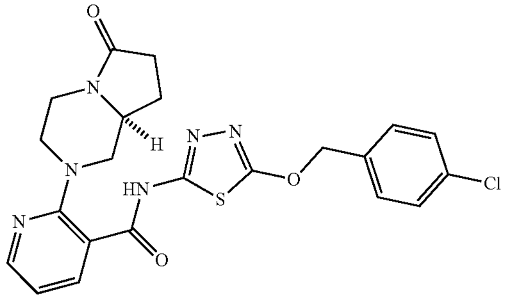

Further elution of Example 69 afforded to title compound as the second eluting isomer. $^1H$ NMR (300 MHz; DMSO-$d_6$): δ 1.52-1.59 (m, 1H), 2.03-2.07 (m, 1H), 2.21-2.30 (m, 2H), 2.60-2.68 (m, 1H), 2.73-2.84 (m, 2H), 3.61-3.68 (m, 2H), 3.77-3.84 (m, 2H), 5.51 (s, 2H), 6.99-7.03 (m, 1H), 7.48-7.58 (m, 4H), 7.91-7.94 (m, 1H), 8.35-8.37 (m, 1H), 12.82 (s, 1H) ppm. m/z 485 (M+H$^+$).

Example 71

Synthesis of N-(5-((4-chlorobenzyl)oxy)-1,3,4-thiadiazol-2-yl)-6-cyano-2-(2-methoxyphenyl)-nicotinamide

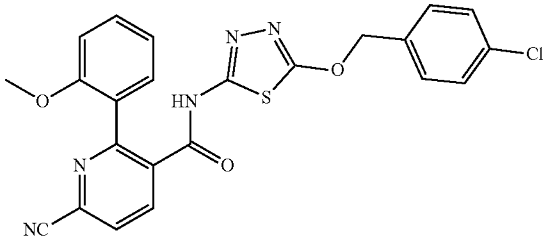

Step 1. Preparation of methyl 2-chloro-6-cyanonicotinate

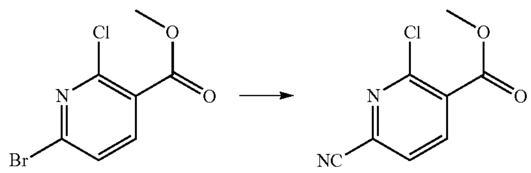

To a solution of methyl 6-bromo-2-chloropyridine-3-carboxylate (1 g, 4.0 mmol) in DMF (10 mL) was added $Zn(CN)_2$ (516 mg, 4.4 mmol). The solution was degassed with bubbling nitrogen for 3 minutes and then $Pd(PPh_3)_4$ (461 mg, 0.40 mmol) was added. The solution was degassed with bubbling with nitrogen for 3 minutes. The mixture was stirred at 80° C. for 14 h. The mixture was cooled to room temperature and diluted with water. The mixture was extracted with EtOAc (3×). The combined organic layers were washed with brine (3×) and concentrated under reduce pressure. The residue was purified by silica gel column chromatograph eluted with 3-9% EtOAc in PE to afford methyl 2-chloro-6-cyanonicotinate as light yellow oil.

Step 2. Preparation of methyl 6-cyano-2-(2-methoxyphenyl)nicotinate

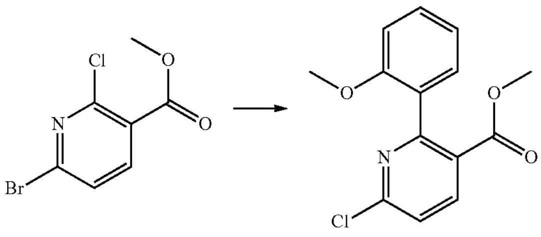

The title compound was prepared using General Procedure E employing methyl 2-chloro-6-cyanopyridine-3-carboxylate and 2-methoxyphenylboronic acid. The mixture was stirred at 80° C. for 4 h. The mixture was cooled to room temperature and diluted with EtOAc. The mixture was washed with brine (2×) and concentrated under reduce pressure. The residue was purified by Prep-TLC (PE:EtOAc, 2:1) to afford methyl 6-cyano-2-(2-methoxyphenyl)nicotinate as a white solid.

Step 3. Preparation of 6-cyano-2-(2-methoxyphenyl)nicotinic acid

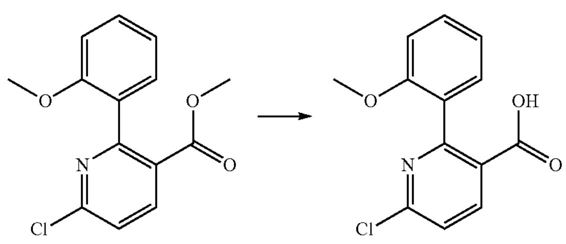

To a solution of methyl 6-cyano-2-(2-methoxyphenyl) pyridine-3-carboxylate (215 mg, 0.80 mmol) in THF (4 mL) was added a solution of LiOH (19 mg, 0.80 mmol) in water (0.8 mL). The mixture was stirred at room temperature for 16 h. The mixture was diluted with EtOAc and washed with brine (2×) The combined aqueous layers were acidified by to pH 3 with HCl (1 M). The mixture was extracted with EtOAc (2×). The combined organic layers were concentrated under reduce pressure to afford 6-cyano-2-(2-methoxyphenyl)nicotinic acid as a white solid.

Step 4. Preparation of N-(5-((4-chlorobenzyl)oxy)-1,3,4-thiadiazol-2-yl)-6-cyano-2-(2-methoxyphenyl) nicotinamide

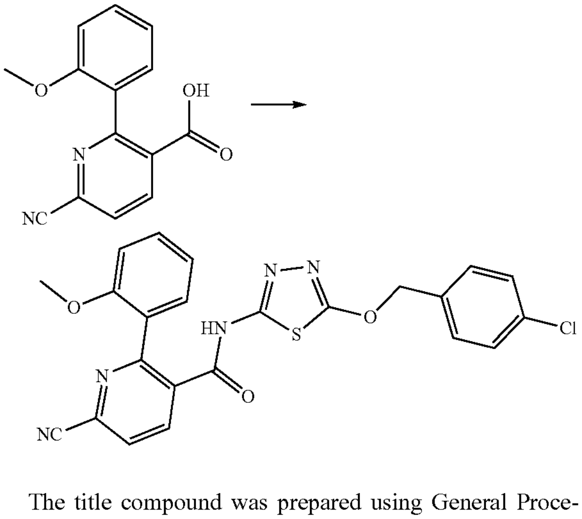

The title compound was prepared using General Procedure A employing 6-cyano-2-(2-methoxyphenyl)nicotinic acid and 5-((4-chlorobenzyl)oxy)-1,3,4-thiadiazol-2-amine (Intermediate B). The mixture was diluted with EtOAc and washed with brine (2×). The organic layer was concentrated under reduced pressure. The residue was purified by Prep-TLC (DCM:MeOH, 80:1). The residue was further purified by trituration with MeOH to afford N-(5-((4-chlorobenzyl) oxy)-1,3,4-thiadiazol-2-yl)-6-cyano-2-(2-methoxyphenyl) nicotinamide as a white solid. $^{1}H$ NMR (300 MHz, DMSO-$d_6$): δ 3.51 (s, 3H), 5.48 (s, 2H), 6.98-7.01 (m, 1H), 7.08-7.13 (m, 1H), 7.42-7.56 (m, 6H), 8.15-8.18 (m, 1H), 8.30-8.33 (m, 1H), 13.00 (s, 1H) ppm. m/z 478 ($M+H^+$).

Example 72

Synthesis of N-(5-((4-chlorobenzyl)oxy)-1,3,4-thiadiazol-2-yl)-4-cyano-2-morpholinobenzamide

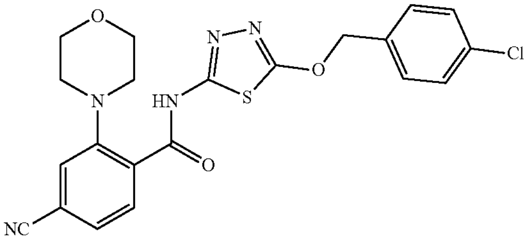

Step 1. Preparation of 4-cyano-2-morpholinobenzoic acid

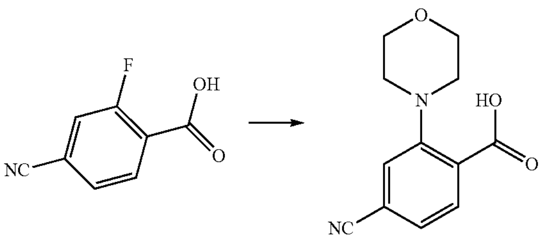 [SMILES: N#Cc1ccc(C(=O)O)c(F)c1 ; N#Cc1ccc(C(=O)O)c(N2CCOCC2)c1]

The title compound was prepared using General Procedure C employing 4-cyano-2-fluorobenzoic acid. The mixture was cooled to room temperature and concentrated under reduce pressure. The residue was purified by silica gel column eluted with 0.9-2% MeOH in (0.05% AcOH in DCM). The residue was further purified by triturating with DCM give 4-cyano-2-morpholinobenzoic acid as a white solid.

Step 2. Preparation of N-(5-((4-chlorobenzyl)oxy)-1,3,4-thiadiazol-2-yl)-4-cyano-2-morpholinobenzamide

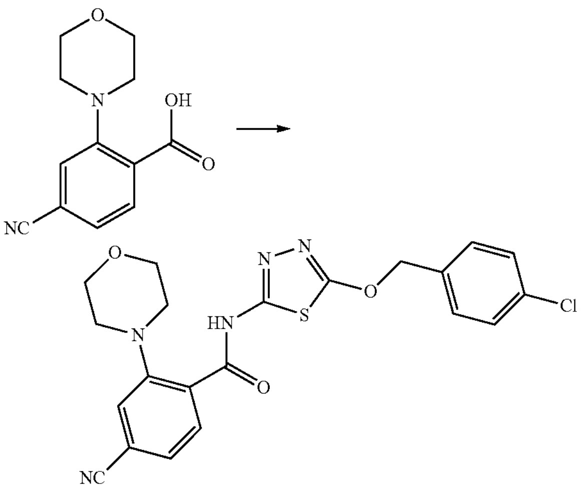

The title compound was prepared using General Procedure A employing and 5-((4-chlorobenzyl)oxy)-1,3,4-thiadiazol-2-amine (Intermediate B). The mixture was diluted with water and stirred at room temperature for 5 minutes. The mixture was filtered and the solid was washed with water (2×). The solid was triturated with MeOH to afford N-(5-((4-chlorobenzyl)oxy)-1,3,4-thiadiazol-2-yl)-4-cyano-2-morpholinobenzamide as a light yellow solid. 1H NMR (300 MHz; DMSO-$d_6$): δ 3.00-3.03 (m, 4H), 3.70-3.73 (m, 4H), 5.52 (s, 2H), 7.48-7.51 (m, 2H), 7.55-7.58 (m, 2H), 7.63-7.66 (m, 1H), 7.77-7.78 (m, 1H), 7.83-7.86 (m, 1H), 13.38 (s, 1H) ppm. m/z 456 (M+H+).

Example 73

Synthesis of $N^5$-(5-((4-chlorobenzyl)oxy)-1,3,4-thiadiazol-2-yl)-N2,N2-dimethyl-4-morpholinopyridine-2,5-dicarboxamide

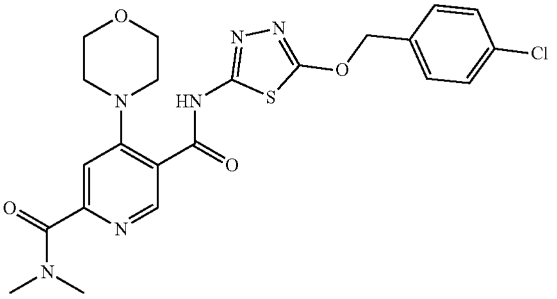 [SMILES: CN(C)C(=O)c1cc(N2CCOCC2)c(C(=O)Nc2nnc(OCc3ccc(Cl)cc3)s2)cn1]

Step 1. Preparation of 6-(dimethylcarbamoyl)-4-(morpholin-4-yl)pyridine-3-carboxylic acid

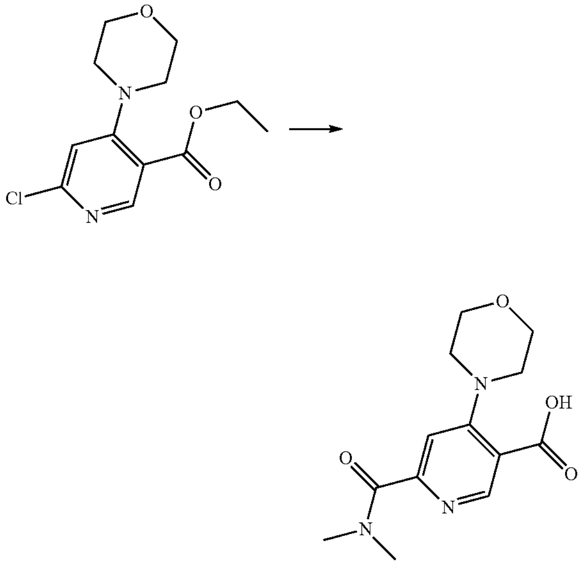

The title compound was prepared using similar procedure as Example 64, Steps 1-2, replacing methylamine with dimethylamine in Step 1.

Step 2. Preparation of $N^5$-(5-((4-chlorobenzyl)oxy)-1,3,4-thiadiazol-2-yl)-N2,N2-dimethyl-4-morpholinopyridine-2,5-dicarboxamide

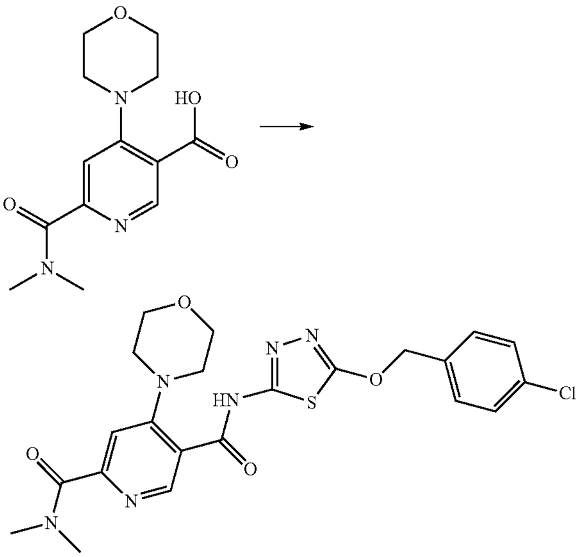

To a solution of 6-(dimethylcarbamoyl)-4-(morpholin-4-yl)pyridine-3-carboxylic acid (100 mg, 0.36 mmol) in DCM (1 mL) was added DMF (5 mg, 0.72 mmol) and oxalyl chloride (68 mg, 0.54 mmol). The mixture was stirred at room temperature for 1 h. The mixture was concentrated under reduced pressure. Then a solution of 5-((4-chlorobenzyl)oxy)-1,3,4-thiadiazol-2-amine (87 mg, 0.36 mmol, Intermediate B) and $Et_3N$ (72 mg, 0.72 mmol) in DCM (1 mL) was added. The mixture was stirred at room temperature for 2 h. The mixture was concentrated under reduce pressure. The residue was triturated with MeOH (1 mL). The residue was further purified by Prep-HPLC with the following condition [column: XBridge Prep OBD $C_{18}$; mobile phase, 13-33% MeCN in (0.05% $NH_4OH$ in water)] to afford $N^5$-(5-((4-chlorobenzyl)oxy)-1,3,4-thiadiazol-2-yl)-N2,N2-dimethyl-4-morpholinopyridine-2,5-dicarboxamide as a white solid. $^1H$ NMR (300 MHz; DMSO-$d_6$): δ 2.92 (s, 3H), 2.99 (s, 3H), 3.16 (s, 4H), 3.63-3.65 (m, 4H), 5.50 (s, 2H), 7.08 (s, 1H), 7.47-7.57 (m, 4H), 8.41 (s, 1H), 12.85 (s, 1H) ppm. m/z 503 ($M+H^+$).

Example 74

Synthesis of N-(5-((4-chlorobenzyl)oxy)-1,3,4-thiadiazol-2-yl)-2'-hydroxy-[2,4'-bipyridine]-3-carboxamide or its tautomer N-(5-((4-chlorobenzyl)oxy)-1,3,4-thiadiazol-2-yl)-2'-oxo-1',2'-dihydro-[2,4'-bipyridine]-3-carboxamide

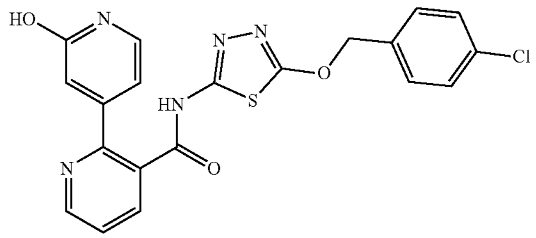

-continued or its tautomeric form

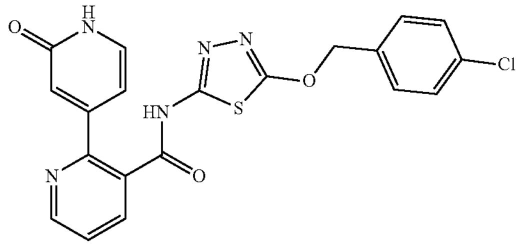

Step 1. Preparation of methyl 2'-methoxy-[2,4'-bipyridine]-3-carboxylate

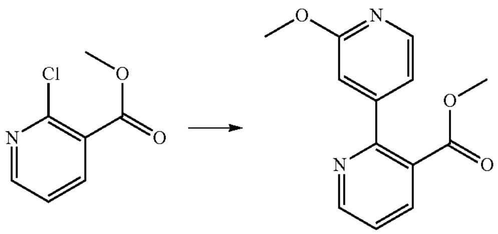

The title compound was prepared using General Procedure D employing methyl 2-chloropyridine-3-carboxylate and 2-methoxypyridin-4-ylboronic acid. The mixture was cooled to room temperature and diluted with EtOAc. The mixture was washed with water (3×) and the organic layer was concentrated under reduced pressure. The residue was purified by silica gel column chromatography, eluted with 9% EtOAc in PE to afford methyl 2'-methoxy-[2,4'-bipyridine]-3-carboxylate as a white solid.

Step 2. Preparation of 2'-methoxy-[2,4'-bipyridine]-3-carboxylic acid

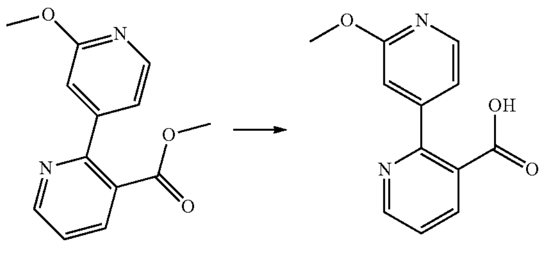

To a solution of methyl 2'-methoxy-[2,4'-bipyridine]-3-carboxylate (1.9 g, 7.8 mmol) in DCM (20 mL) was added $BBr_3$ (19 g, 78 mmol) at 0° C. under nitrogen. The mixture was warmed to room temperature and stirred at room temperature overnight. The mixture was diluted with sat. $NaHCO_3$ (20 mL). The mixture was concentrated under reduced pressure. The residue was purified by silica gel column chromatography, eluted with 17% MeOH in DCM to afford 2'-methoxy-[2,4'-bipyridine]-3-carboxylic acid as a white solid.

Step 3. Preparation of 2'-oxo-1',2'-dihydro-[2,4'-bipyridine]-3-carboxylic acid

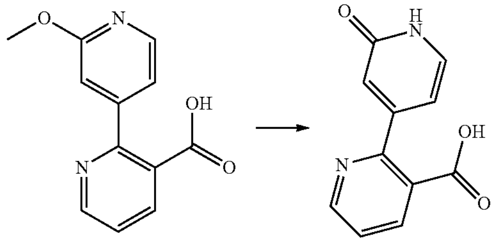 [SMILES: COc1cc(-c2ncccc2C(=O)O)ccn1 ; O=C(O)c1cccnc1-c1cc[nH]c(=O)c1]

To a solution of 2-methoxy-[2,4-bipyridine]-3-carboxylic acid (780 mg, 3.4 mmol) and PTSA (886 mg, 5.1 mmol) in DMF was added LiCl (218 mg, 5.1 mmol). The mixture was stirred for 1 h at 100° C. under nitrogen. The mixture was cooled to room temperature and concentrated under reduced pressure. The residue was purified by Prep-HPLC (column, $C_{18}$; mobile phase, 0-100% MeCN in water) to afford 2'-oxo-1',2'-dihydro-[2,4'-bipyridine]-3-carboxylic acid as a white solid.

Step 4. Preparation of N-(5-((4-chlorobenzyl)oxy)-1,3,4-thiadiazol-2-yl)-2'-oxo-1',2'-dihydro-[2,4'-bipyridine]-3-carboxamide

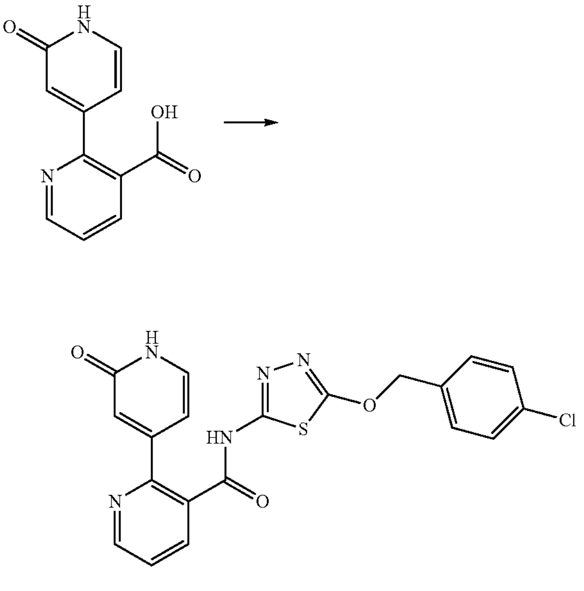

The title compound was prepared using General Procedure A employing 2'-oxo-1',2'-dihydro-[2,4'-bipyridine]-3-carboxylic acid and 5-((4-chlorobenzyl)oxy)-1,3,4-thiadiazol-2-amine (Intermediate B). The mixture was diluted with EtOAc and washed with water (2×). The organic layer was concentrated under reduce pressure and the residue was triturated with MeOH to afford N-(5-((4-chlorobenzyl)oxy)-1,3,4-thiadiazol-2-yl)-2'-oxo-1',2'-dihydro-[2,4'-bipyridine]-3-carboxamide as a white solid. $^1H$ NMR (400 MHz; DMSO-$d_6$): δ 5.49 (s, 2H), 6.30-6.37 (m, 2H), 7.41-7.61 (m, 6H), 8.10-8.13 (m, 1H), 8.79-8.81 (m, 1H), 11.58-11.73 (br s, 1H), 13.01-13.11 (br s, 1H) ppm. m/z 440 ($M+H^+$).

Example 75

Synthesis of N-(5-((4-chlorobenzyl)oxy)-1,3,4-thiadiazol-2-yl)-6-methoxy-4-morpholino-nicotinamide

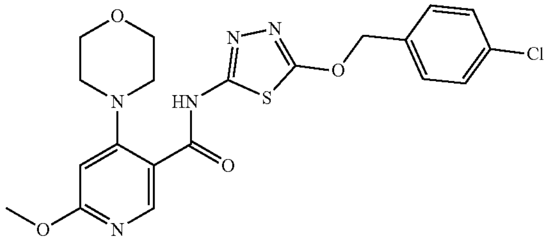 [SMILES: COc1cc(N2CCOCC2)c(C(=O)Nc2nnc(OCc3ccc(Cl)cc3)s2)cn1]

Step 1. Preparation of methyl 6-methoxy-4-morpholinonicotinate

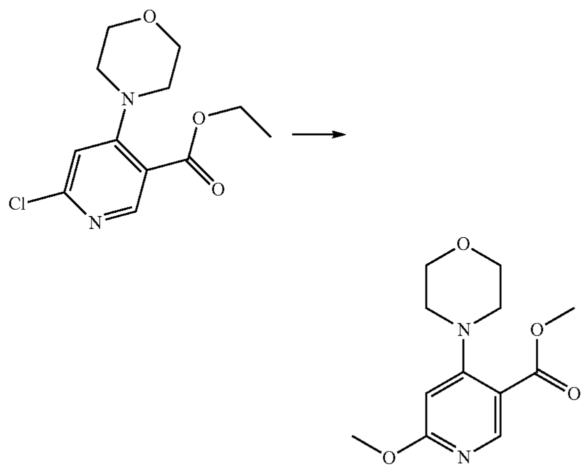

To a solution of ethyl 6-chloro-4-(morpholin-4-yl)pyridine-3-carboxylate (500 mg, 1.8 mmol, Example 35, Step 1) in DMF (5 mL) and MeOH (3.8 mL) was added MeONa (998 mg, 18.5 mmol). The mixture was stirred at 60° C. overnight. The mixture was cooled to room temperature and diluted with sat $NH_4Cl$ (15 mL). The mixture was extracted with EtOAc (3×) and the combined organic layers were concentrated under reduced pressure. The residue was purified by Prep-TLC (PE:EtOAc, 5:1) to afford methyl 6-methoxy-4-morpholinonicotinate as an off-white oil.

Step 2. Preparation of 6-methoxy-4-morpholinonicotinic acid

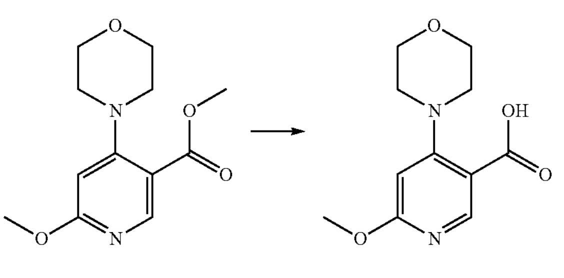

The title compound was prepared using General Procedure F employing methyl 6-methoxy-4-morpholinonicotinate. The mixture was acidified to pH 3 with HCl (1 M). The mixture was concentrated. The residue was purified by Prep-HPLC (column, $C_{18}$; mobile phase, 10-50% MeCN and water, with both eluents containing 0.05% TFA) to afford 6-methoxy-4-morpholinonicotinic acid as an off-white oil.

Step 3. Preparation of N-(5-((4-chlorobenzyl)oxy)-1,3,4-thiadiazol-2-yl)-6-methoxy-4-morpholinonicotinamide

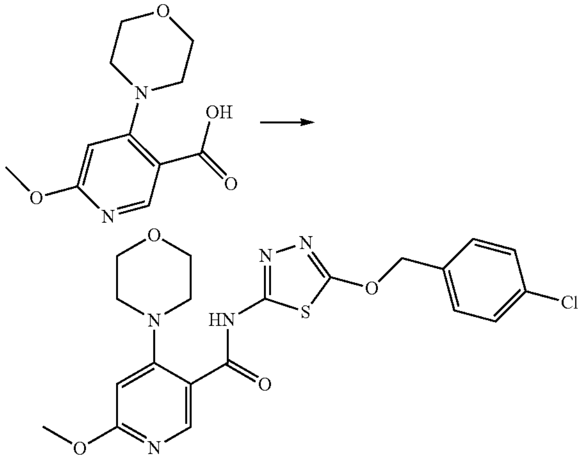

The title compound was prepared using General Procedure A employing 6-methoxy-4-morpholinonicotinic acid and 5-((4-chlorobenzyl)oxy)-1,3,4-thiadiazol-2-amine (Intermediate B). The mixture was diluted with EtOAc and washed with water (2×). The mixture was concentrated under reduce pressure. The residue was triturated with MeOH to afford N-(5-((4-chlorobenzyl)oxy)-1,3,4-thiadiazol-2-yl)-6-methoxy-4-morpholinonicotinamide as a white solid. $^1H$ NMR (300 MHz; DMSO-$d_6$): δ 3.02-3.05 (m, 4H), 3.64-3.69 (m, 4H), 3.88 (s, 3H), 5.50 (s, 2H), 6.37 (s, 1H), 7.48-7.57 (m, 4H), 8.26 (s, 1H), 12.62 (s, 1H) ppm. m/z 462 $(M+H^+)$.

Example 76

Synthesis of N-(5-((4-chlorobenzyl)oxy)-1,3,4-thiadiazol-2-yl)-6-cyano-2-(3-oxopiperazin-1-yl)nicotinamide

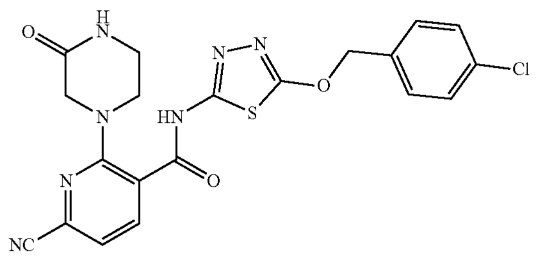 [SMILES: N#Cc1ccc(C(=O)Nc2nnc(OCc3ccc(Cl)cc3)s2)c(N2CCNC(=O)C2)n1]

The title compound was prepared using similar procedure as Example 14, Step 1-3, replacing morpholine with piperazin-2-one in Step 1. The mixture was purified by Prep-HPLC [column $C_{18}$ Spherical; mobile phase, 35-55% MeCN in (0.16% $NH_4HCO_3$ in water)] to afford N-(5-((4-chlorobenzyl)oxy)-1,3,4-thiadiazol-2-yl)-6-cyano-2-(3-oxopiperazin-1-yl)nicotinamide as a white solid. $^1H$ NMR (300 MHz; DMSO-$d_6$): δ 3.24 (s, 2H), 3.51-3.55 (m, 2H), 3.81 (s, 2H), 5.51 (s, 2H), 7.46-7.56 (m, 5H), 8.02-8.05 (m, 1H), 8.13 (s, 1H), 13.11 (s, 1H) ppm. m/z 470 ($M+H^+$).

Example 77

Synthesis of N-[5-[(4-chlorophenyl)methoxy]-1,3,4-thiadiazol-2-yl]-4-(2-methoxyphenyl)pyridine-3-carboxamide

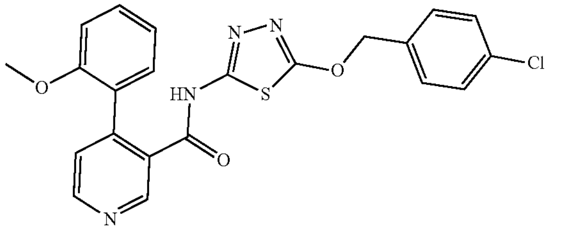 [SMILES: COc1ccccc1-c1ccncc1C(=O)Nc1nnc(OCc2ccc(Cl)cc2)s1]

The title compound was prepared using similar procedure as Example 67, Steps 1-3, replacing methyl 2-chloropyridine-3-carboxylate with methyl 4-chloropyridine-3-carboxylate in Step 1. The residue was purified by Prep-TLC (DCM:MeOH, 15:1) to afford N-[5-[(4-chlorophenyl)methoxy]-1,3,4-thiadiazol-2-yl]-4-(2-methoxyphenyl)pyridine-3-carboxamide as a white solid. $^1H$ NMR (400 MHz; DMSO-$d_6$): δ 3.52 (s, 3H), 5.48 (s, 2H), 6.98-7.00 (m, 1H), 7.06-7.09 (m, 1H), 7.34-7.44 (m, 3H), 7.47-7.54 (m, 4H), 8.75-8.79 (m, 2H), 12.78 (s, 1H) ppm. m/z 453 ($M+H^+$).

Example 78

Synthesis of 6-acetamido-N-(5-((4-chlorobenzyl)oxy)-1,3,4-thiadiazol-2-yl)-4-morpholinonicotinamide

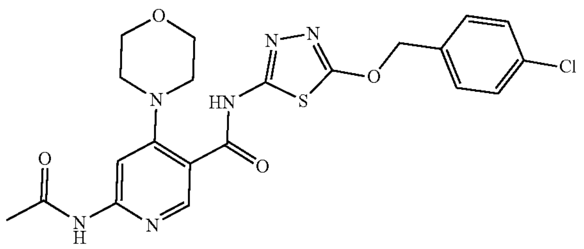 [SMILES: CC(=O)Nc1cc(N2CCOCC2)c(C(=O)Nc2nnc(OCc3ccc(Cl)cc3)s2)cn1]

Step 1. Preparation of ethyl 6-acetamido-4-morpholinonicotinate

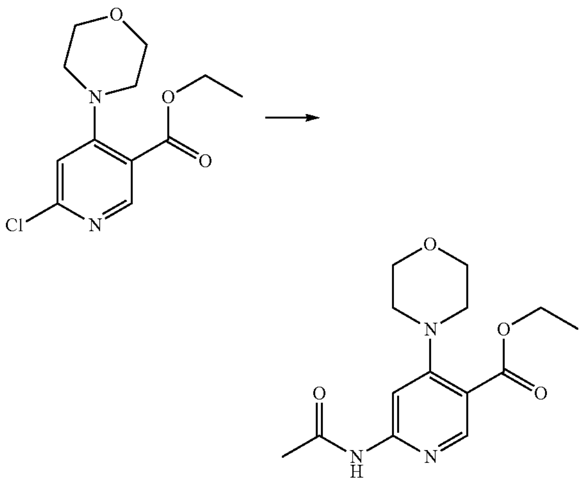

To a stirred solution of ethyl 6-chloro-4-(morpholin-4-yl)pyridine-3-carboxylate (1.0 g, 3.7 mmol, Example 35, Step 1) in dioxane (10 mL) was added acetamide (436 mg, 7.4 mmol), $Pd(OAc)_2$ (124 mg, 0.55 mmol), dppf (204 mg, 0.37 mmol) and $Cs_2CO_3$ (2.4 g, 7.4 mmol) at room temperature under nitrogen. The mixture was stirred at 100° C. for 4 h. The mixture was diluted with EtOAc (10 mL) and was washed with water (3×10 mL). The organic layer was concentrated under reduced pressure. The residue was purified by silica gel column chromatography, eluted with 3% EtOAc in PE to afford ethyl 6-acetamido-4-morpholinonicotinate as an off-white solid.

Step 2. Preparation of 6-acetamido-4-morpholinonicotinic acid

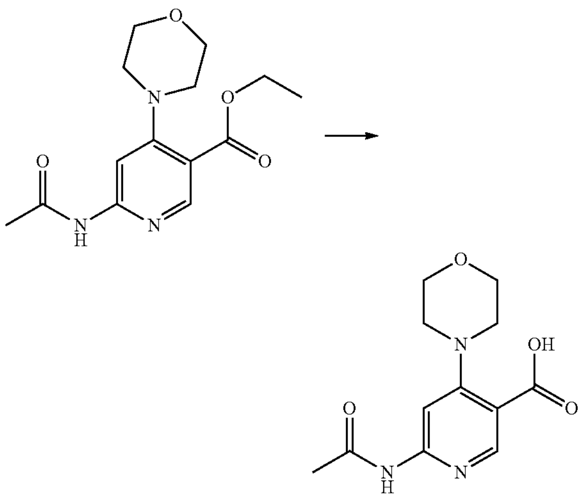

To a solution of ethyl 6-acetamido-4-morpholinonicotinate (300 mg, 1.0 mmol) in DCM (3 mL) was added $BBr_3$ (512 mg, 2.0 mmol) at room temperature under nitrogen. The mixture was stirred for 30 min at room temperature. The diluted with sat. $NaHCO_3$. The mixture was concentrated under reduced pressure. The residue was purified by Prep-HPLC (column, $C_{18}$ silica gel; mobile phase, 0-5% MeCN in water) to afford 6-acetamido-4-morpholinonicotinic acid as a white solid.

Step 3. Preparation of 6-acetamido-N-(5-((4-chlorobenzyl)oxy)-1,3,4-thiadiazol-2-yl)-4-morpholinonicotinamide

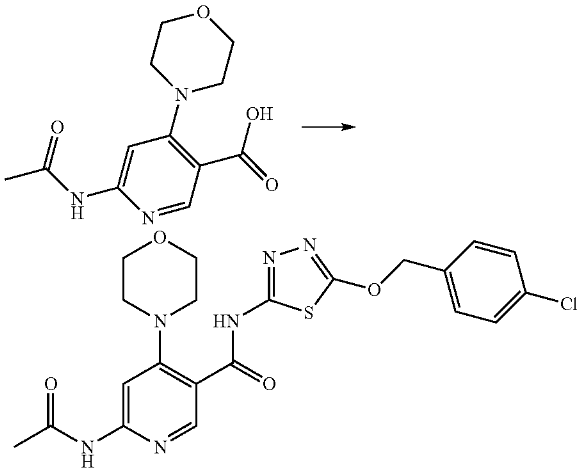

The title compound was prepared using General Procedure A employing 6-acetamido-4-morpholinonicotinic acid and 5-((4-chlorobenzyl)oxy)-1,3,4-thiadiazol-2-amine (Intermediate B). The mixture was diluted with EtOAc and washed with water (3×). The organic layer concentrated under reduced pressure. The residue was purified by Prep-TLC (PE:EtOAc, 2:1). The residue was further purified by triturating with MeOH to afford 6-acetamido-N-(5-((4-chlorobenzyl)oxy)-1,3,4-thiadiazol-2-yl)-4-morpholinonicotinamide as a white solid. $^1H$ NMR (300 MHz; DMSO-$d_6$): δ 2.11 (s, 3H), 3.05 (s, 4H), 3.69 (s, 4H), 5.50 (s, 2H), 7.47-7.57 (m, 4H), 7.79 (s, 1H), 8.31 (s, 1H), 10.61 (s, 1H), 12.59 (s, 1H) ppm. m/z 489 (M+H$^+$).

Example 79

Synthesis of N-(5-((4-chlorobenzyl)oxy)-1,3,4-thiadiazol-2-yl)-6'-oxo-1',6'-dihydro-[2,3'-bipyridine]-3-carboxamide or its tautomer N-(5-((4-chlorobenzyl)oxy)-1,3,4-thiadiazol-2-yl)-6'-hydroxy-[2,3'-bipyridine]-3-carboxamide

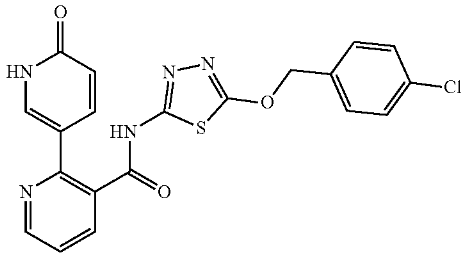

or is tautomer

-continued

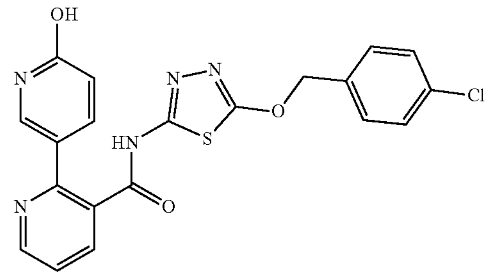

The title compound was prepared using similar procedure as Example 67, Steps 1-3, replacing 2-methoxyphenylboronic acid with 6-oxo-1H-pyridin-3-ylboronic acid in Step 1. The mixture was diluted with water and extracted with EtOAc (2×). The combined organic layers concentrated under reduced pressure. The residue was triturated with MeOH to afford N-(5-((4-chlorobenzyl)oxy)-1,3,4-thiadiazol-2-yl)-6'-oxo-1',6'-dihydro-[2,3'-bipyridine]-3-carboxamide as a light green solid. $^1H$ NMR (300 MHz; DMSO-$d_6$): δ 5.51 (s, 2H), 6.31-6.40 (m, 1H), 7.29-7.65 (m, 7H), 8.03-8.04 (m, 1H), 8.74 (s, 1H), 11.65-11.96 (br s, 1H), 12.73-13.11 (br s, 1H) ppm. m/z 440 (M+H$^+$).

Example 80

Synthesis of N-(5-((4-chlorobenzyl)oxy)-1,3,4-thiadiazol-2-yl)-1'-methyl-6'-oxo-1',6'-dihydro-[2,3'-bipyridine]-3-carboxamide

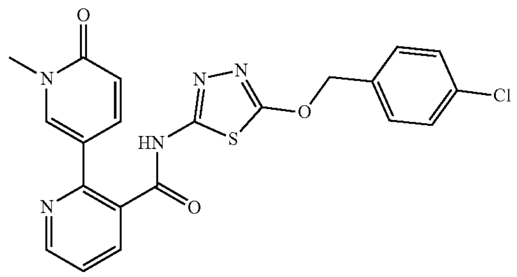 [SMILES: Cn1cc(-c2ncccc2C(=O)Nc2nnc(OCc3ccc(Cl)cc3)s2)ccc1=O]

The title compound was prepared using similar procedure as Example 67, Steps 1-3, replacing 2-methoxyphenylboronic acid with 1-methyl-5-(4,4,5,5-tetramethyl-1,3,2-dioxaborolan-2-yl)pyridin-2-one in Step 1. The mixture was diluted with water and extracted with EtOAc (2×). The combined organic layers concentrated under reduced pressure. The residue was triturated with MeOH to afford N-(5-((4-chlorobenzyl)oxy)-1,3,4-thiadiazol-2-yl)-1'-methyl-6'-oxo-1',6'-dihydro-[2,3'-bipyridine]-3-carboxamide as a white solid. $^1H$ NMR (400 MHz; DMSO-$d_6$): δ 3.48 (s, 3H), 5.50 (s, 2H), 6.38-6.40 (m, 1H), 7.45-7.48 (m, 4H), 7.50-7.56 (m, 2H), 8.05-8.07 (m, 2H), 8.73-8.74 (m, 1H), 12.94 (s, 1H) ppm. m/z 440 (M+H$^+$).

Example 81

Synthesis of N-(5-((4-chlorobenzyl)oxy)-1,3,4-thiadiazol-2-yl)-2-fluoro-5-(2-methoxyphenyl)isonicotinamide

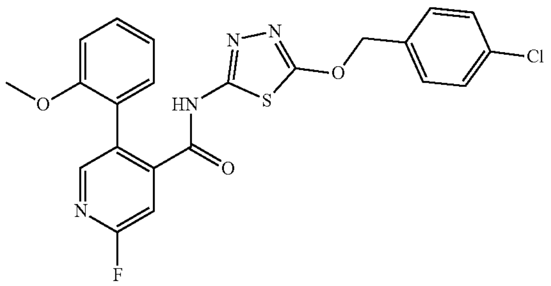 [SMILES: COc1ccccc1-c1cnc(F)cc1C(=O)Nc1nnc(OCc2ccc(Cl)cc2)s1]

Step 1. Preparation of methyl 5-bromo-2-fluoroisonicotinate

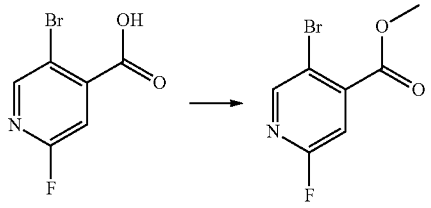

To a solution of 5-bromo-2-fluoropyridine-4-carboxylic acid (1.0 g, 4.5 mmol) in THF (10 mL) was added $Ph_3P$ (2.4 g, 9.1 mmol) and MeOH (0.7 g, 22.7 mmol) at 0° C. The mixture was stirred at 0° C. for 5 min then DIAD (1.8 g, 9.1 mmol) was added and the mixture was warmed to room temperature and stirred for 30 min at room temperature. The mixture was concentrated under reduce pressure. The residue was purified by silica gel column chromatography, eluted with 3% EtOAc in PE to afford methyl 5-bromo-2-fluoroisonicotinate as a white solid.

Step 2. Preparation of methyl 2-fluoro-5-(2-methoxyphenyl)isonicotinate

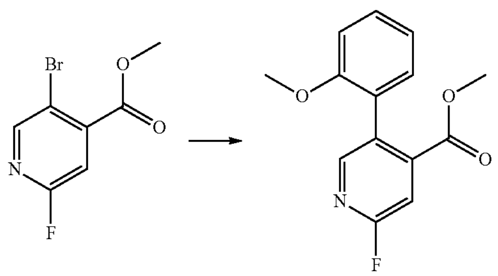

The title compound was prepared using General Procedure E employing methyl 5-bromo-2-fluoroisonicotinate and 2-methoxyphenylboronic acid. The mixture was cooled room temperature and diluted with water. The mixture was extracted with EtOAc (2×). The combined organic layers were concentrated under reduced pressure. The residue was purified by silica gel column chromatography, eluted with 3% EtOAc in PE to afford methyl 2-fluoro-5-(2-methoxyphenyl)isonicotinate as a white solid.

Step 3. Preparation of 2-fluoro-5-(2-methoxyphenyl)pyridine-4-carboxylic acid

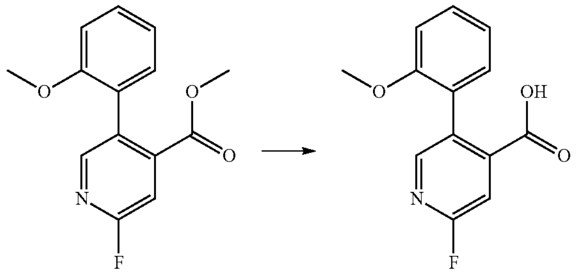

The title compound was prepared using General Procedure F employing methyl 2-fluoro-5-(2-methoxyphenyl) isonicotinate. The mixture was acidified to pH 6 with HCl (1 M). The mixture was extracted with EtOAc (3×) and the combined organic layers were concentrated under reduced pressure to afford 2-fluoro-5-(2-methoxyphenyl)pyridine-4-carboxylic acid as a white solid.

Step 4. Preparation of N-(5-((4-chlorobenzyl)oxy)-1,3,4-thiadiazol-2-yl)-2-fluoro-5-(2-methoxyphenyl) isonicotinamide

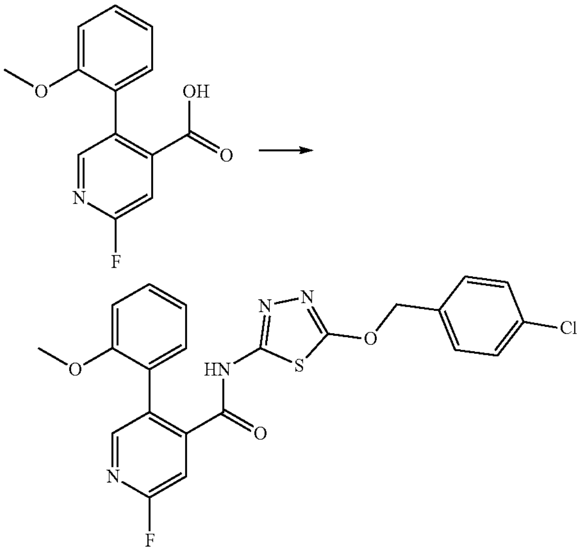

The title compound was prepared using General Procedure A employing 2-fluoro-5-(2-methoxyphenyl)pyridine-4-carboxylic acid and 5-((4-chlorobenzyl)oxy)-1,3,4-thiadiazol-2-amine (Intermediate B). The mixture was diluted with water and extracted with EtOAc (2×). The combined organic layers were concentrated under reduced pressure. The residue was re-crystallized from MeOH:water (10:1) to afford N-(5-((4-chlorobenzyl)oxy)-1,3,4-thiadiazol-2-yl)-2-fluoro-5-(2-methoxyphenyl)isonicotinamide as a white solid. $^{1}H$ NMR (300 MHz; DMSO-$d_6$): δ 3.51 (s, 3H), 5.48 (s, 2H), 6.97-7.08 (m, 2H), 7.34-7.41 (m, 2H), 7.46-7.55 (m, 5H), 8.27 (s, 1H), 12.97 (s, 1H) ppm. m/z 471 (M+H$^{+}$).

Example 82

Synthesis of N-(5-((4-fluorobenzyl)oxy)-1,3,4-thiadiazol-2-yl)-1-(2-methoxyphenyl)-1H-1,2,3-triazole-5-carboxamide

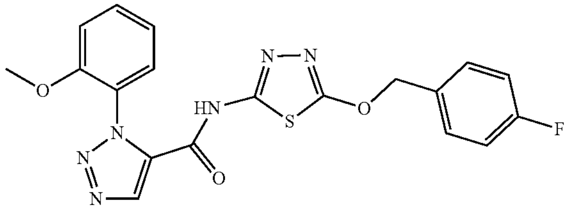 [SMILES: COc1ccccc1-n1nncc1C(=O)Nc1nnc(OCc2ccc(F)cc2)s1]

Step 1. Preparation of ethyl 3-(2-methoxyphenyl)-5-(trimethylsilyl)-1,2,3-triazole-4-carboxylate

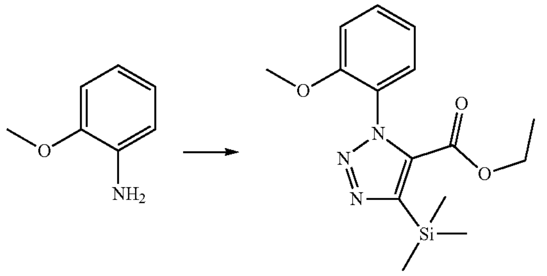

To a solution of 2-methoxyaniline (3 g, 24.4 mmol) in 4 M HCl (30 mL) was added a solution of $NaNO_2$ (1.9 g, 26.8 mmol) in water (10 mL) dropwise at 0° C. The mixture was stirred for 30 min. Then azidosodium (1.9 g, 29.2 mmol) was added in portions. The mixture was slowly warmed to room temperature and stirred 1 h at room temperature. The mixture was extracted with MTBE (3×). The combined organic layers were dried over $Na_2SO_4$ and concentrated under reduced pressure. The residue was diluted with toluene (8 mL) and ethyl 3-(trimethylsilyl)prop-2-ynoate (1.0 g, 5.9 mmol) was added under nitrogen. The mixture was stirred at 80° C. overnight. The mixture was cooled to room temperature and concentrated under reduce pressure to afford ethyl 3-(2-methoxyphenyl)-5-(trimethylsilyl)-1,2,3-triazole-4-carboxylate as brown oil, which was used in the next step without further purification.

Step 2. Preparation of ethyl 3-(2-methoxyphenyl)-1, 2, 3-triazole-4-carboxylate

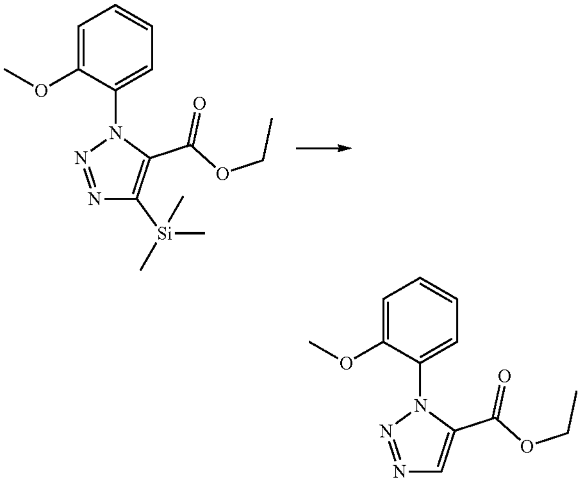

To a solution of ethyl 3-(2-methoxyphenyl)-5-(trimethylsilyl)-1, 2, 3-triazole-4-carboxylate (1.7 g, 5.3 mmol) in THF (20 mL) was added TBAF (2.1 g, 8.0 mmol) under nitrogen. The mixture was stirred at room temperature for 3 h. The mixture was diluted with water (20 mL) and extracted with DCM (3×). The combined organic layers were concentrated under reduced pressure and the residue was purified by Prep-TLC (hexanes:EtOAc, 3:1) to afford ethyl 3-(2-methoxyphenyl)-1, 2, 3-triazole-4-carboxylate as brown oil.

Step 3. Preparation of 3-(2-methoxyphenyl)-1, 2, 3-triazole-4-carboxylic acid

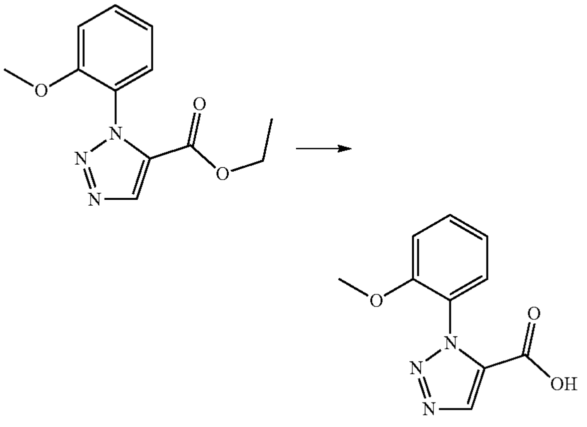

The title compound was prepared using General Procedure F employing ethyl 3-(2-methoxyphenyl)-1, 2, 3-triazole-4-carboxylate. The mixture was diluted with water and acidified to pH 6 with HCl (1 M). The mixture was extracted with EtOAc (2×) and the combined organic layers were concentrated under reduced pressure. The residue was triturated with MeOH to afford 3-(2-methoxyphenyl)-1, 2, 3-triazole-4-carboxylic acid as a white solid.

Step 4. Preparation of N-(5-((4-fluorobenzyl)oxy)-1,3,4-thiadiazol-2-yl)-1-(2-methoxyphenyl)-1H-1,2,3-triazole-5-carboxamide

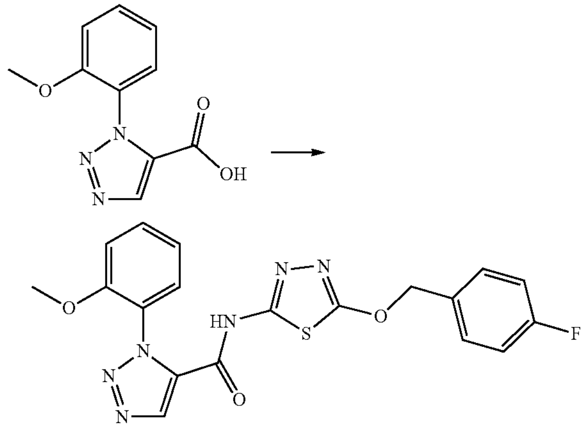

The title compound was prepared using General Procedure A employing 3-(2-methoxyphenyl)-1, 2, 3-triazole-4-carboxylic acid and 5-((4-fluorobenzyl)oxy)-1,3,4-thiadiazol-2-amine (Intermediate A). The mixture was diluted with water and extracted with EtOAc (2×). The combined organic layers were concentrated under reduced pressure. The residue was purified by Prep-TLC (DCM:MeOH, 10:1). The residue was further purified by triturating with MeOH to afford N-(5-((4-fluorobenzyl)oxy)-1,3,4-thiadiazol-2-yl)-1-(2-methoxyphenyl)-1H-1,2,3-triazole-5-carboxamide as a white solid. $^1$H NMR (300 MHz; DMSO-$d_6$): δ 3.66 (s, 3H), 5.47-5.52 (m, 2H), 7.13-7.28 (m, 4H), 7.52-7.59 (m, 4H), 8.57-8.62 (m, 1H), 13.28-13.37 (br s, 1H) ppm. m/z 427 (M+H$^+$).

Example 83

Synthesis of N-[5-[(4-chlorophenyl)methoxy]-1,3,4-thiadiazol-2-yl]-4-[4-[2-(morpholin-4-yl)ethyl]-3-oxopiperazin-1-yl]pyridine-3-carboxamide

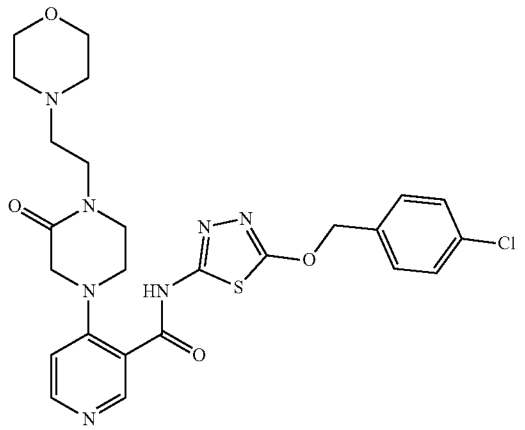 [SMILES: O=C(Nc1nnc(OCc2ccc(Cl)cc2)s1)c1cnccc1N1CCN(CCN2CCOCC2)C(=O)C1]

Step 1. Preparation of benzyl 4-[2-(morpholin-4-yl)ethyl]-3-oxopiperazine-1-carboxylate

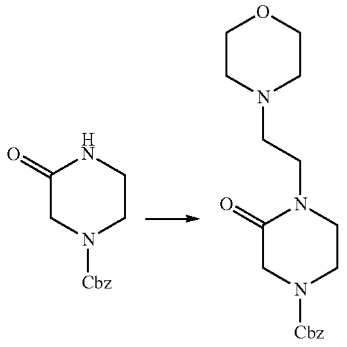 [SMILES: O=C1CN(C(=O)OCc2ccccc2)CCN1 ; O=C1CN(C(=O)OCc2ccccc2)CCN1CCN1CCOCC1]

To a solution of benzyl 3-oxopiperazine-1-carboxylate (2.0 g, 8.5 mmol) in DMF (20 mL) was added NaH (0.68 g, 17.1 mmol, 60% dispersion in oil) under nitrogen at 0° C. The mixture was stirred at 0° C. for 1 h and then 4-(2-bromoethyl)morpholine (1.7 g, 8.5 mmol) was added. The mixture was warmed to room temperature and stirred at room temperature for 3 h. The mixture was diluted with sat. $NH_4Cl$ (60 mL) and extracted with EtOAc (2×20 mL). The combined organic layers were concentrated under reduce pressure. The residue was purified by silica gel column chromatography, eluted with 25% EtOAc in PE to afford benzyl 4-[2-(morpholin-4-yl)ethyl]-3-oxopiperazine-1-carboxylate as a yellow solid.

Step 2. Preparation of 1-[2-(morpholin-4-yl)ethyl]piperazin-2-one

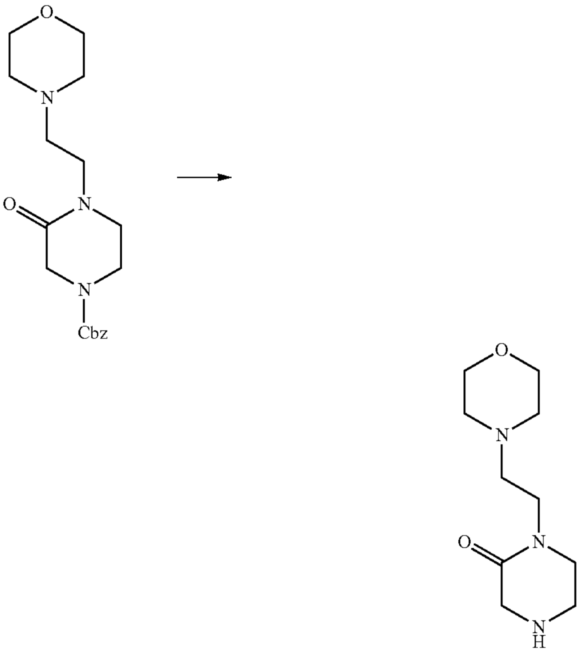

To a solution of benzyl 4-[2-(morpholin-4-yl)ethyl]-3-oxopiperazine-1-carboxylate (500 mg, 1.4 mmol) in MeOH (10 mL) was added 20% Pd/C (100 mg). The mixture was stirred at room temperature for 2 h under an of hydrogen. The mixture was filtered over celite. The filtrate was concentrated under reduce pressure to afford 1-[2-(morpholin-4-yl)ethyl]piperazin-2-one as a yellow solid.

Step 3. Preparation of 4-chloro-N-[5-[(4-chlorophenyl)methoxy]-1,3,4-thiadiazol-2-yl]pyridine-3-carboxamide

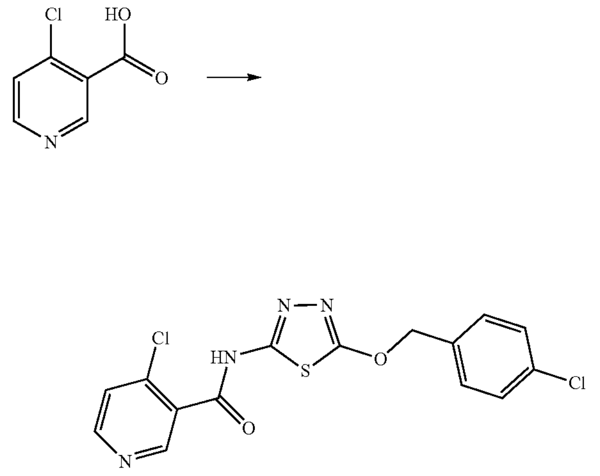

A solution of 4-chloropyridine-3-carboxylic acid (2.0 g, 12.7 mmol) in $SOCl_2$ (20 mL) was stirred at 85° C. for 3 h under nitrogen. The mixture cooled to room temperature and concentrated under reduced pressure. The residue was dissolved in DCM (20 mL) and 5-((4-chlorobenzyl)oxy)-1,3,4-thiadiazol-2-amine (3.1 g, 12.7 mmol, Intermediate B) and $Et_3N$ (2.6 g, 25.4 mmol) were added under nitrogen. The mixture was stirred for 3 h at room temperature. The mixture was diluted with water and extracted with EtOAc (3×). The combined organic layers were concentrated under reduced pressure. The residue was triturated with EtOAc to afford 4-chloro-N-[5-[(4-chlorophenyl)methoxy]-1,3,4-thiadiazol-2-yl]pyridine-3-carboxamide as a yellow solid.

Step 4. Preparation of N-[5-[(4-chlorophenyl)methoxy]-1,3,4-thiadiazol-2-yl]-4-[4-[2-(morpholin-4-yl)ethyl]-3-oxopiperazin-1-yl]pyridine-3-carboxamide

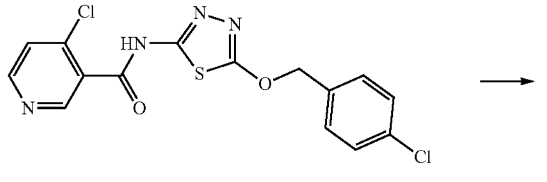

-continued

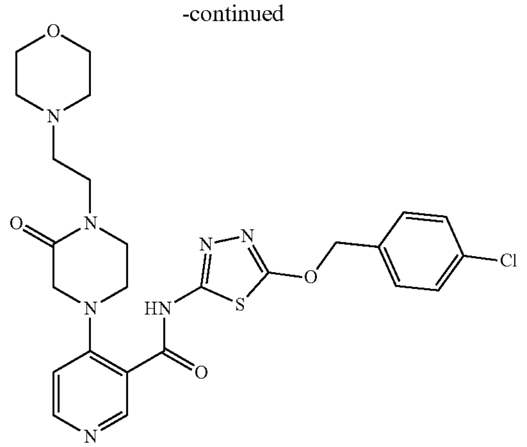

To a solution of 1-[2-(morpholin-4-yl)ethyl]piperazin-2-one (180 mg, 0.84 mmol, Step 2) in MeCN (2 mL) was added 4-chloro-N-[5-[(4-chlorophenyl)methoxy]-1,3,4-thiadiazol-2-yl]pyridine-3-carboxamide (322 mg, 0.84 mmol, Step 3), DIEA (218 mg, 1.7 mmol) under nitrogen. The mixture was stirred at 80° C. for 6 h. The mixture was cooled room temperature and diluted with water. The mixture was extracted with EtOAc (3×). The combined organic layers were concentrated under reduced pressure. The residue was purified by Prep-TLC (DCM:MeOH, 5:1) to afford N-[5-[(4-chlorophenyl)methoxy]-1,3,4-thiadiazol-2-yl]-4-[4-[2-(morpholin-4-yl)ethyl]-3-oxopiperazin-1-yl]pyridine-3-carboxamide as a white solid. $^1H$ NMR (300 MHz; DMSO-$d_6$): δ 2.35-2.39 (m, 4H), 2.42-2.44 (m, 2H), 3.40-3.50 (m, 6H), 3.52 (s, 4H), 3.78 (s, 2H), 5.51 (s, 2H), 6.92-6.97 (m, 1H), 7.48-7.57 (m, 4H), 8.33-8.35 (m, 1H), 8.42 (s, 1H), 12.80-13.03 (br s, 1H) ppm. m/z 558 ($M+H^+$).

Example 84

Synthesis of 5-((5-((4-chlorobenzyl)oxy)-1,3,4-thiadiazol-2-yl)carbamoyl)-4-morpholinopicolinic acid

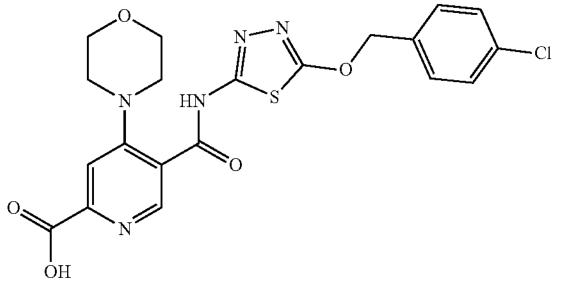 [SMILES: O=C(O)c1cc(N2CCOCC2)c(C(=O)Nc2nnc(OCc3ccc(Cl)cc3)s2)cn1]

Step 1. Preparation of 6-chloro-N-[5-[(4-chlorophenyl)methoxy]-1,3,4-thiadiazol-2-yl]-4-(morpholin-4-yl)pyridine-3-carboxamide

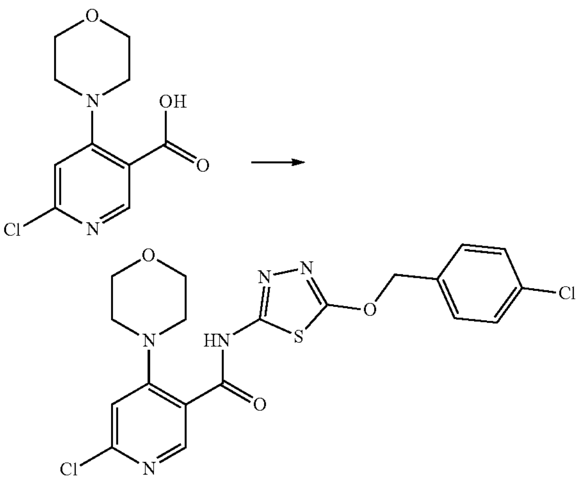

The title compound was prepared using General Procedure A employing 6-chloro-4-(morpholin-4-yl)pyridine-3-carboxylic acid (Example 35, Step 1) and 5-((4-chlorobenzyl)-oxy)-1,3,4-thiadiazol-2-amine (Intermediate B). The mixture was diluted with EtOAc and washed with water (2×). The organic layer was concentrated under reduced pressure. The residue was re-crystallized from MeOH/water (10:1) to afford 6-chloro-N-[5-[(4-chlorophenyl)methoxy]-1,3,4-thiadiazol-2-yl]-4-(morpholin-4-yl)pyridine-3-carboxamide as a white solid.

Step 2. Preparation of methyl 5-((5-((4-chlorobenzyl)oxy)-1,3,4-thiadiazol-2-yl)carbamoyl)-4-morpholinopicolinate

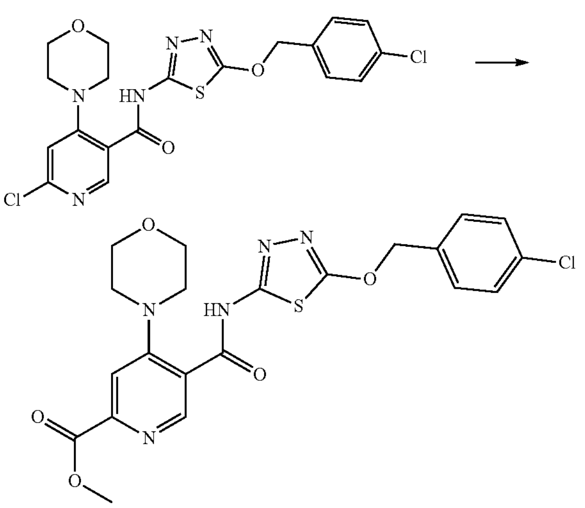

To a solution of 6-chloro-N-[5-[(4-chlorophenyl)methoxy]-1,3,4-thiadiazol-2-yl]-4-(morpholin-4-yl)pyridine-3-carboxamide (5.0 g, 10.7 mmol) in MeOH (300) was added $Et_3N$ (2.2 g, 21.4 mmol), Xantphos (0.3 g, 0.54 mmol)

and $Pd(dppf)Cl_2$ (0.4 g, 0.54 mmol) at room temperature. The mixture was stirred at 80° C. for 12 h under 30 atm of carbon monoxide. The mixture was cooled to room temperature and diluted with EtOAc (500 mL). The resulting mixture was washed with water (3×). The organic layer was concentrated under reduced pressure. The residue was purified by silica gel column chromatography, eluted with 0.3% MeOH in DCM to afford methyl 5-((5-((4-chlorobenzyl)oxy)-1,3,4-thiadiazol-2-yl)carbamoyl)-4-morpholinopicolinate as a white solid.

Step 3. Preparation of 5-((5-((4-chlorobenzyl)oxy)-1,3,4-thiadiazol-2-yl)carbamoyl)-4-morpholinopicolinic acid

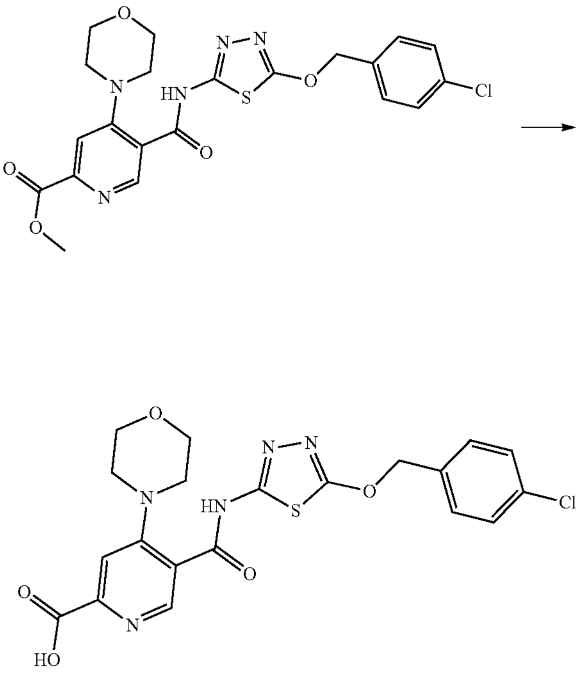

To a solution of methyl 5-((5-((4-chlorobenzyl)oxy)-1,3,4-thiadiazol-2-yl)carbamoyl)-4-morpholinopicolinate (1.2 g, 2.5 mmol) in MeOH (7 mL) and $H_2O$ (7 mL) was added NaOH (0.2 g, 5.1 mmol). The mixture was stirred for 1 h at room temperature. The mixture was acidified to pH 7 with HCl (1 M). The mixture was extracted with EtOAc (3×). The combined organic layers were concentrated under reduced pressure. The residue was re-crystallized from (MeOH:water, 12:1) to afford 5-((5-((4-chlorobenzyl)oxy)-1,3,4-thiadiazol-2-yl)carbamoyl)-4-morpholinopicolinic acid as an off-white solid. $^1$H NMR (300 MHz; DMSO-$d_6$): δ 3.24-3.26 (m, 4H), 3.65-3.68 (m, 4H), 5.49 (s, 2H), 7.47-7.56 (m, 5H), 8.44 (s, 1H) ppm. m/z 476 (M+H$^+$).

Example 85

Synthesis of N-(5-((4-bromobenzyl)oxy)-1,3,4-thiadiazol-2-yl)-6-cyano-2-(4-oxa-7-azaspiro[2.5]octan-7-yl)nicotinamide

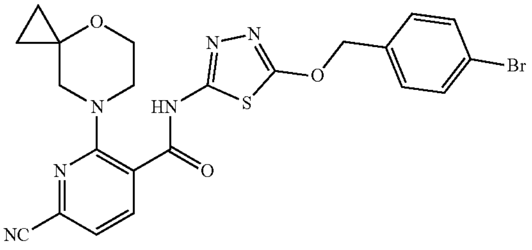 [SMILES: N#Cc1ccc(C(=O)Nc2nnc(OCc3ccc(Br)cc3)s2)c(N2CCOC3(CC3)C2)n1]

The title compound was prepared using General Procedure A employing 6-cyano-2-(4-oxa-7-azaspiro[2.5]octan-7-yl)nicotinic acid (Example 44, Step 1) and 5-((4-bromobenzyl)oxy)-1,3,4-thiadiazol-2-amine (Example 40, Step 1). The mixture was diluted with EtOAc washed with water (2×). The organic layer was concentrated under reduced pressure. The residue was triturated with MeOH to afford N-(5-((4-bromobenzyl)oxy)-1,3,4-thiadiazol-2-yl)-6-cyano-2-(4-oxa-7-azaspiro[2.5]octan-7-yl)nicotinamide as a yellow solid. $^1$H NMR (300 MHz; DMSO-$d_6$): δ 0.48-0.55 (m, 2H), 0.60-0.69 (m, 2H), 3.35-3.38 (m, 4H), 3.68-3.71 (m, 2H), 5.49 (s, 2H), 7.47-7.49 (m, 3H), 7.61-7.64 (m, 2H), 8.00-8.02 (m, 1H), 13.03 (s, 1H) ppm. m/z 527 (M+H$^+$).

Example 86

Synthesis of N-(5-((4-bromobenzyl)oxy)-1,3,4-thiadiazol-2-yl)-1-(2-methoxyphenyl)-1H-imidazole-5-carboxamide

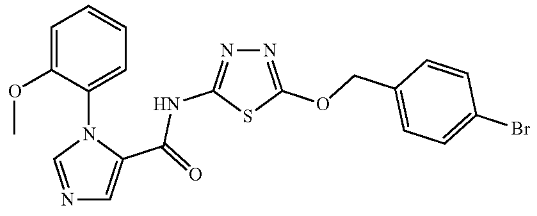 [SMILES: COc1ccccc1-n1cncc1C(=O)Nc1nnc(OCc2ccc(Br)cc2)s1]

The title compound was prepared using similar procedure as Example 18, replacing 4-aminopyridine with 2-methoxyaniline in Step 1 and employing 5-((4-bromobenzyl)oxy)-1,3,4-thiadiazol-2-amine (Example 40, Step 1) in Step 2. The mixture was diluted with water and extracted with EtOAc (2×). The combined organic layers were concentrated under reduced pressure. The residue was triturated with MeOH to afford N-(5-((4-bromobenzyl)oxy)-1,3,4-thiadiazol-2-yl)-1-(2-methoxyphenyl)-1H-imidazole-5-carboxamide as a pink solid. $^1$H NMR (300 MHz; DMSO-$d_6$): δ 3.68 (s, 3H), 5.44 (s, 2H), 7.03-7.08 (m, 1H), 7.16-7.19 (m, 1H), 7.35-7.38 (m, 1H), 7.43-7.48 (m, 3H), 7.59-7.62 (m, 2H), 7.98 (s, 1H), 8.10 (s, 1H), 12.71 (s, 1H) ppm. m/z 486 (M+H$^+$).

Example 87

Synthesis of $N^5$-(5-((4-chlorobenzyl)oxy)-1,3,4-thiadiazol-2-yl)-N2-methyl-4-(5-oxo-1,4-diazepan-1-yl)pyridine-2,5-dicarboxamide

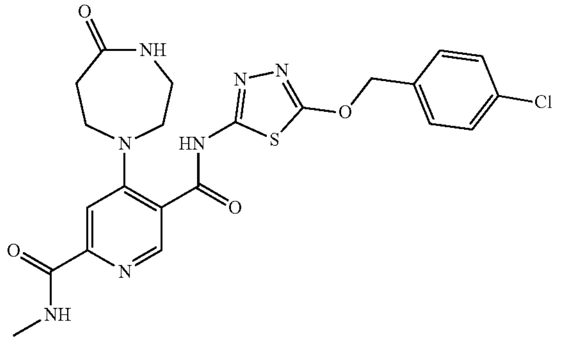 [SMILES: CNC(=O)c1cc(N2CCNC(=O)CC2)c(C(=O)Nc2nnc(OCc3ccc(Cl)cc3)s2)cn1]

Step 1. Preparation of ethyl 6-chloro-4-(5-oxo-1,4-diazepan-1-yl)nicotinate

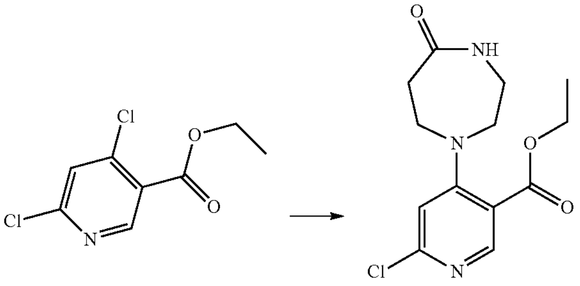 [SMILES: CCOC(=O)c1cnc(Cl)cc1Cl ; CCOC(=O)c1cnc(Cl)cc1N1CCNC(=O)CC1]

The title compound was prepared using similar procedure as Example 35, Step 1 replacing morpholine with 1,4-diazepan-5-one.

Step 2. Preparation of 6-methylcarbamoyl)-4-(5-oxo-1,4-diazepan-1-yl)nicotinic acid

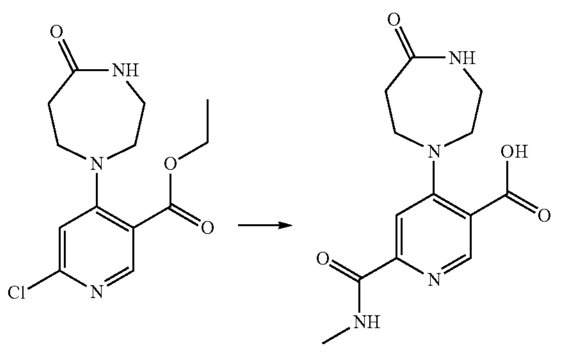 [SMILES: CCOC(=O)c1cnc(Cl)cc1N1CCNC(=O)CC1 ; CNC(=O)c1cc(N2CCNC(=O)CC2)c(C(=O)O)cn1]

The title compound was prepared using similar procedure as Example 64, Steps 1 and 2, replacing ethyl 6-chloro-4-(morpholin-4-yl)pyridine-3-carboxylate in Step 1 with ethyl 6-chloro-4-(5-oxo-1,4-diazepan-1-yl)nicotinate.

Step 3. Preparation of $N^5$-(5-((4-chlorobenzyl)oxy)-1,3,4-thiadiazol-2-yl)-N2-methyl-4-(5-oxo-1,4-diazepan-1-yl)pyridine-2,5-dicarboxamide

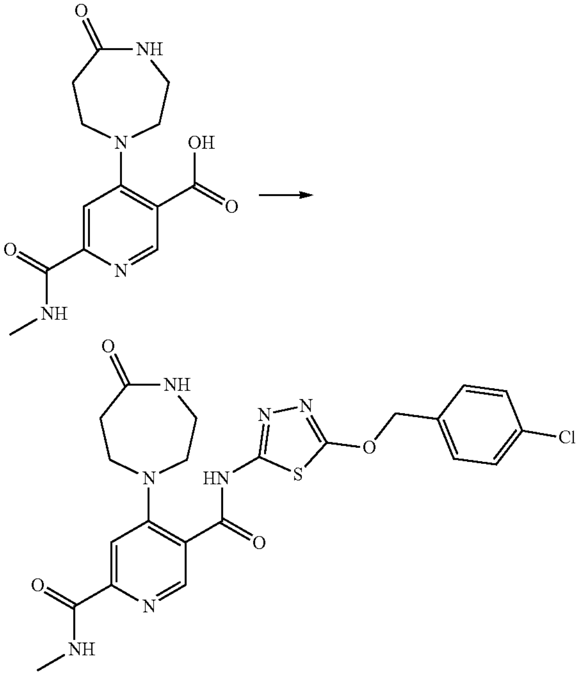

The title compound was prepared using General Procedure D employing 6-(methylcarbamoyl)-4-(5-oxo-1,4-diazepan-1-yl)nicotinic acid and 5-((4-chlorobenzyl)oxy)-1,3,4-thiadiazol-2-amine (Intermediate B). The mixture was stirred overnight at room temperature. The mixture was diluted with EtOAc and washed with water (3×). The aqueous layer was extracted with EtOAc (3×). The combined organic layers were concentrated under reduce pressure and residue was purified by Prep-TLC (DCM:MeOH, 20:1) to afford $N^5$-(5-((4-chlorobenzyl)oxy)-1,3,4-thiadiazol-2-yl)-N2-methyl-4-(5-oxo-1,4-diazepan-1-yl)pyridine-2,5-dicarboxamide as a white solid. $^1H$ NMR (400 MHz, DMSO-$d_6$): δ 2.62-2.68 (m, 2H), 2.80-2.82 (m, 3H), 3.29-3.34 (m, 4H), 3.50-3.51 (m, 2H), 5.51 (s, 2H), 7.49-7.61 (m, 6H), 8.42 (s, 1H), 8.79-8.81 (m, 1H), 12.96 (s, 1H) ppm. m/z 516 (M+H$^+$).

Example 88

Synthesis of N-(5-((4-bromobenzyl)oxy)-1,3,4-thiadiazol-2-yl)-6-cyano-2-(3-oxopiperazin-1-yl)nicotinamide

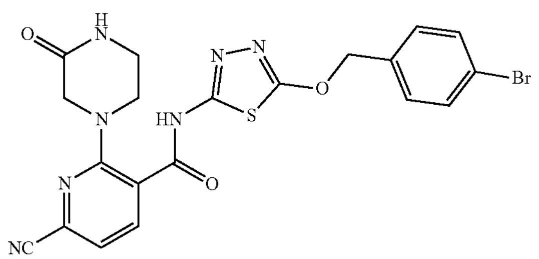 [SMILES: N#Cc1ccc(C(=O)Nc2nnc(OCc3ccc(Br)cc3)s2)c(N2CCNC(=O)C2)n1]

Step 1. Preparation of 6-bromo-2-(3-oxopiperazin-1-yl)nicotinic acid

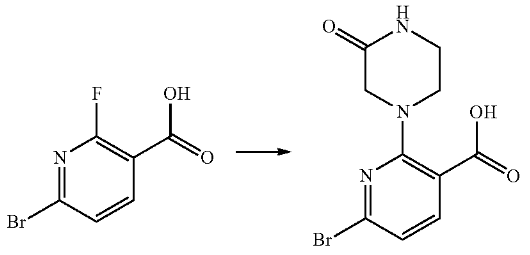 [SMILES: O=C(O)c1ccc(Br)nc1F ; O=C1CN(c2nc(Br)ccc2C(=O)O)CCN1]

The title compound was prepared using similar procedure as Example 14, Step 1 replacing morpholine with piperazin-2-one Step 2. Preparation of 6-cyano-2-(3-oxopiperazin-1-yl)pyridine-3-carboxylic acid

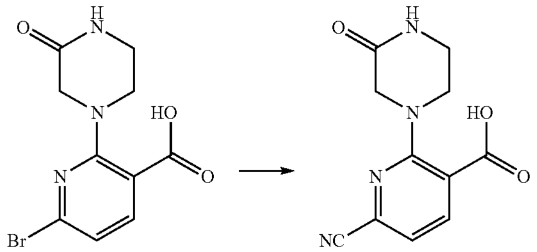 [SMILES: O=C1CN(c2nc(Br)ccc2C(=O)O)CCN1 ; N#Cc1ccc(C(=O)O)c(N2CCNC(=O)C2)n1]

The title compound was prepared using similar procedure as Example 35, Step 2 replacing 6-chloro-4-(morpholin-4-yl)pyridine-3-carboxylic acid with 6-bromo-2-(3-oxopiperazin-1-yl)nicotinic acid Step 3. Preparation of N-(5-((4-bromobenzyl)oxy)-1,3,4-thiadiazol-2-yl)-6-cyano-2-(3-oxopiperazin-1-yl)nicotinamide

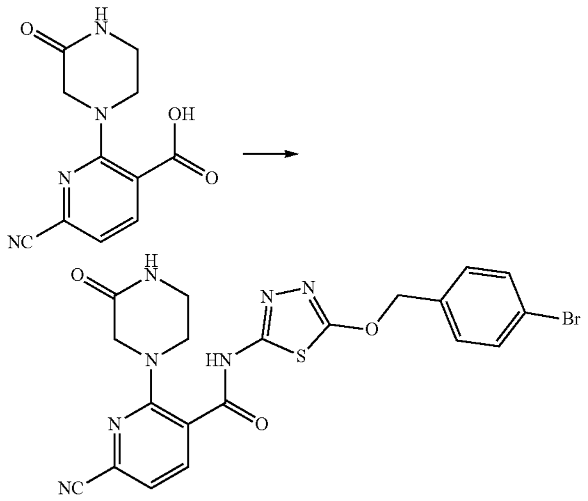

The title compound was prepared using General Procedure A employing 6-cyano-2-(3-oxopiperazin-1-yl)pyridine-3-carboxylic acid and 5-((4-bromobenzyl)oxy)-1,3,4-thiadiazol-2-amine (Example 40, Step 1). The mixture was diluted with EtOAc and washed with water (2×). The organic layer was concentrated under reduce pressure. The residue was triturated with MeOH to afford N-(5-((4-bromobenzyl)oxy)-1,3,4-thiadiazol-2-yl)-6-cyano-2-(3-oxopiperazin-1-yl)nicotinamide as a yellow solid. $^1$H NMR (400 MHz; DMSO-$d_6$): δ 3.24-3.28 (m, 2H), 3.52-3.54 (m, 2H), 3.81 (s, 2H), 5.49 (s, 2H), 7.46-7.52 (m, 3H), 7.58-7.64 (m, 2H), 8.02-8.04 (m, 1H), 8.12 (s, 1H), 13.10 (s, 1H) ppm. m/z 514 (M+H$^+$).

Example 89

Synthesis of N-(5-((5-chloropyridin-2-yl)methoxy)-1,3,4-thiadiazol-2-yl)-4-(2-methoxyphenyl)nicotinamide

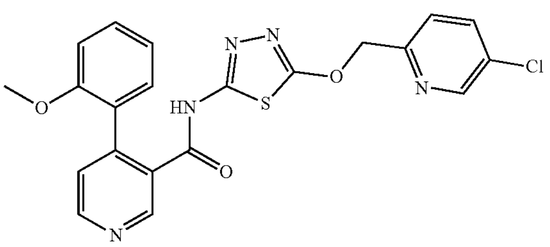 [SMILES: COc1ccccc1-c1ccncc1C(=O)Nc1nnc(OCc2ccc(Cl)cn2)s1]

The title compound was prepared using similar procedure as Example 77, replacing 5-((4-chlorobenzyl)oxy)-1,3,4-thiadiazol-2-amine (Intermediate B) with 5-((5-chloropyridin-2-yl)methoxy)-1,3,4-thiadiazol-2-amine (Intermediate C). $^1$H NMR (300 MHz; DMSO-$d_6$): δ 3.52 (s, 3H), 5.54 (s, 2H), 6.98-7.01 (m, 1H), 7.05-7.10 (m, 1H), 7.34-7.44 (m, 3H), 7.59-7.62 (m, 1H), 7.98-8.02 (m, 1H), 8.65-8.66 (m, 1H), 8.74-8.79 (m, 2H), 12.82 (s, 1H) ppm. m/z 454 (M+H$^+$).

Example 90

Synthesis of N-(5-(cyclopropylmethoxy)-1,3,4-thiadiazol-2-yl)-4-(2-methoxyphenyl)nicotinamide

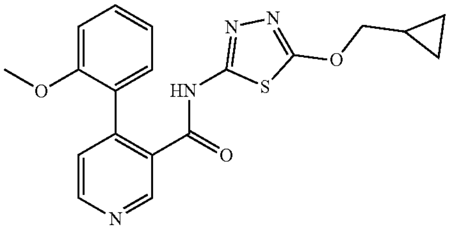 [SMILES: COc1ccccc1-c1ccncc1C(=O)Nc1nnc(OCC2CC2)s1]

Step 1. Preparation of 5-(cyclopropylmethoxy)-1,3,4-thiadiazol-2-amine

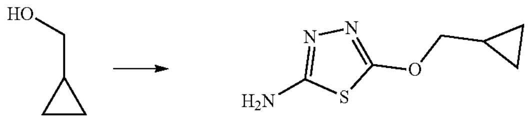 [SMILES: OCC1CC1 ; Nc1nnc(OCC2CC2)s1]

The title compound was prepared using similar procedure as Intermediate A, replacing (4-fluorophenyl)methanol with cyclopropylmethanol in Step 1.

Step 2. Preparation of N-(5-(cyclopropylmethoxy)-1,3,4-thiadiazol-2-yl)-4-(2-methoxyphenyl)nicotinamide

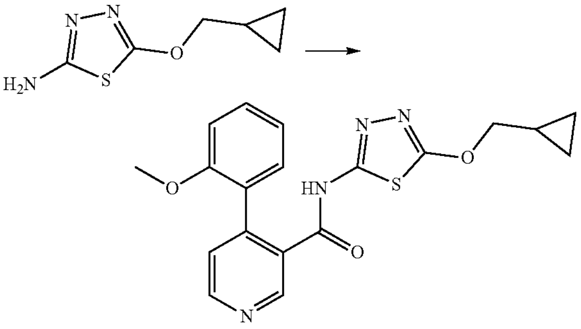

The title compound was prepared using General Procedure A employing 5-(cyclopropylmethoxy)-1,3,4-thiadiazol-2-amine and 4-(2-methoxyphenyl)pyridine-3-carboxylic acid (Example 77). The mixture was diluted with water and extracted with EtOAc (2×). The combined organic layers were concentrated under reduced pressure. The residue was purified by Prep-TLC (DCM:MeOH, 20:1). The residue was further purified by trituration with MeOH to afford N-(5-(cyclopropylmethoxy)-1,3,4-thiadiazol-2-yl)-4-(2-methoxyphenyl)nicotinamide as a white solid. $^1$H NMR (300 MHz; $CD_3OD$): δ 0.38-0.41 (m, 2H), 0.68-0.69 (m, 2H), 1.31-1.40 (m, 1H), 3.00 (s, 1H), 3.63 (s, 3H), 4.25-4.31 (m, 2H), 6.98-7.01 (m, 1H), 7.07-7.12 (m, 1H), 7.39-7.42 (m, 2H), 7.45-7.50 (m, 1H), 8.71-8.72 (m, 1H), 8.79 (s, 1H) ppm. m/z 383 (M+H$^+$).

Example 91

Synthesis of Synthesis of 2-(2-chlorophenyl)-N-[5-[(4-chlorophenyl)methoxy]-1,3,4-thiadiazol-2-yl]pyridine-3-carboxamide

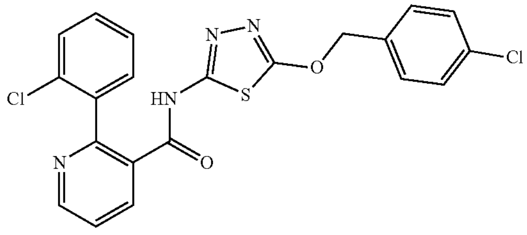 [SMILES: O=C(Nc1nnc(OCc2ccc(Cl)cc2)s1)c1cccnc1-c1ccccc1Cl]

The title compound was prepared using similar procedure as Example 51 employing 5-((4-chlorobenzyl)oxy)-1,3,4-thiadiazol-2-amine (Intermediate B). $^1H$ NMR (300 MHz; DMSO-$d_6$): δ 5.54 (s, 2H), 7.40-7.49 (m, 8H), 7.58-7.63 (m, 1H), 8.20-8.23 (m, 1H), 8.81-8.83 (m, 1H), 13.00 (s, 1H) ppm. m/z 457 (M+H$^+$).

Example 92

N-(5-((4-chlorobenzyl)oxy)-1,3,4-thiadiazol-2-yl)-6-cyano-4-(2-methoxyphenyl)nicotinamide

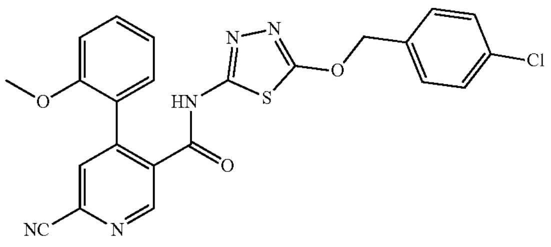 [SMILES: COc1ccccc1-c1cc(C#N)ncc1C(=O)Nc1nnc(OCc2ccc(Cl)cc2)s1]

Step 1. Preparation of benzyl 6-bromo-4-chloropyridine-3-carboxylate

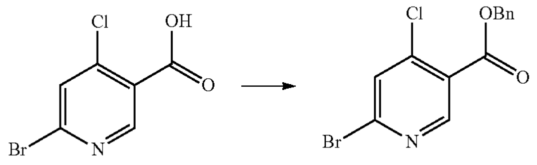 [SMILES: O=C(O)c1cnc(Br)cc1Cl ; O=C(OCc1ccccc1)c1cnc(Br)cc1Cl]

To a solution of 6-bromo-4-chloropyridine-3-carboxylic acid (1.5 g, 6.3 mmol) in DMF (20 mL) was added (bromomethyl)benzene (1.2 g, 7.0 mmol), $K_2CO_3$ (1.8 g, 12.7 mmol). The mixture was stirred at 60° C. for 10 min. The mixture was cooled to room temperature, diluted with water and extracted with EtOAc. The combined organic layers were concentrated under reduced pressure and the residue was purified by silica gel column chromatography, eluted with 8% EtOAc in hexane to afford benzyl 6-bromo-4-chloropyridine-3-carboxylate as a white solid.

Step 2. Preparation of benzyl 4-chloro-6-cyanopyridine-3-carboxylate

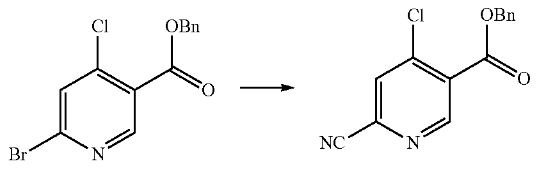 [SMILES: O=C(OCc1ccccc1)c1cnc(Br)cc1Cl ; N#Cc1cc(Cl)c(C(=O)OCc2ccccc2)cn1]

The title compound was prepared using similar procedure as Example 33, Step 2 replacing methyl 5-bromo-2-morpholinonicotinate with benzyl 6-bromo-4-chloropyridine-3-carboxylate.

Step 3. Preparation of benzyl 6-cyano-4-(2-methoxyphenyl)pyridine-3-carboxylate

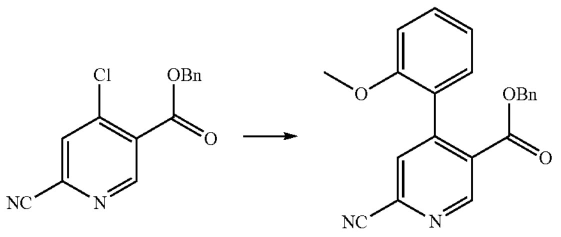 [SMILES: N#Cc1cc(Cl)c(C(=O)OCc2ccccc2)cn1 ; COc1ccccc1-c1cc(C#N)ncc1C(=O)OCc1ccccc1]

The title compound was prepared using similar procedure as Example 67, Step 1, replacing methyl 2-chloropyridine-3-carboxylate with benzyl 4-chloro-6-cyanopyridine-3-carboxylate in Step 1.

Step 4. Preparation of 6-cyano-4-(2-methoxyphenyl)pyridine-3-carboxylic acid

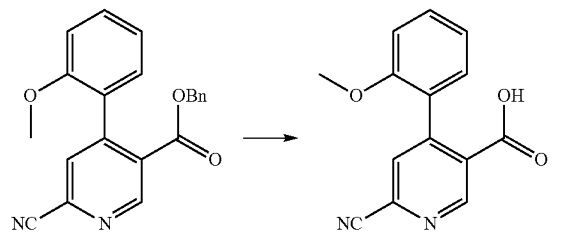 [SMILES: COc1ccccc1-c1cc(C#N)ncc1C(=O)OCc1ccccc1 ; COc1ccccc1-c1cc(C#N)ncc1C(=O)O]

To a solution of benzyl 6-cyano-4-(2-methoxyphenyl)pyridine-3-carboxylate (530 mg, 1.5 mmol) in THF (12 mL) was added 10% Pd/C (106 mg). The mixture was stirred under hydrogen at room temperature for 6 h. The mixture was filtered over celite and the filtrate was concentrated under reduced pressure to afford 6-cyano-4-(2-methoxyphenyl)pyridine-3-carboxylic acid as an off-white solid.

Step 5. Preparation of N-(5-((4-chlorobenzyl)oxy)-1,3,4-thiadiazol-2-yl)-6-cyano-4-(2-methoxyphen 1 nicotinamide

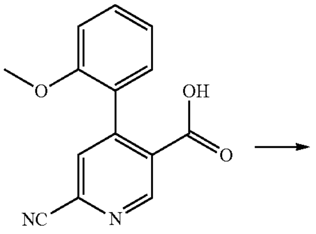

-continued

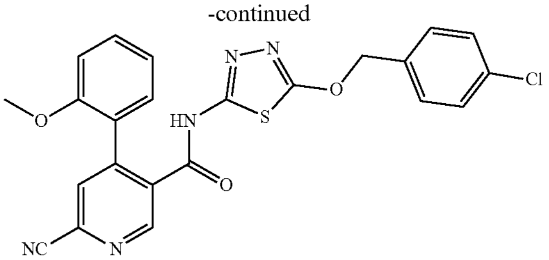

The title compound was prepared using General Procedure D employing 6-cyano-4-(2-methoxyphenyl)pyridine-3-carboxylic acid and 5-((4-chlorobenzyl)oxy)-1,3,4-thiadiazol-2-amine (Intermediate B). The mixture was stirred at room temperature overnight and diluted with water. The mixture was extracted with EtOAc (2×). The combined organic layers were concentrated under reduced pressure. The residue was purified by Prep-TLC (DCM:MeOH, 12:1) to afford N-(5-((4-chlorobenzyl)oxy)-1,3,4-thiadiazol-2-yl)-6-cyano-4-(2-methoxyphenyl)nicotinamide as a light yellow solid. $^{1}$H NMR (300 MHz; DMSO-$d_6$): δ 3.54 (s, 3H), 5.48 (s, 2H), 7.02-7.13 (m, 2H), 7.42-7.55 (m, 6H), 8.14 (s, 1H), 8.96 (s, 1H), 13.07 (s, 1H) ppm. m/z 478 (M+H$^+$).

Example 93

Synthesis of N-(5-((4-chlorobenzyl)oxy)-1,3,4-thiadiazol-2-yl)-4-(2-cyclopropoxyphenyl)nicotinamide

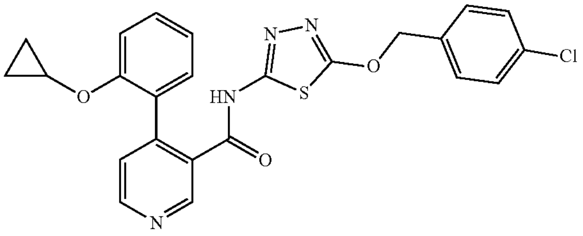 [SMILES: O=C(Nc1nnc(OCc2ccc(Cl)cc2)s1)c1cnccc1-c1ccccc1OC1CC1]

The title compound was prepared using similar procedure as Example 77, replacing 2-methoxyphenylboronic acid with 2-(2-cyclopropoxyphenyl)-4,4,5,5-tetramethyl-1,3,2-dioxaborolane. $^{1}$H NMR (300 MHz; DMSO-$d_6$): δ 0.32-0.55 (m, 4H), 3.49-3.57 (m, 1H), 5.53 (s, 2H), 7.06-7.10 (m, 1H), 7.17-7.66 (m, 8H), 8.70-8.80 (m, 2H), 12.66-12.96 (br s, 1H) ppm. m/z 479 (M+H$^+$).

Example 94

Synthesis of N-(5-((4-chlorobenzyl)oxy)-1,3,4-thiadiazol-2-yl)-2-phenylnicotinamide

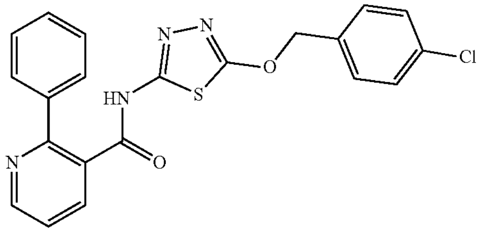 [SMILES: O=C(Nc1nnc(OCc2ccc(Cl)cc2)s1)c1cccnc1-c1ccccc1]

The title compound was prepared using similar procedure as Example 67, replacing 2-methoxyphenylboronic acid in Step 1 with phenyl boronic acid. $^{1}$H NMR (400 MHz; DMSO-$d_6$): δ 5.48 (s, 2H), 7.38 (s, 3H), 7.40-7.58 (m, 7H), 8.05-8.08 (m, 1H), 8.79-8.81 (m, 1H), 12.88 (s, 1H) ppm. m/z 423 (M+H$^+$).

Example 95

Synthesis of N-(5-((4-chlorobenzyl)oxy)-1,3,4-thiadiazol-2-yl)-3-(2-methoxyphenyl)isonicotinamide

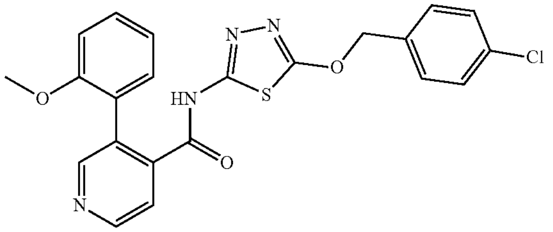

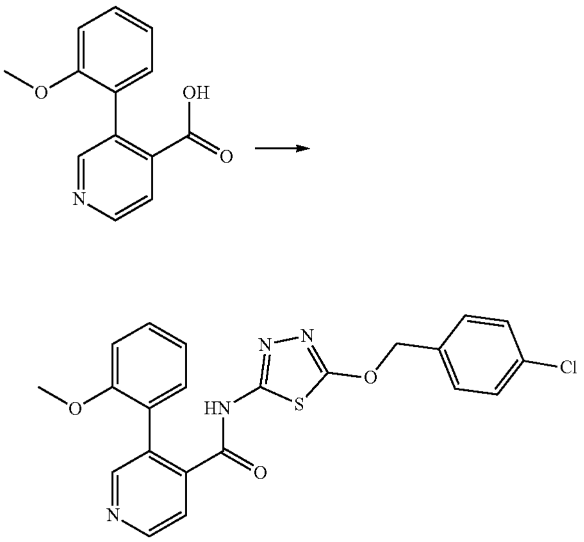

The title compound was prepared using General Procedure A employing 3-(2-methoxyphenyl) pyridine-4-carboxylic acid (Intermediate H) and 5-((4-chlorobenzyl)oxy)-1,3,4-thiadiazol-2-amine (Intermediate B). The mixture was diluted with water and extracted with EtOAc (2×). The combined organic layers were concentrated under reduced pressure. The residue was triturated with MeOH to afford N-(5-((4-chlorobenzyl)oxy)-1,3,4-thiadiazol-2-yl)-3-(2-methoxyphenyl)isonicotinamide as an off-white solid. $^{1}$H NMR (300 MHz; DMSO-$d_6$): δ 3.51 (s, 3H), 5.47 (s, 2H), 6.97-7.00 (m, 1H), 7.04-7.09 (m, 1H), 7.35-7.41 (m, 2H), 7.47-7.54 (m, 4H), 7.62-7.63 (m, 1H), 8.61 (s, 1H), 8.70-8.72 (m, 1H), 12.84 (s, 1H) ppm. m/z 453 (M+H$^+$).

Example 96

Synthesis of N-(5-((5-chloropyridin-2-yl)methoxy)-1,3,4-thiadiazol-2-yl)-6-cyano-4-(2-methoxyphenyl) nicotinamide

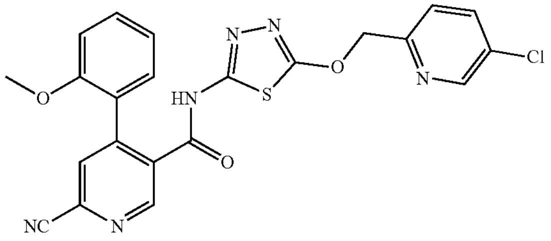 [SMILES: COc1ccccc1-c1cc(C#N)ncc1C(=O)Nc1nnc(OCc2ccc(Cl)cn2)s1]

The title compound was prepared using General Procedure D employing 6-cyano-4-(2-methoxyphenyl)pyridine-3-carboxylic acid (Example 92, Step 4) and 5-((5-chloropyridin-2-yl)methoxy)-1,3,4-thiadiazol-2-amine (Intermediate C). The mixture was stirred at room temperature overnight and diluted with water. The mixture was extracted with EtOAc (2×). The combined organic layers were concentrated under reduced pressure. The residue was purified by Prep-TLC (DCM:MeOH, 12:1) to afford N-(5-((5-chloropyridin-2-yl)methoxy)-1,3,4-thiadiazol-2-yl)-6-cyano-4-(2-methoxyphenyl)nicotinamide as a white solid. $^{1}$H NMR (300 MHz; DMSO-$d_6$): δ 3.54 (s, 3H), 5.54 (s, 2H), 7.02-7.12 (m, 2H), 7.42-7.47 (m, 2H), 7.59-7.62 (m, 1H), 7.98-8.02 (m, 1H), 8.13 (s, 1H), 8.64-8.65 (m, 1H), 8.96 (s, 1H), 13.08 (s, 1H) ppm. m/z 479 (M+H$^+$).

Example 97

Synthesis of N-(5-((5-bromopyridin-2-yl)methoxy)-1,3,4-thiadiazol-2-yl)-4-(2-methoxy-phenyl)nicotinamide

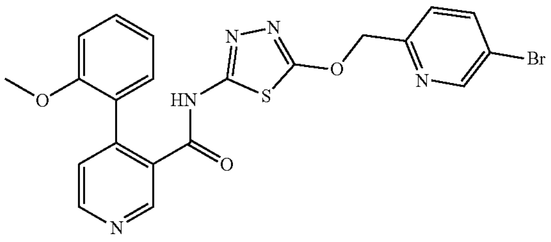 [SMILES: COc1ccccc1-c1ccncc1C(=O)Nc1nnc(OCc2ccc(Br)cn2)s1]

The title compound was prepared using similar procedure as Example 77, replacing 5-((4-chlorobenzyl)oxy)-1,3,4-thiadiazol-2-amine (Intermediate B) with 5-((5-bromopyridin-2-yl)methoxy)-1,3,4-thiadiazol-2-amine (Example 15, Step 1). $^{1}$H NMR (300 MHz; DMSO-$d_6$): δ 3.52 (s, 3H), 5.52 (s, 2H), 6.98-7.01 (m, 1H), 7.05-7.10 (m, 1H), 7.34-7.44 (m, 3H), 7.53-7.56 (m, 1H), 8.11-8.14 (m, 1H), 8.73-8.76 (m, 2H), 8.79 (s, 1H), 12.84 (s, 1H) ppm. m/z 498 (M+H$^+$).

Example 98

Synthesis of N-(5-((4-chlorobenzyl)oxy)-1,3,4-thiadiazol-2-yl)-6-(1H-imidazol-2-yl)-4-morpholinonicotinamide

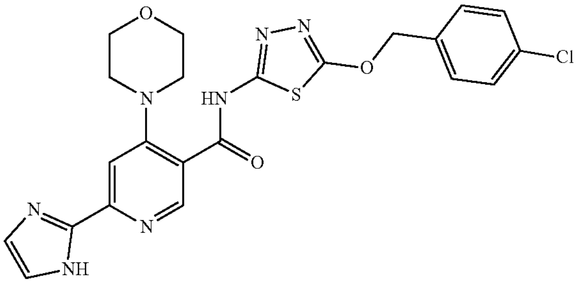 [SMILES: O=C(Nc1nnc(OCc2ccc(Cl)cc2)s1)c1cnc(-c2ncc[nH]2)cc1N1CCOCC1]

Step 1. Preparation of ethyl 6-cyano-4-(morpholin-4-yl)pyridine-3-carboxylate

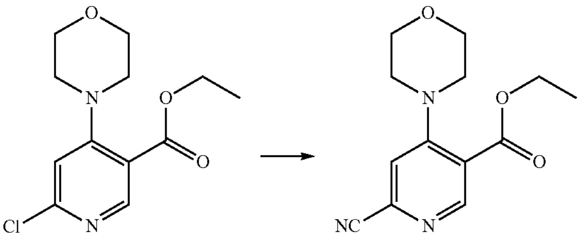 [SMILES: CCOC(=O)c1cnc(Cl)cc1N1CCOCC1 ; CCOC(=O)c1cnc(C#N)cc1N1CCOCC1]

The title compound was prepared using similar procedure as Example 35, Steps 2 replacing 6-chloro-4-(morpholin-4-yl)pyridine-3-carboxylic acid with ethyl 6-chloro-4-(morpholin-4-yl)pyridine-3-carboxylate.

Step. Preparation of methyl 6-(1H-imidazol-2-yl)-4-morpholinonicotinate

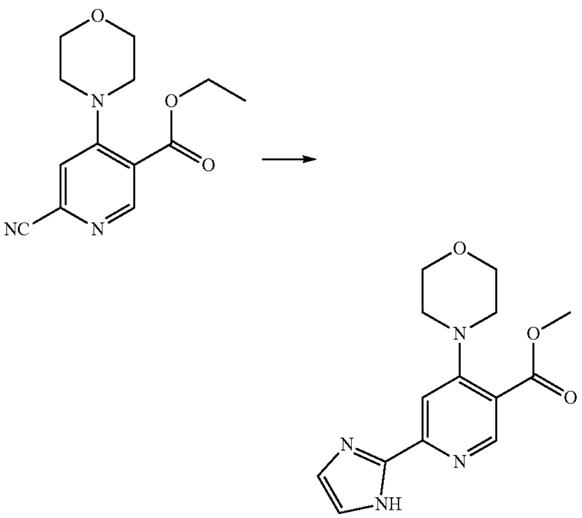

To a solution of ethyl 6-cyano-4-(morpholin-4-yl)pyridine-3-carboxylate (360 mg, 1.38 mmol) in MeOH (4 mL) was added NaOMe (15 mg, 0.28 mmol). The mixture was stirred at 50° C. for 1.5 h, then HOAc (147 mg, 2.4 mmol) and 2,2-dimethoxyethanamine (1289 mg, 1.2 mmol) were added. The mixture was stirred at 50° C. for 2 h. Then HCl (133.97 mg, 3.7 mmol, concentrated) was added. The mixture was stirred at 50° C. for 13 h. The mixture was cooled to room temperature and diluted with sat. $NaHCO_3$ (10 mL). The mixture was extracted with EtOAc (4×) and the combined organic layers were concentrated under reduce pressure. The residue was purified by Prep-TLC (DCM:MeOH, 30:1) to afford methyl 6-(1H-imidazol-2-yl)-4-morpholinonicotinate as a white solid.

Step 2. Preparation of 6-(1H-imidazol-2-yl)-4-morpholinonicotinic acid

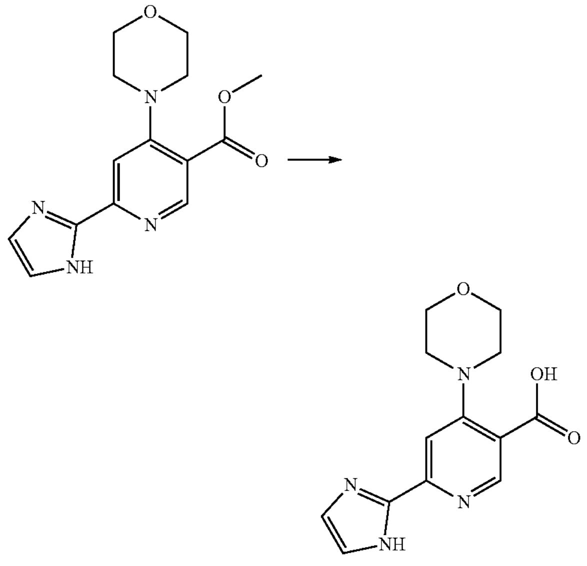

The title compound was prepared using General Procedure F employing methyl 6-(1H-imidazol-2-yl)-4-morpholinonicotinate. The mixture was stirred overnight at room temperature and then acidified to pH 6 with HCl (1M). The mixture was concentrated and the residue was purified by reverse phase chromatography (column, $C_{18}$ silica gel, mobile phase, 0-50% MeCN in water) to afford 6-(1H-imidazol-2-yl)-4-morpholinonicotinic acid as a white solid.

Step 3. Preparation of N-(5-((4-chlorobenzyl)oxy)-1,3,4-thiadiazol-2-yl)-6-(1H-imidazol-2-yl)-4-morpholinonicotinamide

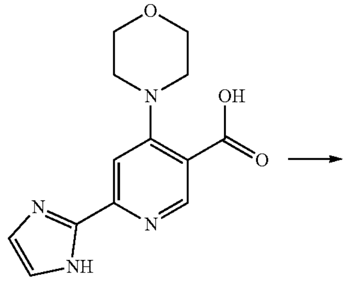

-continued

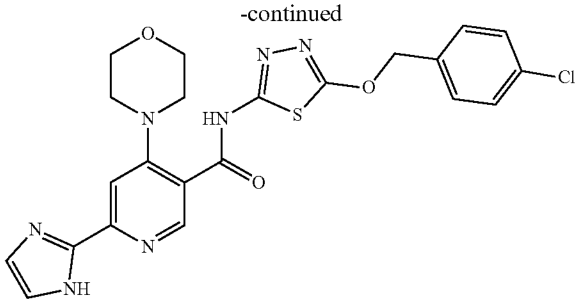

The title compound was prepared using General Procedure A employing 6-(1H-imidazol-2-yl)-4-morpholinonicotinic acid and 5-((4-chlorobenzyl)oxy)-1,3,4-thiadiazol-2-amine (Intermediate B). The mixture was diluted with EtOAc and washed with water (3×). The organic layer was concentrated under reduced pressure and the residue was triturated with MeOH to afford in N-(5-((4-chlorobenzyl)oxy)-1,3,4-thiadiazol-2-yl)-6-(1H-imidazol-2-yl)-4-morpholinonicotinamide as a light yellow solid. $^1H$ NMR (300 MHz; DMSO-$d_6$): δ 3.17 (s, 4H), 3.69-3.70 (m, 4H), 5.51 (s, 2H), 7.19 (s, 2H), 7.48-7.61 (m, 5H), 8.51 (s, 1H), 12.81-12.93 (m, 2H) ppm. m/z 498 ($M+H^+$).

Example 99

Synthesis of N-[5-[(5-chloropyridin-2-yl)methoxy]-1,3,4-thiadiazol-2-yl]-3-(2-methoxyphenyl)pyridine-4-carboxamide

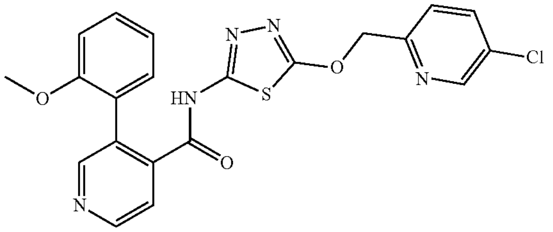 [SMILES: COc1ccccc1-c1cnccc1C(=O)Nc1nnc(OCc2ccc(Cl)cn2)s1]

The title compound was prepared using General Procedure A employing 5-((5-chloropyridin-2-yl)methoxy)-1,3,4-thiadiazol-2-amine (Intermediate C) and 3-(2-methoxyphenyl) pyridine-4-carboxylic acid (Intermediate H). The mixture was diluted with water and extracted with EtOAc (3×). The combined organic layers were dried over $Na_2SO_4$ and concentrated under reduced pressure. The residue was triturated with EtOAc (2×) to give the title compound. $^1H$ NMR (300 MHz, DMSO-$d_6$): δ 12.91 (s, 1H), 8.72-8.61 (m, 3H), 8.00 (d, 1H), 7.65-7.60 (m, 2H), 7.42-7.36 (m, 2H), 7.10-6.99 (m, 2H), 5.55 (s, 2H), 3.52 (s, 3H) ppm. m/z 454 (M+H+).

Example 100

Synthesis of N-(5-((4-chlorobenzyl)oxy)-1,3,4-thiadiazol-2-yl)-3-(2-(difluoromethoxy)phenyl)isonicotinamide

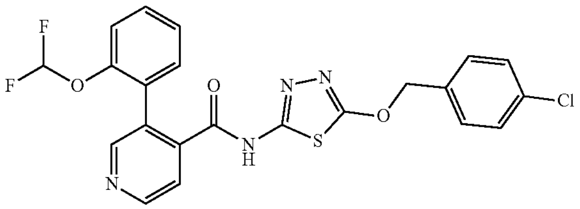 [SMILES: O=C(Nc1nnc(OCc2ccc(Cl)cc2)s1)c1ccncc1-c1ccccc1OC(F)F]

Step 1. Preparation of methyl 3-[2-(difluoromethoxy)phenyl]pyridine-4-carboxylate

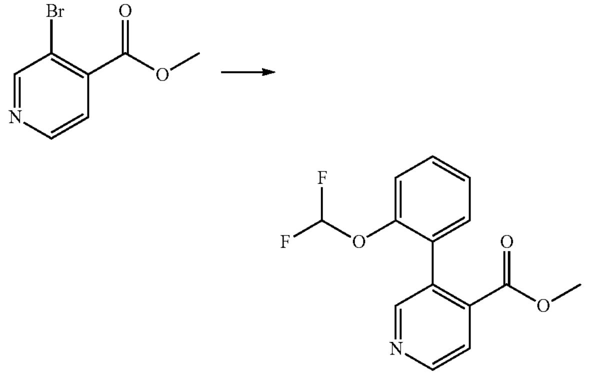

The title compound was prepared using General Procedure E employing methyl 3-bromopyridine-4-carboxylate and 2-(difluoromethoxy)phenylboronic acid. The mixture was stirred at 80° C. for 1 h. The mixture was cooled to it and diluted with EtOAc. The mixture was washed with water (3×). The organic layer was concentrated under reduced pressure. The residue was purified by silica gel column chromatography, eluted with 50% EtOAc in PE to afford the title compound as a yellow oil.

Step 2. Preparation of 3-[2-(difluoromethoxy)phenyl]pyridine-4-carboxylic acid

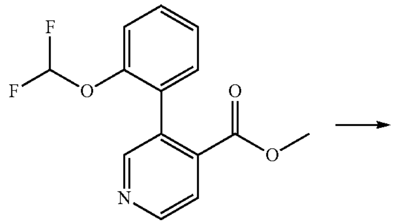

-continued

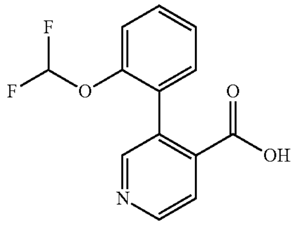

The title compound was prepared using General Procedure F employing methyl 3-[2-(difluoromethoxy)phenyl]pyridine-4-carboxylate. The mixture was stirred at 50° C. for 3 h. The mixture was diluted with water and washed with EtOAc. 2 M HCl was added to the aqueous layer to adjust the pH to 5-6. The precipitate was filtered and the solid was dried in an oven to afford the title compound as a white solid. The residue was purified by Prep-TLC (DCM:MeOH, 20:1) to afford the title compound as a white solid.

Step 3. Preparation of N-(5-((4-chlorobenzyl)oxy)-1,3,4-thiadiazol-2-yl)-3-(2-(difluoromethoxy)phenyl)isonicotinamide

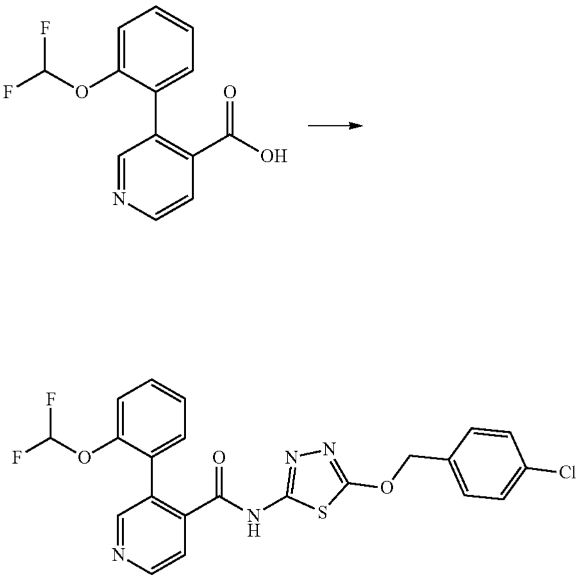

The title compound was prepared using General Procedure A employing 3-[2-(difluoromethoxy)phenyl]pyridine-4-carboxylic acid and 5-((4-chlorobenzyl)oxy)-1,3,4-thiadiazol-2-amine (Intermediate B). The mixture was diluted with EtOAc and washed with water (2×). The organic layer was concentrated under reduced pressure. $^{1}H$ NMR (300 MHz; DMSO-$d_6$): δ 13.06 (s, 1H), 8.78 (d, 1H), 8.63 (s, 1H), 7.74 (d, 1H), 7.51-7.42 (m, 6H), 6.80-7.35 (m, 3H), 5.47 (s, 2H) ppm. m/z 489 ($M+H^+$).

Example 101

Synthesis of N-[5-[(6-cyclopropylpyridin-3-yl)methoxy]-1,3,4-thiadiazol-2-yl]-3-(2-methoxyphenyl)pyridine-4-carboxamide

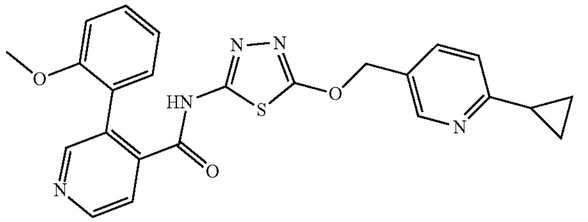 [SMILES: COc1ccccc1-c1cnccc1C(=O)Nc1nnc(OCc2ccc(C3CC3)nc2)s1]

Step 1. Preparation of (6-cyclopropylpyridin-3-yl)methanol

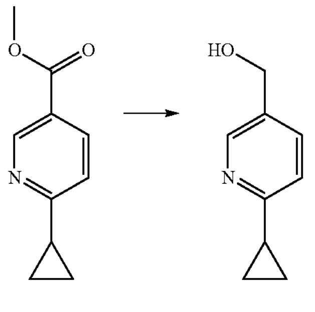

To a solution of methyl 6-cyclopropylpyridine-3-carboxylate (2.0 g, 11.3 mmol) in THF (20 mL) at 0° C. was added $LiAlH_4$ (0.86 g, 22.660 mmol, 2.01 equiv). The mixture was stirred at 0° C. for 1 h. The mixture was warmed to rt and a solution of $NH_4Cl$ (aq.) was added. The mixture was extracted with EtOAc (3×). The combined organic layers were concentrated under reduced pressure. The residue was purified by silica gel column chromatography, eluted with 25% EtOAc in PE to afford the title compound (1.4 g, 79% yield) as a yellow liquid.

Step 2. Preparation of [(6-cyclopropylpyridin-3-yl)methoxy](methylsulfanyl)methanethione

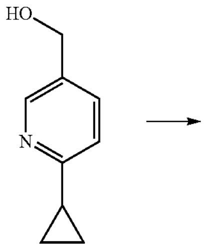

-continued

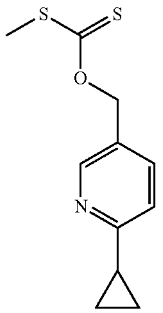

The title compound was prepared using similar procedure as Intermediate A, Step 1, replacing (4-fluorophenyl)methanol with (6-cyclopropylpyridin-3-yl)methanol.

Step 3. Preparation of 5-[(6-cyclopropylpyridin-3-yl)methoxy]-1,3,4-thiadiazol-2-amine

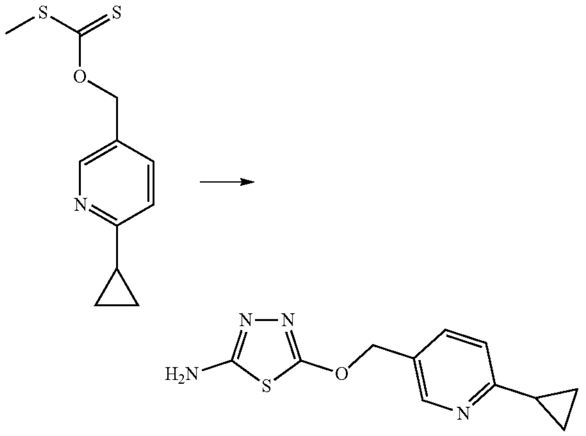

To a solution of [(6-cyclopropylpyridin-3-yl)methoxy](methylsulfanyl)methanethione (920 mg, 3.8 mmol) in MeOH (10 mL) at 0° C. was added hydrazine hydrate (196 mg, 3.9 mmol. The mixture was stirred at 0° C. for 0.5 h. The mixture was filtered and the solid was washed with MeOH (2×). The filtrate was concentrated under reduced pressure to afford a white solid. The solid was diluted with MeOH (7 mL) cooled to 0° C. Then $Et_3N$ (625 mg, 6.2 mmol) and BrCN (393 mg, 3.7 mmol) were added. The mixture was stirred at 0° C. for 1 h. The mixture was filtered and the solid was washed with MeOH (2×) to give the title compound as a yellow solid.

Step 4. Preparation of N-[5-[(6-cyclopropylpyridin-3-yl)methoxy]-1,3,4-thiadiazol-2-yl]-3-(2-methoxyphenyl)pyridine-4-carboxamide

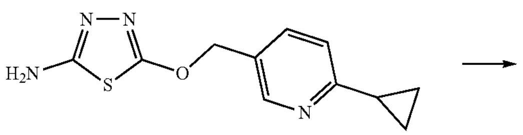

-continued

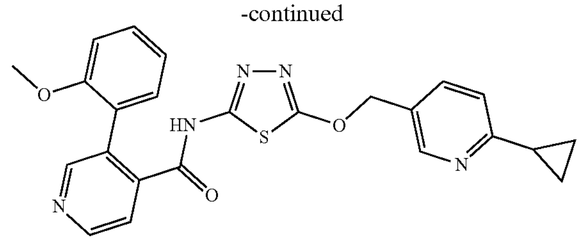

The title compound was prepared using General Procedure A employing 3-(2-methoxyphenyl) pyridine-4-carboxylic acid (Intermediate H) and 5-[(6-cyclopropylpyridin-3-yl)methoxy]-1,3,4-thiadiazol-2-amine. The mixture was stirred for 1 h at rt. The mixture was diluted with EtOAc and washed with water (2×). The organic layer was concentrated under reduced pressure. The residue was purified by Prep-TLC (DCM:MeOH, 20:1) to afford the title compound as a white solid. $^1H$ NMR (300 MHz; DMSO-$d_6$): δ 12.87 (s, 1H), 8.71 (d, 1H), 8.60 (s, 1H), 8.52-8.51 (m, 1H), 7.79-7.76 (m, 1H), 7.63 (d, 1H), 7.37-7.32 (m, 3H), 7.09-7.06 (m, 1H), 6.98 (d, 1H), 5.44 (s, 2H), 3.51 (s, 3H), 2.11-2.07 (m, 1H), 0.98-0.90 (m, 4H) ppm. m/z 460 (M+H+).

Example 102

Synthesis of N-(5-((4-chlorobenzyl)oxy)-1,3,4-thiadiazol-2-yl)-6-(hydroxymethyl)-4-(2-methoxyphenyl)nicotinamide

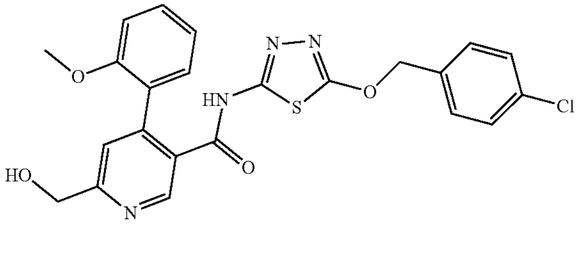 [SMILES: COc1ccccc1-c1cc(CO)ncc1C(=O)Nc1nnc(OCc2ccc(Cl)cc2)s1]

Step 1: Preparation of 5-benzyl 2-isopropyl 4-chloropyridine-2,5-dicarboxylate

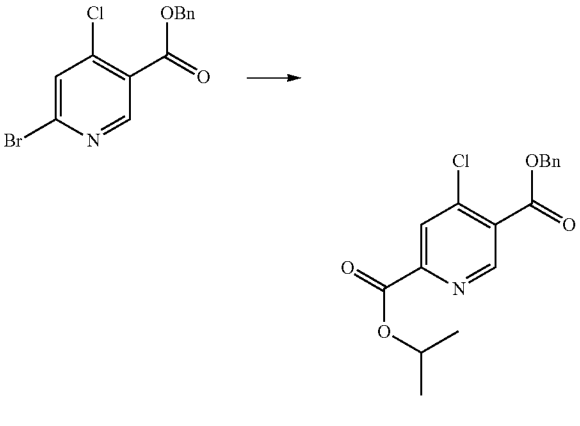

A solution of benzyl 6-bromo-4-chloropyridine-3-carboxylate (8.0 g, 24.5 mmol), $Et_3N$ (5.0 g, 49.0 mmol) and $Pd(dppf)Cl_2$ (2.7 g, 3.7 mmol) in propan-2-ol (1.50 L) was added to 2 L pressure tank reactor. Mixture was purged with CO (30 atm) and stirred at 60° C. overnight under atmosphere of CO (30 atm). The mixture was diluted with water and extracted with DCM (3×). The combined organic layers were concentrated and the residue was purified by silica gel column chromatography, eluted with 9% EtOAc in hexanes to afford the title compound (6.8 g, 75% yield) as a white solid.

Step 2: Preparation of 5-benzyl 2-isopropyl 4-(2-methoxyphenyl)pyridine-2,5-dicarboxylate

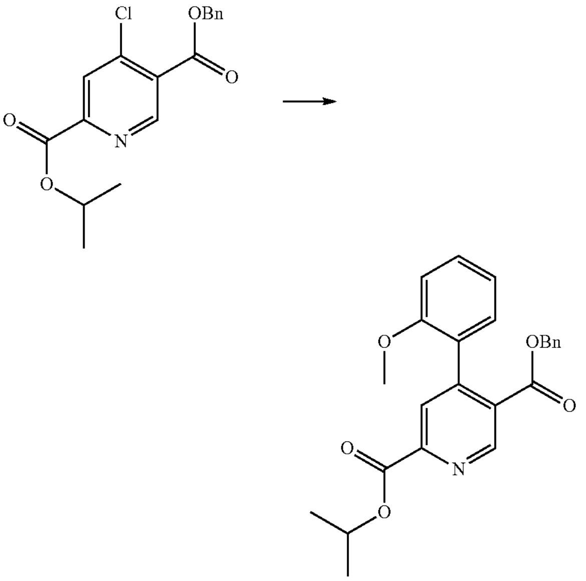

The title compound was prepared using General Procedure E employing 5-benzyl 2-isopropyl 4-chloropyridine-2,5-dicarboxylate and 2-methoxyphenylboronic acid. The mixture was diluted with water and extracted with DCM (3×). The combined organic layers were washed with 1 N NaOH (2×), dried over $Na_2SO_4$, and concentrated under reduced pressure. The residue was purified by silica gel column chromatography, eluted with 14% EtOAc in PE to the title compound (4.4 g, 49% yield) as a light yellow solid.

Step 3: Preparation of 6-(isopropoxycarbonyl)-4-(2-methoxyphenyl)pyridine-3-carboxylic acid

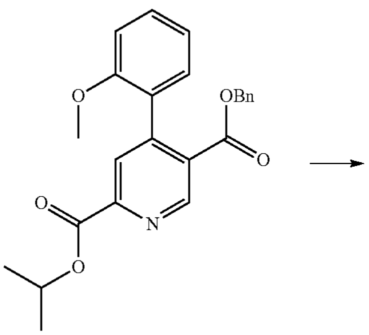

-continued

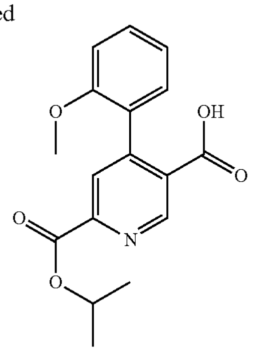

To a solution of 5-benzyl 2-isopropyl 4-(2-methoxyphenyl)pyridine-2,5-dicarboxylate (4.4 g) in THF (180 mL) was added 10% Pd/C (0.80 g). The mixture was stirred for 2 h at room temperature under the atmosphere of $H_2$. The mixture was filtered and the filtration was concentrated under reduced pressure to afford the title compound (3.6 g) as a light yellow solid which was used without further purification.

Step 4: Preparation of isopropyl 5-((5-((4-chlorobenzyl)oxy)-1,3,4-thiadiazol-2-yl)carbamoyl)-4-(2-methoxyphenyl)picolinate

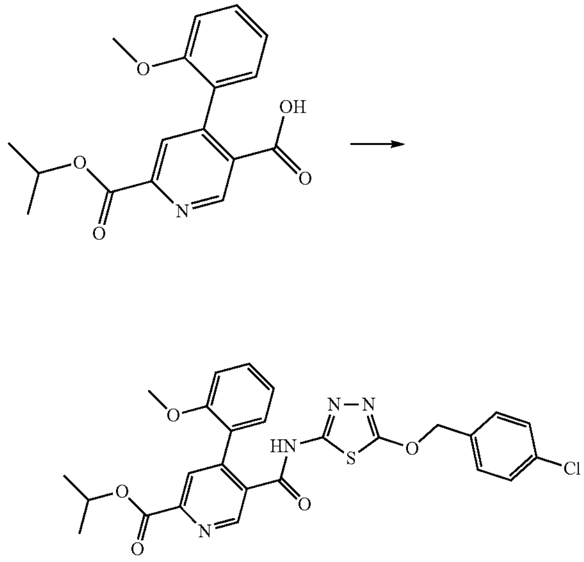

A reaction vial was charged with 6-(isopropoxycarbonyl)-4-(2-methoxyphenyl)pyridine-3-carboxylic acid (200 mg, 0.634 mmol), THF (3 mL), 5-((4-chlorobenzyl)oxy)-1,3,4-thiadiazol-2-amine (Intermediate B) (153 mg, 0.634 mmol), DIEA (163 mg, 1.26 mmol) and propylphosphonic anhydride (50 wt. % in EtOAc, 605 mg, 0.951 mmol) at room temperature. The resulting mixture was stirred for 3 h at room temperature under nitrogen atmosphere. The resulting mixture was diluted with water (15 mL). The aqueous layer was extracted with EtOAc (3×5 mL). The combined organic extracts were concentrated under vacuum. The crude product was triturated with MeOH (5 mL) to afford the title compound (230 mg, 63% yield) as a white solid.

Step 5: Preparation of N-(5-((4-chlorobenzyl)oxy)-1,3,4-thiadiazol-2-yl)-6-(hydroxymethyl)-4-(2-methoxyphenyl)nicotinamide

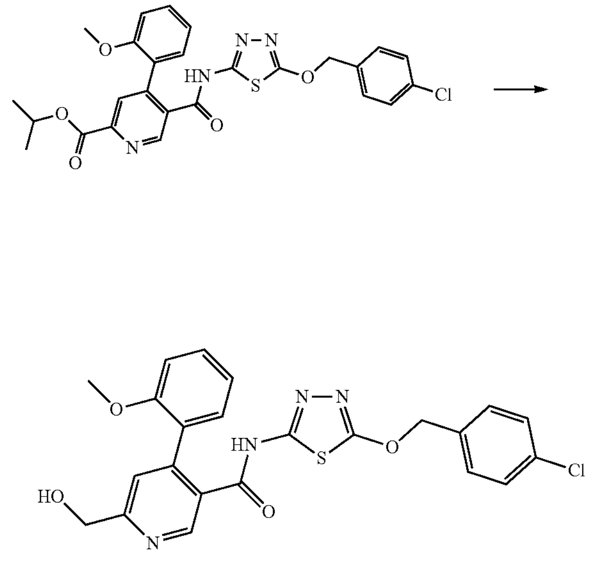

A round bottom flask was charged with isopropyl 5-((5-((4-chlorobenzyl)oxy)-1,3,4-thiadiazol-2-yl)carbamoyl)-4-(2-methoxyphenyl)picolinate (210 mg, 0.390 mmol), MeOH (2 mL, 49 mmol) and $NaBH_4$ (29 mg, 0.779 mmol) at room temperature. The resulting mixture was stirred for 30 minutes at room temperature under a nitrogen atmosphere. The reaction was quenched by the addition of sat. $NH_4Cl$ (aq.) (25 mL) at room temperature. The aqueous layer was extracted with EtOAc (4×10 mL). The resulting mixture was concentrated under vacuum. The residue was purified by Prep-TLC (eluent. 10% MeOH in DCM) to afford the title compound (33 mg, 17% yield) as a yellow solid. $^1H$ NMR (400 MHz; DMSO $d_6$): δ 12.78 (s, 1H), 8.69 (s, 1H), 7.54-7.42 (m, 5H), 7.40-7.38 (m, 1H), 7.35-7.33 (m, 1H), 7.11-7.07 (m, 1H), 6.99 (d, 1H), 5.59 (d, 1H), 5.47 (s, 2H), 4.66 (d, 1H), 3.51 (s, 3H). m/z 483 (M+H$^+$).

Example 103

Synthesis of 3-(benzo[c][1,2,5]thiadiazol-4-yl)-N-(5-((4-chlorobenzyl)oxy)-1,3,4-thiadiazol-2-yl)isonicotinamide

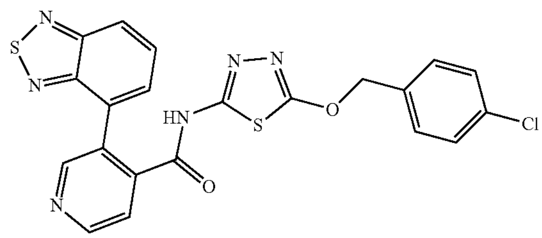 [SMILES: O=C(Nc1nnc(OCc2ccc(Cl)cc2)s1)c1ccncc1-c1cccc2nsnc12]

Step 1: Preparation of 4-(4,4,5,5-tetramethyl-1,3,2-dioxaborolan-2-yl)benzo[c][1,2,5]thiadiazole

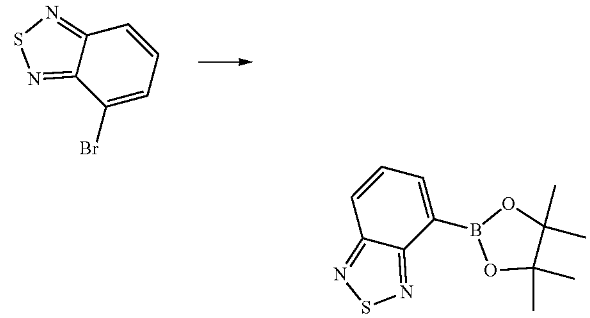

A round bottom flask under a nitrogen atmosphere was charged with 4-bromo-2,1,3-benzothiadiazole (1.00 g, 4.65 mmol), 1,4-dioxane (10 mL), bis(pinacolato)diboron (1.77 g, 6.97 mmol), KOAc (912 mg, 9.29 mmol), Pd(dppf)$Cl_2$ (340 mg, 0.465 mmol). The resulting solution was stirred for 4 hours at 80° C. The resulting mixture was diluted with water (50 mL). The aqueous layer was extracted with EtOAc (50 mL). The combined organic extracts were concentrated under vacuum. The residue was purified by silica gel column chromatography (eluent: 3% EtOAc in PE) to afford the title compound (850 mg, 48% yield) as a yellow solid.

Step 2: Preparation of methyl 3-(benzo[c][1,2,5]thiadiazol-4-yl)isonicotinate

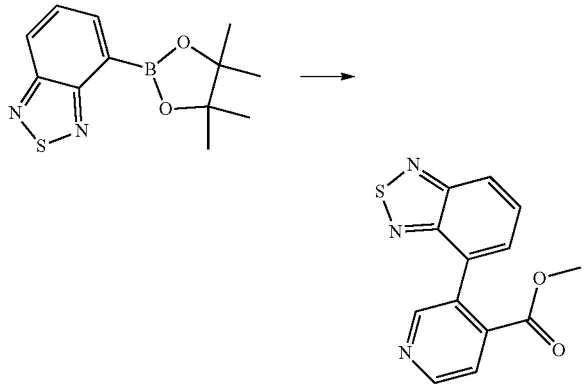

A round bottom flask under a nitrogen atmosphere was charged with 4-(4,4,5,5-tetramethyl-1,3,2-dioxaborolan-2-yl)benzo[c][1,2,5]thiadiazole (830 mg, 3.16 mmol), 1,4-dioxane (8.30 mL), methyl 3-bromopyridine-4-carboxylate (752 mg, 3.48 mmol), $H_2O$ (2.10 mL), $K_2CO_3$ (875 mg, 6.33 mmol), Pd(dppf)$Cl_2$ (231 mg, 0.317 mmol). The resulting solution was stirred for 1.5 hours at 100° C. The resulting mixture was diluted with water (30 mL). The aqueous layer was extracted with EtOAc (40 mL). The combined organic extracts were concentrated under reduced pressure. The residue was purified by silica gel column chromatography (eluent: 25% EtOAc in PE) to afford the title compound (490 mg, 54% yield) as a yellow solid.

Step 3: Preparation of 3-(benzo[c][1,2,5]thiadiazol-4-yl)isonicotinic acid

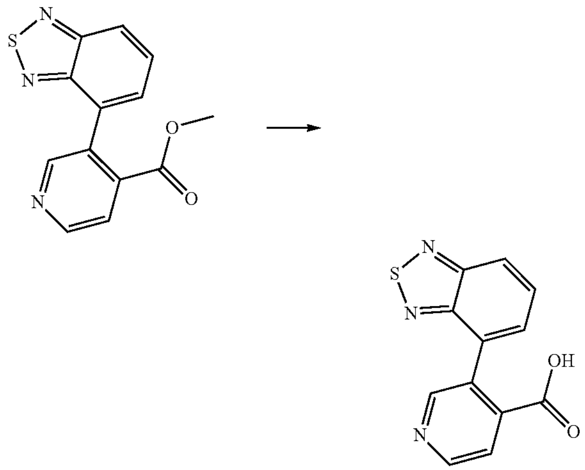

The title compound was prepared according to General Procedure F employing methyl 3-(benzo[c][1,2,5]thiadiazol-4-yl)isonicotinate (470 mg, 1.73 mmol), MeOH (5 mL), $H_2O$ (1.25 mL), NaOH (138 mg, 3.46 mmol). The resulting mixture was diluted with water (20 mL). The aqueous layer was extracted with EtOAc (20 mL). The pH of aqueous solution was adjusted to 5 with HCl (1 M). The aqueous layer was extracted with EtOAc (20 mL). The combined organic extracts were concentrated under reduced pressure to afford the title compound (330 mg, 71% yield) as a white solid.

Step 4: Preparation of 3-(benzo[c][1,2,5]thiadiazol-4-yl)-N-(5-((4-chlorobenzyl)oxy)-1,3,4-thiadiazol-2-yl)isonicotinamide

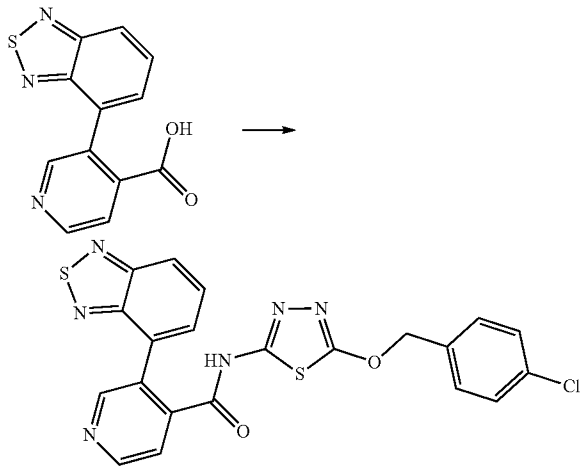

A reaction vial was charged with 3-(benzo[c][1,2,5]thiadiazol-4-yl)isonicotinic acid (150 mg, 0.583 mmol), DMF (1.50 mL), 5-((4-chlorobenzyl)oxy)-1,3,4-thiadiazol-2-amine (Intermediate B) (140 mg, 0.583 mmol), EDCI (167 mg, 0.875 mmol), HOBT (118 mg, 0.875 mmol). The resulting solution was stirred overnight at room temperature.

The precipitated solids were collected by filtration and washed with water (3 mL) followed by MeOH (3 mL) to afford the title compound (167 mg, 58% yield) as an off-white solid. $^{1}H$ NMR (400 MHz; DMSO $d_6$): δ 13.19 (s, 1H), 8.91 (d, 2H), 8.15 (dd, 1H), 7.85-7.79 (m, 3H), 7.51-7.45 (m, 4H), 5.44 (s, 2H); m, z 481 [M+H$^+$].

Example 104

Synthesis of N-(5-((5-chloropyridin-2-yl)methoxy)-1,3,4-thiadiazol-2-yl)-4-(2-(difluoromethoxy)phenyl)-6-(hydroxymethyl)nicotinamide

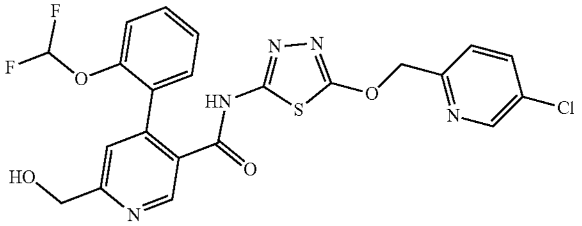 [SMILES: O=C(Nc1nnc(OCc2ccc(Cl)cn2)s1)c1cnc(CO)cc1-c1ccccc1OC(F)F]

Step 1: Preparation of ethyl 6-chloro-4-(2-(difluoromethoxy)phenyl)nicotinate

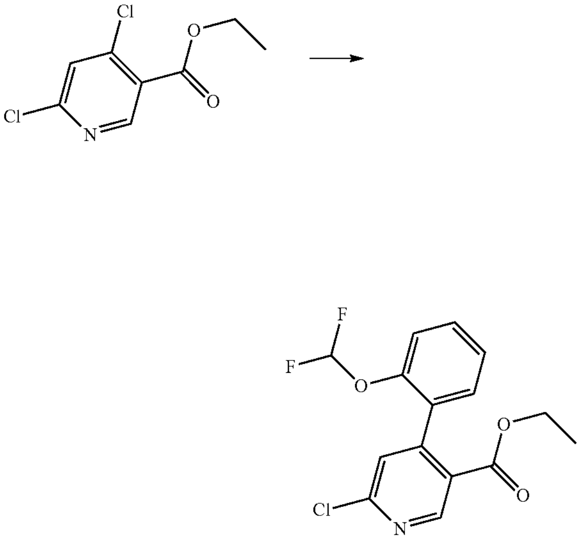

A reaction vial under a nitrogen atmosphere was charged with 2(difluoromethoxy)phenylboronic acid (460 mg, 2.44 mmol), 1,4-dioxane (4.60 mL), ethyl 4,6-dichloropyridine-3-carboxylate (807 mg, 3.67 mmol), $H_2O$ (1.10 mL), $K_2CO_3$ (676 mg, 4.89 mmol), Pd(dtbpf)$Cl_2$ (159 mg, 0.245 mmol). The resulting solution was stirred for 4 hours at 80° C. The resulting mixture was diluted with water (20 mL). The aqueous layer was extracted with EtOAc (20 mL). The resulting mixture was concentrated under reduced pressure. The residue was purified by Prep-TLC (40% EtOAc in PE) to afford the title compound (730 mg, 60% yield) as a white solid.

Step 2: Preparation of ethyl 4-(2-(difluoromethoxy)phenyl)-6-(hydroxymethyl)nicotinate

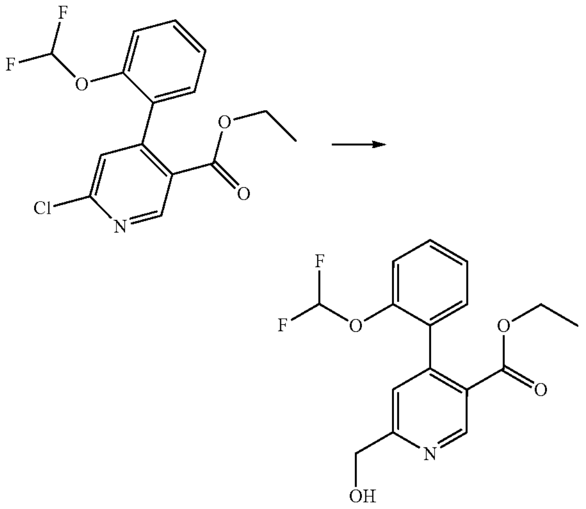

A round bottom flask under an atmosphere of nitrogen was charged with ethyl 6-chloro-4-(2-(difluoromethoxy)phenyl)nicotinate (690 mg, 2.10 mmol), PhMe (7 mL), (tributylstannyl)methanol (1.01 g, 3.15 mmol), $Pd(PPh_3)_4$ (243 mg, 0.211 mmol). The resulting solution was stirred for 4 hours at 80° C. The resulting mixture was diluted with water (20 mL). The aqueous layer was extracted with EtOAc (20 mL). The residue was purified by Prep-TLC (40% EtOAc in PE) to afford the title compound (160 mg, 24% yield) as a yellow oil.

Step 3: Preparation of 4-(2-(difluoromethoxy)phenyl)-6-(hydroxymethyl)nicotinic acid

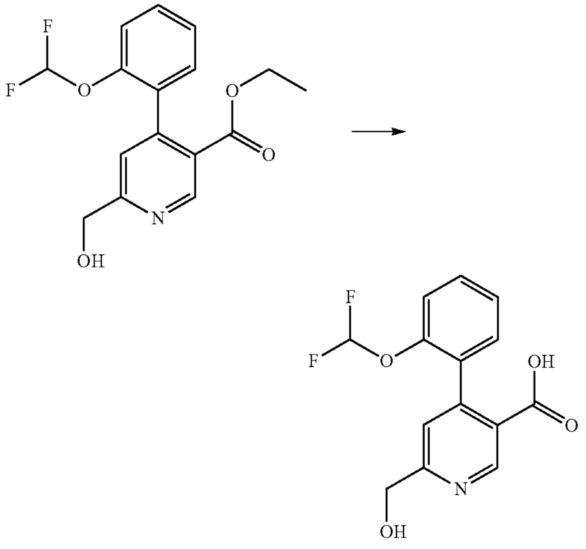

A reaction vial was charged with ethyl 4-(2-(difluoromethoxy)phenyl)-6-(hydroxymethyl)nicotinate (150 mg, 0.464 mmol), EtOH (1.50 mL), $H_2O$ (0.4 ml), NaOH (37 mg, 0.928 mmol). The resulting solution was stirred for 1.5 hours at room temperature. The resulting mixture was diluted with water (10 mL). The aqueous layer was extracted with EtOAc (10 mL). The pH of aqueous solution was adjusted to 5 using HCl (1 M). The aqueous layer was extracted with EtOAc (10 mL). The resulting mixture was concentrated under reduced pressure to afford the title compound (120 mg, 86% yield) as a white solid.

Step 4: Preparation of N-(5-((5-chloropyridin-2-yl)methoxy)-1,3,4-thiadiazol-2-yl)-4-(2-(difluoromethoxy)phenyl)-6-(hydroxymethyl)nicotinamide

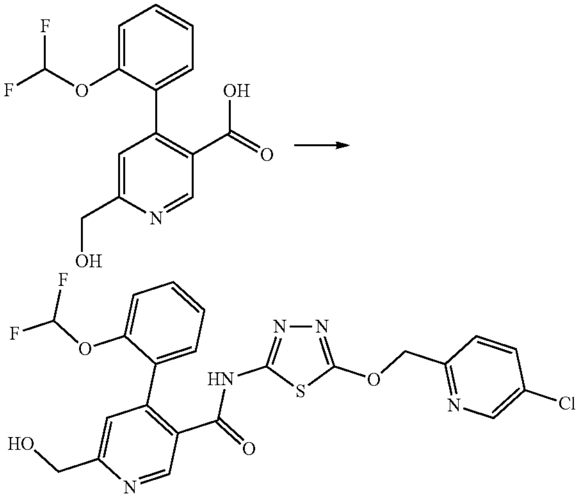

A reaction vial was charged with 4-(2-(difluoromethoxy)phenyl)-6-(hydroxymethyl)nicotinic acid (100 mg, 0.339 mmol), DMF (1 mL), 5-((5-chloropyridin-2-yl)methoxy)-1,3,4-thiadiazol-2-amine (Intermediate C) (82 mg, 0.339 mmol), EDCI (97 mg, 0.508 mmol), HOBT (68 mg, 0.508 mmol). The resulting solution was stirred overnight at room temperature. The precipitated solids were collected by filtration and washed with water (3 mL) followed by MeOH (2 mL) to afford the title compound (25 mg, 14% yield) as an off-white solid. $^1$H NMR (400 MHz; DMSO $d_6$): δ 12.98 (s, 1H), 8.85 (s, 1H), 8.66 (s, 1H), 8.02-8.00 (m, 1H), 7.62 (d, 1H), 7.52 (d, 2H), 7.43-7.36 (m, 2H), 7.24-6.88 (m, 2H), 5.64 (t, 1H), 5.55 (s, 2H), 4.69 (d, 2H); m/z 520 (M+H$^+$).

Example 105

Synthesis of N-(5-((4-chlorobenzyl)oxy)-1,3,4-thiadiazol-2-yl)-6-(cyanomethyl)-4-(2-methoxyphenyl)nicotinamide

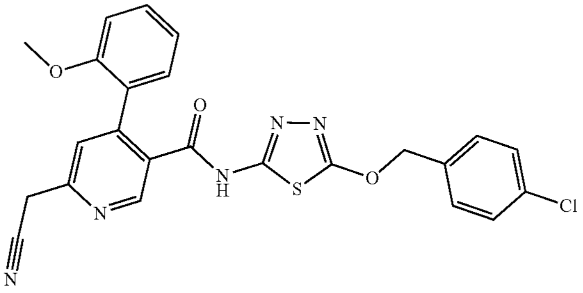 [SMILES: COc1ccccc1-c1cc(CC#N)ncc1C(=O)Nc1nnc(OCc2ccc(Cl)cc2)s1]

Step 1: Preparation of ethyl 6-chloro-4-(2-methoxyphenyl)pyridine-3-carboxylate

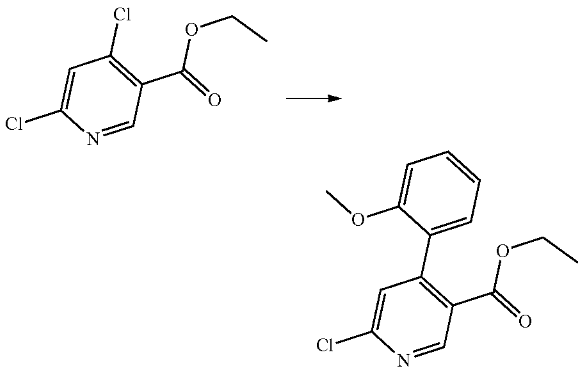

The title compound was prepared using General Procedure E employing ethyl 4,6-dichloropyridine-3-carboxylate and 2-methoxyphenylboronic acid and replacing Pd(dppf)$Cl_2$ (0.2 eq) with Pd(dtbpf)$Cl_2$ (0.1 equiv). The mixture was diluted with water and extracted with EtOAc (2×). The combined organic layers were concentrated under vacuum. The residue was purified by silica gel column chromatography, eluted with 6% EtOAc in PE to afford the title compound as a yellow solid.

Step 2: Preparation of ethyl 6-(hydroxymethyl)-4-(2-methoxyphenyl)pyridine-3-carboxylate

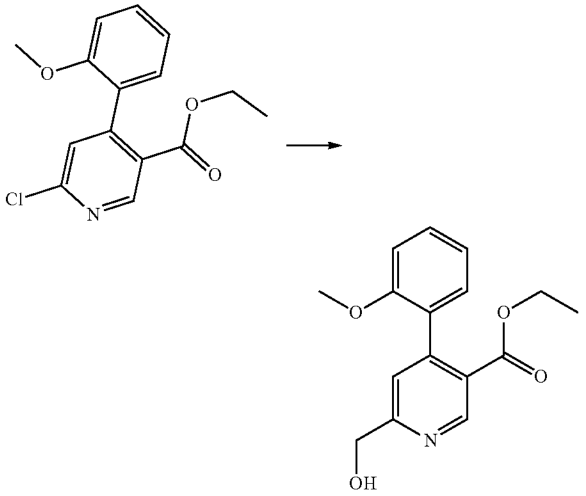

To a stirred solution of ethyl 6-chloro-4-(2-methoxyphenyl)pyridine-3-carboxylate (480 mg, 1.6 mmol) and (tributylstannyl)methanol (792 mg, 2.5 mmol) in toluene was added Pd(dppf)$Cl_2$ (120 mg, 0.17 mmol) at room temperature under nitrogen atmosphere. The mixture was stirred for 2 h at 100° C. under nitrogen atmosphere. The mixture was diluted with water. The aqueous layer was extracted with EtOAc (3×). The combined organic layers were concentrated under vacuum. The residue was purified by Prep-TLC (PE:EtOAc, 1:1) to afford the title compound (300 mg, 63% yield) as a white solid.

Step 3: Preparation of 6-(hydroxymethyl)-4-(2-methoxyphenyl)pyridine-3-carboxylic acid

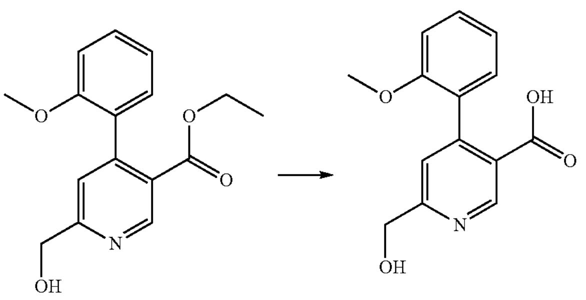 [SMILES: CCOC(=O)c1cnc(CO)cc1-c1ccccc1OC ; COc1ccccc1-c1cc(CO)ncc1C(=O)O]

To a solution of ethyl 6-(hydroxymethyl)-4-(2-methoxyphenyl)pyridine-3-carboxylate (287 mg, 1.0 mmol) in EtOH (5 mL) and water (1 mL) was added LiOH (84 mg, 2.0 mmol). The mixture was stirred at rt overnight. The mixture was acidified to pH 5 with HCl (1 M). The mixture was concentrated under vacuum. The residue was purified by reverse phase chromatography (column, C18 silica gel; mobile phase, with 0-100% MeCN in water) to afford the title compound (77 mg, 30% yield) as a white solid.

Step 4: Preparation of N-(5-((4-chlorobenzyl)oxy)-1,3,4-thiadiazol-2-yl)-6-(hydroxymethyl)-4-(2-methoxyphenyl)nicotinamide

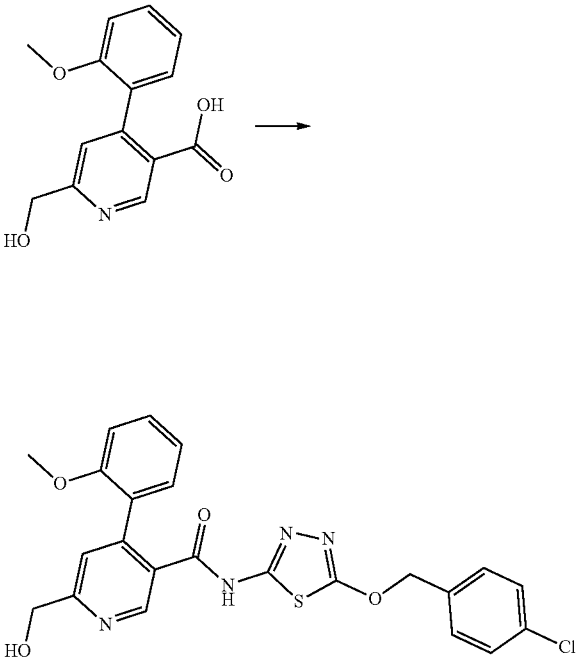

The title compound was prepared according to General Procedure A using 6-(hydroxymethyl)-4-(2-methoxyphenyl) pyridine-3-carboxylic acid (540 mg, 2.08 mmol) and 5-((4-chlorobenzyl)oxy)-1,3,4-thiadiazol-2-amine (Intermediate B) The mixture was stirred for 3 h at room temperature. The mixture was diluted with water. The aqueous layer was extracted with EtOAc (2×). The residue was purified by Prep-TLC (5% MeOH in DCM) to afford the title compound (300 mg, 27% yield) as a brown solid.

Step 5: Preparation of (5-((5-((4-chlorobenzyl)oxy)-1,3,4-thiadiazol-2-yl)carbamoyl)-4-(2-methoxyphenyl)pyridin-2-yl)methyl methanesulfonate

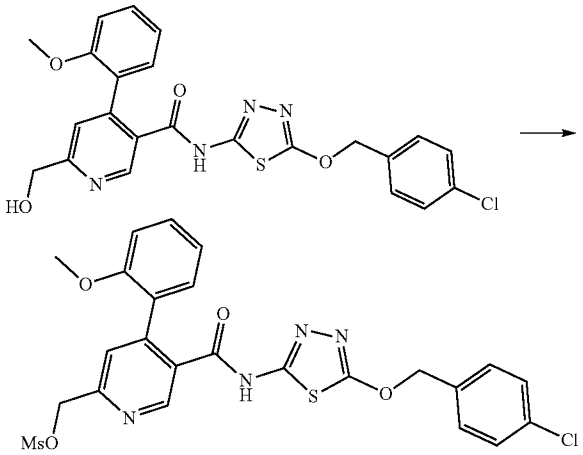

To a solution of N-(5-((4-chlorobenzyl)oxy)-1,3,4-thiadiazol-2-yl)-6-(hydroxymethyl)-4-(2-methoxyphenyl)nicotinamide (290 mg, 0.600 mmol) and $Et_3N$ (121 mg, 1.20 mmol) in DCM was added MsCl (82.54 mg, 0.721 mmol) dropwise at room temperature under nitrogen atmosphere. The mixture was stirred for 2 h at room temperature under nitrogen atmosphere. The mixture was concentrated under vacuum. The residue was purified by Prep-TLC (5% MeOH in DCM) to afford the title compound (110 mg, 29% yield) as an off-white solid.

Step 6: Preparation of N-(5-((4-chlorobenzyl)oxy)-1,3,4-thiadiazol-2-yl)-6-(cyanomethyl)-4-(2-methoxyphenyl)nicotinamide

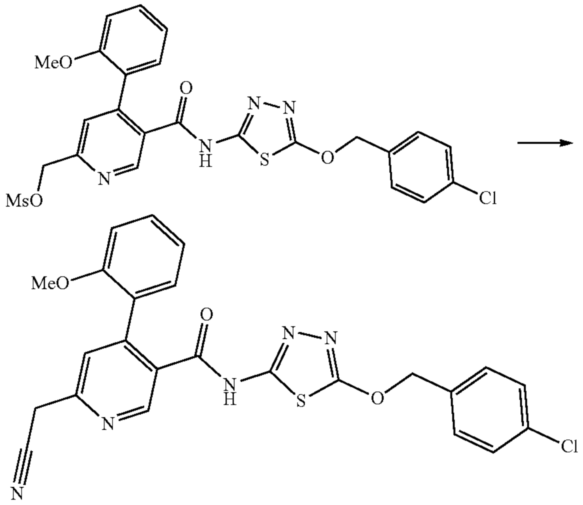

To a solution of [5-([5-[(4-chlorophenyl)methoxy]-1,3,4-thiadiazol-2-yl]carbamoyl)-4-(2-methoxyphenyl)pyridin-2-yl]methyl methanesulfonate (100 mg, 0.178 mmol) in DMSO (2 mL) was added NaCN (34 mg, 0.713 mmol). The mixture was stirred for 2 hours at room temperature. The mixture was diluted with water and extracted with EtOAc (2×). The mixture was concentrated under reduced pressure. The residue was purified by Prep-TLC (2% MeOH in DCM) to afford the title compound (37 mg, 40% yield) as an off-white solid. $^1$H NMR (300 MHz, DMSO-$d_6$) δ 12.88 (s, 1H), 8.79 (s, 1H), 7.59-7.31 (m, 7H), 7.12-7.00 (m, 2H), 5.48 (s, 2H), 4.35 (s, 2H), 3.52 (s, 3H); m/z: $[M+H]^+$ 492.

Example 106

Synthesis of N-(5-((5-chloropyridin-2-yl)methoxy)-1,3,4-thiadiazol-2-yl)-5-(2-methoxyphenyl) pyridazine-4-carboxamide

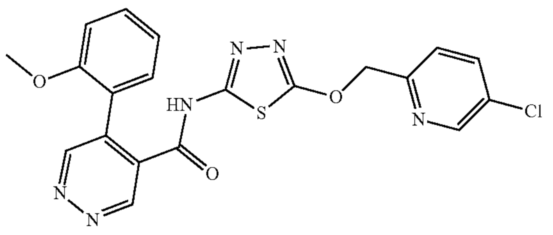 [SMILES: COc1ccccc1-c1cnncc1C(=O)Nc1nnc(OCc2ccc(Cl)cn2)s1]

Step 1: Preparation of 5-(2-methoxyphenyl)-3-oxo-2,3-dihydropyridazine-4-carbonitrile

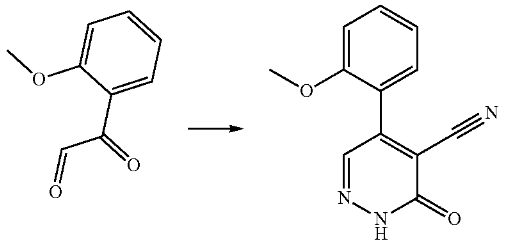 [SMILES: COc1ccccc1C(=O)C=O ; COc1ccccc1-c1cn[nH]c(=O)c1C#N]

To a solution of 2-(2-methoxyphenyl)-2-oxoacetaldehyde (1.90 g, 11.5 mmol) in EtOH (60 mL) was added cyacetacide (1.14 g, 11.5 mmol) and $Na_2SO_4$ (3.28 g, 23.1 mmol). The mixture was stirred for 5 hours at room temperature under an inert atmosphere of nitrogen. The mixture was filtered and washed with EtOAc (3×). The mixture was concentrated to afford a brown solid. The reside was dissolved in EtOH (60 mL). In a separate flask, sodium metal (2.66 g, 11.5 mmol) was added to EtOH (60 mL) and the mixture was cooled 0° C. under nitrogen atmosphere. The brown mixture was added to the sodium ethoxide mixture dropwise at 0° C. The mixture was then stirred at 80° C. overnight. The mixture was cooled to rt and diluted with water. The mixture was concentrated under reduced pressure to half volume. The precipitated were collected by filtration and washed with water and then washed with EtOAc to afford the title compound (1.5 g, 56% yield) as a grey solid.

Step 2: Preparation of 3-chloro-5-(2-methoxyphenyl)pyridazine-4-carbonitrile

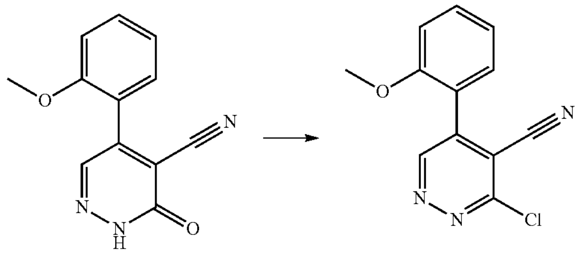 [SMILES: COc1ccccc1-c1cn[nH]c(=O)c1C#N ; COc1ccccc1-c1cnnc(Cl)c1C#N]

A round bottom flask was charged with 5-(2-methoxyphenyl)-3-oxo-2,3-dihydropyridazine-4-carbonitrile (1.50 g, 6.60 mmol), and $POCl_3$ (15 mL). The mixture was stirred at 100° C. overnight. The mixture was cooled to rt and concentrated under reduced pressure. The residue was cooled to 0° C. and ice water was added (50 mL). The aqueous layer was extracted with EtOAc (50 mL). The organic layer was concentrated under reduced pressure. The residue was purified by silica gel column chromatography, eluent: 17% EtOAc in PE to afford the title compound (780 mg, 47% yield) as a brown solid.

Step 3: Preparation of 5-(2-methoxyphenyl)pyridazine-4-carbonitrile

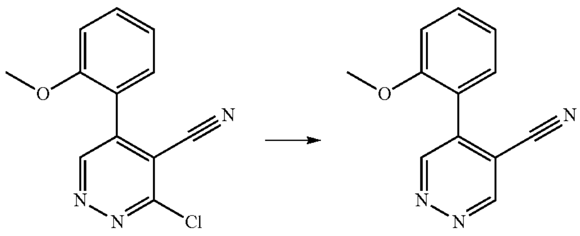 [SMILES: COc1ccccc1-c1cnnc(Cl)c1C#N ; COc1ccccc1-c1cnncc1C#N]

To a solution of 3-chloro-5-(2-methoxyphenyl) pyridazine-4-carbonitrile (720 mg, 2.93 mmol) in THF (72 mL) was added 10% Pd/C (72 mg) and $Et_3N$ (889 mg, 8.79 mmol). The mixture was purged with $H_2$ and stirred under an atmosphere of $H_2$ for 30 mins at room temperature. The mixture was filtered, and the filter cake was washed with THF. The filtrate was concentrated under reduced pressure. The residue was purified by Prep-TLC (eluent: 25% EtOAc in PE) to afford the title compound (300 mg, 45% yield) as a grey solid.

Step 4: Preparation of 5-(2-methoxyphenyl)pyridazine-4-carboxylic acid

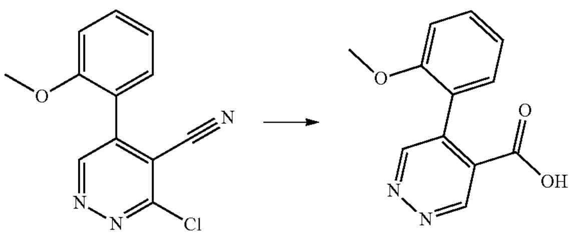 [SMILES: COc1ccccc1-c1cnnc(Cl)c1C#N ; COc1ccccc1-c1cnncc1C(=O)O]

To a solution of 5-(2-methoxyphenyl)pyridazine-4-carbonitrile (285 mg, 1.34 mmol) in water $H_2O$ (2 mL) was added $H_2SO_4$ (1.20 mL, 60% w/w). The mixture was stirred at 100° C. for 5 hours. The mixture was cooled to rt and saturated $NaHCO_3$ (aq.) was added until mixture was pH 5. The mixture was concentrated under reduced pressure. The residue was purified by Prep-TLC (eluent: 5% MeOH in DCM) to afford the title compound (100 mg, 31%) as an off-white solid.

Step 5: Preparation of N-(5-((5-chloropyridin-2-yl)methoxy)-1,3,4-thiadiazol-2-yl)-5-(2-methoxyphenyl)pyridazine-4-carboxamide

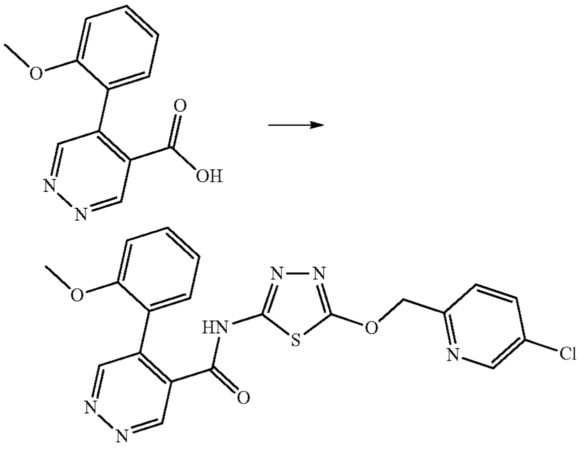

To a solution of 5-(2-methoxyphenyl)pyridazine-4-carboxylic acid (90 mg, 0.391 mmol) in DMF (1 mL) was added EDCI (112 mg, 0.586 mmol), HOBT (79 mg, 0.586 mmol) and 5-((5-chloropyridin-2-yl)methoxy)-1,3,4-thiadiazol-2-amine (Intermediate C) (94 mg, 0.391 mmol). The mixture was stirred for 4 hours at room temperature. The mixture was diluted with water. The aqueous layer was extracted with EtOAc. The organic layer was concentrated under reduced pressure. The residue was triturated with MeOH to afford the title compound (26.7 mg, 14% yield) as a white solid. $^1$H NMR (300 MHz; DMSO $d_6$): δ 13.17 (s, 1H), 9.41 (dd, 2H), 8.66 (d, 1H), 8.01 (dd, 1H), 7.62 (d, 1H), 7.51-7.46 (m, 2H), 7.16-7.06 (m, 2H), 5.56 (s, 2H), 3.55 (s, 3H); m/z 455 (M+H$^+$).

Example 107

Synthesis of N-(5-((7-chloro-1H-indazol-4-yl)methoxy)-1,3,4-thiadiazol-2-yl)-3-(2-methoxyphenyl)isonicotinamide

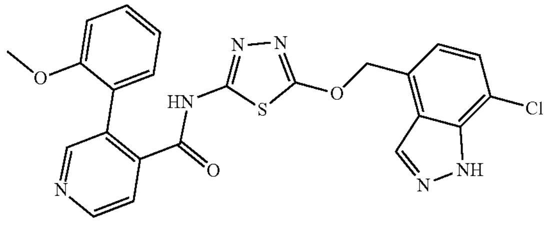 [SMILES: COc1ccccc1-c1cnccc1C(=O)Nc1nnc(OCc2ccc(Cl)c3[nH]ncc23)s1]

Step 1: Preparation of 4-bromo-7-chloro-1-((2-(trimethylsilyl)ethoxy)methyl)-1H-indazole

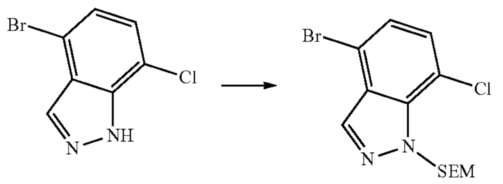 [SMILES: Clc1ccc(Br)c2cn[nH]c12 ; C[Si](C)(C)CCOCn1ncc2c(Br)ccc(Cl)c21]

To a solution of 4-bromo-7-chloro-1H-indazole (1.50 g, 6.48 mmol) in DMF (32 mL) was added sodium hydride (as a 60% dispersion in mineral oil, 518 mg, 12.9 mmol) portion wise at 0° C. The mixture was stirred for 40 min and then SEM-Cl (2.16 g, 12.9 mmol) was added to the mixture and stirred for 4 h. The mixture was diluted with water and extracted with EtOAc (3×). The combined organic layers were concentrated under vacuum. The residue was purified by silica gel column chromatography, eluent: 1% EtOAC in PE to afford the title compound (1.8 g, 76% yield) as a yellow oil.

Step 2: 7-chloro-1-((2-(trimethylsilyl)ethoxy)methyl)-4-vinyl-1H-indazole

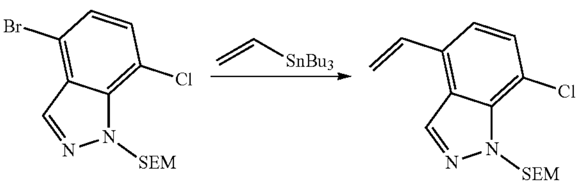

To a solution of 4-bromo-7-chloro-1-[[2-(trimethylsilyl)ethoxy]methyl]indazole (1.80 g, 4.97 mmol) in toluene (15 mL) was added tributyl(ethenyl)stannane (1.89 g, 5.97 mmol) and $Pd(PPh_3)_4$ (862 mg, 0.746 mmol) at room temperature. The mixture was stirred for 4 h at 110° C. under nitrogen atmosphere. The mixture was concentrated under reduced pressure. The residue was purified by silica gel column chromatography, eluent: 100% DCM to afford the title compound (1.3 g, 84% yield) as a yellow oil.

Step 3: 1-(7-chloro-1-((2-(trimethylsilyl)ethoxy)methyl)-1H-indazol-4-yl)ethane-1,2-diol

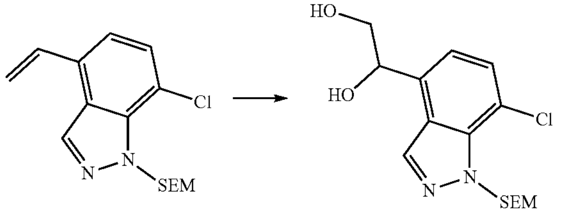 [SMILES: C=Cc1ccc(Cl)c2c1cnn2COCC[Si](C)(C)C ; C[Si](C)(C)CCOCn1ncc2c(C(O)CO)ccc(Cl)c21]

To a solution of 7-chloro-4-ethenyl-1-[[2-(trimethylsilyl)ethoxy] methyl]indazole (1.30 g, 4.20 mmol) in THF (12 mL) was added $OsO_4$ (107 mg, 0.421 mmol) at room temperature. Then a solution of NMO (986 mg, 8.41 mmol)

in $H_2O$ (1 mL) was added at room temperature. The mixture was stirred for 2 h at room temperature. The mixture was diluted with $H_2O$ water and extracted with EtOAc (3×). The combined organic extracts were concentrated under vacuum. The residue was purified by Prep-TLC (5% MeOH in DCM) to afford the title compound (660 mg, 45% yield) as a yellow oil.

Step 4: Preparation of 7-chloro-1-((2-(trimethylsilyl)ethoxy)methyl)-1H-indazole-4-carbaldehyde

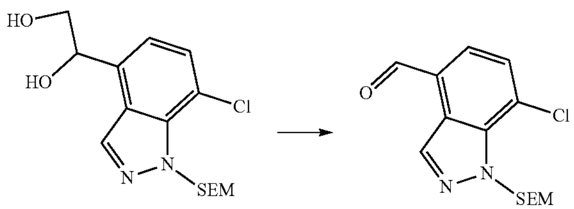 [SMILES: C[Si](C)(C)CCOCn1ncc2c(C(O)CO)ccc(Cl)c21 ; C[Si](C)(C)CCOCn1ncc2c(C=O)ccc(Cl)c21]

To a solution of 1-(7-chloro-1-[[2-(trimethylsilyl)ethoxy]methyl]indazol-4-yl)ethane-1,2-diol (650 mg, 1.89 mmol) in MeOH (5 mL) was added $NaIO_4$ (810 mg, 3.79 mmol) at room temperature. The mixture was stirred for 2 h at room temperature under nitrogen atmosphere. The mixture was diluted with water and extracted with EtOAc (5×). The combined organic extracts were concentrated under vacuum. The residue was purified by Prep-TLC (eluent: 17% EtOAc in PE) to afford the title compound (560 mg, 87% yield) as a yellow solid.

Step 5: (7-chloro-1-((2-(trimethylsilyl)ethoxy)methyl)-1H-indazol-4-yl)methanol

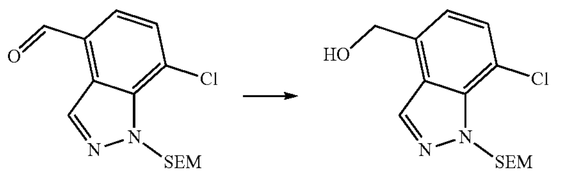 [SMILES: C[Si](C)(C)CCOCn1ncc2c(C=O)ccc(Cl)c21 ; C[Si](C)(C)CCOCn1ncc2c(CO)ccc(Cl)c21]

To a solution of 7-chloro-1-[[2-(trimethylsilyl)ethoxy]methyl]indazole-4-carbaldehyde (560 mg, 1.80 mmol) in MeOH (5 mL) was added $NaBH_4$ (136 mg, 3.60 mmol) at room temperature. The mixture was stirred for 30 min at room temperature. Then sat. $NH_4Cl$ (aq.) was added and the mixture was extracted with EtOAc (3×). The combined organic extracts were concentrated under vacuum. The residue was purified by Prep-TLC (eluent: 5% MeOH in DCM) to afford the title compound (520 mg, 84% yield) as a yellow solid.

Step 6: Preparation of O-((7-chloro-1-((2-(trimethylsilyl)ethoxy)methyl)-1H-indazol-4-yl)methyl) S-methyl carbonodithioate

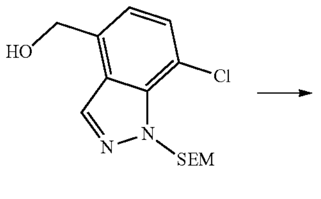

-continued

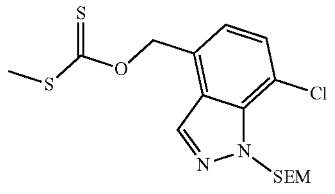

To a solution of (7-chloro-1-[[2-(trimethylsilyl)ethoxy]methyl]indazol-4-yl)methanol (510 mg, 1.63 mmol) in THF (0.5 ml) at 0° C. was added NaH (as a 60% dispersion in mineral oil, 130 mg, 3.25 mmol). The mixture was stirred for 30 min at 0° C., then MeI (254 mg, 1.79 mmol) was added at 0° C. The mixture was stirred for 5 min, then $CS_2$ (5 mg, 0.070 mmol) was then added. The mixture was warmed to room temperature and stirred for 30 min. A sat. $NH_4Cl$ (aq.) solution was added and the was diluted with water. The mixture was extracted with EtOAc (3×). The combined organic layers were concentrated under reduced pressure. The residue was purified by Prep-TLC (eluent: 20% EtOAc in PE) to afford the title compound (445 mg, 67%) as a yellow solid.

Step 7: Preparation of O-((7-chloro-1-((2-(trimethylsilyl)ethoxy)methyl)-1H-indazol-4-yl)methyl) hydrazinecarbothioate

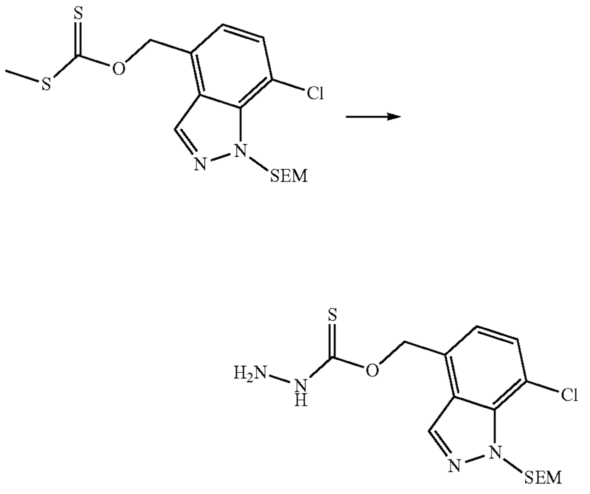

To a solution of O-((7-chloro-1-((2-(trimethylsilyl)ethoxy)methyl)-1H-indazol-4-yl)methyl) S-methyl carbonodithioate (445 mg, 1.10 mmol) in MeOH (5 ml) at 0° C. was added hydrazine hydrate (55 mg, 1.10 mmol) at 0° C. The mixture was warmed to room temperature and stirred for 15 min at rt. The mixture was diluted with EtOAc. The mixture was washed with water (5×). The organic layer was concentrated under reduced pressure. The residue was purified by Prep-TLC (eluent: 50% EtOAc in PE) to afford the title compound (370 mg, 86% yield) as a yellow oil.

Step 8: 5-((7-chloro-1-((2-(trimethylsilyl)ethoxy)methyl)-1H-indazol-4-yl)methoxy)-1,3,4-thiadiazol-2-amine

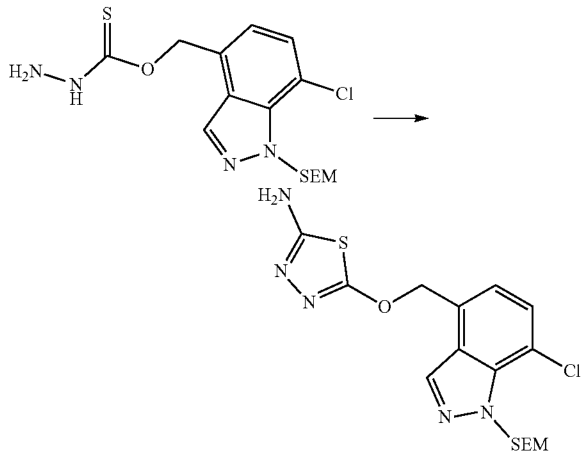

To a solution of O-((7-chloro-1-((2-(trimethylsilyl)ethoxy)methyl)-1H-indazol-4-yl)methyl) hydrazinecarbothioate (370 mg, 0.956 mmol) in MeOH (4 mL) at 0° C. was added $Et_3N$ (193 mg, 1.91 mmol) and BrCN (111 mg, 1.05 mmol) at 0° C. The mixture was stirred for 30 min. The mixture was diluted with water. The aqueous layer was extracted with EtOAc (3×). The combined organic layers were concentrated under reduced pressure. The residue was purified by Prep-TLC (eluent: 7% MeOH in DCM) to afford the title compound (210 mg, 52% yield) as a yellow oil.

Step 9: N-(5-((7-chloro-1-((2-(trimethylsilyl)ethoxy)methyl)-1H-indazol-4-yl)methoxy)-1,3,4-thiadiazol-2-yl)-3-(2-methoxyphenyl)isonicotinamide

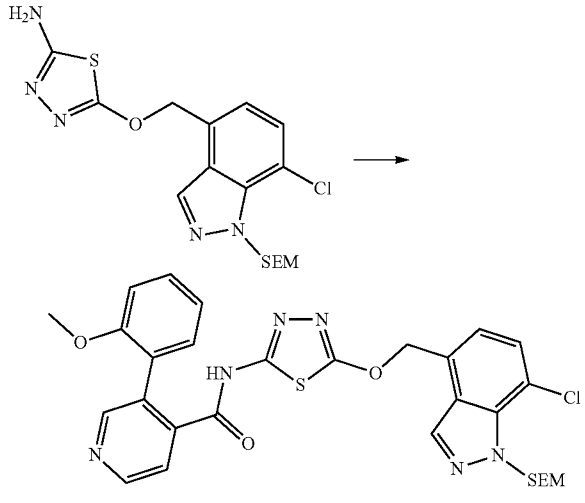

The title compound was prepared according to General Procedure A employing 3-(2-methoxyphenyl)pyridine-4-carboxylic acid (Intermediate H) and 5-((7-chloro-1-((2-(trimethylsilyl)ethoxy)methyl)-1H-indazol-4-yl)methoxy)-1,3,4-thiadiazol-2-amine. The mixture was diluted with EtOAc (25 mL). The mixture was washed with water (3×). The organic layer was concentrated under vacuum. The residue was purified by Prep-TLC (eluent: 5% EtOAc in PE) to afford the title compound (260 mg, 81%) as an off-white solid.

Step 10: N-(5-((7-chloro-1H-indazol-4-yl)methoxy)-1,3,4-thiadiazol-2-yl)-3-(2-methoxyphenyl)isonicotinamide

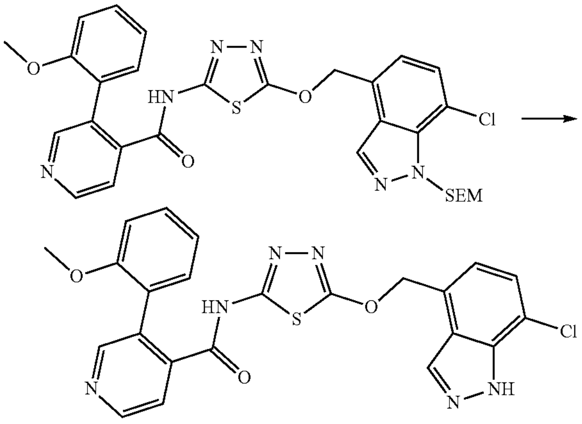

To a solution of N-[5-[(7-chloro-1-[[2-(trimethylsilyl)ethoxy]methyl]indazol-4-yl)methoxy]-1,3,4-thiadiazol-2-yl]-3-(2-methoxyphenyl)pyridine-4-carboxamide N-(5-((7-chloro-1-((2-(trimethylsilyl)ethoxy)methyl)-1H-indazol-4-yl)methoxy)-1,3,4-thiadiazol-2-yl)-3-(2-methoxyphenyl)isonicotinamide (150 mg, 0.241 mmol) in THF (2 mL) was added TBAF (2 M in THF, 0.722 mL, 1.44 mmol) and CsF (365 mg, 2.40 mmol) at room temperature. The mixture was stirred at 60° C. overnight under nitrogen atmosphere. The mixture was diluted with EtOAc. The mixture was washed with water (4×). The organic layer was concentrated under reduced pressure. The residue was purified by Prep-TLC (eluent. 7% MeOH in DCM) to afford the title compound (50 mg, 42% yield) as a white solid. $^1H$ NMR (400 MHz, DMSO $d_6$): δ 13.76 (s, 1H), 12.87 (s, 1H), 8.72 (d, 1H), 8.61 (s, 1H), 8.45 (s, 1H), 7.63 (d, 1H), 7.48 (d, 1H), 7.40-7.35 (m, 2H), 7.26 (d, 1H), 7.08-7.04 (m, 1H), 6.99-6.97 (m, 1H), 5.81 (s, 2H), 3.50 (s, 3H); m/z 493 ($M+H^+$).

Example 108

Synthesis of N-(5-((4-chlorobenzyl)oxy)-1,3,4-thiadiazol-2-yl)-3-(5-cyano-2-(difluoromethoxy)phenyl)isonicotinamide

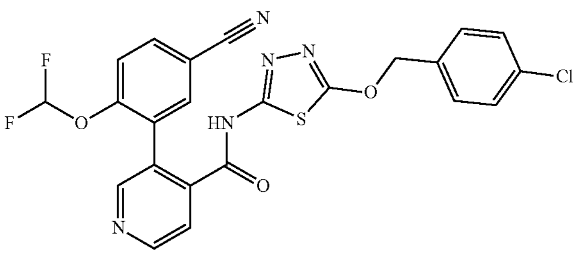 [SMILES: N#Cc1ccc(OC(F)F)c(-c2cnccc2C(=O)Nc2nnc(OCc3ccc(Cl)cc3)s2)c1]

Step 1: Preparation of 3-bromo-4-(difluoromethoxy)benzonitrile

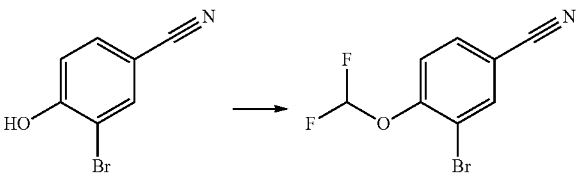 [SMILES: N#Cc1ccc(O)c(Br)c1 ; N#Cc1ccc(OC(F)F)c(Br)c1]

To a solution of 3-bromo-4-hydroxybenzonitrile (5.00 g, 25.2 mmol), (bromodifluoromethyl)trimethylsilane (10.2 g, 50.4 mmol) in DCM (20 mL) at 0° C. was added a solution of KOH (8.50 g, 151.5 mmol) in water (35 mL) was added at 0° C. The mixture was stirred overnight at room temperature. The mixture was diluted with water. The aqueous layer was extracted with EtOAc (3×). The combined organic layers were concentrated under vacuum. The residue was purified by silica gel column chromatography, eluent: 75% EtOAc in PE to afford the title compound (4 g, 63% yield) as a white solid.

Step 2: 4-(difluoromethoxy)-3-(4,4,5,5-tetramethyl-1,3,2-dioxaborolan-2-yl)benzonitrile

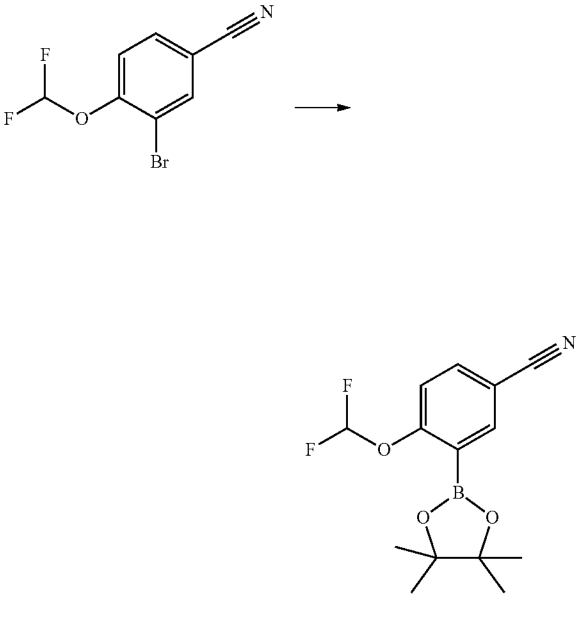

To a solution of 3-bromo-4-(difluoromethoxy)benzonitrile (2.00 g, 8.06 mmol), bis(pinacolato)diboron (2.46 g, 9.67 mmol) in 1,4-dioxane (20 mL) was added KOAc (1.58 g, 16.1 mmol), and Pd(dppf)$Cl_2$ (1.18 g, 1.61 mmol) at room temperature. The mixture was stirred at 80° C. overnight under a nitrogen atmosphere. The mixture was diluted with water and extracted with EtOAc (3×). The combined organic layers were concentrated under vacuum. The residue was purified by silica gel column chromatography, eluent: 33% EtOAc in PE to afford the title compound (400 mg, 16%) as an off-white solid.

Step 3: Preparation of methyl 3-(5-cyano-2-(difluoromethoxy)phenyl)isonicotinate

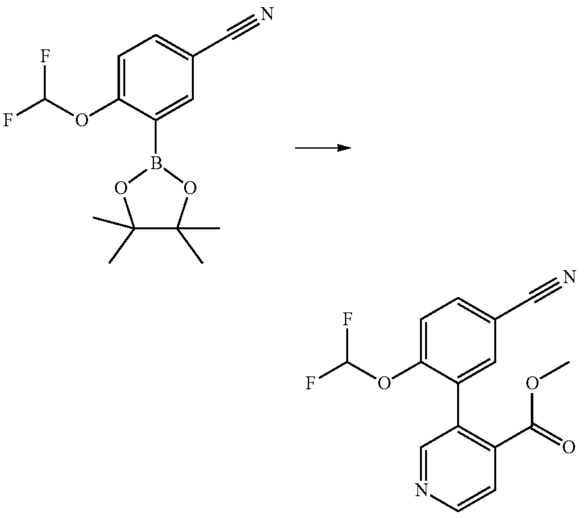

The title compound was prepared according to General Procedure E employing 4-(difluoromethoxy)-3-(4,4,5,5-tetramethyl-1,3,2-dioxaborolan-2-yl)benzonitrile and methyl 3-bromopyridine-4-carboxylate. The mixture was diluted with water and extracted with EtOAc (3×). The combined organic layers were concentrated under vacuum. The residue was purified by Prep-TLC (eluent: 25% EtOAc in PE) to afford the title compound (143 mg, 34% yield) as an off-white solid.

Step 4: Preparation of 3-(5-cyano-2-(difluoromethoxy)phenyl)isonicotinic acid

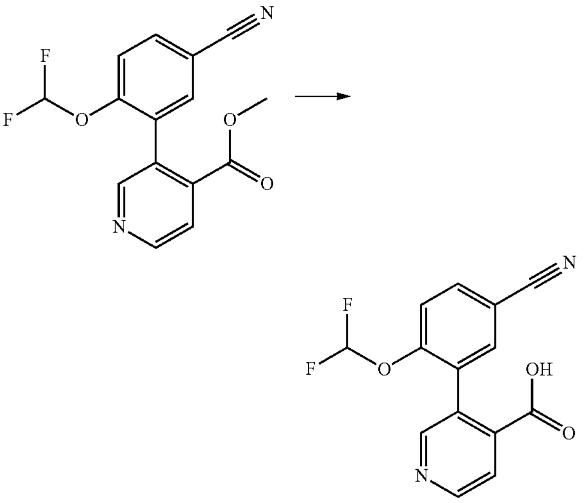

The title compound was prepared according to General Procedure F employing methyl 3-(5-cyano-2-(difluoromethoxy)phenyl)isonicotinate (50 mg, 0.164 mmol) and replacing NaOH (5 eq) with LiOH (1.5 eq). The mixture was acidified with HCl (1 M) to pH 5 and extracted with EtOAc (2×). The combined organic layers were concentrated under vacuum. The residue was purified by reverse phase chromatography (column, C18 silica gel; mobile phase, with 0-100% MeCN in water) to afford the title compound as a white solid.

Step 5: N-(5-((4-chlorobenzyl)oxy)-1,3,4-thiadiazol-2-yl)-3-(5-cyano-2-(difluoromethoxy)phenyl)isonicotinamide

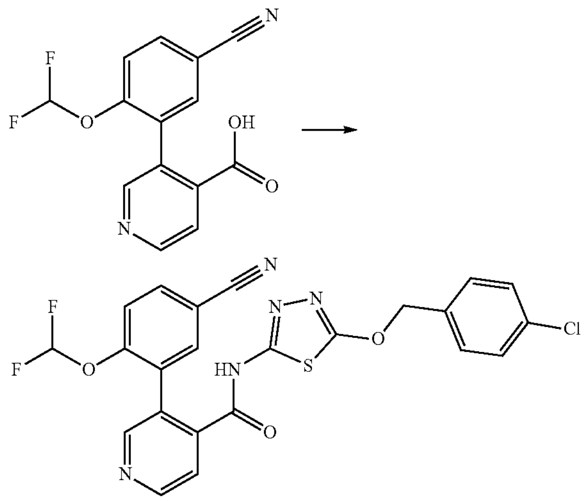

The title compound was prepared according to General Procedure A employing 3-(5-cyano-2-(difluoromethoxy) phenyl)isonicotinic acid and 5-[(4-chlorophenyl)methoxy]-1,3,4-thiadiazol-2-amine 5-((4-chlorobenzyl)oxy)-1,3,4-thiadiazol-2-amine (Intermediate B). The mixture was diluted with water and extracted with EtOAc (2×). The combined organic layers were concentrated under vacuum. The residue was purified by Prep-TLC (eluent: 3% MeOH in DCM) to afford the title compound (10 mg, 18%) as a white solid. $^1$H NMR (300 MHz, DMSO $d_6$): δ 13.12 (s, 1H), 8.84 (d, 1H), 8.69 (s, 1H), 8.03-7.99 (m, 2H), 7.80 (d, 1H), 7.55-7.01 (m, 6H), 5.48 (s, 2H); m/z 514 (M+H$^+$).

Example 109

Synthesis of N-(5-((4-chlorobenzyl)oxy)-1,3,4-thiadiazol-2-yl)-3-(2-(difluoromethoxy)-6-fluorophenyl) isonicotinamide

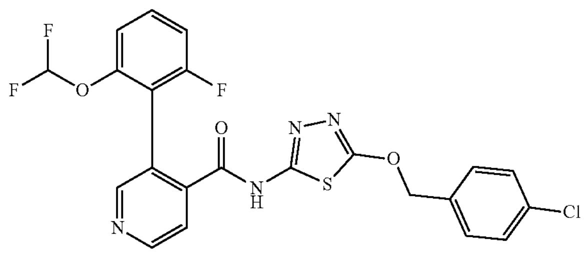 [SMILES: O=C(Nc1nnc(OCc2ccc(Cl)cc2)s1)c1ccncc1-c1c(F)cccc1OC(F)F]

Step 1: Preparation of 2-bromo-1-(difluoromethoxy)-3-fluorobenzene

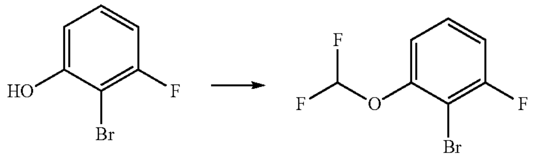 [SMILES: Oc1cccc(F)c1Br ; Fc1cccc(OC(F)F)c1Br]

To a solution of 2-bromo-3-fluorophenol (5 g, 26.1 mmol) and (bromodifluoromethyl)trimethylsilane (10.6 g, 52.3 mmol) in DCM (100 mL) was added a solution of KOH (8.81 g, 157.0 mmol) in water (35 mL) dropwise. The mixture was stirred overnight at room temperature. The mixture was diluted with water (300 mL). The aqueous layer was extracted with DCM (3×100 mL). The combined organic extracts were concentrated under reduced pressure. The residue was purified by silica gel column chromatography (eluent: 10% EtOAc in PE) to afford the title compound (4 g, 63% yield) as a yellow oil.

Step 2: Preparation of 2-(2-(difluoromethoxy)-6-fluorophenyl)-4,4,5,5-tetramethyl-1,3,2-dioxaborolane

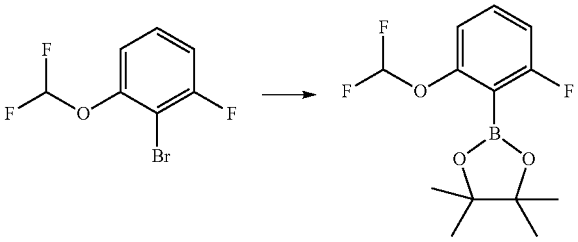 [SMILES: Fc1cccc(OC(F)F)c1Br ; CC1(C)OB(c2c(F)cccc2OC(F)F)OC1(C)C]

To a solution of 2-bromo-1-(difluoromethoxy)-3-fluorobenzene (2.00 g, 8.29 mmol) in 1,4-dioxane (20 mL) was added bis(pinacolato)diboron (3.16 g, 12.4 mmol), KOAc (1.63 g, 16.5 mmol) and Pd(dppf)$Cl_2$ (0.61 g, 0.830 mmol). The mixture was stirred at 80° C. overnight under nitrogen atmosphere. The mixture was diluted with water and extracted with EtOAc (3×). The mixture was concentrated under reduced pressure. The residue was purified by silica gel column chromatography, eluent: 10% EtOAc in PE to afford the title compound (900 mg, 37% yield) as a yellow oil.

Step 3: Preparation of methyl 3-(2-(difluoromethoxy)-6-fluorophenyl)isonicotinate

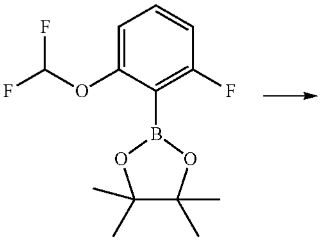

-continued

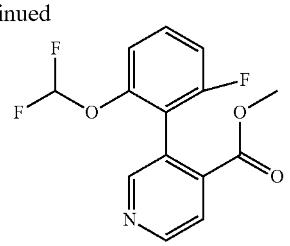

To a solution of 2-(2-(difluoromethoxy)-6-fluorophenyl)-4,4,5,5-tetramethyl-1,3,2-dioxaborolane (840 mg, 2.91 mmol), in 1,4-dioxane (4 mL) and water (1 mL) was added methyl 3-bromopyridine-4-carboxylate (944 mg, 4.374 mmol), $K_2CO_3$ (806 mg, 5.83 mmol) and Pd(dtbpf)$Cl_2$ (380 mg, 0.583 mmol) at room temperature. The mixture was stirred at 100° C. overnight under a nitrogen atmosphere. The mixture was diluted with water and extracted with EtOAc (3×). The combined organic layers were concentrated under reduced pressure. The residue was purified by Prep-TLC (eluent: 10% EtOAc in PE) to afford the title compound (140 mg, 16% yield) as a white solid.

Step 4: Preparation of 3-(2-(difluoromethoxy)-6-fluorophenyl)isonicotinic acid

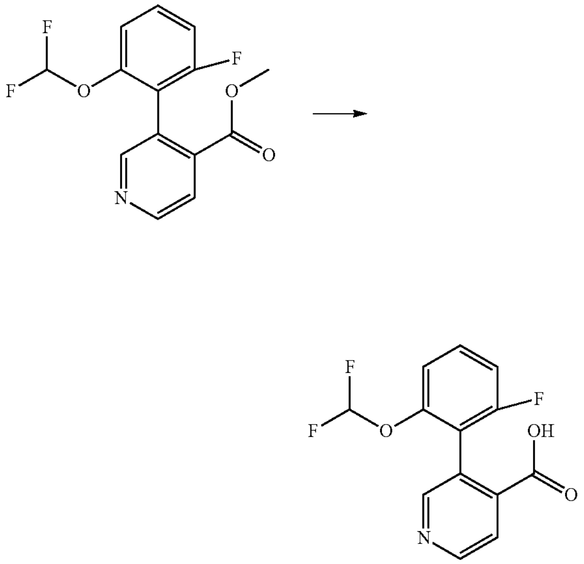 [SMILES: COC(=O)c1ccncc1-c1c(F)cccc1OC(F)F ; O=C(O)c1ccncc1-c1c(F)cccc1OC(F)F]

To a solution of methyl 3-(2-(difluoromethoxy)-6-fluorophenyl)isonicotinate (130 mg, 0.437 mmol) in MeOH (2 mL) was added an aqueous solution of UGH (2 M, 0.44 mL, 0.880 mmol) dropwise at room temperature. The mixture was stirred overnight at room temperature. The mixture was diluted with water and washed with EtOAc. HCl (1 M) was added to the aqueous layer until pH was 5. The solid was collected by filtration and washed with water (3×) to afford the title compound (60 mg, 47% yield) as a white solid.

Step 5: Preparation of N-(5-((4-chlorobenzyl)oxy)-1,3,4-thiadiazol-2-yl)-3-(2-(difluoromethoxy)-6-fluorophenyl)isonicotinamide

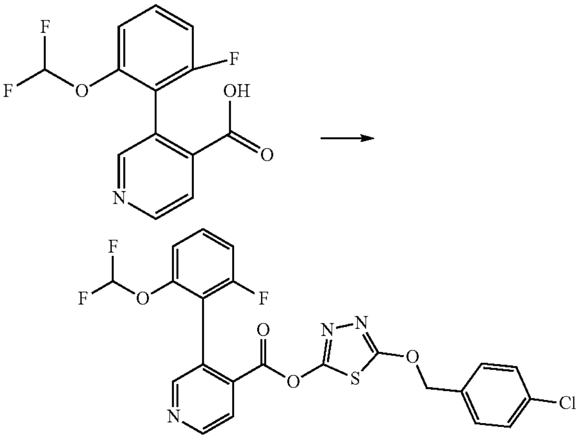

The title compound was prepared according to General Procedure A employing 3-(2-(difluoromethoxy)-6-fluorophenyl)isonicotinic acid and 5-((4-chlorobenzyl)oxy)-1,3,4-thiadiazol-2-amine (Intermediate B). The mixture was diluted with water and extracted with EtOAc (2×). The combined organic extracts were concentrated under reduced pressure. The residue was purified by Prep-TLC (eluent: 5% MeOH in DCM) to afford the title compound (53 mg, 59% yield) as a light yellow solid. $^1$H NMR (300 MHz; DMSO $d_6$): δ 13.13 (s, 1H), 8.83 (d, 1H), 8.66 (s, 1H), 7.84 (d, 1H), 7.54-7.46 (m, 5H), 7.38-6.89 (m, 3H), 5.47 (s, 2H); m/z 507 (M+H$^+$).

Example 110

Synthesis of N-(5-((4-chlorobenzyl)oxy)-1,3,4-thiadiazol-2-yl)-3-((3S,5S)-3,5-dimethylmorpholino)isonicotinamide

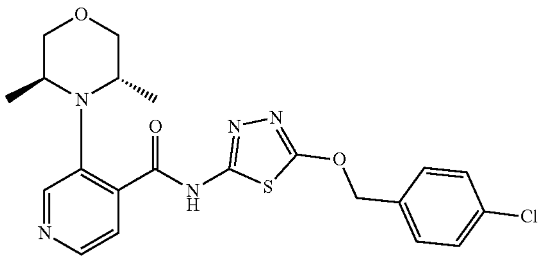 [SMILES: C[C@H]1COC[C@H](C)N1c1cnccc1C(=O)Nc1nnc(OCc2ccc(Cl)cc2)s1]

Step 1: Preparation of 3-fluoro-4-(methoxycarbonyl)pyridine 1-oxide

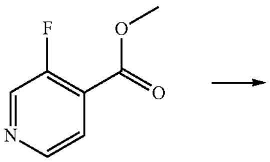

-continued

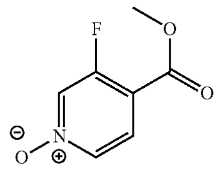

To a solution of methyl 3-fluoropyridine-4-carboxylate (800 mg, 5.2 mmol) in chloroform (8 mL) under and atmosphere of nitrogen was added m-CPBA (85%, 10474 mg, 5.2 mmol). The mixture was stirred for 5 h at room temperature. A solution of sat. NH4Cl (aq.) was added and the mixture was extracted with DCM (3×). The mixture was concentrated under reduced pressure. The residue was purified by silica gel column chromatography, eluted with 5% MdOH in DCM to afford the title compound.

Step 2: Preparation of 3-((3S,5S)-3,5-dimethylmorpholino)-4-(methoxycarbonyl)pyridine 1-oxide

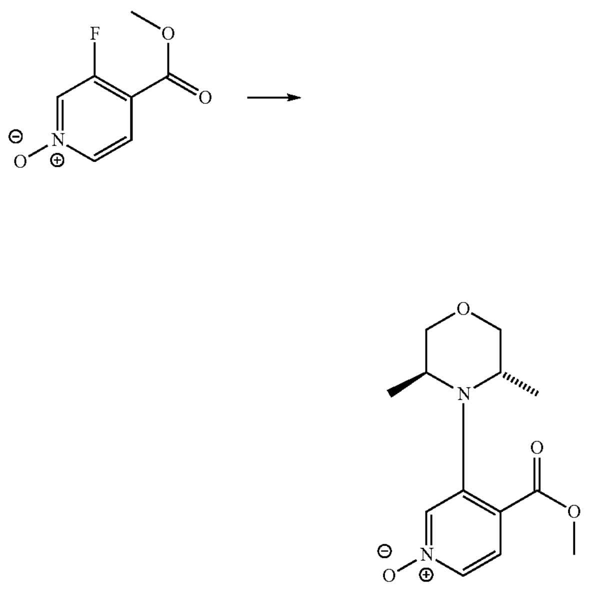

To a solution of 3-fluoro-4-(methoxycarbonyl)pyridine 1-oxide (770 mg, 4.50 mmol) in MeCN (7.70 mL) was added (3S,5S)-3,5-dimethylmorpholine hydrochloride (407 mg, 2.70 mmol) and DIEA (1.04 g, 8.09 mmol). The mixture was stirred at 100° C. for 3 days. The mixture was diluted with water and concentrated under reduced pressure to half volume. The mixture was diluted with EtOAc and the layer were separated. The organic layer was concentrated under vacuum. The residue was purified by Prep-TLC (eluent: 4% MeOH in DCM) to afford the title compound (130 mg, 8% yield) as a yellow oil.

Step 3: Preparation of methyl 3-((3S,5S)-3,5-dimethylmorpholino)isonicotinate

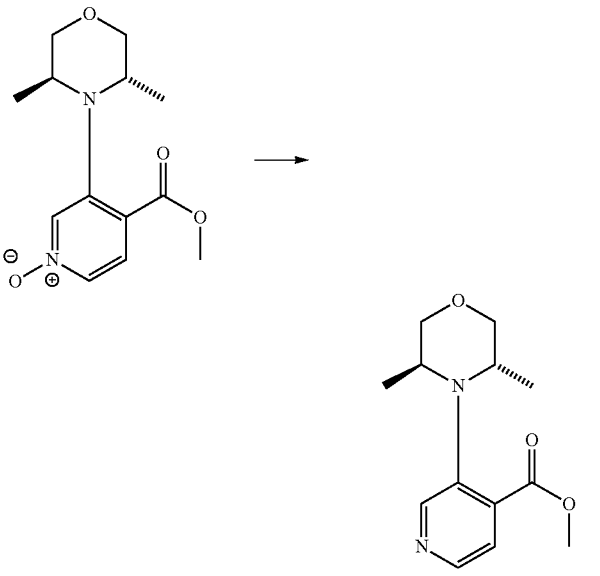

To a solution of 3-((3S,5S)-3,5-dimethylmorpholino)-4-(methoxycarbonyl)pyridine 1-oxide (120 mg, 0.451 mmol) in MeOH (1.20 mL) was added 10% Pd/C (12 mg) and $HCO_2NH_4$ (142 mg, 2.25 mmol). The mixture was stirred for 2 hours at room temperature. The mixture was diluted with MeOH. The solid was removed by filtration and washed with MeOH (2×). The filtrate was concentrated under reduced pressure. The residue was purified by Prep-TLC (eluent: 20% EtOAc in PE) to afford the title compound (78 mg, 67%) as a colorless oil.

Step 4: Preparation of 3-((3S,5S)-3,5-dimethylmorpholino)isonicotinic acid

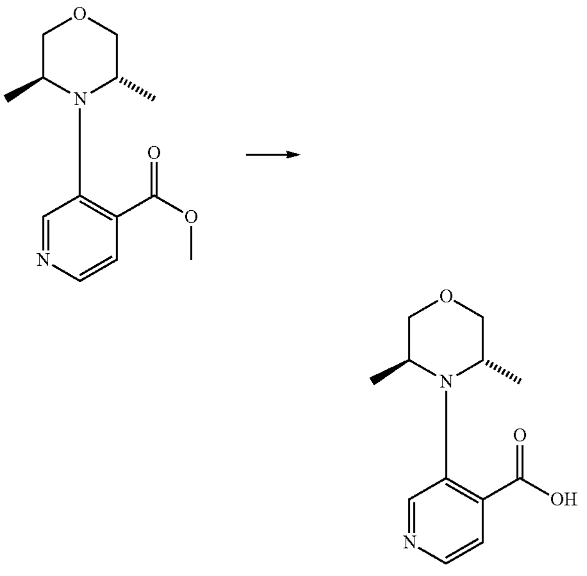

To a solution of methyl 3-((3S,5S)-3,5-dimethylmorpholino)isonicotinate (78 mg, 0.312 mmol) in MeOH (0.80 mL) and water (0.20 mL) was added NaOH (24 mg, 0.623 mmol). The mixture was stirred for 2 hours at room temperature. The mixture was diluted with water and washed with EtOAc. HCl (1 M) was added to aqueous layer until pH was 5. The aqueous layer was extracted with EtOAc (8×). The combined organic layers were concentrated under reduced pressure to afford the title compound (70 mg, 94% yield) as a white solid which was used without further purification.

Step 5: N-(5-((4-chlorobenzyl)oxy)-1,3,4-thiadiazol-2-yl)-3-((3S,5S)-3,5-dimethylmorpholino)isonicotinamide

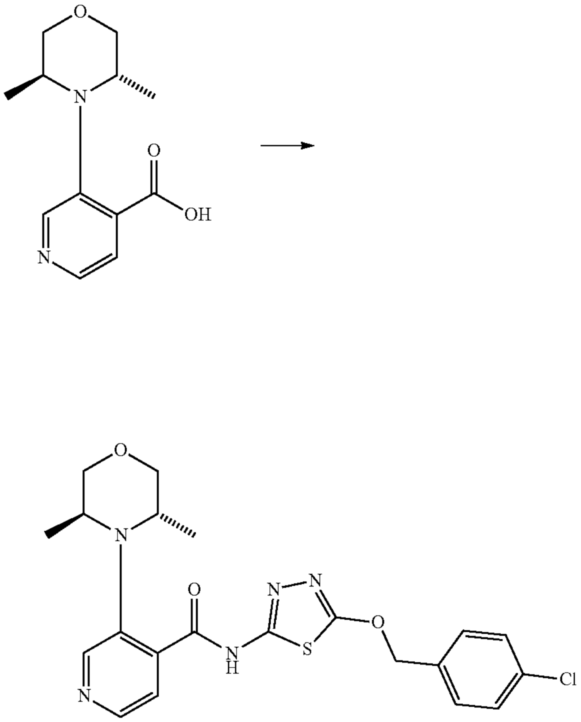 [SMILES: C[C@H]1COC[C@H](C)N1c1cnccc1C(=O)O ; C[C@H]1COC[C@H](C)N1c1cnccc1C(=O)Nc1nnc(OCc2ccc(Cl)cc2)s1]

The title compound was prepared according to General Procedure A employing 3-((3S,5S)-3,5-dimethylmorpholino)isonicotinic acid and 5-((4-chlorobenzyl)oxy)-1,3,4-thiadiazol-2-amine (Intermediate B). The resulting was stirred for 2 h at room temperature. The mixture was diluted with water. The solid was collected by filtration and washed with water. The solid was purified by trituration with MeOH to afford the title compound (61 mg, 43% yield) as a light pink solid. $^1$H-NMR (300 MHz, DMSO-$d_6$): δ 14.24 (s, 1H), 8.74 (s, 1H), 8.62 (d, 1H), 7.90 (d, 1H), 7.57-7.55 (m, 2H), 7.51-7.48 (m, 2H), 5.52 (s, 2H), 3.95 (s, 3H), 3.74 (s, 1H), 3.17 (s, 2H), 1.06 (s, 3H), 0.81 (s, 3H); m/z [M+H]$^+$ 460.

Example 111

Synthesis of 3-(benzo[d]oxazol-7-yl)-N-(5-((4-chlorobenzyl)oxy)-1,3,4-thiadiazol-2-yl)isonicotinamide

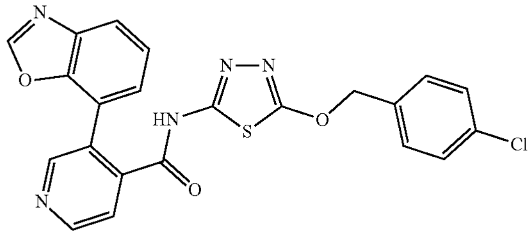 [SMILES: O=C(Nc1nnc(OCc2ccc(Cl)cc2)s1)c1ccncc1-c1cccc2ncoc12]

Step 1: Preparation of 7-(4,4,5,5-tetramethyl-1,3,2-dioxaborolan-2-yl)benzo[d]oxazole

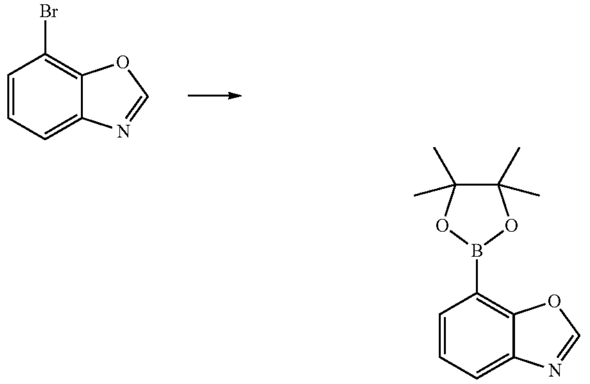

To a solution of 7-bromo-1,3-benzoxazole (2.00 g, 10.1 mmol) in 1,4-dioxane (20 mL) was added 4,4,5,5-tetramethyl-2-(4,4,5,5-tetramethyl-1,3-dioxolan-2-yl)-1,3,2-dioxaborolane (3.88 g, 15.1 mmol), KOAc (1.98 g, 20.2 mmol), Pd(dppf)$Cl_2$ (740 mg, 1.01 mmol). The mixture was stirred at 80° C. for 2 h. The mixture was cooled to rt and diluted with water. The mixture was extracted with EtOAc (3×). The combined organic layers were concentrated under reduced pressure. The residue was purified by silica gel column chromatography, eluent: 2% EtOAc in PE to afford the title compound (2 g, 71% yield) as a white solid.

Step 2: Preparation of methyl 3-(benzo[d]oxazol-7-yl)isonicotinate

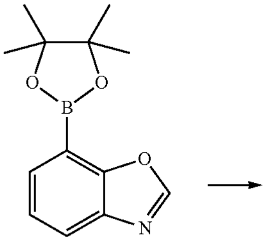

-continued

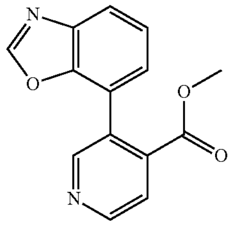

To a solution of 7-(4,4,5,5-tetramethyl-1,3,2-dioxaborolan-2-yl)benzo[d]oxazole (1.00 g, 4.08 mmol) in 1,4-dioxane (10 mL) and water (2 mL) was added methyl 3-bromopyridine-4-carboxylate (1.32 g, 6.12 mmol), $K_2CO_3$ (1.13 g, 8.16 mmol) and Pd(dppf)$Cl_2$ (0.30 g, 0.408 mmol). The mixture was stirred at 80° C. for 2 h. The mixture was diluted with water and extracted with EtOAc (3×). The combined organic layers were concentrated under reduced pressure. The residue was purified by silica gel column chromatography, eluent: 3% EtOAc in PE to afford the title compound (700 mg, 64% yield) as a white solid.

Step 3: Preparation of 3-(benzo[d]oxazol-7-yl)isonicotinic acid

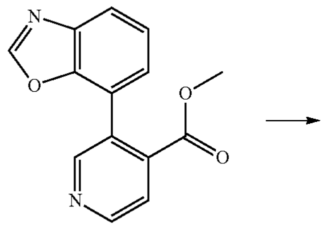

The title compound was prepared according to General Procedure F employing methyl 3-(benzo[d]oxazol-7-yl) isonicotinate. The mixture was acidified to pH 6 with AcOH. The mixture was concentrated under reduced pressure. The residue was purified by reverse phase chromatography (column, C18 silica gel; mobile phase, with 0-10% MeCN in water) to afford the title compound (270 mg, 37% yield) as a yellow solid.

Step 4: Preparation of 3-(benzo[d]oxazol-7-yl)-N-(5-((4-chlorobenzyl)oxy)-1,3,4-thiadiazol-2-yl)isonicotinamide

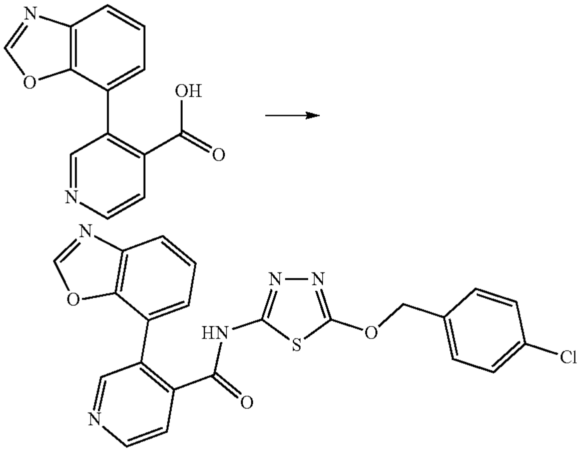

The title compound was prepared according to General Procedure A employing 3-(benzo[d]oxazol-7-yl)isonicotinic acid and 5-((4-chlorobenzyl)oxy)-1,3,4-thiadiazol-2-amine (Intermediate B). The mixture was diluted with water and extracted with EtOAc (2×). The combined organic extracts were concentrated under reduced pressure. The residue was purified by Prep-TLC (eluent: 5% MeOH in DCM) to afford the title compound (15 mg, 7% yield) as a white solid. $^1$H NMR (300 MHz, DMSO-$d_6$): δ 13.13 (s, 1H), 8.93 (s, 1H), 8.85 (d, 1H), 8.72 (s, 1H), 7.85-7.80 (m, 2H), 7.54-7.46 (m, 6H), 5.46 (s, 2H); m/z 464 (M+H$^+$).

Example 112

Synthesis of N-(5-((4-chlorobenzyl)oxy)-1,3,4-thiadiazol-2-yl)-5-(2-(difluoromethoxy)phenyl) pyridazine-4-carboxamide

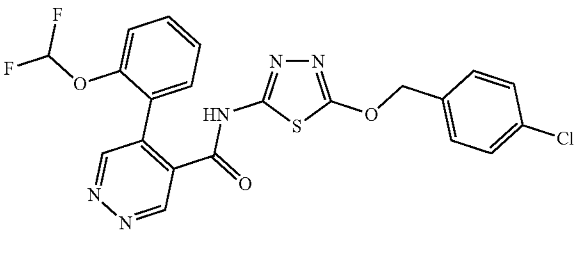 [SMILES: O=C(Nc1nnc(OCc2ccc(Cl)cc2)s1)c1cnncc1-c1ccccc1OC(F)F]

Step 1: Preparation of 2-(2-(difluoromethoxy)phenyl)-2-oxoacetaldehyde

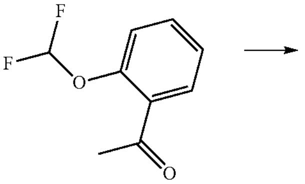

-continued

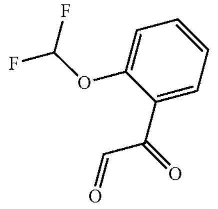

To a solution of 1-[2-(difluoromethoxy)phenyl]ethanone (5.00 g, 26.8 mmol) in 1,4-dioxane (27 mL) and water (3 mL) was added $SeO_2$ (4.47 g, 40.2 mmol). The mixture was stirred at 100° C. overnight. The mixture was diluted with water and extracted with EtOAc. The combined organic layers were concentrated under reduced pressure. The residue was purified by silica gel column chromatography (eluent: 20% EtOAc in PE) to afford the title compound (3.6 g, 26% yield) as a colorless oil.

Step 2: Preparation of 5-(2-(difluoromethoxy)phenyl)-3-oxo-2,3-dihydropyridazine-4-carbonitrile

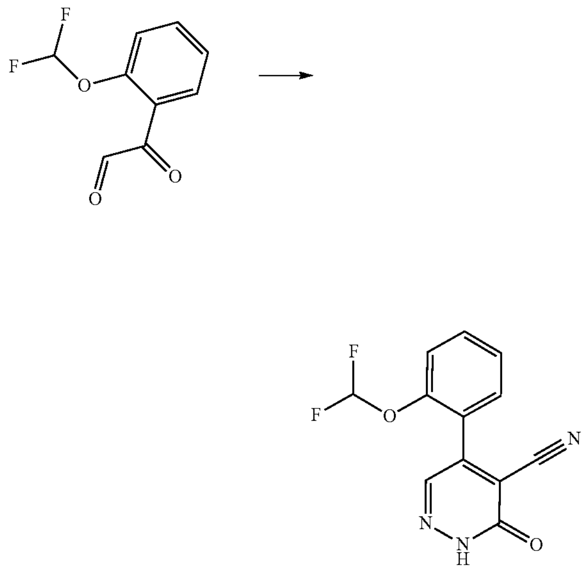

To a solution of 2-(2-(difluoromethoxy)phenyl)-2-oxoacetaldehyde (3.60 g, 17.9 mmol) in EtOH (108 mL) was added $Na_2SO_4$ (5.11 g, 35.9 mmol) and cyacetacide (1.78 g, 17.9 mmol). The mixture was stirred for 5 hours at room temperature. The mixture was filtered and washed with EtOAc (3×). The filtrate was concentrated under vacuum to give a residue. The residue was dissolved in EtOH to give solution A. In a separate flask, a solution of sodium metal (413 mg, 17.9 mmol) in EtOH was cooled to 0° C. under nitrogen atmosphere. The solution A was added to the sodium ethoxide mixture dropwise at 0° C. The mixture was then stirred at 80° C. overnight. The mixture was cooled to rt and diluted with water. The mixture was concentrated under reduced pressure. The precipitated solids were collected by filtration and washed with water followed by EtOAc to afford the title compound (1.14 g, 23% yield) as a brown solid.

Step 3: Preparation 3-chloro-5-(2-(difluoromethoxy)phenyl)pyridazine-4-carbonitrile

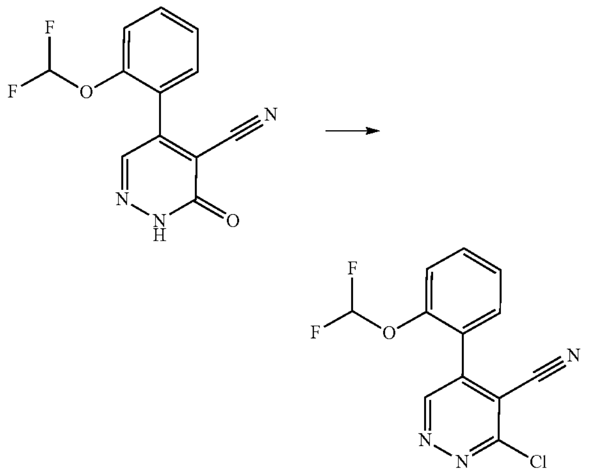

5-(2-(difluoromethoxy)phenyl)-3-oxo-2,3-dihydropyridazine-4-carbonitrile (1.10 g, 4.17 mmol) was diluted with $POCl_3$ (11 mL). The mixture was stirred at 100° C. overnight. The mixture was cooled to 0° C. and ice water was added. The mixture was extracted with EtOAc and the organic layer was concentrated under reduced pressure. During concentration, precipitated solid form. The solid was collected by filtration and washed with MeOH to afford the title compound (780 mg, 63% yield) as a brown solid.

Step 4: Preparation of 5-(2-(difluoromethoxy)phenyl)pyridazine-4-carbonitrile

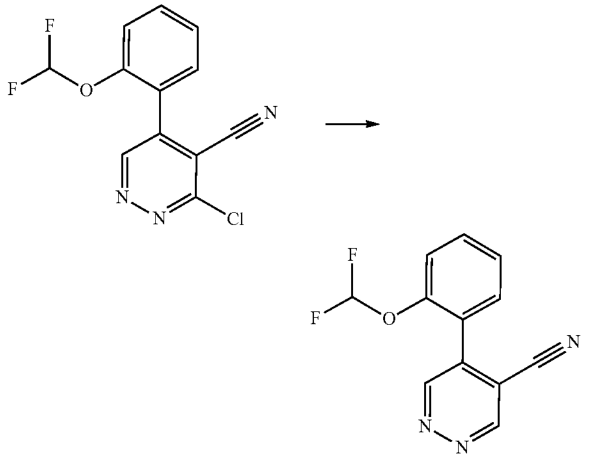

To a solution of 3-chloro-5-(2-(difluoromethoxy)phenyl)pyridazine-4-carbonitrile (340 mg, 1.20 mmol) in MeOH (3.50 mL) and THF (1.70 mL) was added 10% Pd/C (35 mg) and $HCO_2NH_4$ (380 mg, 6.03 mmol). The mixture was stirred at 60° C. overnight. The solids were filtered and washed with MeOH (3×). The mixture was concentrated under reduced pressure. The residue was purified by Prep-TLC (eluent: 3% MeOH in DCM) to afford the title compound (130 mg, 41% yield) as a colorless oil.

Step 5: Preparation of 5-(2-(difluoromethoxy)phenyl)pyridazine-4-carboxylic acid

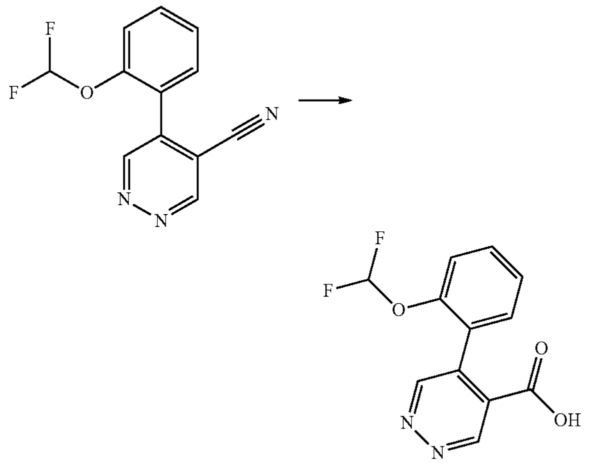

To a solution of 5-(2-(difluoromethoxy)phenyl) pyridazine-4-carbonitrile (110 mg, 0.445 mmol) in EtOH (1.10 mL) was added KOH (99 mg, 1.78 mmol). The mixture was stirred at 100° C. for 3 h. The mixture was diluted with water and washed with EtOAc. AcOH was added to the aqueous layer until the pH was 5. The mixture was extracted with EtOAc. The organic layer was concentrated under reduced pressure to afford the title compound (55 mg, 45% yield) as a yellow solid.

Step 6: Preparation of N-(5-((4-chlorobenzyl)oxy)-1,3,4-thiadiazol-2-yl)-5-(2-(difluoromethoxy)phenyl) pyridazine-4-carboxamide

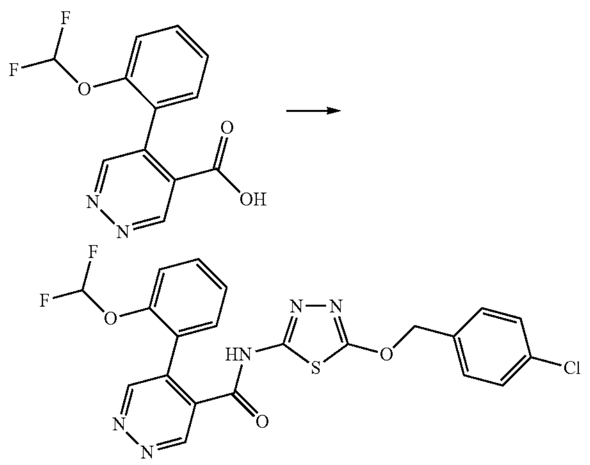

To a solution of 5-(2-(difluoromethoxy)phenyl) pyridazine-4-carboxylic acid (45 mg, 0.169 mmol) in DMF (0.50 mL) was added 5-((4-chlorobenzyl)oxy)-1,3,4-thiadiazol-2-amine (Intermediate B) (40 mg, 0.169 mmol), EDCI (48 mg, 0.254 mmol) and HOBT (34 mg, 0.254 mmol). The mixture was stirred overnight at room temperature. The mixture was diluted with water and extracted with EtOAc. The organic layer was concentrated under reduced pressure. The residue was purified by Prep-TLC (eluent: 3% MeOH in DCM) to afford the title compound (16 mg, 19% yield) as a yellow solid. $^{1}H$ NMR (400 MHz, DMSO-$d_6$): δ13.31 (s, 1H), 9.55 (s, 1H), 9.40 (s, 1H), 7.58-7.46 (m, 6H), 7.41-6.85 (m, 3H), 5.47 (s, 2H); m/z 490 ($M+H^+$).

Example 113

Synthesis of N-(5-((5-chloropyridin-2-yl)methoxy)-1,3,4-thiadiazol-2-yl)-4-(2-methoxyphenyl)-6-methylnicotinamide

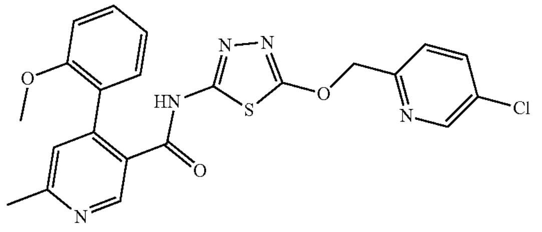 [SMILES: COc1ccccc1-c1cc(C)ncc1C(=O)Nc1nnc(OCc2ccc(Cl)cn2)s1]

Step 1: Preparation of methyl 4-(2-methoxyphenyl)-6-methylnicotinate

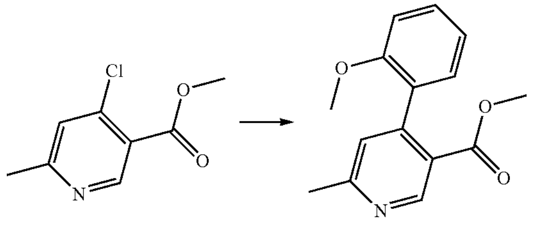

To a solution of methyl 4-chloro-6-methylpyridine-3-carboxylate (300 mg, 1.61 mmol) in 1,4-dioxane (4 mL) and water (0.5 mL), was added 2-methoxyphenylboronic acid (491 mg, 3.23 mmol), $K_2CO_3$ (446 mg, 3.23 mmol), Pd(dtbpf)$Cl_2$ (105 mg, 0.162 mmol). The mixture was stirred for 2 h at 80° C. The mixture was diluted with water and extracted with EtOAc (3×). The combined organic extracts were concentrated under reduced pressure. The residue was purified by Prep-TLC (eluent: 10% MeOH in DCM) to afford the title compound (330 mg, 72% yield) as a brown oil.

Step 2: Preparation of 4-(2-methoxyphenyl)-6-methylnicotinic acid

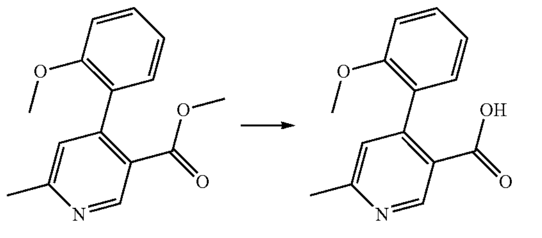

The title compound was prepared according to General Procedure F employing methyl 4-chloro-6-methylpyridine-3-carboxylate. The mixture was diluted with water and MeOH was removed under reduced pressure. The mixture was acidified to pH 5 with HCl (1 M). The precipitated solids were collected by filtration and washed with water (2×) to afford the title compound (140 mg, 41% yield) as a white solid.

Step 3: Preparation of N-(5-((5-chloropyridin-2-yl)methoxy)-1,3,4-thiadiazol-2-yl)-4-(2-methoxyphenyl)-6-methylnicotinamide

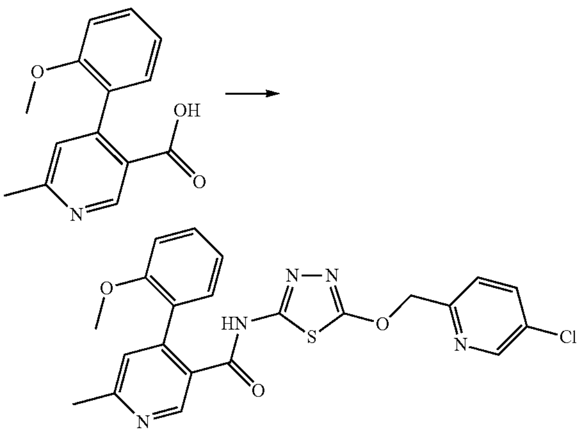

The title compound was prepared according to General Procedure A employing 4-(2-methoxyphenyl)-6-methylnicotinic acid and 5-((5-chloropyridin-2-yl)methoxy)-1,3,4-thiadiazol-2-amine (Intermediate C). The mixture was diluted with water. The mixture was extracted with EtOAc (3×). The combined organic extracts were concentrated under reduced pressure. The residue was purified by Prep-TLC (eluent: 3% MeOH in DCM) to afford the title compound (55 mg, 27%) as a white solid. $^1$H NMR (300 MHz, DMSO-$d_6$): δ 12.76 (s, 1H), 8.66 (s, 2H), 8.00 (d, 1H), 7.60 (d, 1H), 7.39-7.33 (m, 2H), 7.30 (s, 1H), 7.08 (t, 1H), 6.96 (d, 1H), 5.54 (s, 2H), 3.51 (s, 3H), 2.57 (s, 3H); m/z 468 (M+H$^+$).

Example 114

Synthesis of N-[5-[(4-chlorophenyl)methoxy]-1,3,4-thiadiazol-2-yl]-4-[2-(difluoromethoxy)phenyl]-6-methylpyridine-3-carboxamide

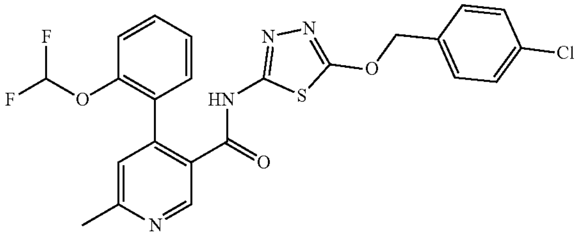

Step 1: Preparation of methyl 4-[2-(difluoromethoxy)phenyl]-6-methylpyridine-3-carboxylate

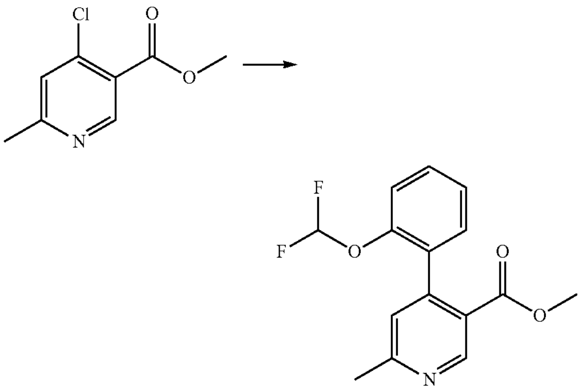

The title compound was prepared using General Procedure E employing methyl 4-chloro-6-methylpyridine-3-carboxylate and 2-[2-(difluoromethoxy)phenyl]-4,4,5,5-tetramethyl-1,3,2-dioxaborolane. The mixture was stirred at 60° C. for 2 h. The mixture was cooled to rt and diluted with water. The mixture was extracted with EtOAc (2×) and the combined organic layers were concentrated under reduced pressure. The residue was purified by Prep-TLC (PE/EtOAc 5:1) to afford the title compound as a yellow oil.

Step 2: Preparation of 4-[2-(difluoromethoxy)phenyl]-6-methylpyridine-3-carboxylic acid

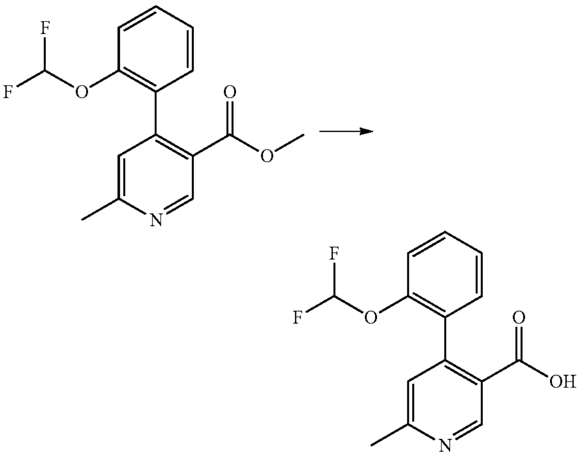

The title compound was prepared according to General Procedure F employing methyl 4-[2-(difluoromethoxy)phenyl]-6-methylpyridine-3-carboxylate. The mixture was stirred at 50° C. for 3 h. The mixture was cooled to rt and diluted with water. The MeOH removed by vacuum. The mixture was acidified to pH 6 with HCl (1 M). The mixture was extracted with EtOAc (3x5). The combined organic layers were concentrated under reduced pressure to afford the title compound as a white solid which was used without further purification.

Step 3: Preparation of N-[5-[(4-chlorophenyl)methoxy]-1,3,4-thiadiazol-2-yl]-4-[2-(difluoromethoxy)phenyl]-6-methylpyridine-3-carboxamide

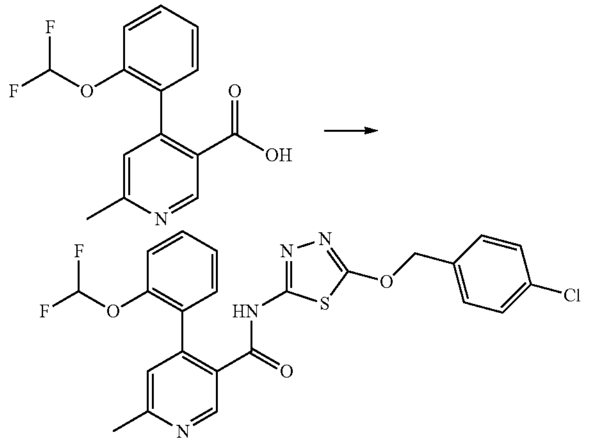

To a solution of 4-[2-(difluoromethoxy)phenyl]-6-methylpyridine-3-carboxylic acid (100 mg, 0.36 mmol) in DMF (1.00 mL) was added 5-((4-chlorobenzyl)oxy)-1,3,4-thiadiazol-2-amine (Intermediate B) (87 mg, 0.36 mmol), HOBt (73 mg, 0.54 mmol) and EDCI (103 mg, 0.54 mmol). The mixture was stirred for at rt for 12 h. The mixture was diluted with water and extracted with EtOAc (2×). The combined organic layers were concentrated under reduced pressure. The residue was purified by Prep-TLC (DCM:MeOH, 20:1) to afford the title compound (88 mg, 47% yield) as a white solid. $^1$H NMR (300 MHz, DMSO-$d_6$): δ 12.90 (s, 1H), 8.80 (s, 1H), 7.54-7.45 (m, 5H), 7.45-7.43 (m, 1H), 7.42-7.39 (m, 2H), 7.32-7.17 (m, 1H), 7.03-6.78 (m, 1H), 5.47 (s, 2H), 2.58 (s, 3H); m/z 503 (M+H$^+$).

Example 115

Synthesis of N-[5-[(5-chloropyridin-2-yl)methoxy]-1,3,4-thiadiazol-2-yl]-4-[2-(difluoromethoxy)phenyl]-6-methylpyridine-3-carboxamide

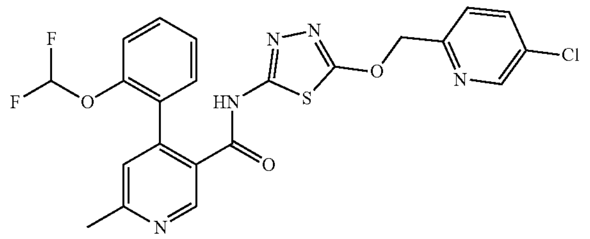 [SMILES: Cc1cc(-c2ccccc2OC(F)F)c(C(=O)Nc2nnc(OCc3ccc(Cl)cn3)s2)cn1]

The title compound was prepared using similar procedure as Example 114, Step 3 replacing 5-((4-chlorobenzyl)oxy)-1,3,4-thiadiazol-2-amine (Intermediate B) with 5-((5-chloropyridin-2-yl)methoxy)-1,3,4-thiadiazol-2-amine (Intermediate C). The residue was purified by Prep-TLC (DCM:MeOH, 20:1) to afford the title compound as a white solid. $^1$H NMR (300 MHz, DMSO-$d_6$): δ 12.93 (s, 1H), 8.81 (s, 1H), 8.65 (s, 1H), 8.02-7.98 (m, 1H), 7.61-7.58 (d, 1H), 7.51-7.46 (m, 1H), 7.46-7.42 (m, 1H), 7.40-7.28 (m, 2H), 7.20-6.79 (m, 2H), 5.54 (s, 2H), 2.58 (s, 3H); m/z 504 (M+H$^+$).

Example 116

Synthesis of N-[5-[(4-chlorophenyl)methoxy]-1,3,4-thiadiazol-2-yl]-4-(5-cyano-2-methoxyphenyl)-6-methylpyridine-3-carboxamide

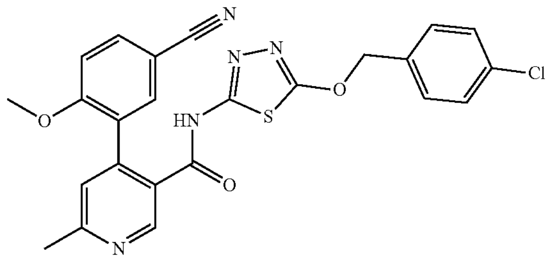

Step 1. Preparation of methyl 4-(5-cyano-2-methoxyphenyl)-6-methylpyridine-3-carboxylate

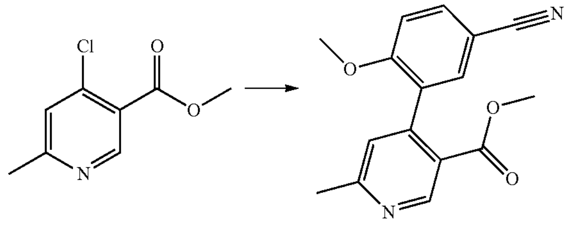

A reaction vial under a nitrogen atmosphere was charged with 5-cyano-2-methoxyphenylboronic acid (1525 mg, 8.6 mmol), 1,4-dioxane (8 mL), methyl 4-chloro-6-methylpyridine-3-carboxylate (800 mg, 4.3 mmol), $H_2O$ (2 mL), $K_2CO_3$ (1191 mg, 8.6 mmol), Pd(dtbpf)$Cl_2$ (281 mg, 0.43 mmol). The mixture was stirred at 80° C. for 4 h. The mixture was cooled to rt and diluted with water. The mixture was extracted with EtOAc (3×) and the combined organic layers were concentrated under reduced pressure. The residue was purified by Prep-TLC (DCM:MeOH, 20:1) to afford the title compound as a yellow oil.

Step 2. Preparation of 4-(5-cyano-2-methoxyphenyl)-6-methylpyridine-3-carboxylic acid

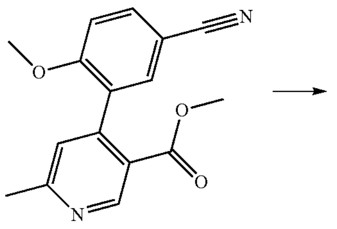

-continued

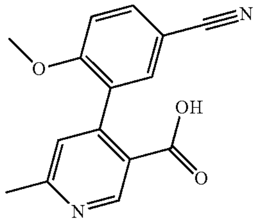

To a solution of methyl 4-(5-cyano-2-methoxyphenyl)-6-methylpyridine-3-carboxylate (600.00 mg, 2.125 mmol) in THF (20 mL), and water (4 mL) was added LiOH (102 mg, 4.3 mmol. The mixture was stirred at rt for 2 h. The mixture was diluted with water and acidified with HCl (1 M) to pH 5. The mixture was extracted with EtOAc (3×) and the combined organic layers were concentrated under reduced pressure. The residue was purified by Prep-TLC (DCM: MeOH, 8:1) to afford the title compound (360 mg, 60% yield) as a brown solid.

Step 3. Preparation of N-[5-[(4-chlorophenyl)methoxy]-1,3,4-thiadiazol-2-yl]-4-(5-cyano-2-methoxyphenyl)-6-methylpyridine-3-carboxamide

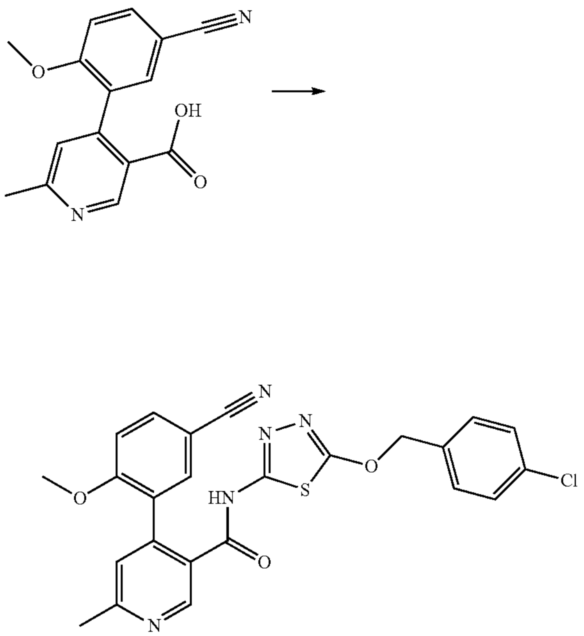

The title compound was prepared using General Procedure A employing 4-(5-cyano-2-methoxyphenyl)-6-methylpyridine-3-carboxylic acid and 5-((4-chlorobenzyl)oxy)-1,3,4-thiadiazol-2-amine (Intermediate B). The mixture was diluted with water and extracted with EtOAc (3×). The combined organic layers were concentrated under reduced pressure. The residue was triturated with MeOH to afford the title compound as a red solid. $^1$H NMR (300 MHz, DMSO-$d_6$): δ 12.88 (s, 1H), 8.82 (s, 1H), 8.08-7.73 (m, 2H), 7.54-7.47 (m, 4H), 7.39 (s, 1H), 7.26-7.16 (d, 1H), 5.38 (s, 2H), 3.59 (s, 3H), 2.58 (s, 3H); m/z 492 (M+H$^+$).

Example 117

Synthesis of N-[5-[(5-chloropyridin-2-yl)methoxy]-1,3,4-thiadiazol-2-yl]-4-(5-cyano-2-methoxyphenyl)-6-methylpyridine-3-carboxamide

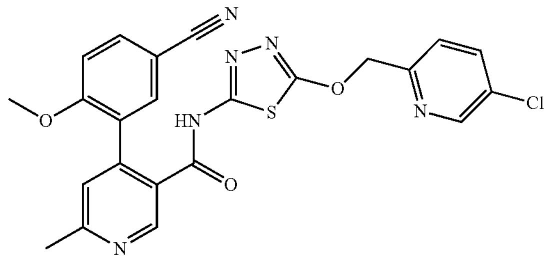

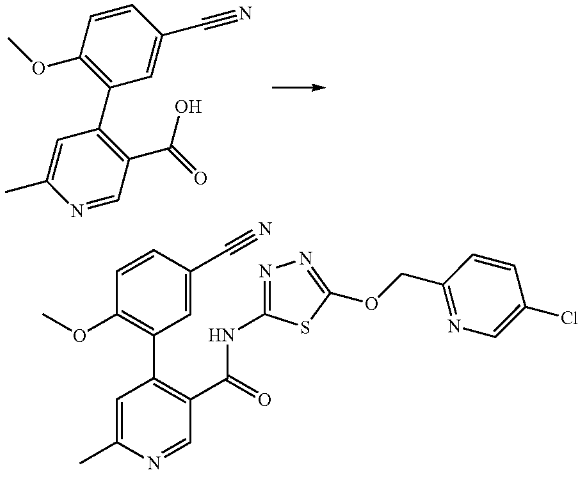

The title compound was prepared using General Procedure A employing 4-(5-cyano-2-methoxyphenyl)-6-methylpyridine-3-carboxylic acid (Example 116, Step 2) and 5-((5-chloropyridin-2-yl)methoxy)-1,3,4-thiadiazol-2-amine (Intermediate C). The mixture was diluted with water and extracted with EtOAc (3×). The combined organic layers were concentrated under reduced pressure. The residue was triturated with MeOH to afford the title compound as a red solid. $^1$H NMR (300 MHz, DMSO-$d_6$): δ 12.81 (s, 1H), 8.73 (s, 1H), 8.65 (s, 1H), 8.02-7.95 (m, 1H), 7.92-7.84 (m, 2H), 7.62-7.54 (d, 1H), 7.39 (s, 1H), 7.19-7.16 (d, 1H), 5.54 (s, 2H), 3.59 (s, 3H), 2.58 (s, 3H); m/z 493 (M+H$^+$).

Example 118

Synthesis of N-(5-((4-chlorobenzyl)oxy)-1,3,4-thiadiazol-2-yl)-3-(4-methyl-1H-pyrazol-5-yl)isonicotinamide

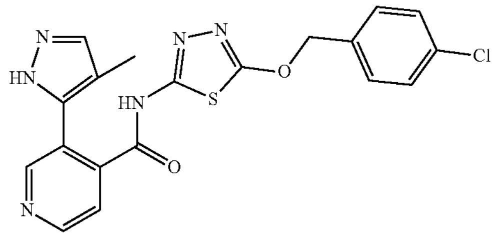 [SMILES: Cc1cn[nH]c1-c1cnccc1C(=O)Nc1nnc(OCc2ccc(Cl)cc2)s1]

Step 1: Preparation of methyl 3-(4-methyl-1-(tetrahydro-2H-pyran-2-yl)-1H-pyrazol-5-yl)isonicotinate

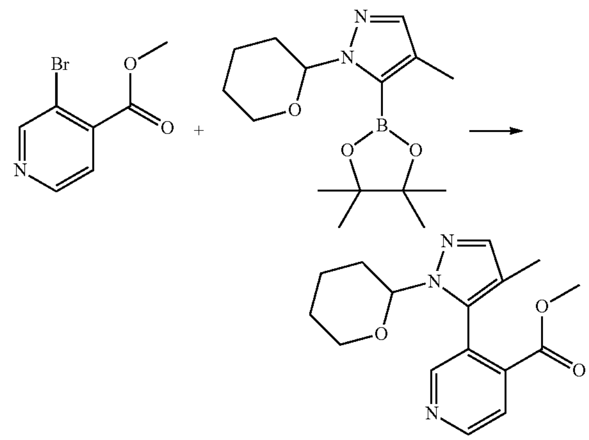

A reaction vial under an atmosphere of nitrogen was charged with methyl 3-bromoisonicotinate (250 mg, 1.15 mmol), 4-methyl-1-(tetrahydro-2H-pyran-2-yl)-5-(4,4,5,5-tetramethyl-1,3,2-dioxaborolan-2-yl)-1H-pyrazole (405 mg, 1.38 mmol), [1,1'-bis(diphenylphosphino)ferrocene]dichloropalladium(II) (128 mg, 0.173 mmol), $K_2CO_3$ (319 mg, 2.31 mmol) and 6 mL of a 9:1 dioxane/water solution. The mixture was sealed under nitrogen and heated to 80° C. for 18 h. The mixture was diluted with water (5 mL), extracted with EtOAc (3×5 mL), dried over $Na_2SO_4$. The combined organic extracts were concentrated under reduced pressure. The residue was purified via silica gel column chromatography (eluent: 0%-100% EtOAc in hexanes) to afford the title compound (125 mg, 36% yield) as a yellow oil.

Step 2: Preparation of 3-(4-methyl-1-(tetrahydro-2H-pyran-2-yl)-1H-pyrazol-5-yl)isonicotinic acid

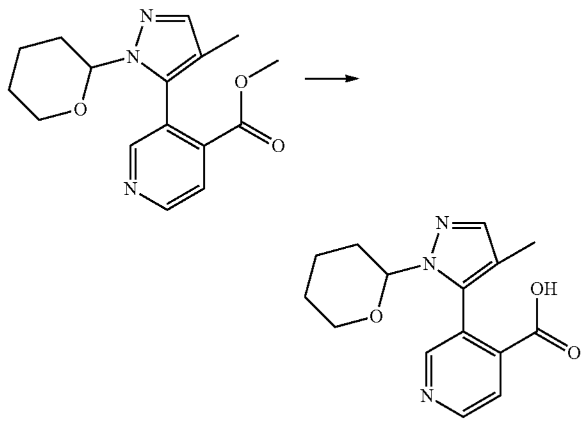

The title compound was prepared according to General Procedure F employing methyl 3-(4-methyl-1-(tetrahydro-2H-pyran-2-yl)-1H-pyrazol-5-yl)isonicotinate (122 mg, 0.404 mmol). The resulting mixture was diluted with water (5 mL). The aqueous layer was extracted with EtOAc (3×8 mL). The pH of aqueous solution was adjusted to 5 with HCl (1 M). The aqueous layer was extracted with EtOAc (20 mL). The combined organic extracts were concentrated under reduced pressure to afford the title compound which was taken forward crude without further purification.

Step 3: Preparation of N-(5-((4-chlorobenzyl)oxy)-1,3,4-thiadiazol-2-yl)-3-(4-methyl-1-(tetrahydro-2H-pyran-2-yl)-1H-pyrazol-5-yl)isonicotinamide

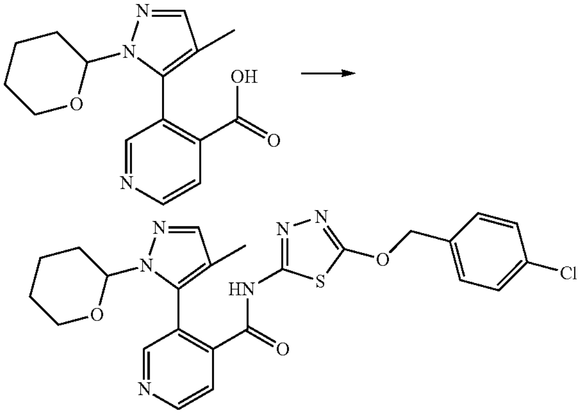

The title compound was prepared according to General Procedure A employing 3-(4-methyl-1-(tetrahydro-2H-pyran-2-yl)-1H-pyrazol-5-yl)isonicotinic acid (120 mg, 0.417 mmol), and 5-[(4-chlorophenyl)methoxy]-1,3,4-thiadiazol-2-amine (Intermediate B) (100 mg, 0.417 mmol). The resulting solution was stirred for 2 hours at room temperature. The mixture was diluted with water (5 mL) and extracted with EtOAc (3×5 mL). The combined organic extracts were concentrated under reduced pressure. The residue was purified using silica gel chromatography (eluent: 0-100% EtOAc hexanes) to afford the title compound (108 mg, 50% yield) as a yellow oil.

Step 4: Preparation of N-(5-((4-chlorobenzyl)oxy)-1,3,4-thiadiazol-2-yl)-3-(4-methyl-1H-pyrazol-5-yl) isonicotinamide

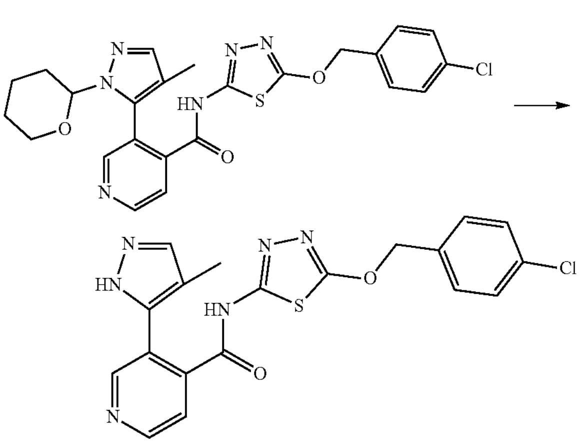

A reaction vial was charged with N-(5-((4-chlorobenzyl) oxy)-1,3,4-thiadiazol-2-yl)-3-(4-methyl-1-(tetrahydro-2H-pyran-2-yl)-1H-pyrazol-5-yl)isonicotinamide (108 mg, 211 mmol), TFA (0.048 mL, 0.634 mmol) and DCM (1 mL) the mixture was stirred for 1 hour at room temperature. The mixture was concentrated under reduced pressure. The residue was purified via reverse phase HPLC (C18 column, 15%-50% MeCN in water) to afford the title compound as a white powder (2 mg, 2% yield). m/z 427 [M+H]+

Example 119

Synthesis of N-(5-((4-chlorobenzyl)oxy)-1,3,4-thiadiazol-2-yl)-3-(1H-indazol-4-yl)isonicotinamide

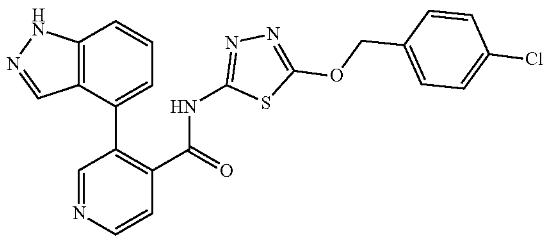 [SMILES: O=C(Nc1nnc(OCc2ccc(Cl)cc2)s1)c1ccncc1-c1cccc2[nH]ncc12]

Step 1: Preparation of methyl 3-(1H-indazol-4-yl)isonicotinate

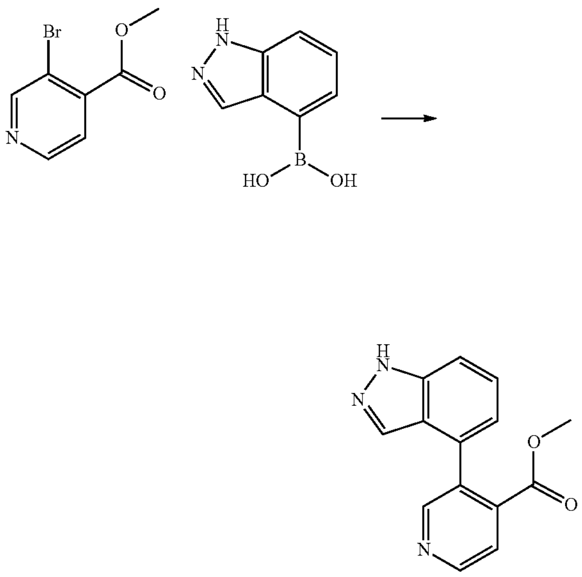

A reaction vial under an atmosphere of nitrogen was charged with methyl 3-bromoisonicotinate (190 mg, 0.879 mmol), 1,4-dioxane (6.9 mL), (1H-indazol-4-yl)boronic acid (170 mg, 1.05 mmol), $K_2CO_3$ (243 mg, 1.75 mmol), [1,1'-bis(diphenylphosphino)ferrocene]dichloropalladium (II) (97 mg, 0.131 mmol). The resulting solution was stirred overnight at 85° C. The mixture was diluted with water (10 mL). The aqueous layer was extracted with EtOAc (3×10 mL). The combined organic extracts were concentrated under reduced pressure. The residue was purified by silica gel column chromatography (eluent: 0-100% EtOAc hexanes) to afford the title compound (90 mg, 40% yield) as a white solid.

Step 2: Preparation of 3-(1H-indazol-4-yl)isonicotinic acid

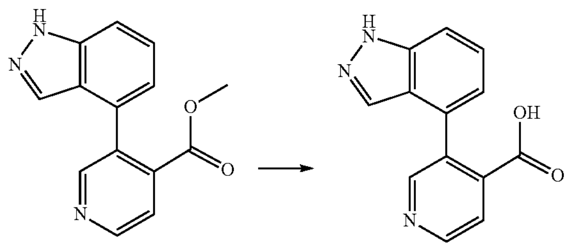 [SMILES: COC(=O)c1ccncc1-c1cccc2[nH]ncc12 ; O=C(O)c1ccncc1-c1cccc2[nH]ncc12]

The title compound was prepared according to General Procedure F employing methyl 3-(1H-indazol-4-yl)isonicotinate (90 mg, 0.355 mmol). The resulting mixture was diluted with water (5 mL). The aqueous layer was extracted with EtOAc (3×8 mL). The pH of aqueous solution was adjusted to 5 with HCl (1 M). The aqueous layer was extracted with EtOAc (20 mL). The combined organic extracts were concentrated under reduced pressure to afford the title compound which was taken forward crude without further purification.

Step 3: Preparation of N-(5-((4-chlorobenzyl)oxy)-1,3,4-thiadiazol-2-yl)-3-(1H-indazol-4-yl)isonicotinamide

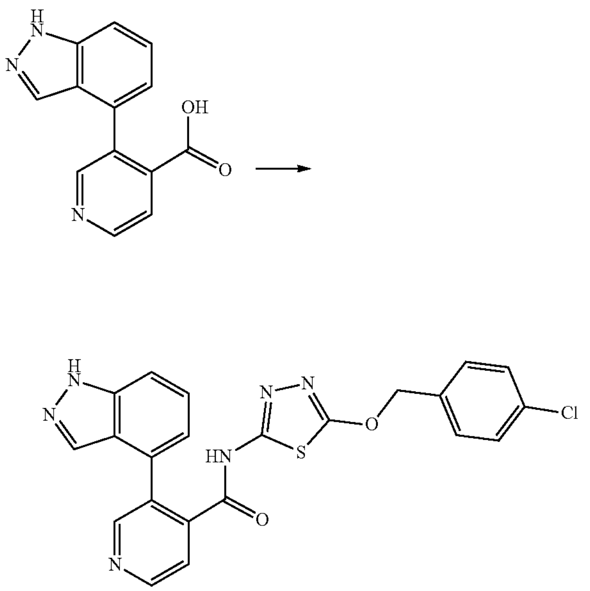

The title compound was prepared according to General Procedure A employing 3-(1H-indazol-4-yl)isonicotinic acid (85 mg, 0.355 mmol), and 5-[(4-chlorophenyl)methoxy]-1,3,4-thiadiazol-2-amine (Intermediate B) (85 mg, 0.355 mmol). The mixture was diluted with water (5 mL) and extracted with EtOAc (3×5 mL). The combined organic extracts were concentrated under reduced pressure. The residue was purified using silica gel chromatography (eluent. 0%-100% EtOAc hexanes) to afford the title compound (1 mg, 1% yield) as a clear oil. m/z 463 [M+H]+

Example 120

Synthesis of N-(5-((4-chlorobenzyl)oxy)-1,3,4-thiadiazol-2-yl)-3-(3-oxo-3,4-dihydro-2H-benzo[b][1,4]oxazin-8-yl)isonicotinamide

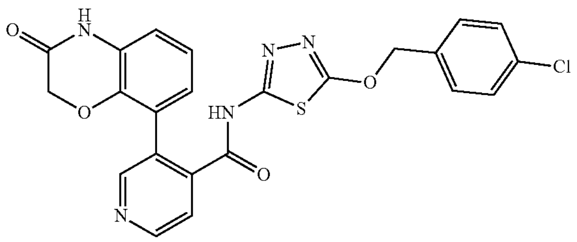 [SMILES: O=C1COc2c(cccc2-c2cnccc2C(=O)Nc2nnc(OCc3ccc(Cl)cc3)s2)N1]

Step 1: Preparation of 8-(4,4,5,5-tetramethyl-1,3,2-dioxaborolan-2-yl)-2H-benzo[b][1,4]oxazin-3(4H)-one

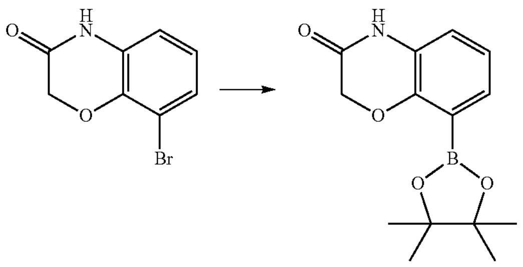 [SMILES: O=C1COc2c(Br)cccc2N1 ; CC1(C)OB(c2cccc3c2OCC(=O)N3)OC1(C)C]

A round bottom flask under an atmosphere of nitrogen was charged with (500 mg, 2.19 mmol), Bis(pinacolato) diboron (1.11 mg, 4.38 mmol), [1,1'-bis(diphenylphosphino) ferrocene]dichloropalladium(II) DCM (181 mg, 0.219 mmol), NaOAc (645 mg, 6.57 mmol) and 1,4-dioxane (11 mL). The mixture was sealed under nitrogen and heated to 100° C. for 2 h. The mixture was diluted with water (5 mL), extracted with EtOAc (3×5 mL), dried over $Na_2SO_4$. The combined organic extracts were concentrated under reduced pressure. The residue was purified via silica gel column chromatography (eluent: 0%-100% EtOAc in hexanes) to afford the title compound (536 mg, 88% yield) as a yellow oil.

Step 2: Preparation of methyl 3-(3-oxo-3,4-dihydro-2H-benzo[b][1,4]oxazin-8-yl)isonicotinate

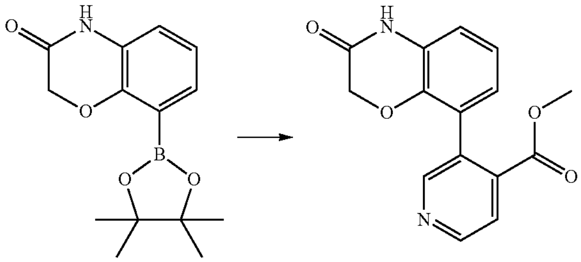 [SMILES: CC1(C)OB(c2cccc3c2OCC(=O)N3)OC1(C)C ; COC(=O)c1ccncc1-c1cccc2c1OCC(=O)N2]

A reaction vial under an atmosphere of nitrogen was charged with methyl 3-bromoisonicotinate (274 mg, 1.27 mmol), 1,4-dioxane (6.4 mL), 8-(4,4,5,5-tetramethyl-1,3,2-dioxaborolan-2-yl)-2H-benzo[b][1,4]oxazin-3(4H)-one (350 mg, 1.27 mmol), $K_2CO_3$ (351 mg, 2.54 mmol), [1,1'-bis(diphenylphosphino)ferrocene]dichloropalladium(II) (141 mg, 0.190 mmol). The resulting solution was stirred overnight at 85° C. The mixture was diluted with water (10 mL). The aqueous layer was extracted with EtOAc (3×10 mL). The combined organic extracts were concentrated under reduced pressure. The residue was purified by silica gel column chromatography (eluent: 0-100% EtOAc hexanes) to afford the title compound (176 mg, 48% yield) as a yellow oil.

Step 3: 3-(3-oxo-3,4-dihydro-2H-benzo[b][1,4]oxazin-8-yl)isonicotinic acid

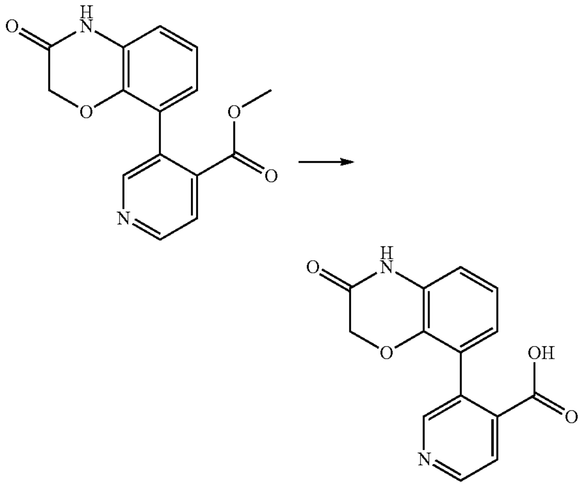

The title compound was prepared according to General Procedure F employing methyl 3-(3-oxo-3,4-dihydro-2H-benzo[b][1,4]oxazin-8-yl)isonicotinate (88 mg, 0.309 mmol). The resulting mixture was diluted with water (5 mL). The aqueous layer was extracted with EtOAc (3×8 mL). The pH of aqueous solution was adjusted to 5 with HCl (1 M). The aqueous layer was extracted with EtOAc (20 mL). The combined organic extracts were concentrated under reduced pressure to afford the title compound which was taken forward crude without further purification.

Step 4: Preparation of N-(5-((4-chlorobenzyl)oxy)-1,3,4-thiadiazol-2-yl)-3-(3-oxo-3,4-dihydro-2H-benzo[b][1,4]oxazin-8-yl)isonicotinamide

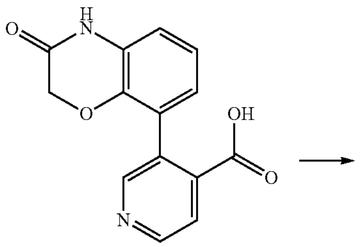

-continued

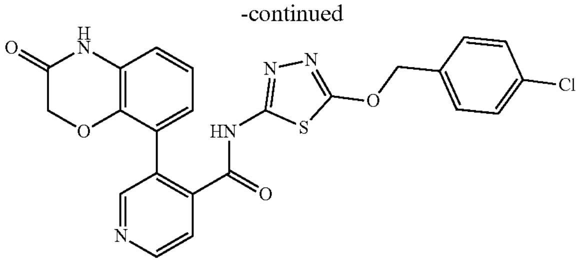

The title compound was prepared according to General Procedure A employing 3-(3-oxo-3,4-dihydro-2H-benzo[b][1,4]oxazin-8-yl)isonicotinic acid (83 mg, 0.307 mmol), and 5-[(4-chlorophenyl)methoxy]-1,3,4-thiadiazol-2-amine (Intermediate B) (74 mg, 0.307 mmol. The mixture was diluted with water (5 mL) and extracted with EtOAc (3×5 mL). The combined organic extracts were concentrated under reduced pressure. The residue was purified using silica gel chromatography (eluent: 0%-100% EtOAc hexanes) to afford the title compound (15 mg, 10% yield) as a white solid. $^1H$ NMR (400 MHz, DMSO-$d_6$) δ 13.05 (s, 1H), 10.82 (s, 1H), 8.74 (d, 1H), 8.66 (s, 1H), 7.69 (d, 1H), 7.58-7.42 (m, 4H), 7.10-6.89 (m, 3H), 5.48 (s, 2H), 4.26 (s, 2H). m/z 494 $[M+H]^+$

Example 121

Synthesis of N-(5-((4-chlorobenzyl)oxy)-1,3,4-thiadiazol-2-yl)-3-(2,2-difluorobenzo[d][1,3]dioxol-4-yl)isonicotinamide

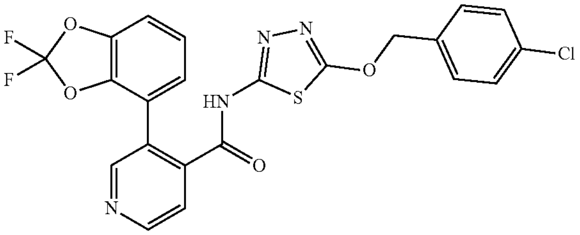 [SMILES: O=C(Nc1nnc(OCc2ccc(Cl)cc2)s1)c1ccncc1-c1cccc2c1OC(F)(F)O2]

The title compound was prepared using General Procedures E, F and A employing methyl 3-bromoisonicotinate and (2,2-difluorobenzo[d][1,3]dioxol-4-yl)boronic acid in General procedure E and 5-((4-chlorobenzyl)oxy)-1,3,4-thiadiazol-2-amine (Intermediate B) in General procedures A. $^1H$ NMR (400 MHz, DMSO-$d_6$) δ 13.24 (s, 1H), 8.86-8.83 (m, 2H), 7.79 (d, 1H), 7.59-7.50 (m, 2H), 7.50-7.46 (m, 3H), 7.35-7.30 (m, 2H), 5.49 (s, 2H). m/z 503 $[M+H]^+$

Example 122

Synthesis of N-(5-((4-chlorobenzyl)oxy)-1,3,4-thiadiazol-2-yl)-1-methyl-6-oxo-1,6-dihydro-[3,4'-bipyridine]-3'-carboxamide

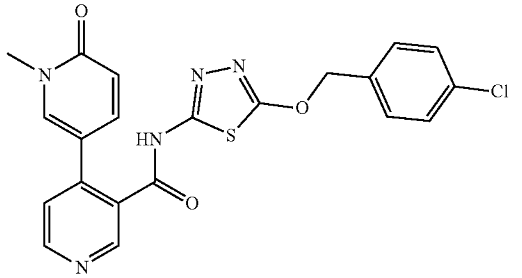 [SMILES: Cn1cc(-c2ccncc2C(=O)Nc2nnc(OCc3ccc(Cl)cc3)s2)ccc1=O]

The title compound was prepared using General Procedures E, F and A. Methyl 4-chloronicotinate and 1-methyl-5-(4,4,5,5-tetramethyl-1,3,2-dioxaborolan-2-yl)pyridin-2(1H)-one were employed in General Procedure E and [1,1'-bis(diphenylphosphino)ferrocene]dichloropalladium(II) was replaced with $Pd(PPh_3)_4$ in General Procedure E. For General Procedure A, 5-((4-chlorobenzyl)oxy)-1,3,4-thiadiazol-2-amine (Intermediate B) was used. m/z 454 $[M+H]^+$

Example 123

Synthesis of N-(5-((4-chlorobenzyl)oxy)-1,3,4-thiadiazol-2-yl)-3-(5-cyano-2-methoxyphenyl)isonicotinamide

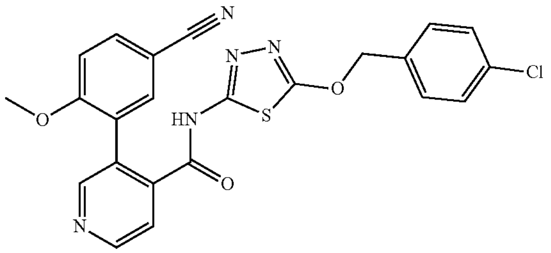 [SMILES: COc1ccc(C#N)cc1-c1cnccc1C(=O)Nc1nnc(OCc2ccc(Cl)cc2)s1]

The title compound was prepared using General Procedures E, F and A. Methyl 3-bromoisonicotinate and (5-cyano-2-methoxyphenyl)boronic acid were employed in General Procedures E. For General Procedure F, NaOH was replaced with LiOH. For General Procedure A, 5-((4-chlorobenzyl)oxy)-1,3,4-thiadiazol-2-amine (Intermediate B) was used. $^1H$ NMR (400 MHz, DMSO-$d_6$) δ 12.95 (s, 1H), 8.78 (s, 1H), 8.68 (s, 1H), 7.89 (s, 2H), 7.70 (s, 1H), 7.62-7.44 (m, 4H), 7.18 (d, 1H), 5.48 (s, 2H), 3.59 (d, 3H). m/z 478 $[M+H]^+$

Example 124

Synthesis of N-(5-((4-chlorobenzyl)oxy)-1,3,4-thiadiazol-2-yl)-3-(2-fluoro-6-methoxyphenyl)isonicotinamide

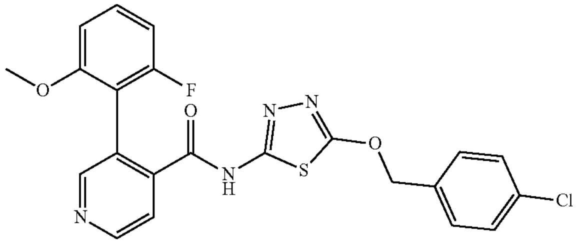 [SMILES: COc1cccc(F)c1-c1cnccc1C(=O)Nc1nnc(OCc2ccc(Cl)cc2)s1]

The title compound was prepared using General Procedures E, F and A. Methyl 3-bromoisonicotinate and 2-fluoro-6-methoxyphenylboronic acid were employed in General Procedures E and [1,1'-bis(diphenylphosphino)ferrocene]dichloropalladium(II) was replaced with [1,1'-bis(diphenylphosphino)ferrocene]dichloropalladium(II), complex with dichloromethane. For General Procedure F, NaOH was replaced with LiOH. For General Procedure A, 5-((4-chlorobenzyl)oxy)-1,3,4-thiadiazol-2-amine (Intermediate B) was used. $^1$H NMR (400 MHz, DMSO-$d_6$) δ 13.03 (s, 1H), 8.76 (d, 1H), 8.63 (s, 1H), 7.74 (s, 1H), 7.66-7.46 (m, 4H), 7.41 (q, 1H), 7.06-6.82 (m, 2H), 5.48 (s, 2H), 3.58 (d, 3H). m/z 471 $[M+H]^+$

Example 125

Synthesis of 3-(2-chloro-6-methoxyphenyl)-N-(5-((4-chlorobenzyl)oxy)-1,3,4-thiadiazol-2-yl)isonicotinamide

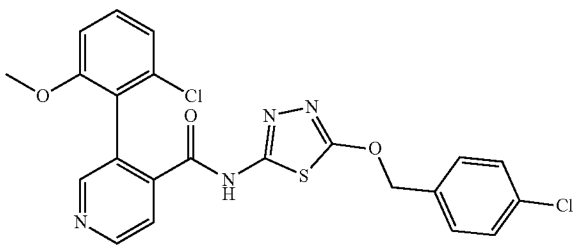 [SMILES: COc1cccc(Cl)c1-c1cnccc1C(=O)Nc1nnc(OCc2ccc(Cl)cc2)s1]

The title compound was prepared using General Procedures E, F and A. Methyl 3-bromoisonicotinate and 2-chloro-6-methoxyphenylboronic acid were employed in General Procedures E and [1,1'-bis(diphenylphosphino)ferrocene]dichloropalladium(II) was replaced with [1,1'-bis(diphenylphosphino)ferrocene]dichloropalladium(II), complex with dichloromethane. For General Procedure F, NaOH was replaced with LiOH. For General Procedure A, 5-((4-chlorobenzyl)oxy)-1,3,4-thiadiazol-2-amine (Intermediate B) was used. $^1$H NMR (400 MHz, DMSO-$d_6$) δ 13.04 (s, 1H), 8.82-8.67 (m, 1H), 8.54 (s, 1H), 7.76 (d, 1H), 7.57-7.43 (m, 4H), 7.42-7.32 (m, 1H), 7.14 (d, 1H), 7.03 (d, 1H), 5.46 (s, 2H), 3.58 (d, 3H). m/z 487 $[M+H]^+$

Example 126

Synthesis of N-(5-((4-chlorobenzyl)oxy)-1,3,4-thiadiazol-2-yl)-3-(2-cyanophenyl)isonicotinamide

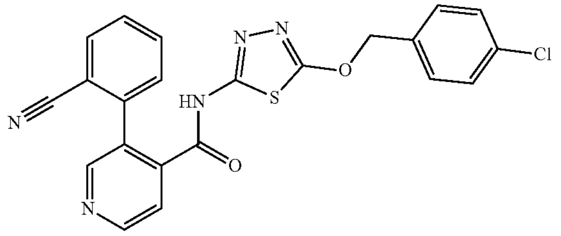 [SMILES: N#Cc1ccccc1-c1cnccc1C(=O)Nc1nnc(OCc2ccc(Cl)cc2)s1]

The title compound was prepared using General Procedures E, F and A. Methyl 3-bromoisonicotinate and 2-cyanophenylboronic acid were employed in General Procedures E and [1,1'-bis(diphenylphosphino)ferrocene]dichloropalladium(II) was replaced with [1,1'-bis(diphenylphosphino)ferrocene]dichloropalladium(II), complex with dichloromethane. For General Procedure F, NaOH was replaced with LiOH. For General Procedure A, 5-((4-chlorobenzyl)oxy)-1,3,4-thiadiazol-2-amine (Intermediate B) was used. $^1$H NMR (400 MHz, DMSO-$d_6$) δ 13.28 (s, 1H), 8.98-8.83 (m, 1H), 8.76 (s, 1H), 7.96 (d, 1H), 7.86 (d, 1H), 7.76 (t, 1H), 7.62 (t, 1H), 7.56-7.45 (m, 5H), 5.47 (d, 2H). m/z 448 $[M+H]^+$

Example 127

Synthesis of N-(5-((4-chlorobenzyl)oxy)-1,3,4-thiadiazol-2-yl)-3-(4-cyano-2-methoxyphenyl)isonicotinamide

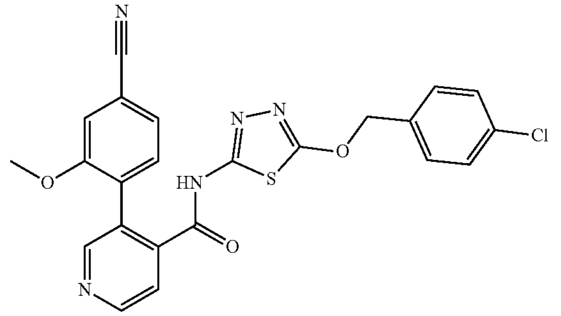 [SMILES: COc1cc(C#N)ccc1-c1cnccc1C(=O)Nc1nnc(OCc2ccc(Cl)cc2)s1]

The title compound was prepared using General Procedures E, F and A. Methyl 3-bromoisonicotinate and 4-cyano-2-methoxycyanophenylboronic acid were employed in General Procedures E and [1,1'-bis(diphenylphosphino)ferrocene]dichloropalladium(II) was replaced with [1,1'-bis(diphenylphosphino)ferrocene]dichloropalladium(II), complex with dichloromethane. For General Procedure F, NaOH was replaced with LiOH. For General Procedure A, 5-((4-chlorobenzyl)oxy)-1,3,4-thiadiazol-2-amine (Intermediate B) was used. $^1$H NMR (400 MHz, DMSO-$d_6$) δ 13.00 (s, 1H), 8.79 (d, 1H), 8.64 (d, 1H), 7.69 (t, 2H), 7.62-7.43 (m, 6H), 5.48 (s, 2H), 3.57 (s, 3H). m/z 478 $[M+H]^+$ Example 128

Synthesis of N-(5-((4-chlorobenzyl)oxy)-1,3,4-thiadiazol-2-yl)-4-(2,6-dimethoxyphenyl)nicotinamide

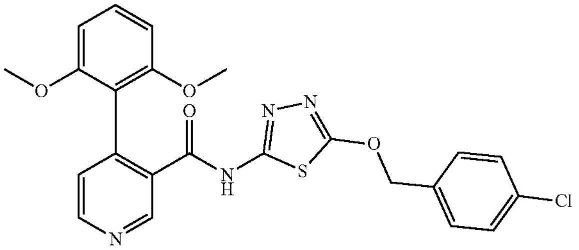 [SMILES: COc1cccc(OC)c1-c1ccncc1C(=O)Nc1nnc(OCc2ccc(Cl)cc2)s1]

The title compound was prepared using General Procedures E and A. 4-bromonicotinic acid and 2,6-dimethoxyphenylboronic acid were employed in General Procedures E and [1,1'-bis(diphenylphosphino)ferrocene]dichloropalladium(II) was replaced with $Pd(PPh_3)_4$. For General Procedure A, 5-((4-chlorobenzyl)oxy)-1,3,4-thiadiazol-2-amine (Intermediate B) was used and HATU was replaced with propylphosphonic anhydride. m/z 483 $[M+H]^+$.

Example 129

Synthesis of N-(5-((4-chlorobenzyl)oxy)-1,3,4-thiadiazol-2-yl)-2-methoxy-[3,4'-bipyridine]-3'-carboxamide

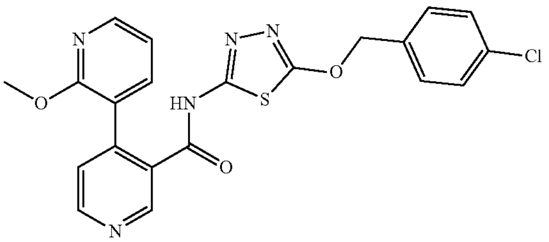

The title compound was prepared using General Procedures E and A. 4-bromonicotinic acid and 2-methoxypyridine-3-boronic acid were employed in General Procedures E and [1,1'-bis(diphenylphosphino)ferrocene]dichloropalladium(II) was replaced with $Pd(PPh_3)_4$. For General Procedure A, 5-((4-chlorobenzyl)oxy)-1,3,4-thiadiazol-2-amine (Intermediate B) was used and HATU was replaced with propylphosphonic anhydride. m/z 454 $[M+H]^+$.

Example 130

Synthesis N-(5-((4-chlorobenzyl)oxy)-1,3,4-thiadiazol-2-yl)-4-(2-(trifluoromethoxy)phenyl)nicotinamide

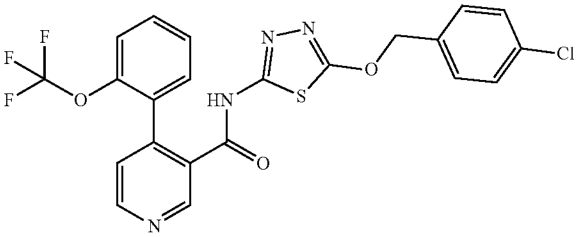 [SMILES: O=C(Nc1nnc(OCc2ccc(Cl)cc2)s1)c1cnccc1-c1ccccc1OC(F)(F)F]

The title compound was prepared using General Procedures E, F and A. Methyl 4-chloronicotinate and (2-(trifluoromethoxy)phenyl)boronic acid were employed in General Procedures E and [1,1'-bis(diphenylphosphino)ferrocene]dichloropalladium(II) was replaced with [1,1'-bis(diphenylphosphino)ferrocene]dichloropalladium(II), complex with dichloromethane. For General Procedure F, NaOH was replaced with LiOH. For General Procedure A, 5-((4-chlorobenzyl)oxy)-1,3,4-thiadiazol-2-amine (Intermediate B) was used. m/z 507 $[M+H]^+$.

Example 131

Synthesis of N-(5-((4-chlorobenzyl)oxy)-1,3,4-thiadiazol-2-yl)-3'-methoxy-[3,4'-bipyridine]-4-carboxamide

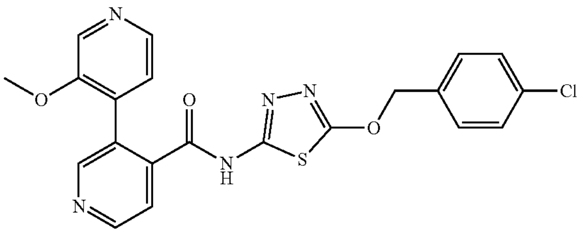 [SMILES: COc1cnccc1-c1cnccc1C(=O)Nc1nnc(OCc2ccc(Cl)cc2)s1]

The title compound was prepared using General Procedures E, F and A. methyl 3-bromoisonicotinate and (3-methoxypyridin-4-yl)boronic acid were employed in General Procedures E. [1,1'-bis(diphenylphosphino)ferrocene]dichloropalladium(II) was replaced with [1,1'-bis(diphenylphosphino)ferrocene]dichloropalladium(II), complex with dichloromethane in General procedure E. For General Procedure F, NaOH was employed instead of LiOH. For General Procedure A, 5-((4-chlorobenzyl)oxy)-1,3,4-thiadiazol-2-amine (Intermediate B) was used. m/z 454 $[M+H]^+$.

Example 132

Synthesis of N-(5-((4-chlorobenzyl)oxy)-1,3,4-thiadiazol-2-yl)-4-(2-(trifluoromethyl)phenyl)nicotinamide

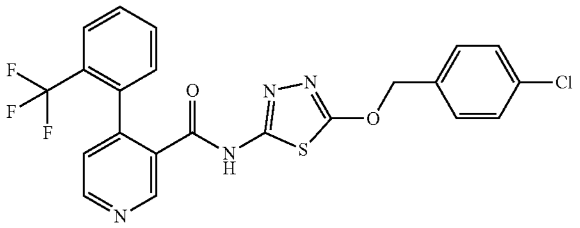 [SMILES: O=C(Nc1nnc(OCc2ccc(Cl)cc2)s1)c1cnccc1-c1ccccc1C(F)(F)F]

The title compound was prepared using General Procedures E and A. 4-bromonicotinic acid and 2-(trifluoromethyl)phenyl boronic acid were employed in General Procedures E [1,1'-bis(diphenylphosphino)ferrocene] dichloropalladium(II) was replaced with $Pd(PPh_3)_4$ in General procedure E. For General Procedure A 5-((4-chlorobenzyl)oxy)-1,3,4-thiadiazol-2-amine (Intermediate B) was used. m/z 491 $[M+H]^+$.

Example 133

Synthesis of N-(5-((4-chlorobenzyl)oxy)-1,3,4-thiadiazol-2-yl)-4'-methoxy-[3,3'-bipyridine]-4-carboxamide

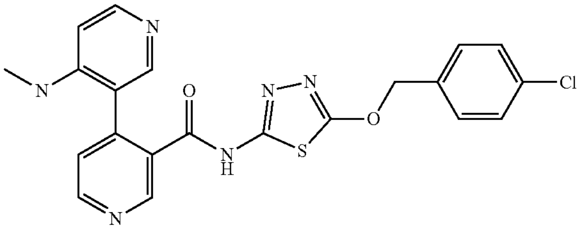 [SMILES: CNc1ccncc1-c1ccncc1C(=O)Nc1nnc(OCc2ccc(Cl)cc2)s1]

The title compound was prepared using General Procedures E, F and A methyl 3-bromoisonicotinate and (4-methoxypyridin-3-yl)boronic acid were employed in General Procedures E. [1,1'-bis(diphenylphosphino)ferrocene]dichloropalladium(II) was replaced with $Pd(PPh3)_4$ in General procedure E. For General Procedure A 5-((4-chlorobenzyl)oxy)-1,3,4-thiadiazol-2-amine (Intermediate B) was used. m/z 454 $[M+H]^+$.

Example 134

Synthesis of N-[5-[(4-chlorophenyl)methoxy]-1,3,4-thiadiazol-2-yl]-3-[2-(oxetan-3-yloxy)phenyl]pyridine-4-carboxamide

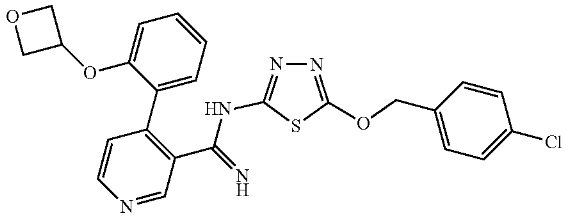 [SMILES: N=C(Nc1nnc(OCc2ccc(Cl)cc2)s1)c1cnccc1-c1ccccc1OC1COC1]

The title compound was prepared using General Procedures E, F and A methyl 3-bromopyridine-4-carboxylate and 4,4,5,5-tetramethyl-2-[2-(oxetan-3-yloxy)phenyl]-1,3,2-dioxaborolane were employed in General Procedures E. For General Procedure A, 5-((4-chlorobenzyl)oxy)-1,3,4-thiadiazol-2-amine (Intermediate B) was used and HATU was replaced with T3P (50% in EtOAc) solution. $^1H$ NMR (300 MHz, DMSO-$d_6$): δ 12.99 (s, 1H), 8.75 (d, 1H), 8.61 (s, 1H), 7.69 (d, 1H), 7.54-7.46 (m, 4H), 7.42-7.35 (m, 1H), 7.32-7.29 (m, 1H), 7.13-7.08 (m, 1H), 6.50 (d, 1H), 5.51 (s, 2H), 5.02-4.95 (m, 1H), 4.66 (t, 2H), 4.35 (t, 2H) ppm m/z 495 $[M+H]^+$ Example 135

Synthesis of N-[5-[(4-chlorophenyl)methoxy]-1,3,4-thiadiazol-2-yl]-3-(2-ethylphenyl)pyridine-4-carboxamide

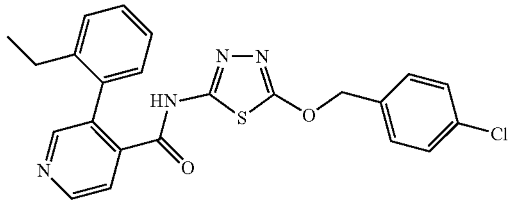 [SMILES: CCc1ccccc1-c1cnccc1C(=O)Nc1nnc(OCc2ccc(Cl)cc2)s1]

The title compound was prepared using General Procedures E, F and A. For General Procedure E, methyl 3-bromopyridine-4-carboxylate and 2-ethylphenylboronic acid were employed. For General procedures A, 5-((4-chlorobenzyl)oxy)-1,3,4-thiadiazol-2-amine (Intermediate B) was used and HATU was replaced with $T_3P$ solution (50% in EtOAc). $^1H$ NMR (400 MHz, DMSO-$d_6$): δ 12.97 (s, 1H), 8.74 (d, 1H), 8.52 (s, 1H), 7.71 (d, 1H), 7.51-7.45 (m, 4H), 7.33-7.28 (m, 2H), 7.19-7.17 (m, 1H), 7.12 (d, 11H), 5.44 (s, 2H), 2.42-2.33 (m, 2H), 0.99 (t, 3H). m/z 451 $[M+H]^+$.

Example 136

Synthesis of N-[5-[(4-chlorophenyl)methoxy]-1,3,4-thiadiazol-2-yl]-3-(3,4-dihydro-2H-1,4-benzoxazin-8-yl)pyridine-4-carboxamide

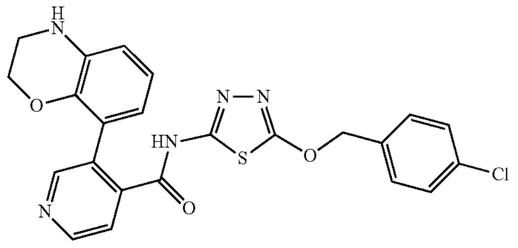 [SMILES: O=C(Nc1nnc(OCc2ccc(Cl)cc2)s1)c1ccncc1-c1cccc2c1OCCN2]

Step 1. Preparation of 8-(4,4,5,5-tetramethyl-1,3,2-dioxaborolan-2-yl)-3,4-dihydro-2H-1,4-benzoxazine

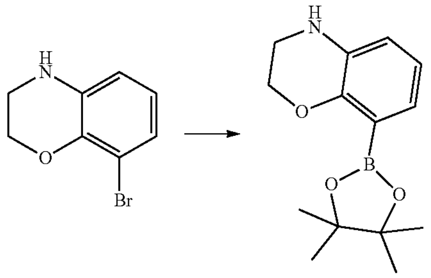 [SMILES: Brc1cccc2c1OCCN2 ; CC1(C)OB(c2cccc3c2OCCN3)OC1(C)C]

To a solution of 8-bromo-3,4-dihydro-2H-1,4-benzoxazine (94 mg, 4.4 mmol) in dioxane (10 mL) was added KOAc (867 mg, 8.8 mmol), bis(pinacolato)diboron (1.7 g, 6.6 mmol) and [1,1'-bis(diphenylphosphino)ferrocene]dichloropalladium(II) (323 mg, 0.44 mmol). The mixture was stirred for 2 h at 80° C. under nitrogen atmosphere. The mixture was diluted with water and extracted with EtOAc (3×). The combined organic layers were concentrated under reduced pressure. The residue was purified by silica gel column chromatography, eluted with 9% EtOAc in PE to afford the title compound (930 mg, 69% yield) as a yellow oil.

Step 2. Preparation of 3-(3,4-dihydro-2H-1,4-benzoxazin-8-yl)pyridine-4-carboxylic acid

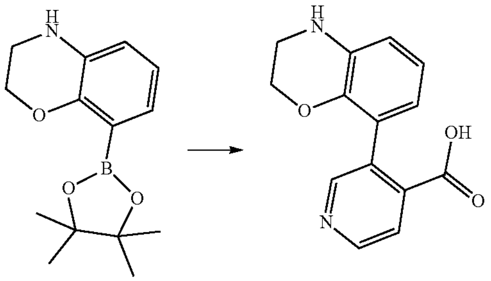 [SMILES: CC1(C)OB(c2cccc3c2OCCN3)OC1(C)C ; O=C(O)c1ccncc1-c1cccc2c1OCCN2]

To a solution of 8-(4,4,5,5-tetramethyl-1,3,2-dioxaborolan-2-yl)-3,4-dihydro-2H-1,4-benzoxazine (900 mg, 3.4 mmol) in dioxane (8 mL) and water (2 mL) was added $K_3PO_4$ (49 mg, 0.23 mmol), methyl 3-bromopyridine-4-carboxylate (745 mg, 3.4 mmol) and [1,1'-bis(diphenylphosphino)ferrocene]dichloropalladium(II) (252 mg, 0.35 mmol) at room temperature. The mixture was stirred for 4 h at 80° C. under nitrogen atmosphere. The mixture was diluted with water and extracted with EtOAc (3×). The residue was purified by silica gel column chromatography, eluted with 6% EtOAc in hexane to afford methyl 3-(3,4-dihydro-2H-benzo[b][1,4]oxazin-8-yl)isonicotinate as a yellow oil. The title compound was prepared following General Procedure F employing methyl 3-(3,4-dihydro-2H-benzo[b][1,4]oxazin-8-yl)isonicotinate.

Step 3. Preparation of 3-[4-[(9H-fluoren-9-ylmethoxy)carbonyl]-2,3-dihydro-1,4-benzoxazin-8-yl]pyridine-4-carboxylic acid

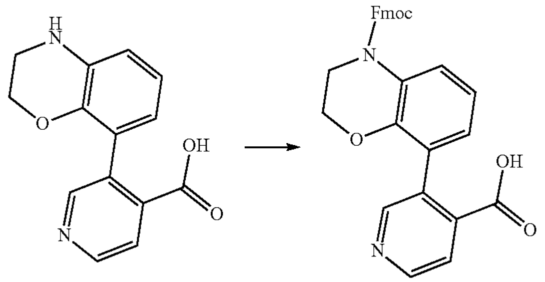

To a solution of 3-(3,4-dihydro-2H-1,4-benzoxazin-8-yl)pyridine-4-carboxylic acid (740 mg, 2.89 mmol) in water (2 mL) and dioxane (2 mL) was added $NaHCO_3$ (485 mg, 5.8 mmol) and 9-fluorenylmethyl chloroformate (1122 mg, 4.3 mmol) at room temperature. The mixture was stirred for 2 h at room temperature under hydrogen atmosphere. The reaction was diluted with water and acidified to pH 6 with HCl (2 M). The mixture was extracted with EtOAc (3×). The combined organic layers were concentrated under vacuum. The residue was purified by reverse phase chromatography (column, C18 silica gel; mobile phase, with 10-50% MeCN in water) to afford the title compound (180 mg, 13% yield) as an off-white solid.

Step 4. Preparation of (9H-fluoren-9-yl)methyl 8-(4-((5-((4-chlorobenzyl)oxy)-1,3,4-thiadiazol-2-yl)carbamoyl)pyridin-3-yl)-2,3-dihydro-4H-benzo[b][1,4]oxazine-4-carboxylate

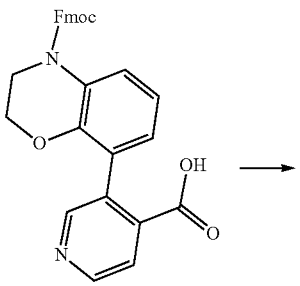

-continued

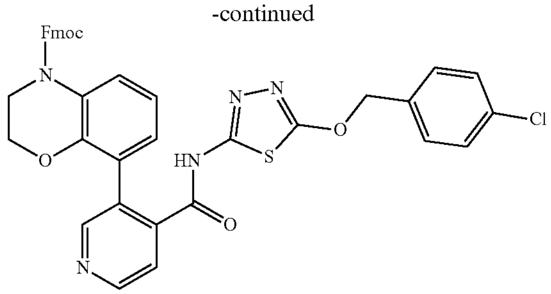

To a solution of 3-[4-[(9H-fluoren-9-ylmethoxy)carbonyl]-2,3-dihydro-1,4-benzoxazin-8-yl]pyridine-4-carboxylic acid (160 mg, 0.33 mmol) in DMF (2 mL) was added EDCI (96 mg, 0.50 mmol), HOBT (50 mg, 0.37 mmol), 5-((4-chlorobenzyl)oxy)-1,3,4-thiadiazol-2-amine (81 mg, 0.33 mmol, Intermediate B). The mixture was stirred for 1 h at rt. The mixture was diluted with water and extracted with EtOAc (3×). The mixture was concentrated under reduced pressure and the reside was triturated with MeOH to afford the title compound (180 mg, 77% yield) as a white solid.

Step 5. Preparation of N-[5-[(4-chlorophenyl) methoxy]-1,3,4-thiadiazol-2-yl]-3-(3,4-dihydro-2H-1,4-benzoxazin-8-yl)pyridine-4-carboxamide

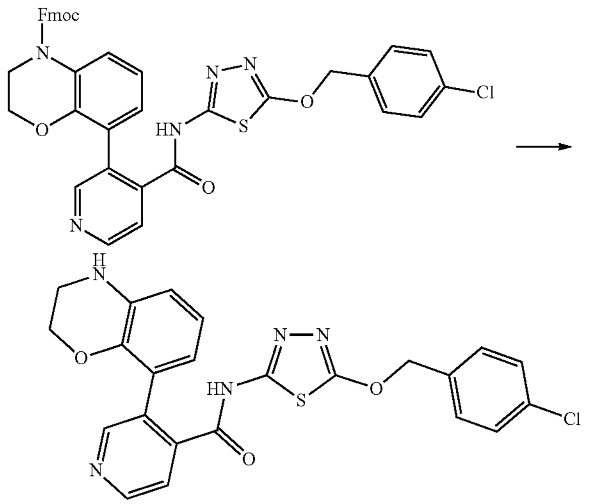

To a solution of 9H-fluoren-9-ylmethyl 8-[4-([5-[(4-chlorophenyl)methoxy]-1,3,4-thiadiazol-2-yl]carbamoyl)pyridin-3-yl]-2,3-dihydro-1,4-benzoxazine-4-carboxylate (170 mg, 0.24 mmol) in DCM (2 mL) was added piperidine (41 mg, 0.48 mmol) at room temperature. The mixture was stirred for 2 h at room temperature under nitrogen atmosphere. The mixture was diluted with DCM and washed with water (4×). The mixture was concentrated under vacuum. The residue was purified by Prep-TLC (DCM:MeOH, 20:1) to afford the title compound (24 mg, 21% yield) as an off-white solid. $^{1}$H NMR (400 MHz, DMSO-$d_6$): δ 2.07 (s, 1H), 3.13 (s, 3H), 3.80 (s, 2H), 5.48 (s, 2H), 5.82 (s, 1H), 6.54-6.59 (m, 2H), 6.74-6.78 (m, 1H), 8.58 (s, 1H), 8.67 (d, 4H), 12.85 (s, 1H). m/z 480 [M+H$^+$].

Example 137

Synthesis of N-[5-[(4-chlorophenyl)methoxy]-1,3,4-thiadiazol-2-yl]-2-(cyanomethyl)-5-(2-methoxyphenyl)pyridine-4-carboxamide

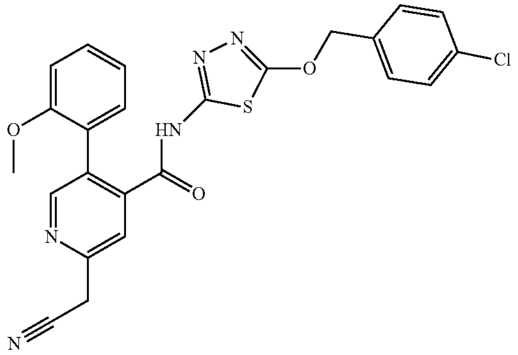 [SMILES: COc1ccccc1-c1cnc(CC#N)cc1C(=O)Nc1nnc(OCc2ccc(Cl)cc2)s1]

Step 1. Preparation of methyl 2-ethenyl-5-(2-methoxyphenyl)pyridine-4-carboxylate

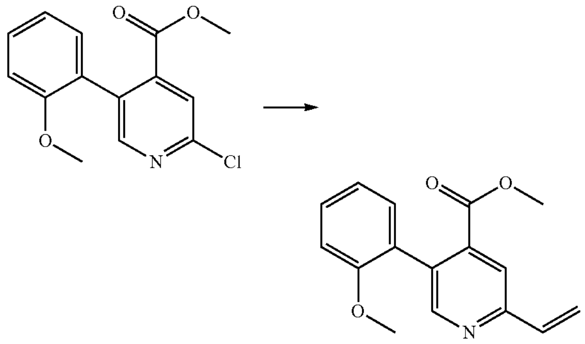

To a solution of methyl 2-chloro-5-(2-methoxyphenyl) pyridine-4-carboxylate (1.9 g, 6.8 mmol, Example 191. Step 1) and tributyl(ethenyl)stannane (3.3 g, 0.010 mmol) in DMF (20 mL) was added and $Pd(PPh_3)_4$ (0.79 g, 0.001 mmol) at room temperature under nitrogen atmosphere. The mixture was stirred overnight at 100° C. under nitrogen atmosphere. The mixture was diluted with water and extracted with EtOAc (2×). The residue was purified by silica gel column chromatography, eluted with 5% EtOAc in hexanes to afford the title compound (1.42 g) as a white solid.

Step 2. Preparation of 4-(methoxycarbonyl)-5-(2-methoxyphenyl)pyridine-2-carboxylic acid

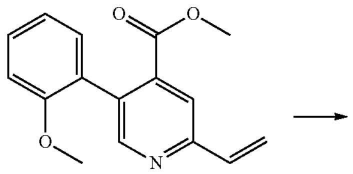

-continued

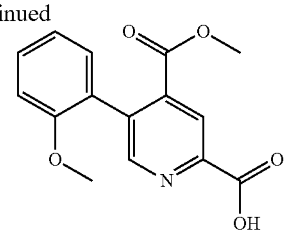

To a solution of methyl 2-ethenyl-5-(2-methoxyphenyl) pyridine-4-carboxylate (1.4 g, 5.2 mmol) in THF (20 mL) and water (4 mL) was added NMO (2.4 g, 20.8 mmol) and OsO4 (0.40 g, 1.6 mmol) at room temperature. The mixture was stirred for 2 h at rt. The mixture was diluted with water and extracted with EtOAc. The mixture was concentrated under vacuum. The residue was purified by reverse phase chromatography (column, C18 silica gel; mobile phase, with 0-100% MeCN in water) to afford the title compound (580 mg, 39% yield) as a colorless oil.

Step 3. Preparation of methyl 2-(hydroxymethyl)-5-(2-methoxyphenyl)pyridine-4-carboxylate

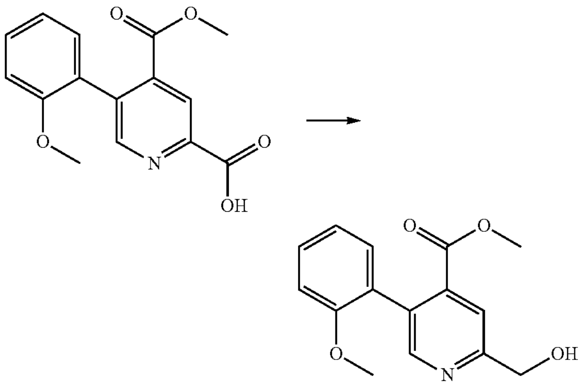

To a solution of 4-(methoxycarbonyl)-5-(2-methoxyphenyl)pyridine-2-carboxylic acid (540 mg, 1.9 mmol) in THF was added $BH_3$ (1 M in THF, 3.8 mL, 3.8 mmol) was dropwise at room temperature. The mixture was stirred overnight at 60° C. The mixture was diluted with water and extracted with EtOAc (2×). The mixture was concentrated under vacuum. The residue was purified by Prep-TLC (DCM:MeOH, 20:1) to afford the title compound (320 mg, 62% yield) as a white solid.

Step 4. Preparation of methyl 2-(chloromethyl)-5-(2-methoxyphenyl)pyridine-4-carboxylate

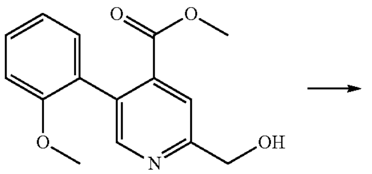

-continued

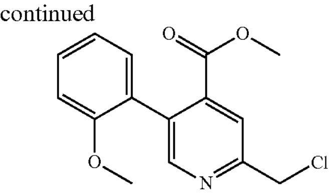

To a solution of methyl 2-(hydroxymethyl)-5-(2-methoxyphenyl)pyridine-4-carboxylate (310 mg, 1.1 mmol) in DCM was added $SOCl_2$ (675 mg, 5.7 mmol). The mixture was stirred for 2 h at room temperature. The mixture was quenched by the addition of $NaHCO_3$ (aq.). The layers were separated, and the aqueous layer was extracted with EtOAc (3×). The combined organic layers were concentrated under vacuum. The residue was purified by Prep-TLC (DCM: MeOH, 15:1) to afford the title compound (300 mg, 91% yield) as a yellow solid.

Step 5. Preparation of methyl 2-(cyanomethyl)-5-(2-methoxyphenyl)pyridine-4-carboxylate

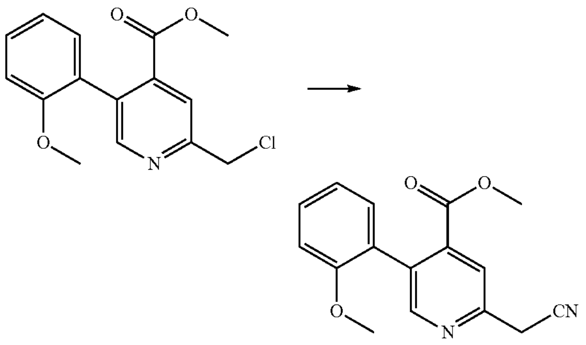

To a solution of methyl 2-(chloromethyl)-5-(2-methoxyphenyl)pyridine-4-carboxylate (240 mg, 0.82 mmol) in DMSO (5 mL) was added NaCN (81 mg, 1.6 mmol) at room temperature. The mixture was stirred overnight at 60° C. The mixture was diluted with water and extracted with EtOAc (2×). The combined organic layers were concentrated under vacuum. The residue was purified by Prep-TLC (DCM: MeOH, 20:1) to afford the title compound (190 mg, 82% yield) as a white solid.

Step 6. Preparation of 2-(cyanomethyl)-5-(2-methoxyphenyl)pyridine-4-carboxylic acid

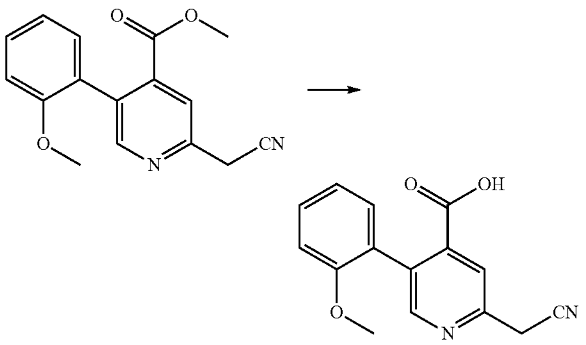

To a solution of methyl 2-(cyanomethyl)-5-(2-methoxyphenyl)pyridine-4-carboxylate (160 mg, 0.57 mmol) water (0.5 mL) and MeOH (2.00 mL) was added LiOH (47 mg, 1.1 mmol) at room temperature. The mixture was stirred for 1 h at 60° C. The solution was acidified to pH 5 with HCl (2 M). The mixture was concentrated under vacuum. The residue was purified by reverse phase chromatography (column, C18 silica gel; mobile phase, with 0-30% MeCN in water) to afford the title compound (65 mg, 43% yield) as a white solid.

Step 7. Preparation of N-[5-[(4-chlorophenyl) methoxy]-1,3,4-thiadiazol-2-yl]-2-(cyanomethyl)-5-(2-methoxyphenyl)pyridine-4-carboxamide

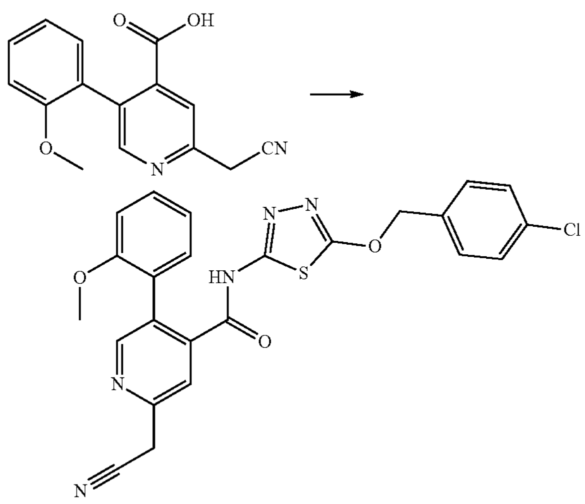

The title compound was prepared using General Procedure A employing 2-(cyanomethyl)-5-(2-methoxyphenyl) pyridine-4-carboxylic acid and 5-((4-chlorobenzyl)oxy)-1,3,4-thiadiazol-2-amine (Intermediate B). $^1H$ NMR (400 MHz, DMSO-$d_6$): δ 12.91 (s, 1H), 8.60 (s, 1H), 7.67 (s, 1H), 7.54-7.46 (m, 4H), 7.38 (d, 2H), 7.08 (d, 1H), 6.99 (d, 1H), 5.47 (s, 2H), 4.34 (s, 2H), 3.51 (s, 3H). m/z 492 [M+H$^+$].

Example 138

Synthesis of N-[5-[(4-chlorophenyl)methoxy]-1,3,4-thiadiazol-2-yl]-4-(2-methoxyphenyl)-6-methylpyridine-3-carboxamide

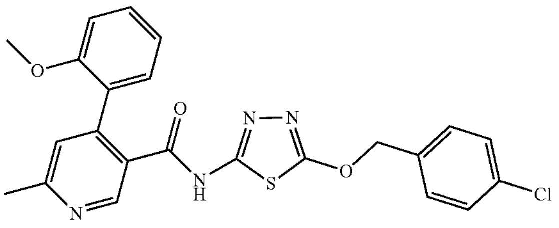 [SMILES: COc1ccccc1-c1cc(C)ncc1C(=O)Nc1nnc(OCc2ccc(Cl)cc2)s1]

The title compound was prepared using General Procedure A employing 4-(2-methoxyphenyl)-6-methylnicotinic acid (Example 113, Step 2) and 5-((4-chlorobenzyl)oxy)-1,3,4-thiadiazol-2-amine (Intermediate B). $^1H$ NMR (300 MHz, DMSO-$d_6$): δ 12.75 (s, 1H), 8.66 (s, 1H), 7.55-7.47 (m, 4H), 7.42-7.30 (m, 3H), 7.08 (t, 1H), 7.04-6.98 (m, 1H), 5.48 (s, 2H), 3.50 (s, 3H), 2.57 (s, 3H). m/z 467 [M+H$^+$].

Example 139

Synthesis of N-[5-[(4-chlorophenyl)methoxy]-1,3,4-thiadiazol-2-yl]-3-(4-methyl-2,3-dihydro-1,4-benzoxazin-8-yl)pyridine-4-carboxamide

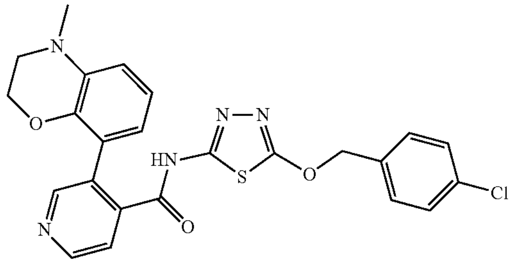 [SMILES: CN1CCOc2c(-c3cnccc3C(=O)Nc3nnc(OCc4ccc(Cl)cc4)s3)cccc21]

Step 1. Preparation of 8-bromo-4-methyl-2,3-dihydro-1,4-benzoxazine

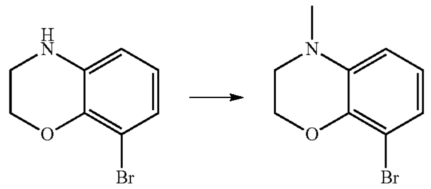

To a solution of 8-bromo-3,4-dihydro-2H-1,4-benzoxazine (900 mg, 4.2 mmol) in THF (10 ml) at 0° C. was added sodium hydride (60% dispersion in oil, 202 mg, 5.0 mmol). The mixture was stirred for 40 min at 0° C. Then MeI (656 mg, 4.63 mmol) was added. The mixture was stirred for 40 min and then warmed to rt and quenched with NH4Cl (aq.). The mixture was extracted with EtOAc (3×). The mixture was concentrated under vacuum. The residue was purified by silica gel column chromatography, eluted with 1% EtOAc in PE to afford the title compound (845 mg, 88% yield) as a light-yellow oil.

Step 2. Preparation of N-[5-[(4-chlorophenyl) methoxy]-1,3,4-thiadiazol-2-yl]-3-(4-methyl-2,3-dihydro-1,4-benzoxazin-8-yl)pyridine-4-carboxamide

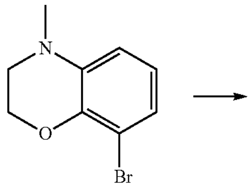

-continued

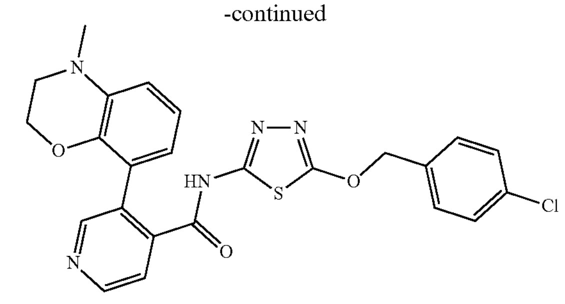

The title compound was prepared using similar procedure as Example 136, Steps 1, 2 and 4 replacing 8-bromo-3,4-dihydro-2H-1,4-benzoxazine with 8-bromo-4-methyl-2,3-dihydro-1,4-benzoxazine in Step 1. $^1$H NMR (300 MHz, DMSO-$d_6$): δ 2.80 (s, 3H), 3.07-3.17 (m, 2H), 3.86-3.94 (m, 2H), 5.48 (s, 2H), 6.64-6.74 (m, 2H), 6.85-6.90 (m, 1H), 7.47-7.60 (m, 5H), 8.59 (s, 1H), 8.68 (d, 1H), 12.86 (s, 1H). m/z 494 [M+H$^+$].

Example 140

Synthesis of N-[5-[(4-chlorophenyl)methoxy]-1,3,4-thiadiazol-2-yl]-3-(3,5-dimethyl-1H-pyrazol-4-yl)pyridine-4-carboxamide

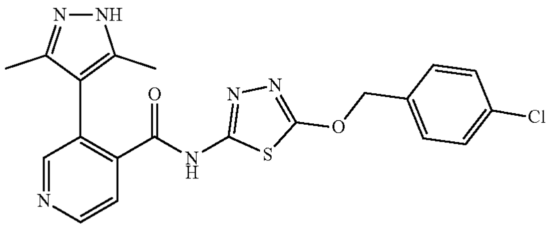 [SMILES: Cc1n[nH]c(C)c1-c1cnccc1C(=O)Nc1nnc(OCc2ccc(Cl)cc2)s1]

The title compound was prepared using General Procedure E, F and A. 3,5-dimethyl-4-(4,4,5,5-tetramethyl-1,3,2-dioxaborolan-2-yl)-1H-pyrazole and methyl 3-bromopyridine-4-carboxylate were employed for General Procedure E. For General Procedure A, 5-((4-chlorobenzyl)oxy)-1,3,4-thiadiazol-2-amine (Intermediate B) was used. $^1$H NMR (300 MHz; DMSO-$d_6$): δ12.82 (s, 1H), 12.32 (s, 1H), 8.66 (d, 1H), 8.53 (s, 1H), 7.64 (d, 1H), 7.54-7.47 (m, 4H), 5.48 (s, 2H), 2.01 (s, 6H). m/z 441 [M+H$^+$].

Example 141

Synthesis of N-(5-[[4-(1-cyanocyclopropyl)phenyl]methoxy]-1,3,4-thiadiazol-2-yl)-3-(2-methoxyphenyl)pyridine-4-carboxamide

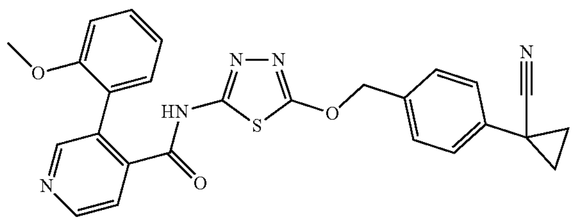 [SMILES: COc1ccccc1-c1cnccc1C(=O)Nc1nnc(OCc2ccc(C3(C#N)CC3)cc2)s1]

Step 1. Preparation of 1-[4-(hydroxymethyl)phenyl]cyclopropane-1-carbonitrile

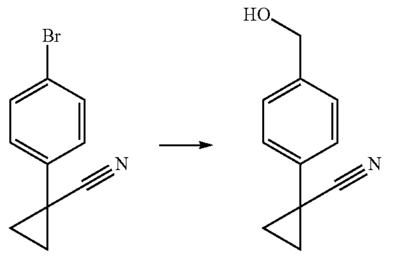 [SMILES: N#CC1(c2ccc(Br)cc2)CC1 ; N#CC1(c2ccc(CO)cc2)CC1]

To a solution of 1-(4-bromophenyl)cyclopropane-1-carbonitrile (1.0 g, 4.5 mmol), in DMF (10 mL) was added (tributylstannyl)methanol (2.2 g, 0.007 mmol) and Pd($PPh_3$). (0.52 g, 0.000 mmol) under nitrogen atmosphere. The solution was stirred overnight at 100° C. The mixture was diluted with water and extracted with EtOAc (3×). The mixture was concentrated under reduced pressure. The residue was purified by Prep-TLC (hexane:EtOAc, 3:1) to afford the title compound (150 mg, 17% yield) as an off-white oil.

Step 2. Preparation of 1-(4-[[(5-amino-1,3,4-thiadiazol-2-yl)oxy]methyl]phenyl) cyclopropane-1-carbonitrile

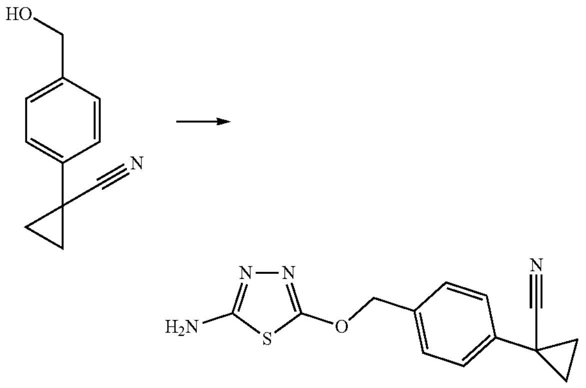

The title compound was prepared using similar procedures as the synthesis of Intermediate C, replacing (5-chloropyridin-2-yl)methanol with 1-[4-(hydroxymethyl)phenyl]cyclopropane-1-carbonitrile in Step 1.

Step 3. Preparation of N-(5-[[4-(1-cyanocyclopropyl)phenyl]methoxy]-1,3,4-thiadiazol-2-yl)-3-(2-methoxyphenyl)pyridine-4-carboxamide

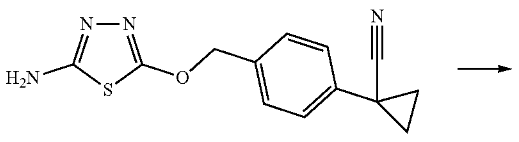

-continued

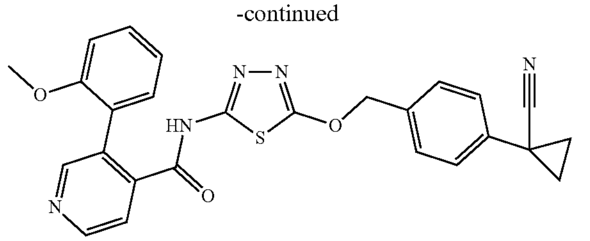

The title compound was prepared using General Procedure A employing 1-(4-[[(5-amino-1,3,4-thiadiazol-2-yl)oxy]methyl]phenyl) cyclopropane-1-carbonitrile and 3-(2-methoxyphenyl) pyridine-4-carboxylic acid (Intermediate H). $^{1}H$ NMR (300 MHz; DMSO-$d_6$): δ12.85 (s, 1H), 8.72-8.70 (d, 1H), 8.61 (s, 1H), 7.63 (d, 1H), 7.52 (d, 2H), 7.41-7.35 (m, 4H), 7.09-7.04 (m, 1H), 7.00-6.97 (m, 1H), 5.47 (s, 2H), 3.51 (s, 3H), 1.78 (t, 2H), 1.52 (t, 2H). m/z 484 [$M+H^+$].

Example 142

Synthesis of N-[5-[(4-chlorophenyl)methoxy]-1,3,4-thiadiazol-2-yl]-3-[5H,6H,7H-pyrazolo[1,5-a]pyrimidin-4-yl]pyridine-4-carboxamide

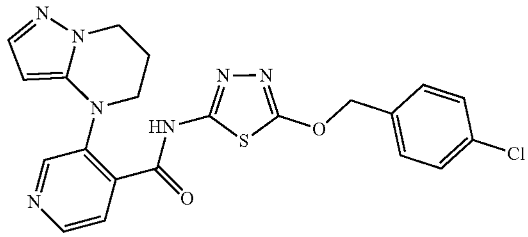 [SMILES: O=C(Nc1nnc(OCc2ccc(Cl)cc2)s1)c1ccncc1N1CCCn2nccc21]

Step 1. Preparation of methyl 3-[5H,6H,7H-pyrazolo[1,5-a]pyrimidin-4-yl]pyridine-4-carboxylate

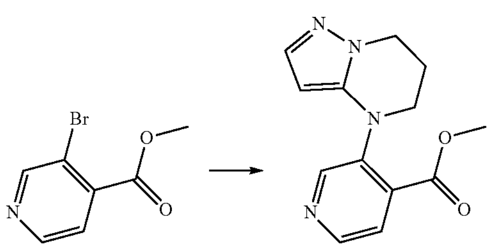 [SMILES: COC(=O)c1ccncc1Br ; COC(=O)c1ccncc1N1CCCn2nccc21]

Into a 50-mL 3-necked round-bottom flask purged and maintained with an inert atmosphere of nitrogen, was placed To a solution of methyl 3-bromopyridine-4-carboxylate (1.0 g, 4.6 mmol) in DMF (10 mL) was added 4H,5H,6H,7H-pyrazolo[1,5-a]pyrimidine (684 mg, 5.6 mmol), $Cs_2CO_3$ (3016 mg, 9.3 mmol), Xantphos (536 mg, 0.93 mmol) and $Pd_2(dba)_3CHCl_3$ (479 mg, 0.46 mmol) under an atmosphere of nitrogen. The mixture was stirred for 5 hours at 80° C. The mixture was diluted with water and extracted with EtOAc. The organic layer was concentrated under reduced pressure. The residue was purified by Prep-TLC (DCM:MeOH, 30:1) to afford the title compound (420 mg, 33% yield) as a black oil.

Step 2. Preparation of 3-[5H,6H,7H-pyrazolo[1,5-a]pyrimidin-4-yl]pyridine-4-carboxylic acid

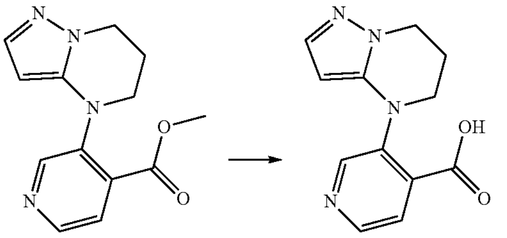 [SMILES: COC(=O)c1ccncc1N1CCCn2nccc21 ; O=C(O)c1ccncc1N1CCCn2nccc21]

The title compound was prepared using General Procedures F using methyl 3-[5H,6H,7H-pyrazolo[1,5-a]pyrimidin-4-yl]pyridine-4-carboxylate.

Step 3. Preparation of N-[5-[(4-chlorophenyl)methoxy]-1,3,4-thiadiazol-2-yl]-3-[5H,6H,7H-pyrazolo[1,5-a]pyrimidin-4-yl]pyridine-4-carboxamide

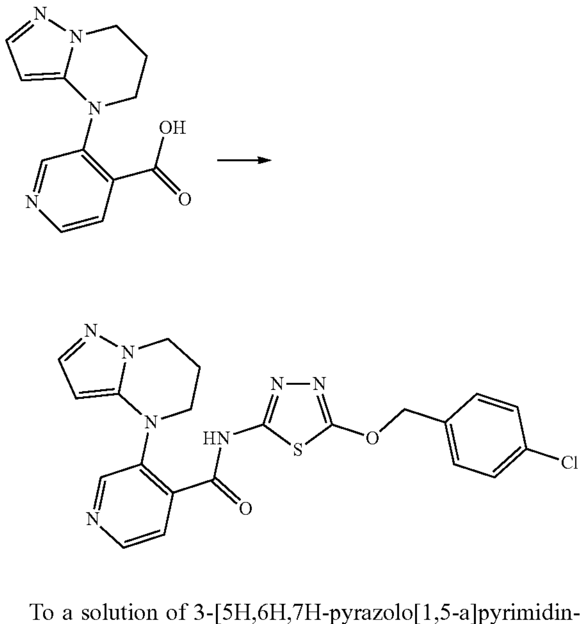

To a solution of 3-[5H,6H,7H-pyrazolo[1,5-a]pyrimidin-4-yl]pyridine-4-carboxylic acid (100 mg, 0.41 mmol) in DMF (1.0 mL) was added EDCI (118 mg, 0.61 mmol), HOBT (83 mg, 0.61 mmol) and 5-((4-chlorobenzyl)oxy)-1,3,4-thiadiazol-2-amine (99 mg, 0.41 mmol, Intermediate B). The mixture was stirred overnight at room temperature. The mixture was diluted with water and extracted with EtOAc. The organic layer was concentrated under reduced pressure. The residue was purified by Prep-TLC (DCM:MeOH, 15:1) to afford the title compound (10.6 mg, 6% yield) as a light yellow solid. $^{1}H$ NMR (300 MHz, DMSO-$d_6$): δ12.93 (s, 1H), 8.75 (s, 1H), 8.53 (s, 1H), 7.74-7.49 (m, 5H), 7.04 (s, 1H), 5.47 (s, 2H), 5.11 (s, 1H), 4.12-4.05 (m, 2H), 3.65-3.55 (m, 2H), 2.39-2.19 (m, 2H). m/z 468 [$M+H^+$].

Example 143

Synthesis of N-(5-((4-chlorobenzyl)oxy)-1,3,4-thiadiazol-2-yl)-3-(2-fluoro-6-(oxetan-3-yloxy)phenyl) isonicotinamide

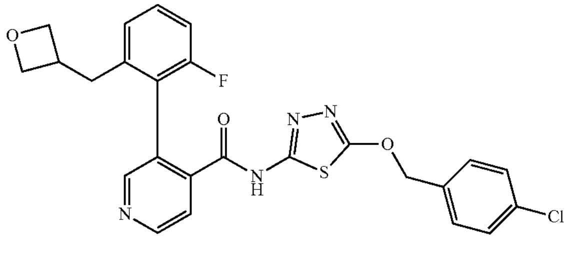 [SMILES: O=C(Nc1nnc(OCc2ccc(Cl)cc2)s1)c1ccncc1Cc1c(F)cccc1CC1COC1]

Step 1. Preparation of 3-(2-bromo-3-fluorophenoxy)oxetane

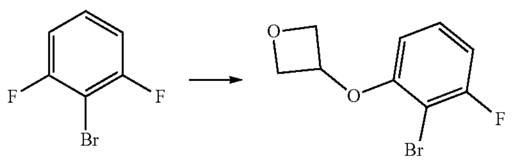 [SMILES: Fc1cccc(F)c1Br ; Fc1cccc(OC2COC2)c1Br]

To a solution of 2-bromo-1,3-difluorobenzene (5.0 g, 25.9 mmol) in DMF (50 mL) was added oxetan-3-ol (2.9 g, 38.9 mmol) and $K_2CO_3$ (7.2 g, 51.8 mmol) at room temperature under nitrogen atmosphere. The mixture was stirred overnight at 140° C. under nitrogen atmosphere. The mixture was diluted with water and extracted with EtOAc (4×). The mixture was concentrated under reduced pressure. The residue was purified by silica gel column chromatography, eluted with 1% EtOAc in PE to afford the title compound (1.6 g, 25% yield) as a yellow solid.

Step 2. Preparation of 2-(2-fluoro-6-(oxetan-3-yloxy)phenyl)-4,4,5,5-tetramethyl-1,3,2-dioxaborolane

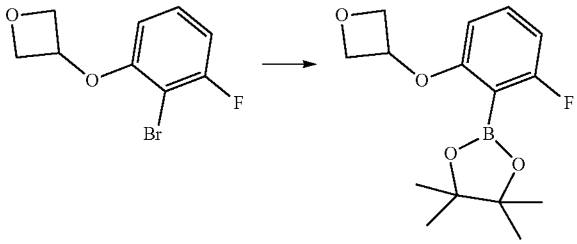 [SMILES: Fc1cccc(OC2COC2)c1Br ; CC1(C)OB(c2c(F)cccc2OC2COC2)OC1(C)C]

To a solution of 3-(2-bromo-3-fluorophenoxy)oxetane (1.5 g, 6.1 mmol) and dioxane (13 mL), was added bis(pinacolato)diboron (1.5 g, 6.1 mmol), KOAc (1.2 g, 12.1 mmol) and [1,1'-bis(diphenylphosphino)ferrocene]dichloropalladium(II) (0.89 g, 1.2 mmol) at room temperature under nitrogen atmosphere. The mixture was stirred overnight at 100° C. under nitrogen atmosphere. The mixture was diluted with water and extracted with EtOAc (3×). The combined organic layers were concentrated under reduced pressure. The residue was purified by silica gel column chromatography, eluted with 17% EtOAc in PE to afford the title compound (960 mg, 54% yield) as a yellow oil.

Step 3. Preparation of N-(5-((4-chlorobenzyl)oxy)-1,3,4-thiadiazol-2-yl)-3-(2-fluoro-6-(oxetan-3-yloxy)phenyl)isonicotinamide

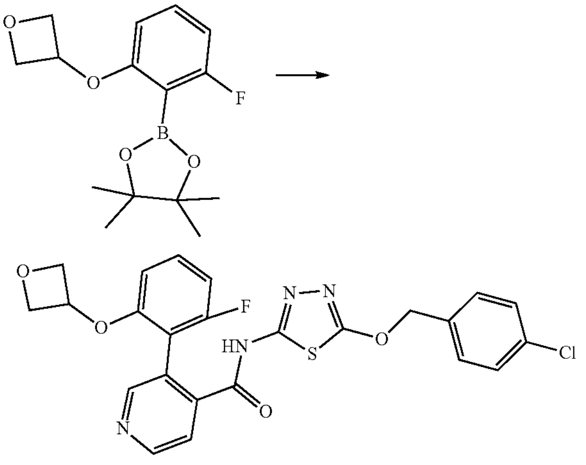

The title compound was prepared using General Procedures E, F and A. For General Procedure E, 2-(2-fluoro-6-(oxetan-3-yloxy)phenyl)-4,4,5,5-tetramethyl-1,3,2-dioxaborolane and methyl 3-bromopyridine-4-carboxylate were employed. For General Procedure A, 5-((4-chlorobenzyl)oxy)-1,3,4-thiadiazol-2-amine (Intermediate B) was used. $^1H$ NMR (400 MHz, DMSO-$d_6$): δ13.13 (s, 1H), 8.79 (d, 1H), 8.66 (s, 1H), 7.80 (s, 1H), 7.54-7.47 (m, 4H), 7.39-7.33 (m, 1H), 7.02-6.98 (m, 1H), 6.44 (d, 1H), 5.49 (t, 2H), 5.10-5.04 (m, 1H), 4.75 (t, 1H), 4.62 (t, 1H), 4.45-4.42 (m, 1H), 4.22-4.19 (m, 1H). m/z 513 [M+H$^+$].

Example 144

Synthesis of N-(5-((4-chlorobenzyl)oxy)-1,3,4-thiadiazol-2-yl)-3-((3R,5R)-3,5-dimethylmorpholino) isonicotinamide

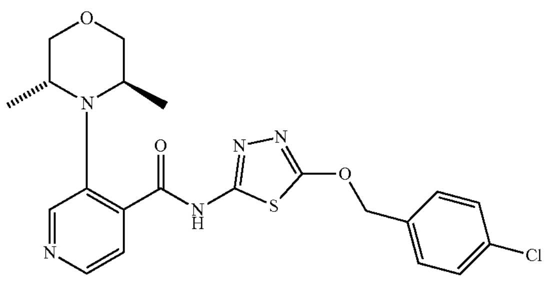 [SMILES: C[C@@H]1COC[C@@H](C)N1Cc1cnccc1C(=O)Nc1nnc(OCc2ccc(Cl)cc2)s1]

Step 1. Preparation of methyl 3-fluoro-1-oxo-1lambda5-pyridine-4-carboxylate

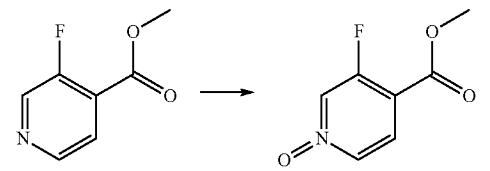

Into a 50-mL 3-necked round-bottom flask purged and maintained with an inert atmosphere of nitrogen, was placed To a solution of methyl 3-fluoropyridine-4-carboxylate (800 mg, 5.2 mmol) in chloroform (8 mL) was added m-CPBA (85%, 1047 mg, 5.2 mmol) under nitrogen atmosphere. The mixture was stirred for 5 hours at room temperature. The mixture was quenched by the addition of sat. NH4Cl (aq.) at room temperature. The layers were separated, and the aqueous layer was extracted with DCM (3×). The mixture was concentrated under reduced pressure. The residue was purified by silica gel column chromatography, eluted with 5% MeOH in DCM to afford the title compound (900 mg, 99% yield) as a white solid.

Step 2. Preparation of 3-((3R,5R)-3,5-dimethylmorpholino)-4-(methoxycarbonyl)pyridine 1-oxide

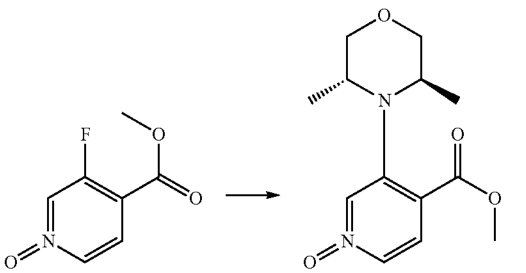 [SMILES: COC(=O)c1cc[n+]([O-])cc1F ; COC(=O)c1cc[n+]([O-])cc1N1[C@H](C)COC[C@H]1C]

To a solution of methyl 3-fluoro-1-oxo-1lambda5-pyridine-4-carboxylate (1.2 g, 7.0 mmol) in MeCN (12 mL) was added (3R,5R)-3,5-dimethylmorpholine hydrochloride (635 mg, 4.2 mmol) and DIEA (1631 mg, 12.6 mmol). The mixture was stirred for 3 days at 100° C. The mixture was cooled to rt, diluted with water and extracted with EtOAc. The organic layer was concentrated under reduced pressure. The residue was purified by Prep-TLC (DCM:MeOH, 25:1) to afford the title compound (180 mg, 8% yield) as a yellow oil.

Step 3. Preparation of methyl 3-((3R,5R)-3,5-dimethylmorpholino)isonicotinate

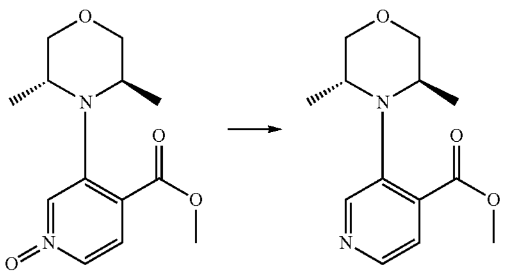

To a solution of 3-((3R,5R)-3,5-dimethylmorpholino)-4-(methoxycarbonyl)pyridine 1-oxide (170 mg, 0.64 mmol) in MeOH (2.00 mL) was added Pd/C (10%, 17 mg,) and $HCOONH_4$ (201 mg, 3.2 mmol). The mixture was stirred for 2 hours at room temperature. The mixture was diluted with MeOH and filtered out. The solids were washed with MeOH (2×). The filtrate was concentrated under reduced pressure. The residue was purified by Prep-TLC (PE:EtOAc, 4:1) to afford the title compound (110 mg, 67% yield) as a yellow oil.

Step 4. Preparation of N-(5-((4-chlorobenzyl)oxy)-1,3,4-thiadiazol-2-yl)-3-((3R,5R)-3,5-dimethylmorpholino)isonicotinamide

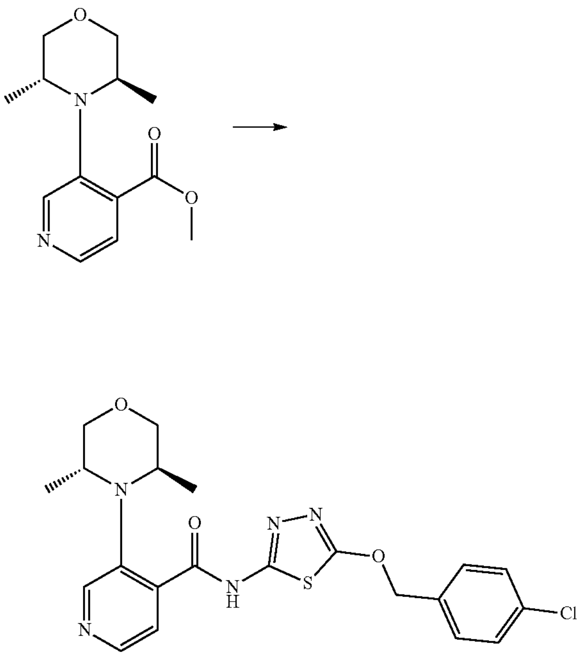

The title compound was prepared using General Procedures F and A. For General Procedure A, 5-((4-chlorobenzyl)oxy)-1,3,4-thiadiazol-2-amine (intermediate B) was used. $^1$H NMR (300 MHz, DMSO-$d_6$): δ14.24 (s, 1H), 8.74 (s, 1H), 8.61 (d, 1H), 7.89 (d, 1H), 7.58-7.48 (m, 4H), 5.52 (s, 2H), 4.10-3.65 (m, 4H), 3.32-3.24 (m, 2H), 1.23-0.81 (m, 6H). m/z 460 [M+H$^+$].

Example 145

Synthesis of N-[5-(1H-1,3-benzodiazol-4-ylmethoxy)-1,3,4-thiadiazol-2-yl]-3-(2-methoxyphenyl)pyridine-4-carboxamide

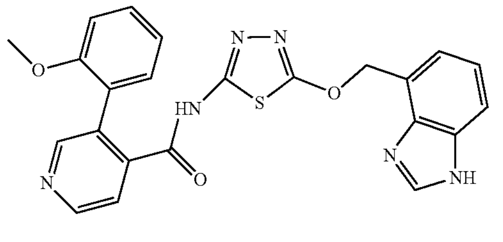 [SMILES: COc1ccccc1-c1cnccc1C(=O)Nc1nnc(OCc2cccc3[nH]cnc23)s1]

Step 1. Preparation of methyl 1-[[2-(trimethylsilyl)ethoxy]methyl]-1,3-benzodiazole-4-carboxylate

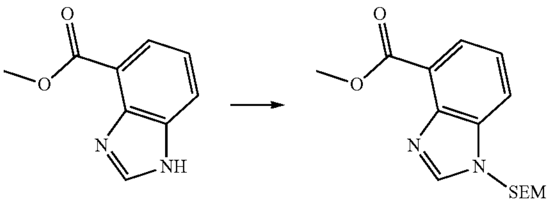 [SMILES: COC(=O)c1cccc2[nH]cnc12 ; COC(=O)c1cccc2c1ncn2COCC[Si](C)(C)C]

To a solution of methyl 1H-1,3-benzodiazole-4-carboxylate (3.0 g, 17.0 mmol) in DMF (30 mL) at 0° C. was added NaH (60% dispersion in oil, 1.0 g, 25.5 mmol). The mixture was stirred for 40 min at 0° C. Then 2-(trimethylsilyl)ethoxymethyl chloride (2.8 g, 17.0 mmol) was added and the mixture was warmed to rt and stirred overnight. The mixture was quenched by NH4Cl (aq.) and extracted with EtOAc (5×). The combined organic layers were concentrated under vacuum. The residue was purified by reverse phase chromatography (column, C18 silica gel; mobile phase, with 5-80% MeCN in water) to afford the title compound (3.1 g, 56% yield) as a brown oil.

Step 2. Preparation of (1-((2-(trimethylsilyl)ethoxy)methyl)-1H-benzo[d]imidazol-4-yl)methanol

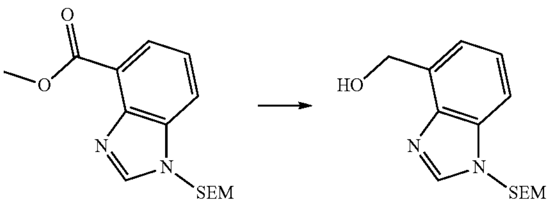 [SMILES: COC(=O)c1cccc2c1ncn2COCC[Si](C)(C)C ; C[Si](C)(C)CCOCn1cnc2c(CO)cccc21]

To a solution of methyl 1-[[2-(trimethylsilyl)ethoxy]methyl]-1,3-benzodiazole-4-carboxylate (1.1 g, 3.4 mmol) in THF (15 mL) was added $LiAlH_4$ (259 mg, 6.8 mmol) at room temperature under nitrogen atmosphere. The mixture was stirred for 1 h at room temperature under nitrogen atmosphere. The mixture was cooled to 0° C. and was quenched by the addition of NH4Cl (aq.) The mixture was extracted with EtOAc (3×). The combined organic layers were concentrated under vacuum. The residue was purified by silica gel column chromatography, 17% EtOAc in PE to afford the title compound (840 mg, 84% yield) as a yellow oil.

Step 3. Preparation of 5-[(1-[[2-(trimethylsilyl)ethoxy]methyl]-1,3-benzodiazol-4-yl)methoxy]-1,3,4-thiadiazol-2-amine

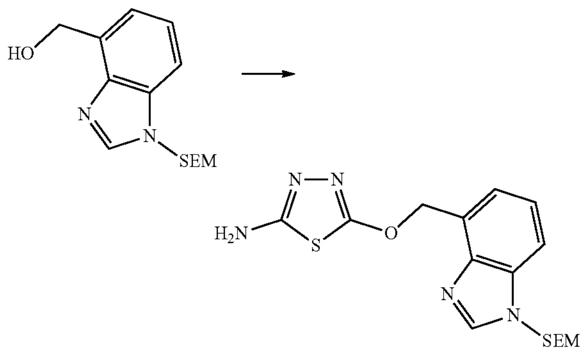

The title compound was prepared using similar procedures as the synthesis of Intermediate C, replacing (5-chloropyridin-2-yl)methanol with (1-[[2-(trimethylsilyl)ethoxy]methyl]-1,3-benzodiazol-4-yl)methanol in Step 1.

Step 4. Preparation of 3-(2-methoxyphenyl)-N-[5-[(1-[[2-(trimethylsilyl)ethoxy]methyl]-1,3-benzodiazol-4-yl)methoxy]-1,3,4-thiadiazol-2-yl]pyridine-4-carboxamide

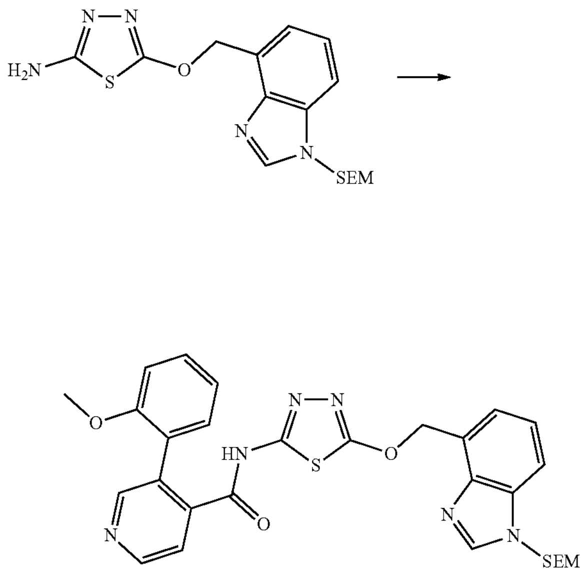

The title compound was prepared using General Procedure A employing 3-(2-methoxyphenyl) pyridine-4-carboxylic acid (Intermediate H) and 5-[(1-[[2-(trimethylsilyl)ethoxy]methyl]-1,3-benzodiazol-4-yl)methoxy]-1,3,4-thiadiazol-2-amine.

Step 5. Preparation of N-[5-(1H-1,3-benzodiazol-4-ylmethoxy)-1,3,4-thiadiazol-2-yl]-3-(2-methoxyphenyl)pyridine-4-carboxamide

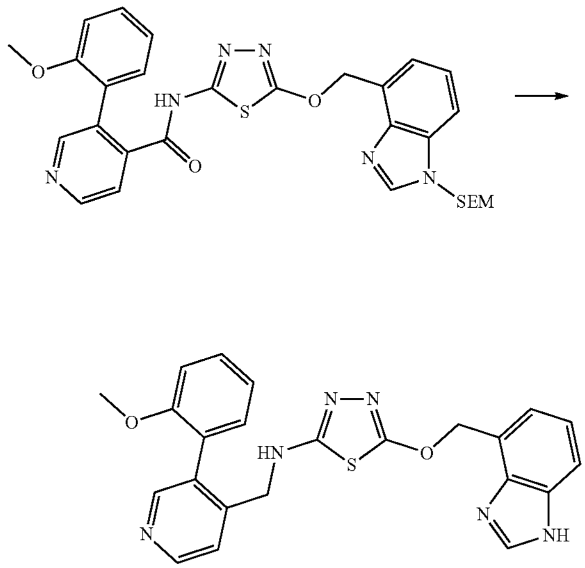

To a solution of 3-(2-methoxyphenyl)-N-[5-[(1-[[2-(trimethylsilyl)ethoxy]methyl]-1,3-benzodiazol-4-yl)methoxy]-1,3,4-thiadiazol-2-yl]pyridine-4-carboxamide (200 mg, 0.34 mmol) in THF (3 mL) was added TBAF (1 M in THF, 1.7 mL, 1.7 mmol) and CsF (1032 mg, 6.80 mmol) at room temperature. The mixture was stirred for 4 h at 70° C. under nitrogen atmosphere. The mixture was diluted with water and extracted with EtOAc (3×). The combined organic layers were concentrated vacuum. The residue was purified by Prep-TLC (DCM:MeOH, 10:1) to afford the title compound (52 mg, 33% yield) as an off-white solid. $^1$H NMR (300 MHz, DMSO-$d_6$): δ12.86-12.61 (m, 2H), 8.72 (d, 1H), 8.61 (s, 1H), 8.27 (s, 1H), 7.65-7.63 (m, 2H), 7.38-7.33 (m, 3H), 7.30-7.20 (m, 1H), 7.09-6.98 (m, 2H), 5.80 (d, 2H), 3.53 (s, 3H). m/z 459 [M+H$^+$].

Example 146

Synthesis of N-[5-[(7-chloro-1-methylindazol-4-yl)methoxy]-1,3,4-thiadiazol-2-yl]-3-(2-methoxyphenyl)pyridine-4-carboxamide

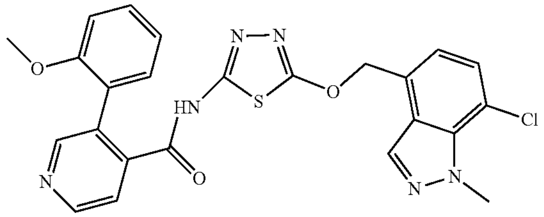 [SMILES: COc1ccccc1-c1cnccc1C(=O)Nc1nnc(OCc2ccc(Cl)c3c2cnn3C)s1]

Step 1. Preparation of 4-bromo-7-chloro-1-methylindazole

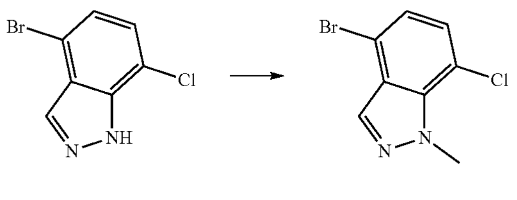

To a solution of 4-bromo-7-chloro-1H-indazole (3.0 g, 13.0 mmol) in DMF (30 mL) at 0° C. was added NaH (60% dispersion in oil, 1.04 g, 26.0 mmol). The mixture was stirred for 40 min at 0° C. Then MeI (1840 mg, 13.0 mmol) was added and the mixture warm to rt and stirred at it overnight. The mixture was quenched by the addition of $NH_4Cl$ (aq.) and extracted with EtOAc (3×). The combined organic layers were concentrated under vacuum. The residue was purified by silica gel column chromatography, eluted with 3% EtOAc in PE to afford the title compound (1.8 g, 57% yield) as an off-white solid.

Step 2. Preparation of 7-chloro-4-ethenyl-1-methylindazole

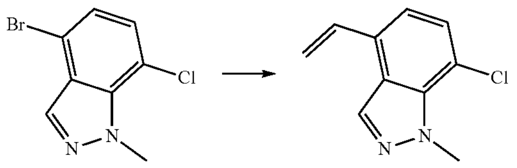

To a solution of 4-bromo-7-chloro-1-methylindazole (1.8 g, 7.3 mmol) in toluene (20 mL) was added tributyl(ethenyl) stannane (5813 mg, 18.3 mmol) and $Pd(PPh_3)_4$ (847 mg, 0.73 mmol) at room temperature. The mixture was stirred for 2 h at 110° C. under nitrogen atmosphere. The mixture was concentrated under vacuum. The residue was purified by silica gel column chromatography, eluted with 9% EtOAc in PE to afford the title compound (1 g, 71% yield) as an off-white solid.

Step 3. Preparation of 1-(7-chloro-1-methylindazol-4-yl)ethane-1,2-diol

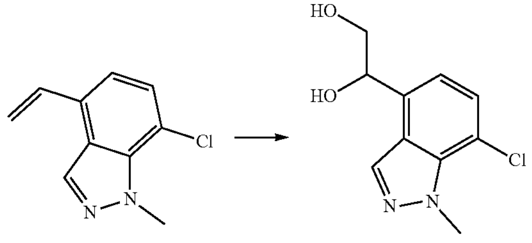

To a solution of 7-chloro-4-ethenyl-1-methylindazole (980 mg, 5.1 mmol) in THF (10 mL) was added $OsO_4$ (129 mg, 0.51 mmol) at room temperature. Then a solution of NMO (1192 mg, 10.2 mmol) in water (5 mL) was added.

The mixture was stirred for 2 h and then diluted with water. The mixture was extracted with EtOAc (3×). The combined organic layers were concentrated under vacuum. The residue was purified by silica gel column chromatography, eluted with 50% EtOAc in DCM to afford the title compound (730 mg, 63% yield) as a black solid.

Step 4. Preparation of 7-chloro-1-methylindazole-4-carbaldehyde

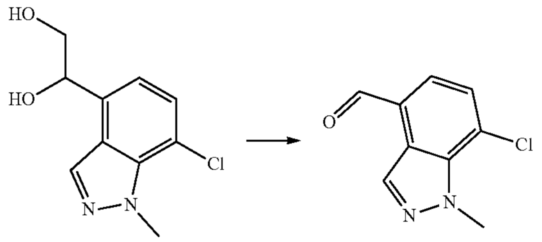

To a solution of 1-(7-chloro-1-methylindazol-4-yl)ethane-1,2-diol (710 mg, 3.1 mmol) in MeOH (7 mL) was added NaIO4 (1340 mg, 6.3 mmol) at room temperature. The mixture was stirred for 4 h at room temperature under nitrogen atmosphere. The mixture was diluted with water and extracted with EtOAc (3×). The combined organic layers were concentrated under vacuum. The residue was purified by Prep-TLC (PE:EtOAc, 5:1) to afford the title compound (560 mg, 92% yield) as a white solid.

Step 5. Preparation of (7-chloro-1-methylindazol-4-yl) methanol

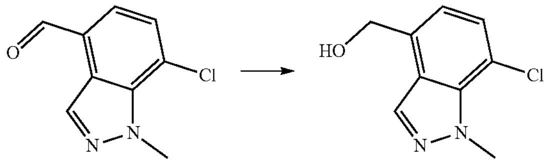

To a solution of 7-chloro-1-methylindazole-4-carbaldehyde (560 mg, 2.9 mmol) in MeOH (10 mL) was added $NaBH_4$ (218 mg, 5.8 mmol) at room temperature. The mixture was stirred for 30 min at room temperature under nitrogen atmosphere. The mixture was quenched by the addition of water at room temperature. The mixture was extracted with EtOAc (3×). The combined organic layers were concentrated under vacuum. The residue was purified by silica gel column chromatography, eluted with 17% EtOAc in DCM to afford the title compound (530 mg, 94% yield) as a white solid.

Step 6. Preparation of 5-[(7-chloro-1-methylindazol-4-yl)methoxy]-1,3,4-thiadiazol-2-amine

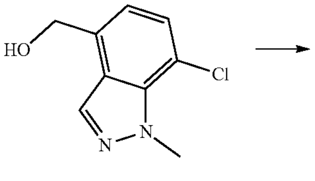

-continued

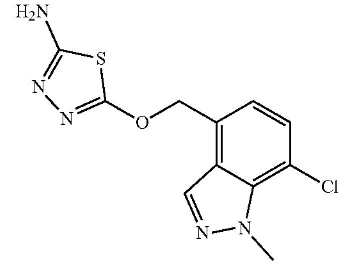

The title compound was prepared using similar procedures as the synthesis of Intermediate C, replacing (5-chloropyridin-2-yl)methanol with (7-chloro-1-methylindazol-4-yl) methanol in Step 1.

Step 7. Preparation of N-[5-[(7-chloro-1-methylindazol-4-yl)methoxy]-1,3,4-thiadiazol-2-yl]-3-(2-methoxyphenyl)pyridine-4-carboxamide

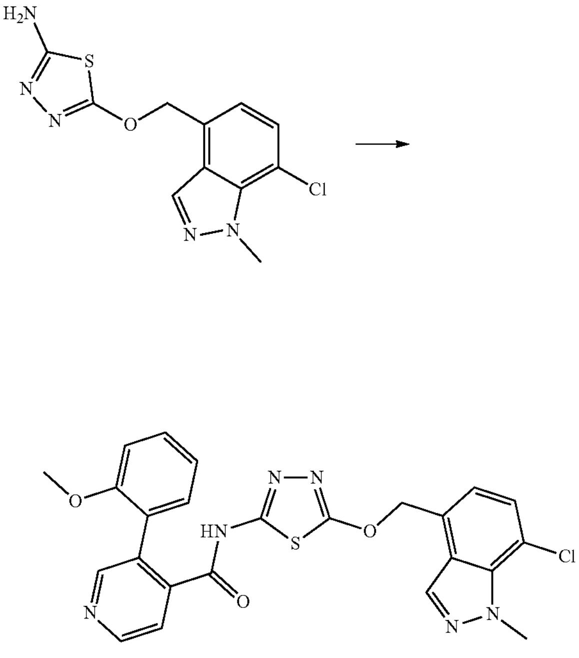

The title compound was prepared using General Procedure A employing 5-[(7-chloro-1-methylindazol-4-yl) methoxy]-1,3,4-thiadiazol-2-amine and 3-(2-methoxyphenyl) pyridine-4-carboxylic acid (Intermediate H). $^1H$ NMR (300 MHz, DMSO-$d_6$): δ12.86 (s, 1H), 8.72 (d, 1H), 8.61 (s, 1H), 8.29 (s, 1H), 7.63 (d, 1H), 7.49 (d, 1H), 7.41-7.36 (m, 2H), 7.26-7.24 (m, 1H), 7.09-6.98 (m, 2H), 5.80 (s, 2H), 4.34 (s, 3H), 3.52 (s, 3H). m/z 507 [M+H$^+$].

Example 147

Synthesis of N-[5-[(4-chlorophenyl)methoxy]-1,3,4-thiadiazol-2-yl]-5-[2-(difluoromethoxy)phenyl]-2-(3-hydroxyprop-1-yn-1-yl)pyridine-4-carboxamide

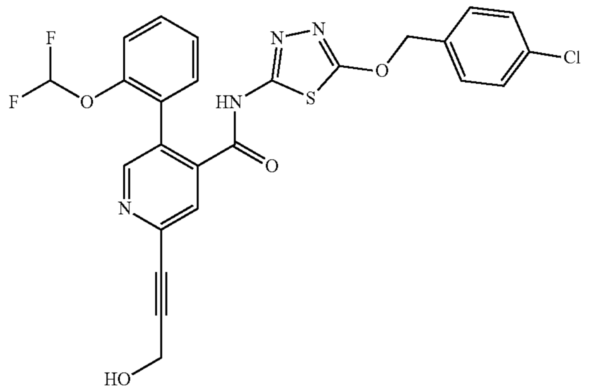 [SMILES: O=C(Nc1nnc(OCc2ccc(Cl)cc2)s1)c1cc(C#CCO)ncc1-c1ccccc1OC(F)F]

Step 1. Preparation of methyl 2-chloro-5-(2-(difluoromethoxy)phenyl)isonicotinate

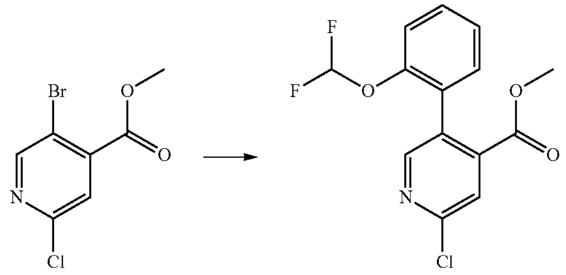 [SMILES: COC(=O)c1cc(Cl)ncc1Br ; COC(=O)c1cc(Cl)ncc1-c1ccccc1OC(F)F]

The title compound was prepared using General Procedure E employing methyl 5-bromo-2-chloropyridine-4-carboxylate and 2-[2-(difluoromethoxy)phenyl]-4,4,5,5-tetramethyl-1,3,2-dioxaborolane.

Step 2. Preparation of methyl 2-[3-[(tert-butyldimethylsilyl)oxy]prop-1-yn-1-yl]-5-[2-(difluoromethoxy)phenyl]pyridine-4-carboxylate

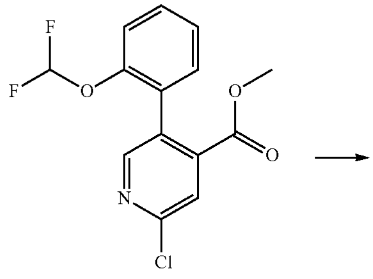

-continued

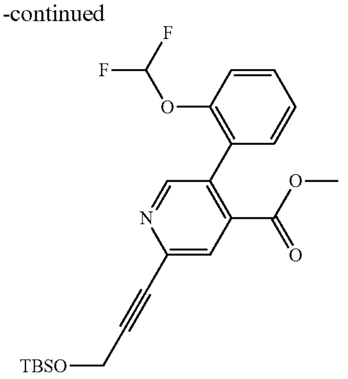

To a solution of methyl 2-chloro-5-[2-(difluoromethoxy)phenyl]pyridine-4-carboxylate (320 mg, 1.0 mmol) in DMF (12 mL) was added diisopropylamine (516 mg, 5.1 mmol), CuI (78 mg, 0.41 mmol), Pd/C (10%, 64 mg) and tert-butyldimethyl(prop-2-yn-1-yloxy)silane (869 mg, 5.1 mmol) at room temperature. The mixture was irradiated with microwave radiation for 40 min at 140° C. The mixture was cooled room temperature. The solids were filtered, and the filtrate was diluted with water and extracted with EtOAc (3×). The combined organic layers were concentrated under reduced pressure. The residue was purified by Prep-TLC (PE:EtOAc, 2:1) to afford the title compound (300 mg, 66% yield) as a yellow oil.

Step 3. Preparation of 5-[2-(difluoromethoxy)phenyl]-2-(3-hydroxyprop-1-yn-1-yl)pyridine-4-carboxylic acid

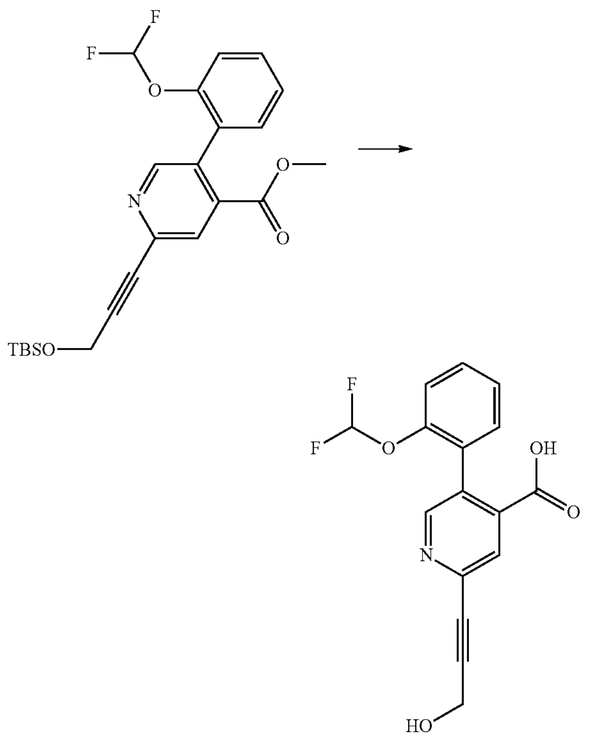

To a solution of methyl 2-[3-[(tert-butyldimethylsilyl)oxy]prop-1-yn-1-yl]-5-[2-(difluoromethoxy)phenyl]pyridine-4-carboxylate (280 mg, 0.63 mmol) in MeOH (3.0 mL) and water (1.0 mL) was added NaOH (51 mg, 1.3 mmol) at room temperature. The mixture was stirred for 30 min at room temperature under nitrogen atmosphere. The mixture was diluted with water and acidified to pH 5 with HCl (1M). The mixture was extracted with EtOAc (5×). The combined organic layers were concentrated under reduced pressure. The residue was purified by Prep-TLC (DCM:MeOH, 10:1) to afford the title compound (140 mg, 71% yield) as a white solid.

Step 4. Preparation of 2-[3-(acetyloxy)prop-1-yn-1-yl]-5-[2-(difluoromethoxy)phenyl]pyridine-4-carboxylic acid

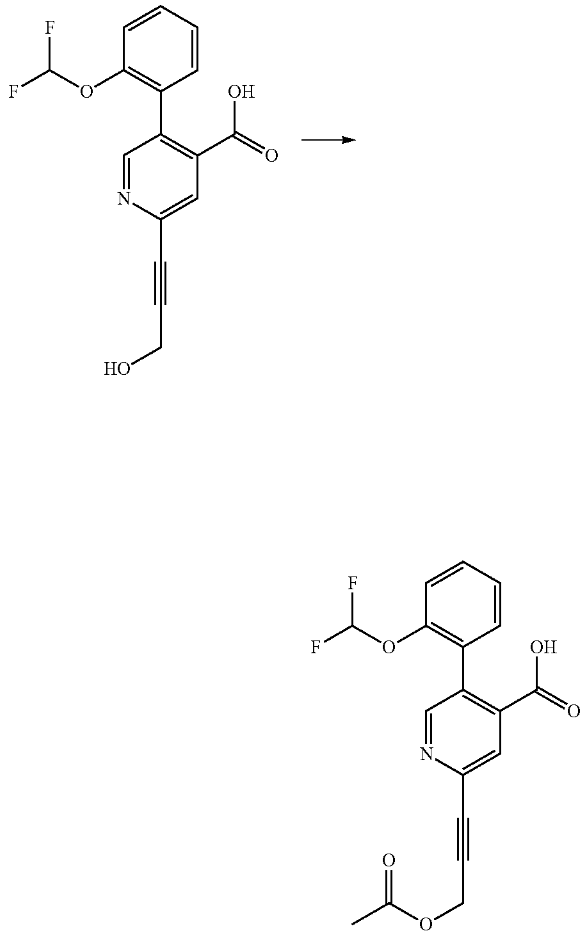

To a solution of 5-[2-(difluoromethoxy)phenyl]-2-(3-hydroxyprop-1-yn-1-yl)pyridine-4-carboxylic acid (135 mg, 0.42 mmol) in DCM (2 mL) was added DIEA (109 mg, 0.85 mmol) and AcCl (33 mg, 0.42 mmol) at 0° C. The mixture was stirred for 30 min at room temperature under nitrogen atmosphere. The mixture was diluted with water and extracted with EtOAc (3×). The combined organic layers were concentrated under vacuum. The residue was purified by Prep-TLC (DCM:MeOH, 15:1) to afford (80 mg, 52% yield) as a white semi-solid.

Step 5. Preparation of 3-[4-([5-[(4-chlorophenyl)methoxy]-1,3,4-thiadiazol-2-yl]carbamoyl)-5-[2-(difluoromethoxy)phenyl]pyridin-2-yl]prop-2-yn-1-yl acetate

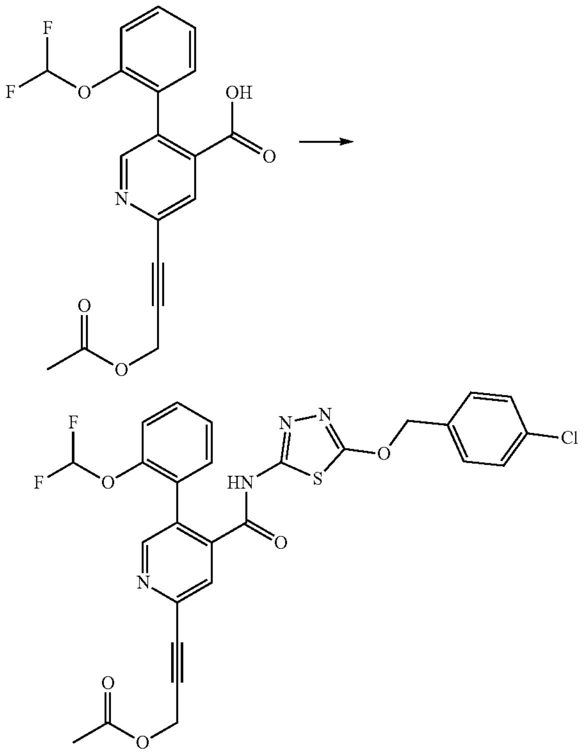

The title compound was prepared using General Procedure A employing 2-[3-(acetyloxy)prop-1-yn-1-yl]-5-[2-(difluoromethoxy)phenyl]pyridine-4-carboxylic acid and 5-((4-chlorobenzyl)oxy)-1,3,4-thiadiazol-2-amine (Intermediate B).

Step 6. Preparation of N-[5-[(4-chlorophenyl)methoxy]-1,3,4-thiadiazol-2-yl]-5-[2-(difluoromethoxy)phenyl]-2-(3-hydroxyprop-1-yn-1-yl)pyridine-4-carboxamide

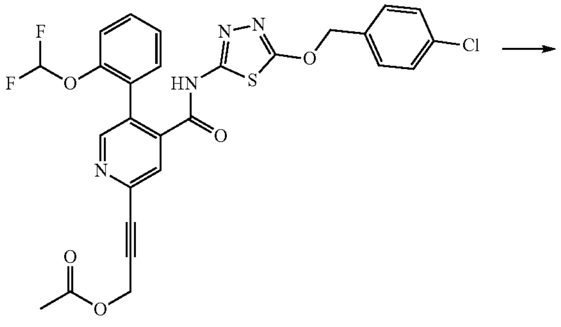

-continued

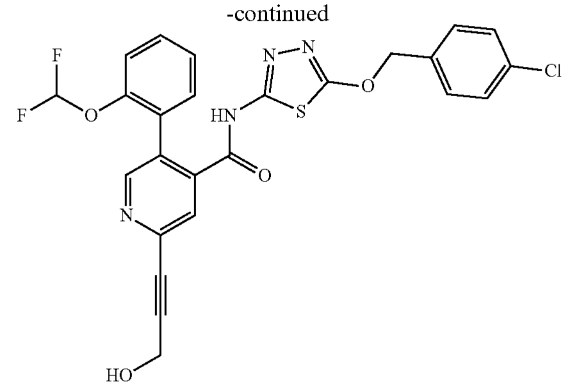

To a solution of 3-[4-([5-[(4-chlorophenyl)methoxy]-1,3,4-thiadiazol-2-yl]carbamoyl)-5-[2-(difluoromethoxy)phenyl]pyridin-2-yl]prop-2-yn-1-yl acetate (95 mg, 0.16 mmol) in MeOH (2 mL) and water (0.5 mL) was added $LiOH \cdot H_2O$ (14 mg, 0.33 mmol) at room temperature. The mixture was stirred for 1 h at room temperature under nitrogen atmosphere. The mixture was diluted with water and acidified to pH 5 with HCl (1 M). The mixture was extracted with EtOAc (3×) and the combined organic layers were concentrated under reduced pressure. The residue was purified by Prep-TLC (DCM:MeOH, 20:1) to afford the title compound (16 mg, 19% yield) as a white solid. $^1H$ NMR (400 MHz, $CD_3OD$): δ 8.56 (s, 1H), 7.84 (s, 1H), 7.48-7.30 (m, 7H), 7.20 (d, 1H), 6.92-6.43 (m, 1H), 5.44 (s, 2H), 4.47 (s, 2H). m/z 543 [$M+H^+$].

Example 148

Synthesis of N-(5-((4-chlorobenzyl)oxy)-1,3,4-thiadiazol-2-yl)-2-fluoro-5-(2-methoxyphenyl)isonicotinamide

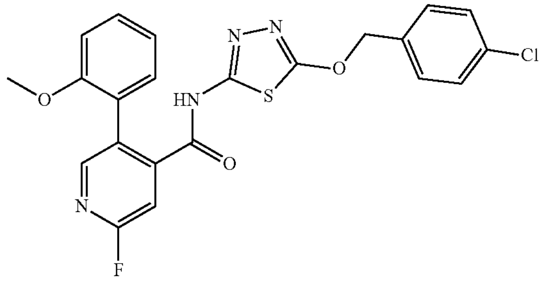 [SMILES: COc1ccccc1-c1cnc(F)cc1C(=O)Nc1nnc(OCc2ccc(Cl)cc2)s1]

Step 1. Preparation of methyl 5-bromo-2-fluoroisonicotinate

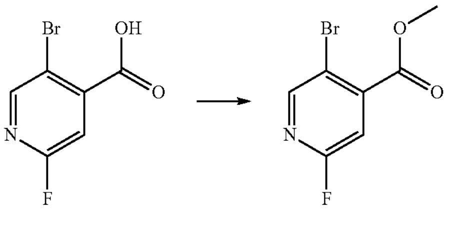

To a solution of 5-bromo-2-fluoropyridine-4-carboxylic acid (1.0 g, 4.5 mmol) in THF (10 mL) was added $Ph_3P$ (2.4 g, 9.1 mmol) and MeOH (0.73 g, 22.7 mmol) at 0° C. The mixture was stirred for 5 min and then DIAD (1.8 g, 9.1 mmol) was added. The mixture was warmed to rt and stirred at rt for 30 min. The mixture was concentrated under vacuum. The residue was purified by silica gel column chromatography, eluted with 3% EtOAc in PE to afford the title compound (0.95 g, 88% yield) as a white solid.

Step 2. Preparation of N-(5-((4-chlorobenzyl)oxy)-1,3,4-thiadiazol-2-yl)-2-fluoro-5-(2-methoxyphenyl)isonicotinamide

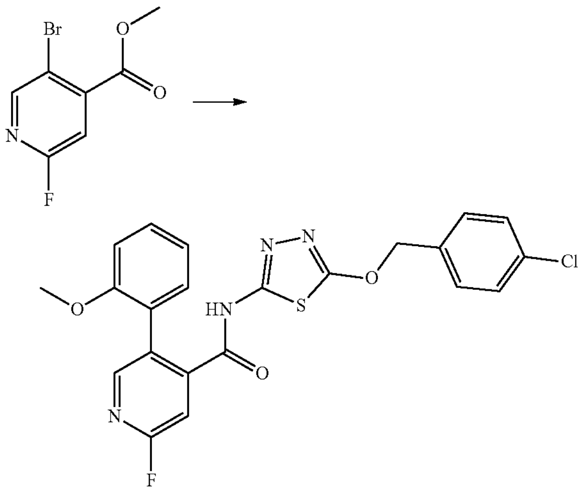

The title compound was prepared using General Procedures E, F and A. For General Procedure E, methyl 5-bromo-2-fluoropyridine-4-carboxylate and 2-methoxyphenylboronic acid were employed. For General Procedure A, 5-((4-chlorobenzyl)oxy)-1,3,4-thiadiazol-2-amine (Intermediate B) was used. $^1H$ NMR (300 MHz, DMSO-$d_6$): δ 3.51 (s, 3H), 5.48 (s, 2H), 6.97-7.08 (m, 2H), 7.34-7.41 (m, 2H), 7.46-7.55 (m, 5H), 8.27 (s, 1H), 12.97 (s, 1H). m/z 471 [$M+H^+$].

Example 149

Synthesis of N-(5-((4-cyclopropylbenzyl)oxy)-1,3,4-thiadiazol-2-yl)-1-(2-methoxyphenyl)-1H-imidazole-5-carboxamide

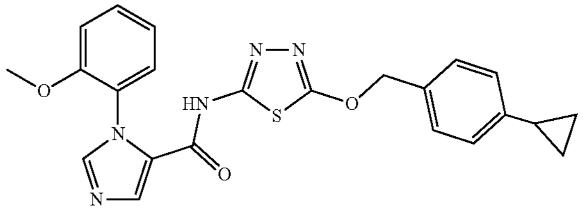 [SMILES: COc1ccccc1-n1cncc1C(=O)Nc1nnc(OCc2ccc(C3CC3)cc2)s1]

The title compound was prepared using similar procedures as the synthesis of Example 50 replacing 5-((4-chlorobenzyl)oxy)-1,3,4-thiadiazol-2-amine (Intermediate B) with 5-[(4-cyclopropylphenyl)methoxy]-1,3,4-thiadiazol-2-amine (Example 47, Step 1). $^1$H NMR (300 MHz, DMSO-$d_6$): δ 0.62-0.66 (m, 2H), 0.94-0.98 (m, 2H), 1.87-1.96 (m, 1H), 3.66 (s, 3H), 5.39 (s, 2H), 7.03-7.11 (m, 3H), 7.17 (d, 1H), 7.33-7.37 (m, 3H), 7.42-7.48 (m, 1H), 7.97 (d, 1H), 8.10 (s, 1H), 12.68 (br s, 1H). m/z 448 [M+H$^+$].

Example 150

Synthesis of N-(5-((4-chlorobenzyl)oxy)-1,3,4-thiadiazol-2-yl)-2-(2-chlorophenyl)nicotinamide

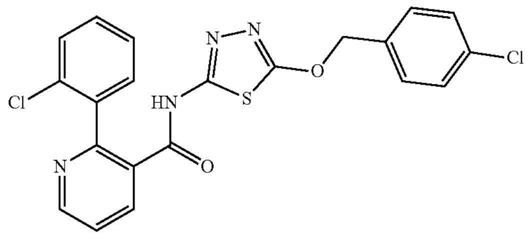 [SMILES: O=C(Nc1nnc(OCc2ccc(Cl)cc2)s1)c1cccnc1-c1ccccc1Cl]

The title compound was prepared using General Procedures E, F and A. For General Procedure E, methyl 2-bromopyridine-3-carboxylate and 2-chlorophenylboronic acid were employed. For General Procedure A, 5-((4-chlorobenzyl)oxy)-1,3,4-thiadiazol-2-amine (Intermediate B) was used. $^1$H NMR (300 MHz, DMSO-$d_6$): δ 5.54 (s, 2H), 7.40-7.63 (m, 8H), 7.98-8.01 (m, 1H), 8.21-8.24 (m, 1H), 8.81-8.83 (m, 1H), 13.00 (s, 1H). m/z 457 [M+H$^+$].

Example 151

Synthesis of N-(5-((4-chlorobenzyl)oxy)-1,3,4-thiadiazol-2-yl)-2-cyano-5-(2-methoxyphenyl)isonicotinamide

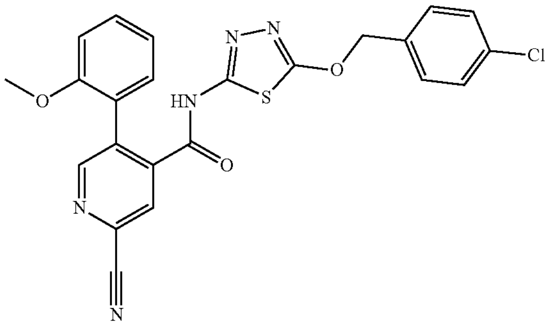 [SMILES: COc1ccccc1-c1cnc(C#N)cc1C(=O)Nc1nnc(OCc2ccc(Cl)cc2)s1]

Step 1. Preparation of benzyl 5-bromo-2-chloropyridine-4-carboxylate

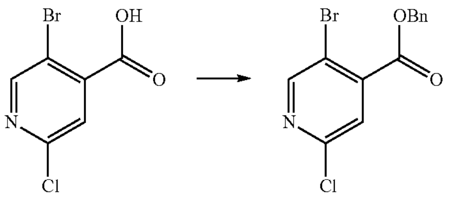 [SMILES: O=C(O)c1cc(Cl)ncc1Br ; O=C(OCc1ccccc1)c1cc(Cl)ncc1Br]

To a solution of 5-bromo-2-chloropyridine-4-carboxylic acid (3 g, 12.7 mmol) and benzyl bromide (2.6 g, 15.2 mmol) in DMF (10 mL) was added $K_2CO_3$ (1.2 g, 8.5 mmol) at room temperature. The mixture was stirred for 2 h at 50° C. The mixture was diluted with EtOAc and washed with (3×). The organic layer was concentrated under reduced pressure. The residue was purified by silica gel column chromatography, eluted with 14% EtOAc in PE to afford the title compound (4 g, 93% yield) as a white solid.

Step 2. Preparation of benzyl 2-chloro-5-(2-methoxyphenyl)pyridine-4-carboxylate

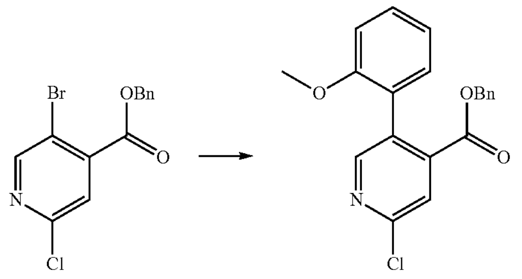 [SMILES: O=C(OCc1ccccc1)c1cc(Cl)ncc1Br ; COc1ccccc1-c1cnc(Cl)cc1C(=O)OCc1ccccc1]

The title compound was prepared using General Procedure E employing benzyl 5-bromo-2-chloropyridine-4-carboxylate and 2-methoxyphenylboronic acid.

Step 3. Preparation of benzyl 2-cyano-5-(2-methoxyphenyl)pyridine-4-carboxylate

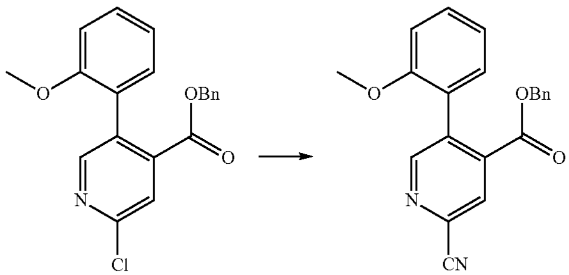 [SMILES: COc1ccccc1-c1cnc(Cl)cc1C(=O)OCc1ccccc1 ; COc1ccccc1-c1cnc(C#N)cc1C(=O)OCc1ccccc1]

To a solution of benzyl 2-chloro-5-(2-methoxyphenyl)pyridine-4-carboxylate (3.4 g, 9.7 mmol) in DMF (34 ml) was added $Zn(CN)_2$ (5.7 g, 48.6 mmol) at room temperature. The mixture was stirred for 2 h at 80° C. under nitrogen atmosphere. The mixture was cooled to rt, diluted with EtOAc and washed with water. The organic layer was concentrated under vacuum. The residue was purified by silica gel column chromatography, eluted with 17% EtOAc in PE to afford the title compound (2 g, 57% yield) as a white solid.

Step 4. Preparation of 2-cyano-5-(2-methoxyphenyl)pyridine-4-carboxylic acid

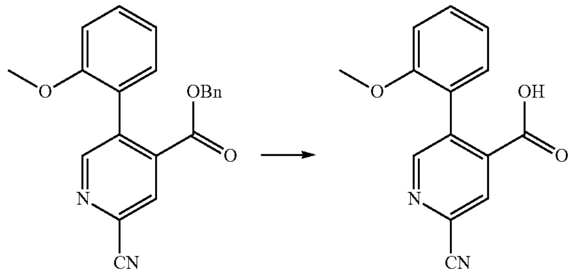 [SMILES: COc1ccccc1-c1cnc(C#N)cc1C(=O)OCc1ccccc1 ; COc1ccccc1-c1cnc(C#N)cc1C(=O)O]

To a solution of benzyl 2-cyano-5-(2-methoxyphenyl) isonicotinate (1 g, 2.9 mmol) in MeOH was added Pd/C (10%, 0.09 g) at room temperature. The mixture was stirred for 8 h at room temperature under hydrogen atmosphere. The mixture was filtered, and the solid was washed with MeOH (3×). The filtrate was concentrated under reduced pressure. The residue was purified by Prep-TLC (DCM: MeOH, 7:1) to afford the title compound (140 mg, 17% yield) as a yellow oil.

Step 5. Preparation of N-(5-((4-chlorobenzyl)oxy)-1,3,4-thiadiazol-2-yl)-2-cyano-5-(2-methoxyphenyl) isonicotinamide

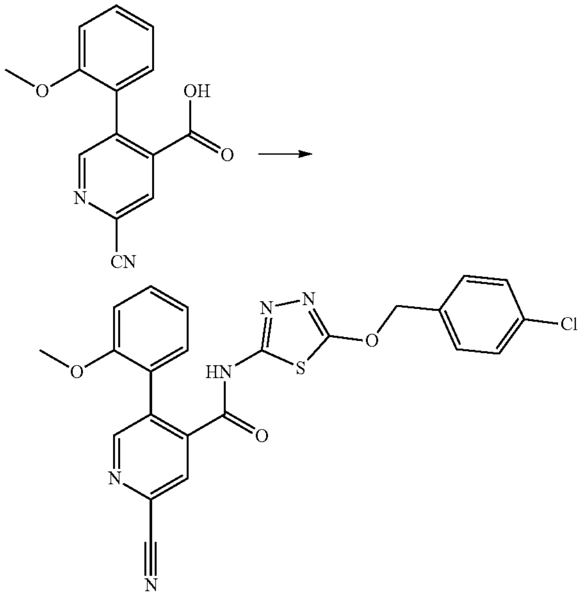

The title compound was prepared using General Procedure A employing 2-cyano-5-(2-methoxyphenyl)pyridine-4-carboxylic acid and 5-((4-chlorobenzyl)oxy)-1,3,4-thiadiazol-2-amine (Intermediate B). $^1H$ NMR (300 MHz, DMSO-$d_6$): δ 3.58 (s, 3H), 5.48 (s, 2H), 7.02-7.12 (m, 2H), 7.41-7.55 (m, 6H), 8.36 (s, 1H), 8.82 (s, 1H), 13.05 (s, 1H). m/z 478 [M+H$^+$].

Example 152

Synthesis of 5-([5-[(4-bromophenyl)methoxy]-1,3,4-thiadiazol-2-yl]carbamoyl)-4-(2-methoxyphenyl) pyridine-2-carboxylic acid

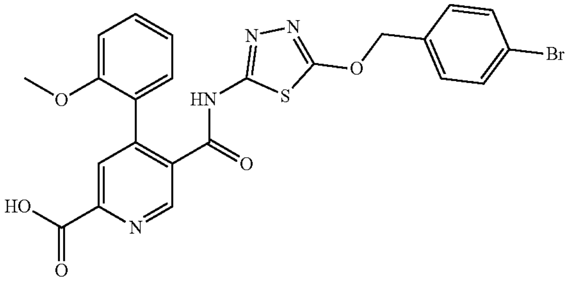 [SMILES: COc1ccccc1-c1cc(C(=O)O)ncc1C(=O)Nc1nnc(OCc2ccc(Br)cc2)s1]

Step 1. Preparation of isopropyl 5-([5-[(4-bromophenyl)methoxy]-1,3,4-thiadiazol-2-yl]carbamoyl)-4-(2-methoxyphenyl)pyridine-2-carboxylate

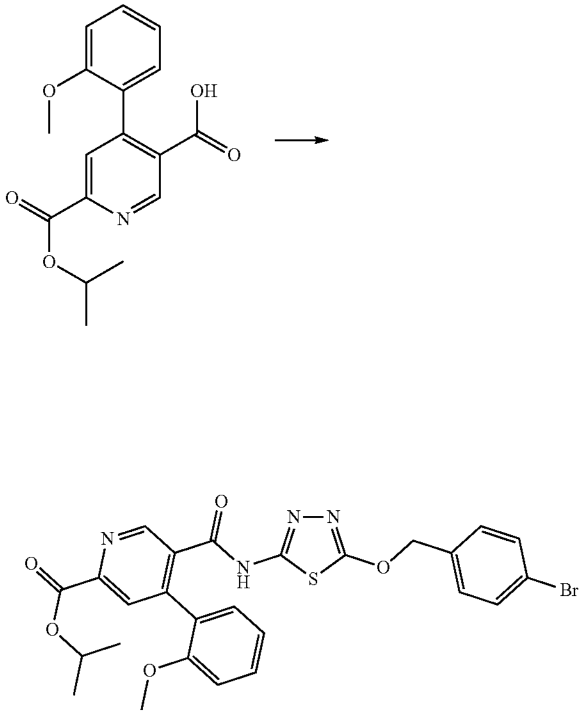

The title compound was prepared using General Procedure A employing 6-(isopropoxycarbonyl)-4-(2-methoxyphenyl)pyridine-3-carboxylic acid (Example 102, Step 3) and 5-((4-bromobenzyl)oxy)-1,3,4-thiadiazol-2-amine (Example 40, Step 1).

Step 2. Preparation of 5-([5-[(4-bromophenyl) methoxy]-1,3,4-thiadiazol-2-yl]carbamoyl)-4-(2-methoxyphenyl)pyridine-2-caboxylic acid

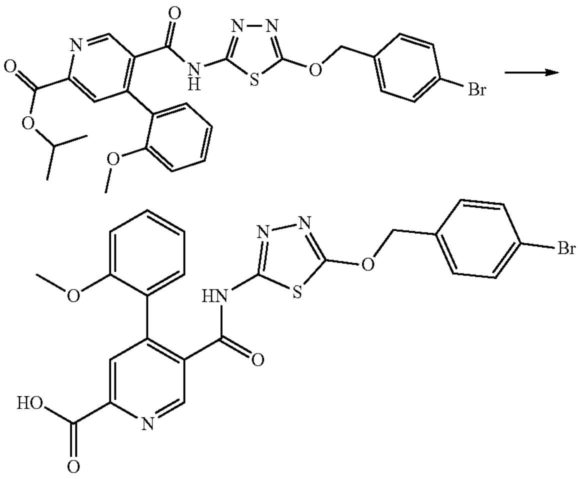

To a solution of isopropyl 5-([5-[(4-bromophenyl) methoxy]-1,3,4-thiadiazol-2-yl]carbamoyl)-4-(2-methoxyphenyl)pyridine-2-carboxylate (2.0 g, 3.4 mmol) in MeOH (50 mL) was added $LiOH \cdot H_2O$ (0.57 g, 13.8 mmol) and water (10 mL) at room temperature. The mixture was stirred for 2 hours. The mixture was diluted with water and MeOH was removed under reduced pressure. The pH of the mixture was adjusted pH 6-7 with formic acid. The solid was collected by filtration to afford the title compound (1.1 g, 57% yield) as an off-white solid. $^1H$ NMR (300 MHz, DMSO-$d_6$): δ 8.81 (s, 1H), 7.87 (s, 1H), 7.60 (d, 2H), 7.47-7.31 (m, 4H), 7.07-6.93 (m, 2H), 5.42 (s, 2H), 3.53 (s, 3H). m/z 541 $[M+H^+]$.

Example 153

Synthesis of N-[5-[(4-bromophenyl)methoxy]-1,3,4-thiadiazol-2-yl]-4-(2-methoxyphenyl)pyridine-3-carboxamide

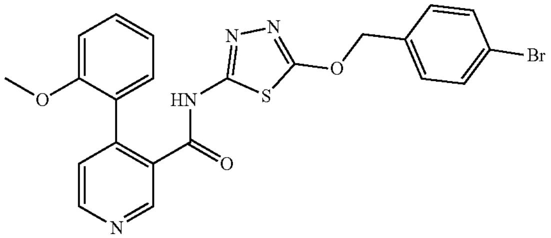 [SMILES: COc1ccccc1-c1ccncc1C(=O)Nc1nnc(OCc2ccc(Br)cc2)s1]

The title compound was prepared using similar procedures as Example 77, replacing 5-((4-chlorobenzyl)oxy)-1,3,4-thiadiazol-2-amine (Intermediate B) with 5-((4-bromobenzyl)oxy)-1,3,4-thiadiazol-2-amine (Example 40, Step 1). $^1H$ NMR (300 MHz, DMSO-$d_6$): δ 3.52 (s, 3H), 5.45 (s, 2H), 7.00 (d, 1H) 7.05-7.09 (m, 1H) 7.34-7.40 (m, 1H), 7.42-7.47 (m, 4H), 7.59-7.62 (m, 2H), 8.74 (s, 1H), 8.75 (s, 1H), 12.79 (s, 1H). m/z 497 $[M+H]^+$.

Example 154

Synthesis of 6-cyano-N-(5-(2-cyclopropylethoxy)-1,3,4-thiadiazol-2-yl)-4-(2-methoxyphenyl)nicotinamide

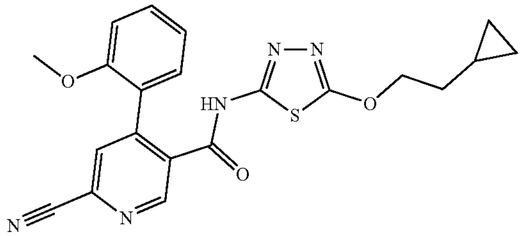 [SMILES: COc1ccccc1-c1cc(C#N)ncc1C(=O)Nc1nnc(OCCC2CC2)s1]

Step 1. Preparation of 5-(2-cyclopropylethoxy)-1,3,4-thiadiazol-2-amine

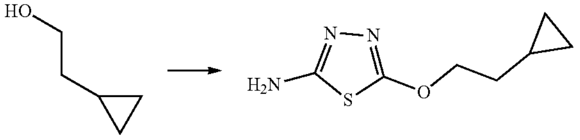 [SMILES: OCCC1CC1 ; Nc1nnc(OCCC2CC2)s1]

The title compound was prepared using similar procedures as the synthesis of Intermediate C, replacing (5-chloropyridin-2-yl)methanol with 2-cyclopropylethanol in Step 1.

Step 2. Preparation of 6-cyano-N-(5-(2-cyclopropylethoxy)-1,3,4-thiadiazol-2-yl)-4-(2-methoxyphenyl) nicotinamide

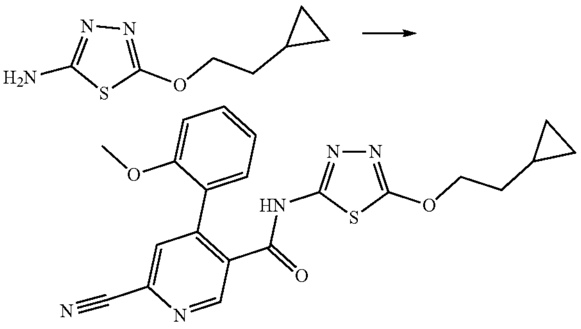

The title compound was prepared using General Procedure A employing 5-(2-cyclopropylethoxy)-1,3,4-thiadiazol-2-amine and 6-cyano-4-(2-methoxyphenyl)pyridine-3-carboxylic acid (Example, 92, Step 4). $^1H$ NMR (300 MHz, DMSO-$d_6$): δ13.02 (s, 1H), 8.95 (s, 1H), 8.14 (s, 1H), 7.45 (d, 2H), 7.10-7.01 (m, 2H), 4.46 (t, 2H), 3.73 (s, 3H), 1.70-1.57 (m, 2H), 0.89-0.74 (m, 1H), 0.46-0.39 (m, 2H), 0.13-0.10 (m, 2H). m/z 422 $[M+H^+]$.

Example 155

Synthesis of N-[5-[(4-chlorophenyl)methoxy]-1,3,4-thiadiazol-2-yl]-4-(4-fluoro-2-methoxyphenyl)pyridine-3-carboxamide

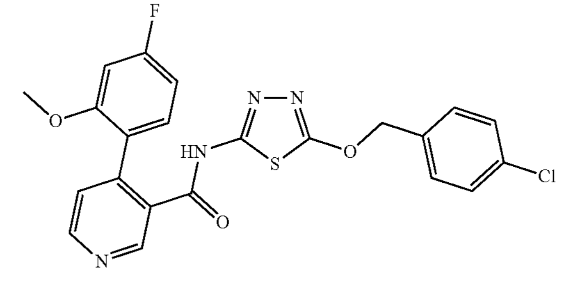 [SMILES: COc1cc(F)ccc1-c1ccncc1C(=O)Nc1nnc(OCc2ccc(Cl)cc2)s1]

The title compound was prepared using General Procedures E, F and A. For General Procedure E, methyl 4-chloropyridine-3-carboxylate and 4-fluoro-2-methoxyphenylboronic acid were employed. For General Procedure A, 5-((4-chlorobenzyl)oxy)-1,3,4-thiadiazol-2-amine (Intermediate B) was used. $^1$H NMR (300 MHz, DMSO-$d_6$): δ12.84 (s, 1H), 8.77 (d, 2H), 7.55-7.47 (m, 4H), 7.43-7.36, (m, 2H), 6.90 (d, 2H), 5.48 (s, 2H), 3.53 (s, 3H). m/z 471 [M+H$^+$].

Example 156

Synthesis of N-[5-[(4-chlorophenyl)methoxy]-1,3,4-thiadiazol-2-yl]-4-(2-methoxyphenyl)-6-(trifluoromethyl)pyridine-3-carboxamide

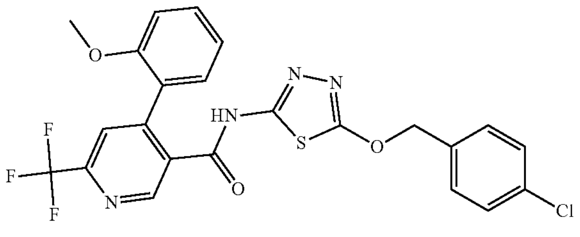 [SMILES: COc1ccccc1-c1cc(C(F)(F)F)ncc1C(=O)Nc1nnc(OCc2ccc(Cl)cc2)s1]

Step 1. Preparation of methyl 4-chloro-6-(trifluoromethyl)pyridine-3-carboxylate

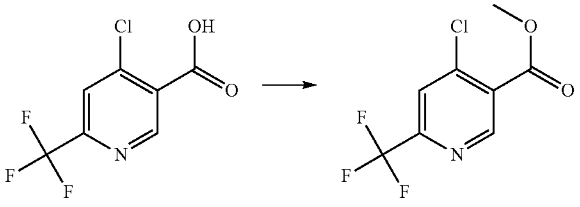

To a solution of 4-chloro-6-(trifluoromethyl)pyridine-3-carboxylic acid (480 mg, 2.1 mmol) in THF (5 mL) was added $Ph_3P$ (2791 mg, 10.6 mmol) and MeOH (682 mg, 21.3 mmol) at 0° C. The mixture was stirred for 2 min at 0° C. and then DIAD (2152 mg, 10.6 mmol) was added and the mixture warmed to rt and stirred for 1 h. The mixture was diluted with water and extracted with EtOAc (3×). The combined organic layers were concentrated under reduced pressure. The residue was purified by silica gel column chromatography, eluted with 2% EtOAc in PE to afford the title compound (415 mg, 81% yield) as a white solid.

Step 2. Preparation of N-[5-[(4-chlorophenyl)methoxy]-1,3,4-thiadiazol-2-yl]-4-(2-methoxyphenyl)-6-(trifluoromethyl)pyridine-3-carboxamide

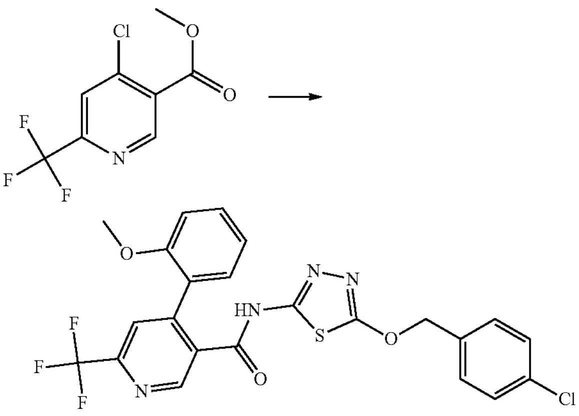

The title compound was prepared using General Procedures E, F and A. For General Procedure E, methyl 4-chloro-6-(trifluoromethyl)pyridine-3-carboxylate and 4-fluoro-2-methoxyphenylboronic acid were employed. For General Procedure A, 5-((4-chlorobenzyl)oxy)-1,3,4-thiadiazol-2-amine (Intermediate B) was used. 1H NMR (300 MHz, DMSO-$d_6$): δ 13.04 (s, 1H), 9.00 (s, 1H), 7.92 (s, 1H), 7.56-7.43 (m, 6H), 7.13-7.02 (m, 2H), 5.49 (s, 2H), 3.54 (s, 3H). m/z 521 [M+H+].

Example 157

Synthesis of N-(5-((3-chlorobenzyl)oxy)-1,3,4-thiadiazol-2-yl)-3-(2-methoxyphenyl)isonicotinamide

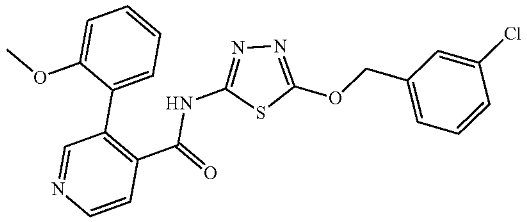 [SMILES: COc1ccccc1-c1cnccc1C(=O)Nc1nnc(OCc2cccc(Cl)c2)s1]

The title compound was prepared using similar procedures as the synthesis of Example 141, Step 2 and 3, replacing 1-[4-(hydroxymethyl)phenyl]cyclopropane-1-carbonitrile with m-chlorobenzyl alcohol in Step 2. $^1$H NMR (300 MHz, DMSO-$d_6$): δ12.88 (s, 1H), 8.72 (d, 1H), 8.61 (s, 1H), 7.63-7.59 (m, 1H), 7.59 (s, 1H), 7.45-7.44 (m, 3H), 7.40-7.35 (m, 2H), 7.09-7.04 (m, 1H), 6.99 (d, 1H), 5.48 (s, 2H), 3.51 (s, 3H). m/z 453 [M+H$^+$].

Example 158

Synthesis of N-[5-[(3,4-dichlorophenyl)methoxy]-1,3,4-thiadiazol-2-yl]-3-(2-methoxyphenyl)pyridine-4-carboxamide

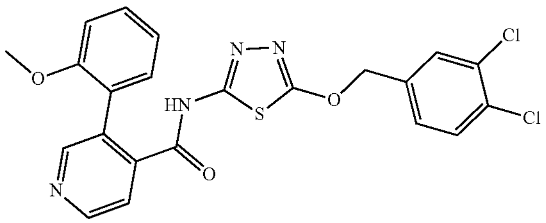 [SMILES: COc1ccccc1-c1cnccc1C(=O)Nc1nnc(OCc2ccc(Cl)c(Cl)c2)s1]

The title compound was prepared using similar procedures as the synthesis of Example 141, Step 2 and 3, replacing 1-[4-(hydroxymethyl)phenyl]cyclopropane-1-carbonitrile with 3,4-dichlorobenzyl alcohol in Step 2. 1H NMR (400 MHz, DMSO-$d_6$): δ12.86 (s, 1H), 8.71 (d, 1H), 8.61 (s, 1H), 7.80 (d, 1H), 7.69 (d, 1H), 7.63-7.62 (m, 1H), 7.52-7.49 (m, 1H), 7.40-7.35 (m, 2H), 7.06 (t, 1H), 6.99 (d, 1H), 5.48 (s, 2H), 3.51 (s, 3H). m/z 487 [M+H+].

Example 159

Synthesis of N-(5-((4-chlorobenzyl)oxy)-1,3,4-thiadiazol-2-yl)-3-(3-cyano-2-methoxyphenyl)isonicotinamide

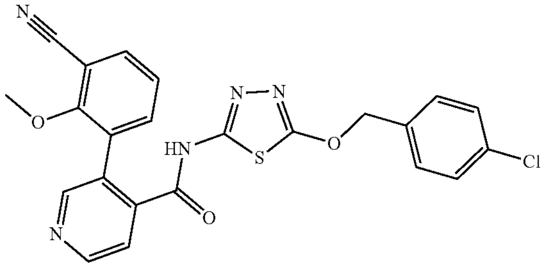 [SMILES: COc1c(C#N)cccc1-c1cnccc1C(=O)Nc1nnc(OCc2ccc(Cl)cc2)s1]

Step 1. Preparation of 2-methoxy-3-(4,4,5,5-tetramethyl-1,3,2-dioxaborolan-2-yl)benzonitrile

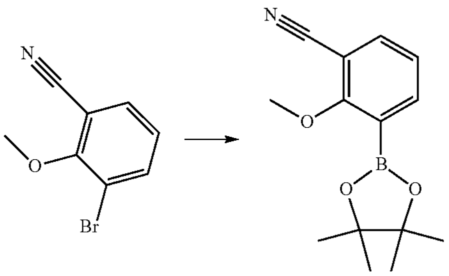

To a solution of 3-bromo-2-methoxybenzonitrile (200 mg, 0.94 mmol) in dioxane (3.0 mL) was added bis(pinacolato) diboron (287 mg, 1.1 mmol), $K_3PO_4$ (400 mg, 1.9 mmol) and [1,1'-bis(diphenylphosphino)ferrocene]dichloropalladium(II) (69 mg, 0.09 mmol) at room temperature. The mixture was stirred for 4 h at 80° C. under nitrogen atmosphere. The mixture was cooled to room temperature, diluted with water and extracted with EtOAc (2×). The combined organic layers were concentrated under reduced pressure. The residue was purified by Prep-TLC (PE:EtOAc, 5:1) to afford the title compound (56 mg, 23% yield) as a yellow oil.

Step 2. Preparation of N-(5-((4-chlorobenzyl)oxy)-1,3,4-thiadiazol-2-yl)-3-(3-cyano-2-methoxyphenyl) isonicotinamide

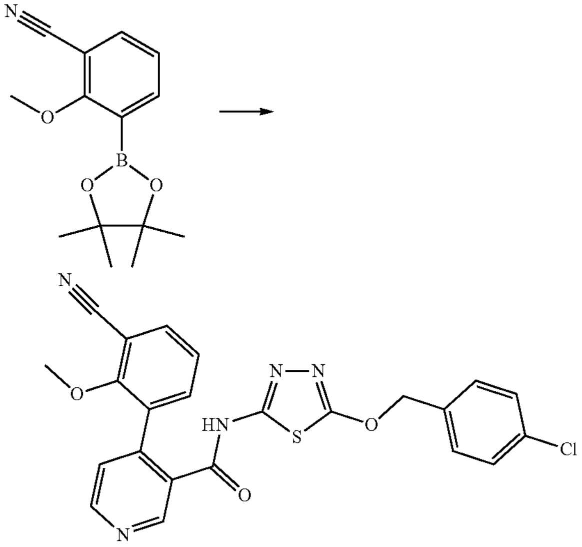

The title compound was prepared using General Procedures E, F and A. For General Procedure E, 2-methoxy-3-(4,4,5,5-tetramethyl-1,3,2-dioxaborolan-2-yl)benzonitrile and methyl 3-bromopyridine-4-carboxylate were employed. For General Procedure A, 5-((4-chlorobenzyl)oxy)-1,3,4-thiadiazol-2-amine (Intermediate B) was used. $^1H$ NMR (300 MHz, DMSO-$d_6$): δ13.10 (s, 1H), 8.79 (d, 1H), 8.64 (s, 1H), 7.83-7.77 (m, 2H), 7.67 (d, 1H), 7.54-7.45 (m, 4H), 7.35 (t, 1H), 5.45 (s, 2H), 3.55 (s, 3H). m/z 478 [$M+H^+$].

Example 160

Synthesis of N-(5-((4-chlorobenzyl)oxy)-1,3,4-thiadiazol-2-yl)-2-methoxy-5-(2-methoxyphenyl)isonicotinamide

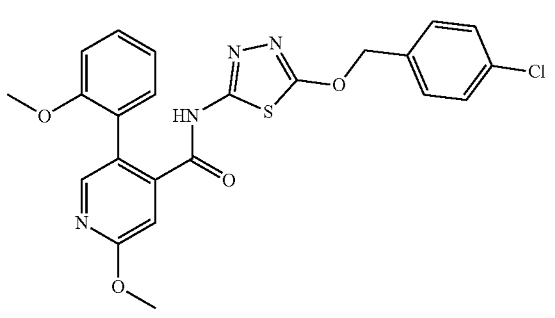 [SMILES: COc1cc(C(=O)Nc2nnc(OCc3ccc(Cl)cc3)s2)c(-c2ccccc2OC)cn1]

Step 1. Preparation of methyl 5-bromo-2-methoxypyridine-4-carboxylate

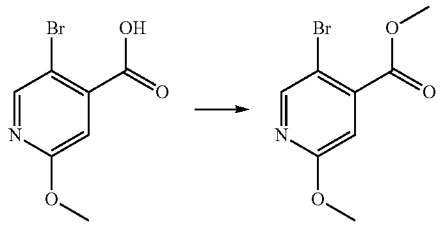

To a solution of 5-bromo-2-methoxypyridine-4-carboxylic acid (800 mg, 3.4 mmol) in THF (8.0 mL) was added MeOH (221 mg, 6.9 mmol), $PPh_3$ (1809 mg, 6.9 mmol) and DIAD (1046 mg, 5.2 mmol) at 0° C. The mixture was stirred for 1 hour at 0° C. The mixture was diluted with water and extracted with EtOAc. The organic layer was concentrated under reduced pressure. The residue was purified by Prep-TLC (PE:EtOAc, 20:1) to afford the title compound (800 mg, 94% yield) as a white solid.

Step 2. Preparation of N-(5-((4-chlorobenzyl)oxy)-1,3,4-thiadiazol-2-yl)-2-methoxy-5-(2-methoxyphen 1 isonicotinamide

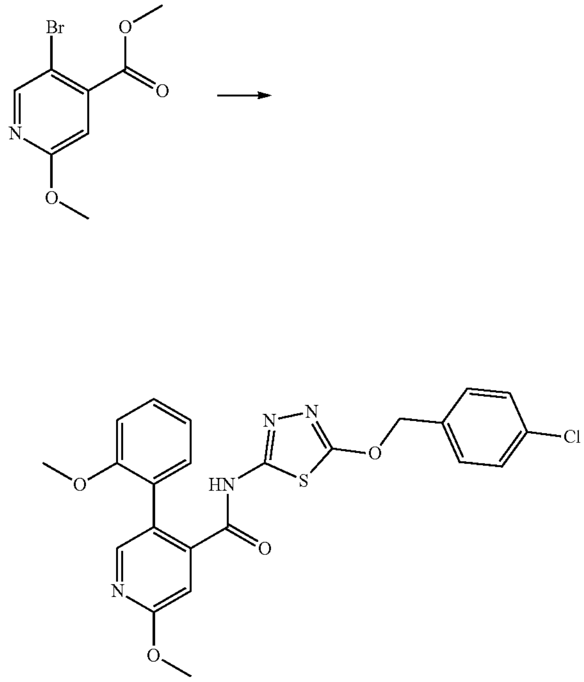

The title compound was prepared using General Procedures E, F and A. For General Procedure E, methyl 5-bromo-2-methoxypyridine-4-carboxylate and 2-methoxyphenylboronic acid were employed. For General Procedure A, 5-((4-chlorobenzyl)oxy)-1,3,4-thiadiazol-2-amine (Intermediate B) was used. $^1$H NMR (300 MHz, DMSO-$d_6$): δ12.83 (s, 1H), 8.17 (s, 1H), 7.55-7.47 (m, 4H), 7.37-7.31 (m, 2H), 7.09 (s, 1H), 7.06-7.01 (m, 1H), 6.95 (d, 1H), 5.48 (s, 2H), 3.95 (s, 3H), 3.49 (s, 3H). m/z 483 [M+H$^+$].

Example 161

Synthesis of N-(5-((4-chlorobenzyl)oxy)-1,3,4-thiadiazol-2-yl)-6-(2-methoxyphenyl)imidazo[1,2-a]pyridine-7-carboxamide

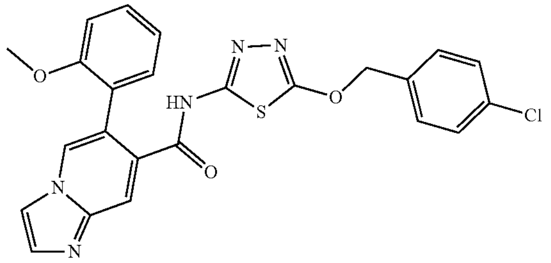 [SMILES: COc1ccccc1-c1cn2ccnc2cc1C(=O)Nc1nnc(OCc2ccc(Cl)cc2)s1]

Step 1. Preparation of methyl 2-amino-5-bromopyridine-4-carboxylate

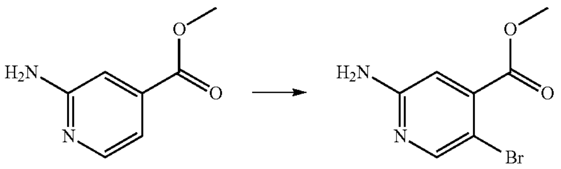

To a solution of methyl 2-aminopyridine-4-carboxylate (5.0 g, 32.9 mmol) in DMF (50 mL) was added NBS (6.3 g, 36.1 mmol) at rt. The mixture was stirred for 2 h at rt under nitrogen atmosphere. The mixture was diluted with water and extracted with EtOAc (3×). The combined organic layers were concentrated under vacuum. The residue was purified by silica gel column chromatography, eluted with 100% $CH_2Cl_2$ to afford the title compound (3.5 g, 46% yield) as a yellow oil.

Step 2. Preparation of methyl 6-bromoimidazo[1,2-a]pyridine-7-carboxylate

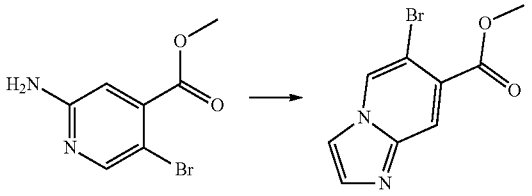

To a solution of methyl 2-amino-5-bromopyridine-4-carboxylate (3.3 g, 14.3 mmol) in EtOH (35 mL), was added $NaHCO_3$ (2.0 g, 24.3 mmol) and chloroacetaldehyde (5.05 g, 64.3 mmol) at room temperature. The mixture was stirred for overnight at 80° C. under nitrogen atmosphere. The mixture was diluted with water and extracted with EtOAc (3×). The combined organic layers were was concentrated under vacuum. The residue was purified by silica gel column chromatography, eluted with 100% $CH_2Cl_2$ to afford the title compound (3.9 g, 96% yield) as a yellow oil.

Step 3. Preparation of N-(5-((4-chlorobenzyl)oxy)-1,3,4-thiadiazol-2-yl)-6-(2-methoxyphenyl)imidazo[1,2-a]pyridine-7-carboxamide

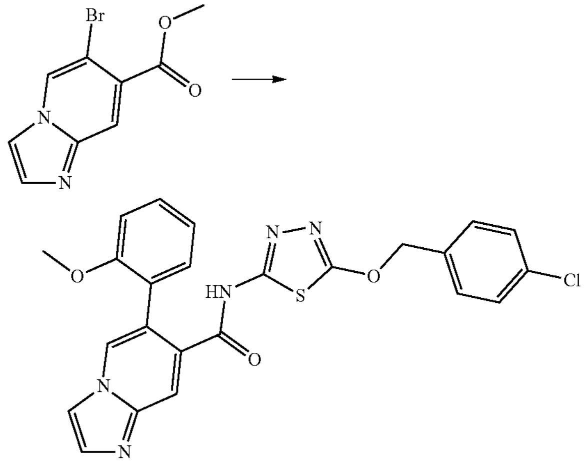

The title compound was prepared using General Procedures E, F and A. For General Procedure E, methyl 6-bromoimidazo[1,2-a]pyridine-7-carboxylate and 2-methoxyphenylboronic acid were employed. For General Procedure A, 5-((4-chlorobenzyl)oxy)-1,3,4-thiadiazol-2-amine (Intermediate B) was used. $^1$H NMR (400 MHz, DMSO-$d_6$): δ12.81 (s, 1H), 8.56 (s, 1H), 8.05 (s, 1H), 7.92 (s, 1H), 7.73 (s, 1H), 7.54-7.47 (m, 4H), 7.39-7.33 (m, 2H), 7.06-7.03 (m, 1H), 6.95-6.93 (m, 1H), 5.47 (s, 2H), 3.49 (s, 3H). m/z 492 [M+H$^+$].

Example 162

Synthesis of N-(5-((4-chlorobenzyl)oxy)-1,3,4-thiadiazol-2-yl)-3-(3-methyl-1H-pyrazol-4-yl)isonicotinamide

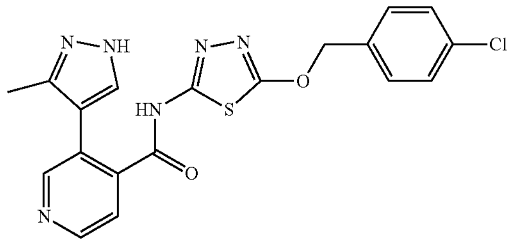 [SMILES: Cc1n[nH]cc1-c1cnccc1C(=O)Nc1nnc(OCc2ccc(Cl)cc2)s1]

The title compound was prepared using General Procedures E, F and A. For General Procedure E, methyl 3-bromopyridine-4-carboxylate and 3-methyl-1H-pyrazol-4-ylboronic acid were employed. For General Procedure A, 5-((4-chlorobenzyl)oxy)-1,3,4-thiadiazol-2-amine (Intermediate B) was used. $^1$H NMR (300 MHz, DMSO-$d_6$): δ 12.80 (s, 2H), 8.65-8.58 (m, 2H), 7.61-7.47 (m, 6H), 5.48 (s, 2H), 2.18 (s, 3H). m/z 427 [M+H$^+$].

Example 163

Synthesis of 6-(3-amino-3-oxopropyl)-N-(5-((4-chlorobenzyl)oxy)-1,3,4-thiadiazol-2-yl)-4-(2-methoxyphenyl)nicotinamide

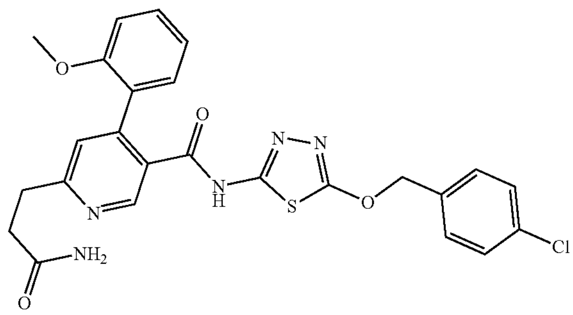

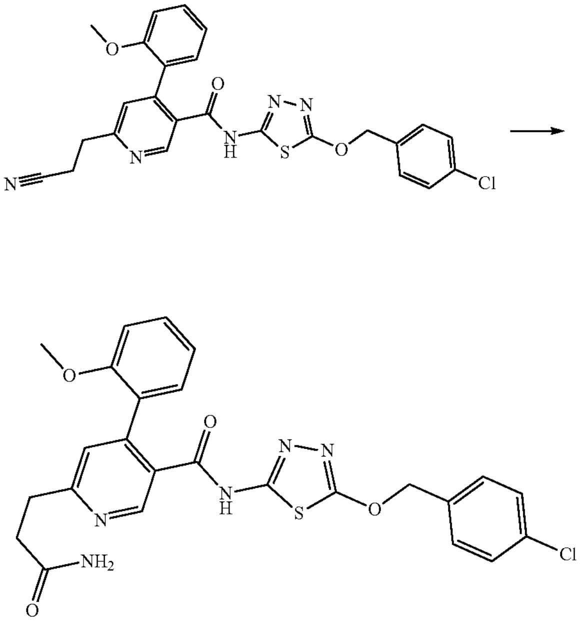

To a solution of N-[5-[(4-chlorophenyl)methoxy]-1,3,4-thiadiazol-2-yl]-6-(2-cyanoethyl)-4-(2-methoxyphenyl)pyridine-3-carboxamide (24 mg, 0.047 mmol, Example 164) in $H_2O_2$ (30%, 21 mg, 0.190 mmol) and EtOH (2 mL) was added a solution of LiOH (2.3 mg, 0.095 mmol) in water (1.0 mL) dropwise at room temperature under air atmosphere. The mixture was stirred for 3 h at 70° C. The mixture was cooled to rt, diluted with water, and extracted with EtOAc (2×). The combined organic layers were concentrated under reduced pressure. The residue was purified by Prep-TLC (DCM:MeOH, 15:1) to afford the title compound (12 mg, 46% yield) as a white solid. $^1$H NMR (300 MHz, DMSO-$d_6$): δ 12.75 (s, 1H), 8.68 (s, 1H), 7.55-7.49 (m, 4H), 7.42-7.35 (m, 3H), 7.30 (s, 1H), 7.10 (t, 1H), 6.98 (d, 1H), 6.81 (s, 1H), 5.47 (s, 2H), 3.50 (s, 3H), 3.05 (t, 2H), 2.59-2.56 (m, 2H). m/z 524 [M+H$^+$].

Example 164

Synthesis of N-[5-[(4-chlorophenyl)methoxy]-1,3,4-thiadiazol-2-yl]-6-(2-cyanoethyl)-4-(2-methoxyphenyl)pyridine-3-carboxamide

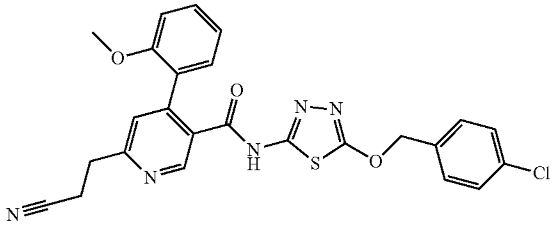 [SMILES: COc1ccccc1-c1cc(CCC#N)ncc1C(=O)Nc1nnc(OCc2ccc(Cl)cc2)s1]

Step 1. Preparation of ethyl 6-chloro-4-(2-methoxyphenyl)pyridine-3-carboxylate

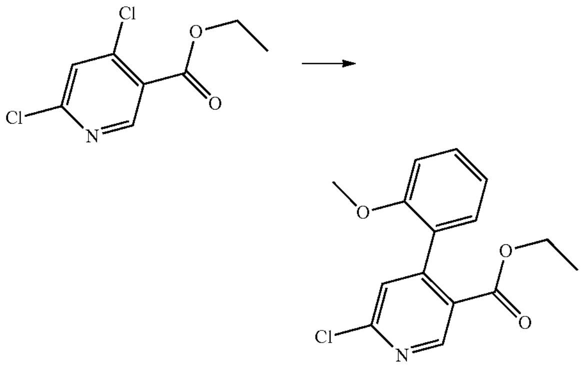

To a solution of ethyl 4,6-dichloropyridine-3-carboxylate (10 g, 45.4 mmol) in dioxane (100 mL) and water (20 mL) was added 2-methoxyphenylboronic acid (6.9 g, 45.5 mmol), $K_2CO_3$ (12.6 g, 90.9 mmol) and Pd(DTBPF)$Cl_2$ (3.0 g, 4.5 mmol) under nitrogen atmosphere. The solution was stirred for 3 hr at 80° C. The mixture was cooled to rt, diluted with water and extracted with EtOAc (2×). The combined organic layers were concentrated under reduced pressure. The residue was purified by silica gel column chromatography, eluted with 6% EtOAc in PE to afford the title compound (4.5 g, 32% yield) as a yellow solid.

Step 2. Preparation of ethyl 6-ethenyl-4-(2-methoxyphenyl)pyridine-3-carboxylate

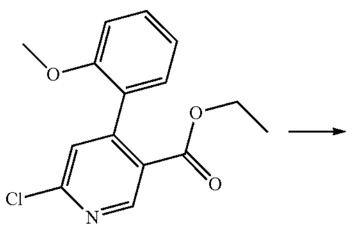

-continued

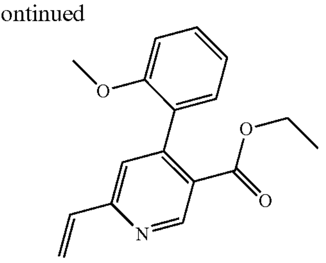

To a solution of ethyl 6-chloro-4-(2-methoxyphenyl)pyridine-3-carboxylate (2 g, 6.9 mmol) in DMF (20 mL) was added tributyl(ethenyl)stannane (2.6 g, 8.2 mmol) and $Pd(PPh_3)_4$ (0.79 g, 0.684 mmol) under nitrogen atmosphere. The solution was stirred for 3 hr at 100° C. The mixture was cooled to rt, diluted with water and extracted with EtOAc (2×). The combined organic layers were concentrated under reduced pressure. The residue was purified by silica gel column chromatography, eluted with 9% EtOAc in PE to afford the title compound (2 g, 99.9/0 yield) as a yellow oil.

Step 3. Preparation of ethyl 6-(2-hydroxyethyl)-4-(2-methoxyphenyl)pyridine-3-carboxylate

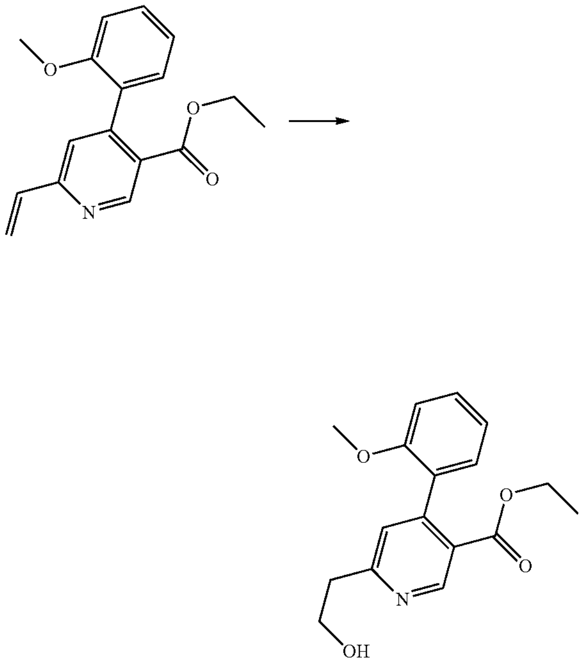

To a solution of ethyl 6-ethenyl-4-(2-methoxyphenyl) pyridine-3-carboxylate (2 g, 7.1 mmol) in THF was added $BH_3$ (1M in THF, 23 mL, 23 mmol) dropwise at room temperature. The mixture was heated to 55° C. for 1 h. The mixture was cooled to 0° C. and then $K_2CO_3$ (1M in water, 24 mL, 24 mmol) was added dropwise followed by $H_2O_2$ (30%, 20 mL, 858 mmol). The mixture was stirred for 2 h at room temperature. The mixture was diluted with water and extracted with EtOAc (2×). The combined organic layers were concentrated under reduced pressure. The residue was purified by silica gel column chromatography, eluted with 17% EtOAc in hexanes to afford the title compound (400 mg, 17% yield) as a light-yellow oil.

Step 4. Preparation of ethyl 6-(2-chloroethyl)-4-(2-methoxyphenyl)pyridine-3-carboxylate

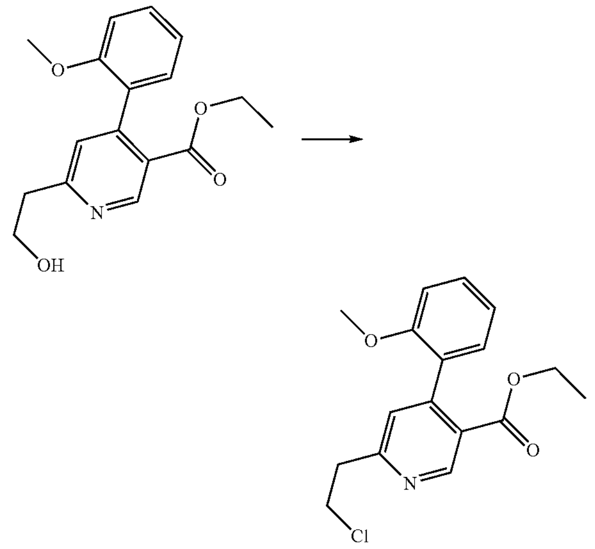

To a solution of ethyl 6-(2-hydroxyethyl)-4-(2-methoxyphenyl)pyridine-3-carboxylate (400 mg, 1.3 mmol) in DCM was added $SOCl_2$ (1579 mg, 13.3 mmol). The mixture was stirred overnight at room temperature. The mixture was quenched with water and extracted with DCM (2×). The combined organic layers were concentrated under reduced pressure. The residue was purified by Prep-TLC (DCM: MeOH, 30:1) to afford the title compound (300 mg, 67% yield) as a light-yellow oil.

Step 5. Preparation of ethyl 6-(2-cyanoethyl)-4-(2-methoxyphenyl)pyridine-3-carboxylate

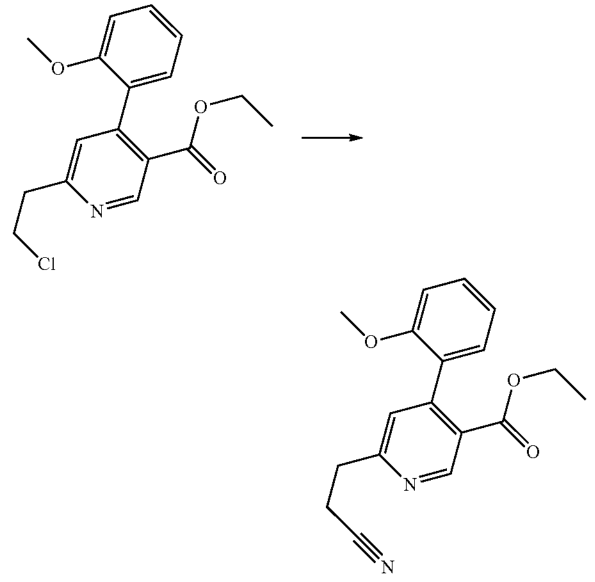

To a solution of ethyl 6-(2-chloroethyl)-4-(2-methoxyphenyl)pyridine-3-carboxylate (300 mg, 0.94 mmol) in DMSO (5 mL) was added NaCN (230 mg, 4.7 mmol). The mixture was stirred for 2 hr at 90° C. The mixture was cooled to rt, diluted with water and extracted with EtOAc (3×). The combined organic layers were concentrated under reduced pressure. The residue was purified by Prep-TLC (hexanes:EtOAc, 5:1) to afford the title compound (180 mg, 59% yield) as a light brown oil.

Step 6. Preparation of 6-(2-cyanoethyl)-4-(2-methoxyphenyl)pyridine-3-carboxylic acid

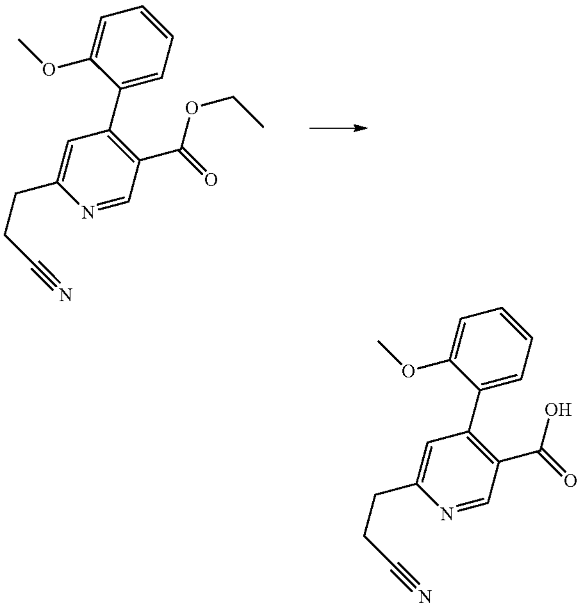

To a solution of ethyl 6-(2-cyanoethyl)-4-(2-methoxyphenyl)pyridine-3-carboxylate (150 mg, 0.48 mmol) in ethanol (3 mL) were added a solution of $LiOH·H_2O$ (40 mg, 0.97 mmol) in water (1 mL) dropwise at room temperature. The mixture was stirred for 3 hr at 60° C. The mixture was acidified to pH 5 with HCl (2 M). The mixture was concentrated under reduced pressure. The residue was purified by reverse phase chromatography (column, C18 silica gel; mobile phase, with 10-30% MeCN in water) to afford the title compound (80 mg, 56% yield) as an off-white solid.

Step 7. Preparation of N-[5-[(4-chlorophenyl)methoxy]-1,3,4-thiadiazol-2-yl]-6-(2-cyanoethyl)-4-(2-methoxyphenyl)pyridine-3-carboxamide

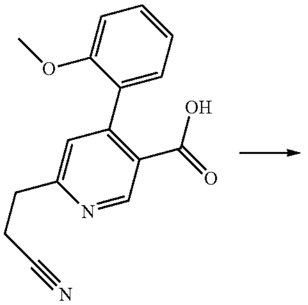

-continued

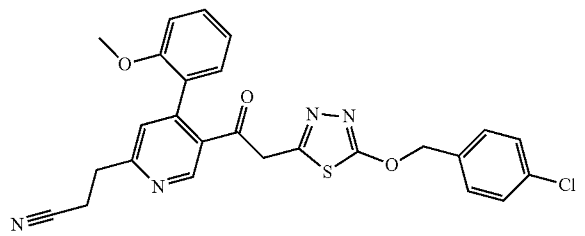

The title compound was prepared using General Procedure A employing 6-(2-cyanoethyl)-4-(2-methoxyphenyl) pyridine-3-carboxylic acid and 5-((4-chlorobenzyl)oxy)-1,3,4-thiadiazol-2-amine (Intermediate B). $^1$H NMR (300 MHz, DMSO-$d_6$): δ 12.82 (s, 1H), 8.74 (s, 1H), 7.56-7.47 (m, 4H), 7.43-7.36 (m, 3H), 7.10 (t, 1H), 7.00 (d, 1H), 5.48 (s, 2H), 3.51 (s, 3H), 3.19 (t, 2H), 3.00 (t, 2H). m/z 506 [M+H$^+$].

Example 165

Synthesis of N-(5-((4-chlorobenzyl)oxy)-1,3,4-thiadiazol-2-yl)-3-(2-(3-hydroxycyclobutoxy)phenyl) isonicotinamide

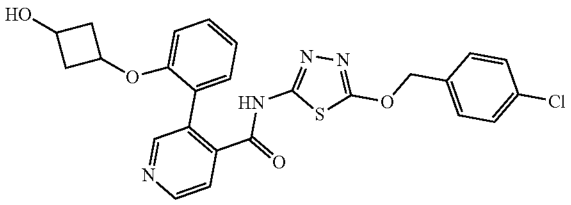 [SMILES: O=C(Nc1nnc(OCc2ccc(Cl)cc2)s1)c1ccncc1-c1ccccc1OC1CC(O)C1]

Step 1. Preparation of 3-(benzyloxy)cyclobutan-1-ol

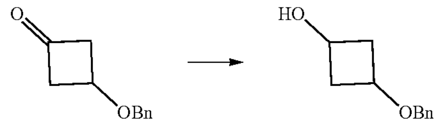 [SMILES: O=C1CC(OCc2ccccc2)C1 ; OC1CC(OCc2ccccc2)C1]

To a solution of 3-(benzyloxy)cyclobutan-1-one (7 g, 39.7 mmol) in MeOH (70 mL) was added $NaBH_4$ (3.0 g, 79.4 mmol) in portions at 0° C. under air atmosphere. The mixture was stirred for overnight at 0° C. under air atmosphere. The mixture was warmed to rt and quenched by the addition of $NH_4Cl$ (aq.) The mixture was extracted with EtOAc (3×). The combined organic layers were concentrated under reduced pressure. The residue was purified by silica gel column chromatography, 9% eluted with EtOAc in PE to afford the title compound (4.2 g, 59% yield) as a yellow oil.

Step 2. Preparation of 1-(3-(benzyloxy)cyclobutoxy)-2-bromobenzene

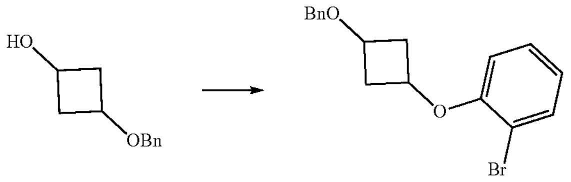 [SMILES: OC1CC(OCc2ccccc2)C1 ; Brc1ccccc1OC1CC(OCc2ccccc2)C1]

To a solution of 3-(benzyloxy)cyclobutan-1-ol (4.2 g, 23.6 mmol) in THF (45 mL) was added 2-bromophenol (6.2 g, 35.3 mmol) and $PPh_3$ (15.5 g, 58.9 mmol) at 0° C. under nitrogen atmosphere. Then DIAD (9.5 g, 47.1 mmol) was added at 0° C. in in portions over 20 min. The mixture was stirred for overnight at 60° C. The mixture was cooled to rt and diluted with water. The mixture was extracted with EtOAc (3×). The organic layers were concentrated under reduced pressure. The residue was purified by silica gel column chromatography, eluted with 1% EtOAc in PE to afford the title compound (5.2 g, 62% yield) as a light yellow solid.

Step 3. Preparation of 2-(2-(3-(benzyloxy)cyclobutoxy)phenyl)-4,4,5,5-tetramethyl-1,3,2-dioxaborolane

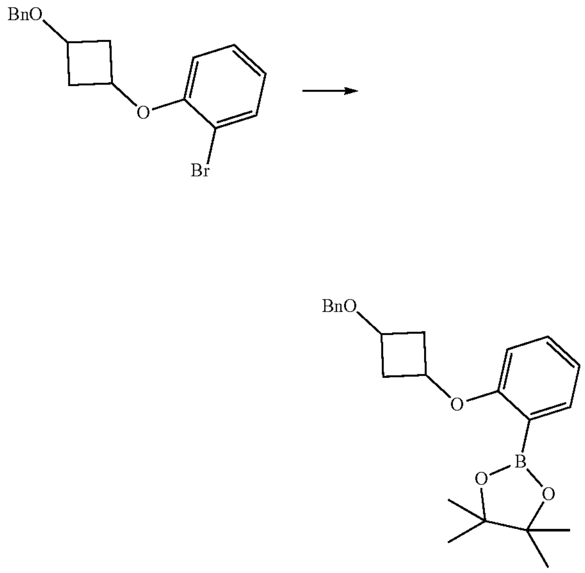

To a solution of 1-(3-(benzyloxy)cyclobutoxy)-2-bromobenzene (1 g, 31 mmol) in dioxane (10 mL) was added and bis(pinacolato)diboron (1.5 g, 6.0 mmol), KOAc (0.6 g, 62 mmol) and [1,1'-bis(diphenylphosphino)ferrocene]dichloropalladium(II) (0.22 g, 0.300 mmol) under nitrogen atmosphere. The mixture was stirred for overnight at 80° C. The mixture was cooled room temperature and diluted with water. The mixture was extracted with EtOAc (3×). The combined organic layers were concentrated under reduced pressure. The residue was purified by silica gel column chromatography, eluted with 2% EtOAc in PE to afford the title compound (900 mg, 79% yield) as a light brown solid.

Step 4. Preparation of methyl 3-(2-(3-(benzyloxy)cyclobutoxy)phenyl)isonicotinate

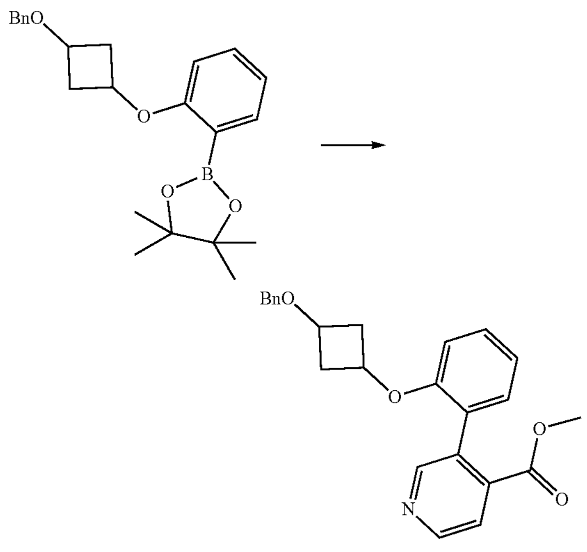

The title compound was prepared using General Procedure E employing 2-(2-(3-(benzyloxy)cyclobutoxy)phenyl)-4,4,5,5-tetramethyl-1,3,2-dioxaborolane and methyl 3-bromopyridine-4-carboxylate.

Step 5. Preparation of methyl 3-(2-(3-hydroxycyclobutoxy)phenyl)isonicotinate

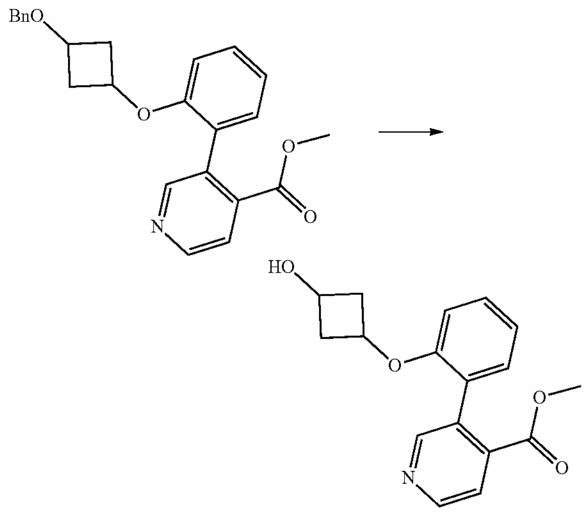

To a solution of methyl 3-(2-(3-(benzyloxy)cyclobutoxy)phenyl)isonicotinate (580 mg, 1.5 mmol) in MeOH (150 mL) was added Pd/C (10%, 0.119 g) under nitrogen atmosphere. The mixture stirred at room temperature overnight under hydrogen atmosphere. The mixture was filtered through a Celite pad and the filtrate was concentrated under reduced pressure to afford the title compound (430 mg, 86% yield) as a light yellow solid.

Step 6. Preparation of N-(5-((4-chlorobenzyl)oxy)-1,3,4-thiadiazol-2-yl)-3-(2-(3-hydroxycyclobutoxy)phenyl)isonicotinamide

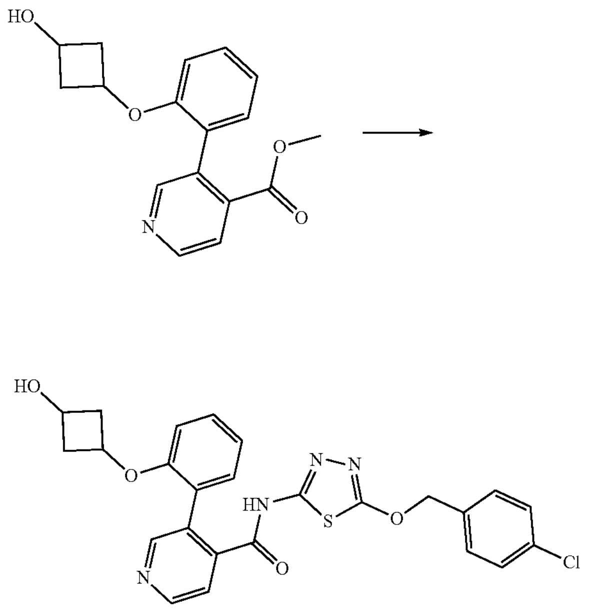

The title compound was prepared using General Procedures F and A. For General Procedure A, 5-((4-chlorobenzyl)oxy)-1,3,4-thiadiazol-2-amine (Intermediate B) was used. $^1$H NMR (300 MHz, DMSO-$d_6$): δ12.97 (s, 1H), 8.74 (d, 1H), 8.59 (s, 1H), 7.66 (d, 1H), 7.52-7.50 (m, 4H), 7.37-7.31 (m, 2H), 7.08-7.06 (m, 1H), 6.69-6.67 (m, 1H), 5.49 (s, 2H), 5.01 (d, 1H), 4.66-4.62 (m, 1H), 3.95-3.92 (m, 1H), 2.10-2.14 (m, 4H). m/z 509 [M+H$^+$].

Example 166

Synthesis of N-(5-((4-chlorobenzyl)oxy)-1,3,4-thiadiazol-2-yl)-6-(2-hydroxyethyl)-4-(2-methoxyphenyl)nicotinamide

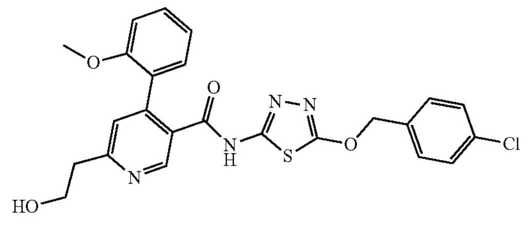 [SMILES: COc1ccccc1-c1cc(CCO)ncc1C(=O)Nc1nnc(OCc2ccc(Cl)cc2)s1]

The title compound was prepared using General Procedures F and A. For General Procedure F ethyl 6-(2-hydroxyethyl)-4-(2-methoxyphenyl)pyridine-3-carboxylate (Example 164, Step 3) was employed. For General Procedure A, 5-((4-chlorobenzyl)oxy)-1,3,4-thiadiazol-2-amine (Intermediate B) was used. $^1$H NMR (300 MHz, DMSO-$d_6$): δ 12.73 (s, 1H), 8.68 (s, 1H), 7.54-7.46 (m, 4H), 7.41-7.34 (m, 2H), 7.30 (s, 1H), 7.09 (t, 1H), 7.00 (d, 1H), 5.46 (s, 2H), 4.70 (t, 1H), 3.83-3.77 (m, 2H), 3.49 (s, 3H), 2.97 (t, 2H). m/z 497 [M+H$^+$].

Example 167

Synthesis of (R)—N-[5-[(4-chlorophenyl)methoxy]-1,3,4-thiadiazol-2-yl]-6-(1-hydroxyethyl)-4-(2-methoxyphenyl)pyridine-3-carboxamide and (S)—N-[5-[(4-chlorophenyl)methoxy]-1,3,4-thiadiazol-2-yl]-6-(1-hydroxyethyl)-4-(2-methoxyphenyl)pyridine-3-carboxamide

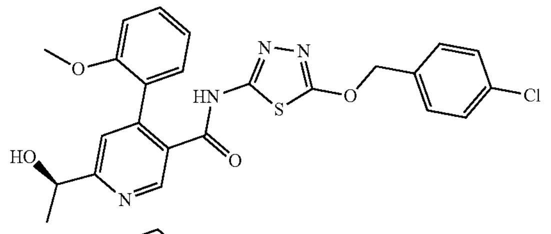

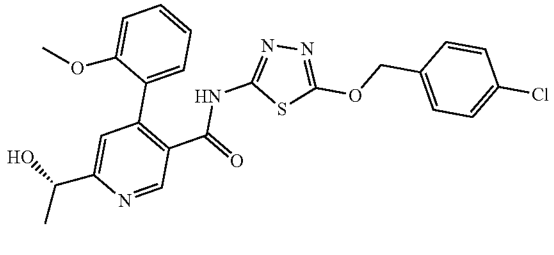

Step 1. Preparation of ethyl 6-(1-ethoxyethenyl)-4-(2-methoxyphenyl)pyridine-3-carboxylate

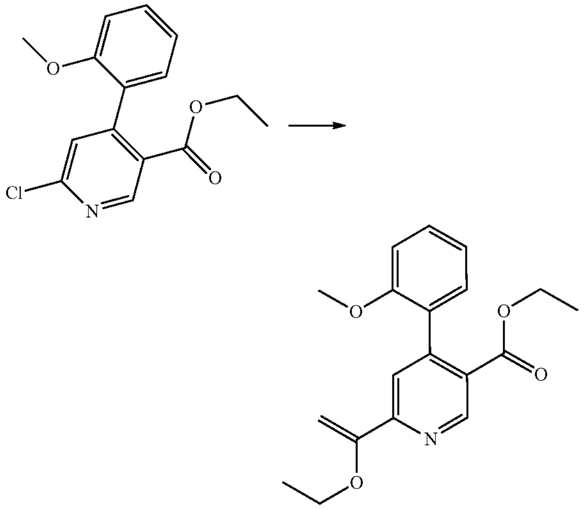

To a solution of ethyl 6-chloro-4-(2-methoxyphenyl)pyridine-3-carboxylate (400 mg, 1.4 mmol, Example 105, Step 1) in toluene (4 mL) was added tributyl(1-ethoxyethenyl) stannane (743 mg, 2.1 mmol) and $Pd(PPh_3)_4$ (158 mg, 0.14 mmol). The mixture was stirred for 4 hours at 100° C.

The mixture was cooled room temperature and diluted with water. The mixture was extracted with EtOAc. The organic layer was concentrated under reduced pressure. The residue was purified by Prep-TLC (PE:EtOAc, 2:1) to afford the title compound (350 mg, yield 73% yield) as a colorless oil.

Step 2. Preparation of ethyl 6-acetyl-4-(2-methoxyphenyl)pyridine-3-carboxylate

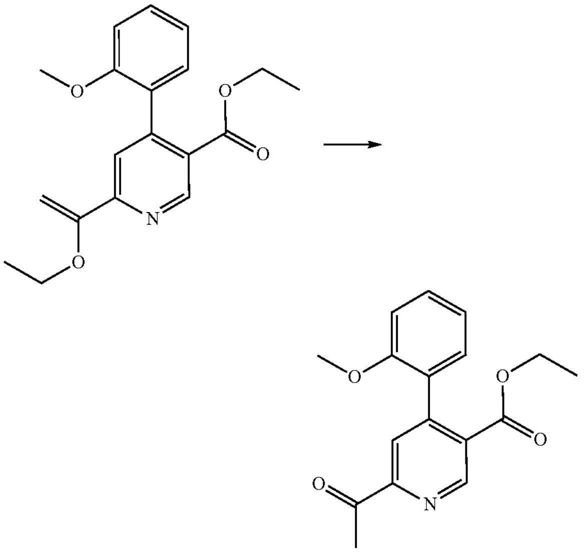

To a solution of ethyl 6-(I-ethoxyethenyl)-4-(2-methoxyphenyl)pyridine-3-carboxylate (350 mg, 1.1 mmol) in water (3 mL) was added HCl in 1,4-dioxane (3 mL). The mixture was stirred for 4 hours at room temperature. The mixture was diluted with water. The mixture was extracted with EtOAc and the organic layer was concentrated under reduced pressure to afford the title compound 410 mg (yield 92% yield) of as an off-white solid.

Step 3. Preparation of 6-acetyl-N-[5-[(4-chlorophenyl)methoxy]-1,3,4-thiadiazol-2-yl]-4-(2-methoxyphenyl)pyridine-3-carboxamide

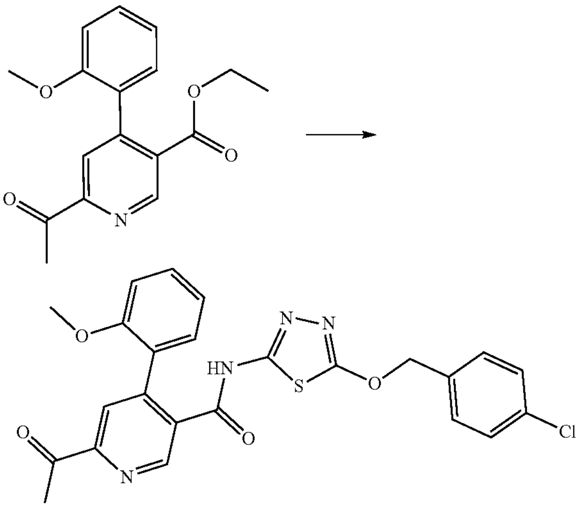

The title compound was prepared using General Procedures F and A. For General Procedure A, 5-((4-chlorobenzyl)oxy)-1,3,4-thiadiazol-2-amine (Intermediate B) was used.

Step 4. Preparation of N-[5-[(4-chlorophenyl) methoxy]-1,3,4-thiadiazol-2-yl]-6-(1-hydroxyethyl)-4-(2-methoxyphenyl)pyridine-3-carboxamide

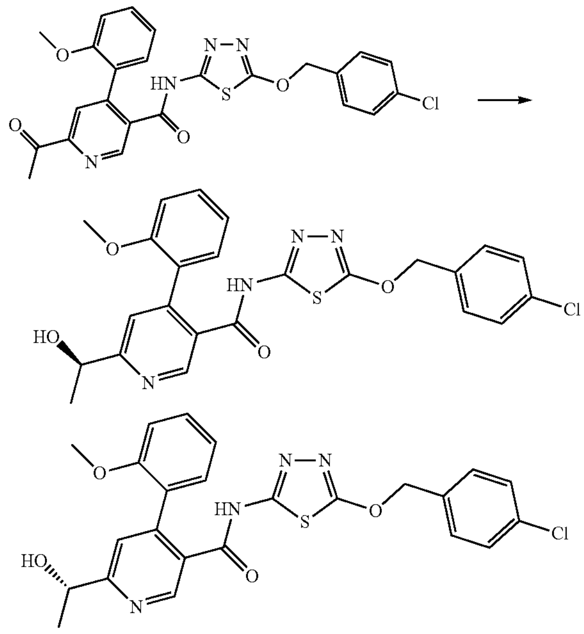

To a solution of 6-acetyl-N-[5-[(4-chlorophenyl) methoxy]-1,3,4-thiadiazol-2-yl]-4-(2-methoxyphenyl)pyridine-3-carboxamide (95 mg, 0.19 mmol) in MeOH (1 mL) at 0° C. was added a solution of $NaBH_4$ (22 mg, 0.58 mmol) in THF (3 mL) under nitrogen atmosphere. The mixture was stirred for 1 hour at 0° C. The mixture was warmed to rt and NH4Cl (aq.) was added. The mixture was extracted with EtOAc and the organic layer was concentrated under reduced pressure. The residue was purified by Prep-TLC (PE:EtOAc, 2:1) to afford the title compound as a racemic mixture (54 mg, yield 56%) as a white solid. $^1$H NMR (300 MHz, DMSO-$d_6$): δ12.76 (s, 1H), 8.70 (s, 1H), 7.35-7.56 (m, 7H), 7.12-7.10 (m, 1H), 6.99 (d, 1H), 5.55-5.48 (m, 3H), 4.84-4.80 (m, 1H), 3.51 (s, 3H), 1.43 (d, 3H). m/z 497 [M+H$^+$].

Example 168

Synthesis of N-[5-[(5-chloropyridin-2-yl)methoxy]-1,3,4-thiadiazol-2-yl]-3-[2-(difluoromethoxy)phenyl] imidazole-4-carboxamide

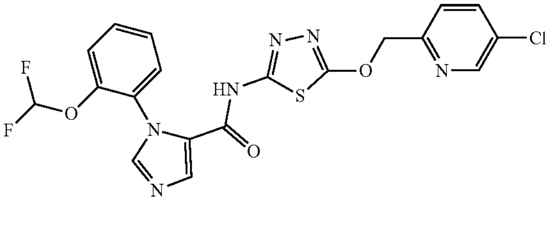 [SMILES: O=C(Nc1nnc(OCc2ccc(Cl)cn2)s1)c1cncn1-c1ccccc1OC(F)F]

Step 1. Preparation of ethyl 2-[[2-(difluoromethoxy)phenyl]imino]acetate

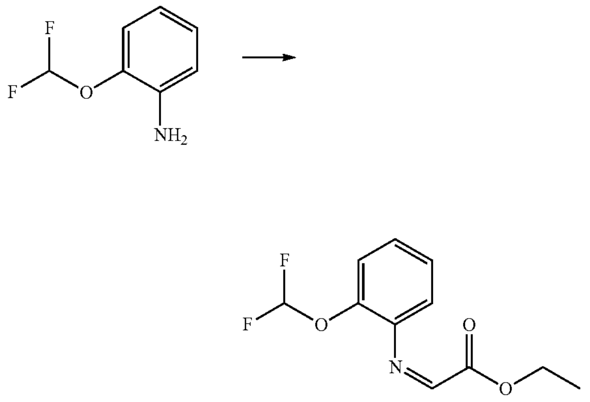

To a solution of 2-(difluoromethoxy) aniline (2.0 g, 12.6 mmol) in MeOH (20 mL) was added ethyl glyoxylate (50% in toluene, 3.1 g, 15.1 mmol) at room temperature. The mixture was stirred for 5 h at room temperature. The mixture was concentrated under reduced pressure to afford the title compound (6 g) as a dark brown oil, which was used in the next step without further purification Step 2. Preparation of ethyl 3-[2-(difluoromethoxy) phenyl]imidazole-4-carboxylate

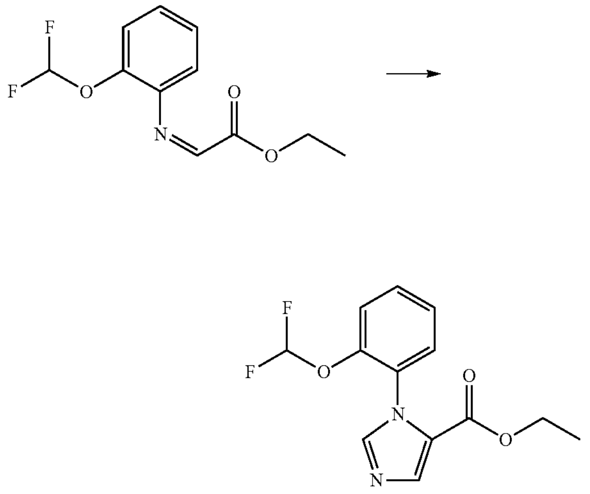

To a solution of ethyl 2-[[2-(difluoromethoxy) phenyl] imino]acetate (6.0 g, 11.1 mmol) in EtOH (20 mL) was added $K_2CO_3$ (3.1 g, 22.2 mmol) and p-toluenesulfonylmethyl isocyanide (2.2 g, 11.1 mmol) at room temperature. The mixture was stirred for overnight at 80° C. under nitrogen atmosphere. The mixture was cooled room temperature and diluted with water. The mixture was extracted with EtOAc (3×). The combined organic layers were concentrated under reduced pressure. The residue was purified by silica gel column chromatography, eluted with 11% EtOAc in hexanes to afford the title compound (2.5 g, 66% yield) as a light-yellow oil.

Step 3. Preparation of N-[5-[(5-chloropyridin-2-yl)methoxy]-1,3,4-thiadiazol-2-yl]-3-[2-(difluoromethoxy)phenyl]imidazole-4-carboxamide

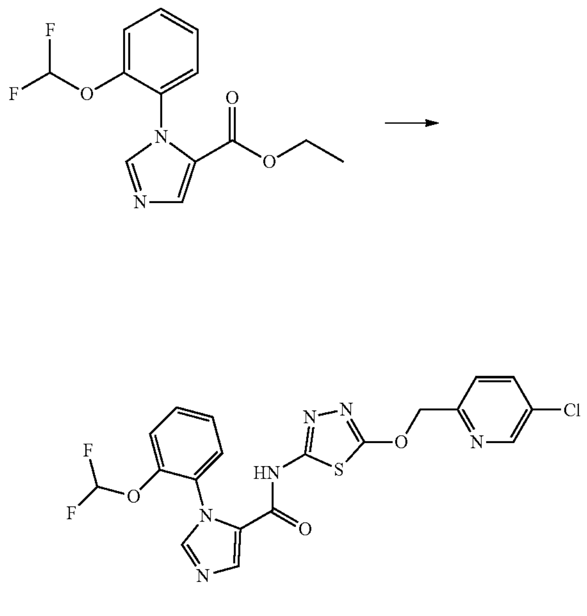

The title compound was prepared using General Procedures F and A. For General Procedure A, 5-((5-chloropyridin-2-yl)methoxy)-1,3,4-thiadiazol-2-amine (Intermediate C) was used. $^1$H NMR (400 MHz, DMSO-$d_6$): δ5.53 (s, 2H), 7.07-7.25 (m, 1H), 7.37-7.39 (m, 2H), 7.56-7.59 (m, 3H), 8.00 (d, 1H), 8.08 (s, 1H), 8.22 (s, 1H), 8.65 (d, 1H), 12.85 (s, 1H). m/z 479 [M+H$^+$].

Example 169

Synthesis of N-[5-[(4-chlorophenyl)methoxy]-1,3,4-thiadiazol-2-yl]-3-(1,3-dimethylpyrazol-4-yl)pyridine-4-carboxamide

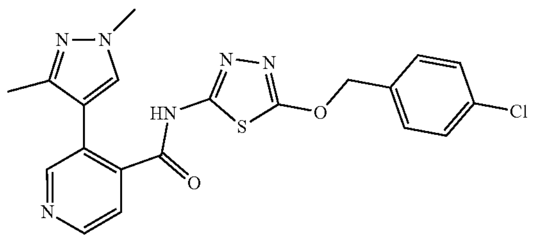 [SMILES: Cc1nn(C)cc1-c1cnccc1C(=O)Nc1nnc(OCc2ccc(Cl)cc2)s1]

The title compound was prepared using General Procedures E, F and A. For General Procedure E, methyl 3-bromopyridine-4-carboxylate and 1,3-dimethylpyrazol-4-ylboronic acid were employed. For General Procedure A, 5-((4-chlorobenzyl)oxy)-1,3,4-thiadiazol-2-amine (Intermediate B) was used. $^1$H NMR (300 MHz, DMSO-$d_6$): δ12.98 (s, 1H), 8.66 (d, 2H), 7.80-7.63 (m, 2H), 7.58-7.47 (m, 4H), 5.53 (s, 2H), 3.78 (s, 3H), 2.14 (s, 3H). m/z 441 [M+H$^+$].

Example 170

Synthesis of N-[5-[(5-chloropyridin-2-yl)methoxy]-1,3,4-thiadiazol-2-yl]-6-(hydroxymethyl)-4-(2-methoxyphenyl)pyridine-3-carboxamide

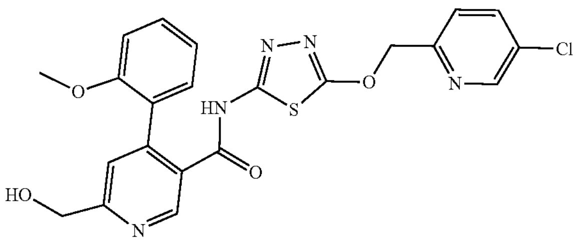 [SMILES: COc1ccccc1-c1cc(CO)ncc1C(=O)Nc1nnc(OCc2ccc(Cl)cn2)s1]

The title compound was prepared using General Procedure A, employing 6-(hydroxymethyl)-4-(2-methoxyphenyl)pyridine-3-carboxylic acid (Example 105, Step 3) and 5-((5-chloropyridin-2-yl)methoxy)-1,3,4-thiadiazol-2-amine (Intermediate C). $^1$H NMR (300 MHz, DMSO-$d_6$): δ12.80 (s, 1H), 8.70 (s, 1H), 8.66 (d, 1H), 8.00 (dd, 1H), 7.60 (d, 1H), 7.44-7.33 (m, 3H), 7.09 (t, 1H), 6.99 (d, 1H), 5.60-5.54 (m, 3H), 4.66-4.64 (m, 2H), 3.51 (s, 3H). m/z 484 [M+H$^+$].

Example 171

Synthesis of N-(5-((4-chlorobenzyl)oxy)-1,3,4-thiadiazol-2-yl)-3-(2-(2-hydroxyethyl)phenyl)isonicotinamide

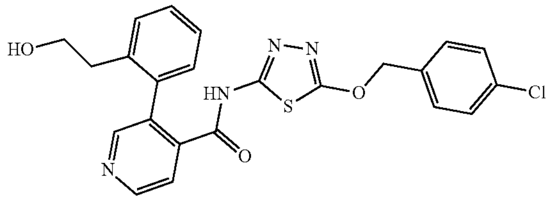 [SMILES: O=C(Nc1nnc(OCc2ccc(Cl)cc2)s1)c1ccncc1-c1ccccc1CCO]

Step 1. Preparation of 2-[2-(4,4,5,5-tetramethyl-1,3,2-dioxaborolan-2-yl)phenyl]ethanol

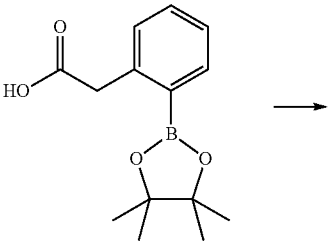

-continued

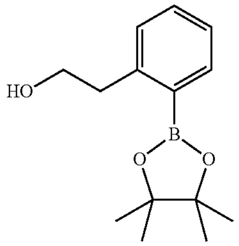

To a solution of [2-(4,4,5,5-tetramethyl-1,3,2-dioxaborolan-2-yl)phenyl]acetic acid (860 mg, 3.3 mmol) in THF (9 mL) was added $BH_3$-THF (1 M, 3.3 mL, 3.3 mmol) at 0° C. under nitrogen atmosphere. The mixture was stirred for 1 hour at 0° C. The mixture was warmed to rt and stirred at rt overnight. The mixture was diluted with MeOH and concentrated under reduced pressure. The residue was purified by Prep-TLC (PE:EtOAc, 5:1) to afford the title compound (250 mg, 29% yield) as a yellow solid.

Step 2. Preparation of 3-[2-(2-hydroxyethyl)phenyl] pyridine-4-carboxylic acid

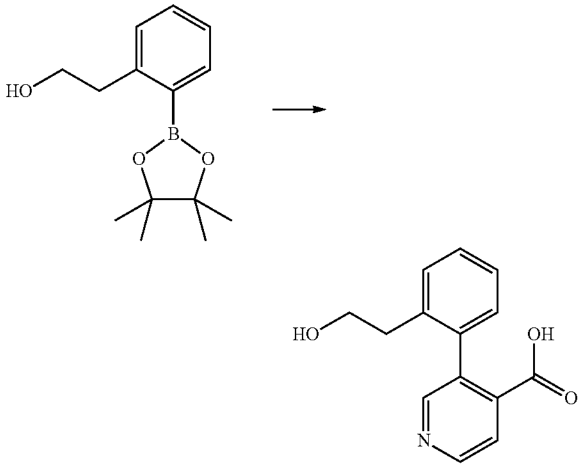

The title compound was prepared using General Procedures E and F. For General Procedure E, 2-[2-(4,4,5,5-tetramethyl-1,3,2-dioxaborolan-2-yl)phenyl]ethanol and methyl 3-bromopyridine-4-carboxylate were employed.

Step 3. Preparation of 3-(2-(2-((tert-butyldimethylsilyl)oxy)ethyl)phenyl)isonicotinic acid

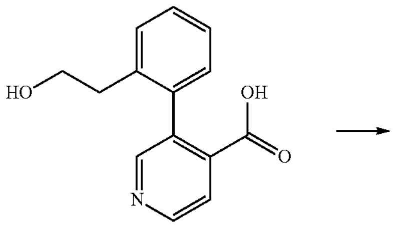

-continued

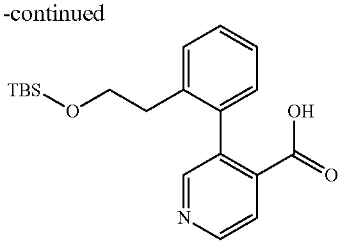

To a solution of 3-[2-(2-hydroxyethyl)phenyl]pyridine-4-carboxylic acid (180 mg, 0.74 mmol) in THF (2 mL) was added TBSCl (245 mg, 1.6 mmol) and imidazole (151 mg, 2.2 mmol). The mixture was stirred for 4 hours at 50° C. The mixture was diluted with MeOH concentrated under reduced pressure. The residue was purified by Prep-TLC (DCM: MeOH, 20:1) to afford the title compound (160 mg, 58% yield) as a white liquid.

Step 4. Preparation of 3-(2-[2-[(tert-butyldimethylsilyl)oxy]ethyl]phenyl)-N-[5-[(4-chlorophenyl)methoxy]-1,3,4-thiadiazol-2-yl]pyridine-4-carboxamide

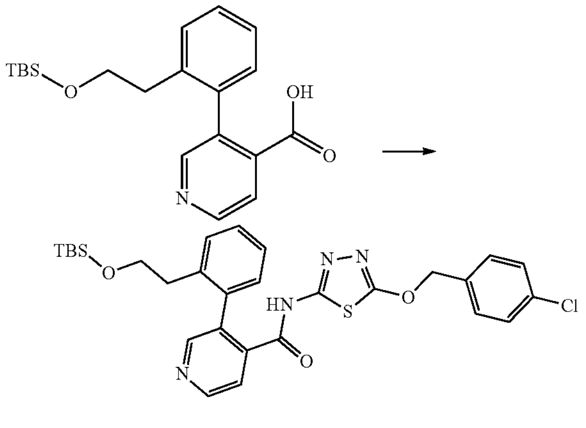

To a solution of 3-(2-[2-[(tert-butyldimethylsilyl)oxy]ethyl]phenyl)pyridine-4-carboxylic acid (100 mg, 0.28 mmol) in DMF (1 mL) was added 5-((4-chlorobenzyl)oxy)-1,3,4-thiadiazol-2-amine (74 mg, 0.31 mmol, Intermediate B), EDCI (80 mg, 0.42 mmol) and HOBt (57 mg, 0.42 mmol) at 0° C. The mixture was stirred for 10 min at 0° C. Then the mixture was warmed to rt and stirred at rt overnight. The mixture was diluted with water and extracted with EtOAc (3×). The combined organic layers were concentrated under reduced pressure. The residue was purified by Prep-TLC (DCM:MeOH, 20:1) to afford the title compound (60 mg, 36% yield) as a white liquid.

Step 5. Preparation of N-(5-((4-chlorobenzyl)oxy)-1,3,4-thiadiazol-2-yl)-3-(2-(2-hydroxyethyl)phenyl) isonicotinamide

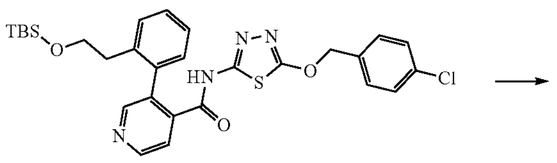

-continued

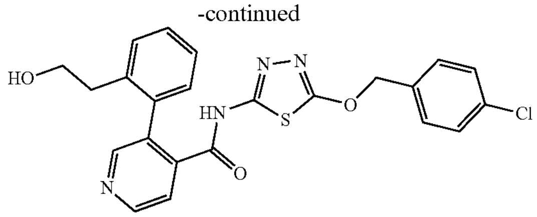

To a solution of 3-(2-[2-[(tert-butyldimethylsilyl)oxy] ethyl]phenyl)-N-[5-[(4-chlorophenyl)methoxy]-1,3,4-thiadiazol-2-yl]pyridine-4-carboxamide (55 mg, 0.095 mmol) in THF (1 mL) was added TBAF (25 mg, 0.095 mmol) and CsF (144 mg, 0.95 mmol). The mixture was stirred for overnight at room temperature. The mixture was diluted with water and extracted with EtOAc (5×). The combined organic layers were concentrated under vacuum. The residue was purified by Prep-TLC (DCM:MeOH, 20:1) to afford the title compound (24 mg, 54% yield) as a white solid. $^1$H NMR (300 MHz, DMSO-$d_6$): δ8.75 (d, 1H), 8.58 (s, 1H), 7.71 (d, 1H), 7.52-7.50 (m, 4H), 7.36-7.28 (m, 2H), 7.23-7.18 (m, 1H), 7.09 (d, 1H), 5.44 (s, 2H), 3.47 (t, 2H), 2.67-2.59 (m, 2H). m/z 467 [M+H$^+$].

Example 172

Synthesis of N-(5-((4-chlorobenzyl)oxy)-1,3,4-thiadiazol-2-yl)-3-(5-cyano-2-(oxetan-3-yloxy)phenyl) isonicotinamide

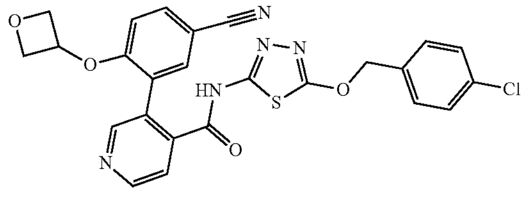 [SMILES: N#Cc1ccc(OC2COC2)c(-c2cnccc2C(=O)Nc2nnc(OCc3ccc(Cl)cc3)s2)c1]

Step 1. Preparation of-bromo-4-(oxetan-3-yloxy)benzonitrile

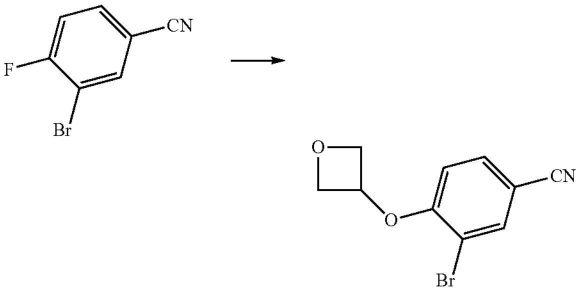

To a solution of 3-bromo-4-fluorobenzonitrile (5 g, 25.0 mmol) in DMF (50 mL) was added oxetan-3-ol (2.8 g, 37.5 mmol) and $K_2CO_3$ (6.9 g, 50.0 mmol). The mixture was stirred for 30 min under nitrogen atmosphere at room temperature. The mixture was stirred for overnight at 100° C. under nitrogen atmosphere. The mixture was cooled room temperature and diluted with water. The mixture was extracted with EtOAc (3×). The combined organic layers were concentrated under reduced pressure. The residue was purified by silica gel column chromatography, eluted with 17% EtOAc in PE to afford the title compound (2.3 g, 36% yield) as a dark yellow oil.

Step 2. Preparation of 4-(oxetan-3-yloxy)-3-(4,4,5,5-tetramethyl-1,3,2-dioxaborolan-2-yl)benzonitrile

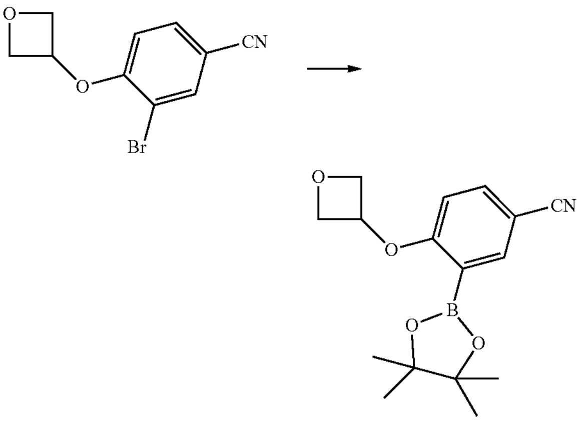

To a solution of 3-bromo-4-(oxetan-3-yloxy)benzonitrile (2.3 g, 9.1 mmol) in dioxane (23 mL) was added bis (pinacolato)diboron (3.5 g, 13.6 mmol). The mixture was stirred for 5 min at room temperature under nitrogen atmosphere. Then KOAc (1.8 g, 18.1 mmol) was added in portions at room temperature under nitrogen atmosphere. Then [1,1'-bis(diphenylphosphino)ferrocene]dichloropalladium(II)(0.66 g, 0.91 mmol) was added in portions at room temperature under nitrogen atmosphere. The mixture was stirred for overnight at 80° C. under nitrogen atmosphere. The mixture was cooled to room temperature and diluted with water. The mixture was extracted with EtOAc (3×). The combined organic layers were concentrated under reduced pressure. The residue was purified by silica gel column chromatography, eluted with 17% EtOAc in PE to afford the title compound (2 g, 73% yield) as a yellow oil.

Step 3. Preparation of N-(5-((4-chlorobenzyl)oxy)-1,3,4-thiadiazol-2-yl)-3-(5-cyano-2-(oxetan-3-yloxy) phenyl)isonicotinamide

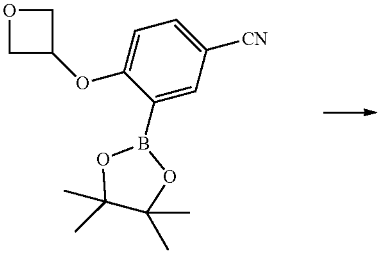

-continued

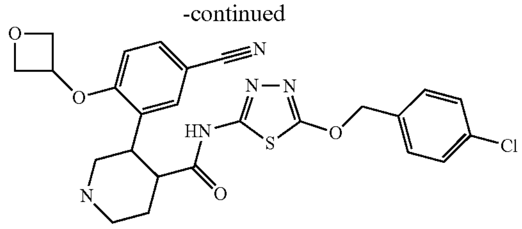

The title compound was prepared using General Procedures E, F and A. For General Procedure E, were employed. For General Procedure A, 5-((4-chlorobenzyl)oxy)-1,3,4-thiadiazol-2-amine (Intermediate B) was used. $^1$H NMR (300 MHz, DMSO-$d_6$): δ 13.09 (s, 1H), 8.81 (d, 1H), 8.67 (s, 1H), 7.94 (s, 1H), 7.85 (d, 1H), 7.76 (d, 1H), 7.54-7.46 (m, 4H), 6.72 (d, 1H), 5.47 (s, 2H), 5.12-5.11 (m, 1H), 4.69 (s, 2H), 4.34 (s, 2H). m/z 520 [M+H$^+$].

Example 173

Synthesis of N-[5-[(5-chloropyridin-2-yl)methoxy]-1,3,4-thiadiazol-2-yl]-3-[4-oxa-7-azaspiro[2.5]octan-7-yl]pyridine-4-carboxamide

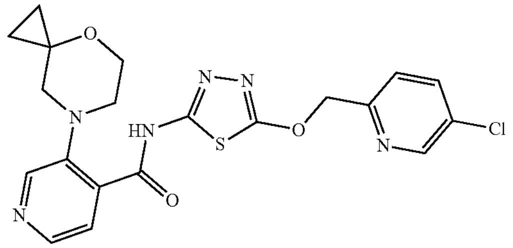 [SMILES: O=C(Nc1nnc(OCc2ccc(Cl)cn2)s1)c1ccncc1N1CCOC2(CC2)C1]

The title compound was prepared using General Procedures C and A. For General Procedures C, 3-fluoropyridine-4-carboxylic acid and 4-oxa-7-azaspiro[2.5]octane were employed. For General Procedures C, MeCN was replaced with NMP and temperature was 120° C. For General Procedure A, 5-((5-chloropyridin-2-yl)methoxy)-1,3,4-thiadiazol-2-amine (Intermediate C) was used and mixture was stirred at 70° C. for 4 h. $^1$H NMR (300 MHz, DMSO-$d_6$): δ 13.85 (s, 1H), 8.76 (s, 1H), 8.67 (d, 1H), 8.52 (d, 1H), 8.04-8.00 (m, 1H), 7.71 (d, 1H), 7.65 (d, 1H), 5.59 (s, 2H), 3.84-3.81 (m, 2H), 3.20-3.16 (m, 2H), 3.09 (s, 2H), 0.75-0.71 (m, 2H), 0.56 (t, 2H). m/z 459 [M+H$^+$].

Example 174

Synthesis of N-(5-(benzyloxy)-1,3,4-thiadiazol-2-yl)-3-(2-methoxyphenyl)isonicotinamide

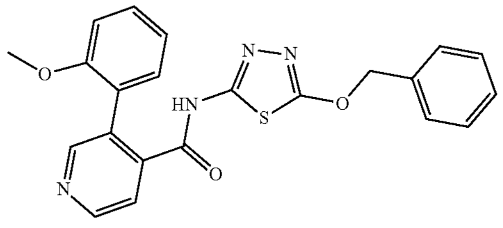 [SMILES: COc1ccccc1-c1cnccc1C(=O)Nc1nnc(OCc2ccccc2)s1]

The title compound was prepared using similar procedures as the synthesis of Example 141, Steps 2 and 3, replacing 1-[4-(hydroxymethyl)phenyl]cyclopropane-1-carbonitrile with benzyl alcohol in Step 2. $^1$H NMR (300 MHz, DMSO-$d_6$): δ12.86 (s, 1H), 8.71 (d, 1H), 8.61 (s, 1H), 7.63 (d, 1H), 7.51-7.50 (m, 2H), 7.48-7.35 (m, 5H), 7.09-6.97 (m, 2H), 5.47 (s, 2H), 3.51 (s, 3H). m/z 419 [M+H$^+$].

Example 175

Synthesis of 3-((1R,6S)-3-oxabicyclo[4.1.0]heptan-6-yl)-N-(5-((4-chlorobenzyl)oxy)-1,3,4-thiadiazol-2-yl)isonicotinamide and 3-((1S,6R)-3-oxabicyclo[4.1.0]heptan-6-yl)-N-(5-((4-chlorobenzyl)oxy)-1,3,4-thiadiazol-2-yl)isonicotinamide

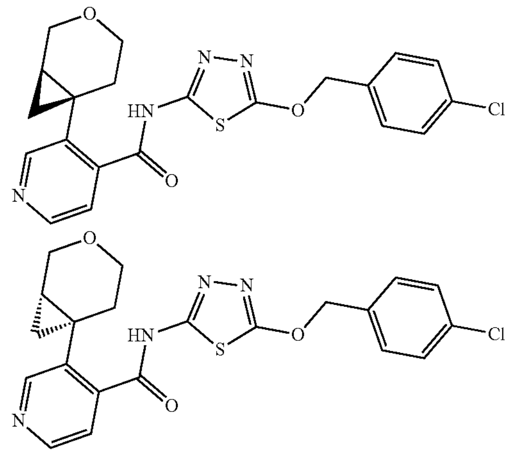

Step 1. Preparation of 2-(3-oxabicyclo[4.1.0]heptan-6-yl)-4,4,5,5-tetramethyl-1,3,2-dioxaborolane

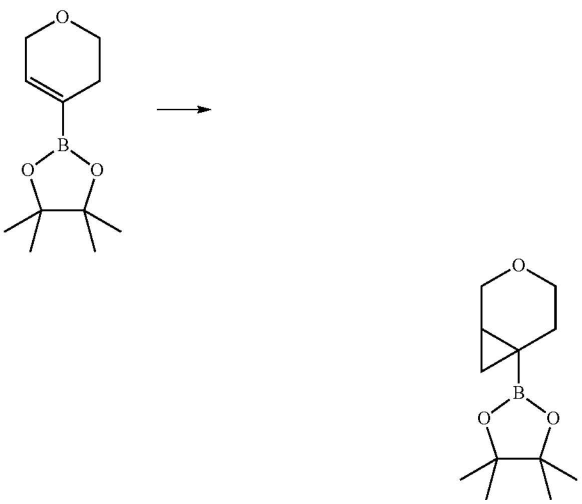

To a solution of 2-(3,6-dihydro-2H-pyran-4-yl)-4,4,5,5-tetramethyl-1,3,2-dioxaborolane (1 g, 4.8 mmol) in fluorobenzene (30 mL) was added diethylzinc (2.94 g, 23.8 mmol) and chloroiodomethane (8.4 g, 47.6 mmol) at −5° C.

The mixture was stirred at −5° C. for 10 min. Then three subsequent additions of diethylzinc (0.29 g, 2.4 mmol) and chloroiodomethane (3.4 g, 19.0 mmol) were added in the same manner. The mixture was stirred overnight at room temperature under nitrogen atmosphere. Then an aq solution of $NH_4Cl$ was added and the mixture was extracted with diethyl ether (3×). The combined organic layers were concentrated under vacuum. The residue was purified by silica gel column chromatography, eluted with 5% EtOAc in hexanes to afford the title compound (450 mg, 42% yield) as a white solid.

Step 2. Preparation of potassium (3-oxabicyclo[4.1.0]heptan-6-yl)trifluoroborate

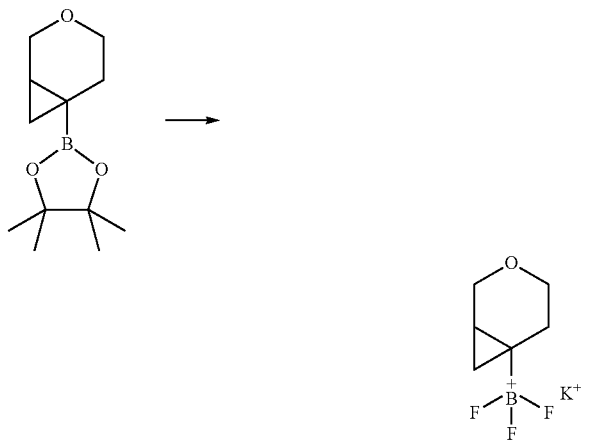

To a solution of 2-(3-oxabicyclo[4.1.0]heptan-6-yl)-4,4,5,5-tetramethyl-1,3,2-dioxaborolane (400 mg, 1.8 mmol) in MeCN (4 mL) and MeOH (4 mL) was added a solution of KF (415 mg, 7.1 mmol) in water (1.6 ml) at room temperature. The mixture was stirred at rt for 10 min and then a solution of L(+)-Tartaric acid (536 mg, 3.57 mmol) in THF (0.20 mL) was added. The mixture was stirred overnight at room temperature. The mixture was diluted with diethyl ether and the precipitate was collected to afford the title compound (350 mg, 96% yield) as a white solid.

Step 3. Preparation of methyl 3-(3-oxabicyclo[4.1.0]heptan-6-yl)isonicotinate

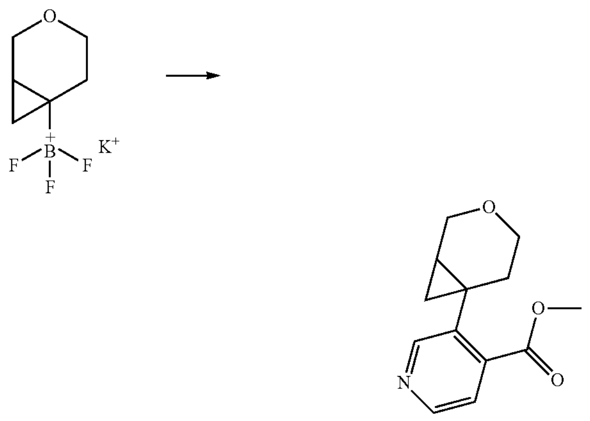

To a solution of potassium (3-oxabicyclo[4.1.0]heptan-6-yl)trifluoroborate (200 mg, 0.98 mmol) in toluene (2 mL) and water (0.20 mL) was added methyl 3-bromopyridine-4-carboxylate (254 mg, 1.2 mmol), $Cs_2CO_3$ (639 mg, 2.0 mmol) and $PdCl_2$ (17 mg, 0.098 mmol) at room temperature. The mixture was stirred for 15 h at 110° C. under nitrogen atmosphere. The mixture was cooled room temperature and diluted with water. The mixture was extracted with EtOAc (3×). The combined organic layers were concentrated under reduced pressure. The residue was purified by Prep-TLC (DCM:MeOH, 10:1) to afford the title compound (165 mg, 72% yield) as a white solid.

Step 4. Preparation of 3-((1R,6S)-3-oxabicyclo[4.1.0]heptan-6-yl)-N-(5-((4-chlorobenzyl)oxy)-1,3,4-thiadiazol-2-yl)isonicotinamide and 3-((1S,6R)-3-oxabicyclo[4.1.0]heptan-6-yl)-N-(5-((4-chlorobenzyl)oxy)-1,3,4-thiadiazol-2-yl)isonicotinamide

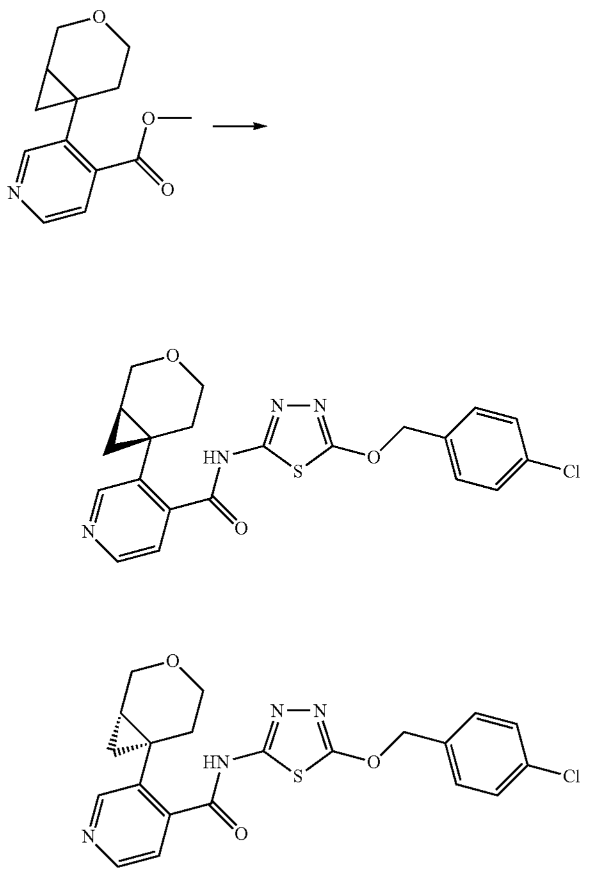

The title compound as a racemic mixture was prepared using General Procedures F and A. For General Procedure A, 5-((4-chlorobenzyl)oxy)-1,3,4-thiadiazol-2-amine (Intermediate B) was used. $^1H$ NMR (400 MHz, DMSO-$d_6$): δ12.98 (s, 1H), 8.67 (s, 1H), 8.58 (d, 1H), 7.57 (d, 2H), 7.53-7.46 (m, 3H), 5.52 (s, 2H), 3.82 (d, 1H), 3.62 (d, 1H), 3.51-3.49 (m, 1H), 3.18-3.15 (m, 1H), 2.03-2 (m, 1H), 1.82-1.74 (m, 1H), 1.23-1.15 (m, 1H), 1.02 (d, 1H), 0.77 (d, 1H). m/z 443 [M+H$^+$].

Example 176

Synthesis of N-[5-[(4-chlorophenyl)methoxy]-1,3,4-thiadiazol-2-yl]-3-[3-oxa-8-azabicyclo[3.2.1]octan-8-yl]pyridine-4-carboxamide

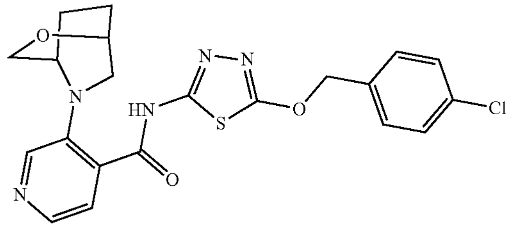 [SMILES: O=C(Nc1nnc(OCc2ccc(Cl)cc2)s1)c1ccncc1N1CC2CCC1CO2]

The title compound was prepared using General Procedures C and A. For General Procedures C, 3-fluoropyridine-4-carboxylic acid and 3-oxa-8-azabicyclo[3.2.1]octane were employed. For General Procedures C, MeCN was replaced with NMP and temperature was 150° C. For General Procedure A, 5-((4-chlorobenzyl)oxy)-1,3,4-thiadiazol-2-amine (Intermediate B) was used. $^1$H NMR (300 MHz, DMSO-$d_6$): δ12.88 (s, 1H), 8.42 (s, 1H), 8.20 (d, 1H), 7.57-7.48 (m, 4H), 7.40 (d, 1H), 5.50 (s, 2H), 3.83 (s, 2H), 3.67 (d, 2H), 3.51-3.48 (m, 2H), 1.90-1.83 (m, 4H). m/z 458 [M+H$^+$].

Example 177

Synthesis of N-[5-[(4-chlorophenyl)methoxy]-1,3,4-thiadiazol-2-yl]-6-cyano-4-[4-oxa-7-azaspiro[2.5]octan-7-yl]pyridine-3-carboxamide

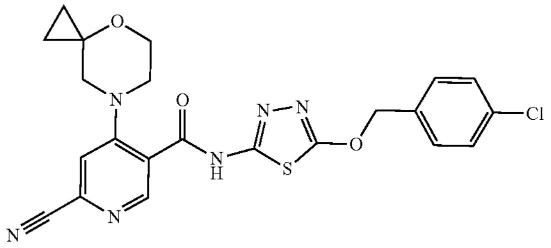 [SMILES: N#Cc1cc(N2CCOC3(CC3)C2)c(C(=O)Nc2nnc(OCc3ccc(Cl)cc3)s2)cn1]

Step 1. Preparation of benzyl 6-cyano-4-[4-oxa-7-azaspiro[2.5]octan-7-yl]pyridine-3-carboxylate

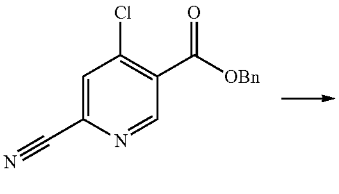

-continued

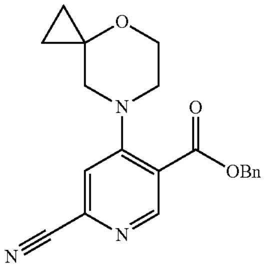

To a solution of benzyl 4-chloro-6-cyanopyridine-3-carboxylate (400 mg, 1.47 mmol) in MeCN (5 mL) was added 4-oxa-7-azaspiro[2.5]octane hydrochloride (241 mg, 1.6 mmol), TEA (594 mg, 5.9 mmol). The mixture was stirred for 4 hr at room temperature. The mixture was diluted with water and extracted with EtOAc (2×). The combined organic layers were concentrated under reduced pressure. The residue was purified by Prep-TLC (hexane:EtOAc, 5:1) to afford the title compound (360 mg, 65% yield) as an off-white solid.

Step 2. Preparation of 6-cyano-4-[4-oxa-7-azaspiro[2.5]octan-7-yl]pyridine-3-carboxylic acid

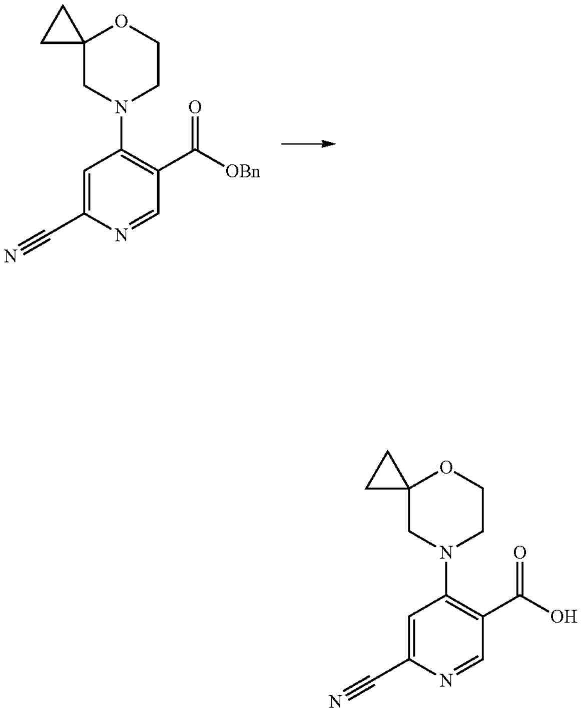

To a solution of benzyl 6-cyano-4-[4-oxa-7-azaspiro[2.5]octan-7-yl]pyridine-3-carboxylate (340 mg, 0.97 mmol) in THF (20 mL) was added Pd/C (10%, 34 mg) under nitrogen. The mixture was stirred at room temperature for 2 h under hydrogen atmosphere. The mixture was filtered through a Celite pad and the filtrate was concentrated under reduced pressure. The residue was purified by Prep-TLC (DCM:MeOH, 5:1) to afford the title compound (105 mg, 40% yield) as a light yellow solid.

Step 3. Preparation of N-[5-[(4-chlorophenyl)methoxy]-1,3,4-thiadiazol-2-yl]-6-cyano-4-[4-oxa-7-azaspiro[2.5]octan-7-yl]pyridine-3-carboxamide

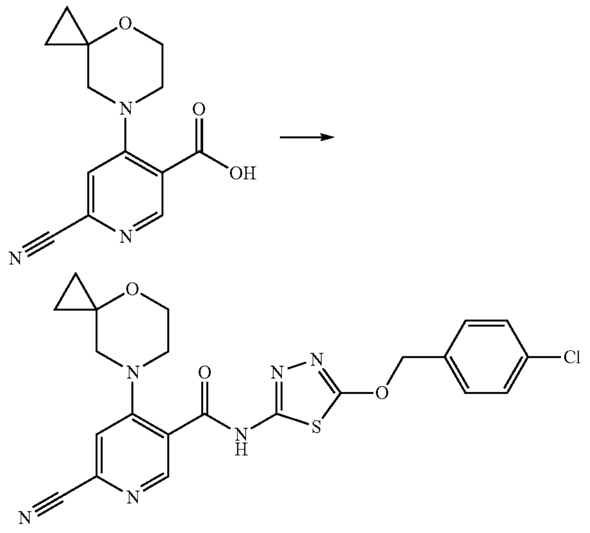

The title compound was prepared using General Procedure A employing 5-((4-chlorobenzyl)oxy)-1,3,4-thiadiazol-2-amine (Intermediate B) and 6-cyano-4-[4-oxa-7-azaspiro[2.5]octan-7-yl]pyridine-3-carboxylic acid. $^1$H NMR (300 MHz, DMSO-$d_6$): δ 9.11 (s, 1H), 7.44-7.37 (m, 5H), 5.47 (s, 2H), 4.01-3.98 (t, 2H), 3.24 (t, 2H), 3.15 (s, 2H), 1.02 (t, 2H), 0.65 (t, 2H). m/z 483 [M+H$^+$].

Example 178

Synthesis of 3-((1R,6S)-2-oxa-5-azabicyclo[4.1.0]heptan-5-yl)-N-(5-((4-chlorobenzyl)oxy)-1,3,4-thiadiazol-2-yl)isonicotinamide and 3-((1S,6R)-2-oxa-5-azabicyclo[4.1.0]heptan-5-yl)-N-(5-((4-chlorobenzyl)oxy)-1,3,4-thiadiazol-2-yl)isonicotinamide

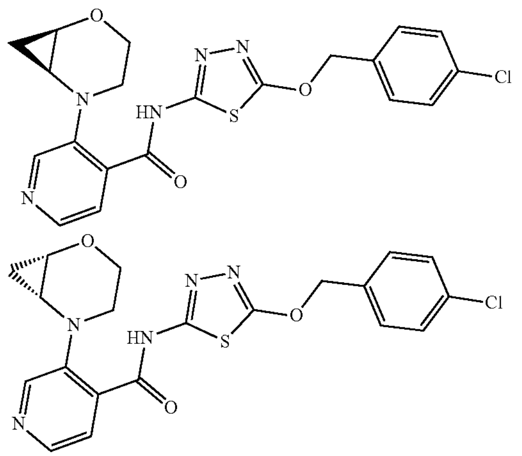

The title compound as a racemic mixture was prepared using similar procedure as Example 144, replacing (3R,5R)-3,5-dimethylmorpholine hydrochloride with 2-oxa-5-azabicyclo[4.1.0]heptane in step 2. $^1$H NMR (300 MHz, DMSO-$d_6$): δ12.99 (s, 1H), 8.50 (s, 1H), 8.08 (d, 1H), 7.56-7.47 (m, 4H), 7.32 (d, 1H), 5.49 (s, 2H), 3.78-3.68 (m, 3H), 3.20-3.11 (m, 2H), 2.57-2.53 (m, 1H), 0.70-0.54 (m, 2H). m/z 444 [M+H$^+$].

Example 179

Synthesis of (S)—N-(5-((5-chloropyridin-2-yl)methoxy)-1,3,4-thiadiazol-2-yl)-3-(2-methyl-3-oxopiperazin-1-yl)isonicotinamide and (R)—N-(5-((5-chloropyridin-2-yl)methoxy)-1,3,4-thiadiazol-2-yl)-3-(2-methyl-3-oxopiperazin-1-yl)isonicotinamide

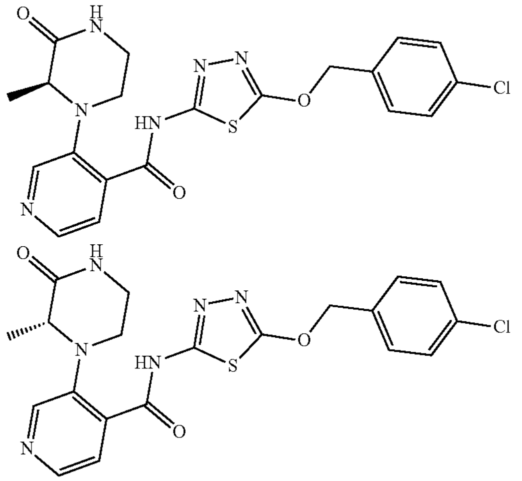

The title compound as a racemic mixture was prepared using similar procedure as Example 144, replacing (3R,5R)-3,5-dimethylmorpholine hydrochloride with 3-methylpiperazin-2-one in step 2 and 5-((4-chlorobenzyl)oxy)-1,3,4-thiadiazol-2-amine (Intermediate B) with 5-((5-chloropyridin-2-yl)methoxy)-1,3,4-thiadiazol-2-amine (Intermediate C) in step 3.1H NMR (300 MHz, DMSO-$d_6$): δ13.50 (s, 1H), 8.75 (s, 1H), 8.66 (d, 1H), 8.50 (d, 1H), 8.03-7.98 (m, 2H), 7.66-7.62 (m, 2H), 5.57 (s, 2H), 3.95 (t, 1H), 3.33-3.26 (m, 4H), 1.11 (d, 3H). m/z 460 [M+H$^+$].

Example 180

Synthesis of N-[5-(3H-1,3-benzodiazol-4-ylmethoxy)-1,3,4-thiadiazol-2-yl]-3-(2-methoxyphenyl)pyridine-4-carboxamide

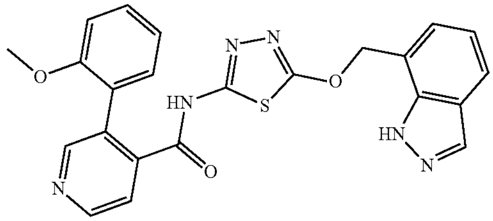 [SMILES: COc1ccccc1-c1cnccc1C(=O)Nc1nnc(OCc2cccc3cn[nH]c23)s1]

Step 1. Preparation of methyl 3-[[2-(trimethylsilyl)ethoxy]methyl]-1,3-benzodiazole-4-carboxylate

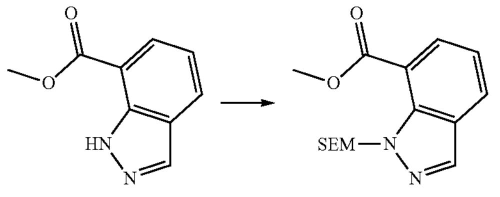 [SMILES: COC(=O)c1cccc2cn[nH]c12 ; COC(=O)c1cccc2cnn(COCC[Si](C)(C)C)c12]

To a solution of methyl 3H-1,3-benzodiazole-4-carboxylate (5000 mg, 28.4 mmol) in DMF (50 mL) was added NaH (60% dispersion in oil, 1.36 g, 34.1 mmol) at 0° C. under nitrogen atmosphere. The mixture was stirred at 0° C. for 30 min. Then, 2-(trimethylsilyl)ethoxymethyl chloride (7098 mg, 42.5 mmol) was added. The mixture was warmed to room temperature and stirred at room temperature for 1 h. The mixture was diluted with water and extracted with EtOAc. The organic layer was washed with water (3×), dried over anhydrous $Na_2SO_4$, and concentrated under reduced pressure. The residue was purified by silica gel column chromatography, eluted with 9% EtOAc in PE to afford the title compound (5500 mg, 63% yield) as a yellow oil.

Step 2. Preparation of (3-[[2-(trimethylsilyl)ethoxy]methyl]-1,3-benzodiazol-4-yl)methanol

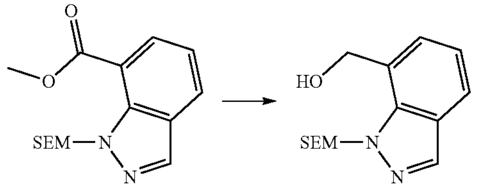 [SMILES: COC(=O)c1cccc2cnn(COCC[Si](C)(C)C)c12 ; C[Si](C)(C)CCOCn1ncc2cccc(CO)c21]

To a solution of methyl 3-[[2-(trimethylsilyl)ethoxy]methyl]-1,3-benzodiazole-4-carboxylate (5500 mg, 17.9 mmol) in THF (50 mL) at 0° C. was added $LiAlH_4$ (1022 mg, 26.9 mmol) in portions under nitrogen atmosphere. The mixture was warmed to rt and stirred for 1 h at rt under nitrogen atmosphere. The mixture was diluted with $NaHCO_3$ (aq.) and extracted with DCM (3×). The combined organic layers were washed with brine, dried over anhydrous $Na_2SO_4$ and concentrated under reduced pressure. The residue was purified by silica gel column chromatography, eluted with 17% EtOAc in PE to afford the title compound (3400 mg, 68% yield) as a light-yellow oil.

Step 3. Preparation of 5-[(3-[[2-(trimethylsilyl)ethoxy]methyl]-1,3-benzodiazol-4-yl)methoxy]-1,3,4-thiadiazol-2-amine

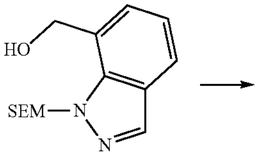

-continued

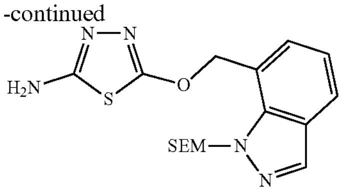

The title compound was prepared using similar procedures as the synthesis of Intermediate C, replacing (5-chloropyridin-2-yl)methanol with (3-[[2-(trimethylsilyl)ethoxy]methyl]-1,3-benzodiazol-4-yl)methanol in Step 1.

Step 4. Preparation of 3-(2-methoxyphenyl)-N-[5-[(3-[[2-(trimethylsilyl)ethoxy]methyl]-1,3-benzodiazol-4-yl)methoxy]-1,3,4-thiadiazol-2-yl]pyridine-4-carboxamide

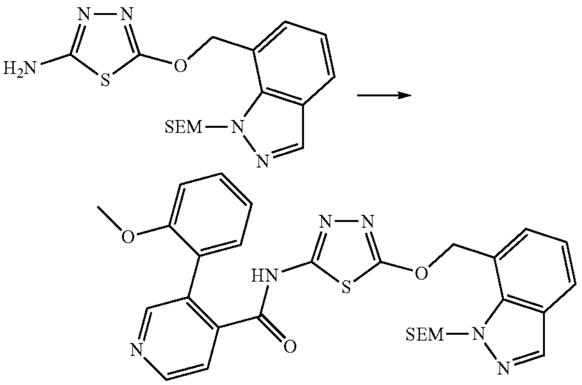

The title compound was prepared using General Procedure A employing 3-(2-methoxyphenyl)pyridine-4-carboxylic acid (Intermediate H) and 5-[(3-[[2-(trimethylsilyl)ethoxy]methyl]-1,3-benzodiazol-4-yl)methoxy]-1,3,4-thiadiazol-2-amine.

Step 5. Preparation of N-[5-(3H-1,3-benzodiazol-4-ylmethoxy)-1,3,4-thiadiazol-2-yl]-3-(2-methoxyphenyl)pyridine-4-carboxamide

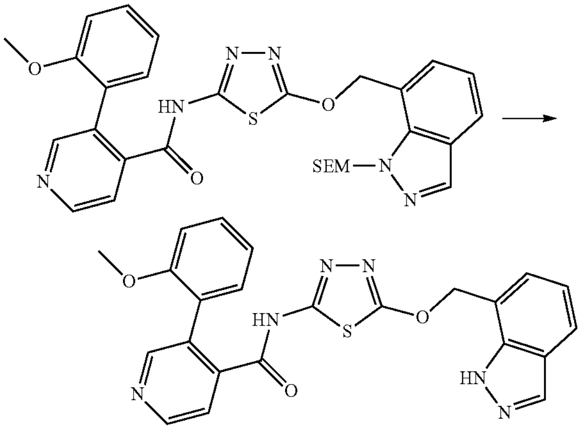

To a solution of 3-(2-methoxyphenyl)-N-[5-[(3-[[2-(trimethylsilyl)ethoxy]methyl]-1,3-benzodiazol-4-yl)methoxy]-1,3,4-thiadiazol-2-yl]pyridine-4-carboxamide (200 mg, 0.34 mmol) in THF (2 mL) was added TBAF (444 mg, 1.7 mmol), CsF (516 mg, 3.4 mmol) at room temperature. The mixture was stirred overnight at 70° C. The mixture was cooled room temperature and diluted with water. The mixture was extracted with EtOAc (2×). The combined organic layers were concentrated under reduced pressure. The residue was purified by Prep-TLC (DCM:MeOH, 20:1) to afford the title compound (14 mg, 9% yield) as a white solid. $^1$H NMR (300 MHz, DMSO-$d_6$): δ13.34 (s, 1H), 12.83 (s, 1H), 8.71 (d, 1H), 8.60 (s, 1H), 8.14 (s, 1H), 7.82-7.79 (m, 1H), 7.63 (d, 1H), 7.48 (d, 1H), 7.40-7.35 (m, 2H), 7.16-6.97 (m, 3H), 5.76 (s, 2H), 3.52 (s, 3H). m/z 459 [M+H$^+$].

Example 181

Synthesis of N-[5-(1H-indazol-4-ylmethoxy)-1,3,4-thiadiazol-2-yl]-3-(2-methoxyphenyl)pyridine-4-carboxamide

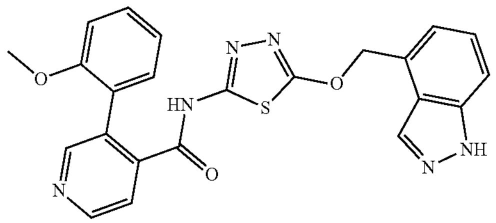 [SMILES: COc1ccccc1-c1cnccc1C(=O)Nc1nnc(OCc2cccc3[nH]ncc23)s1]

Step 1. Preparation of 3-(2-methoxyphenyl)-N-[5-[(1-[[2-(trimethylsilyl)ethoxy]methyl]indazol-4-yl)methoxy]-1,3,4-thiadiazol-2-yl]pyridine-4-carboxamide

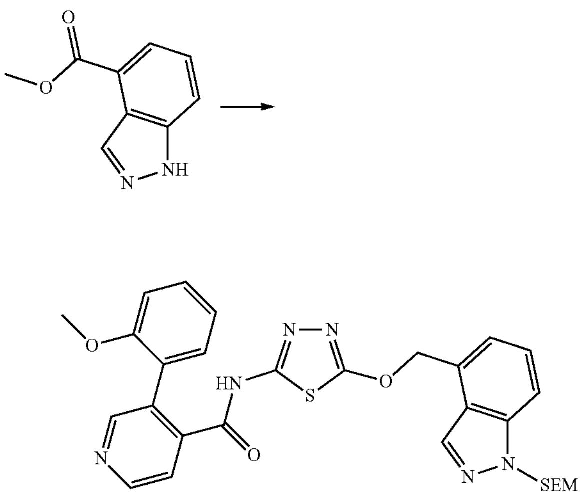

The title compound was prepared using similar procedure as Example 180, Steps 1-4, replacing methyl 3H-1,3-benzodiazole-4-carboxylate with methyl 1H-indazole-4-carboxylate in Step 1.

Step 2. Preparation of N-[5-(1H-indazol-4-ylmethoxy)-1,3,4-thiadiazol-2-yl]-3-(2-methoxyphenyl)pyridine-4-carboxamide

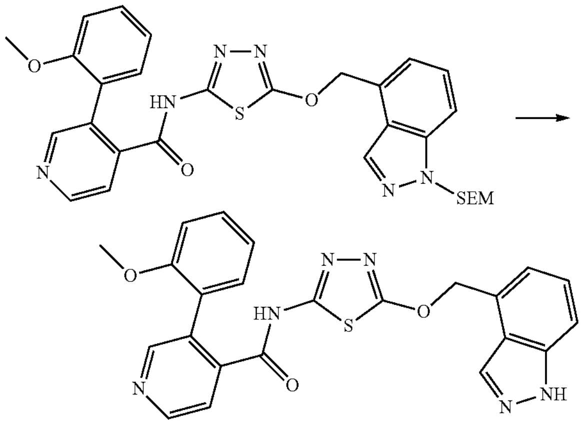

To a solution of 3-(2-methoxyphenyl)-N-[5-[(1-[[2-(trimethylsilyl)ethoxy]methyl]indazol-4-yl)methoxy]-1,3,4-thiadiazol-2-yl]pyridine-4-carboxamide (140 mg, 0.24 mmol) in THF (1.4 mL) was added CsF (722 mg, 4.8 mmol) and TBAF (1 M in THF, 1.2 mL, 1.2 mmol). The mixture was stirred for 2 hr at 70° C. The mixture was cooled room temperature and diluted with water. The mixture was extracted with EtOAc. The organic layer was concentrated under reduced pressure. The residue was purified by Prep-TLC (DCM:MeOH, 15:1) to afford the title compound (42 mg, 38% yield) as a yellow solid. $^1$H NMR (300 MHz, DMSO-$d_6$): δ13.22 (s, 1H), 12.86 (s, 1H), 8.71 (d, 1H), 8.61 (s, 1H), 8.20 (s, 1H), 7.63 (d, 1H), 7.58-7.56 (m, 1H), 7.40-7.35 (m, 3H), 7.23 (d, 1H), 7.09-7.07 (m, 1H), 7.00-6.98 (m, 1H), 5.81 (s, 2H), 3.51 (s, 3H). m/z 459 [M+H$^+$].

Example 182

Synthesis of N-(5-((5-chloropyridin-2-yl)methoxy)-1,3,4-thiadiazol-2-yl)-3-(2-(difluoromethoxy)-6-fluorophenyl)isonicotinamide

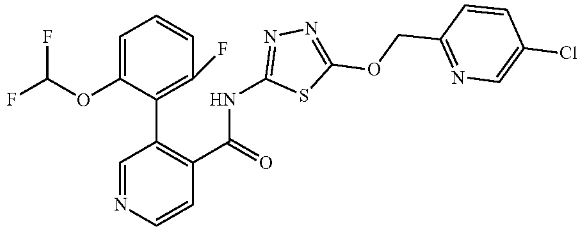 [SMILES: O=C(Nc1nnc(OCc2ccc(Cl)cn2)s1)c1ccncc1-c1c(F)cccc1OC(F)F]

The title compound was prepared using General Procedure A employing 3-(2-(difluoromethoxy)-6-fluorophenyl) isonicotinic acid (Example 109, Step 4) and 5-((5-chloropyridin-2-yl)methoxy)-1,3,4-thiadiazol-2-amine (Intermediate C). $^1$HNMR (300 MHz, DMSO-$d_6$): δ 8.80 (d, 1H), 8.65-8.62 (m, 2H), 8.01-8.00 (m, 1H), 7.89-7.86 (m, 1H), 7.66-7.58 (m, 2H), 7.40-6.91 (m, 3H), 5.53 (s, 3H). m/z 508 [M+H$^+$].

Example 183

Synthesis of N-(5-((4-chlorobenzyl)oxy)-1,3,4-thiadiazol-2-yl)-4-(2-fluoro-6-methoxyphenyl)-6-methylnicotinamide

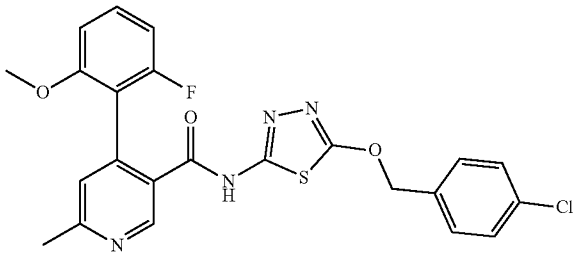 [SMILES: COc1cccc(F)c1-c1cc(C)ncc1C(=O)Nc1nnc(OCc2ccc(Cl)cc2)s1]

The title compound was prepared using General Procedures E, F and A. For General Procedure E, methyl 4-chloro-6-methylpyridine-3-carboxylate and 2-fluoro-6-methoxyphenylboronic acid were employed. For General Procedure A, 5-((4-chlorobenzyl)oxy)-1,3,4-thiadiazol-2-amine (Intermediate B) was used. $^1$H NMR (300 MHz, DMSO-$d_6$): δ2.56 (s, 3H), 3.57 (s, 3H), 5.46 (s, 2H), 6.86-6.94 (m, 2H), 7.32-7.48 (m, 2H), 7.43-7.54 (m, 4H), 8.78 (s, 1H), 12.86 (s, 1H). m/z 485 [M+H$^+$].

Example 184

Synthesis of N-(5-((5-chloropyridin-2-yl)methoxy)-1,3,4-thiadiazol-2-yl)-4-(2-fluoro-6-methoxyphenyl)-6-methylnicotinamide

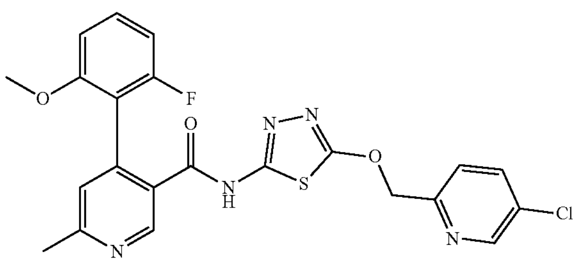 [SMILES: COc1cccc(F)c1-c1cc(C)ncc1C(=O)Nc1nnc(OCc2ccc(Cl)cn2)s1]

The title compound was prepared using General Procedures E, F and A. For General Procedure E, methyl 4-chloro-6-methylpyridine-3-carboxylate and 2-fluoro-6-methoxyphenylboronic acid were employed. For General Procedure A, 5-((5-chloropyridin-2-yl)methoxy)-1,3,4-thiadiazol-2-amine (Intermediate C) was used. $^1$H NMR (300 MHz, DMSO-$d_6$): δ 2.57 (s, 3H), 3.58 (s, 3H), 5.76 (s, 2H), 6.87-6.95 (m, 2H), 7.33 (s, 1H), 7.36-7.44 (m, 1H), 7.59-7.61 (m, 1H), 8.00 (d, 1H), 8.65 (s, 1H), 8.80 (s, 1H), 12.90 (s, 1H). m/z 486 [M+H$^+$].

Example 185

Synthesis of N-(5-((4-chlorobenzyl)oxy)-1,3,4-thiadiazol-2-yl)-6-cyano-4-(2-fluoro-6-methoxyphenyl) nicotinamide

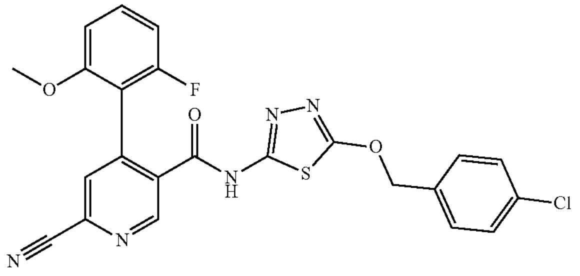 [SMILES: COc1cccc(F)c1-c1cc(C#N)ncc1C(=O)Nc1nnc(OCc2ccc(Cl)cc2)s1]

Step 1. Preparation of benzyl 6-cyano-4-(2-fluoro-6-methoxyphenyl)pyridine-3-carboxylate

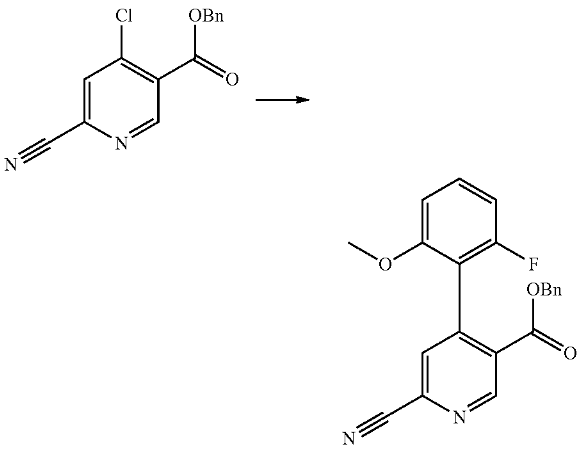 [SMILES: N#Cc1cc(Cl)c(C(=O)OCc2ccccc2)cn1 ; COc1cccc(F)c1-c1cc(C#N)ncc1C(=O)OCc1ccccc1]

The title compound was prepared using General Procedure E employing benzyl 4-chloro-6-cyanopyridine-3-carboxylate (Example 92, Step 2) and 2-fluoro-6-methoxyphenylboronic acid.

Step 2. Preparation of 6-cyano-4-(2-fluoro-6-methoxyphenyl)pyridine-3-carboxylic acid

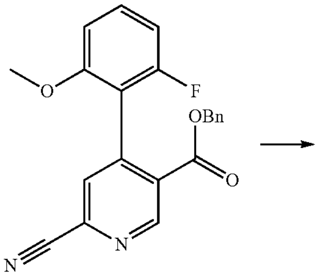

-continued

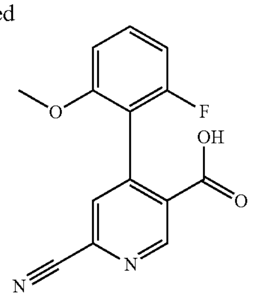

To a solution of benzyl 6-cyano-4-(2-fluoro-6-methoxyphenyl)pyridine-3-carboxylate (610 mg, 1.7 mmol) in THF (20 mL) was added Pd/C (100%, 120 mg) under nitrogen atmosphere. The mixture was stirred at rt for 4 h under hydrogen atmosphere. The mixture was filtered through Celite and the filtrate was concentrated under reduced pressure to afford the title compound (580 mg), which was used in the next step without further purification.

Step 3. Preparation of N-(5-((4-chlorobenzyl)oxy)-1,3,4-thiadiazol-2-yl)-6-cyano-4-(2-fluoro-6-methoxyphenyl)nicotinamide

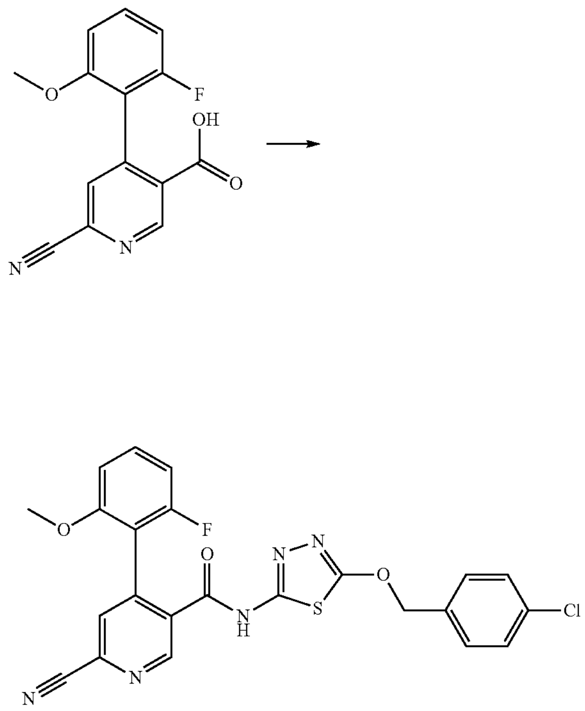

The title compound was prepared using General Procedure A employing 5-((4-chlorobenzyl)oxy)-1,3,4-thiadiazol-2-amine (Intermediate B) and 6-cyano-4-(2-fluoro-6-methoxyphenyl)pyridine-3-carboxylic acid. $^1$H NMR (300 MHz, DMSO-$d_6$): δ 13.2 (s, 1H), 9.08 (s, 1H), 8.24 (s, 1H), 7.54-7.43 (m, 5H), 7.01-6.92 (m, 2H), 5.48 (s, 2H), 3.60 (s, 3H). m/z 496 [M+H$^+$].

Example 186

Synthesis of N-(5-((5-chloropyridin-2-yl)methoxy)-1,3,4-thiadiazol-2-yl)-6-cyano-4-(2-fluoro-6-methoxyphenyl)nicotinamide

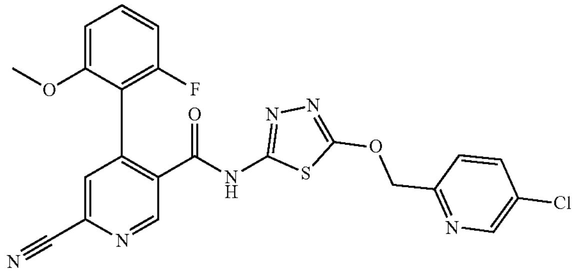

The title compound was prepared using General Procedure A employing 5-((5-chloropyridin-2-yl)methoxy)-1,3,4-thiadiazol-2-amine (Intermediate C) and 6-cyano-4-(2-fluoro-6-methoxyphenyl)pyridine-3-carboxylic acid (Example 185, Step 2). $^1$H NMR (300 MHz, DMSO-$d_6$): δ13.23 (s, 1H), 9.09 (s, 1H), 8.65 (s, 1H), 8.24 (s, 1H), 8.00 (d, 1H), 7.62-7.59 (m, 1H), 7.47 (t, 1H), 7.00-6.92 (m, 2H), 5.55 (s, 2H), 3.60 (s, 3H). m/z 497 [M+H$^+$].

Example 187

Synthesis of N-(5-((5-chloropyridin-2-yl)methoxy)-1,3,4-thiadiazol-2-yl)-3-((3S,5S)-3,5-dimethylmorpholino)isonicotinamide

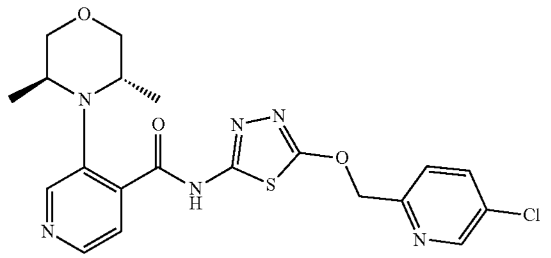 [SMILES: C[C@H]1COC[C@H](C)N1c1cnccc1C(=O)Nc1nnc(OCc2ccc(Cl)cn2)s1]

The title compound was prepared using similar procedures as the synthesis of Example 144, replacing (3R,5R)-3,5-dimethylmorpholine hydrochloride with (3S,5S)-3,5-dimethylmorpholine hydrochloride in Step 2; replacing 5-((4-chlorobenzyl)oxy)-1,3,4-thiadiazol-2-amine (Intermediate B) with 5-((5-chloropyridin-2-yl)methoxy)-1,3,4-thiadiazol-2-amine (Intermediate C) in Step 4. $^1$H NMR (300 MHz, DMSO-d6): δ 14.26 (s, 1H), 8.74 (s, 1H), 8.67 (d, 1H), 8.60 (d, 1H), 8.01 (dd, 1H), 7.89 (d, 1H), 7.64 (d, 1H), 5.58 (s, 2H), 3.94-3.70 (m, 4H), 3.27-3.23 (m, 2H), 1.12-0.96 (m, 3H), 0.94-0.80 (m, 3H). m/z 461 [M+H$^+$].

Example 188

Synthesis of N-(5-((5-chloropyridin-2-yl)methoxy)-1,3,4-thiadiazol-2-yl)-3-((3R,5R)-3,5-dimethylmorpholino)isonicotinamide

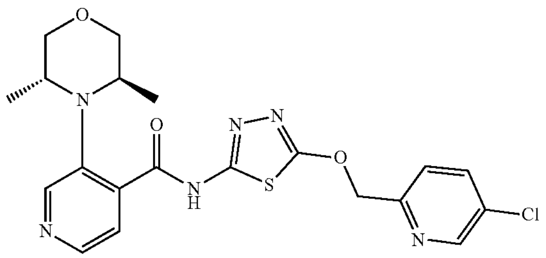 [SMILES: C[C@@H]1COC[C@@H](C)N1c1cnccc1C(=O)Nc1nnc(OCc2ccc(Cl)cn2)s1]

The title compound was prepared using similar procedures as the synthesis of Example 144, replacing 5-((4-chlorobenzyl)oxy)-1,3,4-thiadiazol-2-amine (Intermediate B) with 5-((5-chloropyridin-2-yl)methoxy)-1,3,4-thiadiazol-2-amine (Intermediate C) in Step 4. $^1$H NMR (300 MHz, DMSO-$d_6$): δ 14.27 (s, 11H), 8.74 (s, 11H), 8.67 (d, 1H), 8.61 (d, 1H), 8.01 (dd, 1H), 7.89 (d, 1H), 7.64 (d, 1H), 5.58 (s, 2H), 3.95-3.72 (m, 4H), 3.32-3.24 (m, 2H), 1.12-0.96 (m, 3H), 0.94-0.80 (m, 3H). m/z 461 [M+H$^+$].

Example 189

Synthesis of N-(5-((4-chlorobenzyl)oxy)-1,3,4-thiadiazol-2-yl)-4-(2-(difluoromethoxy)-6-fluorophenyl)-6-methylnicotinamide

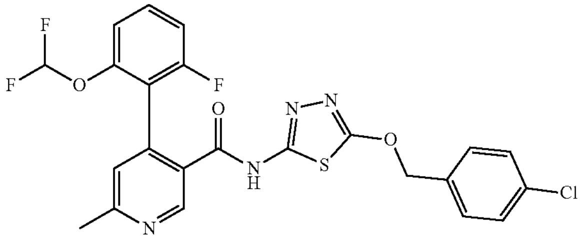 [SMILES: Cc1cc(-c2c(F)cccc2OC(F)F)c(C(=O)Nc2nnc(OCc3ccc(Cl)cc3)s2)cn1]

The title compound was prepared using General Procedures E, F and A. For General Procedure E, ethyl 4-bromo-6-methylpyridine-3-carboxylate and 2-[2-(difluoromethoxy)-6-fluorophenyl]-4,4,5,5-tetramethyl-1,3,2-dioxaborolane were employed. For General Procedure A, 5-((4-chlorobenzyl)oxy)-1,3,4-thiadiazol-2-amine (Intermediate B) was used. $^1$H NMR (300 MHz, DMSO-$d_6$): δ13.02 (s, 1H), 8.93 (s 1H), 7.68-7.47 (m, 5H), 7.47-6.79 (m, 4H), 5.46 (s, 2H), 2.58 (s, 3H). m/z 521 [M+H$^+$].

Example 190

Synthesis of N-(5-((5-chloropyridin-2-yl)methoxy)-1,3,4-thiadiazol-2-yl)-4-(2-(difluoromethoxy)-6-fluorophenyl)-6-methylnicotinamide

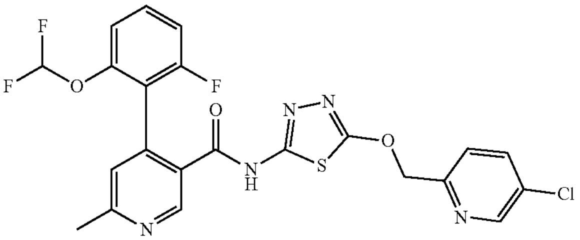

The title compound was prepared using General Procedures E, F and A. For General Procedure E, ethyl 4-bromo-6-methylpyridine-3-carboxylate and 2-[2-(difluoromethoxy)-6-fluorophenyl]-4,4,5,5-tetramethyl-1,3,2-dioxaborolane were employed. For General Procedure A, 5-((5-chloropyridin-2-yl)methoxy)-1,3,4-thiadiazol-2-amine (Intermediate C) was used. $^1$H NMR (300 MHz, DMSO-$d_6$): δ13.03 (s, 1H), 8.98 (s 1H), 8.65 (d, 1H), 8.00 (dd, 1H), 7.68-7.50 (m, 2H), 7.50-6.83 (m, 4H), 5.53 (s, 2H), 2.58 (s, 3H). m/z 522 [M+H$^+$].

Example 191

Synthesis of N-[5-[(5-chloropyridin-2-yl)methoxy]-1,3,4-thiadiazol-2-yl]-5-(2-methoxyphenyl)-2-methylpyridine-4-carboxamide

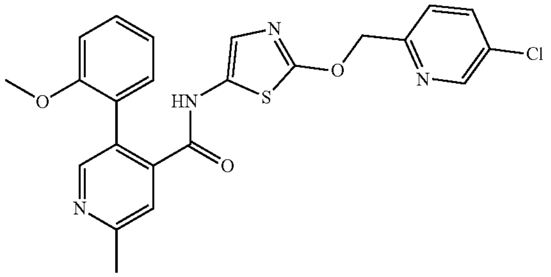 [SMILES: COc1ccccc1-c1cnc(C)cc1C(=O)Nc1cnc(OCc2ccc(Cl)cn2)s1]

Step 1. Preparation of methyl 2-chloro-5-(2-methoxyphenyl)pyridine-4-carboxylate

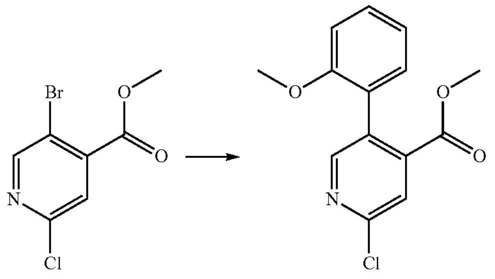

The title compound was prepared using General procedure E employing 5-bromo-2-chloropyridine-4-carboxylate and 2-methoxyphenylboronic acid.

Step 2. Preparation of methyl 5-(2-methoxyphenyl)-2-methylpyridine-4-carboxylate

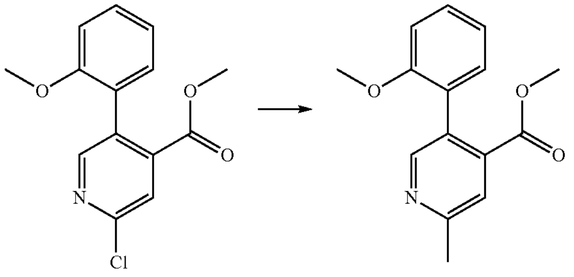 [SMILES: COC(=O)c1cc(Cl)ncc1-c1ccccc1OC ; COC(=O)c1cc(C)ncc1-c1ccccc1OC]

To a solution of methyl 2-chloro-5-(2-methoxyphenyl) pyridine-4-carboxylate (1.0 g, 3.6 mmol), in dioxane (30 mL) was added methylboronic acid (1.1 g, 18.0 mmol), $K_2CO_3$ (1.0 g, 7.2 mmol) and Pd(dtbpf)$Cl_2$ (235 mg, 0.36 mmol). The mixture was stirred overnight at 120° C. under nitrogen atmosphere. The mixture was diluted with water and extracted with EtOAc (2×). The combined organic layers were concentrated under reduced pressure and the residue. The residue was purified using silica gel chromatography (eluent: 25% EtOAc in PE) to afford the title compound (720 mg, 78% yield) as a white solid.

Step 3. Preparation of N-[5-[(5-chloropyridin-2-yl) methoxy]-1,3,4-thiadiazol-2-yl]-5-(2-methoxyphenyl)-2-methylpyridine-4-carboxamide

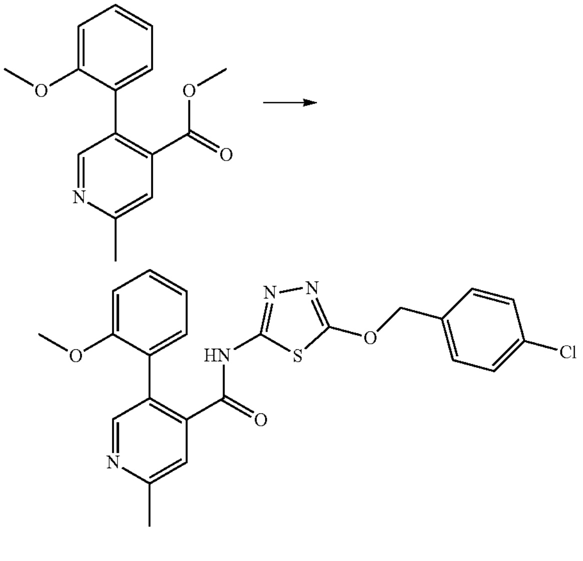

The title compound was prepared using F and A employing in General procedure F methyl 5-(2-methoxyphenyl)-2-methylpyridine-4-carboxylate and 5-((4-chlorobenzyl)oxy)-1,3,4-thiadiazol-2-amine (Intermediate B) in General procedures A. $^1$H NMR (300 MHz, DMSO-$d_6$): δ 2.57 (s, 3H), 3.50 (s, 3H), 5.54 (s, 2H), 6.97 (d, 1H), 7.05 (t, 1H), 7.33-7.38 (m, 2H), 7.52 (s, 1H), 7.61 (d, 1H), 8.00 (dd, 1H), 8.45 (s, 1H), 8.65 (s, 1H), 12.80 (s, 1H) ppm. m/z 468 [M+$H^+$].

Example 192

Synthesis of N-(5-((4-chlorobenzyl)oxy)-1,3,4-thiadiazol-2-yl)-6-cyano-4-(2-(difluoromethoxy)-6-fluorophenyl)nicotinamide

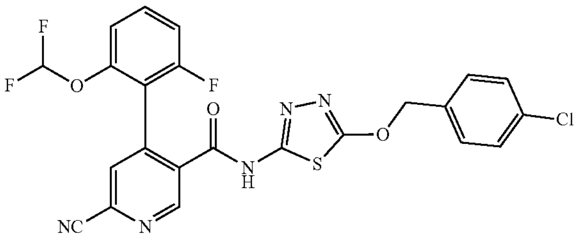 [SMILES: N#Cc1cc(-c2c(F)cccc2OC(F)F)c(C(=O)Nc2nnc(OCc3ccc(Cl)cc3)s2)cn1]

Step 1. Preparation of benzyl 6-cyano-4-[2-(difluoromethoxy)-6-fluorophenyl]pyridine-3-carboxylate

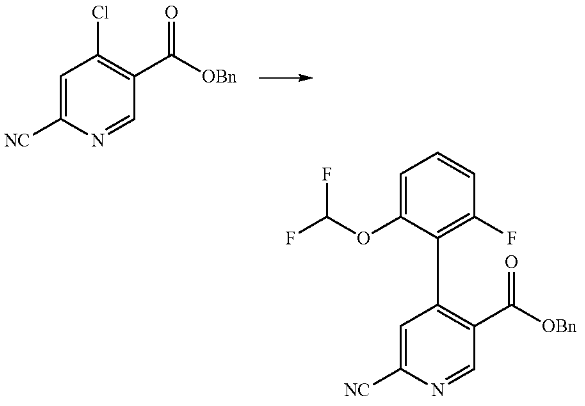

The title compound was prepared using General Procedure E replacing [1,1'-bis(diphenylphosphino)ferrocene]dichloropalladium(II) with [1,1'-bis(diphenylphosphino)ferrocene]dichloropalladium(II) $CH_2Cl_2$.

Step 2. Preparation of 6-cyano-4-[2-(difluoromethoxy)-6-fluorophenyl]pyridine-3-carboxylic acid

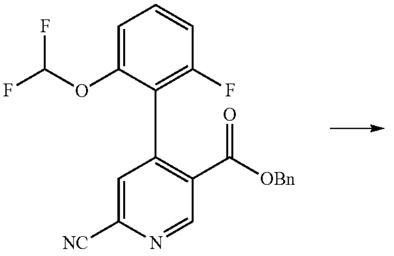

-continued

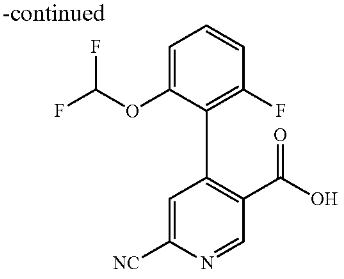

To a solution of benzyl 6-cyano-4-[2-(difluoromethoxy)-6-fluorophenyl]pyridine-3-carboxylate (540 mg, 1.4 mmol) in THF (50 mL) was added 10% Pd/C (54 mg). The mixture was stirred for 40 mins at room temperature. The mixture was diluted with THF and filtered. The solids were washed with THF (2×). The mixture was concentrated under reduced pressure. The residue was purified by Prep-TLC (DCM: MeOH, 20:1) to afford 6-cyano-4-[2-(difluoromethoxy)-6-fluorophenyl]pyridine-3-carboxylic acid (270 mg, yield 63% yield) as a white solid.

Step 3. Preparation of N-(5-((4-chlorobenzyl)oxy)-1,3,4-thiadiazol-2-yl)-6-cyano-4-(2-(difluoromethoxy)-6-fluorophenyl)nicotinamide

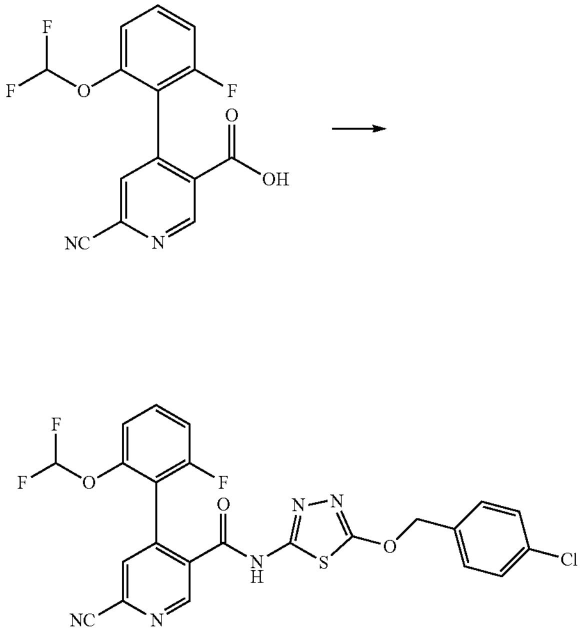

To a solution of 6-cyano-4-[2-(difluoromethoxy)-6-fluorophenyl]pyridine-3-carboxylic acid (100 mg, 0.32 mmol) in DMF (1.0 mL) was added HOBT (66 mg, 0.49 mmol), EDCI (93 mg, 0.49 mmol), 5-((4-chlorobenzyl)oxy)-1,3,4-thiadiazol-2-amine (78 mg, 0.32 mmol, Intermediate B). The mixture was stirred overnight at room temperature. The mixture was diluted with water and filtered. The solids were washed with EtOAc. The solid was purified by trituration with MeCN to afford the title compound (99 mg, 56% yield) as a light pink solid. $^{1}$H NMR (300 MHz, DMSO-$d_6$): δ 13.42 (s, 1H), 9.20 (s, 1H), 8.32 (s, 1H), 7.63-7.46 (m, 5H), 7.40-6.92 (m, 3H), 5.48 (s, 2H) ppm. m/z 532 [M+H$^+$].

Example 193

Synthesis of N-(5-((5-chloropyridin-2-yl)methoxy)-1,3,4-thiadiazol-2-yl)-6-cyano-4-(2-(difluoromethoxy)-6-fluorophenyl) nicotinamide

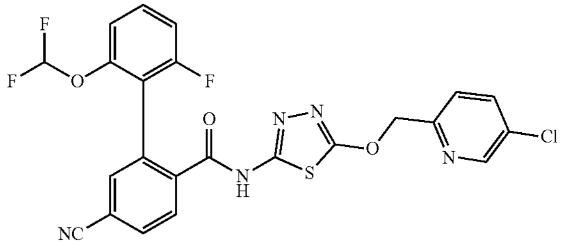 [SMILES: N#Cc1ccc(C(=O)Nc2nnc(OCc3ccc(Cl)cn3)s2)c(Cc2c(F)cccc2OC(F)F)c1]

To a solution of 6-cyano-4-[2-(difluoromethoxy)-6-fluorophenyl]pyridine-3-carboxylic acid (120.00 mg, 0.389 mmol, Example 192, Step 2) in DCM (1.2 mL) was added pyridine (154 mg, 1.9 mmol). The mixture was cooled to 0° C. Then a solution of oxalyl chloride (54 mg, 0.43 mmol) in DCM (0.5 mL) dropwise at 0° C. over 2 mins. The mixture was stirred for 30 mins at 0° C. Then 5-((5-chloropyridin-2-yl)methoxy)-1,3,4-thiadiazol-2-amine (94 mg, 0.39 mmol, Intermediate C), was added in portions at 0° C. over 5 min. The mixture was stirred for 1 h at 0° C. The mixture was warmed to rt and water was added. The layers were separated, and the aqueous layer was extracted with EtOAc. The combined organic layers were concentrated under reduced pressure. The residue was purified by trituration with MeOH to afford the title compound (29 mg, 14% yield as a white solid. $^{1}$H NMR (300 MHz, DMSO-$d_6$): δ13.39 (s, 1H), 9.21 (s, 1H), 8.65 (s, 1H), 8.32 (s, 1H), 8.00 (d, 1H), 7.64-7.56 (m, 2H), 7.41-6.92 (m, 3H), 5.55 (s, 2H). m/z 533 [M+H$^+$].

Example 194

Synthesis of N-(5-((5-chloropyridin-2-yl)methoxy)-1,3,4-thiadiazol-2-yl)-3'-methoxy-6-methyl-[4,4'-bipyridine]-3-carboxamide

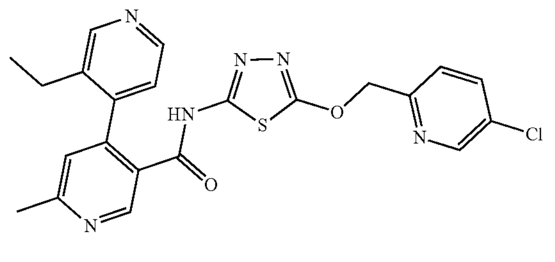 [SMILES: CCc1cnccc1-c1cc(C)ncc1C(=O)Nc1nnc(OCc2ccc(Cl)cn2)s1]

The title compound was prepared using General Procedures E, F and A. For General Procedure E, methyl 4-chloro-6-methylpyridine-3-carboxylate and 3-methoxypyridin-4-ylboronic acid were employed. For General Procedure A, 5-((5-chloropyridin-2-yl)methoxy)-1,3,4-thiadiazol-2-amine (Intermediate C) was used. $^{1}$H NMR (400 MHz, DMSO-$d_6$) δ: 12.94 (s, 1H), 8.78 (s, 1H), 8.66 (d, J=2.4 Hz, 1H), 8.39-8.31 (m, 2H), 8.01 (dd, J=8.4, 2.4 Hz, 1H), 7.61 (d, J=8.4 Hz, 1H), 7.41-7.35 (m, 2H), 5.55 (s, 2H), 3.64 (s, 3H), 2.59 (s, 3H). m/z 469.0 [M+H$^+$].

Example 195

Synthesis of N-[5-[(5-chloropyridin-2-yl)methoxy]-1,3,4-thiadiazol-2-yl]-4-[3-(hydroxymethyl)-2-methoxyphenyl]-6-methylpyridine-3-carboxamide

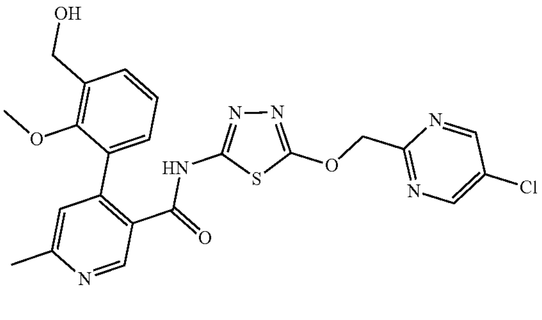 [SMILES: COc1c(CO)cccc1-c1cc(C)ncc1C(=O)Nc1nnc(OCc2ncc(Cl)cn2)s1]

The title compound was prepared using General Procedures E, F and A. For General Procedure E, methyl 4-chloro-6-methylpyridine-3-carboxylate and 3-(hydroxymethyl)-2-methoxyphenylboronic acid were employed. For General Procedure A, 5-((5-chloropyridin-2-yl)methoxy)-1,3,4-thiadiazol-2-amine (Intermediate C) was used. $^1$H NMR (400 MHz, DMSO-$d_6$): δ 12.87 (s, 1H), 8.75 (s, 1H), 8.66 (d, =2.4 Hz, 1H), 8.04-7.97 (m, 1H), 7.61 (d, J=8.4 Hz, 1H), 7.51-7.44 (m, 1H), 7.37 (s, 1H), 7.21 (d, J=4.8 Hz, 2H), 5.55 (s, 2H), 5.19-5.12 (m, 1H), 4.50 (d, J=5.6 Hz, 2H), 3.27 (s, 3H), 2.59 (s, 3H). m/z 498.0 [M+$H^+$].

Example 196

Synthesis of N-(5-((5-chloropyridin-2-yl)methoxy)-1,3,4-thiadiazol-2-yl)-4-(3,5-dimethyl-1H-pyrazol-4-yl)-6methylnicotinamide

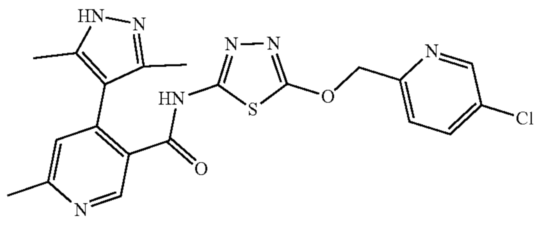 [SMILES: Cc1cc(-c2c(C)n[nH]c2C)c(C(=O)Nc2nnc(OCc3ccc(Cl)cn3)s2)cn1]

The title compound was prepared using General Procedures E, F and A. For General Procedure E, 3,5-dimethyl-4-(4,4,5,5-tetramethyl-1,3,2-dioxaborolan-2-yl)-1H-pyrazole and methyl 4-chloropyridine-3-carboxylate were employed. For General Procedure A, 5-((5-chloropyridin-2-yl)methoxy)-1,3,4-thiadiazol-2-amine (Intermediate C) was used. $^1$HNMR (400 MHz, DMSO-$d_6$): δ 12.51 (s, 1H), 8.72-8.64 (m, 2H), 8.01 (s, 1H), 7.62 (s, 1H), 7.20 (s, 1H), 5.55 (s, 2H), 2.55 (s, 3H), 2.03 (s, 6H). m/z 456.1 [M+$H^+$].

Example 197

Synthesis of N-(5-(2-(5-chloropyridin-2-yl)ethoxy)-1,3,4-thiadiazol-2-yl)-4-(2-methoxyphenyl)-6-methylnicotinamide

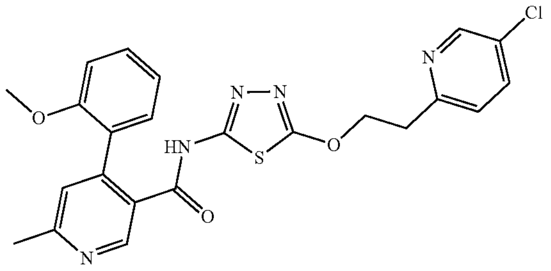 [SMILES: COc1ccccc1-c1cc(C)ncc1C(=O)Nc1nnc(OCCc2ccc(Cl)cn2)s1]

Step-1: Synthesis of 1-(5-chloropyridin-2-yl)ethan-1-ol

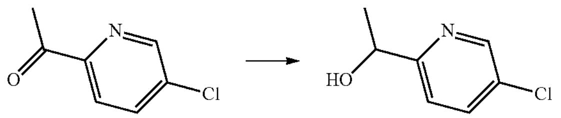

To a solution of 1-(5-chloropyridin-2-yl)ethanone (3.0 g, 19.2 mmol) in MeOH (10 mL) was added $NaBH_4$ (763 mg, 20.1 mmol) in portions at 0° C. The mixture was stirred at room temperature for 2 hours. The reaction mixture was then quenched by the addition of water and extracted with ethyl acetate. The combined organic layers were washed with brine, dried over anhydrous sodium sulfate, filtered, and concentrated under vacuum to afford the title compound (2.5 g, crude) as a yellow oil.

Step-2: Synthesis of O-(2-(5-chloropyridin-2-yl)ethyl) S-methyl carbonodithioate

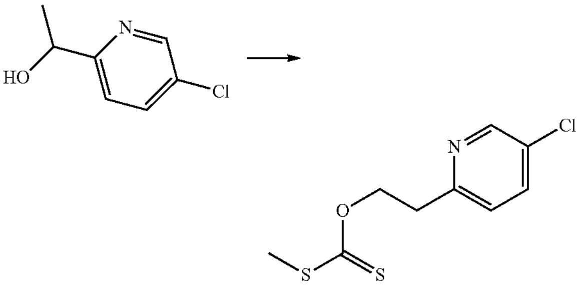

To a solution of 1-(5-chloropyridin-2-yl)ethanol (2.28 g, 14.4 mmol) in THF (10 mL) was added NaH (0.69 g, 28.9 mmol) in portions at 0° C. and stirred at 0° C. for 30 min. Then $CS_2$ (1.65 g, 21.7 mmol) was added to the above mixture at 0° C. and stirred at 0° C. for 20 min, then MeI (3.08 g, 21.7 mmol) was added to the mixture at 0~5° C. under nitrogen. The mixture was stirred at room temperature for 1 hour under nitrogen. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~40% ethyl acetate in petroleum ether to afford the title compound (2.64 g, 74%) (crude) as a colorless oil.

Step-3: Synthesis of O-(2-(5-chloropyridin-2-yl)ethyl) hydrazinecarbothioate

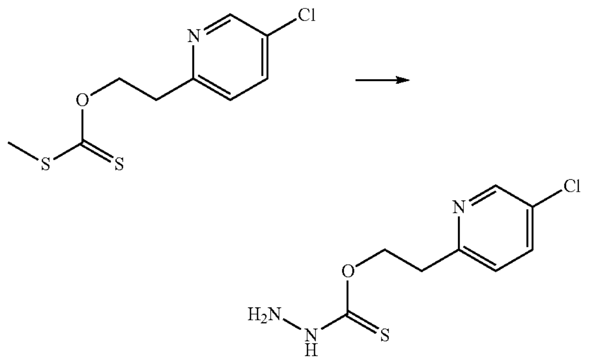

To a solution of 1-(5-chloropyridin-2-yl)ethyl sulfanylmethanethioate (1 g, 4.27 mmol) in MeOH (10 mL) was added $N_2H_4.H_2O$ (250 mg, 4.27 mmol) at room temperature. The mixture was stirred at room temperature for 2 hours. The mixture was diluted with water and extracted with ethyl acetate. The combined organic layers were washed with brine, dried over anhydrous sodium sulfate, filtered, and concentrated under vacuum to afford the title compound (980 mg, crude) as red oil.

Step-4: Synthesis of 5-(2-(5-chloropyridin-2-yl) ethoxy)-1,3,4-thiadiazol-2-amine

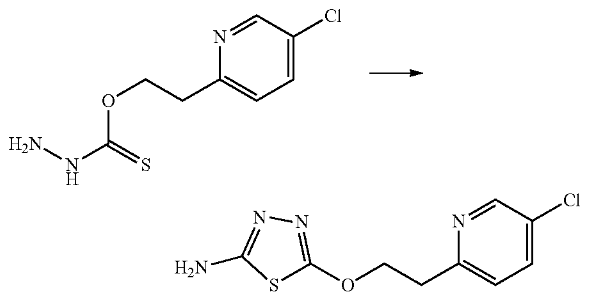

To a solution of ([[1-(5-chloropyridin-2-yl)ethoxy]methanethioyl]amino)amine (1 g, 4.40 mmol) in MeOH (10 mL) were added BrCN (513 mg, 4.84 mmol) and TEA (890 mg, 8.80 mmol). The mixture was stirred at room temperature for 30 min. The mixture was diluted with water and extracted with ethyl acetate. The combined organic layers were washed with brine, dried over anhydrous sodium sulfate, filtered, and concentrated under vacuum, The residue was purified by flash chromatography on silica gel with 0~50% ethyl acetate in petroleum ether to afford the title compound (749 mg, 67%) as a red solid.

Step-5: Synthesis of N-(5-(2-(5-chloropyridin-2-yl) ethoxy)-1,3,4-thiadiazol-2-yl)-4-(2-methoxyphenyl)-6-methylnicotinamide

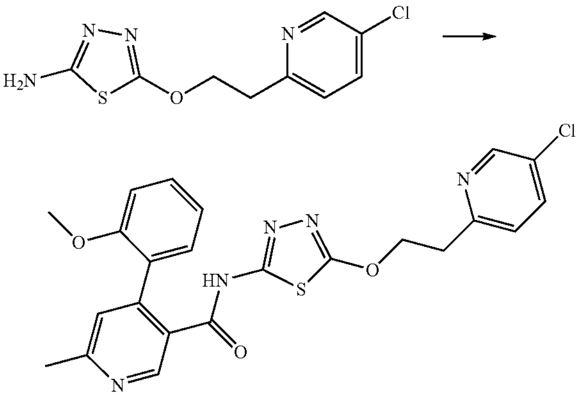

To a solution of 5-(2-(5-chloropyridin-2-yl)ethoxy)-1,3,4-thiadiazol-2-amine (670 mg, 2.60 mmol) in DMF (5 mL) were added DIEA (1.02 g, 7.81 mmol), HATU (1.48 g, 3.90 mmol) and 4-(2-methoxyphenyl)-6-methylpyridine-3-carboxylic acid (Example 113, Step 2, 635 mg, 2.60 mmol). The mixture was stirred at room temperature for 12 h. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purified by prep-HPLC (column, C18 silica gel; mobile phase, water (10 mM $NH_4HCO_3$+0.1% $NH_3 \cdot H_2O$) and ACN) to afford the title compound (121 mg, 14%) as a white solid. $^1H$ NMR (400 MHz, DMSO-$d_6$): δ 12.71 (s, 1H), 8.65 (s, 1H), 8.36-8.35 (m, 1H), 7.85-7.82 (m, 1H), 7.49-7.47 (m, 1H), 7.41-7.33 (m, 2H), 7.30 (s, 1H), 7.09-7.07 (m, 1H), 7.05-6.96 (m, 1H), 4.65 (d, J=6.4 Hz, 2H), 3.49 (s, 3H), 3.13 (d, J=6.4 Hz, 2H), 2.50 (s, 3H). m/z 482.1 [M+H$^+$].

Example 198

Synthesis of N-(5-((5-chloropyridin-2-yl)methoxy)-1,3,4-thiadiazol-2-yl)-4-(3,4-dihydro-2H-benzo[b][1,4]oxazin-8-yl)-6-methylnicotinamide

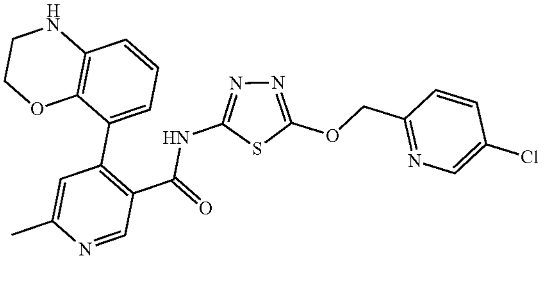 [SMILES: Cc1cc(-c2cccc3c2OCCN3)c(C(=O)Nc2nnc(OCc3ccc(Cl)cn3)s2)cn1]

Step-1: Synthesis of tert-butyl 8-bromo-2,3-dihydro-4H-benzo[b][1,4]oxazine-4-carboxylate

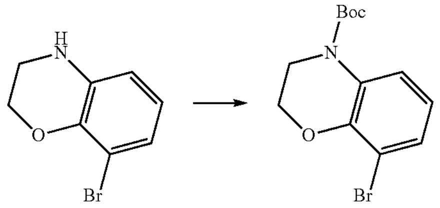 [SMILES: Brc1cccc2c1OCCN2 ; CC(C)(C)OC(=O)N1CCOc2c(Br)cccc21]

To a stirred mixture of 8-bromo-3,4-dihydro-2H-benzo[b][1,4]oxazine (500.0 mg, 2.33 mmol) in 1,4-dioxane (10.0 mL) were added TEA (709.0 mg, 7.00 mmol), $Boc_2O$ (152.9 mg, 0.70 mmol) and DMAP (57.0 mg, 0.46 mmol). The resulting mixture was stirred for overnight at 50° C. before concentrated under vacuum. The residue was purified by flash column chromatography with 0~12% ethyl acetate in petroleum ether to afford the title compound (549 mg, 74%) as a colorless oil.

Step-2: Synthesis of tert-butyl 8-(4,4,5,5-tetramethyl-1,3,2-dioxaborolan-2-yl)-2,3-dihydro-4H-benzo[b][1,4]oxazine-4-carboxylate

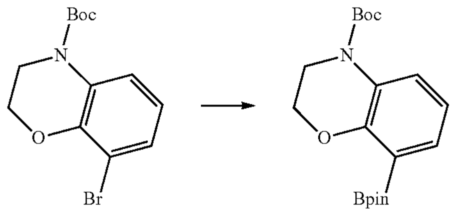

To a stirred solution of tert-butyl 8-bromo-2,3-dihydro-4H-benzo[b][1,4]oxazine-4-carboxylate (540.0 mg, 2.30 mmol) in 1,4-dioxane (10.0 mL) were added $(B_2pin)_2$ (1063.2 mg, 5.76 mmol), KOAc (615.3 mg, 6.92 mmol) and $Pd(dppf)Cl_2$ (153 mg, 0.23 mmol) under nitrogen. The resulting mixture was stirred for overnight at 80° C. under $N_2$. The resulting mixture was quenched with water and extracted with ethyl acetate. The combined organic layers were washed with brine, dried over anhydrous $Na_2SO_4$. After filtration, the filtrate was concentrated under reduced pressure. The residue was purified by flash column chromatography with 0~12% ethyl acetate in petroleum ether to afford the title compound (410 mg, 76%) as a colorless oil.

Step-3: Synthesis of tert-butyl 8-(5-(methoxycarbonyl)-2-methylpyridin-4-yl)-2,3-dihydro-4H-benzo[b][1,4]oxazine-4-carboxylate

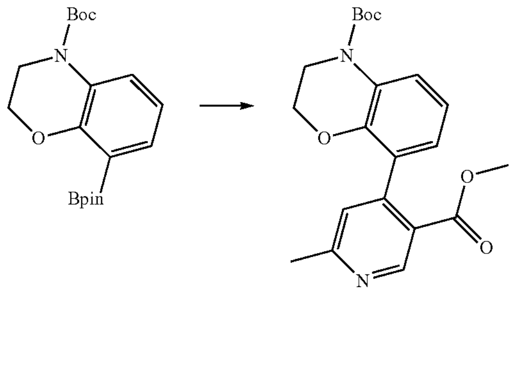

To a degassed mixture of tert-butyl 8-(4,4,5,5-tetramethyl-1,3,2-dioxaborolan-2-yl)-2,3-dihydro-4H-benzo[b][1,4]oxazine-4-carboxylate (390 mg, 1.66 mmol) in 1,4-dioxane (5.0 mL) and $H_2O$ (1.0 mL) were added $K_2CO_3$ (690 mg, 4.99 mmol), methyl 4-chloro-6-methylnicotinate (463 mg, 2.49 mmol) and $Pd(dppf)Cl_2$ (121 mg, 0.16 mmol) under nitrogen atmosphere. The resulting mixture was stirred for 4 h at 80° C. under $N_2$. The resulting mixture was quenched with water and extracted with ethyl acetate. The combined organic layers were washed with brine, dried over anhydrous $Na_2SO_4$. After filtration, the filtrate was concentrated under reduced pressure. The residue was purified by flash column chromatography with 0~37% ethyl acetate in petroleum ether to afford the title compound (260 mg, 40%) as a yellow solid.

Step-4: Synthesis of 4-(4-(tert-butoxycarbonyl)-3,4-dihydro-2H-benzo[b][1,4]oxazin-8-yl)-6-methylnicotinic acid

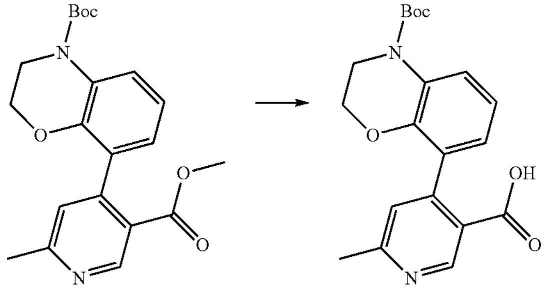

To a stirred solution of tert-butyl 8-(5-(methoxycarbonyl)-2-methylpyridin-4-yl)-2,3-dihydro-4H-benzo[b][1,4]oxazine-4-carboxylate (235 mg, 0.61 mmol) in MeOH (3.0 mL) were added NaOH (48.9 mg, 1.22 mmol) and $H_2O$ (3.0 mL). The resulting mixture was stirred at 50° C. for 2 h. The reaction mixture was acidified to pH ~6 with HCl (1 N) and extracted with ethyl acetate. The combined organic layers were washed with brine, dried over anhydrous $Na_2SO_4$. After filtration, the filtrate was concentrated under reduced pressure to afford the title compound (224 mg, 98%) as an orange solid.

Step-5: Synthesis of tert-butyl 8-(5-((5-((5-chloropyridin-2-yl)methoxy)-1,3,4-thiadiazol-2-yl)carbamoyl)-2-methylpyridin-4-yl)-2,3-dihydro-4H-benzo[b][1,4]oxazine-4-carboxylate

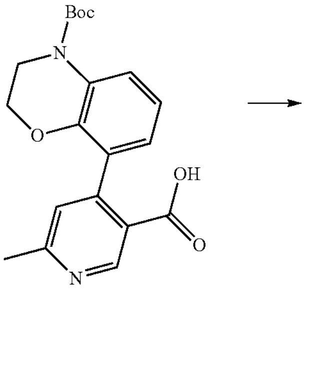

-continued

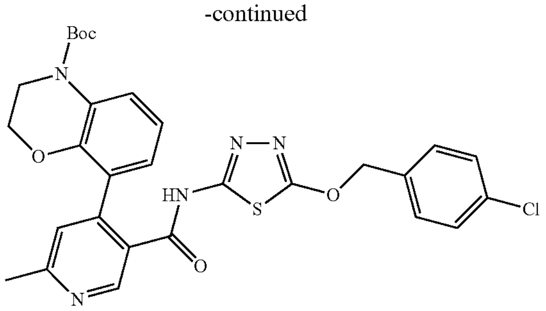

To a stirred mixture of 4-(4-(tert-butoxycarbonyl)-3,4-dihydro-2H-benzo[b][1,4]oxazin-8-yl)-6-methylnicotinic acid (200 mg, 0.54 mmol) in DMF (4.0 mL) were added HATU (410 mg, 1.08 mmol). The resulting mixture was stirred for 5 min at room temperature. To the above mixture were added 5-((5-chloropyridin-2-yl)methoxy)-1,3,4-thiadiazol-2-amine (Intermediate C, 196 mg, 0.81 mmol) and DIEA (209 mg, 1.62 mmol). The resulting mixture was stirred for additional 2 h at room temperature. The resulting mixture was quenched with water and extracted with ethyl acetate. The combined organic layers were washed with brine, dried over anhydrous $Na_2SO_4$ and filtered. The filtrate was collected and concentrated under vacuum. The residue was purified by flash column chromatography with 0~12% ethyl acetate in petroleum ether to afford the title compound (239 mg, 74%) as a yellow oil.

Step-6: Synthesis of N-(5-((5-chloropyridin-2-yl)methoxy)-1,3,4-thiadiazol-2-yl)-4-(3,4-dihydro-2H-benzo[b][1,4]oxazin-8-yl)-6-methylnicotinamide

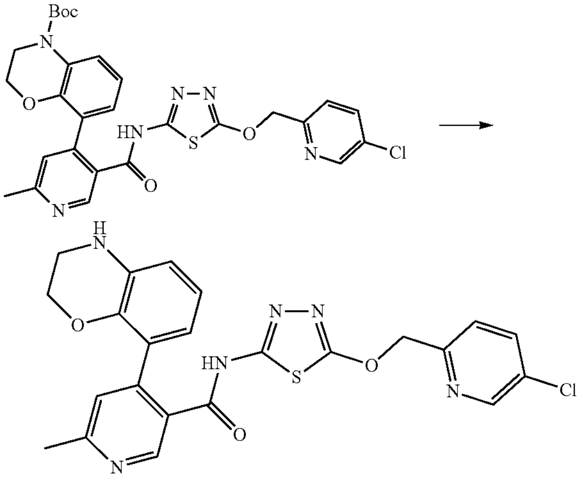

To a mixture of tert-butyl 8-(5-((5-((5-chloropyridin-2-yl)methoxy)-1,3,4-thiadiazol-2-yl)carbamoyl)-2-methylpyridin-4-yl)-2,3-dihydro-4H-benzo[b][1,4]oxazine-4-carboxylate (210 mg, 0.35 mmol) in DCM (4.0 mL) was added TFA (4.0 mL) dropwise at 0° C. The resulting mixture was stirred for 1 h at room temperature before concentrated under vacuum. The residue was basified to pH 7 with saturated $NaHCO_3$ aqueous solution and extracted with ethyl acetate. The combined organic layers were washed with brine, dried over anhydrous $Na_2SO_4$ and filtered. The filtrate was collected and concentrated under vacuum. The crude product was purified by Prep-HPLC (column, C18 silica gel; mobile phase, water (10 mM $NH_4HCO_3$+0.1% $NH_3 \cdot H_2O$) and ACN) to afford the title compound (17.9 mg, 10%) as a white solid. $^1H$ NMR (400 MHz, $CD_3OD$): δ 8.64 (s, 1H), 8.59 (d, J=2.0 Hz, 1H), 7.94-7.92 (m, 1H), 7.62 (d, J=8.4 Hz, 1H), 7.36 (s, 1H), 6.86-6.82 (m, 1H), 6.72-6.68 (m, 2H), 5.56 (s, 2H), 3.97-3.95 (m, 2H), 3.21-3.19 (m, 2H), 2.64 (s, 3H). m/z 495.1 [M+H$^+$].

Example 199

Synthesis of N-(5-((4-fluoropyridin-2-yl)methoxy)-1,3,4-thiadiazol-2-yl)-4-(2-methoxyphenyl)-6-methylnicotinamide

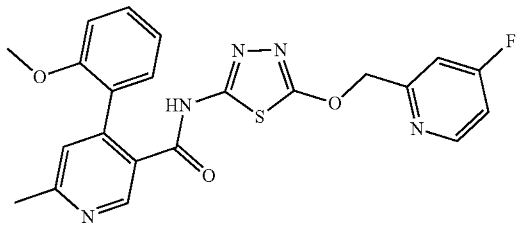 [SMILES: COc1ccccc1-c1cc(C)ncc1C(=O)Nc1nnc(OCc2cc(F)ccn2)s1]

Step-1: Synthesis of (4-fluoropyridin-2-yl)methanol

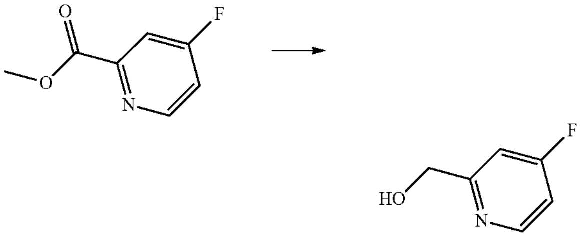

To a solution of methyl 4-fluoropyridine-2-carboxylate (500 mg, 3.22 mmol) in MeOH (15 mL) was added $NaBH_4$ (245 mg, 6.44 mmol) in portions at 0° C. and stirred at room temperature for 4 h. The reaction mixture was then quenched by the addition of water and extracted with ethyl acetate. The combined organic layers were washed with brine, dried over anhydrous sodium sulfate, filtered, and concentrated under vacuum to afford the title compound (420 mg, 84%) as a yellow solid.

Step-2: Synthesis of 5-((4-fluoropyridin-2-yl)methoxy)-1,3,4-thiadiazol-2-amine

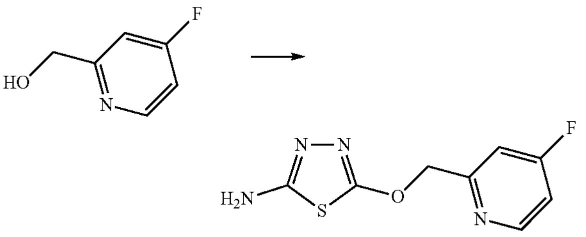

To a solution of NaH (175 mg, 4.36 mmol, 60%) in THF (20 mL) was added (4-fluoropyridin-2-yl)methanol (370 mg, 2.91 mmol) in portions at 0~5° C. and stirred at 5° C. for 1 h. Then 5-bromo-1,3,4-thiadiazol-2-amine (629 mg, 3.49 mmol) was added to the mixture in small portions at 5° C. and stirred at 5° C. for 5 h. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~50% ethyl acetate in petroleum ether to afford (198 mg, 54%) as a white solid.

Step-3: Synthesis of N-(5-((4-fluoropyridin-2-yl)methoxy)-1,3,4-thiadiazol-2-yl)-4-(2-methoxyphenyl)-6-methylnicotinamide

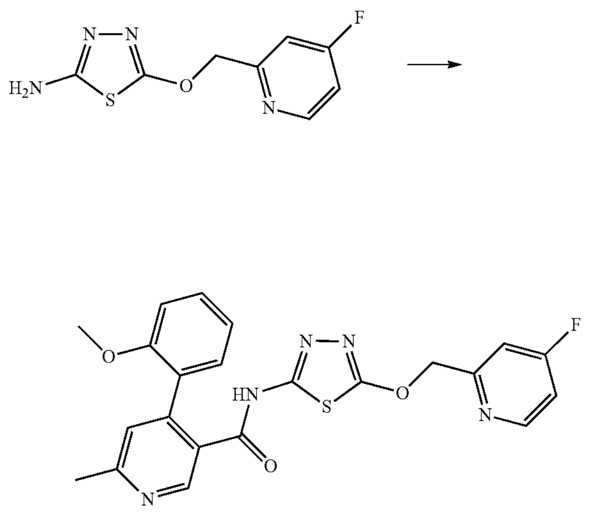

To a solution of 4-(2-methoxyphenyl)-6-methylpyridine-3-carboxylic acid (Example 113, Step 2, 122 mg, 0.502 mmol) in DMF (5 mL) were added DIEA (195 mg, 1.51 mmol), HATU (382 mg, 1.00 mmol) and 5-((4-fluoropyridin-2-yl)methoxy)-1,3,4-thiadiazol-2-amine (170 mg, 0.752 mmol). The mixture was stirred at room temperature for 16 h. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purified by prep-HPLC (column, C18 silica gel; mobile phase, water (0.1% FA) and ACN) to afford the title compound (3.9 mg, 0.03%) as a white solid. $^1$H NMR (400 MHz, $CD_3OD$): δ 8.67 (s, 1H), 8.60 (s, 1H), 7.48-7.36 (m, 4H), 7.24 (s, 1H), 7.11 (s, 1H), 6.99 (s, 1H), 5.59 (s, 2H), 3.62 (s, 3H), 2.66 (s, 3H). m/z 452.1 [M+H$^+$].

Example 200

Synthesis of N-(5-((5-chloropyridin-2-yl)methoxy)-1,3,4-thiadiazol-2-yl)-4-(5-(hydroxymethyl)-2-methoxyphenyl)-6-methylnicotinamide

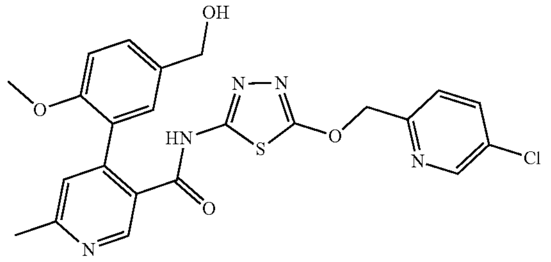 [SMILES: COc1ccc(CO)cc1-c1cc(C)ncc1C(=O)Nc1nnc(OCc2ccc(Cl)cn2)s1]

Step-1: Synthesis of methyl 4-(5-(hydroxymethyl)-2-methoxyphenyl)-6-methylnicotinate

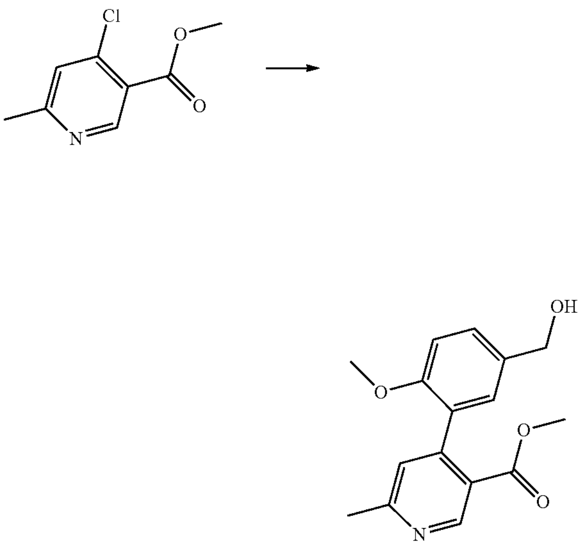

To a solution of methyl 4-chloro-6-methylpyridine-3-carboxylate (500 mg, 2.69 mmol) in dioxane (25 mL) and $H_2O$ (5 mL) were added 5-(hydroxymethyl)-2-methoxyphenylboronic acid (735 mg, 4.04 mmol mmol), $K_2CO_3$ (1.12 g, 8.08 mmol) and Pd(dppf)$Cl_2$ (197 mg, 0.269 mmol) under nitrogen. The resulting solution was stirred at 80° C. for 8 hours under nitrogen. The aqueous solution was concentrated under vacuum. The residue was purified by flash chromatography on silica gel with 0~70% ethyl acetate in petroleum ether to afford the title compound (370 mg, 74%) as a white solid.

Step-2: Synthesis of methyl 4-(2-methoxy-5-(((tetrahydro-2H-pyran-2-yl)oxy)methyl)phenyl)-6-methylnicotinate

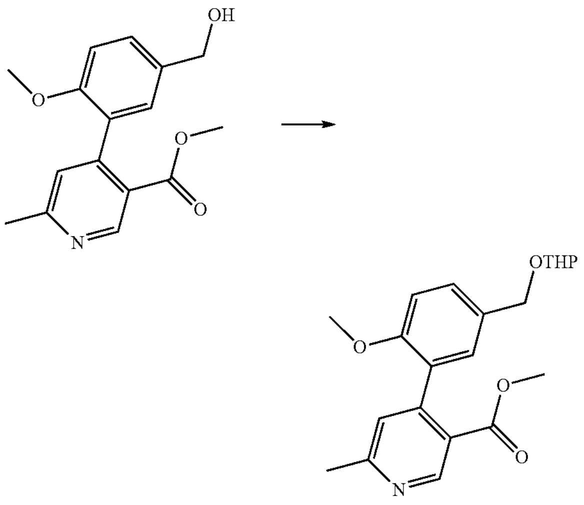

To a solution of methyl 4-[5-(hydroxymethyl)-2-methoxyphenyl]-6-methylpyridine-3-carboxylate (250 mg, 0.870 mmol) in THF (5 mL) were added DHP (147 mg, 1.74 mmol) and TsOH (75 mg, 0.435 mmol). The resulting mixture was stirred at room temperature for 16 h. The aqueous solution was quenched with saturated $NaHCO_3$ aqueous solution and extracted with ethyl acetate. The organic layers were combined, washed with brine, dried over anhydrous sodium sulfate and filtered. The filtrate was concentrated under vacuum to afford the title compound (230 mg, crude) as an off-yellow solid.

Step-3: Synthesis of 4-(2-methoxy-5-(((tetrahydro-2H-pyran-2-yl)oxy)methyl)phenyl)-6-methylnicotinic acid

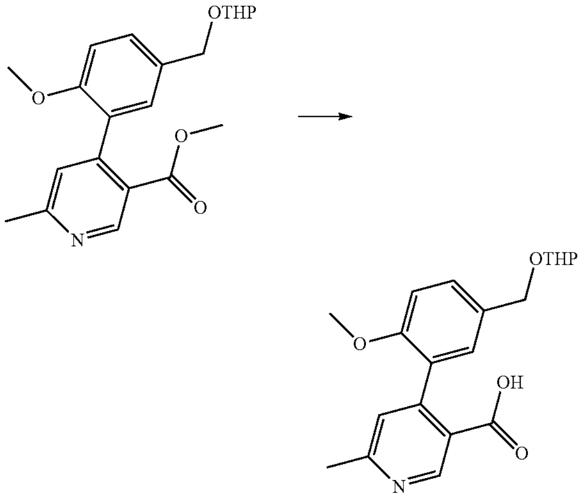

To a solution of 4-(2-methoxy-5-(((tetrahydro-2H-pyran-2-yl)oxy)methyl)phenyl)-6-methylnicotinate (200 mg, 0.563 mmol) in MeOH (10 mL) and $H_2O$ (5 mL) was added NaOH (45 mg, 1.12 mmol). The mixture was stirred at 50° C. for 2 hours. The aqueous solution was neutralized with HCl (1 N) to pH ~6. The aqueous solution was extracted with ethyl acetate. The organic layers were combined, washed with brine, dried over anhydrous sodium sulfate and filtered. The filtrate was concentrated under vacuum to afford the title compound (131 mg, crude) as a white solid.

Step-4: Synthesis of N-(5-((5-chloropyridin-2-yl)methoxy)-1,3,4-thiadiazol-2-yl)-4-(2-methoxy-5-(((tetrahydro-2H-pyran-2-yl)oxy)methyl)phenyl)-6-methylnicotinamide

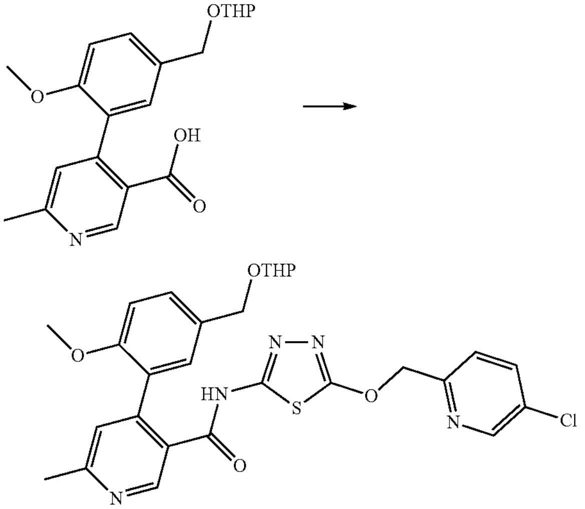

To a mixture of 4-[2-methoxy-5-[(oxan-2-yloxy)methyl]phenyl]-6-methylpyridine-3-carboxylic acid (120 mg, 0.336 mmol) in DMF (2 mL) were added DIEA (130 mg, 1.00 mmol), HATU (191 mg, 0.504 mmol) and 5-[(5-chloropyridin-2-yl)methoxy]-1,3,4-thiadiazol-2-amine (Intermediate C, 123 mg, 0.504 mmol). The mixture was stirred at room temperature for 2 h. The residue was purified by flash chromatography on silica gel with 0~10% methanol in dichloromethane to afford the title compound (25 mg, 21%) as a white solid.

Step-5: Synthesis of N-(5-((5-chloropyridin-2-yl)methoxy)-1,3,4-thiadiazol-2-yl)-4-(5-(hydroxymethyl)-2-methoxyphenyl)-6-methylnicotinamide

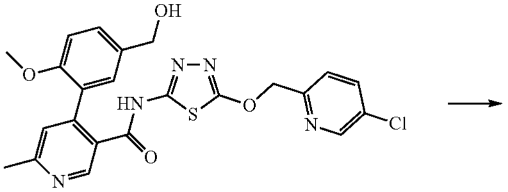

-continued

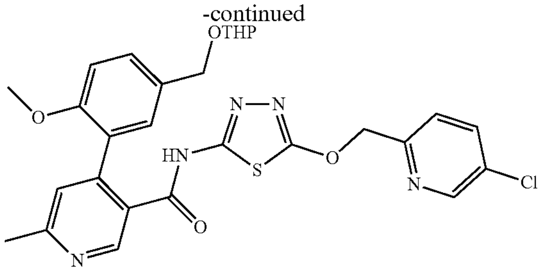

To a mixture of N-[5-[(5-chloropyridin-2-yl)methoxy]-1,3,4-thiadiazol-2-yl]-4-[2-methoxy-5-[(oxan-2-yloxy)methyl]phenyl]-6-methylpyridine-3-carboxamide (25 mg, 0.043 mmol) in $CH_2Cl_2$ (5 mL) were added TFA (1 mL). The mixture was stirred at room temperature for 2 h before concentrated under vacuum. The residue was purified by prep-HPLC (column, C18 silica gel; mobile phase, water (0.1% FA) and ACN) to afford the title compound (10.2 mg, 41%) as a white solid. $^1$H NMR (400 MHz, $CD_3OD$): δ 8.66 (s, 1H), 8.59 (s, 1H), 7.94-7.93 (m, 1H), 7.62 (s, 1H), 7.45-7.40 (m, 3H), 7.00-6.93 (m, 1H), 5.57 (s, 2H), 4.64 (s, 2H), 3.61 (s, 3H), 2.66 (s, 3H). m/z 498.1 [M+H$^+$].

Example 201 and 202

Synthesis of N-[5-[(1R)-1-(4-chlorophenyl)ethoxy]-1,3,4-thiadiazol-2-yl]-4-(2-methoxyphenyl)-6-methylpyridine-3-carboxamide (Example 201) and N-[5-[(1S)-1-(4-chlorophenyl)ethoxy]-1,3,4-thiadiazol-2-yl]-4-(2-methoxyphenyl)-6-methylpyridine-3-carboxamide (Example 202)

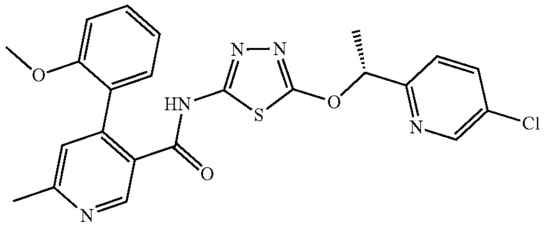

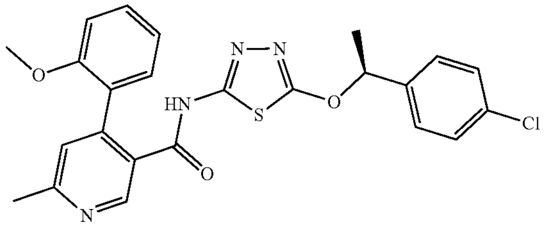

Step-1: Synthesis of [1-(4-chlorophenyl)ethoxy](methylsulfanyl)methanethione

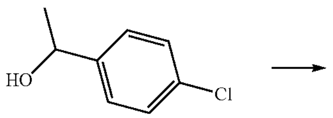

-continued

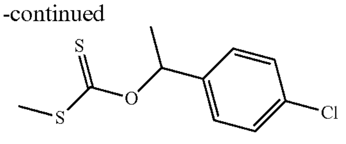

To a solution of NaH (153 mg, 6.38 mmol) in THF (2 mL) was added a solution of methyl 1-(4-chlorophenyl)ethanol (500 mg, 3.19 mmol) in THF (5 mL) dropwise at 0° C. under nitrogen. The resulting solution was stirred at 0° C. for 30 mins under nitrogen atmosphere, then $CS_2$ (364 mg, 4.78 mmol) and MeI (679 mg, 4.78 mmol) were sequentially added dropwise at 0° C. The resulting solution was stirred at 0° C. for additional 1 hour under nitrogen atmosphere. The reaction mixture was quenched with water and extracted with ethyl acetate. The combined organic layers were washed with brine, dried over anhydrous sodium sulfate, filtered, and concentrated under vacuum. The residue was purified by flash column chromatography with 0~50% ethyl acetate in petroleum ether to afford the title compound (403 mg, 46%) as a yellow oil.

Step-2: Synthesis of ([[1-(4-chlorophenyl)ethoxy]methanethioyl]amino)amine

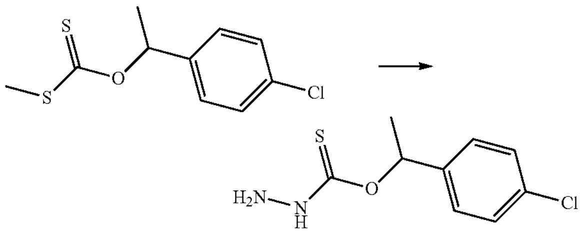

To a solution of [1-(4-chlorophenyl)ethoxy](methylsulfanyl)methanethione (380 mg, 1.54 mmol) in MeOH (5 mL) was added $NH_2NH_2 \cdot H_2O$ (84.8 mg, 1.69 mmol) at 0° C. The resulting solution was stirred at 0° C. for 0.5 h. The resulting mixture was extracted with ethyl acetate. The combined organic layers were washed with water, dried over anhydrous $Na_2SO_4$. After filtration, the filtrate was concentrated under reduced pressure to afford the title compound (356 mg, crude) as a yellow oil.

Step-3: Synthesis of methyl 5-[1-(4-chlorophenyl)ethoxy]-1,3,4-thiadiazol-2-amine

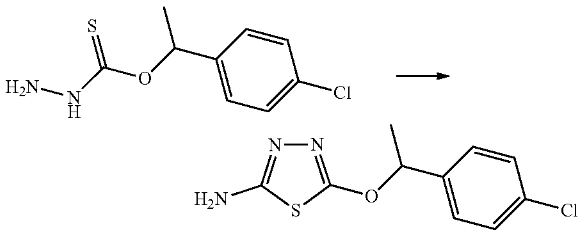

To a solution of methyl ([[1-(4-chlorophenyl)ethoxy]methanethioyl]amino)amine (356 mg, 1.54 mmol) and $Et_3N$ (298 mg, 2.95 mmol) in MeOH (5 mL) was added cyanic bromide (179 mg, 1.69 mmol) at 0° C. The resulting mixture was stirred for 30 min at 0° C. The resulting mixture was diluted with water and extracted with ethyl acetate. The combined organic layers were washed with brine, dried over anhydrous $Na_2SO_4$. After filtration, the filtrate was concentrated under reduced pressure to afford the title compound (377 mg, 86%) as a pink solid.

Step-4: Synthesis of N-[5-[(1R)-1-(4-chlorophenyl)ethoxy]-1,3,4-thiadiazol-2-yl]-4-(2-methoxyphenyl)-6-methylpyridine-3-carboxamide and N-[5-[(1S)-1-(4-chlorophenyl)ethoxy]-1,3,4-thiadiazol-2-yl]-4-(2-methoxyphenyl)-6-methylpyridine-3-carboxamide

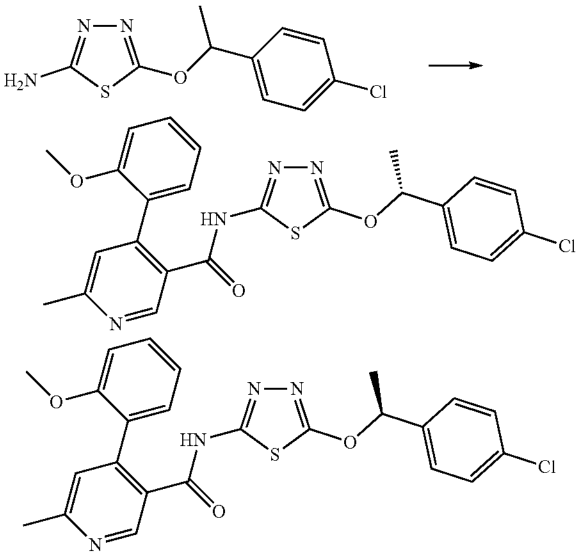

To a solution of 4-(2-methoxyphenyl)-6-methylpyridine-3-carboxylic acid (Example 113, Step 2, 326 mg, 1.34 mmol) in DMF (3 mL) were added HATU (765 mg, 2.01 mmol), DIEA (520 mg, 4.02 mmol) and 5-[1-(4-chlorophenyl)ethoxy]-1,3,4-thiadiazol-2-amine (343 mg, 1.34 mmol) in portions at 0° C. under nitrogen atmosphere. The resulting mixture was stirred at 50° C. for 16 hours under nitrogen atmosphere. The mixture was purified by reverse phase flash column chromatography with 5~40% acetonitrile in water to afford N-[5-[1-(4-chlorophenyl)ethoxy]-1,3,4-thiadiazol-2-yl]-4-(2-methoxyphenyl)-6-methylpyridine-3-carboxamide (213 mg, 32%) as a white solid. The racemic product was separated by prep-chiral-HPLC (Column: CHIRALPAK IG, mobile Phase A: Hex(0.5% 2M $NH_3$-MeOH), Mobile Phase B: EtOH:DCM=1:1) to afford N-[5-[(1S)-1-(4-chlorophenyl)ethoxy]-1,3,4-thiadiazol-2-yl]-4-(2-methoxyphenyl)-6-methylpyridine-3-carboxamide (72.1 mg) as a white solid with shorter retention time and N-[5-[(1R)-1-(4-chlorophenyl)ethoxy]-1,3,4-thiadiazol-2-yl]-4-(2-methoxyphenyl)-6-methylpyridine-3-carboxamide (70.2 mg) as a white solid with longer retention time.

N-[5-[(1R)-1-(4-chlorophenyl)ethoxy]-1,3,4-thiadiazol-2-yl]-4-(2-methoxyphenyl)-6-methylpyridine-3-carboxamide. $^1$H NMR (400 MHz, DMSO-$d_6$): δ 12.68 (s, 1H), 8.64 (s, 1H), 7.53-7.42 (m, 4H), 7.42-7.35 (m, 1H), 7.33 (dd, J=7.6, 2.0 Hz, 1H), 7.28 (s, 1H), 7.06 (dd, J=8.0, 6.8 Hz, 1H), 6.97 (d, J=8.4 Hz, 1H), 6.00 (q, J=6.4 Hz, 1H), 3.47 (s, 3H), 2.56 (s, 3H), 1.64 (d, J=6.4 Hz, 3H). m/z 481.0 [M+H$^+$].

N-[5-[(1S)-1-(4-chlorophenyl)ethoxy]-1,3,4-thiadiazol-2-yl]-4-(2-methoxyphenyl)-6-methylpyridine-3-carboxamide. $^1$H NMR (400 MHz, DMSO-$d_6$): δ 12.68 (s, 1H), 8.63 (s, 1H), 7.53-7.42 (m, 4H), 7.39 (td, J=8.0, 2.0 Hz, 1H), 7.34 (dd, J=7.6, 2.0 Hz, 1H), 7.29 (s, 1H), 7.07 (td, J=7.4, 1.2 Hz, 1H), 6.97 (dd, J=8.4, 1.2 Hz, 1H), 6.01 (q, J=6.4 Hz, 1H), 3.47 (s, 3H), 2.56 (s, 3H), 1.64 (d, J=6.4 Hz, 3H). m/z 481.1 [M+H$^+$].

Example 203

Synthesis of N-[5-[(5-chloropyridin-2-yl)methoxy]-1,3,4-thiadiazol-2-yl]-4-[2-(hydroxymethyl)phenyl]-6-methylpyridine-3-carboxamide

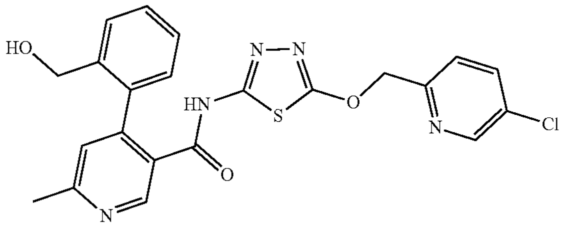 [SMILES: Cc1cc(-c2ccccc2CO)c(C(=O)Nc2nnc(OCc3ccc(Cl)cn3)s2)cn1]

Step-1: Synthesis of 2-methylbenzo[5,6]oxepino[3,4-c]pyridin-5(7H)-one

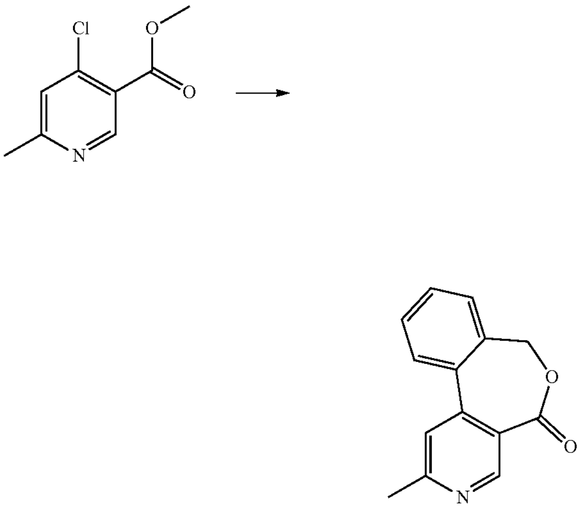

To a degassed solution of methyl 4-chloro-6-methylpyridine-3-carboxylate (1.0 g, 5.38 mmol) and [2-(4,4,5,5-tetramethyl-1,3,2-dioxaborolan-2-yl)phenyl]methanol (1.26 g, 5.38 mmol) in dioxane (10 mL) and $H_2O$ (1 mL) were added Pd(dppf)$Cl_2$ (390 mg, 0.533 mmol) and $K_2CO_3$ (2.23 g, 16.1 mmol) under nitrogen atmosphere. The resulting mixture was stirred at 80° C. for 2 h under nitrogen atmosphere. The resulting mixture was concentrated under vacuum. The residue was purified by flash column chromatography with 0~20% MeOH in DCM to afford the title compound (563 mg, 32%) as a brown solid.

Step-2: Synthesis of N-[5-[(5-chloropyridin-2-yl) methoxy]-1,3,4-thiadiazol-2-yl]-4-[2-(hydroxymethyl)phenyl]-6-methylpyridine-3-carboxamide

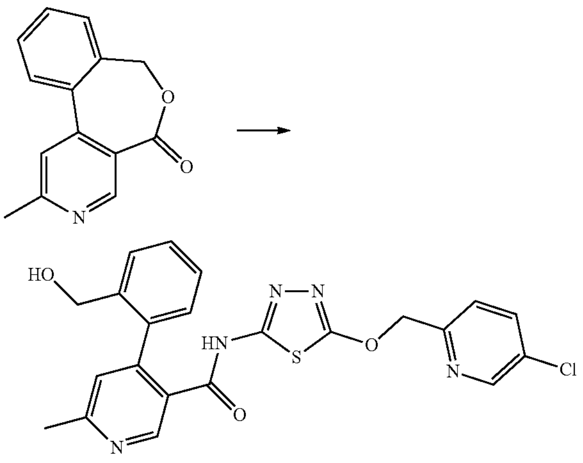

To a degassed solution of 5-[(5-chloropyridin-2-yl) methoxy]-1,3,4-thiadiazol-2-amine (Intermediate C, 116 mg, 0.48 mmol) in THF (10 mL) was added $AlMe_3$ (2 M in hexane) (2 mL) dropwise at 0° C. under nitrogen. The resulting mixture was stirred at room temperature for 30 min. To the above solution was added 2-methylbenzo[5,6] oxepino[3,4-c]pyridin-5(7H)-one (90.0 mg, 0.400 mmol) in THE (5 mL) dropwise at 0° C. under nitrogen. The resulting solution was stirred at 60° C. for overnight under nitrogen. The reaction mixture was quenched by the addition of $H_2O$ and extracted with chloroform. The combined organic layers were washed with brine, dried over anhydrous sodium sulfate, filtered, and concentrated under vacuum. The residue was purified by Prep-HPLC (column, C18 silica gel; mobile phase, water (10 mM $NH_4HCO_3$) and ACN) to afford the title compound (34.0 mg, 71%) as a white solid. $^1H$ NMR (400 MHz, DMSO-$d_6$) δ 12.85 (s, 1H), 8.77 (s, 1H), 8.64 (d, =2.4 Hz, 1H), 8.01-7.97 (m, 1H), 7.61-7.50 (m, 2H), 740-7.38 (m, 1H), 7.31-7.23 (m, 2H), 7.05-7.03 (m, 1H), 5.52 (s, 2H), 4.32 (s, 2H), 2.56 (s, 3H). m/z 468 [M+$H^+$].

Example 204

Synthesis of 6-(aminomethyl)-N-[5-[(5-chloropyridin-2-yl)methoxy]-1,3,4-thiadiazol-2-yl]-4-(2-methoxyphenyl)pyridine-3-carboxamide

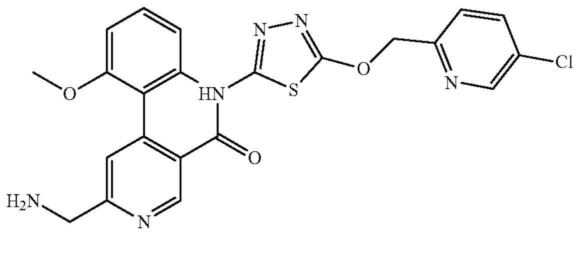 [SMILES: COc1cccc2c1c1cc(CN)ncc1c(=O)n2-c1nnc(OCc2ccc(Cl)cn2)s1]

Step 1. Synthesis of N-[5-[(5-chloropyridin-2-yl) methoxy]-1,3,4-thiadiazol-2-yl]-6-formyl-4-(2-methoxyphenyl)pyridine-3-carboxamide

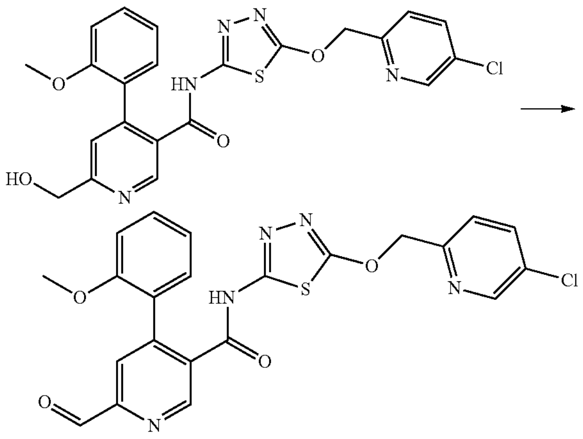

To a solution of N-[5-[(5-chloropyridin-2-yl)methoxy]-1,3,4-thiadiazol-2-yl]-6-(hydroxymethyl)-4-(2-methoxyphenyl)pyridine-3-carboxamide (Example 170, 100 mg, 0.207 mmol) in DCM (6.00 mL) were added Dess-Martin's reagent (132 mg, 0.310 mmol). The resulting mixture was stirred at room temperature for 1 hour. The resulting mixture was quenched with water and extracted with ethyl acetate. The organic layers were combined, washed with brine, dried over anhydrous sodium sulfate and filtered. The filtrate was concentrated under vacuum to afford the title compound (90 mg, crude) as a light yellow solid, which was used for the next step without further purification.

Step 2. Synthesis of (E)-N-[5-([5-[(5-chloropyridin-2-yl)methoxy]-1,3,4-thiadiazol-2-yl]carbamoyl)-4-(2-methoxyphenyl)pyridin-2-yl]carboximidic acid

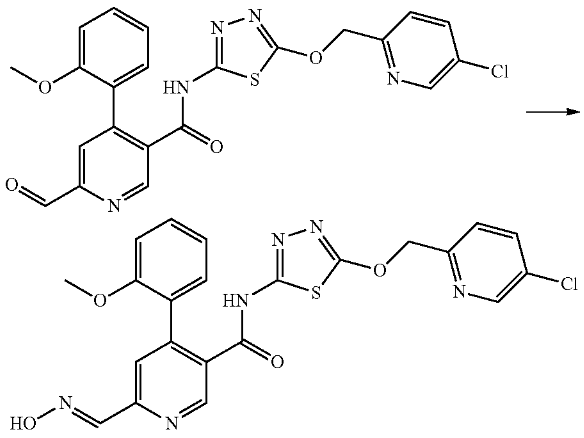

To a solution of N-[5-[(5-chloropyridin-2-yl)methoxy]-1,3,4-thiadiazol-2-yl]-6-formyl-4-(2-methoxyphenyl)pyridine-3-carboxamide (80 mg, 0.166 mmol) in MeOH (2.00 mL) were added $NH_2OH·HCl$ (23 mg, 0.332 mmol) and $NaHCO_3$ (14 mg, 0.166 mmol). The resulting mixture was stirred at room temperature for 16 hours. The resulting mixture was quenched with water and extracted with ethyl acetate. The organic layers were combined, washed with brine, dried over anhydrous sodium sulfate and filtered. The filtrate was concentrated under vacuum to afford the title compound (76 mg, crude) as a light yellow solid. MS (ESI) calc'd for ($C_{22}H_{17}ClN_6O_4S$) $[M+1]^+$, 497.1; found 497.0.

Step 3. Synthesis of 6-(aminomethyl)-N-(5-((5-chloropyridin-2-yl)methoxy)-1,3,4-thiadiazol-2-yl)-4-(2-methoxyphenyl)nicotinamide

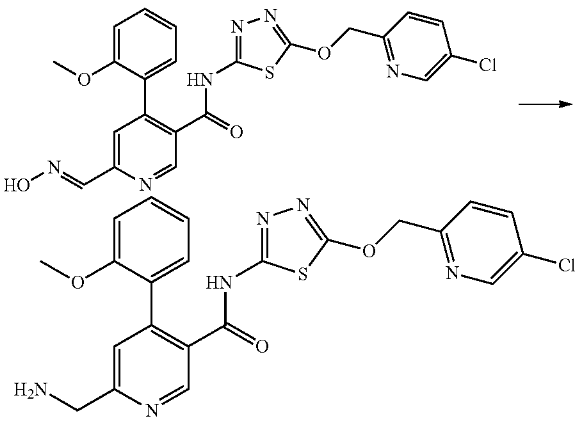

To a mixture of (E)-N-[5-([5-[(5-chloropyridin-2-yl)methoxy]-1,3,4-thiadiazol-2-yl]carbamoyl)-4-(2-methoxyphenyl)pyridin-2-yl]carboximidic acid (76 mg, 0.153 mmol) in methanol (3 mL) were added TFA (322 mg, 2.82 mmol) and Zn (55 mg, 0.841 mmol). The mixture was stirred at room temperature for 4 hours. The resulting mixture was filtered, the filtrate was concentrated under reduced pressure. The crude product was purified by Prep-HPLC (column, C18 silica gel; mobile phase, 15-45% MeCN in water, with both eluents containing 0.1% FA) to afford the title compound as a formate salt (20.2 mg, 29%, white solid). $^1H$ NMR (400 MHz, DMSO-$d_6$) δ 12.95 (s, 1H), 8.84 (s, 1H), 8.66 (d, J=2.4 Hz, 1H), 8.42 (s, 1H), 8.02 (dd, J=8.4, 2.4 Hz, 1H), 7.62 (d, J=8.4 Hz, 1H), 7.57 (s, 1H), 7.49-7.40 (m, 1H), 7.37 (dd, J=7.6, 1.6 Hz, 1H), 7.13 (t, J=7.6 Hz, 1H), 7.03 (d, J=8.4 Hz, 1H), 5.56 (s, 2H), 4.33 (s, 2H), 3.53 (s, 3H). m/z 483 $[M+H^+]$.

Example 205

Synthesis of 4-(2-methoxyphenyl)-6-methyl-N-(5-((5-methylpyridin-2-yl)methoxy)-1,3,4-thiadiazol-2-yl)nicotinamide

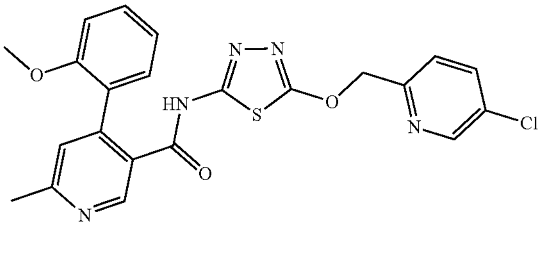 [SMILES: COc1ccccc1-c1cc(C)ncc1C(=O)Nc1nnc(OCc2ccc(Cl)cn2)s1]

Step-1: Synthesis of 5-((5-methylpyridin-2-yl)methoxy)-1,3,4-thiadiazol-2-amine

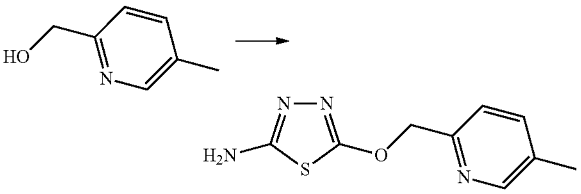

To a stirred mixture of (5-methylpyridin-2-yl)methanol (500.0 mg, 4.06 mmol) in dry THF (7.0 mL) were added NaH (324.7 mg, 8.12 mmol, 60%) in portions at 5° C. and stirred for 30 min under nitrogen atmosphere. To the above mixture was added 5-bromo-1,3,4-thiadiazol-2-amine (877 mg, 4.87 mmol) in portions at 0~5° C. The resulting mixture was stirred for additional 4 h at the same temperature. The resulting mixture was quenched by the addition of water and extracted with ethyl acetate. The combined organic layers were washed with brine, dried over anhydrous $Na_2SO_4$. After filtration, the filtrate was concentrated under reduced pressure. The residue was purified by flash column chromatography with 0~90% ethyl acetate in petroleum ether to afford the title compound (430 mg, 47%) as a grey solid.

Step-2: Synthesis of 4-(2-methoxyphenyl)-6-methyl-N-(5-((5-methylpyridin-2-yl)methoxy)-1,3,4-thiadiazol-2-yl)nicotinamide

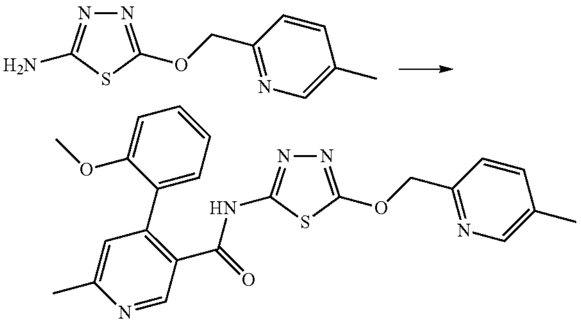

To a stirred mixture of 4-(2-methoxyphenyl)-6-methylpyridine-3-carboxylic acid (Example 113, Step 2, 240 mg, 0.99 mmol) in DMF (5.0 mL) were added HATU (684 mg, 1.80 mmol). The resulting mixture was stirred for 5 min at room temperature. To the above mixture were added 5-[(5-methylpyridin-2-yl)methoxy]-1,3,4-thiadiazol-2-amine (200 mg, 0.90 mmol) and DIEA (348.8 mg, 2.69 mmol). The resulting mixture was stirred for additional 5 h at room temperature. The resulting mixture was diluted with water and extracted with ethyl acetate. The combined organic layers were washed with brine, dried over anhydrous $Na_2SO_4$. After filtration, the filtrate was concentrated under reduced pressure. The residue was purified by flash column chromatography with 0~8% methanol in ethyl acetate. The product was further purified by washed with methanol and dried under vacuum to afford the title compound (38 mg, 9%) as a white solid. $^1H$ NMR (400 MHz, DMSO-$d_6$): δ 12.73 (s, 1H), 8.66 (s, 1H), 8.43 (s, 1H), 7.67 (d, J=7.2 Hz, 1H), 7.45 (d, J=8.0 Hz, 1H), 7.41-7.34 (m, 2H), 7.30 (s, 1H), 7.09-7.05 (m, 1H), 6.98 (d, J=8.4 Hz, 1H), 5.48 (s, 2H), 3.51 (s, 3H), 2.56 (s, 3H), 2.31 (s, 3H). m/z 448.1 [M+H+].

Example 206

Synthesis of N-[5-[(5-chloropyridin-2-yl)methoxy]-1,3,4-thiadiazol-2-yl]-4-(2-fluoro-6-methoxyphenyl)-6-(hydroxymethyl)pyridine-3-carboxamide

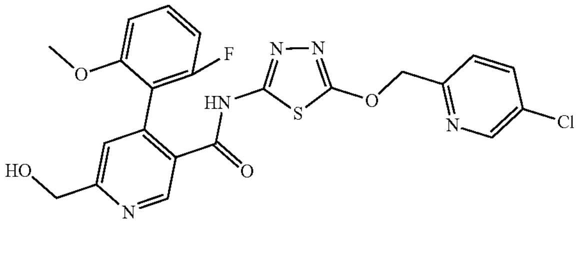 [SMILES: COc1cccc(F)c1-c1cc(CO)ncc1C(=O)Nc1nnc(OCc2ccc(Cl)cn2)s1]

Step-1: Synthesis of methyl 4-(2-fluoro-6-methoxyphenyl)-6-(hydroxymethyl)pyridine-3-carboxylate

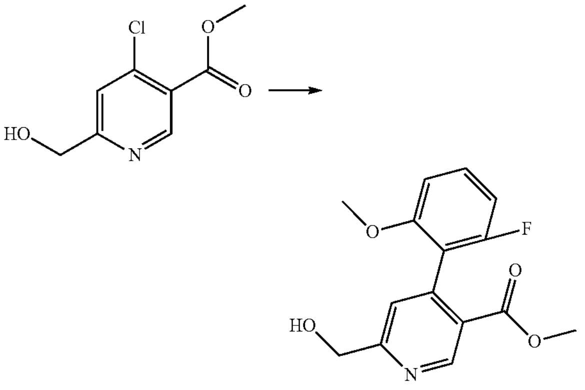

To a mixture of methyl 4-chloro-6-(hydroxymethyl)pyridine-3-carboxylate (200 mg, 0.992 mmol) and 2-fluoro-6-methoxyphenylboronic acid (169 mg, 0.992 mmol) in dioxane (5 mL) and water (1 mL) were added $K_2CO_3$ (411 mg, 2.97 mmol) and Pd(dppf)$Cl_2$ (73 mg, 0.099 mmol). The resulting mixture was stirred at 80° C. for 2 h under nitrogen atmosphere. The resulting mixture was concentrated under reduced pressure. The residue was purified by flash column chromatography with 0-5% MeOH in DCM to afford the title compound (280 mg, 96%) as a yellow oil.

Step-2: Synthesis of methyl 4-(2-fluoro-6-methoxyphenyl)-6-[(oxan-2-yloxy)methyl]pyridine-3-carboxylate

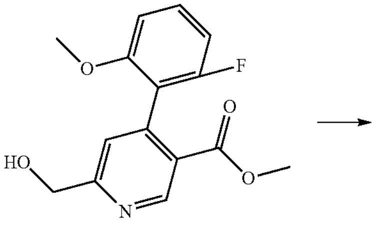

-continued

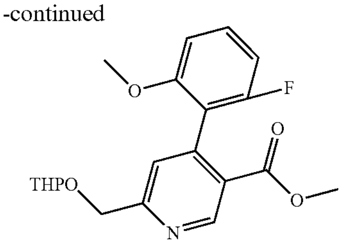

To a mixture of methyl 4-(2-fluoro-6-methoxyphenyl)-6-(hydroxymethyl)pyridine-3-carboxylate (355 mg, 1.21 mmol) in DCM (5 mL) were added DHP (205 mg, 2.43 mmol) and TsOH (21 mg, 0.122 mmol). The resulting mixture was stirred at 50° C. for 2 hours under nitrogen atmosphere. The resulting mixture was concentrated under reduced pressure. The residue was purified by flash column chromatography with 0-5% MeOH in $CH_2C_2$ to afford the title compound (300 mg, 65%) as a yellow oil.

Step-3: Synthesis of 4-(2-fluoro-6-methoxyphenyl)-6-[(oxan-2-yloxy)methyl]pyridine-3-carboxylic acid

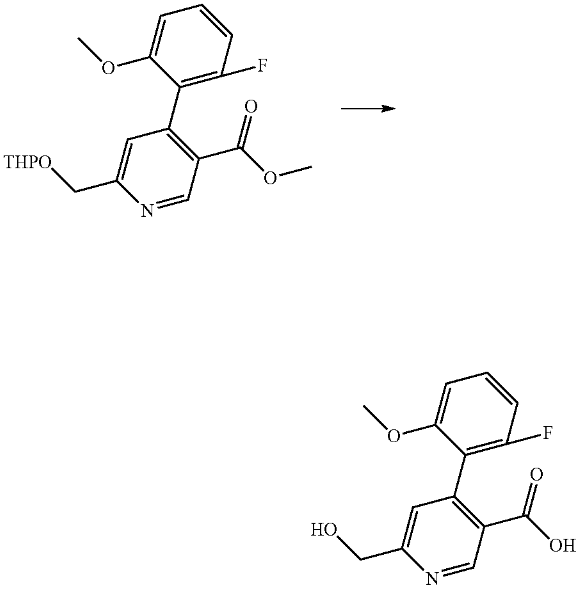

To a mixture of methyl 4-(2-fluoro-6-methoxyphenyl)-6-[(oxan-2-yloxy)methyl]pyridine-3-carboxylate (280 mg, 0.746 mmol) in THF (5 mL) and water (5 mL) was added NaOH (120 mg, 2.98 mmol). The resulting mixture was stirred at 50° C. for 4 h. The mixture was acidified with HCl (1 N) to pH 2-3. The resulting mixture was concentrated under reduced pressure. The residue was purified by reverse phase flash column chromatography with 0-20% acetonitrile in water to afford the title compound (200 mg, 74%) as a green solid.

Step-4: Synthesis of N-[5-[(5-chloropyridin-2-yl)methoxy]-1,3,4-thiadiazol-2-yl]-4-(2-fluoro-6-methoxyphenyl)-6-(hydroxymethyl)pyridine-3-carboxamide

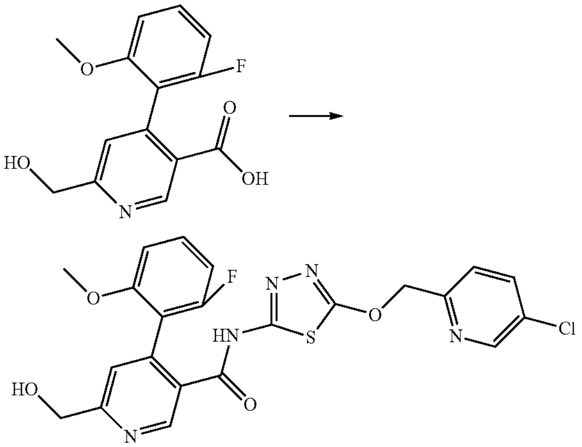

To a mixture of 4-(2-fluoro-6-methoxyphenyl)-6-(hydroxymethyl)pyridine-3-carboxylic acid (200 mg, 0.721 mmol) and 5-[(5-chloropyridin-2-yl)methoxy]-1,3,4-thiadiazol-2-amine (Intermediate C, 263 mg, 1.08 mmol) in DMF (10 mL) were added HATU (820 mg, 2.16 mmol) and DIEA (140 mg, 1.08 mmol). The resulting mixture was stirred at room temperature for 2 hours. The residue was purified by reverse phase flash chromatography with 10~40% acetonitrile in water and further purified by prep-HPLC (column, C18 silica gel; mobile phase, water (10 mM $NH_4HCO_3$+ 0.1% $NH_3 \cdot H_2O$) and ACN) to afford The title compound (77 mg, 21%) as a white solid. $^1$H NMR (400 MHz, DMSO-$d_6$): δ 12.82 (s, 1H), 9.00-8.89 (m, 1H), 7.77-7.69 (m, 1H), 7.98-7.89 (m, 1H), 7.81 (s, 1H), 7.49-7.31 (m, 2H), 7.01-6.91 (m, 2H), 5.71-5.601 (m, 1H), 5.61 (s, 2H), 4.81-4.75 (m, 2H), 3.59 (s, 3H). m/z 502.0 [M+H$^+$].

Example 207

Synthesis of N-(5-((5-chloropyridin-2-yl)methoxy)-1,3,4-thiadiazol-2-yl)-6-(2-hydroxypropan-2-yl)-4-(2-methoxyphenyl)nicotinamide

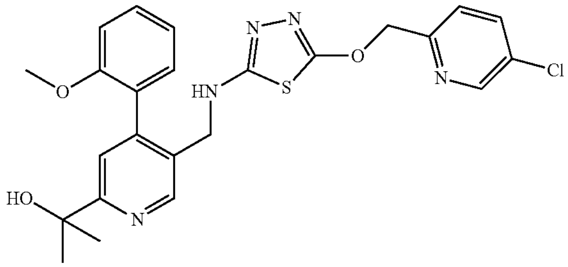 [SMILES: COc1ccccc1-c1cc(C(C)(C)O)ncc1CNc1nnc(OCc2ccc(Cl)cn2)s1]

Step-1: Synthesis of isopropyl 5-([5-[(5-chloropyridin-2-yl)methoxy]-1,3,4-thiadiazol-2-yl]carbamoyl)-4-(2-methoxyphenyl)pyridine-2-carboxylate

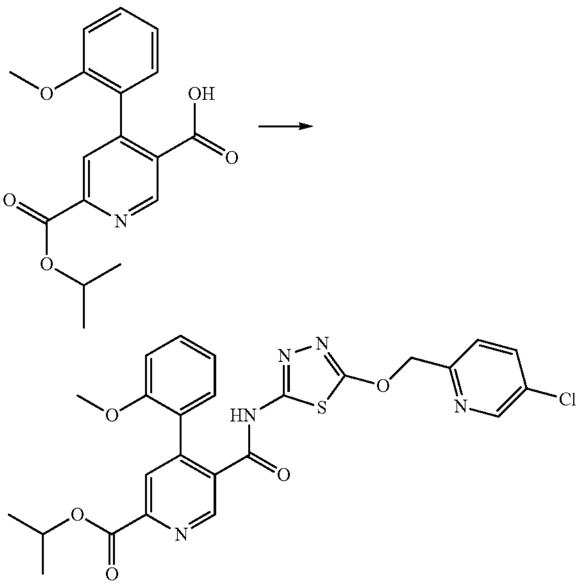

To a mixture of 6-(isopropoxycarbonyl)-4-(2-methoxyphenyl)pyridine-3-carboxylic acid (Step 3 of Example 102, 2 g, 6.343 mmol), HATU (7.2 g, 19.0 mmol) and DIEA (1.23 g, 9.51 mmol) in DMF (20 mL) was added 5-[(5-chloropyridin-2-yl)methoxy]-1,3,4-thiadiazol-2-amine (Intermediate C, 1.54 g, 6.34 mmol). The resulting mixture was stirred at room temperature for 2 h before concentrated under vacuum. The residue was purified by flash column chromatography with 0-8% MeOH in $CH_2Cl_2$ to afford the title compound (2.77 g, 81%) as a yellow solid.

Step-2: Synthesis of N-(5-((5-chloropyridin-2-yl)methoxy)-1,3,4-thiadiazol-2-yl)-6-(2-hydroxypropan-2-yl)-4-(2-methoxyphenyl)nicotinamide

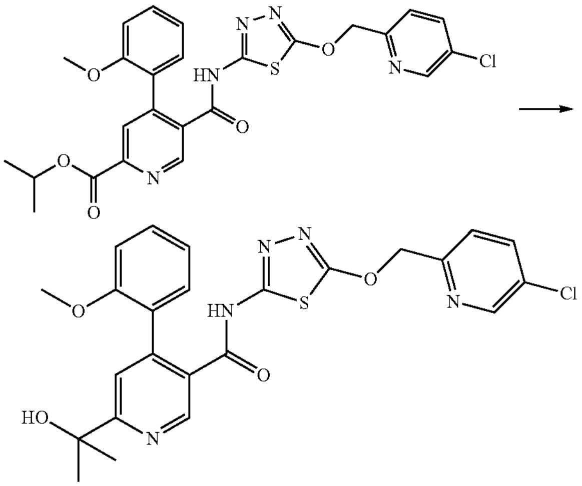

To a mixture of isopropyl 5-((5-((5-chloropyridin-2-yl)methoxy)-1,3,4-thiadiazol-2-yl)carbamoyl)-4-(2-methoxyphenyl)picolinate (200 mg, 0.35 mmol) in THF (5 mL) was added MeMgBr (3 M, 0.5 mL) at −78° C. under nitrogen. The mixture was stirred at room temperature for 8 hours. The reaction was then quenched by the addition of MeOH and then concentrated under vacuum. The residue was purified by flash chromatography on silica gel with 0~10% dichloromethane in methanol and further purified by prep-HPLC (column, C18 silica gel; mobile phase, water (10 mM $NH_4HCO_3$+0.1% $NH_3 \cdot H_2O$) and ACN) to afford the title compound (20.2 mg, 10%) as an off-white solid. $^1$H NMR (400 MHz, DMSO-$d_6$); δ 12.67 (s, 1H), 8.71 (s, 1H), 8.66 (s, 1H), 8.02-7.99 (m, 1H), 7.65-7.60 (m, 2H), 7.43-7.35 (m, 2H), 7.11-7.10 (m, 1H), 7.09-6.98 (m, 1H), 5.54 (s, 2H), 5.42 (s, 1H), 3.51 (s, 3H), 1.50 (s, 6H). m/z 512.1 [M+H$^+$].

Example 208

Synthesis of N-(5-((5-chloropyridin-2-yl)methoxy)-1,3,4-thiadiazol-2-yl)-4-(2,2-difluorobenzo[d][1,3]dioxol-4-yl)-6-methylnicotinamide

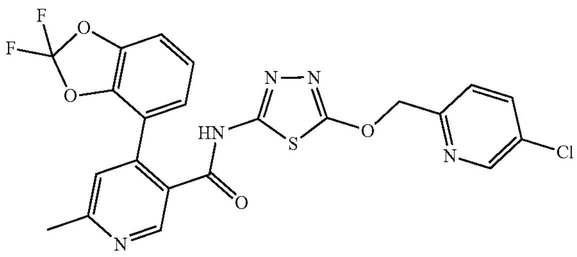 [SMILES: Cc1cc(-c2cccc3c2OC(F)(F)O3)c(C(=O)Nc2nnc(OCc3ccc(Cl)cn3)s2)cn1]

The title compound was prepared using General Procedure E, F and A. Methyl 4-chloro-6-methylpyridine-3-carboxylate and 2,2-difluoro-3a,7a-dihydro-1,3-benzodioxol-4-ylboronic acid were employed for General Procedure E. For General Procedure A, 5-[(5-chloropyridin-2-yl)methoxy]-1,3,4-thiadiazol-2-amine (Intermediate C) was used. $^1$H NMR (400 MHz, DMSO-$d_6$); δ 13.17 (s, 1H), 8.88 (s, 1H), 8.65-8.64 (m, 1H), 8.01-7.98 (m, 1H), 7.59-7.51 (m, 1H), 7.48-7.44 (m, 2H), 7.36-7.28 (m, 2H), 5.51 (s, 2H), 2.50 (s, 3H). m/z 518.0 [M+H$^+$].

Example 209

Synthesis of N-(5-((5-chloropyridin-2-yl)methoxy)-1,3,4-thiadiazol-2-yl)-5-(2-methoxyphenyl)pyrimidine-4-carboxamide

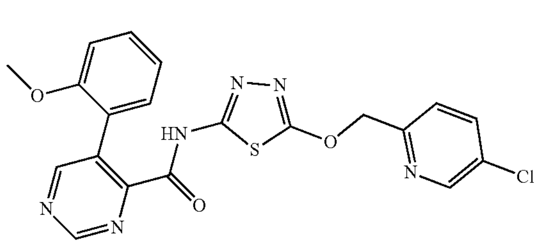 [SMILES: COc1ccccc1-c1cncnc1C(=O)Nc1nnc(OCc2ccc(Cl)cn2)s1]

The title compound was prepared using General Procedure E, F and A. Methyl 5-bromopyrimidine-4-carboxylate and (2-methoxyphenyl)boronic acid were employed for General Procedure E. For General Procedure A, 5-[(5-chloropyridin-2-yl) methoxy]-1,3,4-thiadiazol-2-amine (Intermediate C) was used. $^1$H NMR (400 MHz, DMSO-$d_6$): δ 13.07 (s, 1H), 9.33-9.34 (m, 1H), 8.98 (s, 1H), 8.66-8.65 (m, 1H), 8.02-7.99 (m, 1H), 7.62-7.60 (m, 1H), 7.45-7.41 (m, 2H), 7.11-7.03 (m, 2H), 5.56 (s, 2H), 3.55 (s, 3H). m/z 455.0 [M+H$^+$].

Example 210

Synthesis of N-[5-[(3-fluoropyridin-2-yl)methoxy]-1,3,4-thiadiazol-2-yl]-4-(2-methoxyphenyl)-6-methylpyridine-3-carboxamide

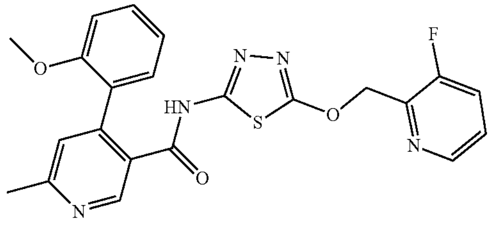 [SMILES: COc1ccccc1-c1cc(C)ncc1C(=O)Nc1nnc(OCc2ncccc2F)s1]

Step-1. Synthesis of 5-((3-fluoropyridin-2-yl) methoxy)-1,3,4-thiadiazol-2-amine

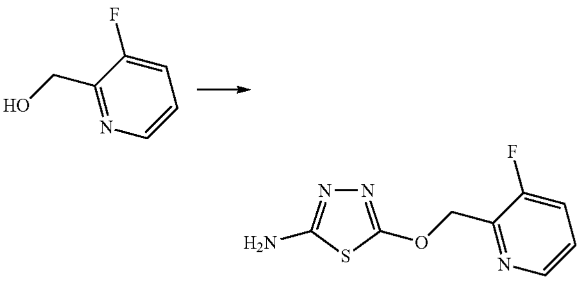

To a solution of NaH (0.70 g, 17.5 mmol, 60%) in THF (10 mL) was added (3-fluoropyridin-2-yl) methanol (1.50 g, 11.8 mmol) in portions at 0~5° C. and stirred at 5° C. for 1 h under nitrogen. Then 5-bromo-1,3,4-thiadiazol-2-amine (2.55 g, 14.1 mmol) was added to the mixture in small portions at 5° C. and stirred at 5° C. for 5 h under nitrogen. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~50% ethyl acetate in petroleum ether to afford the title compound (1.96 g, 74%) as a white solid.

Step-2: Synthesis of N-(5-((3-fluoropyridin-2-yl) methoxy)-1,3,4-thiadiazol-2-yl)-4-(2-methoxyphenyl)-6-methylnicotinamide

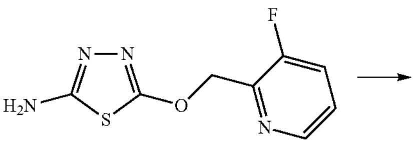

-continued

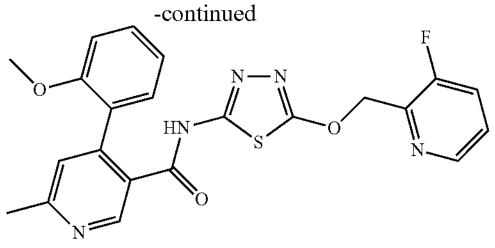

To a mixture of 5-[(3-fluoropyridin-2-yl)methoxy]-1,3,4-thiadiazol-2-amine (280 mg, 1.23 mmol) in DMF (5 mL) were added DIEA (480 mg, 3.71 mmol), HATU (706 mg, 1.85 mmol) and 4-(2-methoxyphenyl)-6-methylpyridine-3-carboxylic acid (Example 113, Step 2, 302 mg, 1.23 mmol). The mixture was stirred at room temperature for 16 h. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% dichloromethane in methanol and further purified by prep-HPLC (column, C18 silica gel; mobile phase, water (10 mM $NH_4HCO_3$+0.1% $NH_3 \cdot H_2O$) and ACN) to afford the title compound (25 mg, 5%) as a white solid. $^1H$ NMR (400 MHz, DMSO-$d_6$): δ 12.77 (s, 1H), 8.69 (s, 1H), 8.48-8.46 (m, 1H), 7.84-7.79 (m, 1H), 7.57-7.53 (m, 1H), 7.42-7.34 (m, 3H), 7.10-6.98 (m, 2H), 5.62 (s, 2H), 3.51 (s, 3H), 2.67 (s, 3H). m/z 452.2 [$M+H^+$].

Example 211

Synthesis of N-[5-[(6-fluoropyridin-2-yl)methoxy]-1,3,4-thiadiazol-2-yl]-4-(2-methoxyphenyl)-6-methylpyridine-3-carboxamide

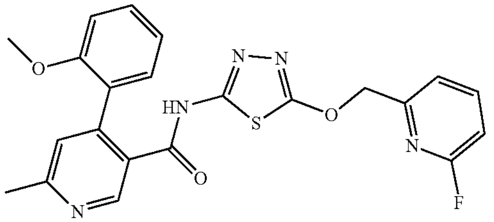 [SMILES: COc1ccccc1-c1cc(C)ncc1C(=O)Nc1nnc(OCc2cccc(F)n2)s1]

Step-1: Synthesis of [(6-fluoropyridin-2-yl)methoxy](methylsulfanyl)methanethione

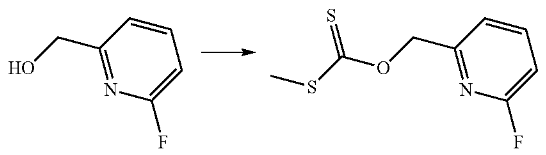

To a solution of (6-fluoropyridin-2-yl)methanol (500 mg, 3.93 mmol) in THF (3.0 mL) was added NaH (188 mg, 7.86 mmol) slowly at 5° C. under nitrogen atmosphere, the resulting mixture was stirred at 5° C. for 30 min. To the above mixture was added $CS_2$ (449 mg, 5.90 mmol), the resulting mixture was stirred at 5° C. for 10 min, then to the above mixture was added MeI (837 mg, 5.90 mmol), the resulting mixture was stirred at 5° C. for additional 10 min. The reaction mixture was quenched with water and extracted with ethyl acetate. The combined organic solution was dried over sodium sulfate, filtered, and concentrated under vacuum to afford the title compound (300 mg, crude) as a yellow oil.

Step-2: Synthesis of ([[(6-fluoropyridin-2-yl)methoxy]methanethioyl]amino)amine

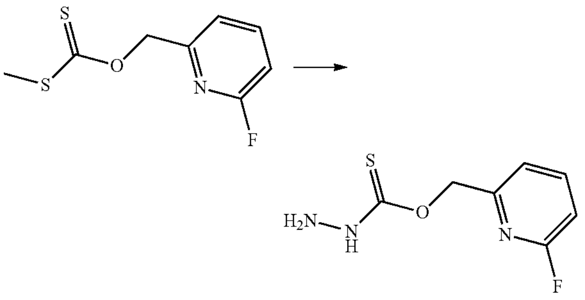

To a solution of [(6-fluoropyridin-2-yl)methoxy](methylsulfanyl)methanethione (300 mg, 1.38 mmol) in MeOH (3.0 mL) was added hydrazine hydrate (80%) (138 mg, 2.76 mmol). The reaction mixture was quenched with water and extracted with ethyl acetate. The combined organic solution was dried over sodium sulfate, filtered, and concentrated under vacuum to afford the title compound (280 mg, crude) as a yellow oil.

Step-3: Synthesis of 5-[(6-fluoropyridin-2-yl)methoxy]-1,3,4-thiadiazol-2-amine

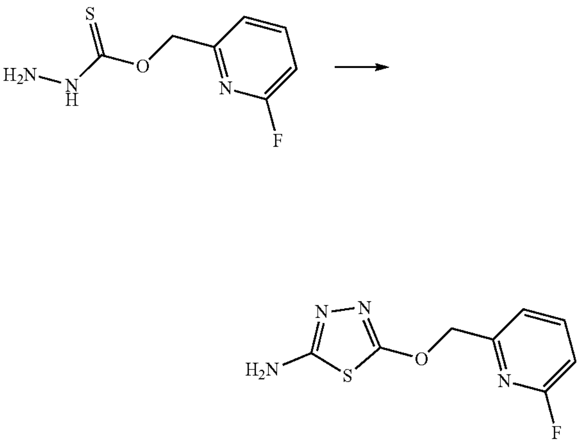

To a solution of ([[(6-fluoropyridin-2-yl)methoxy]methanethioyl]amino)amine (280 mg, 1.39 mmol) in MeOH (5.0 mL) was added TEA (211 mg, 2.08 mmol) and cyanogen bromide (221 mg, 2.08 mmol) slowly. The resulting mixture were stirred at room temperature for 30 min under nitrogen atmosphere. The resulting mixture was concentrated under vacuum to afford the title compound (90 mg, crude) as a yellow oil.

Step-4: Synthesis of N-[5-[(6-fluoropyridin-2-yl)methoxy]-1,3,4-thiadiazol-2-yl]-4-(2-methoxyphenyl)-6-methylpyridine-3-carboxamide

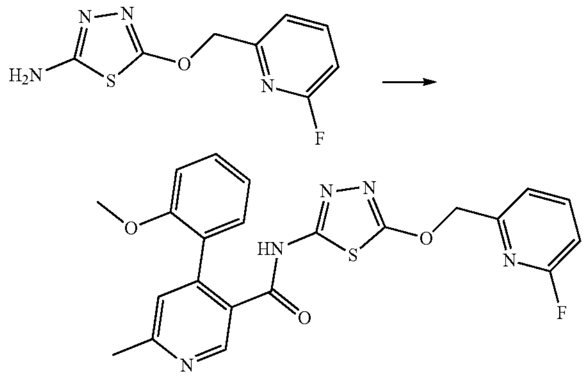

To a solution of 5-[(6-fluoropyridin-2-yl)methoxy]-1,3,4-thiadiazol-2-amine (90 mg, 0.39 mmol) in DMF (3.0 mL) were added 4-(2-methoxyphenyl)-6-methylpyridine-3-carboxylic acid (Example 113, Step 2, 145 mg, 0.59 mmol), DIEA (154 mg, 1.19 mmol), HATU (226 mg, 0.59 mmol) at 0° C. The resulting mixture was stirred at room temperature for 16 h. The reaction mixture was quenched with water and extracted with ethyl acetate. The combined organic solution was dried over sodium sulfate, filtered, and concentrated under vacuum. The crude product was purified by Prep-HPLC (column, C18 silica gel, mobile phase, water (10 mM $NH_4HCO_3$+0.1% $NH_3 \cdot H_2O$) and ACN) to afford the title compound (23.9 mg, 13%) as a white solid. $^1H$ NMR (400 MHz, DMSO-$d_6$): δ 12.85 (s, 1H), 8.66 (s, 1H), 8.09-8.02 (m, 1H), 7.54-7.48 (m, 1H), 7.42-7.32 (m, 2H), 7.29 (s, 1H), 7.21-7.16 (m, 1H), 7.10-7.04 (t, J=7.6 Hz, 1H), 7.00-6.95 (d, J=8.4 Hz, 1H), 5.50 (s, 2H), 3.51 (s, 3H), 2.56 (s, 3H). m/z 452.1 [M+H$^+$].

Example 212

Synthesis of N-[5-[(5-chloropyrazin-2-yl)methoxy]-1,3,4-thiadiazol-2-yl]-4-(2-methoxyphenyl)-6-methylpyridine-3-carboxamide

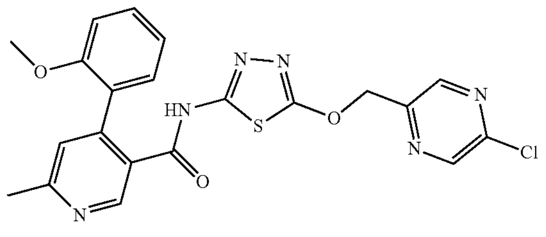 [SMILES: COc1ccccc1-c1cc(C)ncc1C(=O)Nc1nnc(OCc2cnc(Cl)cn2)s1]

Step-1: Synthesis of [(5-chloropyrazin-2-yl)methoxy](methylsulfanyl)methanethione

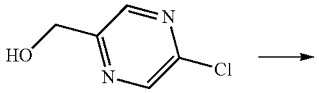

-continued

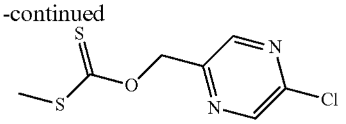

To a solution of NaH (166.01 mg, 6.91 mmol) in THF (2 mL) was added a solution of (5-chloropyrazin-2-yl)methanol (500 mg, 3.45 mmol) in THF (5 mL) under nitrogen. The resulting solution was stirred at 0° C. for 30 mins under nitrogen atmosphere, then $CS_2$ (395 mg, 5.18 mmol) and MeI (736 mg, 5.18 mmol) were sequentially added to the above mixture at 0° C. The resulting solution was stirred at 0° C. for 1 hours under nitrogen atmosphere. The resulting mixture was quenched by the addition of water and extracted with ethyl acetate. The combined organic layers were washed with brine, dried over anhydrous sodium sulfate, filtered, and concentrated under vacuum. The residue was purified by flash column chromatography with 0~10% MeOH in dichloromethane to afford the title compound (450 mg, 49%) as a light yellow solid.

Step-2: Synthesis of ([[(5-chloropyrazin-2-yl)methoxy]methanethioyl]amino)amine

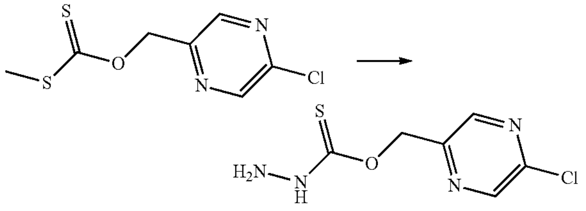

To a solution of [(5-chloropyrazin-2-yl)methoxy](methylsulfanyl)methanethione (400 mg, 1.70 mmol) in MeOH (5 mL) was added $NH_2NH_2 \cdot H_2O$ (93.8 mg, 1.87 mmol) at 0° C. The resulting solution was stirred at 0° C. for 0.5 h. The resulting mixture was diluted with water and extracted with ethyl acetate. The combined organic layers were washed with brine, dried over anhydrous $Na_2SO_4$. After filtration, the filtrate was concentrated under reduced pressure to afford the title compound (380 mg, crude) as a colorless oil.

Step-3: Synthesis of 5-[(5-chloropyrazin-2-yl)methoxy]-1,3,4-thiadiazol-2-amine

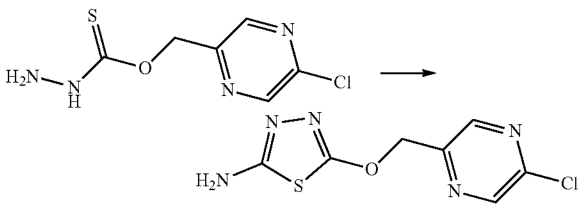

To a solution of ([[(5-chloropyrazin-2-yl)methoxy]methanethioyl]amino)amine (380 mg, 1.73 mmol) and $Et_3N$ (350 mg, 3.47 mmol) in MeOH (5 mL) was added BrCN (202 mg, 1.91 mmol) at 0° C. under nitrogen. The resulting mixture was stirred at 0° C. for 30 min. The resulting mixture was diluted with water and extracted with ethyl acetate. The combined organic layers were washed with brine, dried over anhydrous $Na_2SO_4$. After filtration, the filtrate was concentrated under vacuum to afford the title compound (240 mg, crude) as a reddish solid.

Step-4: Synthesis of N-[5-[(5-chloropyrazin-2-yl)methoxy]-1,3,4-thiadiazol-2-yl]-4-(2-methoxyphenyl)-6-methylpyridine-3-carboxamide

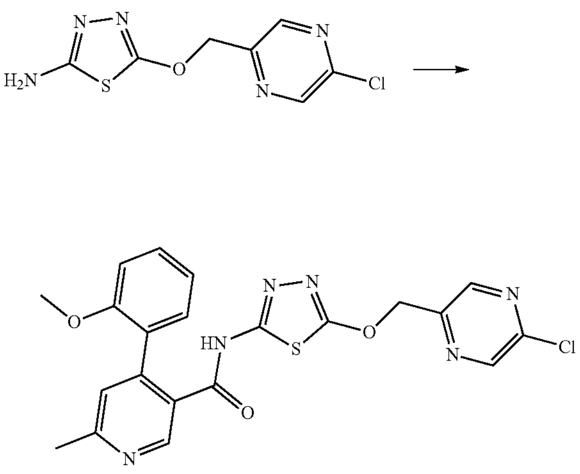

To a solution of 4-(2-methoxyphenyl)-6-methylpyridine-3-carboxylic acid (Example 113, Step 2, 99.8 mg, 0.410 mmol) in DMF (2 mL) were added HATU (234 mg, 0.616 mmol), DIEA (159 mg, 1.23 mmol) and 5-[(5-chloropyrazin-2-yl)methoxy]-1,3,4-thiadiazol-2-amine (100 mg, 0.410 mmol). The resulting mixture was stirred at 50° C. for 2 hours under nitrogen atmosphere. The residue was purified by flash column chromatography with 5~30% acetonitrile in water to afford the title compound (19 mg, 9.8%) as a white solid. $^1H$ NMR (400 MHz, DMSO-$d_6$): δ 12.83 (s, 1H), 8.85 (d, J=1.2 Hz, 1H), 8.75-8.69 (m, 2H), 7.46-7.33 (m, 3H), 7.09 (t, J=7.6 Hz, 1H), 7.00 (d, J=8.4 Hz, 1H), 5.64 (s, 2H), 3.51 (s, 3H), 2.60 (s, 3H). m/z 469.1 [M+H$^+$].

Example 213

Synthesis of N-[5-[(7-chloro-1H-indazol-4-yl)methoxy]-1,3,4-thiadiazol-2-yl]-4-(2-methoxyphenyl)-6-methylpyridine-3-carboxamide

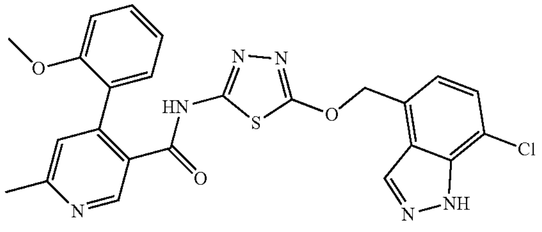 [SMILES: COc1ccccc1-c1cc(C)ncc1C(=O)Nc1nnc(OCc2ccc(Cl)c3[nH]ncc23)s1]

Step-1: Synthesis of 4-bromo-7-chloro-1-[[2-(trimethylsilyl)ethoxy]methyl]indazole

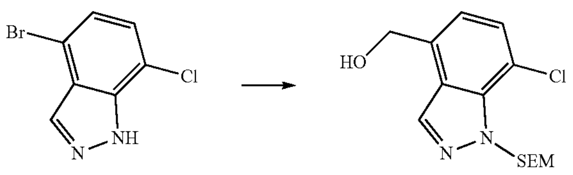 [SMILES: Clc1ccc(Br)c2cn[nH]c12 ; C[Si](C)(C)CCOCn1ncc2c(CO)ccc(Cl)c21]

To a solution of 4-bromo-7-chloro-1H-indazole (4 g, 17.2 mmol) in anhydrous DMF (6.0 mL) was added NaH (1.03 g, 25.9 mmol, 60%) in portions at 0° C. The resulting mixture was stirred at 0° C. for 20 min. To the above mixture was added 2-(trimethylsilyl)ethoxymethyl chloride (4.3 g, 25.9 mmol) dropwise at 0° C. The resulting mixture was stirred at room temperature for 16 h. The resulting mixture was quenched by the addition of water and extracted with ethyl acetate. The organic layers were combined, washed with brine, dried over anhydrous sodium sulfate and filtered. The filtrate was concentrated under vacuum. The residue was purified by flash chromatography on silica gel with 0~20% ethyl acetate in petroleum ether to afford the title compound (6 g, 96%) as a colorless oil.

Step-2: Synthesis of [(7-chloro-1-[[2-(trimethylsilyl)ethoxy]methyl]indazol-4-yl)methoxy](methylsulfanyl)methanethione

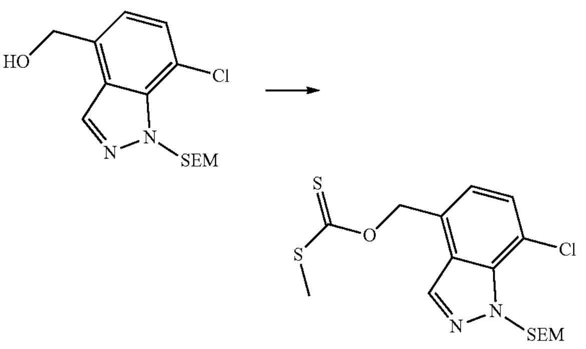

To a solution of NaH (250 mg, 6.38 mmol, 60%) in THF (6.0 mL) was added (7-chloro-1-[[2-(trimethylsilyl)ethoxy]methyl]indazol-4-yl)methanol (1.00 g, 3.19 mmol) dropwise at 0° C. The resulting mixture was stirred at 0° C. for 30 min. To the above mixture was added $CS_2$ (370 mg, 5 mmol) dropwise at 0° C. and stirred at 0° C. for 20 min. Then MeI (680 mg, 5 mmol) was added to the above mixture dropwise at 0° C. The resulting mixture was stirred at room temperature for 1 hour. The resulting mixture was quenched by the addition of water and extracted with ethyl acetate. The organic layers were combined, washed with brine, dried over anhydrous sodium sulfate and filtered. The filtrate was concentrated under vacuum. The residue was purified by flash chromatography on silica gel with 0~30% ethyl acetate in petroleum ether to afford the title compound (820 mg, 64%) as a yellow oil.

Step-3: Synthesis of ([[(7-chloro-1-[[2-(trimethylsilyl)ethoxy]methyl]indazol-4-yl)methoxy]methanethioyl]amino)amine

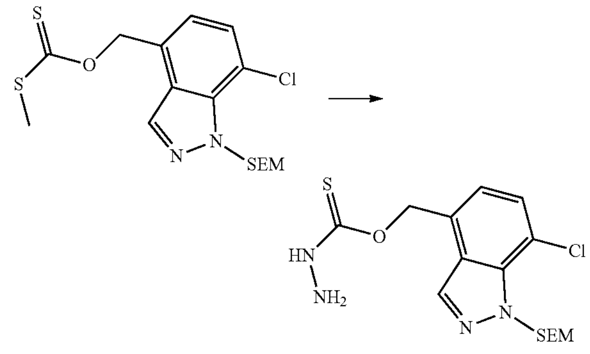

To a mixture of [(7-chloro-1-[[2-(trimethylsilyl)ethoxy]methyl]indazol-4-yl)methoxy](methylsulfanyl)methanethione (820 mg, 2.0 mmol) in MeOH (8.0 mL) was added $NH_2NH_2 \cdot H_2O$ (102 mg, 2.0 mmol). The mixture was stirred at 0° C. for 1 hour before concentrated under vacuum. The residue was purified by flash column chromatography with 5-50% acetonitrile in water to afford the title compound (370 mg, 47%) as a yellow solid.

Step-4: Synthesis of 5-[(7-chloro-1-[[2-(trimethylsilyl)ethoxy]methyl]indazol-4-yl)methoxy]-1,3,4-thiadiazol-2-amine

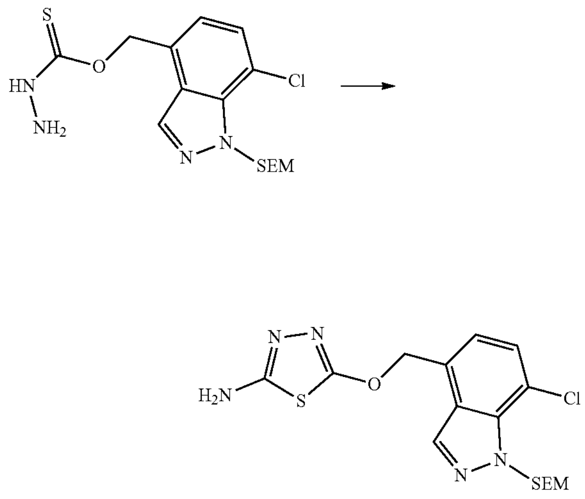

To a mixture of ([[(7-chloro-1-[[2-(trimethylsilyl)ethoxy]methyl]indazol-4-yl)methoxy]methanethioyl]amino)amine (115 mg, 0.30 mmol) and $Et_3N$ (60.1 mg, 0.60 mmol) in MeOH (3 mL) was added BrCN (34.6 mg, 0.33 mmol) at 0° C. The mixture was stirred at 0° C. for 1 hour. The resulting mixture was quenched with water and extracted with ethyl acetate. The organic layers were combined, washed with brine, dried over anhydrous sodium sulfate and filtered. The filtrate was concentrated under vacuum to afford the title compound (80 mg, crude) as a yellow solid.

Step-5: Synthesis of N-[5-[(7-chloro-1-[[2-(trimethylsilyl)ethoxy]methyl]indazol-4-yl)methoxy]-1,3,4-thiadiazol-2-yl]-4-(2-methoxyphenyl)-6-methylpyridine-3-carboxamide

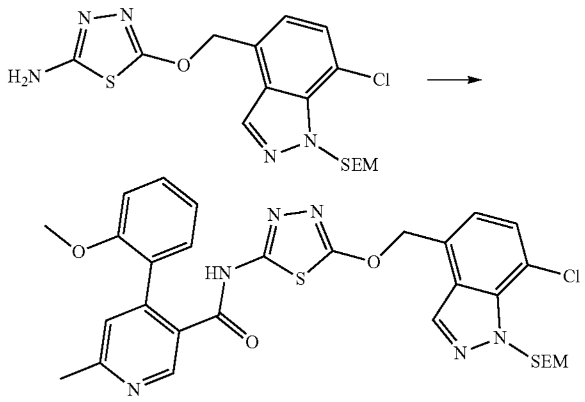

To a mixture of 4-(2-methoxyphenyl)-6-methylpyridine-3-carboxylic acid (Example 113, Step 2, 71 mg, 0.29 mmol) and HATU (82 mg, 0.21 mmol) in DMF (1 mL) were added DIEA (50 mg, 0.388 mmol). The resulting mixture was stirred at room temperature for 30 min. To the above mixture was added 5-[(7-chloro-1-[[2-(trimethylsilyl)ethoxy]methyl]indazol-4-yl)methoxy]-1,3,4-thiadiazol-2-amine (80 mg, 0.194 mmol). The mixture was stirred at room temperature for 16 hours under nitrogen atmosphere. The resulting mixture was quenched with water and extracted with ethyl acetate. The organic layers were combined, washed with brine, dried over anhydrous sodium sulfate and filtered. The filtrate was concentrated under vacuum. The residue was purified by flash chromatography on silica gel with 0~5% methanol in dichloromethane to afford the title compound (110 mg, 88%) as a light yellow solid.

Step-6: Synthesis of N-[5-[(7-chloro-1H-indazol-4-yl)methoxy]-1,3,4-thiadiazol-2-yl]-4-(2-methoxyphenyl)-6-methylpyridine-3-carboxamide

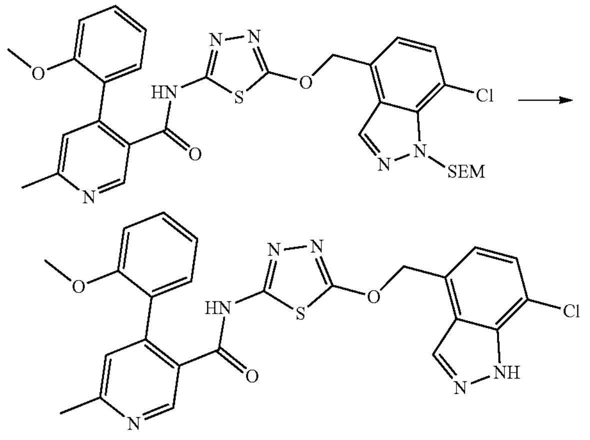

To a mixture of N-[5-[(7-chloro-1-[[2-(trimethylsilyl)ethoxy]methyl]indazol-4-yl)methoxy]-1,3,4-thiadiazol-2-yl]-4-(2-methoxyphenyl)-6-methylpyridine-3-carboxamide (100 mg, 0.157 mmol) and TBAF (246 mg, 0.942 mmol) in THF (5 mL) was added CsF (238 mg, 1.56 mmol). The resulting mixture was stirred at 70° C. for 16 hours. The residue was purified by flash chromatography on silica gel with 0~5% methanol in dichloromethane and further purified by prep-HPLC (column, C18 silica gel; mobile phase, water (10 mM $NH_4HCO_3$) and ACN) to afford the title compound (18 mg, 21%) as a white solid. $^1H$ NMR (400 MHz, DMSO-$d_6$) δ 13.75 (s, 1H), 12.73 (s, 1H), 8.65 (s, 1H), 8.33 (s, 1H), 7.48 (d, J=7.6 Hz, 1H), 7.43-7.31 (m, 2H), 7.31-7.22 (m, 2H), 7.11-7.03 (m, 1H), 6.97 (d, J=8.0 Hz, 1H), 5.80 (s, 2H), 3.50 (s, 3H), 2.55 (s, 3H). m/z 507 [M+H$^+$].

Example 214

Synthesis of N-(5-((5-cyclopropylpyridin-2-yl)methoxy)-1,3,4-thiadiazol-2-yl)-4-(2-methoxyphenyl)-6-methylnicotinamide

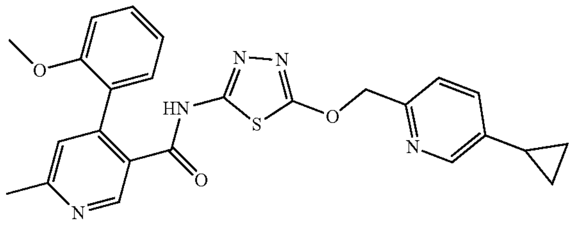 [SMILES: COc1ccccc1-c1cc(C)ncc1C(=O)Nc1nnc(OCc2ccc(C3CC3)cn2)s1]

Step-1: Synthesis of 5-bromo-2-(((tert-butyldimethylsilyl)oxy)methyl)pyridine

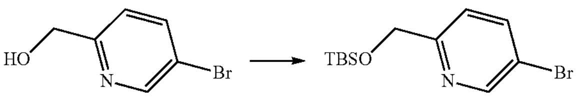 [SMILES: OCc1ccc(Br)cn1 ; CC(C)(C)[Si](C)(C)OCc1ccc(Br)cn1]

To a stirred mixture of (5-bromopyridin-2-yl)methanol (3.00 g, 15.9 mmol) in DCM (30 mL) were added imidazole (3.25 g, 47.8 mmol) and t-butyldimethylchlorosilane (3.60 g, 23.9 mmol). The resulting mixture was stirred at room temperature for 2 h. After the reaction was completed, the resulting mixture was quenched with water and extracted with DCM. The combined organic layer was washed with brine, dried over anhydrous sodium sulfate and filtered. The filtrate was concentrated under vacuum. The residue was purified by flash column chromatography with 0~12% ethyl acetate in petroleum ether to afford the title compound (4.6 g, 95%) as a colorless oil.

Step-2: Synthesis of 2-(((tert-butyldimethylsilyl)oxy)methyl)-5-cyclopropylpyridine

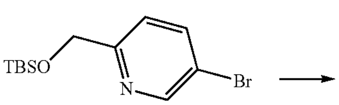

-continued

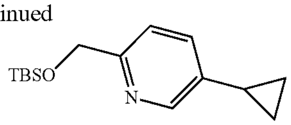

To a degassed solution of 5-bromo-2-(((tert-butyldimethylsilyl)oxy)methyl)pyridine (1.00 g, 3.30 mmol) in 1,4-dioxane (10 mL) and water (1 mL) were added $K_2CO_3$ (1.37 g, 9.92 mmol), cyclopropylboronic acid (568 mg, 6.61 mmol) and Pd(dppf)$Cl_2$ (242 mg, 0.33 mmol). The resulting mixture was stirred at 100° C. for 16 h under $N_2$ before concentrated under vacuum. The residue was diluted with water and extracted with EtOAc. The combined organic layers were washed with brine, dried over anhydrous $Na_2SO_4$. After filtration, the filtrate was concentrated under vacuum. The residue was purified by flash column chromatography with 0~20% ethyl acetate in petroleum ether to afford the title compound (840 mg, 96%) as a yellow oil.

Step-3: Synthesis of (5-cyclopropylpyridin-2-yl)methanol

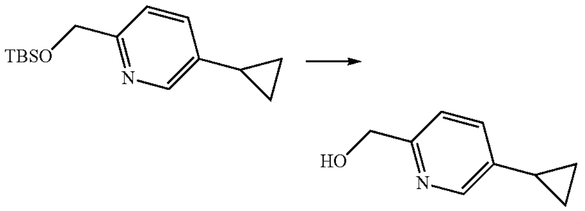

To a stirred mixture of 2-[[(tert-butyldimethylsilyl)oxy]methyl]-5-cyclopropylpyridine (500 mg, 1.89 mmol) in THF (7.0 mL) was added TBAF (744 mg, 2.84 mmol). The resulting mixture was stirred at room temperature for 1 h. The resulting mixture was concentrated under reduced pressure. The residue was purified by flash column chromatography with 0~10% methanol in DCM to afford the title compound (200 mg, 70%) as a yellow solid.

Step-4: Synthesis of 5-((5-cyclopropylpyridin-2-yl)methoxy)-1,3,4-thiadiazol-2-amine

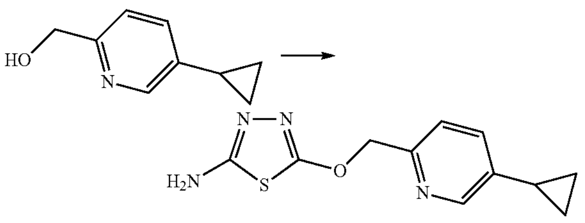

To a stirred mixture of (5-cyclopropylpyridin-2-yl)methanol (180 mg, 1.20 mmol) in THF (5.0 mL) was added NaH (96.7 mg, 2.41 mmol, 60%) at 0~5° C. under nitrogen. The resulting mixture was maintained this temperature and stirred 1 h under nitrogen. 5-Bromo-1,3,4-thiadiazol-2-amine (260.6 mg, 1.44 mmol) was added to the above mixture at 0° C. The resulting mixture was stirred at 0~5° C. for 3 h. The resulting mixture was quenched by the addition of water and extracted with ethyl acetate. The combined organic layers were washed with brine, dried over anhydrous $Na_2SO_4$. After filtration, the filtrate was concentrated under vacuum. The residue was purified by reverse phase flash chromatography with 5~45% acetonitrile in water to afford the title compound (390 mg, 50%) as a grey solid.

Step-5: Synthesis of N-(5-((5-cyclopropylpyridin-2-yl)methoxy)-1,3,4-thiadiazol-2-yl)-4-(2-methoxy-phenyl-6-methylnicotinamide

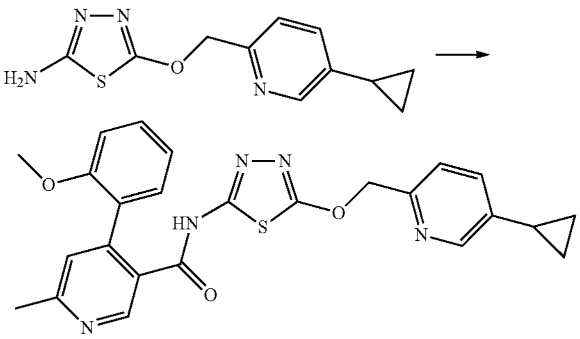

To a stirred mixture of 4-(2-methoxyphenyl)-6-methylpyridine-3-carboxylic acid (Example 113, Step 2, 108 mg, 0.44 mmol) in DMF (4.0 mL) were added HATU (306 mg, 0.80 mmol). The resulting mixture was stirred for 5 min at room temperature. To the above mixture were added 5-((5-cyclopropylpyridin-2-yl)methoxy)-1,3,4-thiadiazol-2-amine (100 mg, 0.40 mmol) and DIEA (156 mg, 1.20 mmol). The resulting mixture was stirred for additional 3 h at room temperature. The resulting mixture was quenched with water and extracted with ethyl acetate. The combined organic layers were washed with brine, dried over anhydrous $Na_2SO_4$. After filtration, the filtrate was concentrated under reduced pressure. The residue was purified by flash column chromatography with 0~10% methanol in ethyl acetate. The product was washed with methanol and dried under vacuum to afford the title compound (31.7 mg, 16%) as a white solid. $^1H$ NMR (400 MHz, DMSO-$d_6$) δ 12.74 (s, 1H), 8.66 (s, 1H), 8.41 (s, 1H), 7.52-7.49 (m, 1H), 7.43-7.39 (m, 3H), 7.29 (s, 1H), 7.09-7.05 (m, 1H), 6.98 (d, J=8.0 Hz, 1H), 5.47 (s, 2H), 3.50 (s, 3H), 2.56 (s, 3H), 2.01-1.94 (m, 1H), 1.08-1.02 (m, 2H), 0.80-0.76 (m, 2H). m/z 472.2 $[M+H^+]$.

Example 215

Synthesis of N-(5-((5-chloropyridin-2-yl)methoxy)-1,3,4-thiadiazol-2-yl)-5-fluoro-4-(2-methoxyphenyl)-6-methylnicotinamide

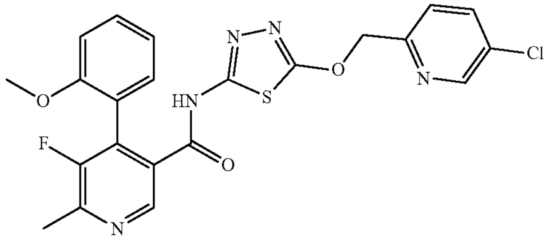 [SMILES: COc1ccccc1-c1c(C(=O)Nc2nnc(OCc3ccc(Cl)cn3)s2)cnc(C)c1F]

Step-1. Synthesis of ethyl 4-chloro-5-fluoro-6-methylnicotinate

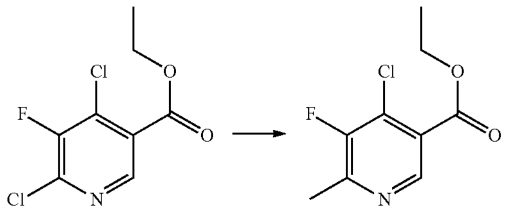

To a solution of ethyl 4,6-dichloro-5-fluoronicotinate (1 g, 4.237 mmol) in dioxane (10 mL) and water (1 mL) were added $K_2CO_3$ (1.75 g, 12.7 mmol), Pd(dppf)$Cl_2$ (0.35 g, 0.424 mmol) and 2,4,6-trimethyl-1,3,5,2,4,6-trioxatriborinane (427 mg, 3.39 mmol) under nitrogen. The mixture was stirred at 80° C. for 5 hours under nitrogen. The reaction mixture was concentrated under vacuum. The residue was purified by flash chromatography on silica gel with 0~30% ethyl acetate in petroleum ether to afford the title compound (990 mg, 60%) as a yellow solid.

Step-2: Synthesis of ethyl 5-fluoro-4-(2-methoxyphenyl)-6-methylnicotinate

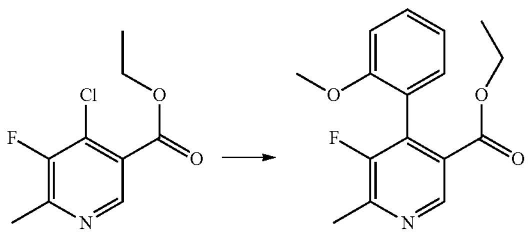 [SMILES: CCOC(=O)c1cnc(C)c(F)c1Cl ; CCOC(=O)c1cnc(C)c(F)c1-c1ccccc1OC]

To a solution of ethyl 4-chloro-5-fluoro-6-methylnicotinate (110 mg, 0.507 mmol) in dioxane (5 mL) and water (1 mL) was added $K_2CO_3$ (220 mg, 1.52 mmol), (2-methoxyphenyl)boronic acid (115 mg, 0.760 mmol) and Pd(dppf)$Cl_2$ (44 mg, 0.051 mmol) under nitrogen. The mixture was stirred at 80° C. for 5 hours under nitrogen. The mixture was concentrated under vacuum. The residue was purified by flash chromatography on silica gel with 0~20% ethyl acetate in petroleum ether to afford the title compound (80 mg, 73%) as a yellow oil.

Step-3: Synthesis of 5-Fluoro-4-(2-methoxyphenyl)-6-methylnicotinic acid

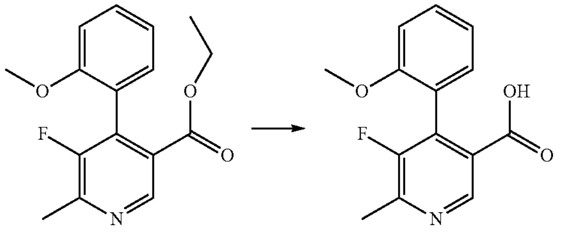 [SMILES: CCOC(=O)c1cnc(C)c(F)c1-c1ccccc1OC ; COc1ccccc1-c1c(C(=O)O)cnc(C)c1F]

To a solution of ethyl 5-fluoro-4-(2-methoxyphenyl)-6-methylnicotinate (80 mg, 0.277 mmol) in MeOH (2 mL) and $H_2O$ (1 mL) was added NaOH (22 mg, 0.55 mmol). The mixture was stirred at 70° C. for 2 hours. The aqueous solution was acidified with HCl (1 N) to pH 5-6. The aqueous solution was extracted with ethyl acetate. The organic layers were combined, washed with brine, dried over anhydrous sodium sulfate and filtered. The filtrate was concentrated under vacuum to afford the title compound (60 mg, crude) as a yellow solid.

Step-4: Synthesis of N-(5-((5-chloropyridin-2-yl)methoxy)-1,3,4-thiadiazol-2-yl)-5-fluoro-4-(2-methoxyphenyl)-6-methylnicotinamide

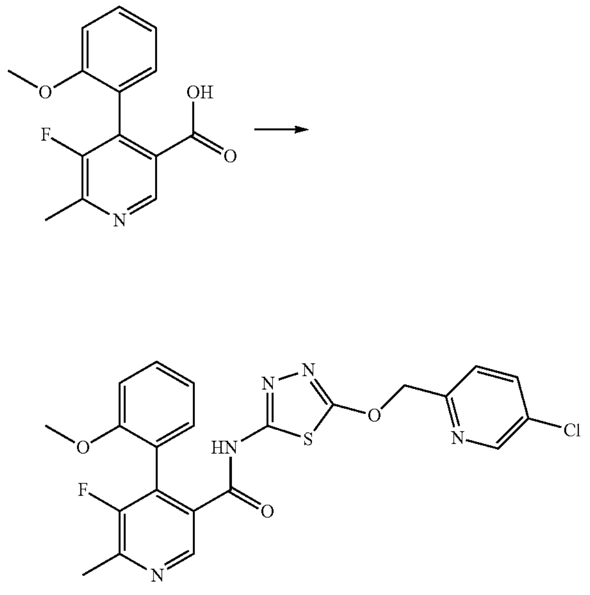

To a solution of 5-fluoro-4-(2-methoxyphenyl)-6-methylnicotinic acid (60 mg, 0.223 mmol) in DMF (1 mL) was added DIEA (86 mg, 0.669 mmol), HATU (127 mg, 0.334 mmol) and 5-((5-chloropyridin-2-yl)methoxy)-1,3,4-thiadiazol-2-amine (Intermediate C, 54 mg, 0.223 mmol). The mixture was stirred at room temperature for 16 h. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purified by prep-HPLC (column, C18 silica gel; mobile phase, water (0.1% FA) and ACN) to afford the title compound (19 mg, 14.4%) as a white solid. $^1H$ NMR (400 MHz, DMSO-$d_6$): δ 13.06 (s, 1H), 8.98 (s, 1H), 8.66-8.65 (m, 1H), 8.01-7.99 (m, 1H), 7.62-7.60 (m, 1H), 7.48-7.39 (m, 2H), 7.11-7.08 (m, 1H), 7.05-7.03 (m, 1H), 5.56 (s, 2H), 3.55 (s, 3H), 2.70-2.40 (m, 3H). m/z 486.2 [M+H$^+$].

Example 216

Synthesis of N-[5-[(5-chloropyridin-2-yl)methoxy]-1,3,4-thiadiazol-2-yl]-6-cyclopropyl-4-(2-methoxyphenyl)pyridine-3-carboxamide

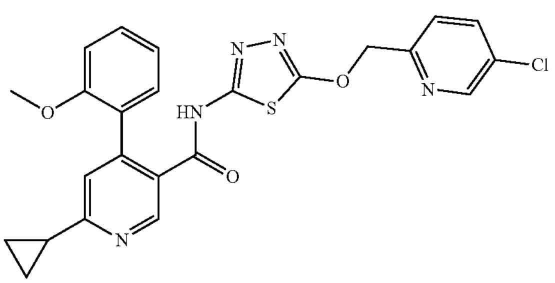 [SMILES: COc1ccccc1-c1cc(C2CC2)ncc1C(=O)Nc1nnc(OCc2ccc(Cl)cn2)s1]

Step-1: Synthesis of benzyl 6-cyclopropyl-4-(2-methoxyphenyl)pyridine-3-carboxylate

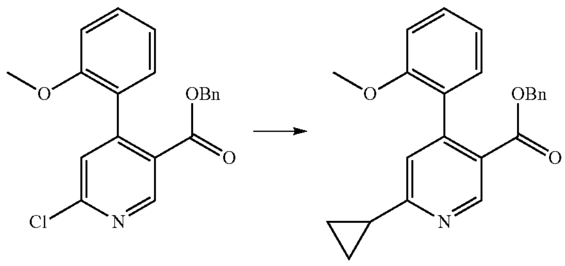 [SMILES: COc1ccccc1-c1cc(Cl)ncc1C(=O)OCc1ccccc1 ; COc1ccccc1-c1cc(C2CC2)ncc1C(=O)OCc1ccccc1]

A degassed mixture of benzyl 6-chloro-4-(2-methoxyphenyl)pyridine-3-carboxylate (200 mg, 0.56 mmol), cyclopropylboronic acid (97.1 mg, 1.13 mmol), $Pd(PPh_3)_4$ (130 mg, 0.11 mmol) and cesium carbonate (368 mg, 1.13 mmol) in dioxane (2.0 mL) and water (0.2 mL) was stirred at 80° C. for 2 h under nitrogen atmosphere. The resulting mixture was quenched with water and the aqueous phase was extracted with ethyl acetate. The combined organic solution was dried over sodium sulfate, filtered, and concentrated under vacuum. The residue was purified by silica gel column chromatography, eluted with 0~19% acetate ethyl in petroleum ether to afford the title compound (145 mg, 71%) as a colorless oil.

Step-2: Synthesis of 6-cyclopropyl-4-(2-methoxyphenyl)pyridine-3-carboxylic acid

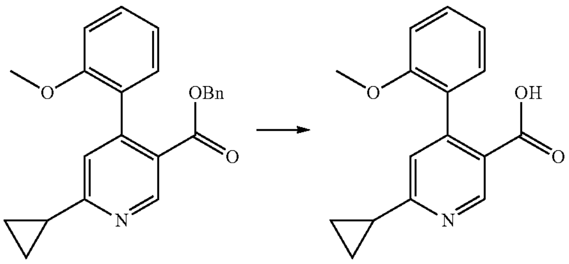 [SMILES: COc1ccccc1-c1cc(C2CC2)ncc1C(=O)OCc1ccccc1 ; COc1ccccc1-c1cc(C2CC2)ncc1C(=O)O]

A solution of benzyl 6-cyclopropyl-4-(2-methoxyphenyl) pyridine-3-carboxylate (350 mg, 0.97 mmol) and sodium hydroxide (155 mg, 3.89 mmol) in water (3.0 mL) and THF (3.0 mL) was stirred at 70° C. for 16 h. The residue was diluted with water and acidified to pH 4-5 with HCl (2 N). The aqueous layer was extracted with ethyl acetate. The combined organic solution was dried over sodium sulfate, filtered, and concentrated under vacuum to afford the title compound (240 mg, crude) as a white solid, which was used for the next step without further purification.

Step-3: Synthesis of N-[5-[(5-chloropyridin-2-yl) methoxy]-1,3,4-thiadiazol-2-yl]-6-cyclopropyl-4-(2-methoxyphenyl)pyridine-3-carboxamide

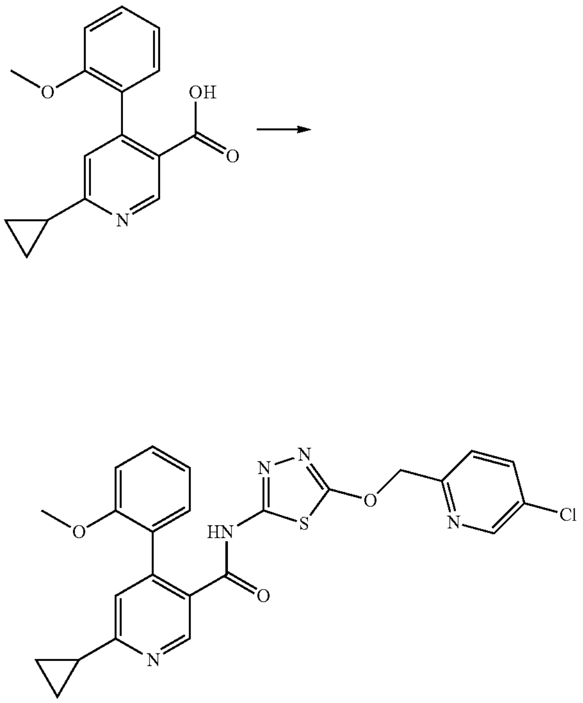

To a solution of 6-cyclopropyl-4-(2-methoxyphenyl)pyridine-3-carboxylic acid (180 mg, 0.66 mmol) in DMF (4.0 mL) were added 5-[(5-chloropyridin-2-yl)methoxy]-1,3,4-thiadiazol-2-amine (Intermediate C, 243 mg, 1.00 mmol), HATU (381 mg, 1.00 mmol) and DIEA (259 mg, 2.00 mmol). The resulting mixture was stirred for 16 h at room temperature. The resulting mixture was quenched with water and the aqueous phase was extracted with ethyl acetate. The combined organic solution was dried over sodium sulfate, filtered, and concentrated under vacuum. The residue was purified by reverse phase flash column chromatography with 5~55% acetonitrile in water and further purified by Prep-HPLC (column, C18 silica gel; mobile phase, water (10 mM $NH_4HCO_3$+0.1% $NH_3 \cdot H_2O$) and ACN) to afford the title compound (113 mg, 39%) as a white solid. $^1$H NMR (400 MHz, DMSO-$d_6$): δ 12.68 (s, 1H), 8.68-8.64 (d, J=2.4 Hz, 1H), 8.61 (s, 1H), 8.04-7.97 (m, 1H), 7.64-7.56 (d, J=8.4 Hz, 1H), 7.44-7.30 (m, 3H), 7.12-7.04 (t, J=5.6 Hz, 1H), 7.01-6.96 (d, J=8.4 Hz, 1H), 5.54 (s, 2H), 3.51 (s, 3H), 2.29-2.20 (m, 1H), 1.09-0.98 (m, 4H). m/z 494.0 [M+H$^+$].

Example 217

Synthesis of N-(5-((5-(1-cyanocyclopropyl)pyridin-2-yl)methoxy)-1,3,4-thiadiazol-2-yl)-4-(2-fluoro-6-methoxyphenyl)-6-methylnicotinamide

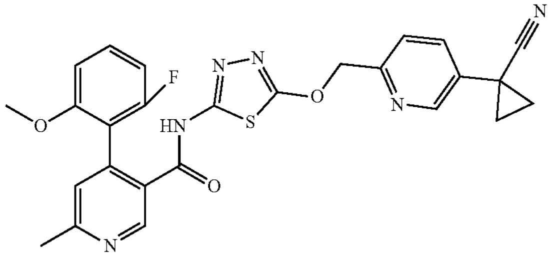 [SMILES: COc1cccc(F)c1-c1cc(C)ncc1C(=O)Nc1nnc(OCc2ccc(C3(C#N)CC3)cn2)s1]

The title compound was prepared using General Procedures E, F and A. For General Procedure E, methyl 4-chloro-6-methylpyridine-3-carboxylate and 2-fluoro-6-methoxyphenylboronic acid were employed. For General Procedure A, 1-(6-[[(5-amino-1,3,4-thiadiazol-2-yl)oxy]methyl]pyridin-3-yl)cyclopropane-1-carbonitrile (Example 220, Step 5) was used. $^1$H NMR (400 MHz, DMSO-$d_6$): δ 12.83 (s, 1H), 8.81 (s, 1H), 8.59 (s, 1H), 7.82-7.81 (m, 1H), 7.57-7.55 (m, 1H), 7.41-7.39 (m, 1H), 7.32 (s, 1H), 6.91-6.88 (m, 2H), 5.54 (s, 2H), 3.59 (s, 3H), 2.57 (s, 3H), 1.86-1.74 (m, 2H), 1.71-1.59 (m, 2H). m/z 517.1 [M+H$^+$].

Example 218

Synthesis of N-(5-[[5-(1-cyanocyclopropyl)pyridin-2-yl]methoxy]-1,3,4-thiadiazol-2-yl)-4-[2-(difluoromethoxy)phenyl]-6-methylpyridine-3-carboxamide

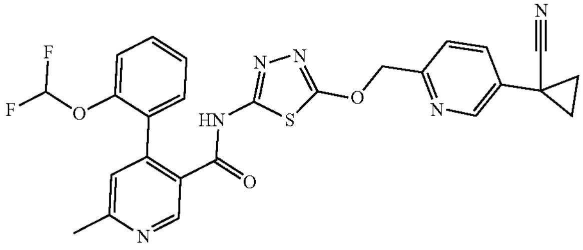 [SMILES: Cc1cc(-c2ccccc2OC(F)F)c(C(=O)Nc2nnc(OCc3ccc(C4(C#N)CC4)cn3)s2)cn1]

Step-1 & Step-2: Synthesis of methyl 4-(2-(difluoromethoxy)phenyl)-6-methylnicotinate

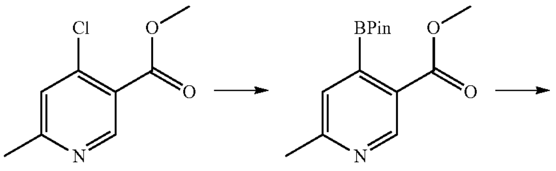

-continued

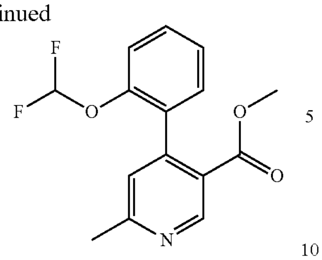

To a degassed solution of methyl 4-chloro-6-methylpyridine-3-carboxylate (2.0 g, 10.7 mmol) and $B_2Pin_2$ (5.45 g, 21.5 mmol) and AcOK (3.17 g, 32.3 mmol) in dioxane (10 mL) was added $Pd(dppf)Cl_2$ (2.37 g, 3.23 mmol) under nitrogen. The resulting solution was stirred at 80° C. for 3 hours under nitrogen atmosphere. Then 1-bromo-2-(difluoromethoxy)benzene (724 mg, 3.24 mmol), $K_2CO_3$ (1.34 g, 9.74 mmol), $Pd(dppf)Cl_2$ (712 mg, 0.974 mmol) and water (1.0 mL) was added to the above mixture. The resulting mixture was stirred at 80° C. for 16 h under nitrogen. The solids were filtered out and the filtrate was concentrated under vacuum. The residue was purified by reverse phase flash column chromatography with 5%-50% acetonitrile in water to afford the title compound (850 mg, 90%) as a white solid.

Step-3: Synthesis of 4-[2-(difluoromethoxy)phenyl]-6-methylpyridine-3-carboxylic acid

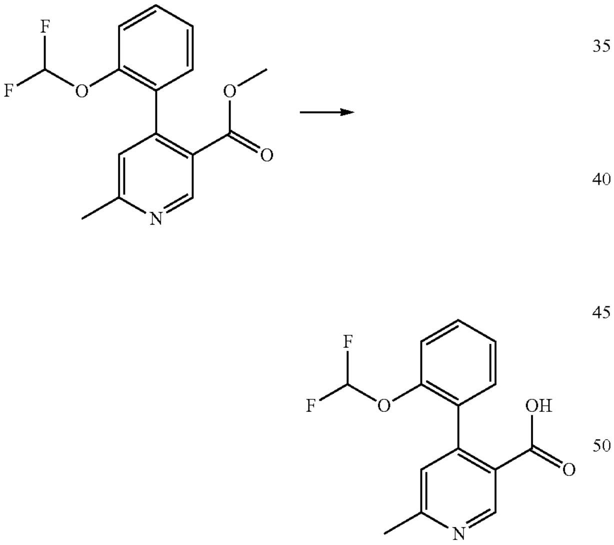

A mixture of 4-[2-(difluoromethoxy)phenyl]-6-methylpyridine-3-carboxylate (850 mg, 2.89 mmol) and NaOH (463 mg, 11.5 mmol) in $H_2O$ (1.0 mL) and THF (5.0 mL). The resulting solution was stirred at 50° C. for 16 h. The reaction mixture was acidified with HCl (1 N) to pH 1~2, and then extracted with ethyl acetate. The organic layers were combined, washed with brine, dried over anhydrous sodium sulfate and filtered. The filtrate was concentrated under vacuum. The residue was purified by reverse phase flash column chromatography with 5-50% acetonitrile in water to afford the title compound (290 mg, 32%) as a white solid.

Step-4: Synthesis of N-(5-[[5-(1-cyanocyclopropyl)pyridin-2-yl]methoxy]-1,3,4-thiadiazol-2-yl)-4-[2-(difluoromethoxy)phenyl]-6-methylpyridine-3-carboxamide

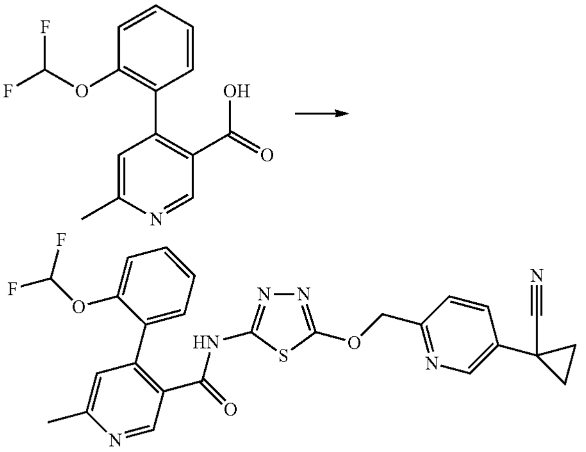

To a solution of 4-[2-(difluoromethoxy)phenyl]-6-methylpyridine-3-carboxylic acid (100 mg, 0.358 mmol) in DMF (1.5 mL) was added HATU (204 mg, 0.573 mmol), DIEA (138 mg, 1.07 mmol) and 1-(6-[[(5-amino-1,3,4-thiadiazol-2-yl)oxy]methyl]pyridin-3-yl)cyclopropane-1-carbonitrile (Example 220, Step 5, 97 mg, 0.358 mmol). The resulting mixture was stirred at 50° C. for 16 h. The residue was purified by reverse phase flash column chromatography with 5-30% acetonitrile in water to afford the title compound (29.3 mg, 15%) as a white solid. $^1H$ NMR (400 MHz, DMSO-$d_6$) δ 12.95 (s, 1H), 8.83 (s, 1H), 8.59 (d, J=2.4 Hz, 1H), 7.80 (dd, J=8.4, 2.4 Hz, 1H), 7.55 (d, J=8.4 Hz, 1H), 7.52-7.43 (m, 1H), 7.41-7.26 (m, 3H), 7.24-7.15 (m, 1H), 5.52 (s, 2H), 2.56 (s, 3H), 1.85-1.77 (m, 2H), 1.66-1.58 (m, 2H). m/z 535.1 $[M+H^+]$.

Example 219

Synthesis of N-(5-((5-cyanopyridin-2-yl)methoxy)-1,3,4-thiadiazol-2-yl)-4-(2-methoxyphenyl)-6-methylnicotinamide

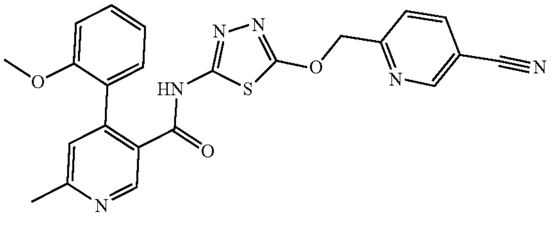 [SMILES: COc1ccccc1-c1cc(C)ncc1C(=O)Nc1nnc(OCc2ccc(C#N)cn2)s1]

Step-1: Synthesis of 6-(((5-amino-1,3,4-thiadiazol-2-yl)oxy)methyl)nicotinonitrile

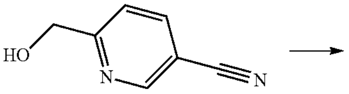

-continued

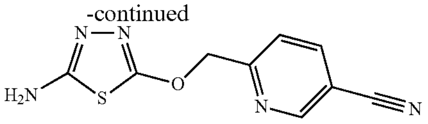

To a stirred mixture of 6-(hydroxymethyl)nicotinonitrile (500 mg, 3.72 mmol) in THF (5.0 mL) was added NaH (298 mg, 7.45 mmol, 60%) in portions at 0~5° C. The resulting mixture was stirred at the same temperature for 1 h under nitrogen atmosphere. To the above mixture was added 5-bromo-1,3,4-thiadiazol-2-amine (805 mg, 4.47 mmol) in portions at 0° C. The resulting mixture was stirred for additional 4 h at 0~5° C. The reaction was quenched by the addition of water and extracted with ethyl acetate. The combined organic layers were washed with brine, dried over anhydrous sodium sulfate, filtered, and concentrated under vacuum. The residue was purified by reverse phase flash chromatography with 5~35% acetonitrile in water to afford the title compound (130 mg, 14%) as an orange solid.

Step-2: Synthesis of N-(5-((5-cyanopyridin-2-yl)methoxy)-1,3,4-thiadiazol-2-yl)-4-(2-methoxyphenyl)-6-methylnicotinamide

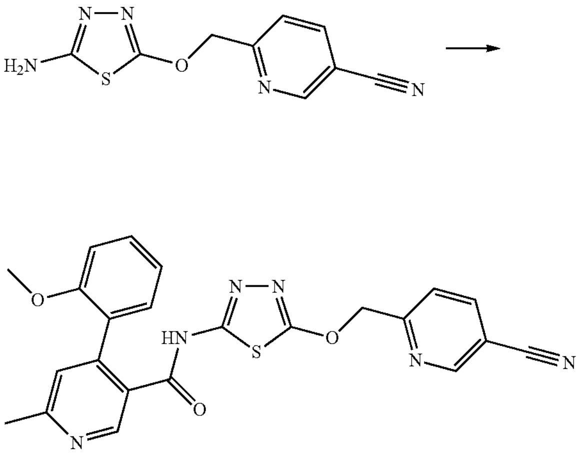

To a stirred mixture of 4-(2-methoxyphenyl)-6-methylpyridine-3-carboxylic acid (Example 113, Step 2, 187 mg, 0.77 mmol) in DMF (4.0 mL) were added HATU (391 mg, 1.02 mmol). The resulting mixture was stirred for 5 min at room temperature. To the above mixture were added 6-(((5-amino-1,3,4-thiadiazol-2-yl)oxy)methyl)nicotinonitrile (120 mg, 0.51 mmol) and DIEA (199 mg, 1.54 mmol). The resulting mixture was stirred at room temperature for 16 h. The resulting mixture was quenched with water and extracted with ethyl acetate. The combined organic layers were washed with brine, dried over anhydrous $Na_2SO_4$ and concentrated under reduced pressure. The residue was purified by flash column chromatography with 20-90% ethyl acetate in petroleum ether. The product was washed with MeOH and dried under vacuum to afford the title compound (60 mg, 24%) as a white solid. $^1H$ NMR (400 MHz, DMSO-$d_6$): δ 12.77 (s, 1H), 9.04 (s, 1H), 8.65 (s, 1H), 8.38-8.36 (m, 1H), 7.72 (d, J=8.0 Hz, 1H), 7.41-7.34 (m, 2H), 7.30 (s, 1H), 7.09-7.05 (m, 1H), 6.98 (d, J=8.0 Hz, 1H), 5.64 (s, 2H), 3.50 (s, 3H), 3.15 (s, 3H). m/z 459.1 [M+H$^+$].

Example 220

Synthesis of N-(5-[[5-(1-cyanocyclopropyl)pyridin-2-yl]methoxy]-1,3,4-thiadiazol-2-yl)-4-(2-methoxyphenyl)-6-methylpyridine-3-carboxamide

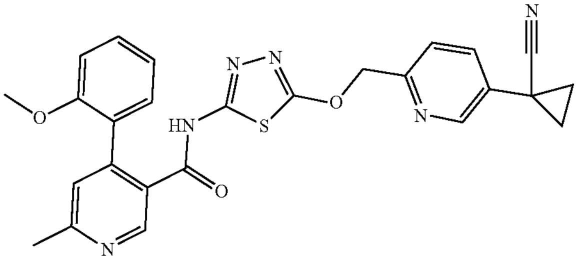 [SMILES: COc1ccccc1-c1cc(C)ncc1C(=O)Nc1nnc(OCc2ccc(C3(C#N)CC3)cn2)s1]

Step-1: Synthesis of 1-(6-chloropyridin-3-yl)cyclopropane-1-carbonitrile

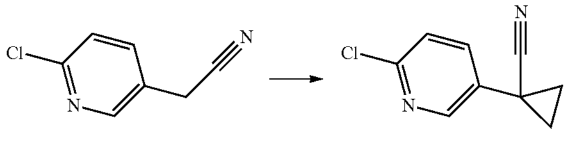 [SMILES: N#CCc1ccc(Cl)nc1 ; N#CC1(c2ccc(Cl)nc2)CC1]

To a solution of NaOH (100 g) in $H_2O$ (100 mL) were added 2-(6-chloropyridin-3-yl)acetonitrile (20 g, 131.079 mmol) and dibromoethane (27 g, 142 mmol). The mixture was stirred at 50° C. for 16 hours. The resulting mixture was extracted with ethyl acetate. The combined organic layers was dried over anhydrous sodium sulfate, filtered, and concentrated under vacuum. The residue was purified by flash chromatography on silica gel with 0~50% ethyl acetate in petroleum ether to afford the title compound (18 g, 77%) as a yellow solid.

Step-2: Synthesis of 1-(6-vinylpyridin-3-yl)cyclopropane-1-carbonitrile

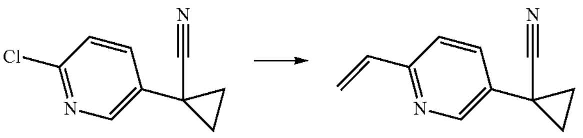

To a solution of ethenyltrifluoro-lambda4-borane potassium (11.5 g, 0.084 mmol) in dioxane (100 mL) and $H_2O$ (20 mL) were added 1-(6-chloropyridin-3-yl)cyclopropane-1-carbonitrile (10 g, 55 mmol), $K_2CO_3$ (23.2 g, 0.168 mmol) and Pd(dppf)$Cl_2$ (4.1 g, 5.4 mmol). The resulting mixture was stirred at 80° C. for 12 hours under nitrogen. The resulting mixture was extracted with ethyl acetate. The combined organic layers was dried over anhydrous sodium sulfate, filtered, and concentrated under vacuum. The residue was purified by flash chromatography on silica gel with 0~50% ethyl acetate in petroleum ether to afford the title compound (6.84 g, 72%) as a yellow solid.

Step-3: Synthesis of 1-(6-formylpyridin-3-yl)cyclopropane-1-carbonitrile

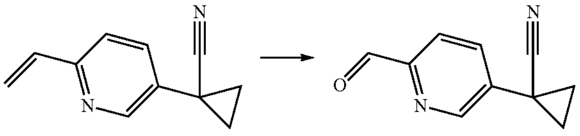

To a solution of 1-(6-ethenylpyridin-3-yl)cyclopropane-1-carbonitrile (6.84 g, 40.1 mmol) in THF (120 mL) and $H_2O$ (40 mL) were added $OsO_4$ (1.02 g, 4.01 mmol) and $NaIO_4$ (34.5 g, 160 mmol). The resulting mixture was stirred at room temperature for 16 h. The resulting mixture was extracted with ethyl acetate. The combined organic layers were washed with brine, dried over anhydrous sodium sulfate, filtered, and concentrated under vacuum. The residue was purified by flash chromatography on silica gel with 0~50% ethyl acetate in petroleum ether to afford the title compound (2.11 g, 40%) as a yellow solid.

Step-4: Synthesis of 1-(6-(hydroxymethyl)pyridin-3-yl)cyclopropane-1-carbonitrile

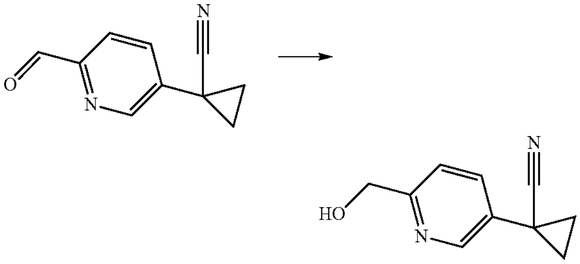

To a solution of 1-(6-formylpyridin-3-yl)cyclopropane-1-carbonitrile (2.12 g, 12.2 mmol) in MeOH (20 mL) was added $NaBH_4$ (0.46 g, 12.254 mmol) at 0° C. The mixture was stirred at room temperature for 1 h. The reaction was then quenched by the addition of water and extracted with ethyl acetate. The combined organic layers were washed with brine, dried over anhydrous sodium sulfate, filtered, and concentrated under vacuum to afford the title compound (1.11 g, 70%) as a yellow solid.

Step-5: Synthesis of 1-(6-(((5-amino-1,3,4-thiadiazol-2-yl)oxy)methyl)pyridin-3-yl)cyclopropane-1-carbonitrile

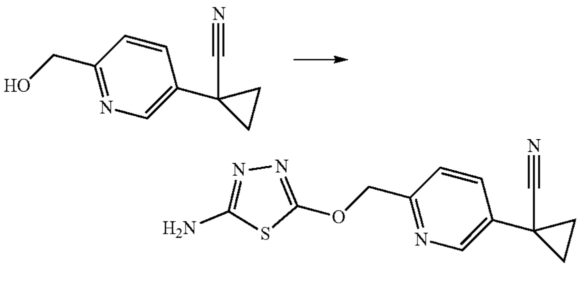

To a solution of NaH (0.73 g, 17.5 mmol, 60%) in THF (10 mL) was added 1-[6-(hydroxymethyl)pyridin-3-yl]cyclopropane-1-carbonitrile (2.11 g, 12.1 mmol) in portions at 0~5° C. and stirred at 5° C. for 1 h. Then 5-bromo-1,3,4-thiadiazol-2-amine (2.62 g, 14.5 mmol) was added to the mixture in small portions at 5° C. and stirred at 5° C. for 5 h. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford the title compound (1.11 g, 33%) as a white solid.

Step-6: Synthesis of N-(5-((5-(1-cyanocyclopropyl)pyridin-2-yl)methoxy)-1,3,4-thiadiazol-2-yl)-4-(2-methoxyphenyl)-6-methylnicotinamide

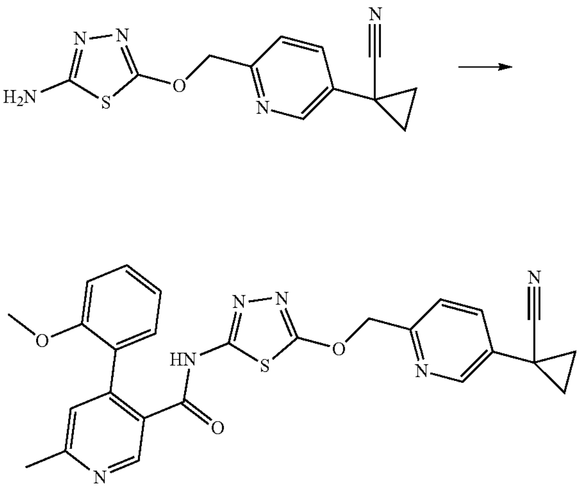

To a solution 1-(6-[[(5-amino-1,3,4-thiadiazol-2-yl)oxy]methyl]pyridin-3-yl)cyclopropane-1-carbonitrile (Example 220, Step 5, 200 mg, 0.732 mmol) in DMF (10 mL) were added HATU (418 mg, 1.09 mmol), DIEA (283 mg, 2.19 mmol) and 4-(2-methoxyphenyl)-6-methylpyridine-3-carboxylic acid (Example 113, Step 2, 178 mg, 0.732 mmol). The mixture was stirred at room temperature for 2 hours. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane. The product was further purified by washed with methanol and dried under vacuum to afford the title compound (50 mg, 13%) as a white solid. $^1H$ NMR (400 MHz, DMSO-$d_6$): δ 12.75 (s, 1H), 8.66 (s, 1H), 8.59 (s, 1H), 7.83-7.80 (m, 1H), 7.58-7.56 (m, 1H), 7.41-7.30 (m, 3H), 7.09-7.05 (m, 1H), 6.99-6.97 (m, 1H), 5.54 (s, 2H), 3.57 (s, 3H), 2.67 (s, 3H), 1.84-1.80 (m, 2H), 1.64-1.61 (m, 2H). m/z 499.2 [M+H$^+$].

Example 221

Synthesis of N-[5-[(5-fluoropyridin-2-yl)methoxy]-1,3,4-thiadiazol-2-yl]-4-(2-methoxyphenyl)-6-methylpyridine-3-carboxamide

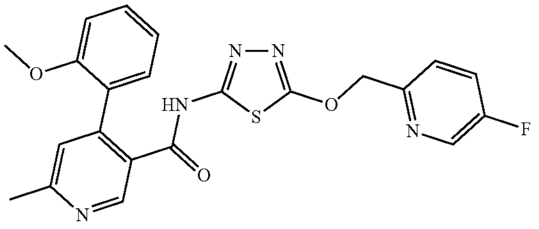 [SMILES: COc1ccccc1-c1cc(C)ncc1C(=O)Nc1nnc(OCc2ccc(F)cn2)s1]

The title compound was prepared using procedures from Example 219. For Step 1, (5-fluoropyridin-2-yl)methanol was used. For Step 2, -(2-methoxyphenyl)-6-methylpyridine-3-carboxylic acid (Example 113, Step 2) was used. $^1$H NMR (400 MHz, $CD_3OD$): δ 8.66 (s, 1H), 8.50 (t, J=1.8 Hz, 1H), 7.73-7.66 (m, 2H), 7.47-7.36 (m, 3H), 7.11 (td, J=7.6, 1.2 Hz, 1H), 6.98 (d, J=8.0 Hz, 1H), 5.56 (s, 2H), 3.62 (s, 3H), 2.66 (s, 3H). m/z 452.1 [M+H$^+$].

Example 222

Synthesis of N-(5-((5-chloropyridin-2-yl)methoxy)-1,3,4-thiadiazol-2-yl)-6-methoxy-4-(2-methoxyphenyl)nicotinamide

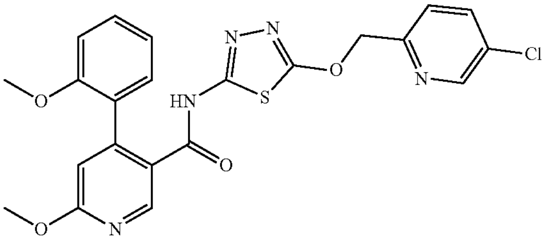 [SMILES: COc1cc(-c2ccccc2OC)c(C(=O)Nc2nnc(OCc3ccc(Cl)cn3)s2)cn1]

Step 1. Synthesis of 6-methoxy-4-(2-methoxyphenyl)nicotinic acid

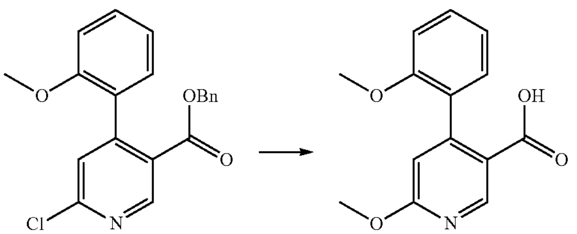 [SMILES: COc1ccccc1-c1cc(Cl)ncc1C(=O)OCc1ccccc1 ; COc1cc(-c2ccccc2OC)c(C(=O)O)cn1]

To a solution of benzyl 6-chloro-4-(2-methoxyphenyl) nicotinate (1.0 g, 2.82 mmol) in MeOH (10.0 mL) was added NaOMe (763.4 mg, 14.1 mmol). The resulting mixture was stirred at 70° C. for 16 h. The resulting mixture was concentrated under vacuum. The residue was dissolved in tetrahydrofuran (5 mL) and $H_2O$ (5 mL) and added NaOH (565 mg, 14.1 mmol) at room temperature. The resulting mixture was stirred for additional 2 h at room temperature. The reaction mixture was diluted with water and acidified to pH ~3 with HCl (1 N), the mixture was concentrated under vacuum. The residue was purified by reverse flash chromatography with 0~60% acetonitrile in water to afford the title compound (880 mg, 82%) as an off-white solid.

Step 2. Synthesis of N-(5-((5-chloropyridin-2-yl) methoxy)-1,3,4-thiadiazol-2-yl)-6-methoxy-4-(2-methoxyphenyl)nicotinamide

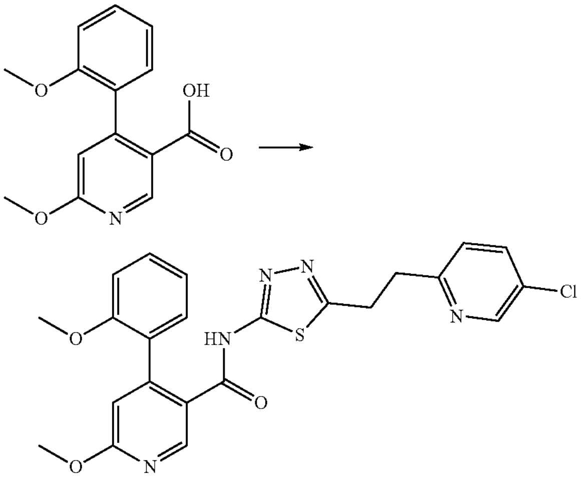

The title compound was prepared using General Procedures A employing 6-methoxy-4-(2-methoxyphenyl)nicotinic acid and 5-((5-chloropyridin-2-yl)methoxy)-1,3,4-thiadiazol-2-amine (Intermediate C). $^1$H NMR (400 MHz, DMSO-$d_6$): δ 12.67 (s, 1H), 8.65 (d, J=2.4 Hz, 1H), 8.45 (s, 1H), 8.01-7.99 (m, 1H), 7.60 (d, J=8.4 Hz, 1H), 7.41-7.33 (m, 2H), 7.07-7.04 (m, 1H), 6.98-6.96 (d, J=0.8 Hz, 1H), 6.80 (s, 1H), 5.54 (s, 2H), 3.95 (s, 3H), 3.51 (s, 3H). m/z 484.0 [M+H$^+$].

Example 223

Synthesis of N-[5-[(5-chloropyridin-2-yl)methoxy]-1,3,4-thiadiazol-2-yl]-5-(2-methoxyphenyl)-[1,2,3] triazolo[1,5-a]pyridine-6-carboxamide

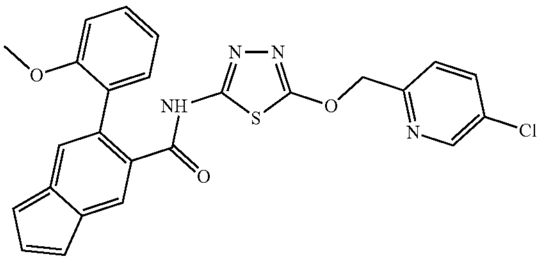

Step-1: Synthesis of ethyl 4-chloro-6-methanehydrazonoylpyridine-3-carboxylate

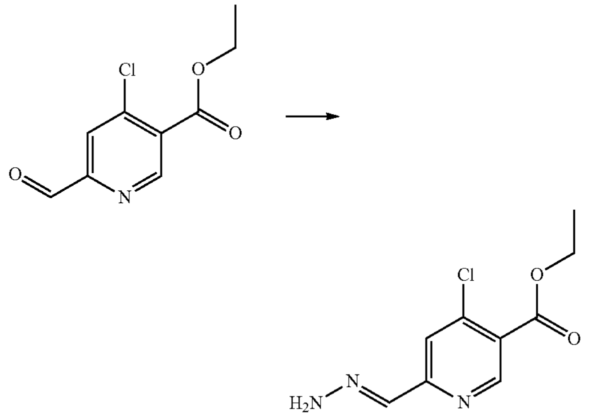

To a solution of ethyl 4-chloro-6-formylpyridine-3-carboxylate (600 mg, 2.80 mmol) in EtOH (10 mL) were added $NH_2NH_2 \cdot H_2O$ (421 mg, 8.42 mmol). The resulting mixture was stirred for 1 h at room temperature under nitrogen atmosphere. The resulting mixture was quenched with water and extracted with DCM. The combined organic layers were washed with brine, dried over anhydrous $Na_2SO_4$. After filtration, the filtrate was concentrated under vacuum to afford the title compound (450 mg, 37%) as a yellow solid.

Step-2: Synthesis of ethyl 5-chloro-[1,2,3]triazolo[1,5-a]pyridine-6-carboxylate

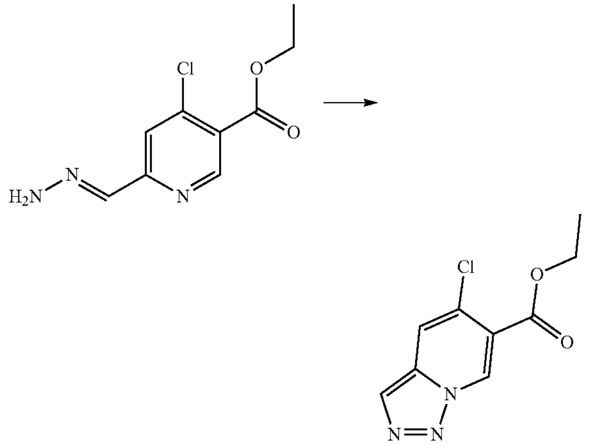

To a stirred solution of ethyl 4-chloro-6-methanehydrazonoylpyridine-3-carboxylate (450 mg, 1.97 mmol) in DCM (5 mL) was added $PhI(OAc)_2$ (700 mg, 2.17 mmol) in portions. The resulting mixture was stirred at room temperature for overnight. The reaction mixture was quenched with saturated $NaHCO_3$ aqueous solution and extracted with DCM. The combined organic layers were washed with brine, dried over anhydrous sodium sulfate, filtered, and concentrated under vacuum. The residue was purified by flash column chromatography with 0-45% ethyl acetate in petroleum ether to afford the title compound (310 mg, 69%) as a yellow solid.

Step-3: Synthesis of ethyl 5-(2-methoxyphenyl)-[1,2,3]triazolo[1,5-a]pyridine-6-carboxylate

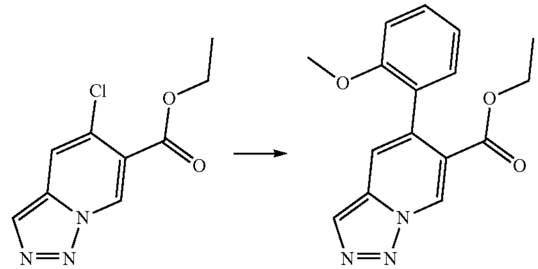 [SMILES: CCOC(=O)c1cn2nncc2cc1Cl ; CCOC(=O)c1cn2nncc2cc1-c1ccccc1OC]

To a mixture of ethyl 5-chloro-[1,2,3]triazolo[1,5-a]pyridine-6-carboxylate (150 mg, 0.665 mmol) and 2-methoxyphenylboronic acid (151 mg, 0.997 mmol) in dioxane (2 mL) and $H_2O$ (0.40 mL) were added $K_2CO_3$ (275 mg, 1.994 mmol) and $Pd(PPh_3)_4$ (76 mg, 0.066 mmol) under nitrogen atmosphere. The resulting mixture was stirred at 80° C. for 2 h under nitrogen atmosphere. After filtered, the filtrate was collected and concentrated under vacuum. The residue was purified by reverse phase flash column chromatography with 5~30% acetonitrile in water to afford the title compound (100 mg, 51%) as a white solid.

Step-4: Synthesis of 5-(2-methoxyphenyl)-[1,2,3]triazolo[1,5-a]pyridine-6-carboxylic acid

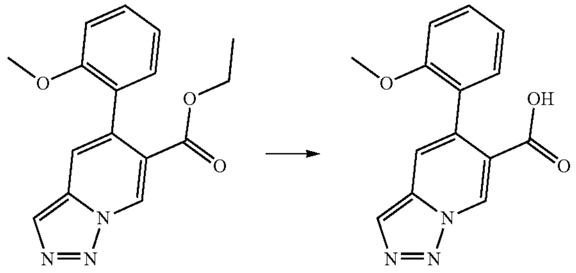 [SMILES: CCOC(=O)c1cn2nncc2cc1-c1ccccc1OC ; COc1ccccc1-c1cc2cnnn2cc1C(=O)O]

To a mixture of ethyl 5-(2-methoxyphenyl)-[1,2,3]triazolo[1,5-a]pyridine-6-carboxylate (100 mg, 0.336 mmol) in THF (1.0 mL) and $H_2O$ (1.0 mL) was added NaOH (54 mg, 1.34 mmol). The resulting mixture was stirred at 80° C. for 2 h. The aqueous solution was acidified with HCl (1 N) to pH 1~2. The residue was purified by reverse phase flash column chromatography with 5~40% acetonitrile in water to afford the title compound (54 mg, 59%) as a pink solid.

Step-5: Synthesis of N-[5-[(5-chloropyridin-2-yl)methoxy]-1,3,4-thiadiazol-2-yl]-5-(2-methoxyphenyl)-[1,2,3]triazolo[1,5-a]pyridine-6-carboxamide

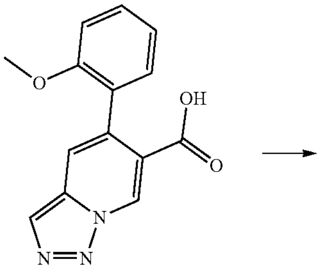

-continued

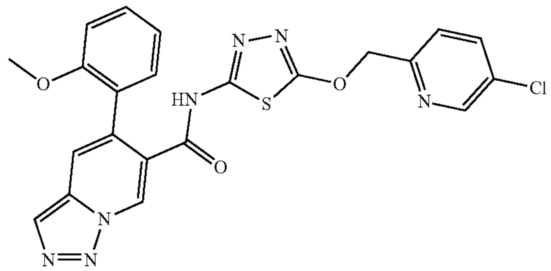

To a mixture of 5-(2-methoxyphenyl)-[1,2,3]triazolo[1,5-a]pyridine-6-carboxylic acid (20 mg, 0.074 mmol), TCFH (27 mg, 0.097 mmol) and NMI (21 mg, 0.260 mmol) in MeCN (1.00 mL) was added 5-[(5-chloropyridin-2-yl)methoxy]-1,3,4-thiadiazol-2-amine (Intermediate C, 23 mg, 0.097 mmol) under nitrogen atmosphere. The resulting mixture was stirred at room temperature for 1 h under nitrogen atmosphere. The residue was purified by reverse phase flash column chromatography with 5~60% acetonitrile in water to afford the title compound (7.2 mg, 20%) as a white solid. $^1$H NMR (400 MHz, DMSO-$d_6$): δ 13.01 (s, 1H), 9.50 (s, 1H), 8.66 (d, J=2.4 Hz, 1H), 8.29 (s, 1H), 8.05-7.98 (m, 1H), 7.94 (s, 1H), 7.62 (d, J=8.4 Hz, 1H), 7.46-7.36 (m, 2H), 7.13-7.05 (m, 1H), 6.98 (d, J=8.0 Hz, 1H), 5.56 (s, 2H), 3.51 (s, 3H). m/z 494.0 [M+H$^+$].

Example 224

Synthesis of N-[5-[(5-chloropyridin-2-yl)methoxy]-1,3,4-thiadiazol-2-yl]-7-(2-methoxyphenyl)imidazo[1,5-a]pyridine-6-carboxamide

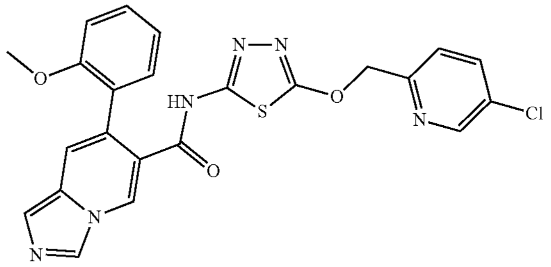 [SMILES: COc1ccccc1-c1cc2cncn2cc1C(=O)Nc1nnc(OCc2ccc(Cl)cn2)s1]

Step-1: Synthesis of ethyl 6-(hydroxymethyl)-4-(2-methoxyphenyl)pyridine-3-carboxylate

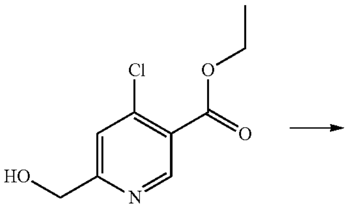

-continued

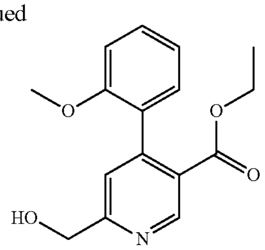

To a stirred mixture of ethyl 4-chloro-6-(hydroxymethyl)pyridine-3-carboxylate (2.0 g, 9.27 mmol), 2-methoxyphenylboronic acid (1.7 g, 11.1 mmol) and $K_2CO_3$ (2.56 g, 18.5 mmol) in dioxane (20 mL) and $H_2O$ (4.0 mL) was added Pd(dppf)$Cl_2$ (680 mg, 0.928 mmol) under nitrogen. The resulting mixture was stirred at 80° C. for 2 hours under nitrogen atmosphere. The residue was purified by reverse phase flash column chromatography with 5~50% acetonitrile in water to afford the title compound (2.19 g, 70%) as a light yellow oil.

Step-2: Synthesis of ethyl 6-(azidomethyl)-4-(2-methoxyphenyl)pyridine-3-carboxylate

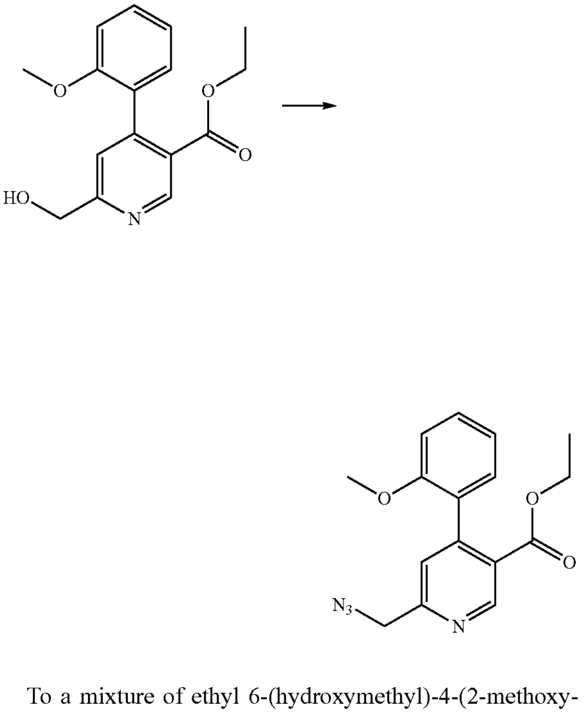

To a mixture of ethyl 6-(hydroxymethyl)-4-(2-methoxyphenyl)pyridine-3-carboxylate (1.5 g, 5.22 mmol) in THF (10 mL) were added DPPA (1.7 g, 6.26 mmol) and DBU (955 mg, 6.26 mmol) sequentially at 0° C. under nitrogen atmosphere. The resulting mixture was stirred at room temperature for overnight under nitrogen atmosphere. The reaction mixture was quenched with water and extracted with ethyl acetate. The combined organic layers were washed with brine, dried over anhydrous sodium sulfate, filtered, and concentrated under vacuum. The residue was purified by reverse phase flash column chromatography with 5~40% acetonitrile in water to afford the title compound (1.2 g, 74%) as a yellow oil.

Step-3: Synthesis of ethyl 6-(aminomethyl)-4-(2-methoxyphenyl)pyridine-3-carboxylate

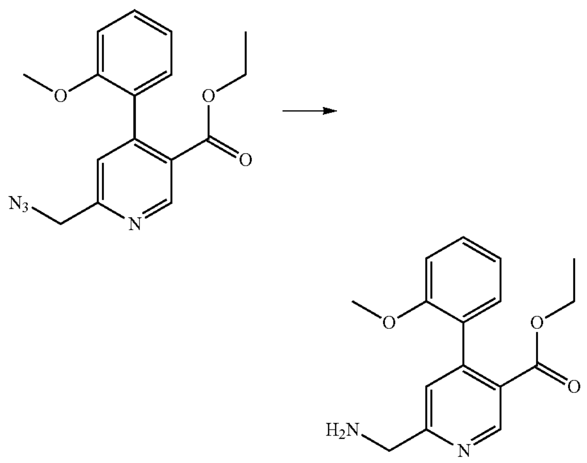

To a mixture of ethyl 6-(azidomethyl)-4-(2-methoxyphenyl)pyridine-3-carboxylate (1.2 g, 3.84 mmol) in ethanol (10 mL) were added Pd/C (150 mg, 1.41 mmol) under nitrogen atmosphere. The resulting mixture was stirred for 2 h at room temperature under hydrogen atmosphere. The suspension was filtered. The filtrate was collected and concentrated under vacuum to afford the title compound (1.2 g, crude) as a yellow oil.

Step-4: Synthesis of ethyl 6-(formamidomethyl)-4-(2-methoxyphenyl)pyridine-3-carboxylate

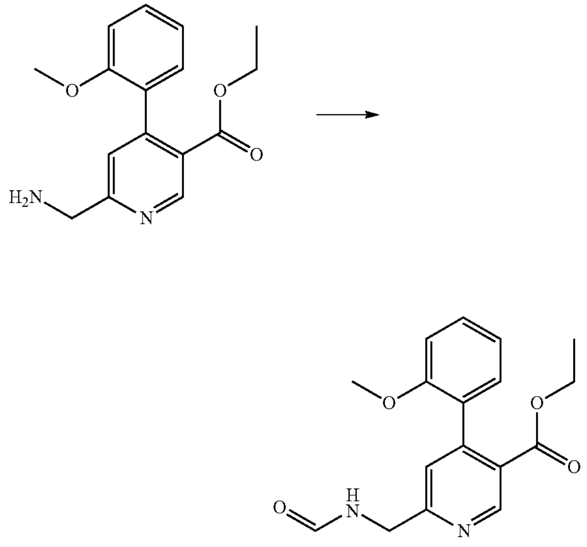

To a mixture of ethyl 6-(aminomethyl)-4-(2-methoxyphenyl)pyridine-3-carboxylate (300 mg, 1.04 mmol) in THF (4 mL) was added acetyl formate (184 mg, 2.09 mmol) at 0° C. The resulting mixture was stirred at room temperature for 1 h. The resulting mixture was concentrated under reduced pressure to afford the title compound (290 mg, 88%) as a yellow solid.

Step-5: Synthesis of ethyl 7-(2-methoxyphenyl)imidazo[1,5-a]pyridine-6-carboxylate

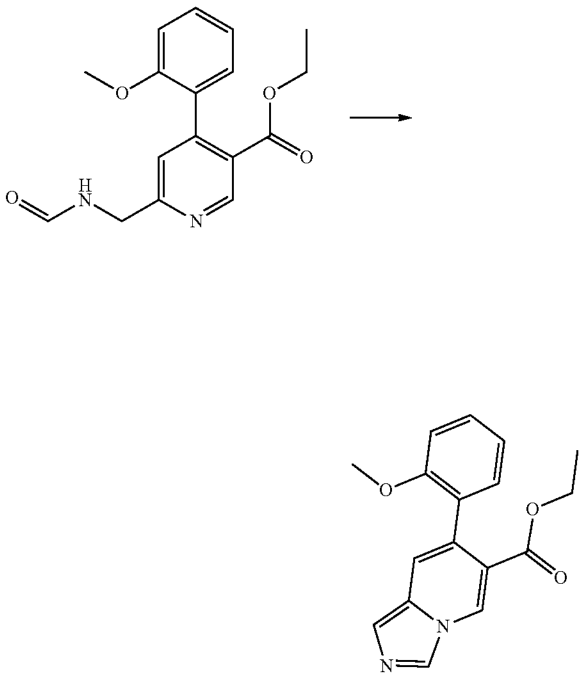

To a mixture of ethyl 6-(formamidomethyl)-4-(2-methoxyphenyl)pyridine-3-carboxylate (270 mg, 0.859 mmol) in Toluene (5 mL) was added $POCl_3$ (263 mg, 1.71 mmol). The resulting mixture was stirred at 100° C. for 2 hours before concentrated under vacuum. The residue was basified with $NH_3 \cdot H_2O$ to pH 9~10 and purified by reverse phase flash column chromatography with 5~50% acetonitrile in water to afford the title compound (113 mg, 44%) as a yellow oil.

Step-6: Synthesis of 7-(2-methoxyphenyl)imidazo[1,5-a]pyridine-6-carboxylic acid

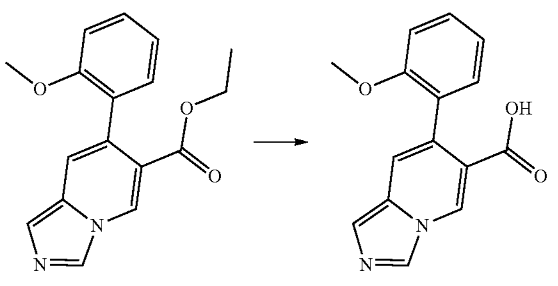 [SMILES: CCOC(=O)c1cn2cncc2cc1-c1ccccc1OC ; COc1ccccc1-c1cc2cncn2cc1C(=O)O]

To a mixture of ethyl 7-(2-methoxyphenyl)imidazo[1,5-a]pyridine-6-carboxylate (113 mg, 0.381 mmol) in THF (1.0 mL) and $H_2O$ (1.0 mL) was added NaOH (61 mg, 1.52 mmol). The resulting mixture was stirred at 80° C. for overnight. The aqueous solution was acidified with HCl (1 N) to pH 1~2. The residue was purified by reverse phase flash column chromatography with 5~30% acetonitrile in water to afford the title compound (77 mg, 75%) as a white solid.

Step-7: Synthesis of N-[5-[(5-chloropyridin-2-yl)methoxy]-1,3,4-thiadiazol-2-yl]-7-(2-methoxyphenyl)imidazo[1,5-a]pyridine-6-carboxamide

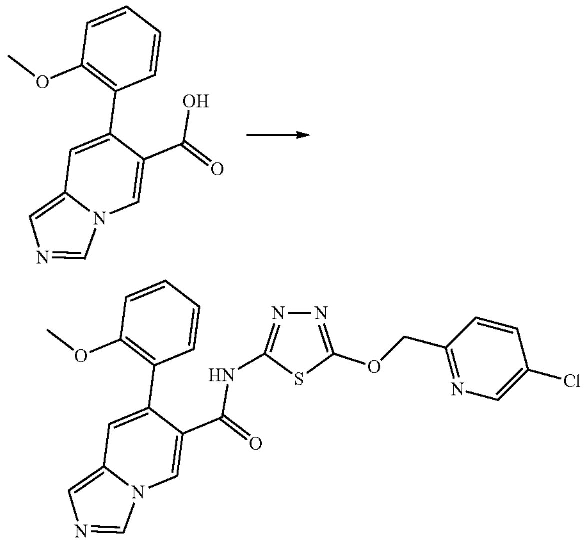

To a mixture of 7-(2-methoxyphenyl)imidazo[1,5-a]pyridine-6-carboxylic acid (60 mg, 0.224 mmol), TCFH (82 mg, 0.291 mmol), NMI (64 mg, 0.783 mmol) in MeCN (1 mL) was added 5-[(5-chloropyridin-2-yl)methoxy]-1,3,4-thiadiazol-2-amine (70 mg, 0.291 mmol) at room temperature under nitrogen atmosphere. The resulting mixture was stirred at room temperature for 2 h under nitrogen atmosphere. The residue was purified by reverse phase flash column chromatography with 5~60% acetonitrile in water to afford the title compound (37.5 mg, 21%) as a white solid. $^1$H NMR (400 MHz, DMSO-$d_6$): δ 12.76 (s, 1H), 8.83 (s, 1H), 8.66 (d, J=2.4 Hz, 1H), 8.53 (s, 1H), 8.05-7.98 (m, 1H), 7.62 (d, J=8.4 Hz, 1H), 7.52 (s, 1H), 7.46 (s, 1H), 7.41-7.29 (m, 2H), 7.08-7.00 (m, 1H), 6.92 (d, J=8.4 Hz, 1H), 5.55 (s, 2H), 3.49 (s, 3H). m/z 493.0 [M+H$^+$].

Example 225

Synthesis of N-[5-[(5-chloropyridin-2-yl)methoxy]-1,3,4-thiadiazol-2-yl]-5-(2-methoxyphenyl)-1H-pyrrolo[3,2-b]pyridine-6-carboxamide

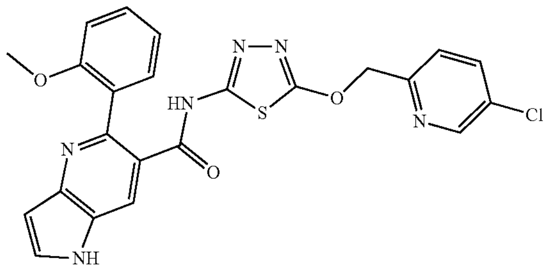 [SMILES: COc1ccccc1-c1nc2cc[nH]c2cc1C(=O)Nc1nnc(OCc2ccc(Cl)cn2)s1]

Step-1: Synthesis of 1-(benzenesulfonyl)-6-bromopyrrolo[3,2-b]pyridine

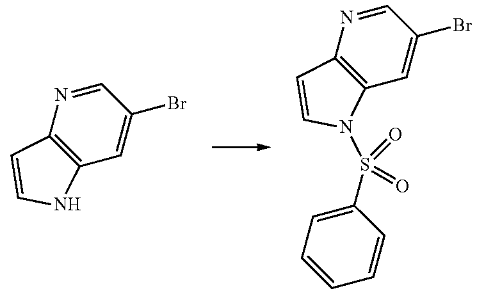 [SMILES: Brc1cnc2cc[nH]c2c1 ; O=S(=O)(c1ccccc1)n1ccc2ncc(Br)cc21]

To a solution of NaH (550 mg, 22.8 mmol) in THF (30 mL) was added 6-bromo-1H-pyrrolo[3,2-b]pyridine (3.0 g, 15.2 mmol) in small portions at 0° C. The resulting mixture was stirred at 0° C. for 15 minutes. A solution of benzenesulfonyl chloride (4.0 g, 22.8 mmol) in THF (24 mL) was then added to the above mixture dropwise at 0° C. The resulting mixture was then stirred at room temperature for 1 hour. The resulting mixture was quenched with water and extracted with ethyl acetate. The organic layers were combined, washed with brine, dried over anhydrous sodium sulfate and filtered. The filtrate was concentrated under vacuum to afford the title compound (5 g, crude) as a yellow solid.

Step-2: Synthesis of 1-(benzenesulfonyl)-6-bromo-4lambda5-pyrrolo[3,2-b]pyridin-4-one

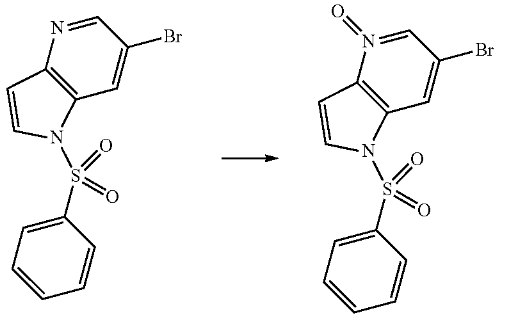 [SMILES: O=S(=O)(c1ccccc1)n1ccc2ncc(Br)cc21 ; O=S(=O)(c1ccccc1)n1ccc2c1cc(Br)c[n+]2[O-]]

To a solution of 1-(benzenesulfonyl)-6-bromopyrrolo[3,2-b]pyridine (5.0 g, 14.8 mmol) in DCM (70 mL) was added mCPBA (3.3 g, 19.3 mmol) at 0° C. The resulting mixture was stirred at room temperature for 16 hours. The solution was washed with saturated aqueous $NaHCO_3$ (20 mL×3) and extracted with ethyl acetate. The organic layers were dried over anhydrous $Na_2SO_4$ and concentrated under vacuum. The residue was purified by flash chromatography on silica gel with 0~15% methanol in dichloromethane to afford the title compound (3.5 g, 67%) as an off-white solid.

Step-3: Synthesis of 1-(benzenesulfonyl)-6-bromo-5-chloropyrrolo[3,2-b]pyridine

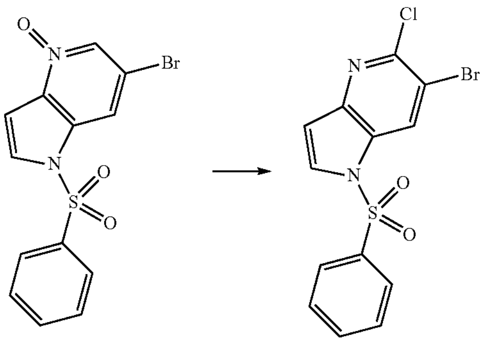 [SMILES: O=S(=O)(c1ccccc1)n1ccc2c1cc(Br)c[n+]2[O-] ; O=S(=O)(c1ccccc1)n1ccc2nc(Cl)c(Br)cc21]

To a mixture of 1-(benzenesulfonyl)-6-bromo-4lambda5-pyrrolo[3,2-b]pyridin-4-one (3.50 g, 9.9 mmol) in toluene (20 mL) was added phosphorus oxychloride (5.0 mL). The mixture was stirred at 80° C. for 3 before concentrated under vacuum. The residue was quenched with water and extracted with ethyl acetate. The organic layers were separated, washed with saturated aqueous $NaHCO_3$ brine, dried over anhydrous sodium sulfate and concentrated under vacuum. The residue was purified by flash chromatography on silica gel with 0~5% methanol in dichloromethane to afford the title compound (1.8 g, 49%) as a white solid.

Step-4: Synthesis of 1-(benzenesulfonyl)-5-chloro-pyrrolo[3,2-b]pyridine-6-carboxylic acid

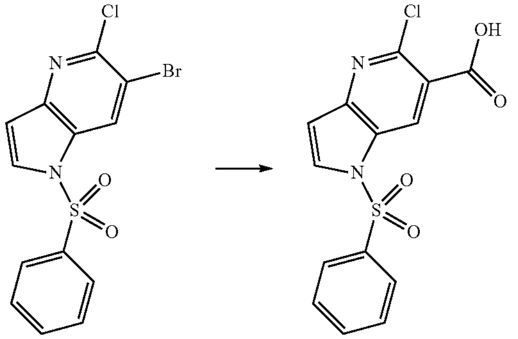 [SMILES: O=S(=O)(c1ccccc1)n1ccc2nc(Cl)c(Br)cc21 ; O=C(O)c1cc2c(ccn2S(=O)(=O)c2ccccc2)nc1Cl]

To a mixture of 1-(benzenesulfonyl)-6-bromo-5-chloro-pyrrolo[3,2-b]pyridine (1.2 g, 3.23 mmol) and oxalic acid hydrate (435 mg, 4.84 mmol) in DMF (5 mL) were added acetic anhydride (494 mg, 4.84 mmol), DIEA (626 mg, 4.84 mmol) and $Pd(OAc)_2$ (72.5 mg, 0.323 mmol). The mixture was stirred at 80° C. for 2 hours under nitrogen atmosphere. The residue was purified by reverse phase flash chromatography with 5~50% acetonitrile in water to afford the title compound (800 mg, 73%) as a yellow solid.

Step-5: Synthesis of 1-(benzenesulfonyl)-5-(2-methoxyphenyl)pyrrolo[3,2-b]pyridine-6-carboxylic acid

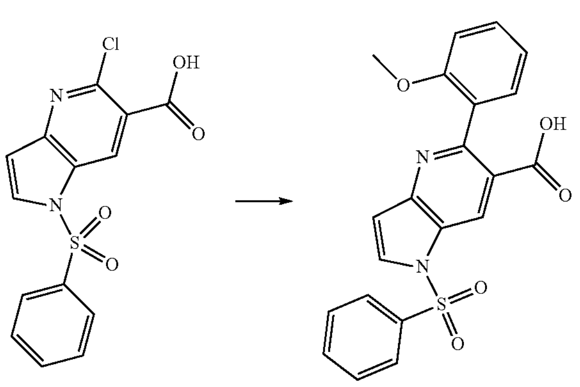 [SMILES: O=C(O)c1cc2c(ccn2S(=O)(=O)c2ccccc2)nc1Cl ; COc1ccccc1-c1nc2ccn(S(=O)(=O)c3ccccc3)c2cc1C(=O)O]

To a mixture of 1-(benzenesulfonyl)-5-chloropyrrolo[3,2-b]pyridine-6-carboxylic acid (800 mg, 2.37 mmol) and 2-methoxyphenylboronic acid (541 mg, 3.56 mmol) in dioxane (10 mL) and $H_2O$ (2.0 mL) were added $K_2CO_3$ (985 mg, 7.12 mmol) and $Pd(PPh_3)_4$ (274 mg, 0.238 mmol). The mixture was stirred at 80° C. for 2 hours under nitrogen atmosphere. The resulting mixture was extracted with ethyl acetate. The aqueous solution was acidified to pH 2 with citric acid and then concentrated. The residue was purified by reverse phase flash chromatography with 5~50% acetonitrile in water to afford the title compound (40 mg, 64%) as a yellow solid.

Step-6: Synthesis of 1-(benzenesulfonyl)-N-[5-[(5-chloropyridin-2-yl)methoxy]-1,3,4-thiadiazol-2-yl]-5-(2-methoxyphenyl)pyrrolo[3,2-b]pyridine-6-carboxamide

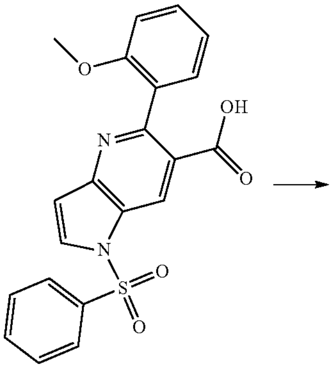

-continued

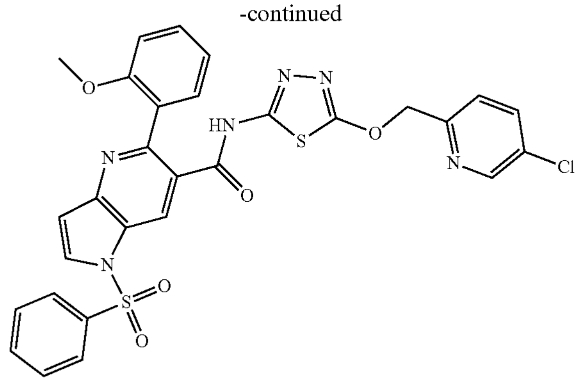

To a solution of 1-(benzenesulfonyl)-5-(2-methoxyphenyl)pyrrolo[3,2-b]pyridine-6-carboxylic acid (40 mg, 0.098 mmol) and 5-[(5-chloropyridin-2-yl)methoxy]-1,3,4-thiadiazol-2-amine (Intermediate C, 30.9 mg, 0.127 mmol) in MeCN (0.50 mL) and DMF (0.50 mL) were added TCFH (35.7 mg, 0.127 mmol) and NMI (40.2 mg, 0.490 mmol). The resulting mixture was stirred at room temperature for 1 hour under nitrogen atmosphere. The resulting mixture was quenched with water and the aqueous phase was extracted with ethyl acetate. The combined organic solution was dried over sodium sulfate, filtered, and concentrated under vacuum to afford the title compound (40 mg, crude) as a yellow solid.

Step-7: Synthesis of N-[5-[(5-chloropyridin-2-yl)methoxy]-1,3,4-thiadiazol-2-yl]-5-(2-methoxyphenyl)-1H-pyrrolo[3,2-b]pyridine-6-carboxamide

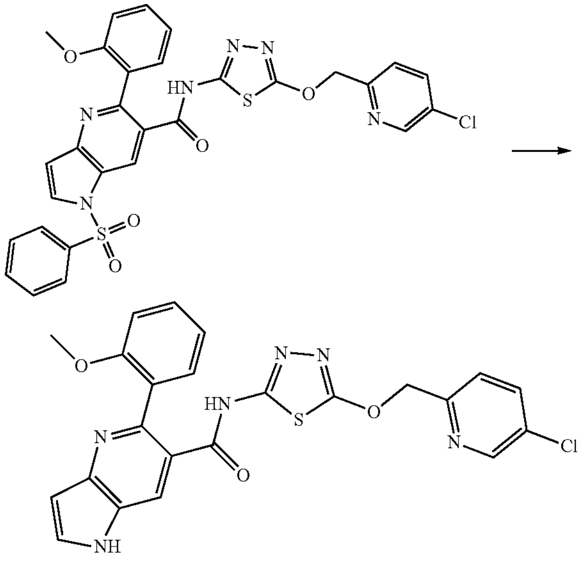

To a mixture of 1-(benzenesulfonyl)-N-[5-[(5-chloropyridin-2-yl)methoxy]-1,3,4-thiadiazol-2-yl]-5-(2-methoxyphenyl)pyrrolo[3,2-b]pyridine-6-carboxamide (40.00 mg, 0.063 mmol) in MeOH (1.00 mL) was added NaOH (2 M, 1 mL). The resulting mixture was stirred at 50° C. for 30 minutes. The residue was acidified to pH 2 with citric acid. The residue was purified by reverse phase flash chromatography with 5~50% acetonitrile in water to afford to afford the title compound (9.3 mg, 29%) as a white solid. $^1$H NMR (400 MHz, DMSO-$d_6$) δ 12.55 (s, 1H), 11.70 (s, 1H), 8.66 (d, J=2.4 Hz, 1H), 8.07 (s, 1H), 8.05-7.98 (m, 1H), 7.84 (t, J=2.8 Hz, 1H), 7.61 (d, J=8.4 Hz, 1H), 7.56-7.49 (m, 1H), 7.37-7.29 (m, 1H), 7.05 (t, J=7.6 Hz, 1H), 6.92 (d, J=8.4 Hz, 1H), 6.66 (d, J=3.2 Hz, 1H), 5.54 (s, 2H), 3.49 (s, 3H). m/z 493.0 [M+H$^+$].

Example 226

Synthesis of N-[5-[(5-chloropyridin-2-yl)methoxy]-1,3,4-thiadiazol-2-yl]-6-(2-methoxyphenyl)-1H-pyrrolo[2,3-b]pyridine-5-carboxamide

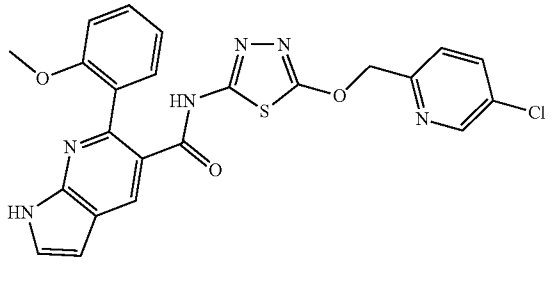 [SMILES: COc1ccccc1-c1nc2[nH]ccc2cc1C(=O)Nc1nnc(OCc2ccc(Cl)cn2)s1]

Step-1: Synthesis of 1-(benzenesulfonyl)-5-bromo-6-chloropyrrolo[2,3-b]pyridine

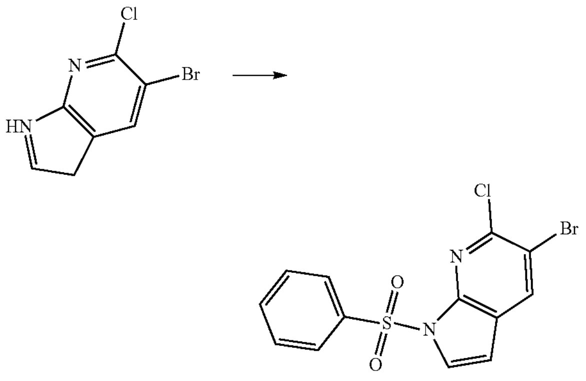

To a solution of NaH (54.4 mg, 2.26 mmol) in THF (3.0 mL) was added 5-bromo-6-chloro-1H-pyrrolo[2,3-b]pyridine (350 mg, 1.51 mmol) in small portions at 0° C. The resulting mixture was stirred at 0° C. for 15 minutes. A solution of benzenesulfonyl chloride (400 mg, 2.26 mmol) in THF (3.0 mL) was then added to the above mixture dropwise at 0° C. The resulting mixture was then stirred at room temperature for 1 hour under nitrogen. The resulting mixture was quenched with water and extracted with ethyl acetate. The organic layers were combined, washed with brine, dried over anhydrous sodium sulfate and filtered. The filtrate was concentrated under vacuum. The residue was purified by flash column chromatography with 0~20% ethyl acetate in petroleum ether to afford the title compound (500 mg, 88%) as a white solid.

Step-2: Synthesis of 1-(benzenesulfonyl)-6-chloro-pyrrolo[2,3-b]pyridine-5-carboxylic acid

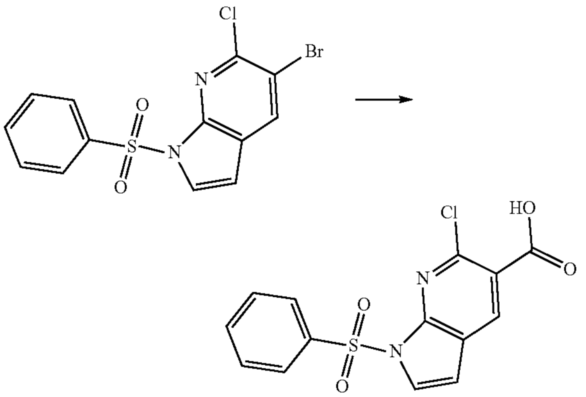

To a mixture of 1-(benzenesulfonyl)-5-bromo-6-chloro-pyrrolo[2,3-b]pyridine (450 mg, 1.21 mmol) in DMF (3.0 mL) were added acetic anhydride (165 mg, 1.81 mmol), DIEA (234 mg, 1.81 mmol) XantPhos (70.1 mg, 1.21 mmol) and $Pd(OAc)_2$ (27.2 mg, 1.21 mmol). The mixture was stirred at 80° C. for 2 hours under nitrogen atmosphere. The residue was purified by reverse phase flash chromatography with 5~70% acetonitrile in water to afford the title compound (120 mg, 29%) as a white solid.

Step-3: Synthesis of 1-(benzenesulfonyl)-6-(2-methoxyphenyl)pyrrolo[2,3-b]pyridine-5-carboxylic acid

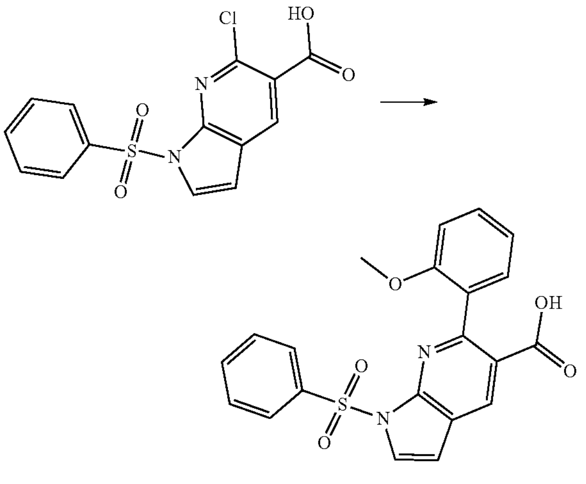

To a mixture of 1-(benzenesulfonyl)-6-chloropyrrolo[2,3-b]pyridine-5-carboxylic acid (120.0 mg, 0.356 mmol) and 2-methoxyphenylboronic acid (81.2 mg, 0.535 mmol) in dioxane (2.00 mL) and $H_2O$ (0.40 mL) were added $K_2CO_3$ (147.7 mg, 1.069 mmol) and $Pd(PPh_3)_4$ (41.2 mg, 0.036 mmol). The mixture was stirred at 80° C. for 2 hours under nitrogen atmosphere. The resulting mixture was extracted with ethyl acetate. The aqueous solution was acidified to pH 2 with citric acid and then concentrated. The residue was purified by reverse phase flash chromatography with 5~50% acetonitrile in water to afford the title compound (40 mg, 27%) as a yellow solid.

Step-4: Synthesis of 1-(benzenesulfonyl)-N-[5-[(5-chloropyridin-2-yl)methoxy]-1,3,4-thiadiazol-2-yl]-6-(2-methoxyphenyl)pyrrolo[2,3-b]pyridine-5-carboxamide

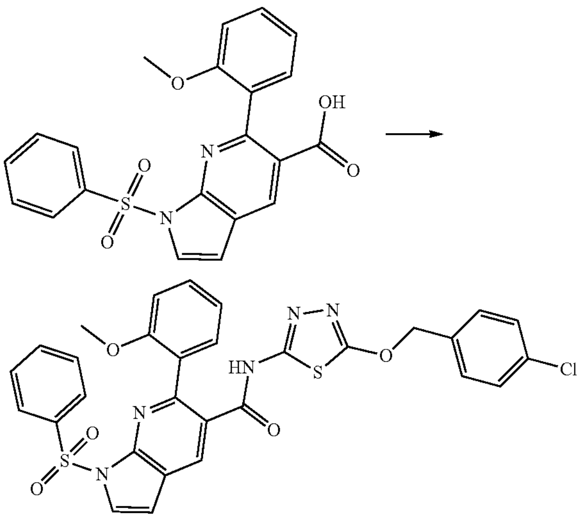

To a solution of 1-(benzenesulfonyl)-6-(2-methoxyphenyl)pyrrolo[2,3-b]pyridine-5-carboxylic acid (30 mg, 0.073 mmol) and 5-[(5-chloropyridin-2-yl)methoxy]-1,3,4-thiadiazol-2-amine (Intermediate C, 23 mg, 0.095 mmol) in MeCN (0.50 mL) and DMF (0.50 mL) were added TCFH (26.8 mg, 0.095 mmol) and NMI (30.2 mg, 0.367 mmol). The resulting mixture was stirred for 1 hour at room temperature under nitrogen atmosphere. The resulting mixture was quenched with water and the aqueous phase was extracted with ethyl acetate. The combined organic solution was dried over sodium sulfate, filtered, and concentrated under vacuum to afford the title compound (30 mg, 641%) as a yellow solid.

Step-5: Synthesis of N-[5-[(5-chloropyridin-2-yl)methoxy]-1,3,4-thiadiazol-2-yl]-6-(2-methoxyphenyl)-1H-pyrrolo[2,3-b]pyridine-5-carboxamide

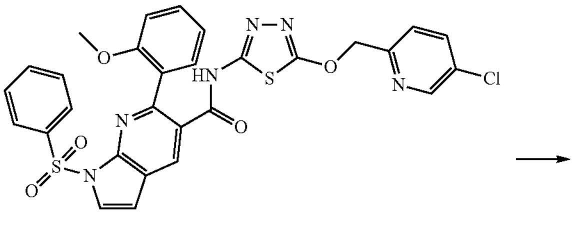

-continued

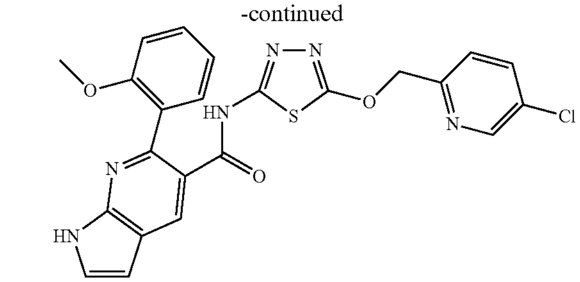

To a solution of 1-(benzenesulfonyl)-N-[5-[(5-chloropyridin-2-yl)methoxy]-1,3,4-thiadiazol-2-yl]-6-(2-methoxyphenyl)pyrrolo[2,3-b]pyridine-5-carboxamide (30 mg, 0.047 mmol) in MeOH (1.0 mL) was added NaOH (2 M, 0.75 mL). The resulting mixture was stirred at 50° C. for 30 minutes. The residue was acidified to pH 2 with citric acid. The residue was purified by reverse phase flash chromatography with 5~50% acetonitrile in water to afford to afford the title compound (8.8 mg, 37%) as a white solid. $^1$H NMR (400 MHz, DMSO-$d_6$): δ 11.72 (s, 1H), 8.64 (d, J=2.4 Hz, 1H), 8.40-8.31 (m, 1H), 8.07-7.91 (m, 1H), 7.56 (d, J=8.4 Hz, 1H), 7.51 (s, 1H), 7.39 (d, J=7.6 Hz, 1H), 7.33-7.23 (m, 1H), 7.01-6.93 (m, 1H), 6.91 (d, J=8.4 Hz, 1H), 6.53 (d, J=3.2 Hz, 1H), 5.45 (s, 2H), 3.48 (s, 3H). m/z 493.1 [M+H$^+$].

Example 227

Synthesis of N-(5-((5-chloropyridin-2-yl)methoxy)-1,3,4-thiadiazol-2-yl)-7-(2-methoxyphenyl)imidazo[1,2-a]pyridine-6-carboxamide

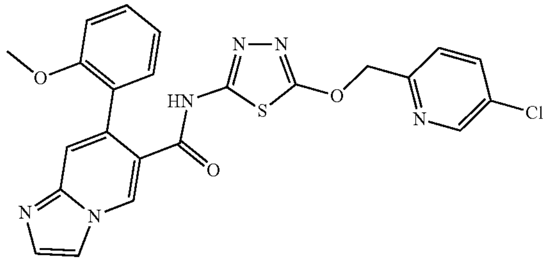 [SMILES: COc1ccccc1-c1cc2nccn2cc1C(=O)Nc1nnc(OCc2ccc(Cl)cn2)s1]

Step-1: Synthesis of ethyl 6-chloro-4-(2-methoxyphenyl)nicotinate

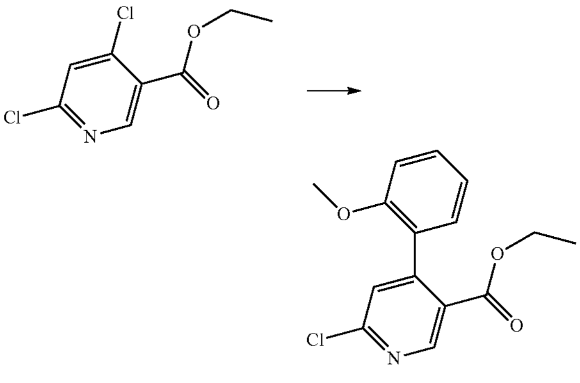

To a degassed solution of ethyl 4,6-dichloronicotinate (5.0 g, 22.8 mmol) in dioxane (50 mL) and $H_2O$ (10 mL) were added $K_2CO_3$ (9.4 g, 68.4 mmol) and Pd(dtbpf)$Cl_2$ (1.48 g, 2.28 mmol) at room temperature under nitrogen. The mixture was stirred at 80° C. for 5 hours under nitrogen before concentrated under vacuum. The residue was purified by flash chromatography on silica gel with 0~50% ethyl acetate in petroleum ether to afford the title compound (3.34 g, 50%) as a yellow oil.

Step-2: Synthesis of ethyl 6-((diphenylmethylene)amino)-4-(2-methoxyphenyl)nicotinate

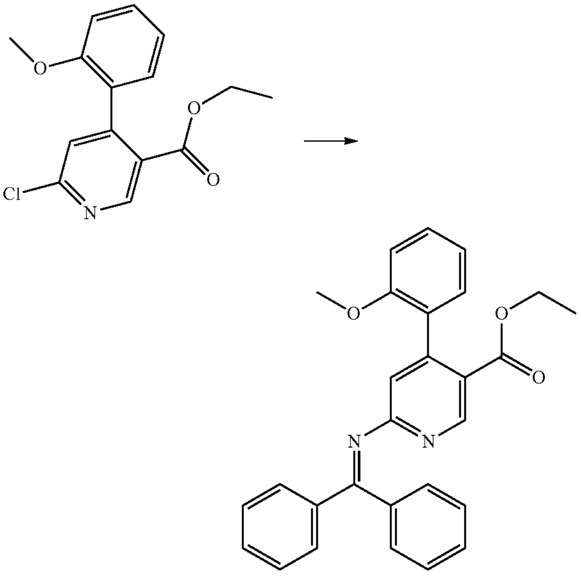

To a degassed solution of ethyl 6-chloro-4-(2-methoxyphenyl)nicotinate (1.0 g, 3.4 mmol) in toluene (10 mL) were added diphenylmethanimine (1.24 g, 3.4 mmol), t-BuONa (500 mg, 5.1 mmol), BINAP (656 mg, 0.68 mmol) and $Pd_2(dba)_3$ (356 mg, 0.34 mmol) under nitrogen. The mixture was stirred at 100° C. for 5 hours under nitrogen. The mixture was concentrated under vacuum. The residue was purified by flash chromatography on silica gel with 0~50% ethyl acetate in petroleum ether to afford the title compound (550 mg, 36%) as a yellow solid.

Step-3: Synthesis of ethyl 6-amino-4-(2-methoxyphenyl)nicotinate

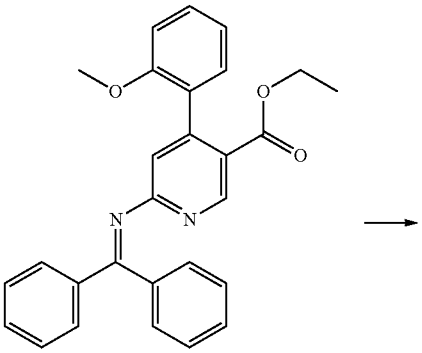

-continued

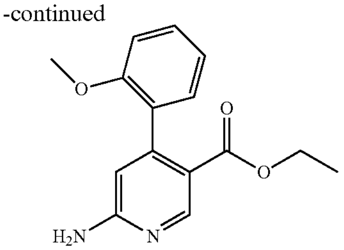

To a solution of ethyl 6-((diphenylmethylene)amino)-4-(2-methoxyphenyl)nicotinate (550 mg, 1.26 mmol) in MeOH (2 mL) was added $H_2NOH \cdot HCl$ (175 mg, 2.52 mmol) and KOAc (371 mg, 3.78 mmol). The mixture was stirred at room temperature for 2 hours. The mixture was diluted with water and extracted with ethyl acetate. The combined organic layers were washed with brine, dried over anhydrous sodium sulfate, filtered, and concentrated under vacuum to afford the title compound (400 mg, 45%) as a yellow solid.

Step-4: Synthesis of methyl 7-bromoimidazo[1,2-a]pyridine-6-carboxylate

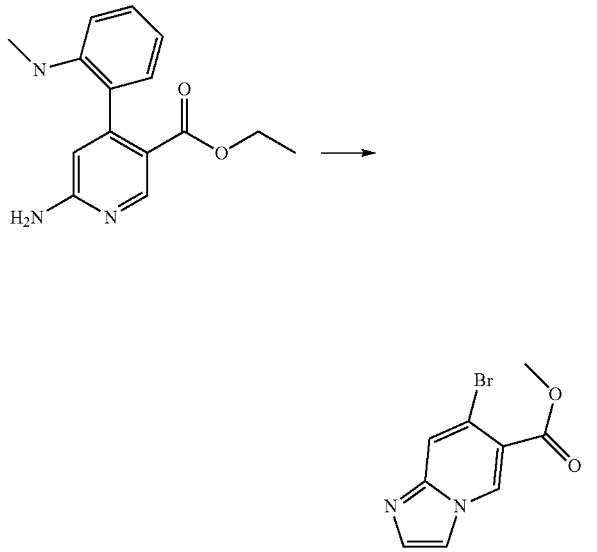

To a solution of ethyl 6-amino-4-(2-methoxyphenyl)nicotinate (400 mg, 1.46 mmol) in EtOH (2.0 mL) was added $NaHCO_3$ (234 mg, 2.92 mmol) and 2-chloroacetaldehyde (497 mg, 6.5 mmol). The mixture was stirred at 80° C. for overnight. The mixture was diluted with water and extracted with ethyl acetate. The combined organic layers were dried over anhydrous sodium sulfate, filtered, and concentrated under vacuum. The residue was purified by flash chromatography on silica gel with 0~50% ethyl acetate in petroleum ether to afford the title compound (307 mg, 76%) as a yellow oil.

Step-5: Synthesis of 7-(2-methoxyphenyl)imidazo[1,2-a]pyridine-6-carboxylic acid

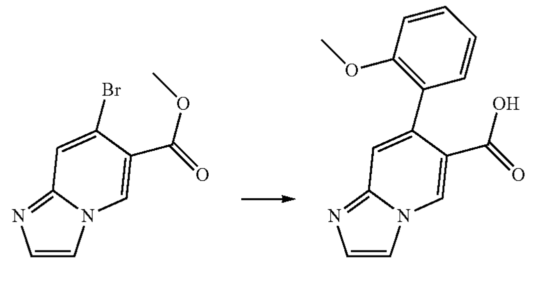 [SMILES: COC(=O)c1cn2ccnc2cc1Br ; COc1ccccc1-c1cc2nccn2cc1C(=O)O]

To a solution of methyl 7-bromoimidazo[1,2-a]pyridine-6-carboxylate (307 mg, 1.2 mmol) in EtOH (2.0 mL) and water (1.0 mL) was added NaOH (96 mg, 2.4 mmol). The mixture was stirred at room temperature for overnight. The aqueous solution was acidified with HCl (1 N) to PH-5. The mixture was diluted with water and extracted with ethyl acetate. The combined organic layers were washed with brine, dried over anhydrous sodium sulfate, filtered, and concentrated under vacuum to afford the title compound (245 mg, crude) as a yellow solid.

Step-6: Synthesis of N-(5-((5-chloropyridin-2-yl)methoxy)-1,3,4-thiadiazol-2-yl)-7-(2-methoxyphenyl)imidazo[1,2-a]pyridine-6-carboxamide

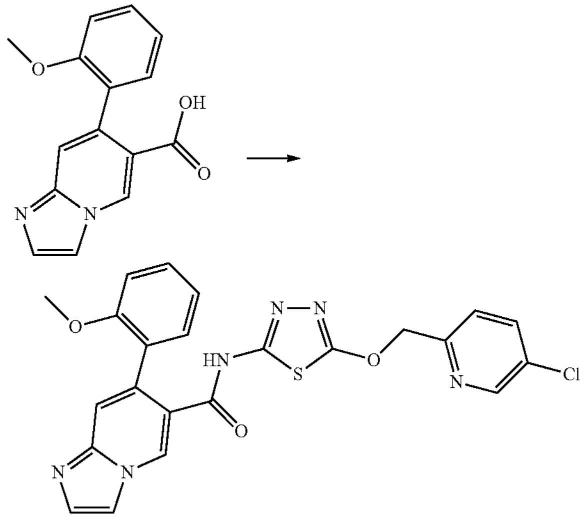

To a solution of 7-(2-methoxyphenyl)imidazo[1,2-a]pyridine-6-carboxylic acid (245 mg, 0.91 mmol) in DMF (2.0 mL) was added DIEA (354 mg, 2.73 mmol), HATU (520 mg, 1.35 mmol) and 5-[(5-chloropyridin-2-yl)methoxy]-1,3,4-thiadiazol-2-amine (Intermediate C, 431 mg, 0.91 mmol). The mixture was stirred at 50° C. for 12 hours. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purified by prep-HPLC (column, C18 silica gel; mobile phase, water (10 mM $NH_4HCO_3$+0.1% $NH_3 \cdot H_2O$) and ACN) to afford the title compound (1.3 mg, 1%) as a white solid. $^1H$ NMR (400 MHz, DMSO-$d_6$): δ 12.77 (s, 1H), 9.03 (s, 1H), 8.66-8.62 (m, 1H), 8.08-8.00 (m, 2H), 7.71-7.61 (m, 2H), 7.49-7.34 (m, 3H), 7.08-6.95 (m, 2H), 5.55 (s, 2H), 3.51 (s, 3H). m/z 493.0 [M+H$^+$].

Example 228

Synthesis of N-[5-[(5-chloropyridin-2-yl)methoxy]-1,3,4-thiadiazol-2-yl]-5-(2-methoxyphenyl)pyrazolo[1,5-a]pyridine-6-carboxamide

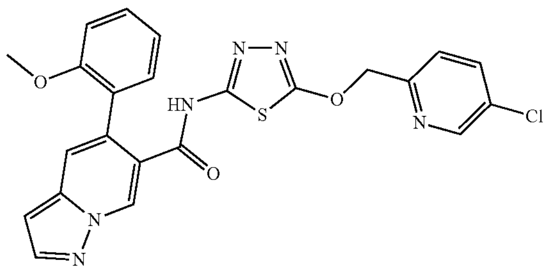 [SMILES: COc1ccccc1-c1cc2ccnn2cc1C(=O)Nc1nnc(OCc2ccc(Cl)cn2)s1]

Step-1: Synthesis of ethyl 4-(2-methoxyphenyl)pyridine-3-carboxylate

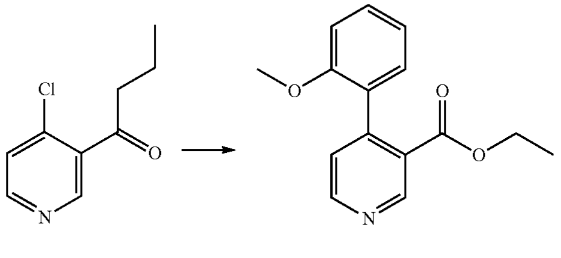 [SMILES: CCCC(=O)c1cnccc1Cl ; CCOC(=O)c1cnccc1-c1ccccc1OC]

A degassed mixture of ethyl 4-chloropyridine-3-carboxylate hydrochloride (1.0 g, 4.50 mmol), 2-methoxyphenylboronic acid (1.37 g, 9.01 mmol), $Pd(PPh_3)_4$ (0.52 g, 0.45 mmol) and Potassium carbonate (1.24 g, 9.01 mmol) in dioxane (40.0 mL) and Water (8.0 mL) was stirred at 80° C. for 2 h under nitrogen atmosphere. The reaction mixture was quenched with water and the aqueous layer was extracted with ethyl acetate. The combined organic layer was dried over sodium sulfate, filtered, and concentrated under vacuum. The residue was purified by silica gel column chromatography, eluted with acetate ethyl in petroleum ether (0~30%) to afford the title compound (900 mg, 77%) as a yellow oil.

Step-2: Synthesis of 6-ethyl 3-methyl 5-(2-methoxyphenyl)pyrazolo[1,5-a]pyridine-3,6-dicarboxylate

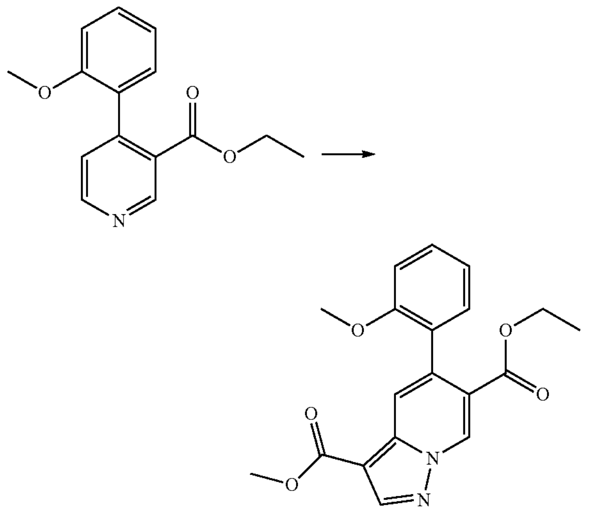

To a mixture of ethyl 4-(2-methoxyphenyl)pyridine-3-carboxylate (900 mg, 3.61 mmol) in DCM (20 mL) amino 2,4,6-trimethylbenzenesulfonate (1.16 g, 5.42 mmol) at 0° C. The resulting mixture was stirred at room temperature for 18 h under nitrogen atmosphere before concentrated under vacuum. The resulting mixture was washed with 100 mL of $Et_2O$ to afford 1-amino-3-(ethoxycarbonyl)-4-(2-methoxyphenyl)pyridin-1-ium (1.3.0 g, crude) as a yellow solid. To a mixture of 1-amino-3-(methoxycarbonyl)-4-(2-methoxyphenyl)pyridin-1-ium (1.30 g, 5.014 mmol) and Potassium carbonate (2.08 g, 15.0 mmol) in DMF (20 mL) was added propiolic acid methyl ester (0.63 g, 7.49 mmol) and stirred at room temperature for 18 h under nitrogen atmosphere. The reaction mixture was quenched with water and the aqueous layer was extracted with ethyl acetate. The combined organic solution was dried over sodium sulfate, filtered, and concentrated under vacuum. The residue was purified by silica gel column chromatography, eluted with acetate ethyl in petroleum ether (0~35%) to afford the title compound (200 mg, 38%) as a yellow solid.

Step-3: Synthesis of 5-(2-methoxyphenyl)pyrazolo[1,5-a]pyridine-6-carboxylic acid

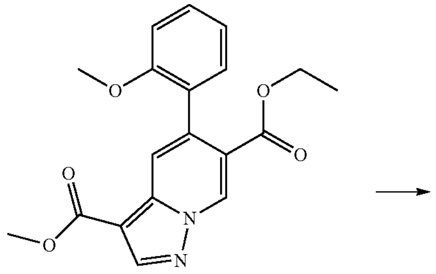

-continued

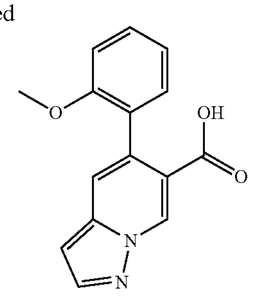

A mixture of 6-ethyl 3-methyl 5-(2-methoxyphenyl)pyrazolo[1,5-a]pyridine-3,6-dicarboxylate (200 mg) in concentrated HCl (3.0 mL) was stirred at 100° C. for 2 h. The reaction mixture was diluted with water and the aqueous layer was extracted with ethyl acetate. The combined organic layer was dried over sodium sulfate, filtered, and concentrated under vacuum. The residue was purified by flash column chromatography with 5~33% acetonitrile in water to afford the title compound (55 mg, 27%) as a white solid.

Step-4: Synthesis of N-[5-[(5-chloropyridin-2-yl)methoxy]-1,3,4-thiadiazol-2-yl]-5-(2-methoxyphenyl)pyrazolo[1,5-a]pyridine-6-carboxamide

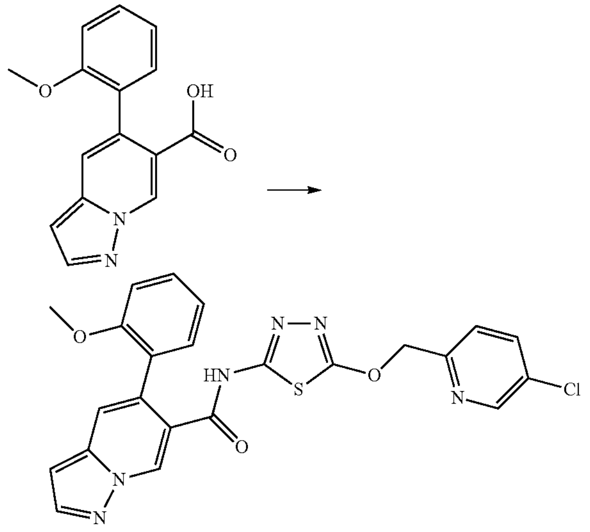

A mixture of 5-(2-methoxyphenyl)pyrazolo[1,5-a]pyridine-6-carboxylic acid (55.0 mg, 0.20 mmol), 5-[(5-chloropyridin-2-yl)methoxy]-1,3,4-thiadiazol-2-amine (Intermediate C, 59.7 mg, 0.24 mmol), TCFH (63.2 mg, 0.22 mmol), NMI (35.3 mg, 0.43 mmol) in DMF (1.0 mL) was stirred at room temperature for 2 h. The crude mixture was purified by Prep-HPLC (column, C18 silica gel; mobile phase, water (10 mM $NH_4HCO_3$) and ACN) to afford the title compound (36.5 mg, 36%) as a white solid. $^1H$ NMR (400 MHz, DMSO-d6): δ 12.80 (s, 1H), 9.07 (s, 1H), 8.66 (d, J=2.4 Hz, 1H), 8.17 (d, J=2.4 Hz, 1H), 8.01 (d, J=2.4 Hz, 1H), 7.65 (s, 1H), 7.62 (d, J=8.4 Hz, 1H), 7.42-7.33 (m, 2H), 7.07 (t, J=7.4 Hz, 1H), 6.96 (d, J=8.4 Hz, 1H), 6.73 (d, J=2.4 Hz, 1H), 5.55 (s, 2H), 3.51 (s, 3H). m/z 493.1 [M+H$^+$].

Example 229

Synthesis of N-(5-((5-chloropyridin-2-yl)methoxy)-1,3,4-thiadiazol-2-yl)-6-(2-methoxyphenyl)-[1,2,4]triazolo[1,5-a]pyridine-7-carboxamide

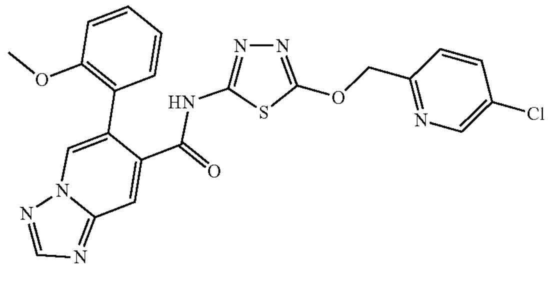 [SMILES: COc1ccccc1-c1cn2ncnc2cc1C(=O)Nc1nnc(OCc2ccc(Cl)cn2)s1]

Step-1: Synthesis of ethyl (E)-5-bromo-2-(((dimethylamino)methylene)amino)isonicotinate

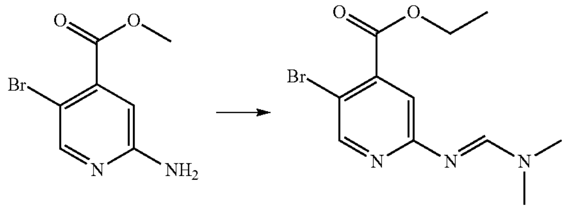 [SMILES: COC(=O)c1cc(N)ncc1Br ; CCOC(=O)c1cc(/N=C/N(C)C)ncc1Br]

A mixture of methyl 2-amino-5-bromoisonicotinate (1.3 g, 5.65 mmol) in DMF-DMA (5.0 mL) and isopropanol (5.0 mL) was stirred at 80° C. for 8 hours. The mixture was concentrated under vacuum to afford the title compound (1.6 g, crude) as an off-white solid.

Step-2: Synthesis of methyl (E)-5-bromo-2-(N'-hydroxyformimidamido)isonicotinate

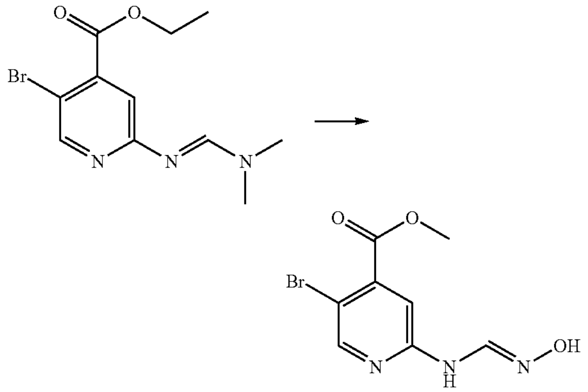

To a mixture of ethyl (E)-5-bromo-2-(((dimethylamino)methylene)amino)isonicotinate (1.6 g, 5.33 mmol) in isopropanol (10 mL) was added hydroxylamine hydrochloride (783 mg, 11.1 mmol). The mixture was stirred at 50° C. for 8 hours before concentrated under vacuum. The residue was purified by flash chromatography on silica gel with 0~10% methanol in dichloromethane to afford the title compound (760 mg, 47%) as a yellow solid.

Step-3: Synthesis of methyl 6-bromo-[1,2,4]triazolo[1,5-a]pyridine-7-carboxylate

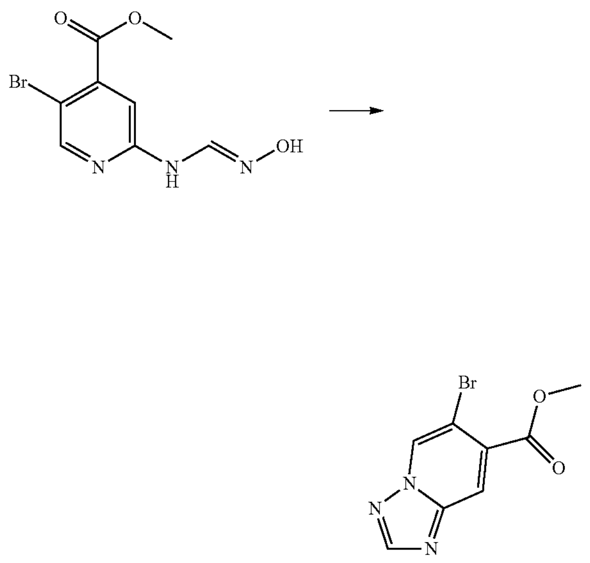

A mixture of methyl (E)-5-bromo-2-(N'-hydroxyformimidamido)isonicotinate (760 mg, 2.78 mmol) in trifluoromethanesulfonic anhydride (10 mL) and THF (10 mL) was stirred at 40° C. for 4 hours. The mixture was concentrated under vacuum and purified by flash chromatography on silica gel with 0~10% methanol in dichloromethane to afford the title compound (588 mg, 77%) as a yellow solid.

Step-4: Synthesis of methyl 6-(2-methoxyphenyl)-[1,2,4]triazolo[1,5-a]pyridine-7-carboxylate

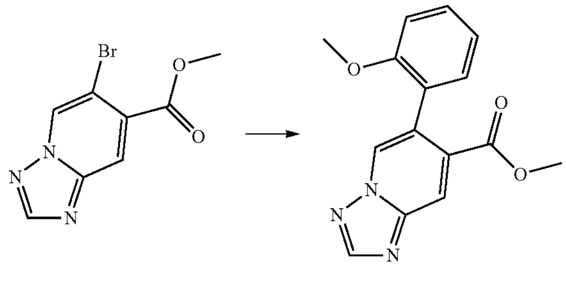

To a solution of methyl 6-bromo-[1,2,4]triazolo[1,5-a]pyridine-7-carboxylate (588 mg, 2.30 mmol) in dioxane (10 mL) and $H_2O$ (1 mL) were added 2-methoxyphenylboronic acid (445 mg, 2.92 mmol), $K_2CO_3$ (955 mg, 6.92 mmol) and Pd(dppf)$Cl_2$ (189 mg, 0.232 mmol) under nitrogen. The resulting solution was stirred at 80° C. for 8 hours under nitrogen before concentrated under vacuum. The residue was purified by flash chromatography on silica gel with 0~50% ethyl acetate in petroleum ether to afford the title compound (483 mg, 82%) as a white solid.

Step-5: 6-(2-methoxyphenyl)-[1,2,4]triazolo[1,5-a]pyridine-7-carboxylic acid

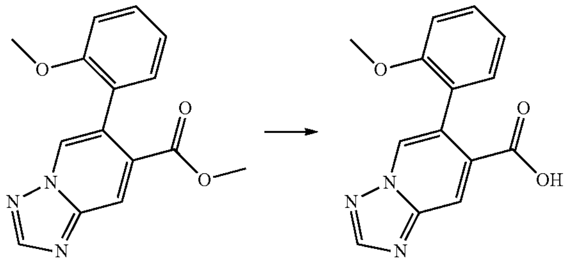

To a solution of methyl 6-(2-methoxyphenyl)-[1,2,4]triazolo[1,5-a]pyridine-7-carboxylate (483 mg, 1.70 mmol) in MeOH (5 mL) and $H_2O$ (2.5 mL) was added NaOH (136 mg, 3.4 mmol). The mixture was stirred at 70° C. for 2 hours. The aqueous solution was acidified with HCl (1 N) to pH 5~6. The aqueous solution was extracted with ethyl acetate. The organic layers were combined, washed with brine, dried over anhydrous sodium sulfate and filtered. The filtrate was concentrated under vacuum to afford the title compound (236 mg, 48%) as an off-white solid.

Step-6: Synthesis of N-(5-((5-chloropyridin-2-yl)methoxy)-1,3,4-thiadiazol-2-yl)-6-(2-methoxyphenyl)-[1,2,4]triazolo[1,5-a]pyridine-7-carboxamide

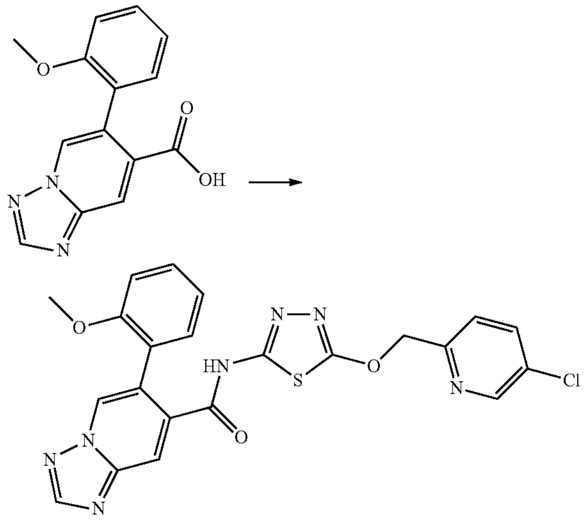

To a solution of 6-(2-methoxyphenyl)-[1,2,4]triazolo[1,5-a]pyridine-7-carboxylic acid (236 mg, 0.874 mmol) in DMF (5.0 mL) were added DIEA (329 mg, 2.55 mmol), HATU (484 mg, 1.27 mmol) and 5-[(5-chloropyridin-2-yl)methoxy]-1,3,4-thiadiazol-2-amine (Intermediate C, 310 mg, 1.27 mmol). The mixture was stirred at room temperature for 3 hours. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purified by prep-HPLC (column, C18 silica gel, mobile phase, water (0.1% FA) and ACN) to afford the title compound (29.8 mg, 12%) as a white solid. $^1$H NMR (400 MHz, DMSO-$d_6$): δ 12.77 (s, 1H), 8.95 (s, 1H), 8.66-8.65 (m, 2H), 8.19 (s, 1H), 8.02-8.01 (m, 1H), 7.61 (s, 1H), 7.46-7.34 (m, 2H), 7.06 (s, 1H), 6.99 (s, 1H), 5.54 (s, 2H), 3.52 (s, 3H). m/z 494.1 [M+$H^+$].

Example 230

Synthesis of N-[5-[(5-chloropyridin-2-yl)methoxy]-1,3,4-thiadiazol-2-yl]-6-(2-methoxyphenyl)pyrazolo[1,5-a]pyridine-5-carboxamide

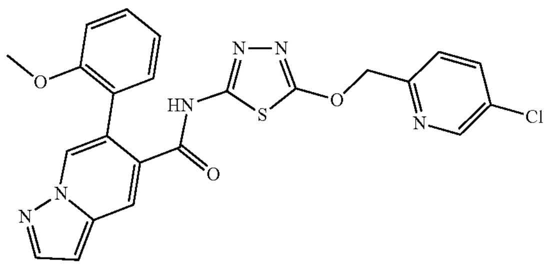 [SMILES: COc1ccccc1-c1cn2nccc2cc1C(=O)Nc1nnc(OCc2ccc(Cl)cn2)s1]

Step-1: Synthesis of methyl 3-(2-methoxyphenyl)pyridine-4-carboxylate

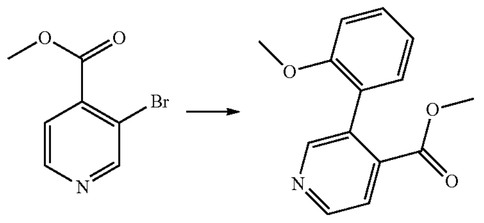

A mixture of methyl 3-bromopyridine-4-carboxylate (1.00 g, 4.62 mmol), 2-methoxyphenylboronic acid (1.41 g, 9.25 mmol), Pd(dppf)$Cl_2$ (0.34 g, 0.463 mmol) and Potassium carbonate (1.28 g, 9.25 mmol) in dioxane (15 mL) and water (3.0 mL) was stirred at 80° C. for 2 h under nitrogen atmosphere. The reaction mixture was quenched with water and the aqueous layer was extracted with ethyl acetate. The combined organic solution was dried over sodium sulfate, filtered, and concentrated under vacuum. The solution was purified by silica gel column chromatography, eluted with acetate ethyl in petroleum ether (0~42%) to afford the title compound (1.0 g, 88%) as a yellow solid.

Step-2: Synthesis of 3,5-dimethyl 6-(2-methoxyphenyl)pyrazolo[1,5-a]pyridine-3,5-dicarboxylate

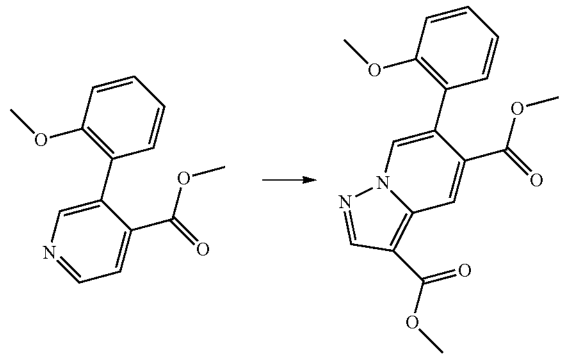

A mixture of methyl 3-(2-methoxyphenyl)pyridine-4-carboxylate (500 mg, 2.05 mmol), amino 2,4,6-trimethylbenzenesulfonate (663 mg, 3.08 mmol) in DCM (10 mL) was stirred at room temperature for 18 h under nitrogen atmosphere. The resulting mixture was concentrated under vacuum and the residue was washed with 100 mL of $Et_2O$ to afford 1-amino-4-(methoxycarbonyl)-3-(2-methoxyphenyl)pyridin-1-ium (510 mg, crude) as a yellow solid. To a mixture of 1-amino-4-(methoxycarbonyl)-3-(2-methoxyphenyl)pyridin-1-ium (510 mg, 1.96 mmol) and potassium carbonate (815 mg, 5.90 mmol) in DMF (15 mL) was added propiolic acid methyl ester (248 mg, 2.95 mmol) and stirred at room temperature for 18 h under nitrogen atmosphere. The reaction mixture was quenched with water and the aqueous layer was extracted with ethyl acetate. The combined organic solution was dried over sodium sulfate, filtered, and concentrated under vacuum. The solution was purified by silica gel column chromatography, eluted with acetate ethyl in petroleum ether (0~24%) to afford the title compound (160 mg, 23%) as a yellow solid.

Step-3: Synthesis of 6-(2-methoxyphenyl)pyrazolo[1,5-a]pyridine-5-carboxylic acid

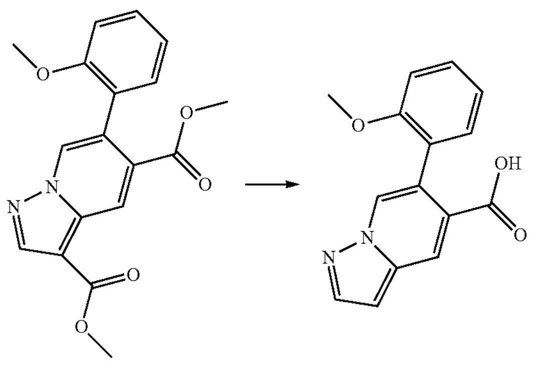

A mixture of 3,5-dimethyl 6-(2-methoxyphenyl)pyrazolo[1,5-a]pyridine-3,5-dicarboxylate (110 mg) in concentrated HCl (3.0 mL) was stirred at 100° C. for 2 h. The resulting mixture was diluted with water and extracted with ethyl acetate. The combined organic solution was dried over sodium sulfate, filtered, and concentrated under vacuum. the resulting solution was purified by reverse phase flash column chromatography with 5~39% acetonitrile in water to afford the title compound (50 mg, 57%) as a white solid.

Step-4: Synthesis of N-[5-[(5-chloropyridin-2-yl)methoxy]-1,3,4-thiadiazol-2-yl]-6-(2-methoxyphenyl)pyrazolo[1,5-a]pyridine-5-carboxamide

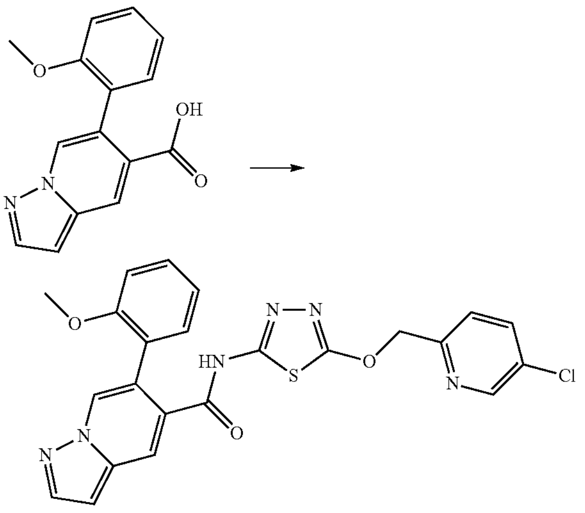

A mixture of 6-(2-methoxyphenyl)pyrazolo[1,5-a]pyridine-5-carboxylic acid (50.0 mg, 0.18 mmol), 5-[(5-chloropyridin-2-yl)methoxy]-1,3,4-thiadiazol-2-amine (Intermediate C, 54.2 mg, 0.22 mmol), TCFH (57.5 mg, 0.20 mmol) NMI (42 mg, 0.52 mmol) in DMF (1.0 mL) was stirred at room temperature for 2 h. The mixture was purified by Prep-HPLC (column, C18 silica gel; mobile phase, water (10 mM $NH_4HCO_3$+0.1% $NH_3 \cdot H_2O$) and ACN) to afford the title compound (35.9 mg, 38%) as a white solid. $^1H$ NMR (400 MHz, DMSO-$d_6$): δ 12.82 (s, 1H), 8.69-8.62 (m, 2H), 8.14 (d, J=2.4 Hz, 1H), 8.10 (s, 1H), 8.01 (dd, J=2.4 Hz, 1H), 7.61 (d, J=8.4 Hz, 1H), 7.47 (d, J=6.4 Hz, 1H), 7.40-7.32 (m, 1H), 7.05 (t, J=7.6 Hz, 1H), 6.96 (d, J=8.4 Hz, 1H), 6.87 (d, J=2.4 Hz, 1H), 5.55 (s, 2H), 3.51 (s, 3H). m/z 493.0 [M+H$^+$].

Example 231

Synthesis of N-(5-((5-chloropyridin-2-yl)methoxy)-1,3,4-thiadiazol-2-yl)-2-(2-methoxyphenyl)-1,6-naphthyridine-3-carboxamide

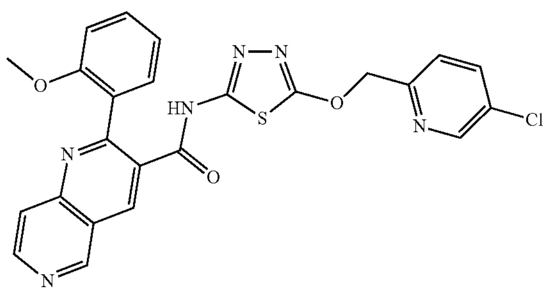 [SMILES: COc1ccccc1-c1nc2ccncc2cc1C(=O)Nc1nnc(OCc2ccc(Cl)cn2)s1]

Step-1: Synthesis of methyl 2-oxo-1,2-dihydro-1,6-naphthyridine-3-carboxylate

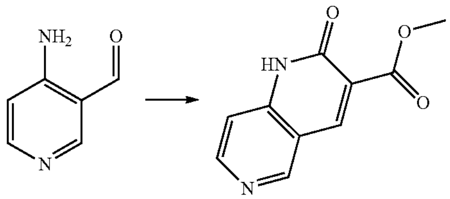

To a stirred solution of 4-aminonicotinaldehyde (4.0 g, 32.7 mmol) in MeOH (30.0 mL) were added diethyl malonate (14.2 g, 88.4 mmol), AcOH (196 mg, 3.27 mmol) and piperidine (7.5 g, 88.4 mmol) at room temperature. The resulting mixture was stirred at 60° C. for 18 h under $N_2$. The resulting mixture was concentrated under vacuum. The precipitated solids were washed with ethyl ether and collected by filtration. The resulting solid was dried under vacuum to afford the title compound (5.2 g, 77%) as a yellow solid.

Step-2: Synthesis of methyl 2-chloro-1,6-naphthyridine-3-carboxylate

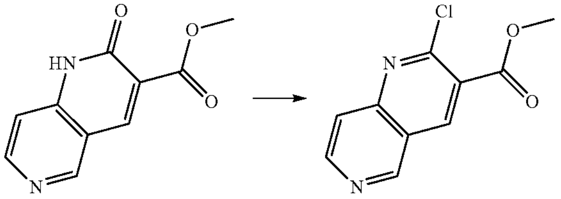

To a stirred solution of methyl 2-oxo-1,2-dihydro-1,6-naphthyridine-3-carboxylate (3.0 g) in $POCl_3$ (200 mL) was stirred at 130° C. for 48 h under $N_2$. The mixture was allowed to cool down to room temperature. The resulting mixture was concentrated under vacuum. The residue was dissolved in ice water. The residue was basified to pH 9 with saturated $Na_2CO_3$ (aq.). The resulting mixture was extracted with ethyl acetate. The combined organic layers were washed with brine, dried over anhydrous $Na_2SO_4$. After filtration, the filtrate was concentrated under reduced pressure. The residue was purified by flash chromatography with 5~45% ethyl acetate in petroleum ether to afford the title compound (292 mg, 10%) as a yellow solid.

Step-3: Synthesis of methyl 2-(2-methoxyphenyl)-1,6-naphthyridine-3-carboxylate

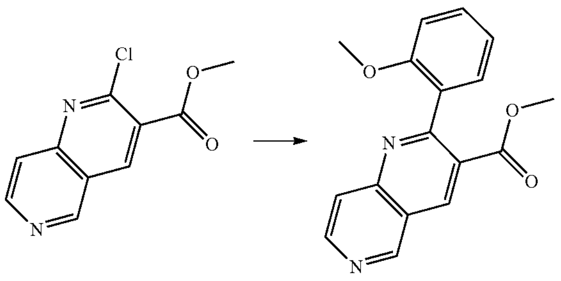 [SMILES: COC(=O)c1cc2cnccc2nc1Cl ; COC(=O)c1cc2cnccc2nc1-c1ccccc1OC]

To a stirred solution of methyl 2-chloro-1,6-naphthyridine-3-carboxylate (270 mg, 1.21 mmol) in 1,4-dioxane (5.0 mL) and $H_2O$ (1.0 mL) were added (2-methoxyphenyl) boronic acid (221 mg, 1.45 mmol), $K_2CO_3$ (502 mg, 3.63 mmol) and Pd(dppf)$Cl_2$ (88.7 mg, 0.12 mmol). The resulting mixture was stirred for 2 h at 80° C. under $N_2$. The resulting mixture was quenched with water and extracted with ethyl acetate. The combined organic layers were washed with brine, dried over anhydrous $Na_2SO_4$. After filtration, the filtrate was concentrated under reduced pressure to afford methyl 2-(2-methoxyphenyl)-1,6-naphthyridine-3-carboxylate (300 mg, crude) as a brown solid.

Step-4: Synthesis of 2-(2-methoxyphenyl)-1,6-naphthyridine-3-carboxylic acid

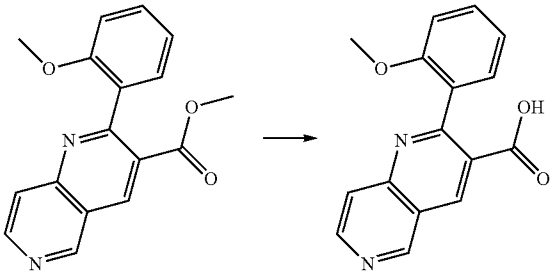 [SMILES: COC(=O)c1cc2cnccc2nc1-c1ccccc1OC ; COc1ccccc1-c1nc2ccncc2cc1C(=O)O]

To a stirred solution of methyl 2-(2-methoxyphenyl)-1,6-naphthyridine-3-carboxylate (270 mg, 0.91 mmol) in EtOH (4.0 mL) were added $H_2O$ (4.0 mL) and NaOH (183 mg, 4.58 mmol). The resulting mixture was stirred at room temperature for 1.5 h. The reaction mixture was diluted with water and extracted with ethyl acetate. The aqueous solution was acidified to pH 7 with HCl (1 N). The resulting mixture was extracted with ethyl acetate. The combined organic layers were washed with brine, dried over anhydrous $Na_2SO_4$. After filtration, the filtrate was concentrated under reduced pressure to afford the title compound (200 mg, crude) as a light yellow solid.

Step-5: Synthesis of N-(5-((5-chloropyridin-2-yl)methoxy)-1,3,4-thiadiazol-2-yl)-2-(2-methoxyphenyl)-1,6-naphthyridine-3-carboxamide

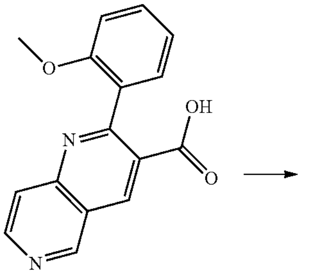

-continued

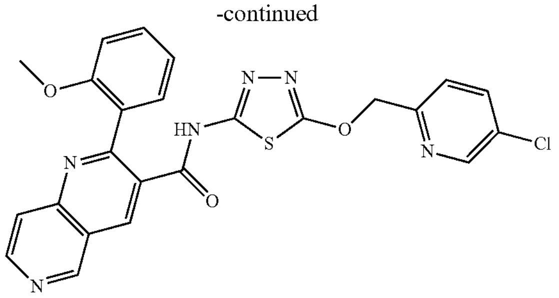

To a stirred solution of 2-(2-methoxyphenyl)-1,6-naphthyridine-3-carboxylic acid (100 mg, 0.35 mmol) in acetonitrile (3.0 mL) were added TCFH (110.1 mg, 0.39 mmol), 5-4(5-chloropyridin-2-yl)methoxy)-1,3,4-thiadiazol-2-amine (Intermediate C, 103 mg, 0.42 mmol) and NMI (61.5 mg, 0.74 mmol). The resulting mixture was stirred for 1.5 h at room temperature. The resulting mixture was concentrated under vacuum. The residue was purified by reverse flash chromatography with 0~60% acetonitrile in water and further purified by Prep-HPLC (column, C18 silica gel; mobile phase, water (10 mM $NH_4HCO_3$) and ACN) to afford the title compound (35 mg, 19%) as an off-white solid. $^1H$ NMR (400 MHz, DMSO-$d_6$): δ 13.05 (s, 1H), 9.53 (s, 1H), 8.93 (s, 1H), 8.86 (d, J=6.0 Hz, 1H), 8.67 (d, J=2.0 Hz, 1H), 8.03-7.99 (m, 2H), 7.68-7.62 (m, 2H), 7.49-7.45 (m, 1H), 7.16-7.12 (m, 1H), 7.02 (d, J=8.4 Hz, 1H), 5.57 (s, 2H), 3.53 (s, 3H). m/z 505.0 [M+$H^+$].

Example 232

Synthesis of N-(5-((5-chloropyridin-2-yl)methoxy)-1,3,4-thiadiazol-2-yl)-2-(2-methoxyphenyl)-1,7-naphthyridine-3-carboxamide

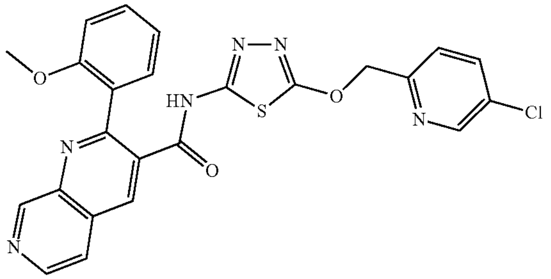 [SMILES: COc1ccccc1-c1nc2cnccc2cc1C(=O)Nc1nnc(OCc2ccc(Cl)cn2)s1]

Step-1: Synthesis of methyl 2-chloro-1,7-naphthyridine-3-carboxylate

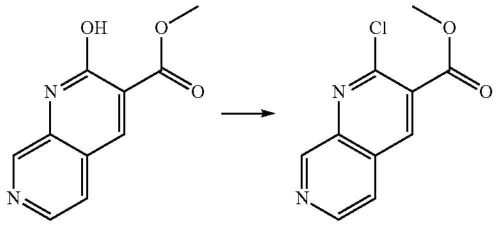

A solution of methyl 2-hydroxy-1,7-naphthyridine-3-carboxylate (500 mg, 2.45 mmol) in $POCl_3$ (5.0 mL) was stirred at 120° C. for 5 hours. The reaction mixture was concentrated under vacuum. The aqueous solution was quenched with water and extracted with ethyl acetate. The combined organic layers were washed with brine, dried over anhydrous sodium sulfate, filtered, and concentrated under vacuum. The residue was purified by flash chromatography on silica gel with 0~50% ethyl acetate in petroleum ether to afford the title compound (500 mg, 92%) as a yellow solid.

Step-2: Synthesis of methyl 2-(2-methoxyphenyl)-1,7-naphthyridine-3-carboxylate

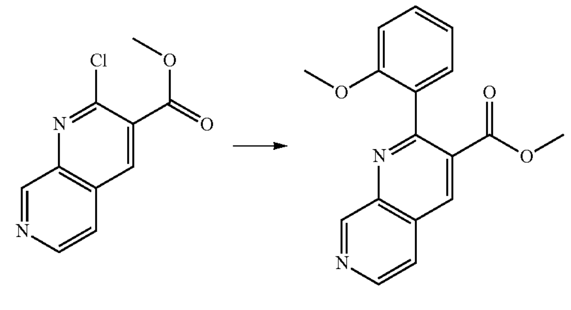

To a solution of ethyl methyl 2-chloro-1,7-naphthyridine-3-carboxylate (500 mg, 2.3 mmol) in dioxane (5.0 mL) and water (1.0 mL) were added $K_2CO_3$ (932 mg, 6.75 mmol) and Pd(dppf)$Cl_2$ (180 mg, 0.23 mmol) under nitrogen. The mixture was stirred at 80° C. for 5 hours before concentrated under vacuum. The residue was purified by flash chromatography on silica gel with 0~50% ethyl acetate in petroleum ether to the title compound (218 mg, 78%) as a yellow oil.

Step-3: Synthesis of 2-(2-methoxyphenyl)-1,7-naphthyridine-3-carboxylic acid

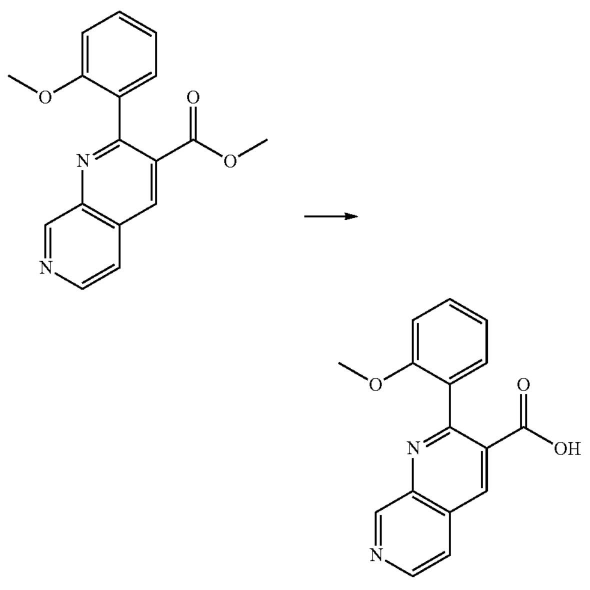

To a solution of methyl 2-(2-methoxyphenyl)-1,7-naphthyridine-3-carboxylate (518 mg, 1.76 mmol) in MeOH (2.0 mL) and $H_2O$ (2.0 mL) was added NaOH (137 mg, 3.52 mmol). The mixture was stirred at room temperature for 2 hours. The aqueous solution was acidified with HCl (1 N) to PH~5. The mixture extracted with ethyl acetate. The combined organic layers were washed with brine, dried over anhydrous sodium sulfate, filtered, and concentrated under vacuum to afford the title compound (341 mg, crude) as a yellow solid.

Step-4: Synthesis of N-(5-((5-chloropyridin-2-yl)methoxy)-1,3,4-thiadiazol-2-yl)-2-(2-methoxyphenyl)-1,7-naphthyridine-3-carboxamide

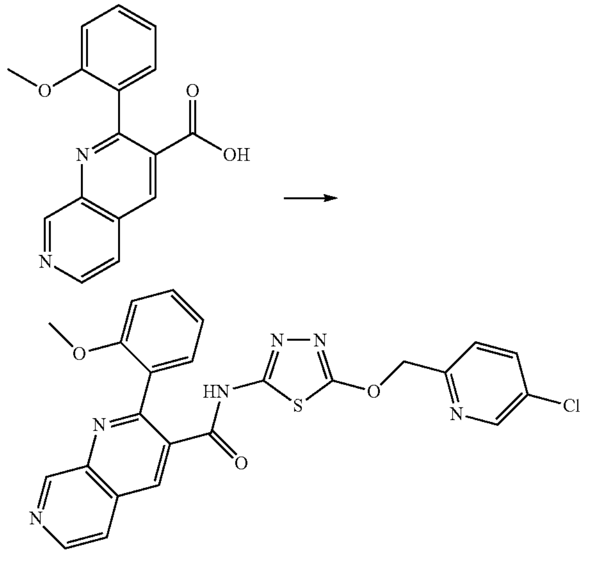

To a solution of 2-(2-methoxyphenyl)-1,7-naphthyridine-3-carboxylic acid (341 mg, 1.21 mmol) in DMF (2.0 mL) were added DIEA (471 mg, 3.63 mmol), HATU (684 mg, 1.8 mmol) and 4-(2-methoxyphenyl)-6-methylpyridine-3-carboxylic acid (294 mg, 1.21 mmol). The mixture was stirred at room temperature for 12 hours. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purified by prep-HPLC (column, C18 silica gel; mobile phase, water (0.1% FA) and ACN) to afford the title compound (6.4 mg, 0.18%) as a white solid. $^1$H NMR (400 MHz, DMSO-$d_6$): δ 13.09 (s, 1H), 9.49 (s, 1H), 8.80 (s, 1H), 8.74-8.73 (m, 1H), 8.67-8.66 (m, 1H), 8.07-8.01 (m, 2H), 7.70-7.62 (m, 2H), 7.49-7.44 (m, 1H), 7.16-7.13 (m, 1H), 7.03-7.01 (m, 1H), 5.57 (s, 2H), 3.53 (s, 3H). m/z 505.1 [M+H$^+$].

BIOLOGICAL EXAMPLES

Example 1

The ability of the compounds of Formula (I) to inhibit ATPase activity of Pol theta (1-899) was determined using the assay described below.

Pol Theta ATPase activity was determined by measuring the rate of ATP turn over in a NADH oxidation-coupled enzymatic assay. 10-point dilution series of compounds were used in a 384 well format for the inhibition assays. Pol theta (1-899) (10 nM) in assay buffer (20 mM Tris HCl (pH 7.80), 80 mM KCl, 10 mM $MgCl_2$, 1 mM DTT, 0.01% BSA, 0.01% Tween, 5% glycerol) was transferred to the test wells (20 μL), except the low control wells (20 μL of assay buffer was added to the low control wells). The plate was then incubated at room temperature for 15 min. An equal volume (20 μL) of 100 μM ATP, 300 nM $dT_{50}$ (single-stranded DNA (ssDNA) containing 50 thymine bases), 300 μM NADH, 6 mM PEP, 10 U/mL lactate dehydrogenase and 20 U/mL pyruvate kinase in assay buffer was added to all the test wells. The plate was then centrifuged at 1000 rpm for 1 min. The reaction was monitored for 30 min by measuring absorbance (λ=340 nm) in a Tecan Spark multimode plate reader every minute. The high control (DMSO with enzyme) with low absorbance intensity represents no inhibition of ATPase reaction while the low control (DMSO with buffer) with high absorbance intensity represents full inhibition of ATPase activity. Slope of the reaction progress curves were used to calculate the rate of ATP hydrolysis. The rates were used to determine the percent inhibition using a four-parameter inhibition model to generate $IC_{50}$, Hill slope and max inhibition.

The $IC_{50}$ of the compounds in Table 1 above are disclosed in Table 2 below:

| Cpd # | ATPase NADH coupling:Standard Screening:hPolQ IC50 (uM) |
|---|---|
| 1 | + |
| 2 | ++ |
| 3 | + |
| 4 | ++ |
| 5 | +++ |
| 6 | +++ |
| 7 | +++ |
| 8 | + |
| 9 | +++ |
| 10 | ++ |
| 11 | + |
| 12 | +++ |
| 13 | +++ |
| 14 | ++++ |
| 15 | + |
| 16 | + |
| 17 | ++ |
| 18 | ++ |
| 19 | + |
| 20 | + |
| 21 | + |
| 22 | + |
| 23 | + |
| 24 | + |
| 25 | + |
| 26 | +++ |
| 27 | +++ |
| 28 | + |
| 29 | + |
| 30 | ++++ |
| 31 | ++++ |
| 32 | +++ |
| 33 | ++ |
| 34 | + |
| 35 | ++++ |
| 36 | + |
| 37 | + |
| 38 | + |
| 39 | + |
| 40 | +++ |
| 41 | + |
| 42 | ++++ |

-continued

| Cpd # | ATPase NADH coupling:Standard Screening:hPolQ IC50 (uM) |
|---|---|
| 43 | +++ |
| 44 | ++++ |
| 45 | ++ |
| 46 | +++ |
| 47 | +++ |
| 48 | +++ |
| 49 | ++ |
| 50 | ++++ |
| 51 | + |
| 52 | +++ |
| 53 | ++ |
| 54 | ++ |
| 55 | + |
| 56 | + |
| 57 | ++ |
| 58 | ++ |
| 59 | +++ |
| 60 | ++++ |
| 61 | ++ |
| 62 | ++++ |
| 63 | + |
| 64 | ++ |
| 65 | + |
| 66 | + |
| 67 | + |
| 68 | + |
| 69 | + |
| 70 | ++ |
| 71 | ++++ |
| 72 | +++ |
| 73 | + |
| 74 | ++ |
| 75 | ++ |
| 76 | ++++ |
| 77 | ++++ |
| 78 | + |
| 79 | ++ |
| 80 | +++ |
| 81 | ++++ |
| 82 | ++++ |
| 83 | ++ |
| 84 | + |
| 85 | ++++ |
| 86 | ++++ |
| 87 | ++ |
| 88 | ++++ |
| 89 | ++++ |
| 90 | ++ |
| 91 | +++ |
| 92 | ++++ |
| 93 | ++++ |
| 94 | + |
| 95 | ++++ |
| 96 | ++++ |
| 97 | ++++ |
| 98 | ++ |
| 99 | ++++ |
| 100 | ++++ |
| 101 | ++++ |
| 102 | ++++ |
| 103 | ++++ |
| 104 | ++++ |
| 105 | ++++ |
| 106 | ++++ |
| 107 | ++++ |
| 108 | ++++ |
| 109 | ++++ |
| 110 | ++++ |
| 111 | ++++ |
| 112 | ++++ |
| 113 | ++++ |
| 114 | ++++ |
| 115 | ++++ |
| 116 | ++++ |
| 117 | ++++ |
| 118 | +++ |

-continued

| Cpd # | ATPase NADH coupling:Standard Screening:hPolQ IC50 (uM) |
|---|---|
| 119 | ++++ |
| 120 | ++++ |
| 121 | ++++ |
| 122 | ++++ |
| 123 | ++++ |
| 124 | ++++ |
| 125 | ++++ |
| 126 | ++++ |
| 127 | ++++ |
| 128 | ++ |
| 129 | +++ |
| 130 | ++++ |
| 131 | ++++ |
| 132 | ++++ |
| 133 | ++ |
| 134 | ++++ |
| 135 | ++++ |
| 136 | ++++ |
| 137 | ++++ |
| 138 | ++++ |
| 139 | ++++ |
| 140 | ++++ |
| 141 | ++++ |
| 142 | ++++ |
| 143 | ++++ |
| 144 | ++++ |
| 145 | ++++ |
| 146 | ++++ |
| 147 | ++++ |
| 148 | ++++ |
| 149 | ++++ |
| 150 | +++ |
| 151 | ++++ |
| 152 | ++++ |
| 153 | ++++ |
| 154 | ++++ |
| 155 | ++++ |
| 156 | ++++ |
| 157 | ++++ |
| 158 | ++++ |
| 159 | ++++ |
| 160 | ++++ |
| 161 | ++++ |
| 162 | ++++ |
| 163 | ++++ |
| 164 | ++++ |
| 165 | ++++ |
| 166 | ++++ |
| 167 | +++ |
| 168 | ++++ |
| 169 | ++++ |
| 170 | ++++ |
| 171 | ++++ |
| 172 | ++++ |
| 173 | +++ |
| 174 | ++++ |
| 175 | ++++ |
| 176 | ++++ |
| 177 | ++++ |
| 178 | ++++ |
| 179 | ++++ |
| 180 | ++++ |
| 181 | ++++ |
| 182 | ++++ |
| 183 | ++++ |
| 184 | ++++ |
| 185 | ++++ |
| 186 | ++++ |
| 187 | ++++ |
| 188 | ++++ |
| 189 | ++++ |
| 190 | ++++ |
| 191 | +++ |
| 192 | ++++ |
| 193 | ++++ |
| 194 | ++++ |

-continued

| Cpd # | ATPase NADH coupling:Standard Screening:hPolQ IC50 (uM) |
|---|---|
| 195 | ++++ |
| 196 | ++++ |
| 197 | +++ |
| 198 | ++++ |
| 199 | +++ |
| 200 | ++++ |
| 201 | ++ |
| 202 | ++++ |
| 203 | ++++ |
| 204 | + |
| 205 | ++++ |
| 206 | ++++ |
| 207 | + |
| 208 | ++++ |
| 209 | ++++ |
| 210 | ++++ |
| 211 | ++++ |
| 212 | ++++ |
| 213 | ++++ |
| 214 | ++++ |
| 215 | ++++ |
| 216 | ++++ |
| 217 | ++++ |
| 218 | ++++ |
| 219 | ++++ |
| 220 | ++++ |
| 221 | ++++ |
| 222 | ++++ |
| 223 | ++++ |
| 224 | ++++ |

$IC_{50}$: 10 uM ≥ (+) > 1 uM;
1 uM ≥ (++) > 500 nM;
500 nM ≥ (+++) > 200 nM;
200 nM ≥ (++++)

Certain examples resulted in mixtures of compounds with at least one stereocenter (e.g., Examples 167, 175, 178, and 179). The data above reports the activity measured when testing a mixture of the stereocenters.

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

The invention claimed is:
1. A compound selected from the group consisting of:
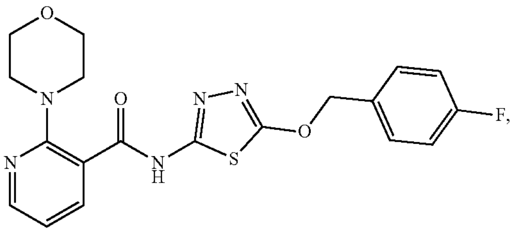
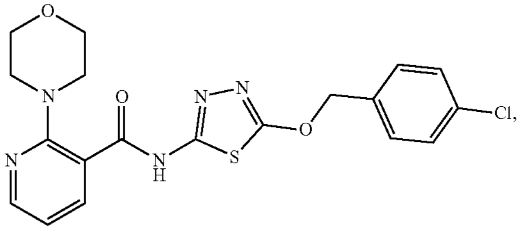
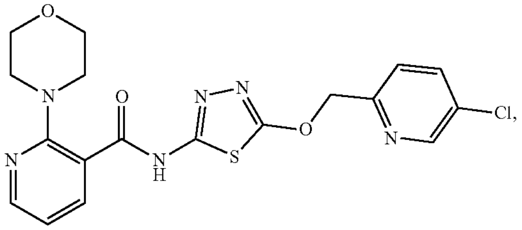
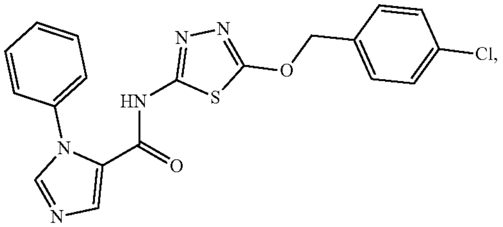
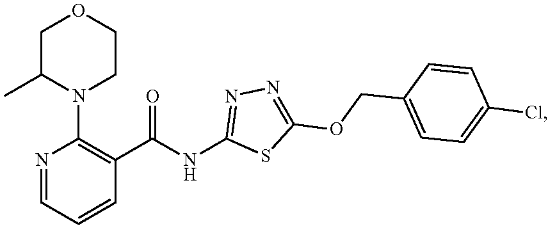
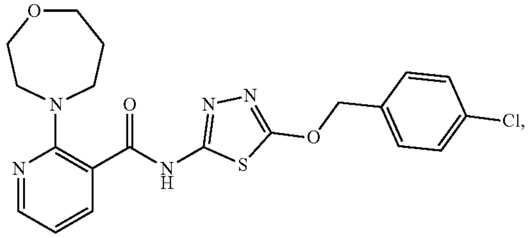
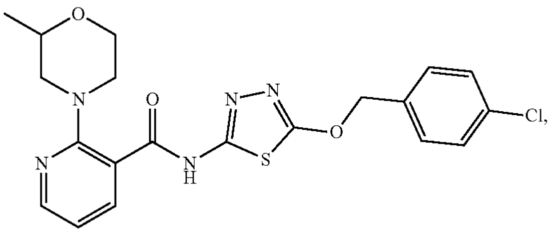
-continued
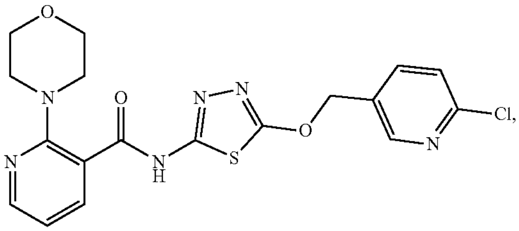
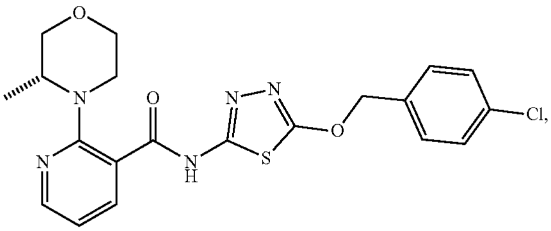
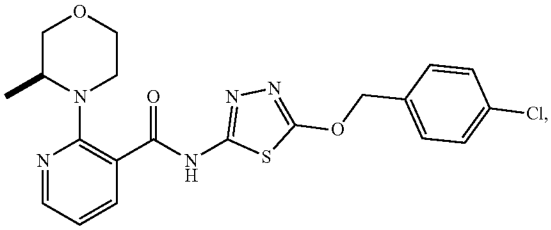
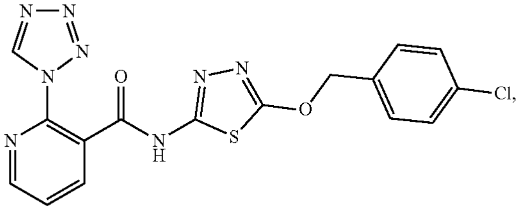
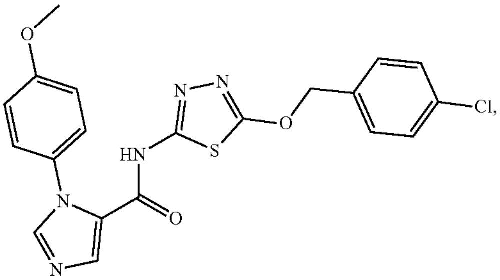
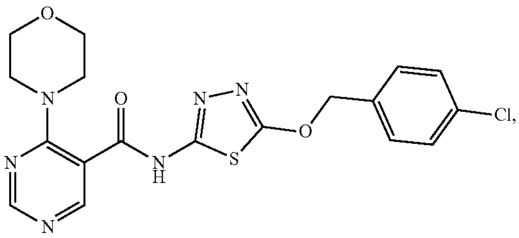
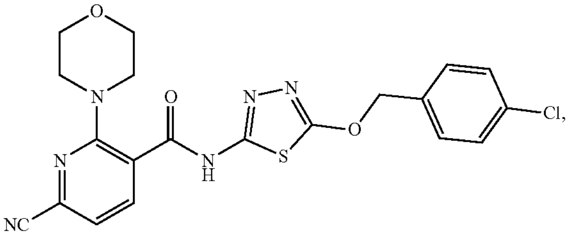

-continued
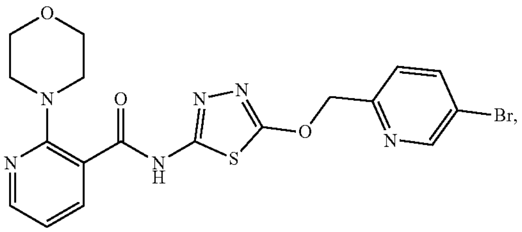
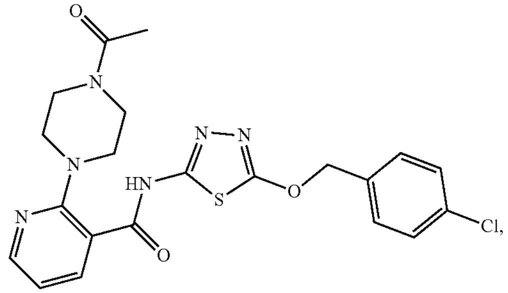
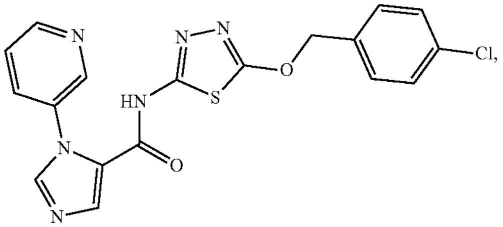
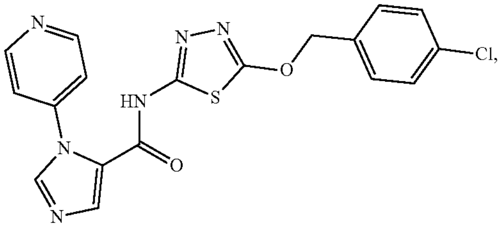
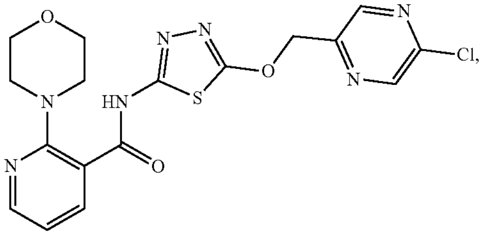
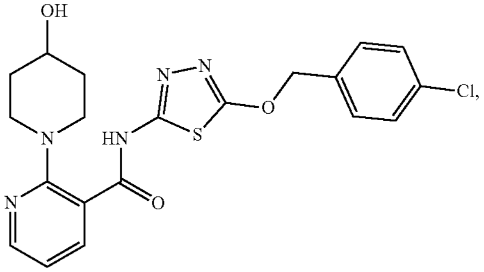
-continued
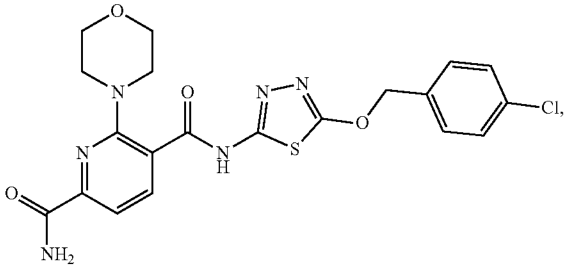
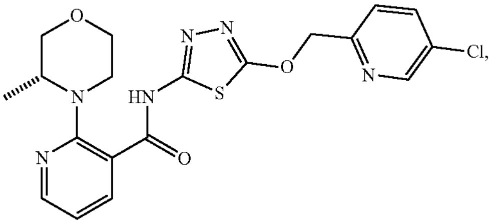
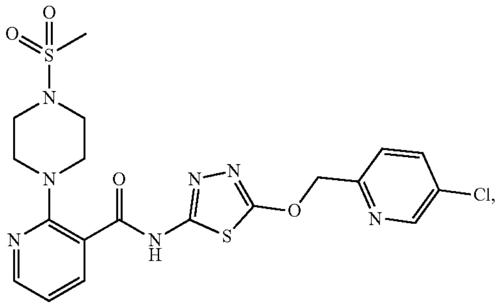
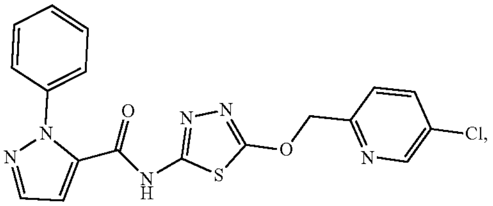
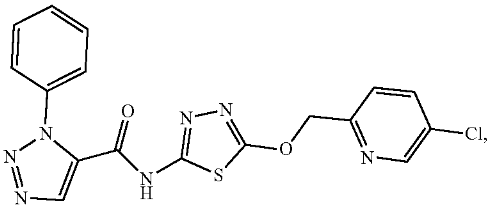
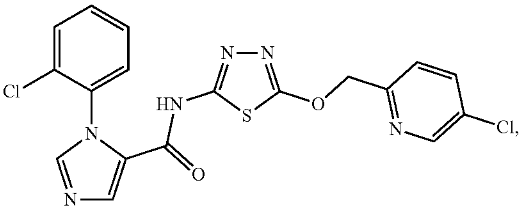
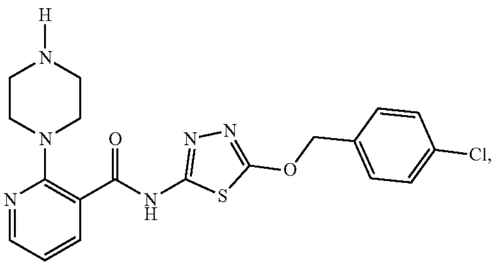

-continued
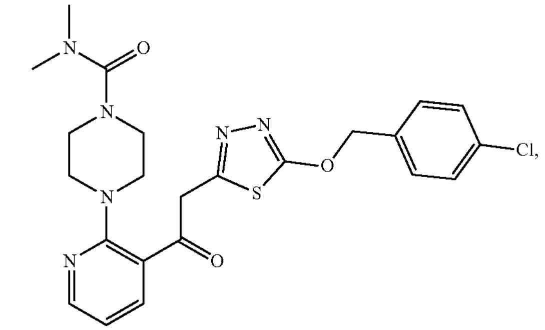
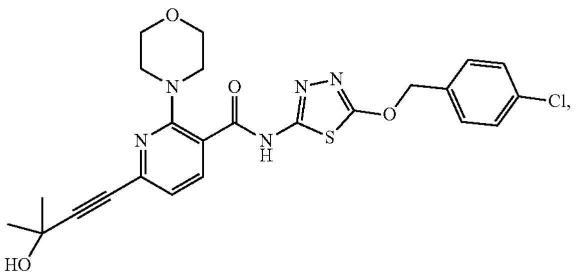
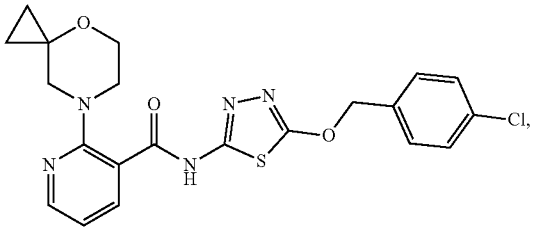
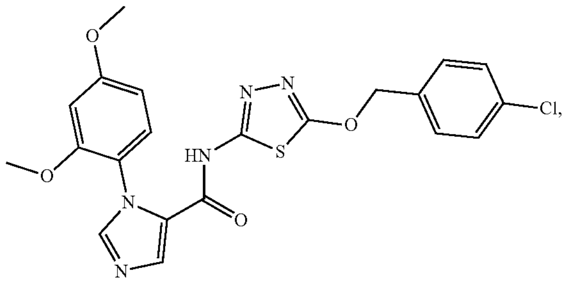
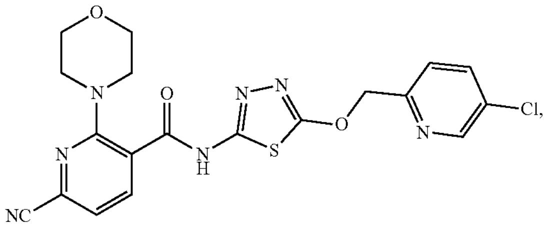
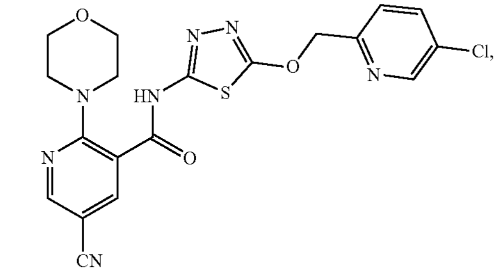
-continued
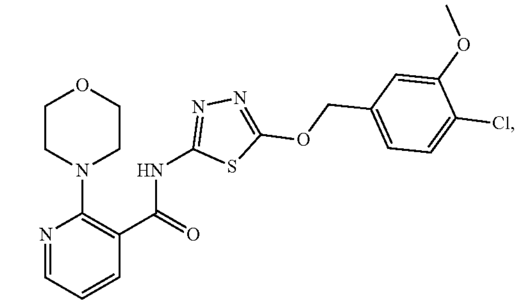
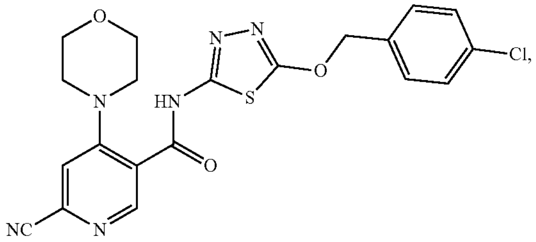
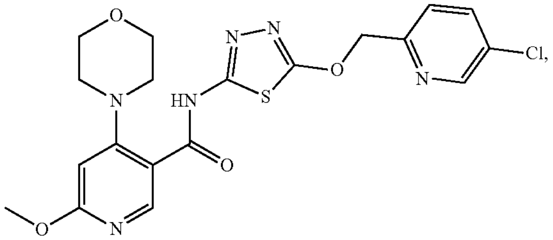
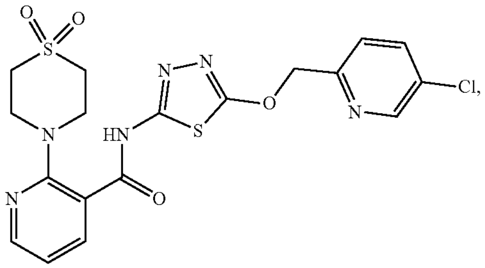
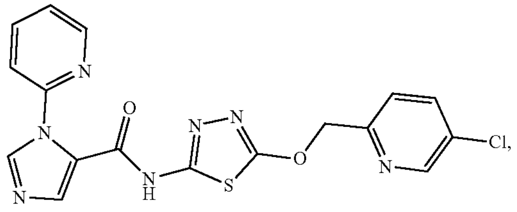
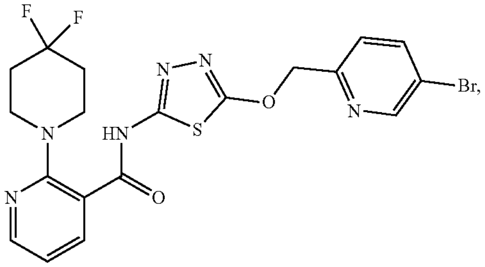

-continued
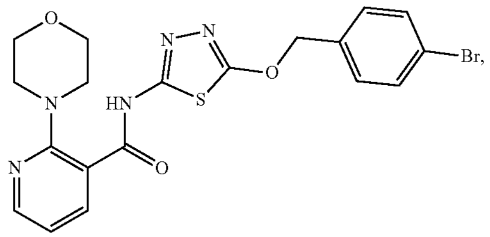
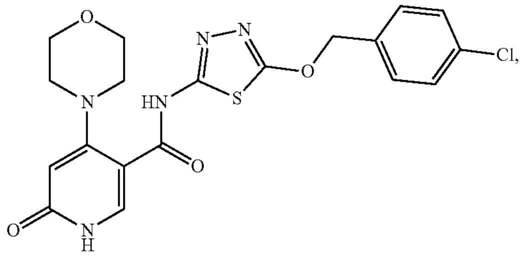
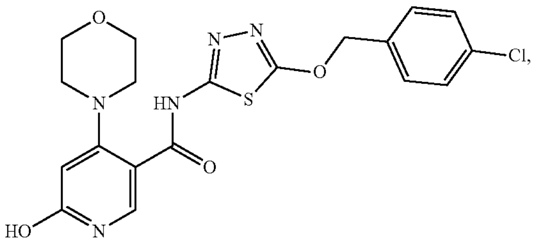
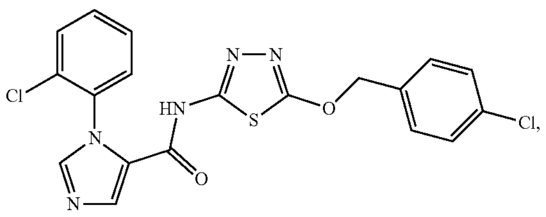
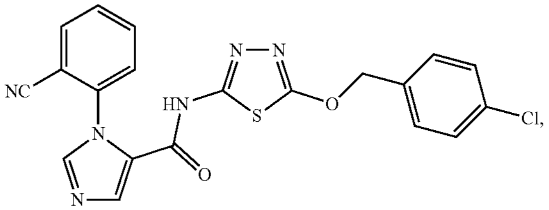
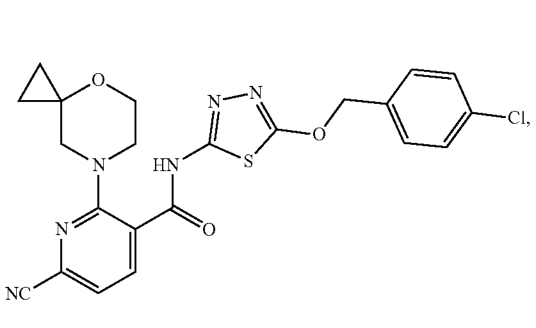
-continued
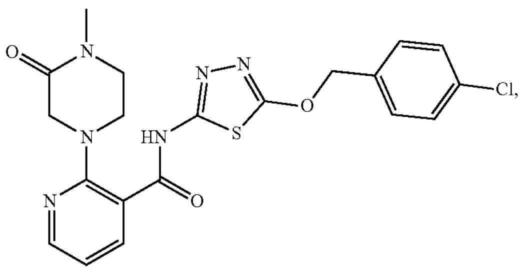
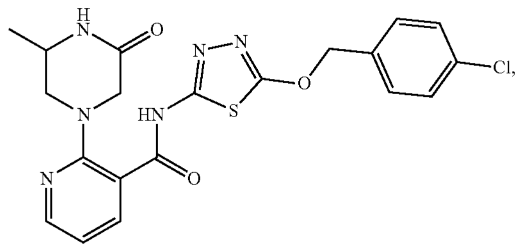
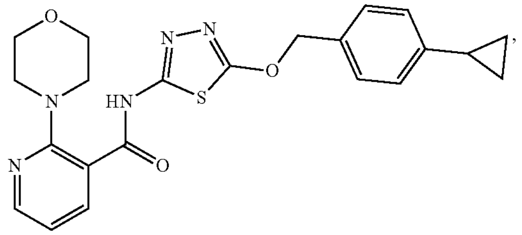
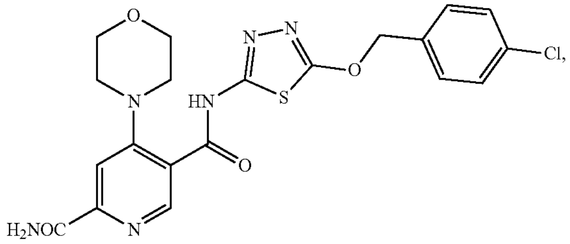
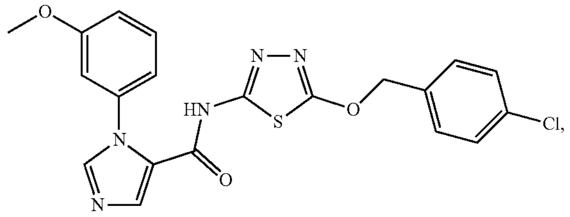
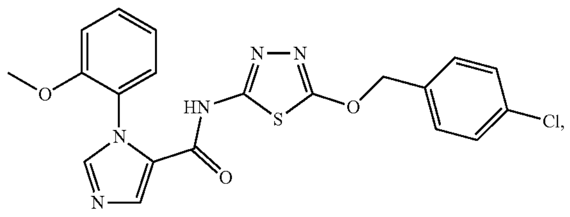
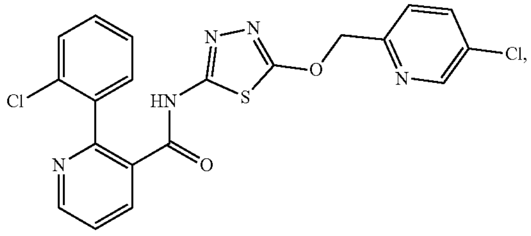

-continued
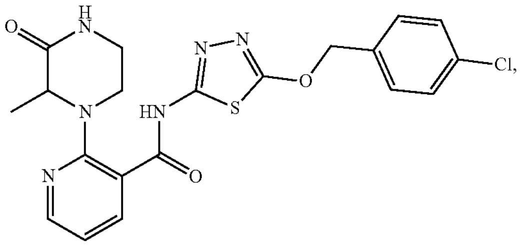,
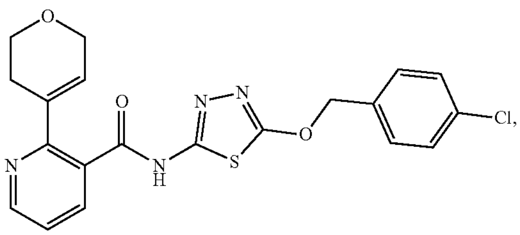,
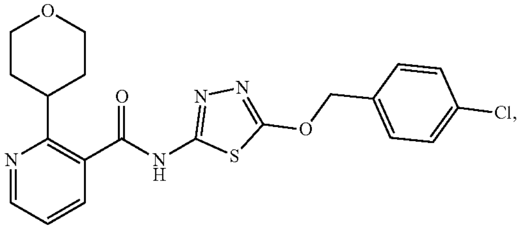,
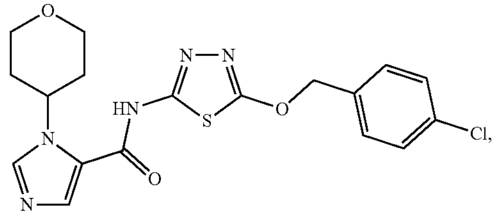,
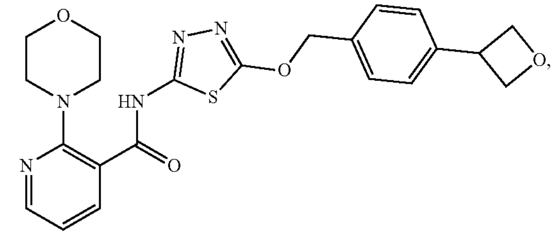,
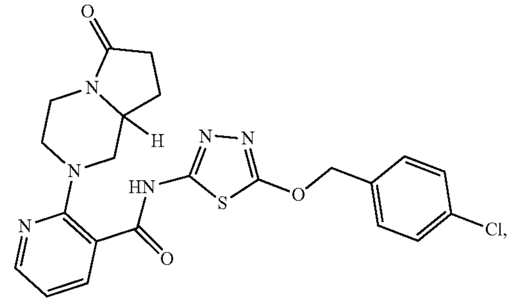,
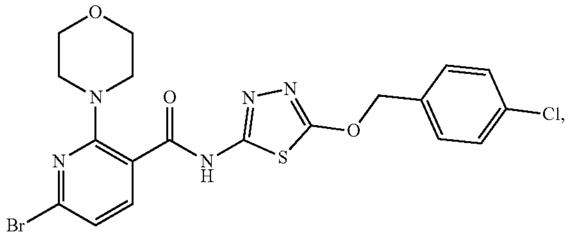,
-continued
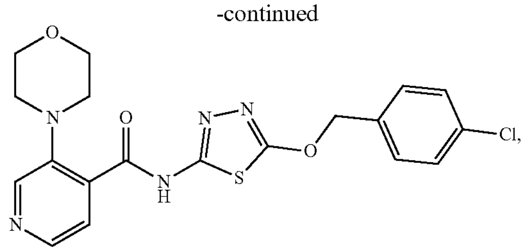,
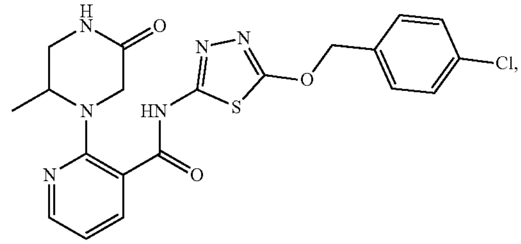,
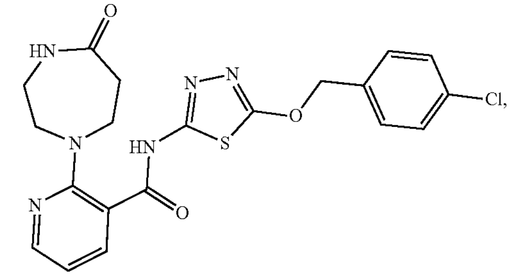,
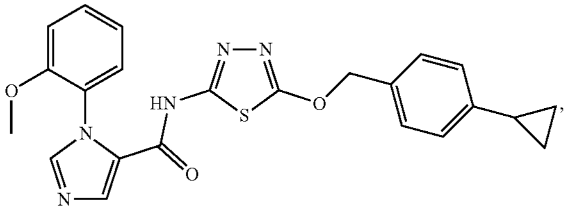,
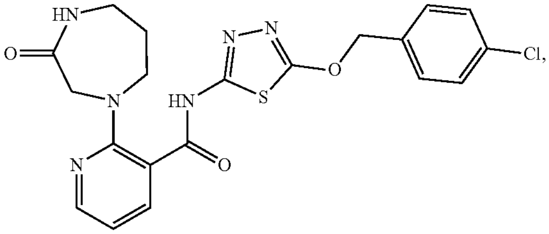,
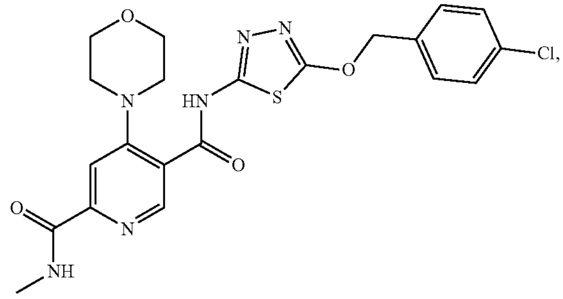,
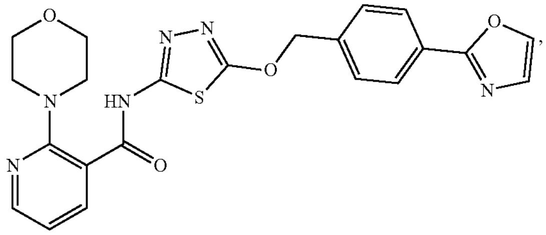, -continued
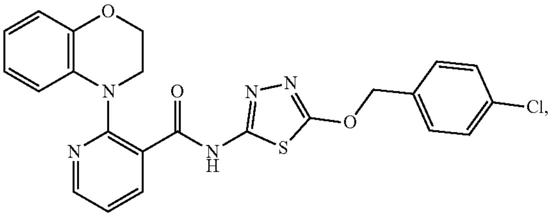
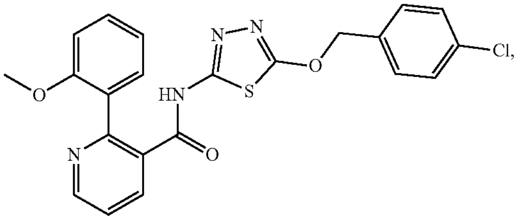
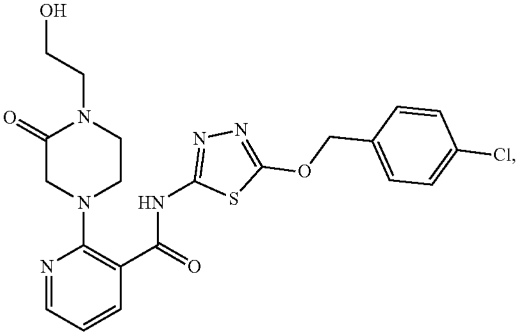
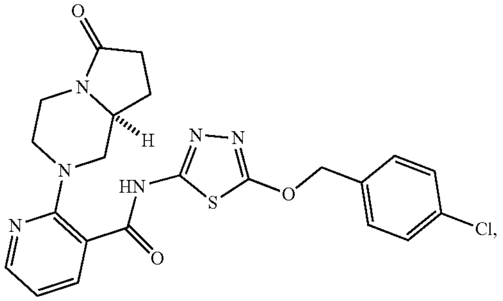
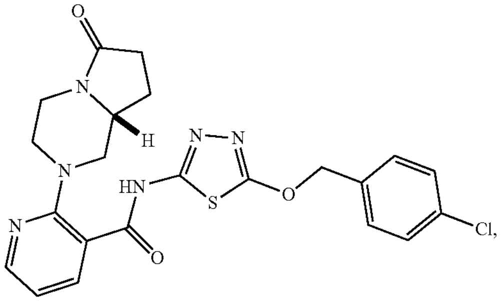
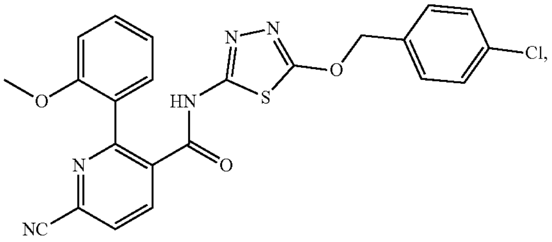
-continued
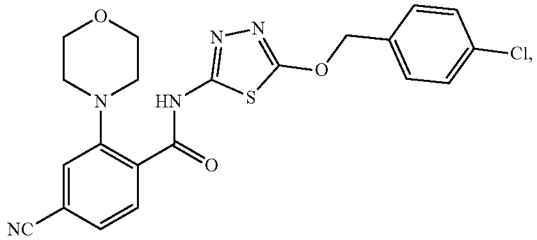
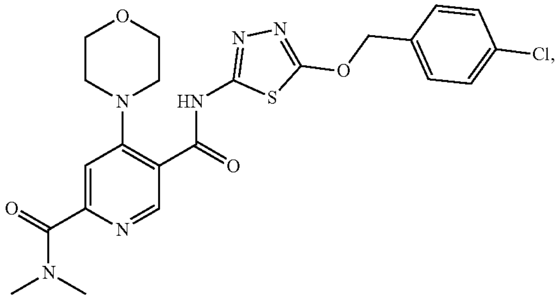
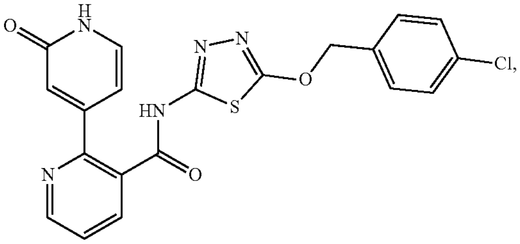
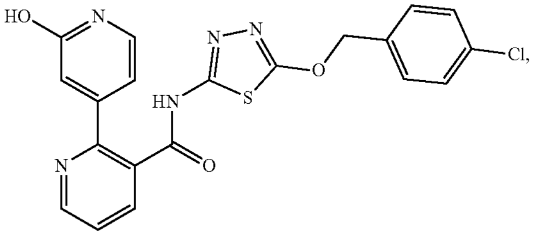
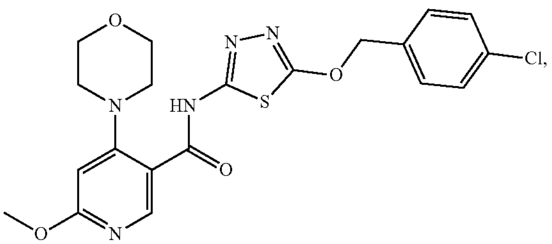
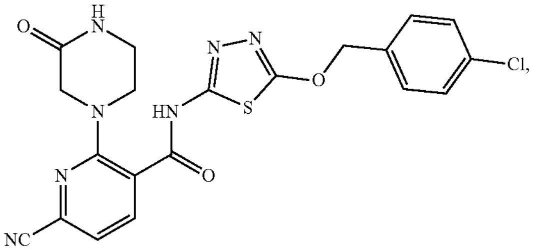

-continued
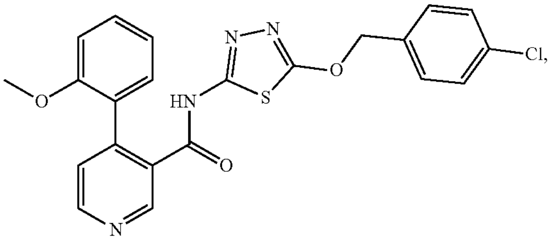
,
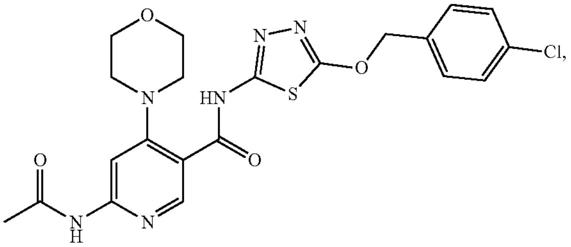
,
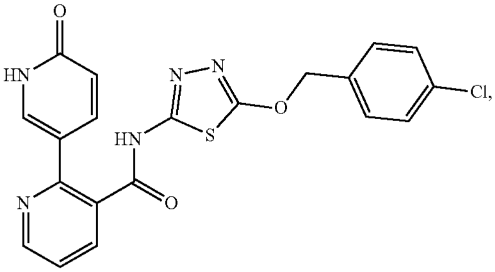
,
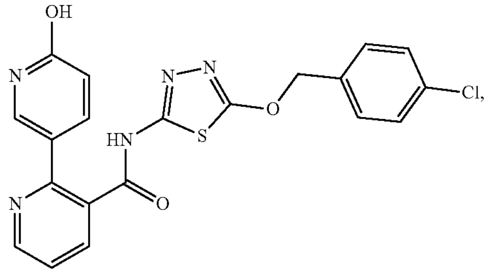
,
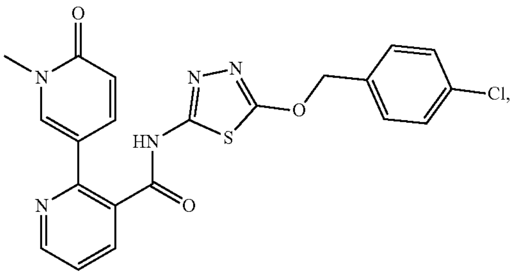
,
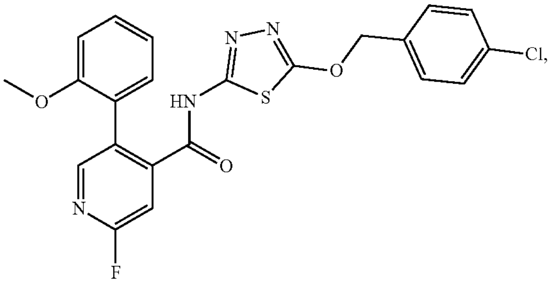
,
-continued
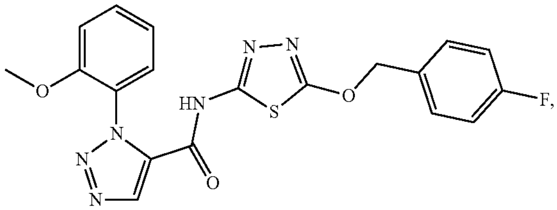
,
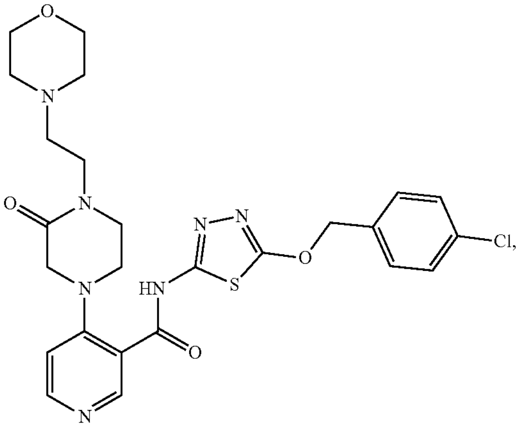
,
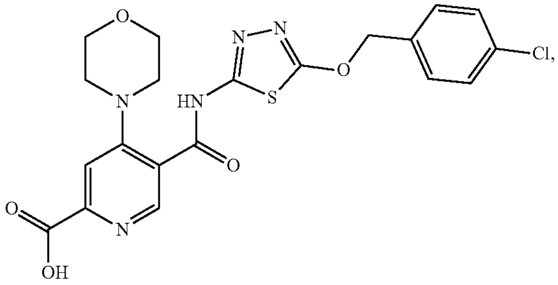
,
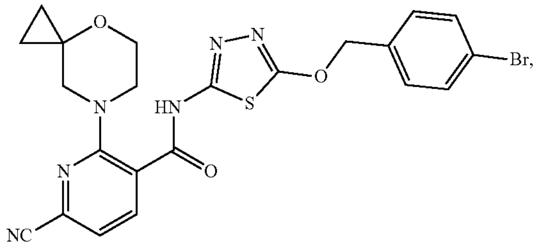
,
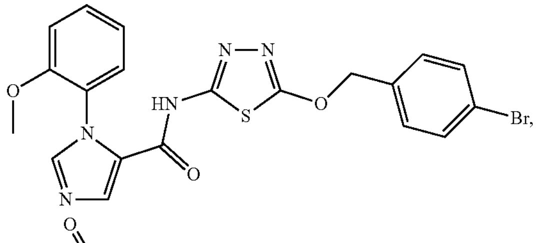
,
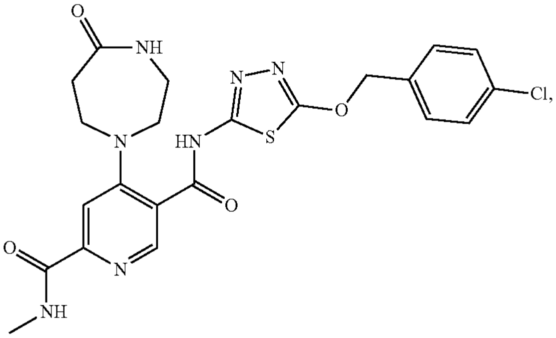
, -continued
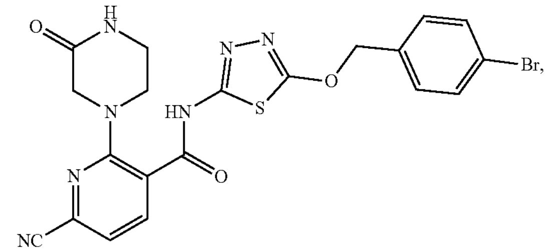
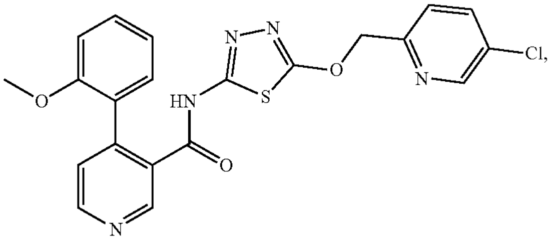
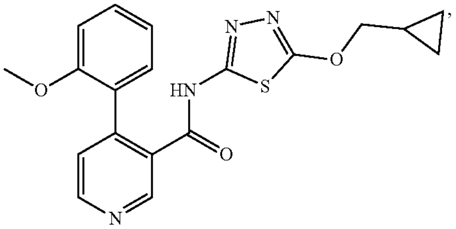
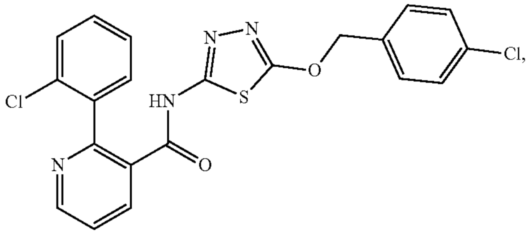
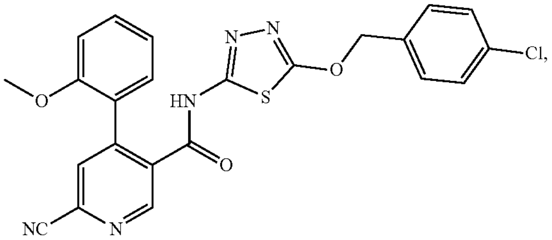
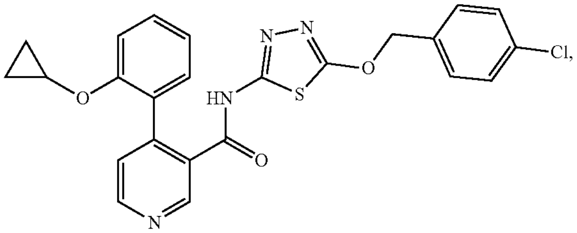
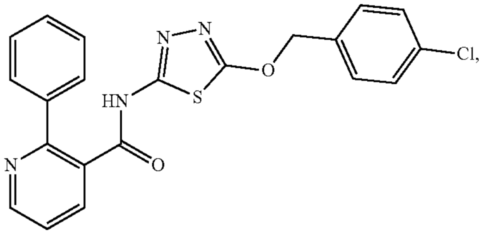
-continued
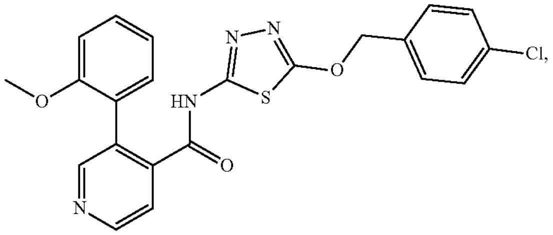
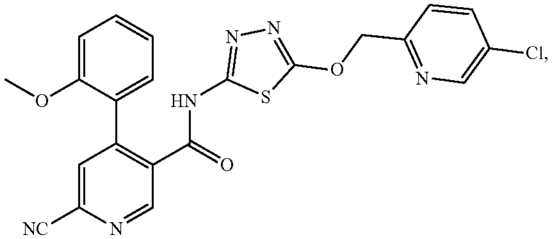
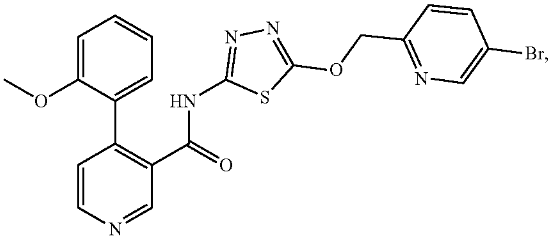
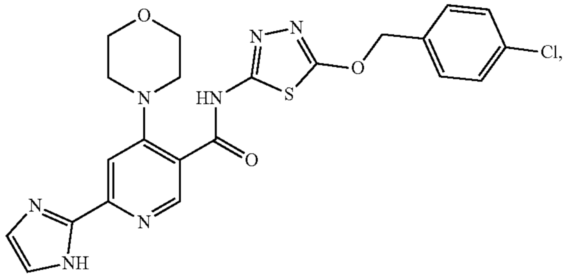
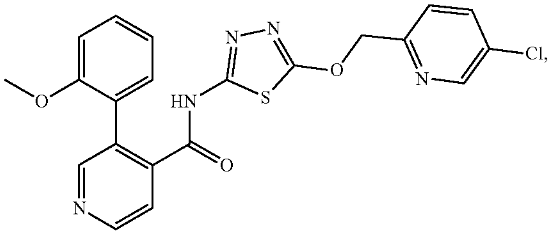
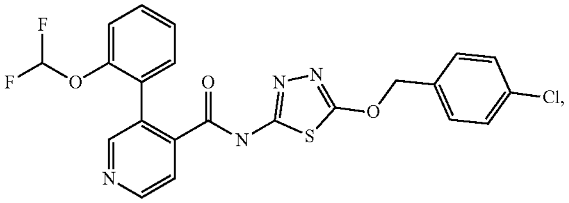
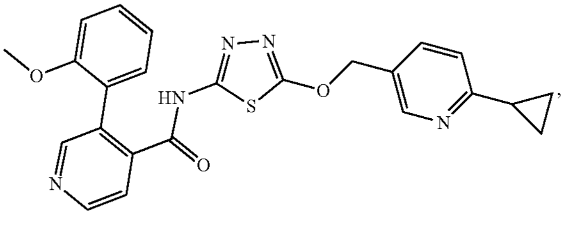

-continued
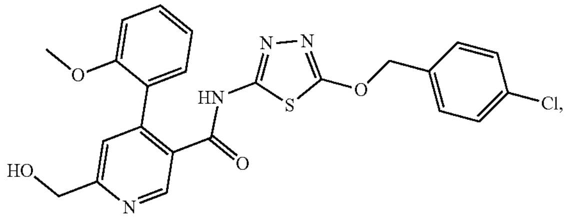
,
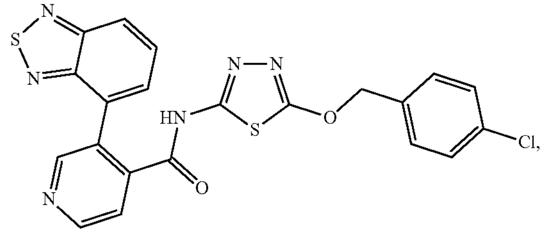
,
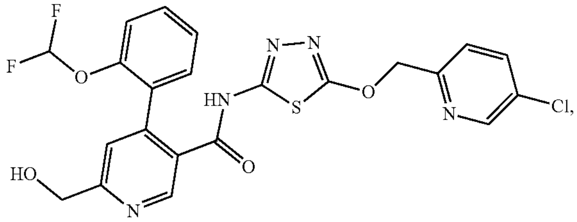
,
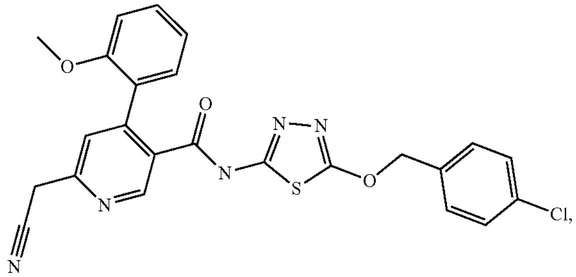
,
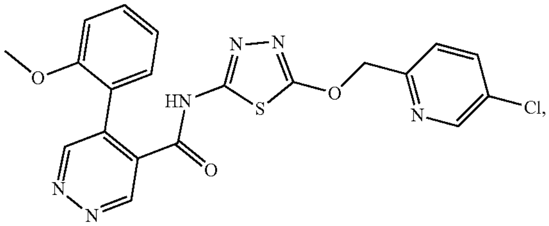
,
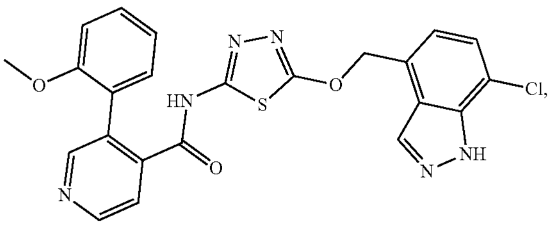
,
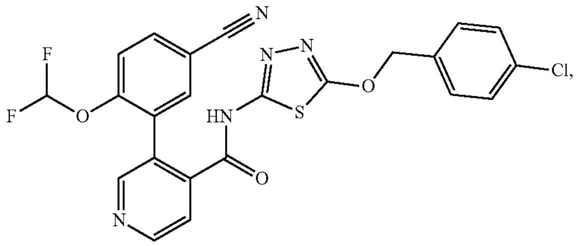
,
-continued
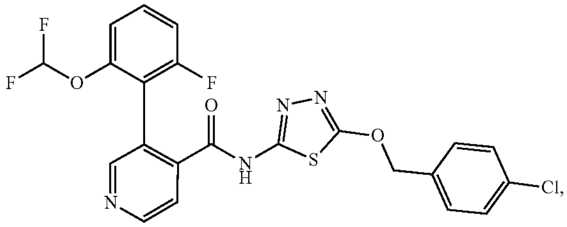
,
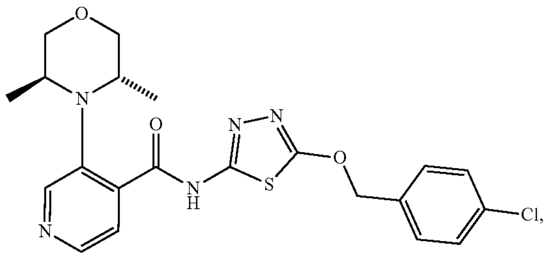
,
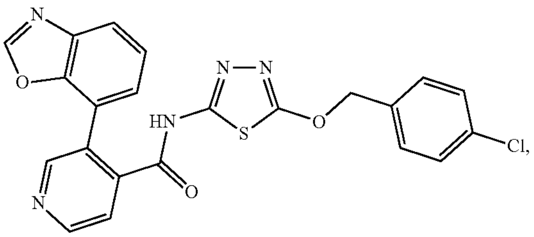
,
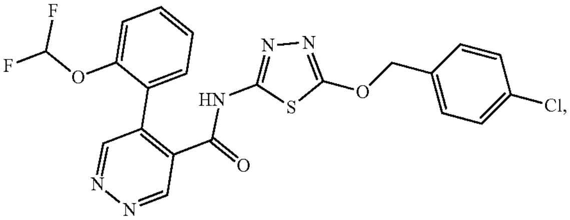
,
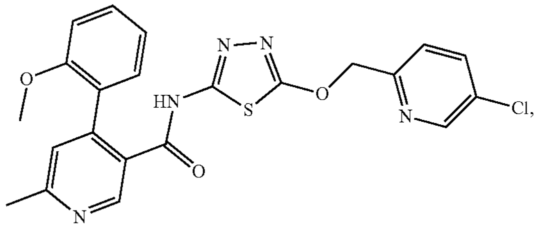
,
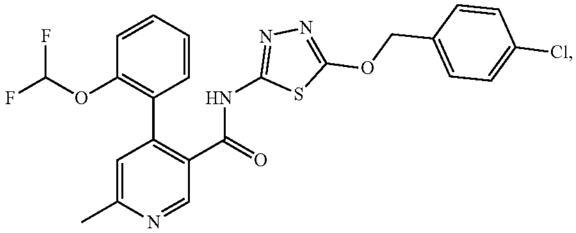
,
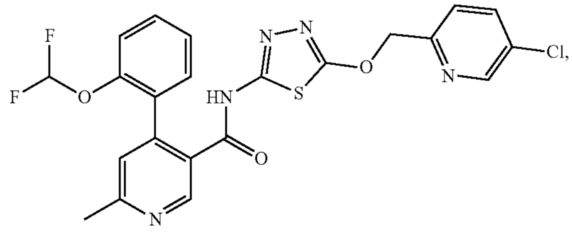
, -continued
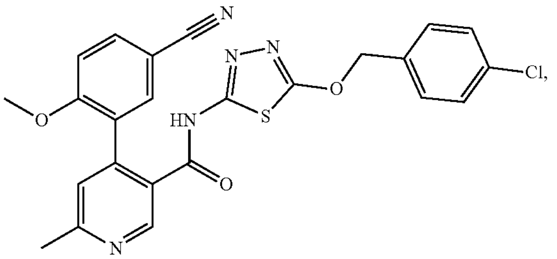
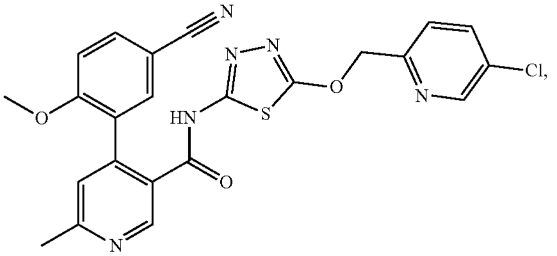
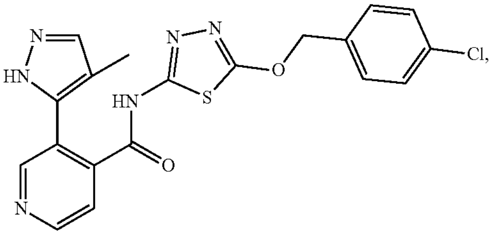
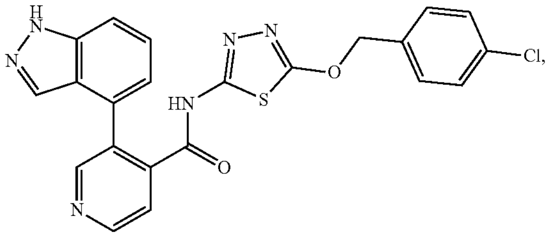
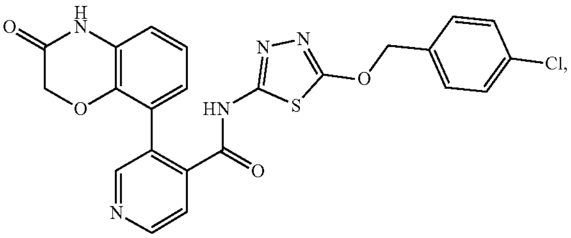
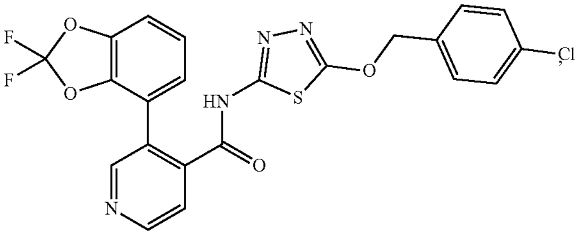
-continued
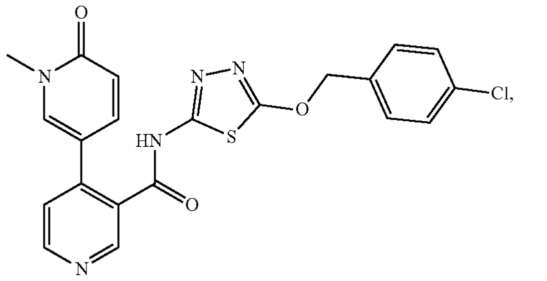
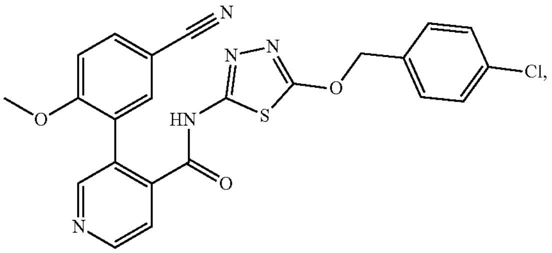
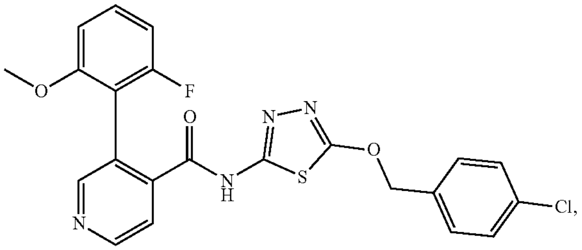
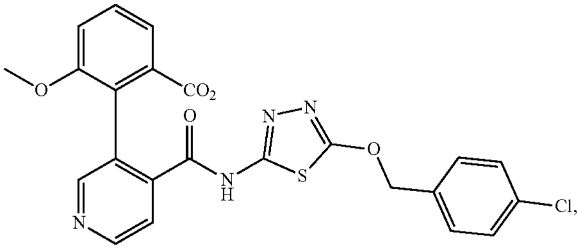
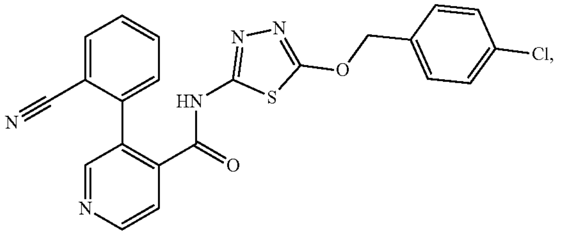
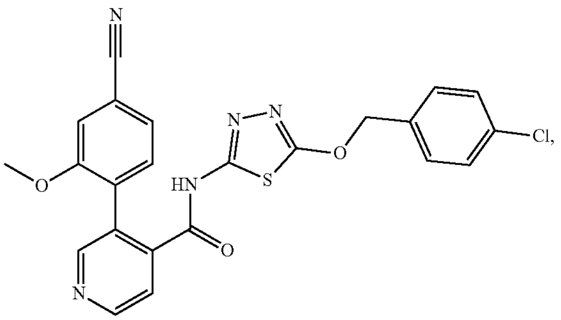

-continued
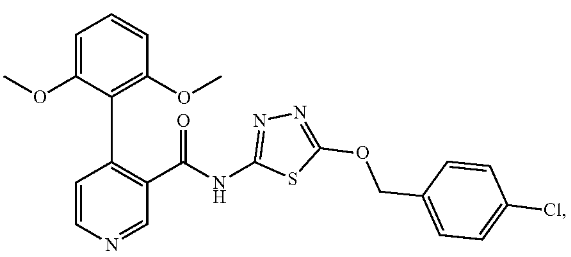
,
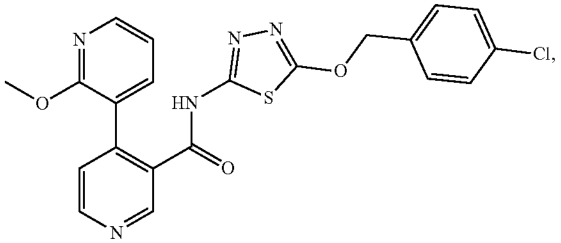
,
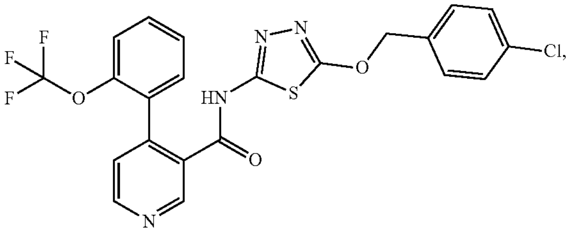
,
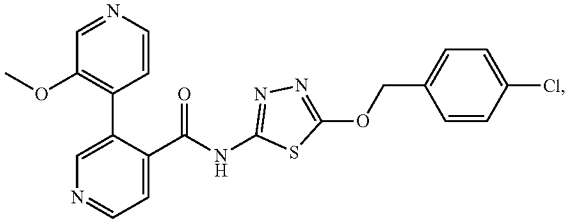
,
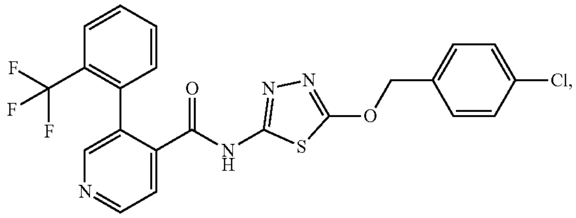
,
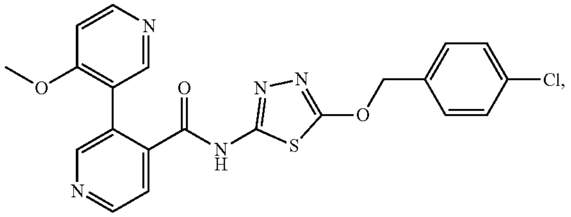
,
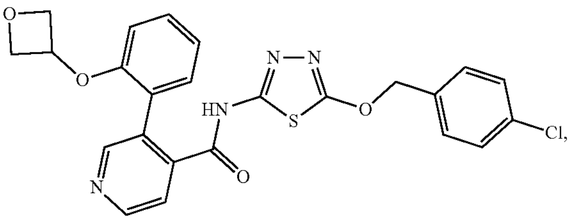
,
-continued
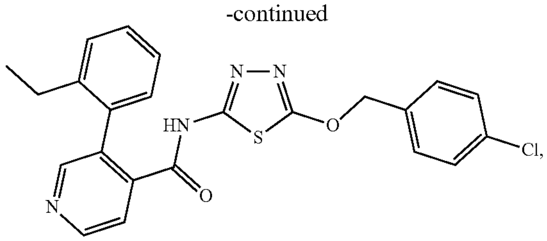
,
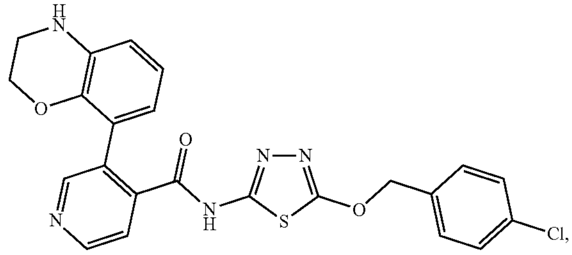
,
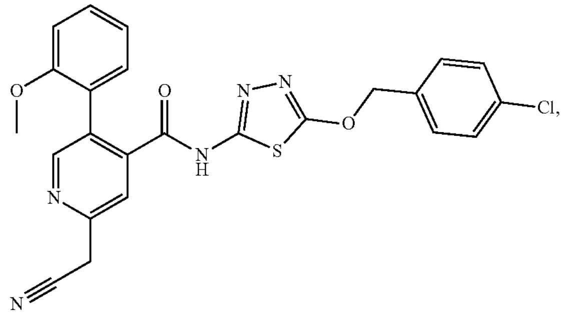
,
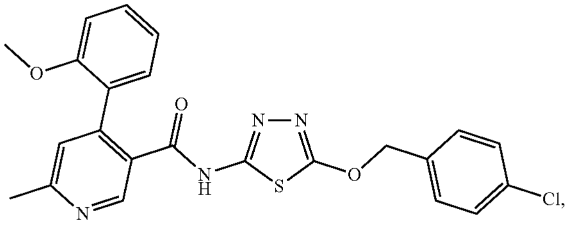
,
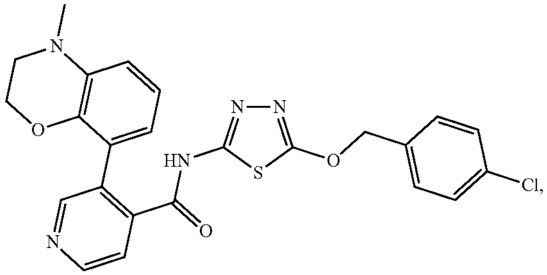
,
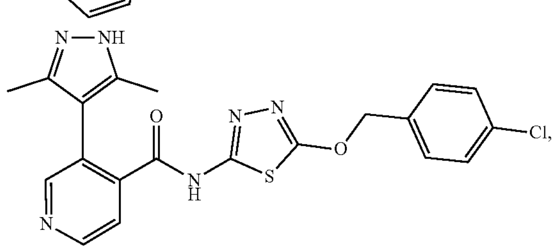
,
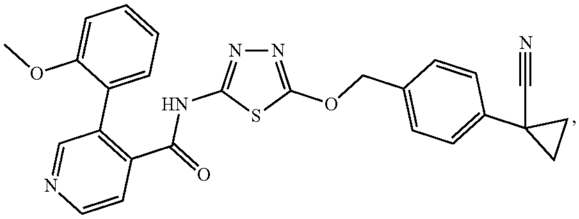
, -continued
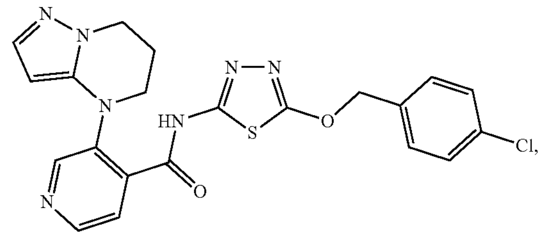
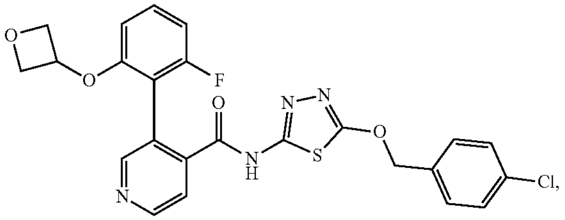
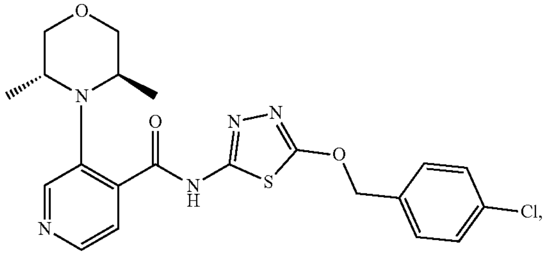
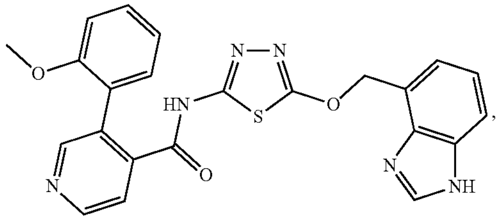
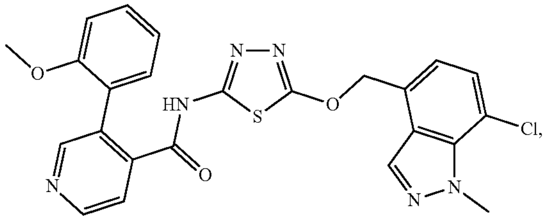
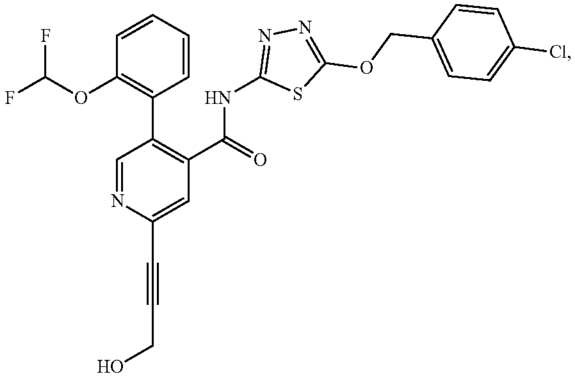
-continued
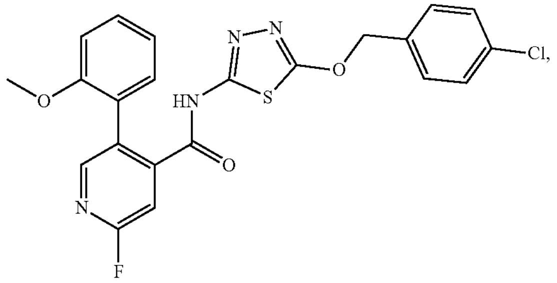
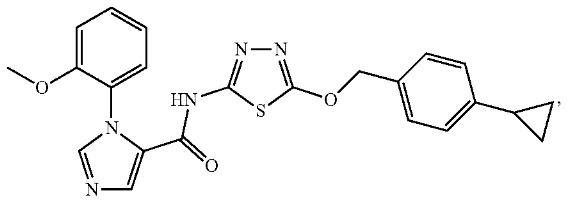
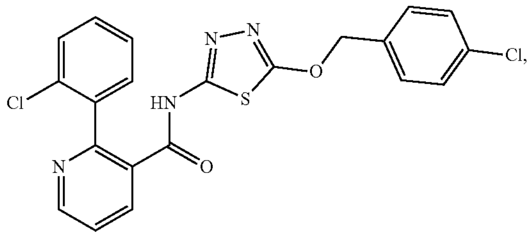
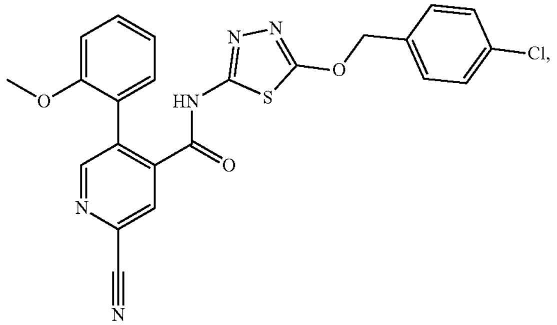
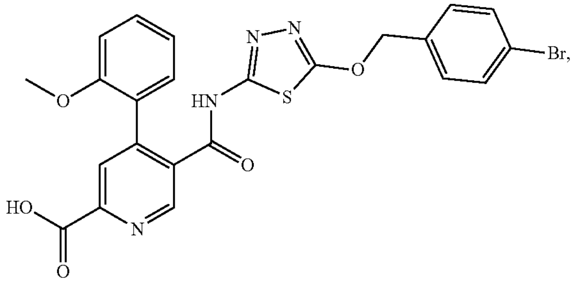
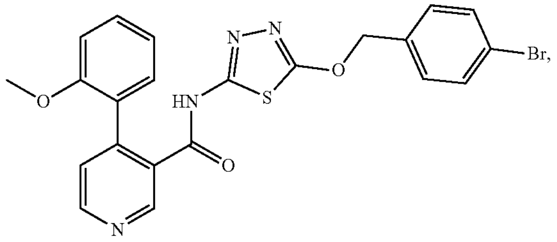

-continued
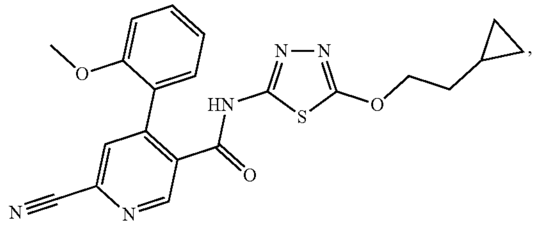
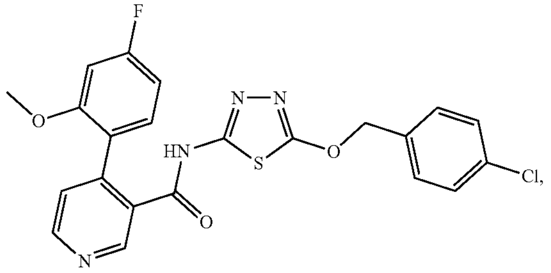
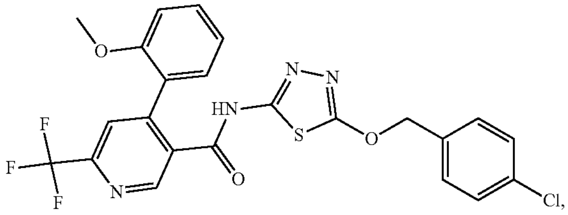
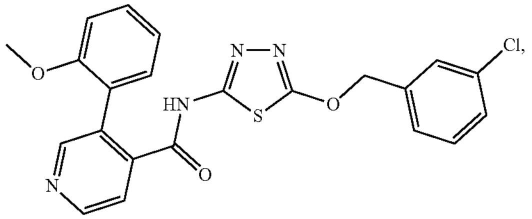
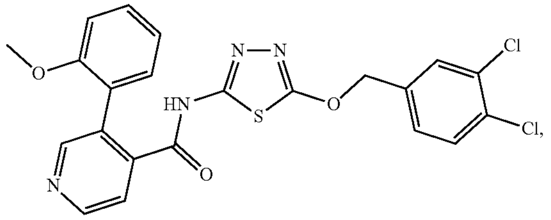
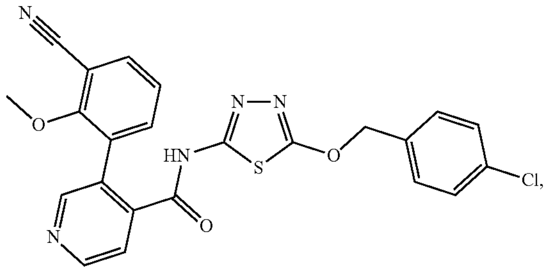
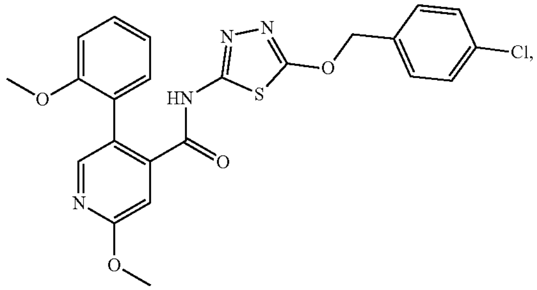
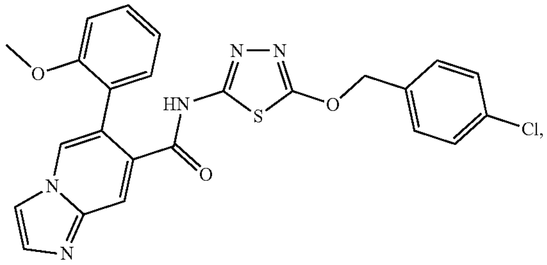
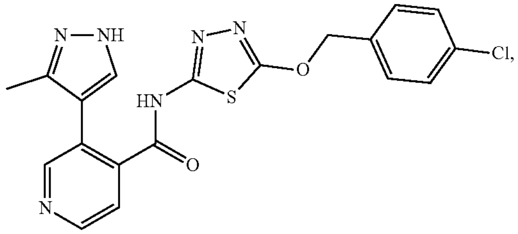
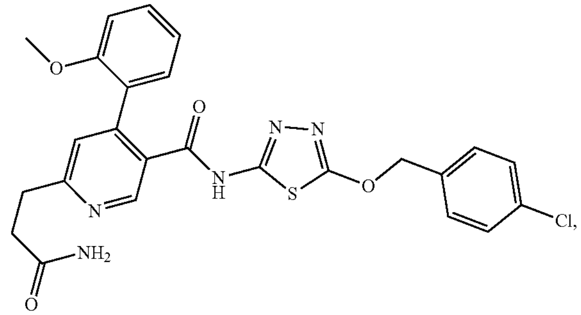
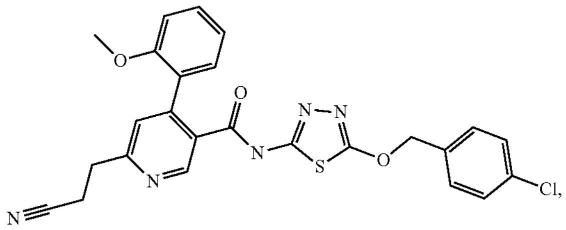
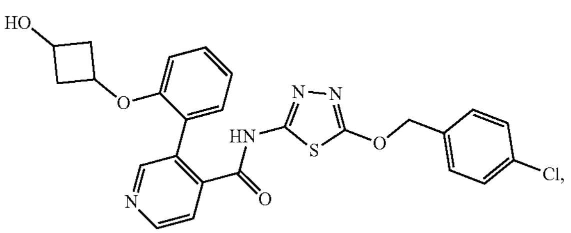

-continued
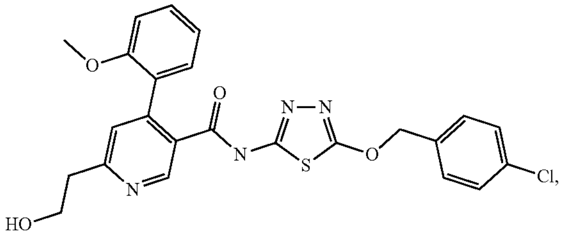
,
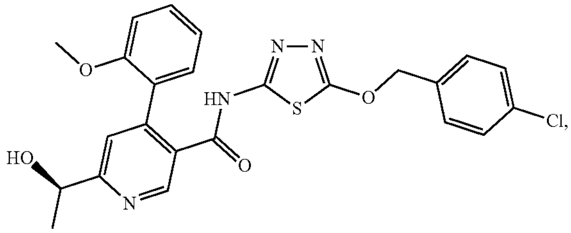
,
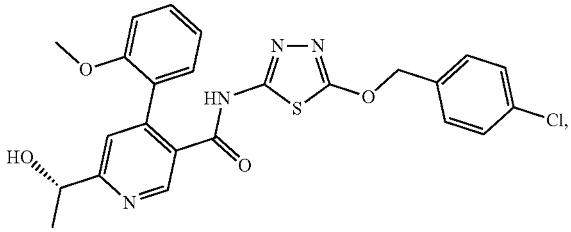
,
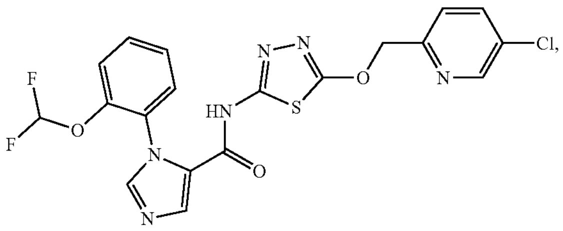
,
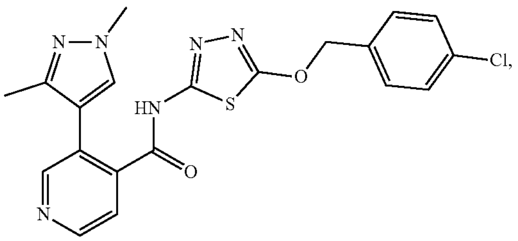
,
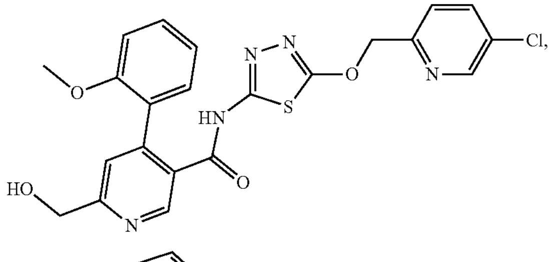
,
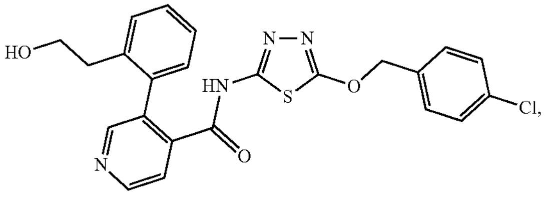
,
-continued
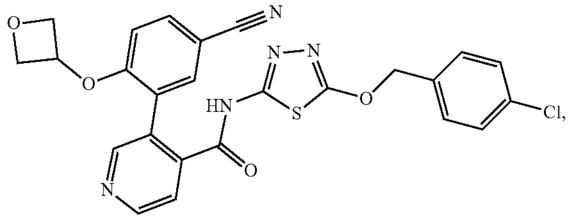
,
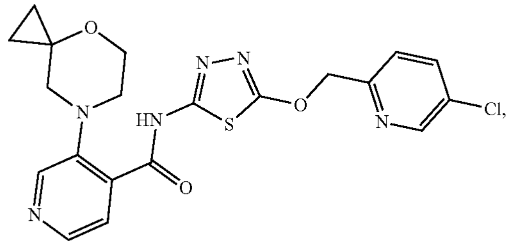
,
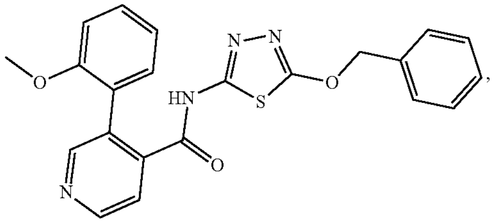
,
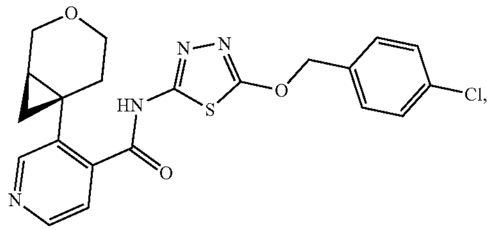
,
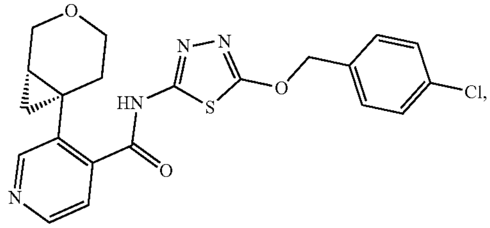
,
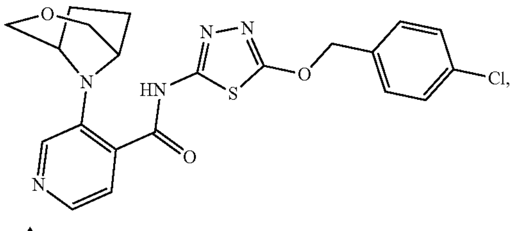
,
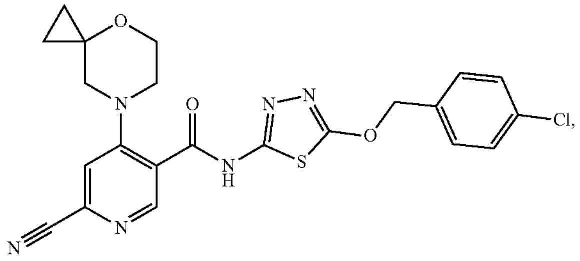
, -continued
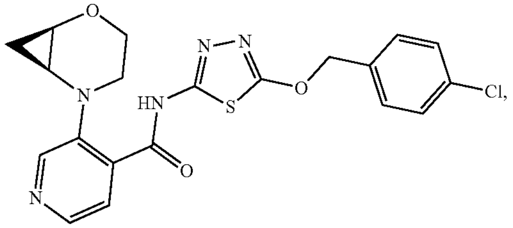
,
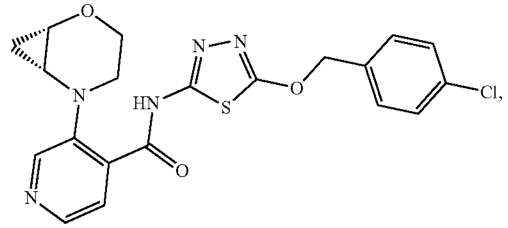
,
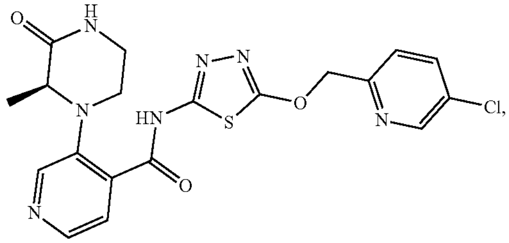
,
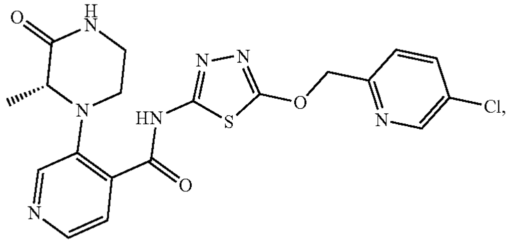
,
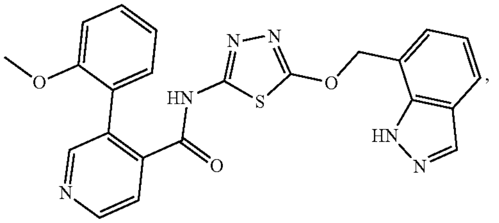
,
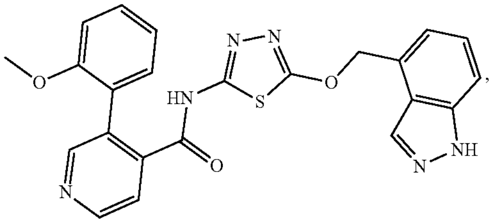
,
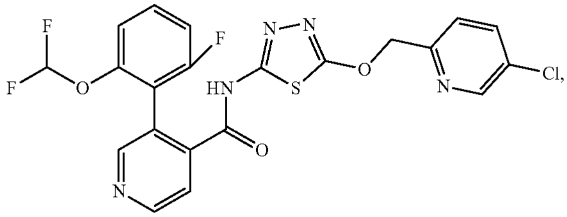
,
-continued
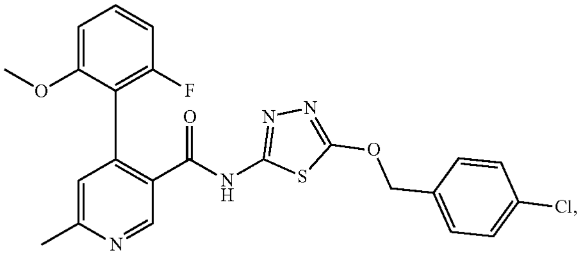
,
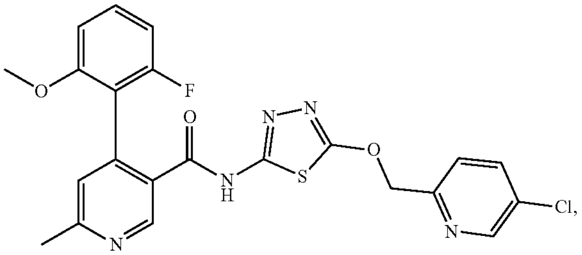
,
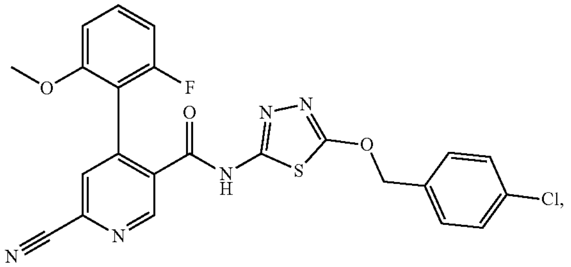
,
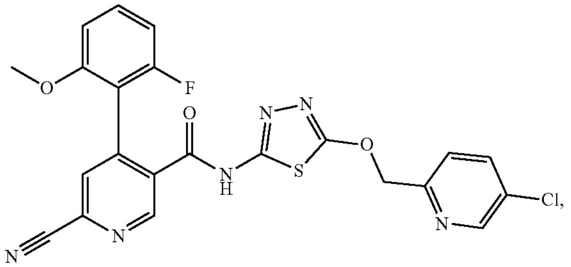
,
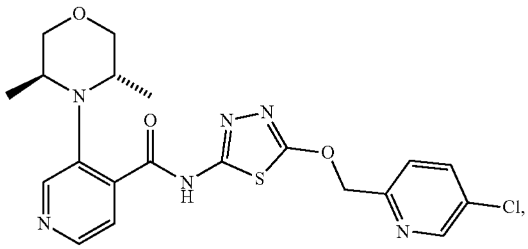
,
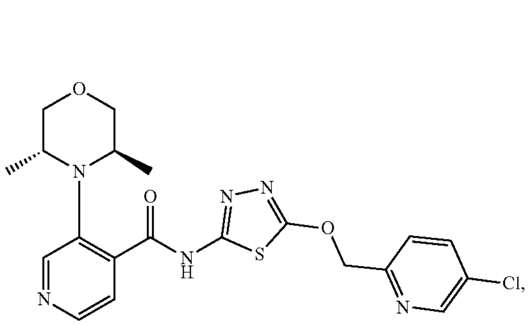
, -continued
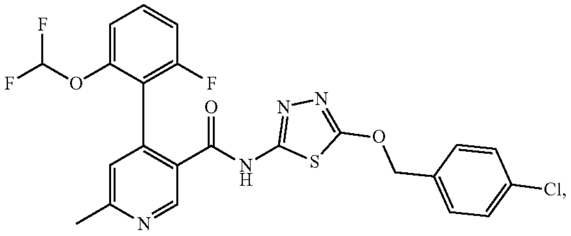
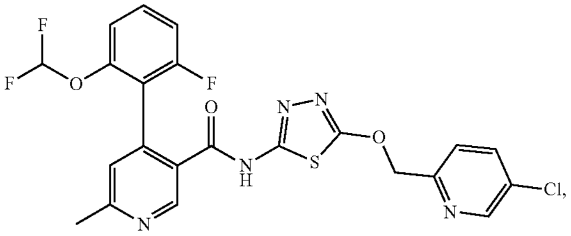
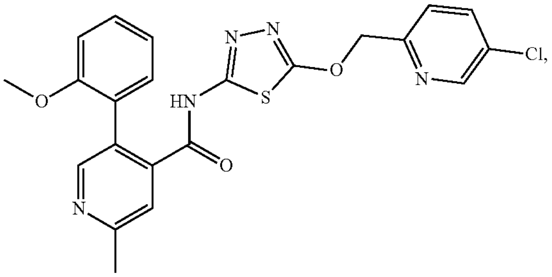
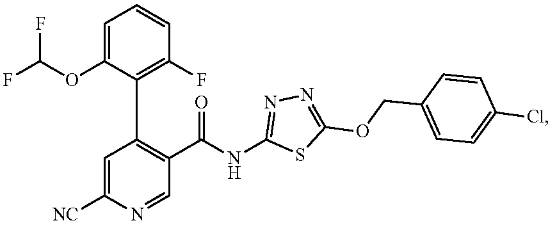
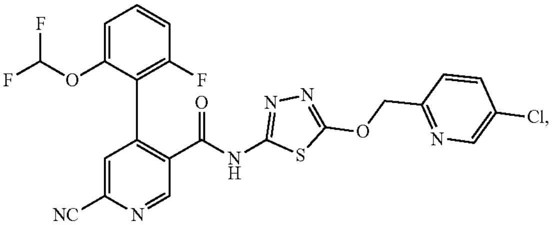
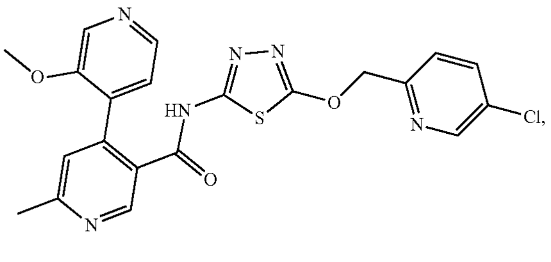
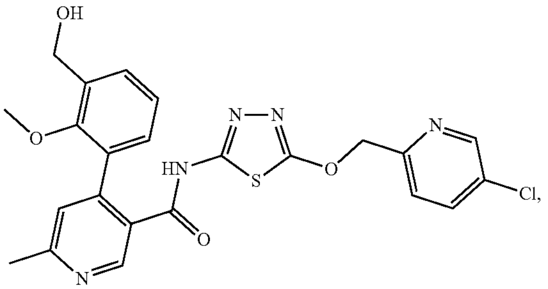
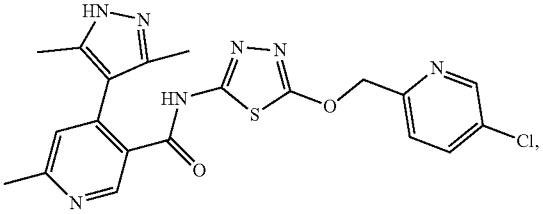
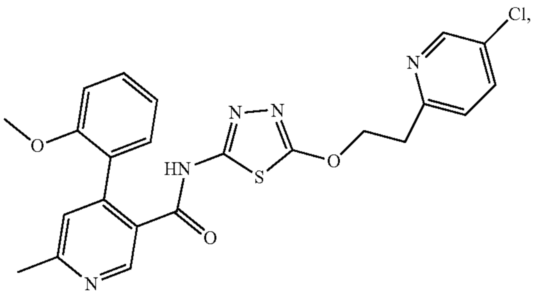
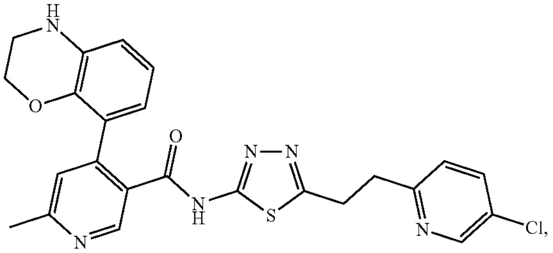
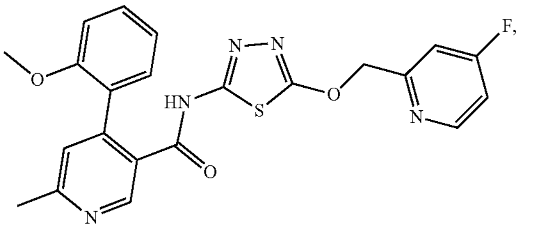
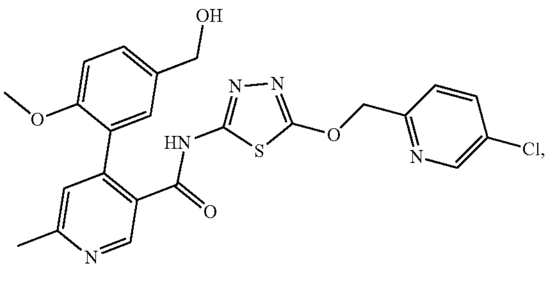

-continued
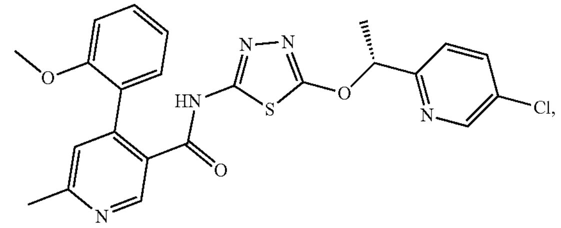
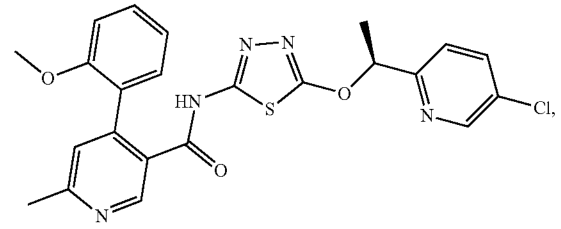
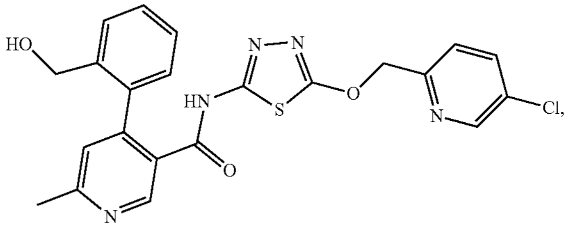
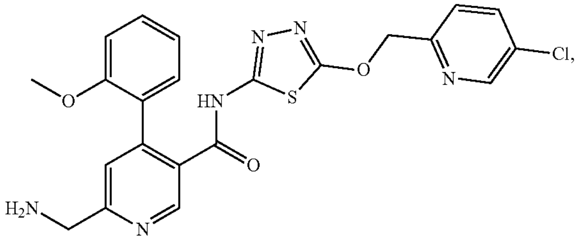
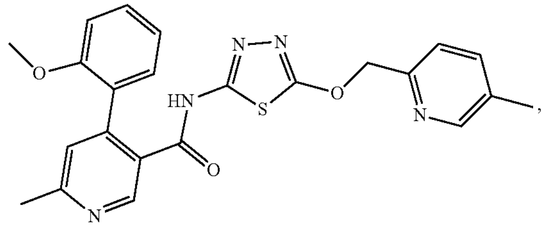
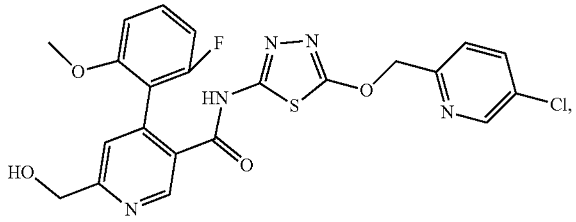
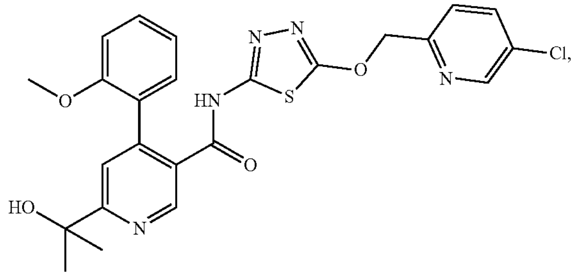
-continued
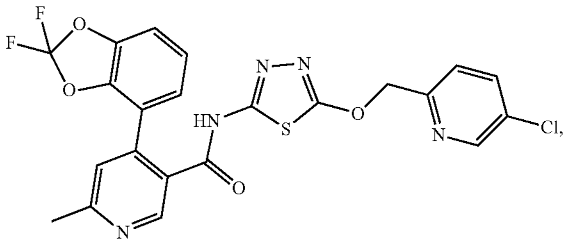
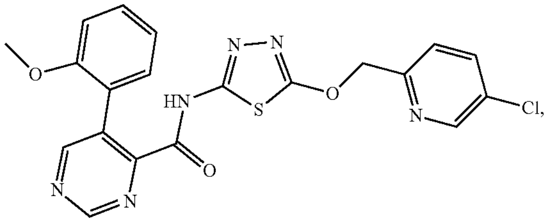
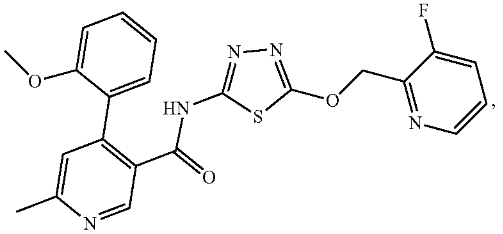
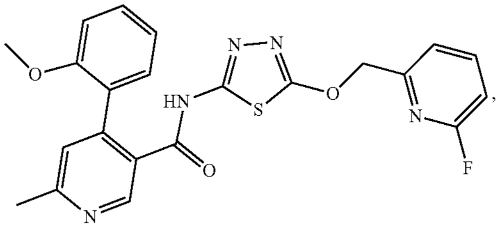
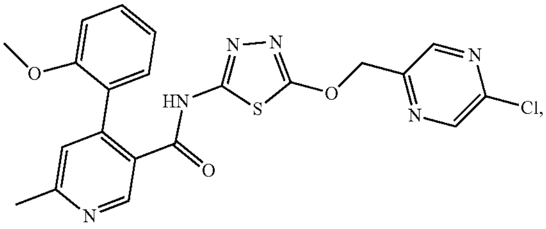
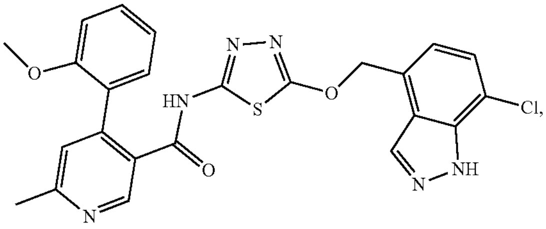
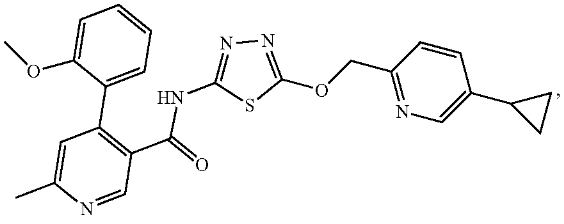

-continued
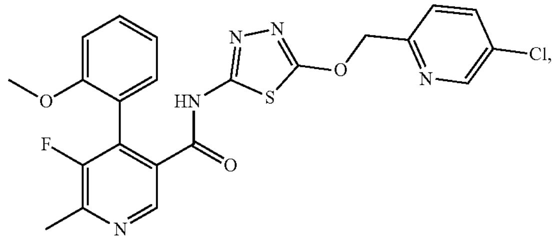,
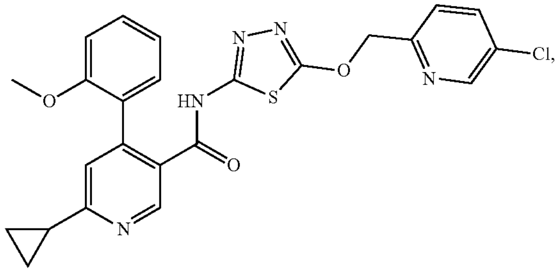,
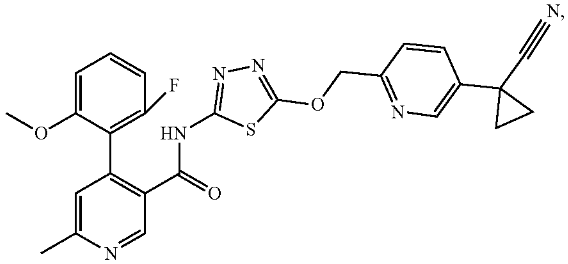,
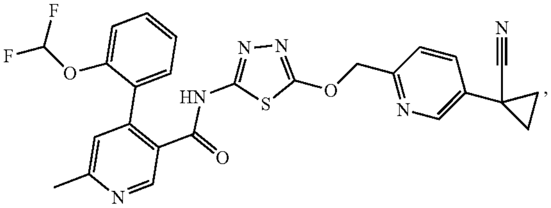,
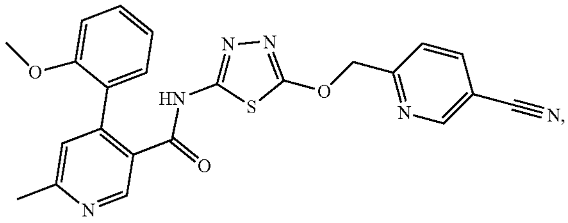,
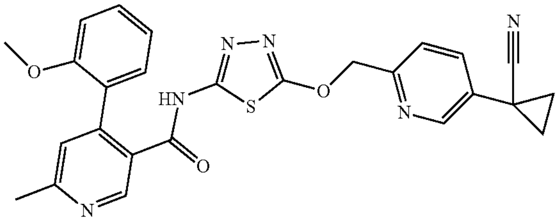,
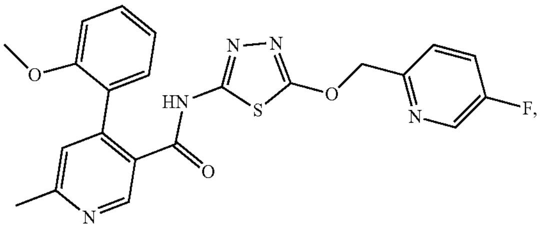,
-continued
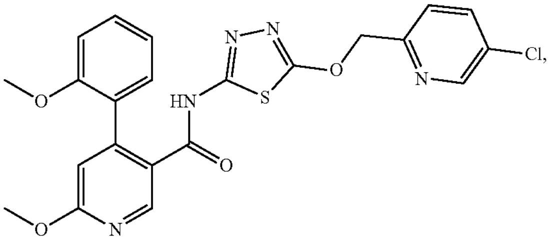,
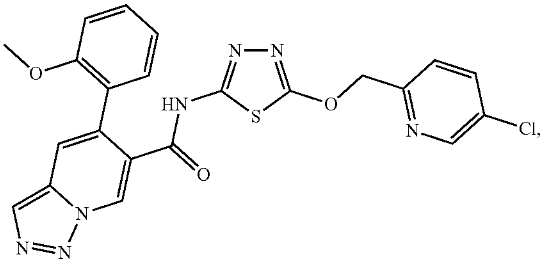,
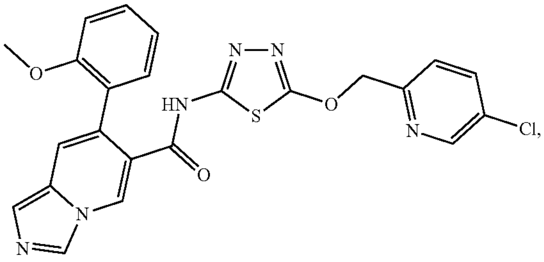,
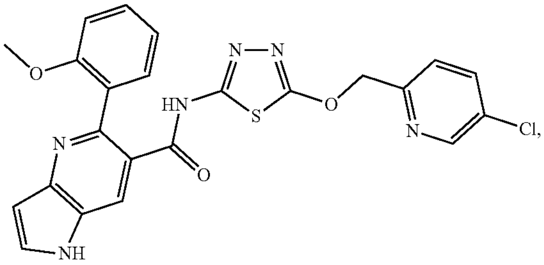,
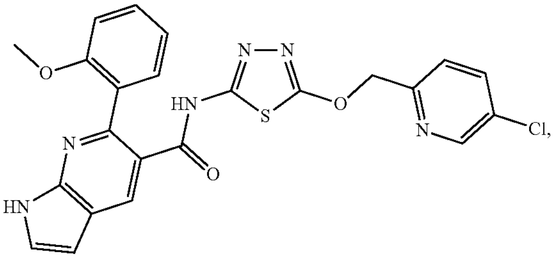,
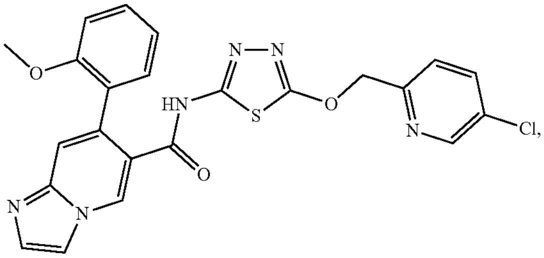, -continued

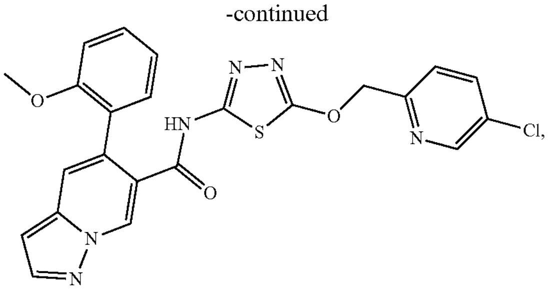

,

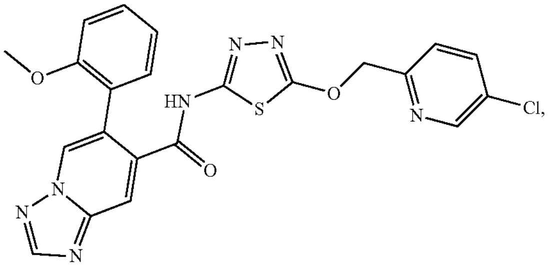

,

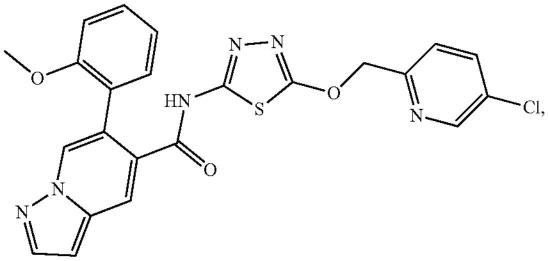

,

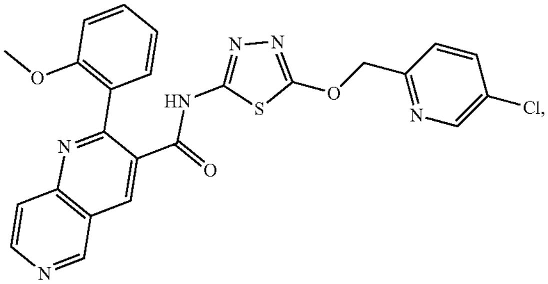

, and

-continued

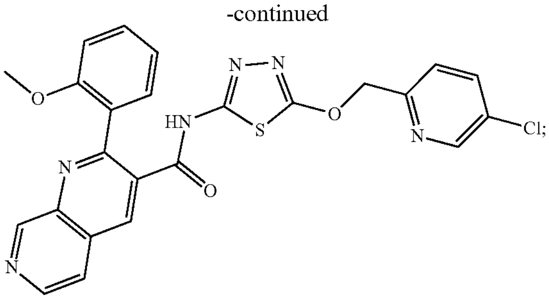

;

or a pharmaceutically acceptable salt thereof.

2. A pharmaceutical composition comprising a compound of claim 1 and at least one pharmaceutically acceptable excipient.

3. A method for treating a disease characterized by overexpression of Polθ in a human patient comprising administering to the human patient in need of such treatment a therapeutically effective amount of a compound of claim 1.

4. The method of claim 3, wherein the human patient is in recognized need of such treatment and the disease is a cancer.

5. A method of treating a homologous recombinant (HR) deficient cancer in a human patient comprising administering to the human patient in need of such treatment a therapeutically effective amount of a compound of claim 1.

6. A method for treating a cancer in a human patient, wherein the cancer is characterized by a reduction or absence of BRCA gene expression, the absence of the BRCA gene, or reduced function of BRCA protein, comprising administering to the human patient in need of such treatment a therapeutically effective amount of a compound of claim 1.

7. The method of claim 4, wherein the cancer is lymphoma, soft tissue, rhabdoid, multiple myeloma, uterus, gastric, peripheral nervous system, rhabdomyosarcoma, bone, colorectal, mesothelioma, breast, ovarian, lung, fibroblast, central nervous system, urinary tract, upper aerodigestive, leukemia, kidney, skin, esophagus, and pancreas.

* * * * *